United States Patent
Urlinger et al.

(10) Patent No.: US 9,541,559 B2
(45) Date of Patent: Jan. 10, 2017

(54) COLLECTION AND METHODS FOR ITS USE

(71) Applicant: MorphoSys AG, Martinsried/Planegg (DE)

(72) Inventors: Stefanie Urlinger, Munich (DE); Thomas Tiller, Munich (DE); Ingrid Schuster, Munich (DE); Yvonne Stark, Munich (DE)

(73) Assignee: MORPHOSYS AG, Martinsried, Planegg (DE)

( * ) Notice: Subject to any disclaimer, the term of this patent is extended or adjusted under 35 U.S.C. 154(b) by 170 days.

(21) Appl. No.: 14/242,906

(22) Filed: Apr. 2, 2014

(65) Prior Publication Data

US 2014/0206575 A1    Jul. 24, 2014

Related U.S. Application Data

(62) Division of application No. 13/884,975, filed as application No. PCT/EP2011/070473 on Nov. 18, 2011, now Pat. No. 8,728,981.

(60) Provisional application No. 61/415,367, filed on Nov. 19, 2010, provisional application No. 61/494,452, filed on Jun. 8, 2011.

(30) Foreign Application Priority Data

Nov. 19, 2010 (EP) ..................... 10191910

(51) Int. Cl.
| C40B 40/08 | (2006.01) |
| G01N 33/68 | (2006.01) |
| C07K 16/00 | (2006.01) |
| C12N 15/10 | (2006.01) |

(52) U.S. Cl.
CPC ......... *G01N 33/6854* (2013.01); *C07K 16/005* (2013.01); *C12N 15/1037* (2013.01); *C07K 2317/55* (2013.01); *C07K 2317/567* (2013.01); *C40B 40/08* (2013.01)

(58) Field of Classification Search
None
See application file for complete search history.

(56) References Cited

U.S. PATENT DOCUMENTS

| 5,091,513 A | 2/1992 | Huston |
| 5,223,409 A | 6/1993 | Ladner |
| 5,395,750 A | 3/1995 | Dillon |
| 5,403,484 A | 4/1995 | Ladner |
| 5,476,786 A | 12/1995 | Huston |
| 5,482,858 A | 1/1996 | Huston |

(Continued)

FOREIGN PATENT DOCUMENTS

| EP | 0368684 | 5/1990 |
| EP | 2088432 | 8/2009 |

(Continued)

OTHER PUBLICATIONS

Curnow et al. (Invest. Opthalmol Visual Sci. (2005) 46, 4251-9).

(Continued)

*Primary Examiner* — Christian Boesen
(74) *Attorney, Agent, or Firm* — Licata & Tyrrell P.C.

(57) ABSTRACT

The present disclosure enables collections of variable heavy chain and variable light chain pairs comprising, in part, germline protein sequences that are pre-selected for functional properties relevant to developability, wherein the collections may be used to select against any antigen using, for example, phage display.

32 Claims, 73 Drawing Sheets

(56) References Cited

U.S. PATENT DOCUMENTS

| | | | |
|---|---|---|---|
| 5,565,332 | A | 10/1996 | Hoogenboom |
| 5,571,698 | A | 11/1996 | Ladner |
| 5,580,717 | A | 12/1996 | Dower |
| 5,693,493 | A | 12/1997 | Robinson |
| 5,780,225 | A | 7/1998 | Wigler |
| 5,837,500 | A | 11/1998 | Ladner |
| 5,840,479 | A | 11/1998 | Little |
| 5,855,885 | A | 1/1999 | Smith |
| 5,859,205 | A | 1/1999 | Adair |
| 5,885,793 | A | 3/1999 | Griffiths |
| 5,969,108 | A | 10/1999 | McCafferty |
| 5,977,322 | A | 11/1999 | Marks |
| 6,096,551 | A | 8/2000 | Barbas |
| 6,248,516 | B1 | 6/2001 | Winter |
| 6,291,158 | B1 | 9/2001 | Winter |
| 6,291,159 | B1 | 9/2001 | Winter |
| 6,291,160 | B1 | 9/2001 | Lerner |
| 6,291,161 | B1 | 9/2001 | Lerner |
| 6,297,053 | B1 | 10/2001 | Stemmer |
| 6,300,064 | B1 | 10/2001 | Knappik |
| 6,303,313 | B1 | 10/2001 | Wigler |
| 6,696,248 | B1 | 2/2004 | Knappik |
| 6,706,484 | B1 | 3/2004 | Knappik |
| 6,828,422 | B1 | 12/2004 | Achim |
| 6,979,538 | B2 | 12/2005 | Ladner |
| 7,117,096 | B2 | 10/2006 | Luo |
| 7,118,879 | B2 | 10/2006 | Ladner |
| 7,208,293 | B2 | 4/2007 | Ladner |
| 7,244,592 | B2 | 7/2007 | Hoogenboom |
| 7,264,963 | B1 | 9/2007 | Knappik |
| 7,288,249 | B2 | 10/2007 | Carter |
| 8,143,007 | B2 | 3/2012 | Devinder |
| 2001/0049107 | A1 | 12/2001 | Sharon |
| 2004/0180327 | A1 | 9/2004 | Ladner |
| 2005/0037358 | A1 | 2/2005 | Muyldermans |
| 2006/0018898 | A1 | 1/2006 | Waldmann |
| 2006/0078898 | A1 | 4/2006 | Curry |
| 2006/0188896 | A1 | 8/2006 | Seul |
| 2008/0003566 | A1 | 1/2008 | Vaux |
| 2009/0082221 | A1 | 3/2009 | Wang |
| 2010/0035241 | A1 | 2/2010 | Achatz |

FOREIGN PATENT DOCUMENTS

| | | |
|---|---|---|
| WO | 9002809 | 3/1990 |
| WO | 9005144 | 5/1990 |
| WO | 9014424 | 11/1990 |
| WO | 9014430 | 11/1990 |
| WO | 9201047 | 1/1992 |
| WO | 9215678 | 9/1992 |
| WO | 9215679 | 9/1992 |
| WO | 9306213 | 9/1992 |
| WO | 9220791 | 11/1992 |
| WO | 9303151 | 2/1993 |
| WO | 9306213 | 4/1993 |
| WO | 9311236 | 6/1993 |
| WO | 9319172 | 9/1993 |
| WO | 9511998 | 5/1995 |
| WO | 9522625 | 8/1995 |
| WO | 9708320 A | 3/1997 |
| WO | 9906587 | 2/1999 |
| WO | 9920749 | 4/1999 |
| WO | 9014443 | 11/1999 |
| WO | 0105950 | 1/2001 |
| WO | 03029456 | 4/2003 |
| WO | 03052416 | 6/2003 |
| WO | 2004013276 | 2/2004 |
| WO | 2004094474 | 11/2004 |
| WO | 2005023993 | 3/2005 |
| WO | 2005042774 | 5/2005 |
| WO | 2005094159 | 10/2005 |
| WO | 2006014498 | 2/2006 |
| WO | 2006084050 | 8/2006 |
| WO | 2007056441 | 5/2007 |
| WO | 2008053275 | 5/2008 |
| WO | 2009024593 | 2/2009 |
| WO | 2009036379 | 3/2009 |
| WO | 2009085462 | 7/2009 |
| WO | 2009100896 | 8/2009 |
| WO | 2009114815 | 9/2009 |
| WO | 2010028791 | 3/2010 |
| WO | 2010054007 | 5/2010 |
| WO | 2010/130824 | 11/2010 |
| WO | 2010136598 | 12/2010 |
| WO | 2011092313 | 8/2011 |

OTHER PUBLICATIONS

Chapal, Biotechniques, 23(3), Sep. 1, 1997, 518-524.
Coronella, Nucleic Acids Research, 28(20), Oct. 15, 2000, E85.
Database WPI Week 200656, Aug. 3, 2006.
de Wildt et al., J Mol Biol. 22;285(3):895-901 (Jan. 1999).
Demaison C. et al. (1995) Immunogenetics 42, 342.
Ewert, J. Mol. Biol. 325(3), Jan. 17, 2003, 531-553.
Ewert, Methods: A companion to methods in enzymology, 34(2), Oct. 1, 2004, 184-199.
Foster SJ. et al. (1997) J. Clin. Invest. 99, 1614.
Fuh et al., Expert Opin Biol Ther.,7(1 ):73-87 (Jan. 2007).
Glanville et al., Proc Natl Acad Sci 1 ;106(48):20216-21 (Dec. 2009).
Meijer et al., J Mol Biol., 358(3):764-72 (May 5, 2006).
Ponsel, Molecules. May 3, 2011;16(5):3675-700.
Scott, Phage Display, A Laboratory Manual, Jan. 1, 2001, pp. 2-1, figure 2.3.
Shi et al., J Mol Biol., 397(2):385-96 (Mar. 26, 2010).
Thirion, European Journal of Cancer Prevention, 5(6), Dec. 1, 1996, 507-511.
Wang, Journal of Immunogical Methods, 244(1-2), Oct. 20, 2000, 217-225.
Knappik A, Gel L, Honegger A, Pack P, Fischer M, Wellnhofer G, Hoess A, Mlle J, Plueckthun A, VirnekAs B, 'Fully synthetic human combinatorial antibody libraries (HuCAL) based on modular consensus frameworks and CDRs randomized with trinucleotides', J Mol Biol. Feb. 11, 2000; 296(1):57-86.
Kruif Selection and Application of Human Chain scFv antibody fragments from a semi-synthetic Phage Antibody Display Library with Designed CDR3 regions, J. Mol. Biol. (1995) 248, 97-105.
Robert Schier et al., 'Identification of functional and structural amino-acid residues by parsimonious mutagenesis', Gene, 169, 1996, pp. 147-155.
Carlos F. Barbas, III, 'Semisynthetic combinatorial antibody libraries: A Chemical solution to the diversity problem', Proc. Natl. Acad. Sci. USA, vol. 89, May 1992, p. 4457-4461.
Collett A binarly plasmid system for shuffling combinatorial antibodies libraries PNAC, vol. 89, No. 21, Nov. 1, 1992, p. 10026-10030.
Knappik and Pluckthun Engineered turns of a recombinant antibody improve ist in vivo folding, Protein Engineering, 8(1), 81-89 (1995).
Cox A directory of human germ-line Vk segments reveals a strong bias in their usage, Eur. J. Immunol. 1994, 24:827-836.
Tomlinson The repertoire of human germline Vh sequences reveals about 50 groups of Vh segments with different hypervariable loops, J. Mol. Biol. (1992) 227, 776-799.
Foote Antibody framework residues affecting the conformation of the hypervariable loops, J. Mol. Biol. 224, 487-499 (1992).
Gram In vitro and affinity maturation of antibodies from a naive conbinatorial immunoglobulin library, PNAS, 89 (8), 3576-3580 (1992).
Waterhouse Combinatorial infection and in vivo recombination: as strategy for making large phage antibody repertoires, Nucl. Acids Res. 21(9), 2265-2266 (1993).
Williams Cloning and sequences of human Vlambda gene segments, Eur. J. Immunol. 23, 1456-1461 (1993).
Marks By passing immunization: building high affinity antibodies by chain shuffling, 1992 Biotechnology 10:779-783.
Hoogenboom, Building antibodies from their genes, 1992 Immunlogical review, 130: 41-68.

(56) References Cited

OTHER PUBLICATIONS

Griffiths isolation of high affinity human antibodies directly from large synthetic repertoires, 1994 EMBO J. 13:3245-3260.
Winter and Milstein, Man made antibodies, 1991 Nature 349:293-299.
Matsuda et al. (1998), "The complete nucleotide sequence of the human immunoglobulin heavy chain variable region locus" J Exp Med 188(11):2151-62.
Embleton et al in Nucleic Acid Res. 20, 3831-3837, 1992.
Marks 1991, J.Mol.Biol. 222, 581-597, by passing immunization, human abs from V-gene libraries.
Pini "Design and Use of Phage Display Library", Journal of BioChemistry 1998, vol. 273,No. 34, Issue of Aug. 21.
Söderlind 2000 Nature Biotechnology, 18; 852-856.
de Haard 1999vol. 274, No. 26, Issue of Jun. 25, pp. 18218-18230, 1999.
Sheets Proc. Natl. Acad. Sci. USA, vol. 95, pp. 6157-6162, May 1998, Cell Biology.
Ignotovich Mol. Biol. (1997) 268, 69±77.
EP10191910.8 search report and opinion dated Jun. 8, 2011.
Rothe et al. "The Human Combinatorial Antibody Library HuCAL GOLD Combines Diversification of All Six CDRs According to the Natural Immune System with a Novel Display Method for Efficient Selection of High-Affinity Antibodies" J Mol. Biol. 2008 376:1182-1200.
EP09162724.0 search report dated Nov. 9, 2009.
PCT/EP2010/057507 International Preliminary Report on Patentability dated Nov. 29, 2011.
Jones et al. Nature, vol. 321, 1986, p. 522-525.
Söderlind 2000 Nature Biotechnology, 18; 852-856 (2000).
Nissim et al., 1994, Antibody fragments from a single pot phage display library as immunochemical reagents, The EMBO Journal, 13(3): 692-698.
Schier et al., J. Mol. Biol. (1996) 263, 551-567.
Anderson DE, et al.: "Hypervariable epitope constructs as a means of accounting for epitope variability", Vaccine. Jun. 1994;12(8):736-40.
PCT/EP2011/070473 ISR and Written Opinion dated Jan. 24, 2012.
Scaviner et al. (1999) Experimental and Clinical Immunogenetics vol. 16, pp. 234 to 240.
Brezinschek H.P. et al. (1997) J. Clin. Invest. 99, 2488.
Prank, et al.: "Light Chain replacement: A New Model for Antibody gene Rearrangement", 1995Prank.
Krawinkel Ulrich, et al.: "Recombination between antibody heavy chain variable-region genes: Evidence for gene conversion", Proc Nat. Acad. Scl. USA, vol. 80, pp. 4997-5001, Aug. 1983.
Davis Julian, et al.: "An antibody VH domain with a lox-Cre site integrated into ist coding region: bacterial recombination with a single polypeptide chain", FEBS Letter 377 (1995) 92-96.

Figure 2

Summary 20 VH region genes

| | Heavy chain germline genes | CDR lengths | | VNTI pI | Ranking pos | PTMs (w/o NxS/T) | NxS/T | Met in CDRs | Cysteine (to be removed) | Epibase check | | Aggresolve Theoretical aggregation propensity |
|---|---|---|---|---|---|---|---|---|---|---|---|---|
| | | Kabat CDR-H1 | Kabat CDR2-H2 | | | | | | | Deviations from germline | Strong T-cell epitope | |
| 1 | hVH_1_2 | 5 | 17 | 9.4 | 14 | 2 | 0 | 1 | 0 | 0 | 0 | intermediate |
| 2 | hVH_1_18 | 5 | 17 | 9.2 | 9 | 2 | 0 | 0 | 0 | 0 | 0 | high |
| 3 | hVH_1_69 | 5 | 17 | 9.3 | 7 | 0 | 0 | 0 | 0 | 0 | 0 | intermediate |
| 4 | hVH_1_46 | 5 | 17 | 9.2 | 21 | 0 | 0 | 1 | 0 | 0 | 0 | n.d. |
| 5 | hVH_3_7 | 5 | 17 | 8.6 | 8 | 4 | 0 | 1 | 0 | 0 | 0 | low |
| 6 | hVH_3_11 | 5 | 17 | 9.0 | 17 | 2 | 0 | 1 | 0 | 0 | 0 | n.d. |
| 7 | hVH_3_15 | 5 | 19 | 9.0 | 12 | 3 | 0 | 1 | 0 | 0 | 0 | low |
| 8 | hVH_3_21 | 5 | 17 | 9.0 | 11 | 3 | 0 | 1 | 0 | 0 | 0 | intermediate |
| 9 | hVH_3_23 | 5 | 17 | 8.7 | 1 | 3 | 0 | 1 | 0 | 0 | 0 | intermediate |
| 10 | hVH_3_30 | 5 | 17 | 9.3 | 2 | 4 | 0 | 1 | 0 | 0 | 0 | intermediate |
| 11 | hVH_3_33 | 5 | 17 | 9.3 | 15 | 4 | 0 | 1 | 0 | 0 | 0 | n.d. |
| 12 | hVH_3_48 | 5 | 17 | 8.0 | 10 | 3 | 0 | 1 | 0 | 0 | 0 | intermediate |
| 13 | hVH_3_53 | 5 | 16 | 8.7 | 16 | 3 | 0 | 1 | 0 | 0 | 0 | intermediate |
| 14 | hVH_3_73 | 5 | 19 | 9.5 | 33 | 3 | 0 | 1 | 0 | 0 | 0 | n.d. |
| 15 | hVH_3_74 | 5 | 17 | 9.1 | 19 | 4 | 0 | 1 | 0 | 0 | 0 | n.d. |
| 16 | hVH_4_4 | 6 | 16 | 9.3 | 20 | 0 | 0 | 0 | 1 | 0 | 0 | n.d. |
| 17 | hVH_4_31 | 7 | 16 | 9.2 | 13 | 0 | 0 | 0 | 0 | 0 | 0 | n.d. |
| 18 | hVH_4_39 | 7 | 16 | 9.0 | 3 | 0 | 0 | 0 | 0 | 0 | 0 | n.d. |
| 19 | hVH_5_51 | 5 | 17 | 8.6 | 6 | 1 | 0 | 0 | 0 | 0 | 0 | intermediate |
| 20 | hVH_6_1 | 7 | 18 | 9.3 | 39 | 3 | 0 | 1 | 0 | 0 | 0 | n.d. |

Figure 3

Summary 20 VL region genes

| | Light chain germline genes | Kabat CDR-L1 | Kabat CDR-L2 | VNTI pI | Ranking pos | PTMs (w/o NxS/T) | NxS/T | Met in CDRs | Cysteine (to be removed) | Deviations from germline | Strong T-cell epitope | Theoretical aggregation propensity |
|---|---|---|---|---|---|---|---|---|---|---|---|---|
| 1 | hVL_1-40 | 14 | 7 | 4.9 | 2 | 1 | 0 | 0 | 0 | 0 | 0 | intermediate |
| 2 | hVL_1-47 | 13 | 7 | 5.0 | 5 | 0 | 0 | 0 | 0 | 0 | 0 | intermediate |
| 3 | hVL_1-51 | 13 | 7 | 6.2 | 4 | 0 | 0 | 0 | 0 | 1 | 0 | intermediate |
| 4 | hVL_2-11 | 14 | 7 | 6.7 | 8 | 0 | 0 | 0 | 0 | 0 | 0 | n.d. |
| 5 | hVL_2-23 | 14 | 7 | 6.7 | 6 | 0 | 0 | 0 | 0 | 0 | 0 | n.d. |
| 6 | hVL_2-14 | 14 | 7 | 5.6 | 1 | 0 | 0 | 0 | 0 | 0 | 0 | high |
| 7 | hVL_3-1 | 11 | 7 | 4.5 | 9 | 2 | 0 | 0 | 1 | 2 | 1* | n.d. |
| 8 | hVL_3-21 | 11 | 7 | 4.8 | 7 | 2 | 0 | 0 | 0 | 1 | 1* | n.d. |
| 9 | hVK_1_5 | 11 | 7 | 5.0 | 3 | 1 | 0 | 0 | 0 | 0 | 0 | high |
| 10 | hVK_1_6 | 11 | 7 | 8.0 | 16 | 0 | 0 | 0 | 0 | 0 | 0 | n.d. |
| 11 | hVK_1_9 | 11 | 7 | 8.0 | 9 | 0 | 0 | 0 | 0 | 0 | 0 | n.d. |
| 12 | hVK_1_12 | 11 | 7 | 8.0 | 15 | 0 | 0 | 0 | 0 | 0 | 0 | n.d. |
| 13 | hVK_1_16 | 11 | 7 | 8.0 | 14 | 0 | 0 | 0 | 0 | 0 | 0 | n.d. |
| 14 | hVK_1_17 | 11 | 7 | 8.7 | 11 | 0 | 0 | 0 | 0 | 0 | 0 | n.d. |
| 15 | hVK_1_27 | 11 | 7 | 8.7 | 12 | 0 | 0 | 0 | 0 | 0 | 0 | n.d. |
| 16 | hVK_1_39 | 11 | 7 | 8.0 | 2 | 0 | 0 | 0 | 0 | 0 | 0 | high |
| 17 | hVK_2_30 | 16 | 7 | 8.0 | 10 | 0 | 0 | 0 | 0 | 0 | 0 | n.d. |
| 18 | hVK_3_11 | 11 | 7 | 6.3 | 6 | 0 | 0 | 0 | 0 | 0 | 0 | intermediate |
| 19 | hVK_3_15 | 11 | 7 | 8.0 | 4 | 0 | 0 | 0 | 0 | 0 | 0 | intermediate |
| 20 | hVK_3_20 | 12 | 7 | 6.3 | 1 | 0 | 0 | 0 | 0 | 0 | 0 | low |
| alt. | hVK_1_8 | 11 | 7 | 8.9 | 13 | 0 | 0 | 0 | 1 | n.d. | n.d. | n.d. |

Figure 4

| 1358.0 | IGKV3-20 | IGKV1-39/1D-39 | IGKV1-5 | IGKV3-15 | IGKV4-1 | IGKV3-11 | IGKV2-28/2D-28 | IGKV1-33/1D-33 | IGKV1-9 | IGKV2-30 | IGKV1-17 | IGKV1-27 | IGKV1-8 | IGKV1-16 | IGKV1-12 | IGKV1-6 | IGKV2D-29 | IGKV1-13 | IGKV2-24 | IGKV1D-8 | IGKV2-29 | IGKV5-2 | IGKV3D-20 | IGKV1D-12 | IGKV2-40/2D-40 | IGKV1D-43 | IGKV2D-30 | IGKV1D-16 | IGKV3D-15 | IGKV1D-13 | IGKV1D-17 |
|---|---|---|---|---|---|---|---|---|---|---|---|---|---|---|---|---|---|---|---|---|---|---|---|---|---|---|---|---|---|---|---|
| >VH3-23 | 24 | 12 | 27 | 20 | 13 | 9 | 7 | 6 | 3 | 1 | 5 | 4 | 4 | 3 | 1 | 0 | 2 | 0 | 0 | 0 | 2 | 0 | 1 | 1 | 2 | 0 | 0 | 0 | 0 | 1 | 0 |
| >VH3-30 | 14 | 12 | 9 | 9 | 11 | 12 | 4 | 2 | 7 | 2 | 1 | 1 | 2 | 1 | 0 | 2 | 1 | 1 | 2 | 2 | 0 | 1 | 0 | 0 | 0 | 0 | 1 | 0 | 0 | 0 | 0 |
| >VH4-39 | 13 | 18 | 14 | 22 | 5 | 6 | 5 | 4 | 0 | 2 | 1 | 4 | 0 | 0 | 0 | 3 | 0 | 0 | 0 | 0 | 0 | 0 | 0 | 0 | 0 | 0 | 0 | 0 | 1 | 0 | 0 |
| >VH4-59 | 15 | 19 | 3 | 8 | 10 | 4 | 0 | 2 | 0 | 1 | 1 | 3 | 1 | 1 | 2 | 0 | 0 | 0 | 0 | 0 | 0 | 0 | 0 | 0 | 0 | 1 | 1 | 0 | 0 | 0 | 1 |
| >VH4-34 | 25 | 18 | 9 | 8 | 7 | 6 | 6 | 3 | 2 | 0 | 2 | 1 | 1 | 2 | 1 | 0 | 0 | 0 | 0 | 0 | 0 | 0 | 0 | 0 | 0 | 0 | 0 | 0 | 0 | 0 | 0 |
| >VH5-51 | 10 | 7 | 4 | 7 | 8 | 6 | 4 | 3 | 1 | 2 | 1 | 1 | 0 | 0 | 1 | 0 | 0 | 6 | 0 | 0 | 0 | 0 | 0 | 0 | 0 | 0 | 0 | 0 | 0 | 0 | 0 |
| >VH1-69 | 12 | 14 | 5 | 7 | 8 | 8 | 3 | 3 | 0 | 1 | 0 | 2 | 2 | 1 | 0 | 1 | 1 | 0 | 0 | 0 | 0 | 0 | 0 | 0 | 0 | 0 | 1 | 1 | 2 | 0 | 0 |
| >VH3-7 | 6 | 10 | 10 | 8 | 5 | 4 | 3 | 0 | 2 | 4 | 2 | 2 | 3 | 0 | 0 | 1 | 0 | 2 | 0 | 1 | 0 | 0 | 0 | 0 | 0 | 0 | 0 | 0 | 0 | 0 | 1 |
| >VH1-18 | 15 | 8 | 5 | 4 | 2 | 4 | 5 | 7 | 0 | 2 | 1 | 0 | 1 | 1 | 1 | 0 | 0 | 1 | 0 | 0 | 0 | 0 | 0 | 0 | 0 | 1 | 0 | 0 | 0 | 0 | 0 |
| >VH3-48 | 12 | 8 | 1 | 6 | 6 | 7 | 3 | 6 | 2 | 0 | 2 | 1 | 3 | 2 | 0 | 1 | 1 | 0 | 0 | 0 | 0 | 0 | 1 | 1 | 0 | 0 | 0 | 0 | 0 | 0 | 0 |
| >VH3-21 | 5 | 7 | 9 | 9 | 4 | 2 | 2 | 0 | 0 | 0 | 0 | 2 | 2 | 0 | 0 | 2 | 1 | 0 | 0 | 0 | 0 | 0 | 0 | 0 | 0 | 0 | 0 | 0 | 0 | 0 | 0 |
| >VH3-15 | 10 | 6 | 6 | 4 | 4 | 3 | 3 | 4 | 3 | 1 | 0 | 1 | 0 | 0 | 0 | 0 | 1 | 1 | 0 | 0 | 0 | 0 | 0 | 0 | 0 | 1 | 0 | 0 | 0 | 0 | 0 |
| >VH4-31 | 7 | 4 | 4 | 4 | 2 | 7 | 4 | 3 | 0 | 0 | 2 | 2 | 0 | 0 | 0 | 1 | 0 | 0 | 0 | 0 | 1 | 0 | 0 | 0 | 1 | 0 | 0 | 0 | 0 | 0 | 0 |
| >VH1-2 | 12 | 6 | 3 | 2 | 3 | 0 | 2 | 1 | 0 | 1 | 0 | 2 | 1 | 0 | 0 | 1 | 0 | 0 | 0 | 0 | 0 | 0 | 0 | 0 | 0 | 0 | 0 | 0 | 0 | 0 | 0 |
| >VH3-33 | 6 | 6 | 5 | 8 | 6 | 2 | 4 | 2 | 2 | 0 | 1 | 0 | 1 | 1 | 0 | 0 | 0 | 0 | 1 | 0 | 0 | 0 | 0 | 0 | 0 | 0 | 0 | 0 | 0 | 0 | 0 |
| >VH3-53 | 2 | 5 | 8 | 6 | 4 | 4 | 1 | 5 | 1 | 0 | 1 | 2 | 2 | 0 | 1 | 0 | 0 | 0 | 0 | 0 | 1 | 0 | 0 | 0 | 0 | 0 | 0 | 1 | 0 | 0 | 0 |
| >VH3-11 | 3 | 5 | 6 | 5 | 2 | 3 | 3 | 1 | 1 | 0 | 1 | 0 | 0 | 0 | 1 | 2 | 0 | 0 | 0 | 1 | 0 | 0 | 0 | 0 | 0 | 0 | 0 | 0 | 0 | 0 | 0 |
| >VH3-9 | 1 | 3 | 3 | 2 | 3 | 2 | 1 | 0 | 0 | 0 | 1 | 1 | 1 | 2 | 1 | 0 | 3 | 0 | 0 | 1 | 0 | 0 | 0 | 0 | 0 | 0 | 0 | 0 | 0 | 0 | 0 |
| >VH3-74 | 4 | 3 | 3 | 3 | 3 | 2 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH4-4 | 6 | 5 | 4 | 3 | 3 | 3 | 2 | 0 | 0 | 0 | 1 | 1 | 0 | 0 | 0 | 1 | 2 | 0 | 0 | 1 | 0 | 0 | 0 | 0 | 0 | 0 | 0 | 0 | 0 | 0 | 0 |
| >VH1-46 | 6 | 5 | 3 | 3 | 1 | 2 | 0 | 1 | 4 | 0 | 0 | 2 | 1 | 2 | 0 | 0 | 0 | 0 | 0 | 0 | 0 | 0 | 0 | 0 | 0 | 0 | 0 | 0 | 0 | 0 | 0 |
| >VH4-61 | 0 | 3 | 0 | 2 | 5 | 1 | 1 | 0 | 0 | 0 | 0 | 0 | 0 | 1 | 1 | 0 | 0 | 1 | 0 | 0 | 0 | 0 | 0 | 0 | 0 | 0 | 0 | 0 | 0 | 0 | 0 |
| >VH1-8 | 2 | 1 | 1 | 4 | 2 | 1 | 1 | 1 | 1 | 0 | 0 | 0 | 0 | 0 | 0 | 0 | 0 | 0 | 0 | 0 | 1 | 0 | 0 | 0 | 0 | 0 | 0 | 0 | 0 | 0 | 0 |
| >VH1-24 | 1 | 3 | 0 | 3 | 1 | 4 | 2 | 1 | 0 | 2 | 0 | 0 | 0 | 0 | 0 | 0 | 0 | 1 | 0 | 0 | 0 | 0 | 1 | 0 | 0 | 0 | 0 | 0 | 0 | 0 | 0 |
| >VH1-3 | 2 | 4 | 1 | 3 | 0 | 0 | 0 | 1 | 0 | 1 | 0 | 0 | 0 | 0 | 1 | 1 | 0 | 0 | 0 | 0 | 0 | 0 | 0 | 0 | 0 | 0 | 0 | 0 | 0 | 0 | 0 |
| >VH3-49 | 2 | 4 | 2 | 1 | 0 | 1 | 1 | 0 | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 |
| >VH4-28 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-43 | 0 | 0 | 3 | 1 | 1 | 2 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-64 | 0 | 0 | 2 | 1 | 0 | 2 | 0 | 0 | 1 | 0 | 0 | 0 | 0 | 0 | 0 | 0 | 1 | 0 | 0 | 0 | 0 | 0 | 0 | 0 | 0 | 0 | 0 | 0 | 0 | 0 | 0 |
| >VH7-81 | 3 | 2 | 1 | 0 | 1 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-13 | 0 | 3 | 1 | 0 | 2 | 0 | 0 | 1 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-72 | 1 | 0 | 2 | 2 | 0 | 0 | 0 | 1 | 0 | 1 | 0 | 0 | 1 | 0 | 0 | 0 | 0 | 0 | 0 | 0 | 0 | 0 | 0 | 0 | 0 | 0 | 0 | 0 | 0 | 0 | 0 |
| >VH3-73 | 0 | 0 | 0 | 0 | 0 | 1 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH1-58 | 2 | 0 | 1 | 0 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-66 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH4-30.2 | 0 | 1 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH7-4.1 | 0 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH2-5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH6-1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH4-30.4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-20 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Figure 5

| 779.0 | IGLV 2-14 | IGLV 1-40 | IGLV 1-44 | IGLV 1-51 | IGLV 1-47 | IGLV 2-23 | IGLV 3-21 | IGLV 2-11 | IGLV 3-1 | IGLV 2-8 | IGLV 6-57 | IGLV 1-36 | IGLV 3-25 | IGLV 4-69 | IGLV 7-43 | IGLV 7-46 | IGLV 2-18 | IGLV 3-27 | IGLV 9-49 | IGLV 3-10 | IGLV 3-9 | IGLV 8-61 | IGLV 3-12 | IGLV 3-19 | IGLV 3-22 | IGLV 4-60 |
|---|---|---|---|---|---|---|---|---|---|---|---|---|---|---|---|---|---|---|---|---|---|---|---|---|---|---|
| >VH3-23 | 13 | 6 | 5 | 3 | 1 | 4 | 6 | 5 | 5 | 1 | 0 | 2 | 0 | 0 | 1 | 0 | 1 | 0 | 0 | 0 | 0 | 0 | 0 | 1 | 0 | 0 |
| >VH3-30 | 7 | 5 | 4 | 9 | 1 | 2 | 3 | 2 | 3 | 1 | 1 | 0 | 0 | 0 | 0 | 0 | 0 | 1 | 2 | 2 | 0 | 0 | 0 | 0 | 0 | 0 |
| >VH4-39 | 10 | 6 | 7 | 5 | 3 | 5 | 13 | 0 | 2 | 10 | 2 | 0 | 0 | 0 | 0 | 1 | 3 | 0 | 0 | 0 | 1 | 0 | 0 | 0 | 0 | 0 |
| >VH4-59 | 4 | 8 | 4 | 4 | 3 | 2 | 2 | 2 | 5 | 1 | 1 | 0 | 0 | 0 | 0 | 0 | 0 | 0 | 0 | 0 | 0 | 1 | 0 | 0 | 0 | 0 |
| >VH4-34 | 10 | 6 | 2 | 9 | 6 | 2 | 2 | 1 | 0 | 4 | 0 | 1 | 2 | 0 | 1 | 0 | 0 | 0 | 1 | 0 | 0 | 0 | 0 | 0 | 0 | 0 |
| >VH5-51 | 11 | 14 | 5 | 0 | 4 | 3 | 3 | 0 | 0 | 0 | 0 | 2 | 2 | 0 | 1 | 0 | 0 | 0 | 0 | 0 | 0 | 0 | 0 | 0 | 0 | 0 |
| >VH1-69 | 8 | 7 | 8 | 5 | 2 | 3 | 2 | 5 | 2 | 4 | 1 | 0 | 1 | 0 | 0 | 0 | 0 | 0 | 0 | 1 | 0 | 0 | 0 | 0 | 0 | 0 |
| >VH3-7 | 2 | 4 | 3 | 3 | 3 | 1 | 3 | 0 | 1 | 1 | 0 | 0 | 0 | 0 | 0 | 1 | 0 | 1 | 0 | 0 | 0 | 0 | 0 | 0 | 0 | 0 |
| >VH1-18 | 5 | 5 | 3 | 3 | 0 | 1 | 0 | 1 | 0 | 2 | 2 | 1 | 1 | 0 | 0 | 0 | 0 | 0 | 0 | 1 | 0 | 0 | 0 | 0 | 0 | 0 |
| >VH3-48 | 6 | 1 | 1 | 1 | 6 | 1 | 1 | 2 | 3 | 0 | 0 | 0 | 1 | 0 | 0 | 1 | 0 | 0 | 1 | 0 | 0 | 0 | 0 | 0 | 0 | 0 |
| >VH3-21 | 5 | 2 | 2 | 9 | 3 | 1 | 2 | 2 | 1 | 1 | 1 | 0 | 1 | 2 | 0 | 1 | 0 | 0 | 0 | 0 | 0 | 0 | 0 | 0 | 0 | 0 |
| >VH3-15 | 1 | 2 | 4 | 2 | 1 | 1 | 1 | 0 | 2 | 2 | 1 | 0 | 1 | 0 | 2 | 3 | 1 | 0 | 0 | 0 | 0 | 0 | 0 | 0 | 1 | 0 |
| >VH4-31 | 8 | 3 | 1 | 3 | 3 | 4 | 2 | 1 | 1 | 0 | 0 | 0 | 0 | 1 | 1 | 0 | 0 | 0 | 0 | 0 | 0 | 0 | 0 | 0 | 0 | 0 |
| >VH1-2 | 8 | 6 | 5 | 3 | 0 | 3 | 1 | 1 | 3 | 2 | 0 | 0 | 0 | 0 | 0 | 2 | 0 | 1 | 0 | 0 | 0 | 0 | 0 | 0 | 0 | 0 |
| >VH3-33 | 4 | 1 | 1 | 1 | 4 | 4 | 4 | 1 | 1 | 0 | 2 | 0 | 0 | 1 | 0 | 0 | 0 | 1 | 1 | 0 | 1 | 0 | 0 | 0 | 0 | 0 |
| >VH3-53 | 2 | 0 | 9 | 1 | 1 | 1 | 0 | 1 | 1 | 1 | 0 | 0 | 0 | 0 | 0 | 1 | 0 | 0 | 0 | 0 | 0 | 0 | 0 | 0 | 0 | 0 |
| >VH3-11 | 3 | 1 | 3 | 1 | 1 | 2 | 2 | 3 | 3 | 1 | 0 | 0 | 1 | 2 | 0 | 1 | 0 | 0 | 1 | 0 | 0 | 1 | 0 | 0 | 0 | 0 |
| >VH3-9 | 6 | 1 | 4 | 1 | 3 | 7 | 2 | 3 | 0 | 2 | 0 | 0 | 0 | 1 | 0 | 0 | 0 | 0 | 0 | 0 | 0 | 0 | 0 | 0 | 0 | 1 |
| >VH3-74 | 2 | 0 | 0 | 0 | 1 | 3 | 3 | 1 | 1 | 1 | 0 | 0 | 0 | 0 | 1 | 1 | 0 | 0 | 0 | 0 | 0 | 0 | 0 | 0 | 0 | 0 |
| >VH4-4 | 4 | 3 | 6 | 2 | 0 | 2 | 0 | 1 | 1 | 2 | 0 | 0 | 1 | 0 | 0 | 0 | 0 | 1 | 0 | 0 | 0 | 0 | 0 | 0 | 0 | 0 |
| >VH1-46 | 3 | 1 | 3 | 4 | 1 | 1 | 1 | 2 | 0 | 0 | 1 | 0 | 0 | 0 | 0 | 0 | 0 | 0 | 0 | 0 | 0 | 0 | 0 | 0 | 0 | 0 |
| >VH4-61 | 3 | 0 | 4 | 0 | 0 | 1 | 1 | 2 | 1 | 0 | 0 | 0 | 0 | 0 | 1 | 0 | 0 | 0 | 0 | 0 | 0 | 0 | 0 | 0 | 0 | 0 |
| >VH1-8 | 4 | 0 | 0 | 1 | 2 | 0 | 0 | 1 | 0 | 1 | 0 | 0 | 0 | 0 | 0 | 0 | 0 | 1 | 0 | 0 | 0 | 0 | 0 | 0 | 0 | 0 |
| >VH1-24 | 1 | 1 | 1 | 0 | 0 | 2 | 1 | 1 | 0 | 0 | 0 | 0 | 0 | 0 | 0 | 0 | 0 | 0 | 0 | 0 | 0 | 0 | 0 | 0 | 0 | 0 |
| >VH1-3 | 2 | 1 | 0 | 0 | 0 | 2 | 0 | 0 | 2 | 0 | 0 | 0 | 0 | 0 | 0 | 0 | 0 | 0 | 0 | 0 | 0 | 0 | 0 | 0 | 0 | 0 |
| >VH3-49 | 1 | 1 | 0 | 0 | 0 | 1 | 2 | 0 | 0 | 1 | 0 | 0 | 0 | 0 | 0 | 0 | 0 | 0 | 0 | 0 | 0 | 0 | 0 | 0 | 0 | 0 |
| >VH4-28 | 1 | 0 | 2 | 2 | 0 | 4 | 0 | 0 | 0 | 0 | 0 | 2 | 0 | 0 | 0 | 0 | 0 | 0 | 0 | 0 | 0 | 0 | 0 | 0 | 0 | 0 |
| >VH3-43 | 1 | 0 | 0 | 2 | 0 | 0 | 0 | 1 | 1 | 0 | 0 | 1 | 0 | 0 | 0 | 0 | 0 | 1 | 0 | 0 | 0 | 0 | 0 | 0 | 0 | 0 |
| >VH3-64 | 1 | 0 | 0 | 0 | 0 | 0 | 2 | 0 | 0 | 0 | 0 | 0 | 0 | 0 | 1 | 0 | 0 | 0 | 0 | 0 | 0 | 0 | 0 | 0 | 0 | 0 |
| >VH7-81 | 2 | 1 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 |
| >VH3-13 | 0 | 1 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-72 | 0 | 0 | 0 | 1 | 0 | 0 | 0 | 0 | 0 | 0 | 0 | 0 | 0 | 1 | 0 | 0 | 0 | 0 | 0 | 0 | 0 | 0 | 0 | 0 | 0 | 0 |
| >VH3-73 | 0 | 1 | 0 | 1 | 1 | 0 | 0 | 1 | 0 | 0 | 1 | 0 | 0 | 0 | 0 | 0 | 0 | 0 | 0 | 0 | 0 | 0 | 0 | 0 | 0 | 0 |
| >VH1-58 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-66 | 0 | 0 | 1 | 0 | 1 | 0 | 0 | 0 | 0 | 0 | 1 | 0 | 0 | 0 | 0 | 0 | 0 | 0 | 0 | 0 | 0 | 0 | 0 | 0 | 0 | 0 |
| >VH4-30.2 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| >VH7-4.1 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH2-5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH6-1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH4-30.4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-20 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Figure 6A

| | Matsuda et al | Tomlinson et al | Protein sequence |
|---|---|---|---|
| IGHV1-2 | VH 1-2 | DP-75 | QVQLVQSGAEVKKPGASVKVSCKASGYTFTGYYMHWVRQAPGQGLEWMG WINPNSGGTNYAQKFQGRVTMTRDTSISTAYMELSRLRSDDTAVYYCAR |
| IGHV1-3 | VH 1-3 | DP-25 | QVQLVQSGAEVKKPGASVKVSCKASGYTFTSYAMHWVRQAPGQRLEWMG WSNAGNGNTKYSQEFQGRVTITRDTSASTAYMELSSLRSEDMAVYYCAR |
| IGHV1-8 | VH 1-8 | DP-15 | QVQLVQSGAEVKKPGASVKVSCKASGYTFTSYDINWVRQATGQGLEWMGW MNPNSGNTGYAQKFQGRVTMTRNTSISTAYMELSSLRSEDTAVYYCARG |
| IGHV1-18 | VH 1-18 | DP-14 | QVQLVQSGAEVKKPGASVKVSCKASGYTFTSYGISWVRQAPGQGLEWMGW ISAYNGNTNYAQKLQGRVTMTTDTSTSTAYMELRSLRSDDTAVYYCAR |
| IGHV1-24 | VH 1-24 | DP-5 | QVQLVQSGAEVKKPGASVKVSCKVSGYTLTELSMHWVRQAPGKGLEWMG GFDPEDGETIYAQKFQGRVTMTEDTSTDTAYMELSSLRSEDTAVYYCAT |
| IGHV1-45 | VH 1-45 | -- | QMQLVQSGAEVKKTGSSVKVSCKASGYTFTYRYLHWVRQAPGQALEWMG WITPFNGNTNYAQKFQDRVTITRDRSMSTAYMELSSLRSEDTAMYYCAR |
| IGHV1-46 | VH 1-46 | DP-7 | QVQLVQSGAEVKKPGASVKVSCKASGYTFTSYYMHWVRQAPGQGLEWMGI INPSGGSTSYAQKFQGRVTMTRDTSTSTVYMELSSLRSEDTAVYYCAR |
| IGHV1-58 | VH 1-58 | DP-2 | QMQLVQSGPEVKKPGTSVKVSCKASGFTFTSSAMQWVRQARGQRLEWIGW IVVGSGNTNYAQKFQERVTITRDMSTSTAYMELSSLRSEDTAVYYCAA |
| IGHV1-69*01 | VH 1-69 | DP-10 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAR |
| IGHV1-69*06, IGHV1-e | VH 1-69 | DP-88 | QVQLVQSGAEVKKPGSSVKVSCKASGGTFSSYAISWVRQAPGQGLEWMGG IIPIFGTANYAQKFQGRVTITADKSTSTAYMELSSLRSEDTAVYYCAR |
| IGHV1-c | -- | -- | KSGASVKVSCSFSGFTITSYGIHWVQQSPGQGLEWMGWINPGNGSPSYAKK FQGRFTMTRDMSTTTAYTDLSSLTSEDMAVYYYAR |
| IGHV1-f | -- | DP-3 | EVQLVQSGAEVKKPGATVKISCKVSGYTFTDYYMHWVQQAPGKGLEWMGL VDPEDGETIYAEKFQGRVTITADTSTDTAYMELSSLRSEDTAVYYCAT |
| IGHV2-5 | VH 2-5 | DP-76 | QITLKESGPTLVKPTQTLTLTCTFSGFSLSTSGVGVGWIRQPPGKALEWLALI YWNDDKRYSPSLKSRLTITKDTSKNQVVLTMTNMDPVDTATYYCAHR |
| IGHV2-26 | VH 2-26 | DP-26 | QVTLKESGPVLVKPTETLTLTCTVSGFSLSNARMGVSWIRQPPGKALEWLAH IFSNDEKSYSTSLKSRLTISKDTSKSQVVLTMTNMDPVDTATYYCARI |
| IGHV2-70 | VH 2-70 | DP-27 | QVTLRESGPALVKPTQTLTLTCTFSGFSLSTSGMCVSWIRQPPGKALEWLALI DWDDDKYYSTSLKTRLTISKDTSKNQVVLTMTNMDPVDTATYYCARI |
| IGHV3-7 | VH 3-7 | DP-54 | EVQLVESGGGLVQPGGSLRLSCAASGFTFSSYWMSWVRQAPGKGLEWVA NIKQDGSEKYYVDSVKGRFTISRDNAKNSLYLQMNSLRAEDTAVYYCAR |
| IGHV3-9 | VH 3-9 | DP-31 | EVQLVESGGGLVQPGRSLRLSCAASGFTFDDYAMHWVRQAPGKGLEWVSG ISWNSGSIGYADSVKGRFTISRDNAKNSLYLQMNSLRAEDTALYYCAKD |

Figure 6B

| IGHV3-11 | VH 3-11 | DP-35 | QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCAR |
|---|---|---|---|
| IGHV3-13 | VH 3-13 | DP-48 | EVQLVESGGGLVQPGGSLRLSCAASGFTFSSYDMHWVRQATGKGLEWVSAIGTAGDTYYPGSVKGRFTISRENAKNSLYLQMNSLRAGDTAVYYCAR |
| IGHV3-15 | VH 3-15 | DP-38 | EVQLVESGGGLVKPGGSLRLSCAASGFTFSNAWMSWVRQAPGKGLEWVGRIKSKTDGGTTDYAAPVKGRFTISRDDSKNTLYLQMNSLKTEDTAVYYCTT |
| IGHV3-16 | VH 3-16 |  | EVQLVESGGGLVQPGGSLRLSCAASGFTFSNSDMNWARKAPGKGLEWVSGVSWNGSRTHYVDSVK.RRFIISRDNSRNSLYLQKNRRRAEDMAVYYCVR |
| IGHV3-20 | VH 3-20 | DP-32 | EVQLVESGGGVVRPGGSLRLSCAASGFTFDDYGMSWVRQAPGKGLEWVSGINWNGGSTGYADSVKGRFTISRDNAKNSLYLQMNSLRAEDTALYHCAR |
| IGHV3-21 | VH 3-21 | DP-77 | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCAR |
| IGHV3-23 | VH 3-23 | DP-47 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAK |
| IGHV3-30 | VH 3-30 | DP-49 | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAR |
| IGHV3-30-3 | -- | DP-46 | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCAR |
| IGHV3-30-5 | -- | -- | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAK |
| IGHV3-33 | VH 3-33 | DP-50 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCAR |
| IGHV3-35 | VH 3-35 | DP-59 | EVQLVESGGGLVQPGGSLRLSCAASGFTFSNSDMNWVHQAPGKGLEWVSGVSWNGSRTHYADSVKGRFIISRDNSRNTLYLQTNSLRAEDTAVYYCVR |
| IGHV3-38 | VH 3-38P | -- | EVQLVESGGGLVQPRGSLRLSCAASGFTVSSNEMSWIRQAPGKGLEWVSSISGGSTYYADSRKGRFTISRDNSKNTLYLQMNNLRAEGTAAYYCARY |
| IGHV3-43 | VH 3-43 | DP-33 | EVQLVESGGVVVQPGGSLRLSCAASGFTFDDYTMHWVRQAPGKGLEWVSLISWDGGSTYYADSVKGRFTISRDNSKNSLYLQMNSLRTEDTALYYCAKD |
| IGHV3-48 | VH 3-48 | DP-51 | EVQLVESGGGLVQPGGSLRLSCAASGFTFSSYSMNWVRQAPGKGLEWVSYISSSSSTIYYADSVKGRFTISRDNAKNSLYLQMNSLRDEDTAVYYCAR |
| IGHV3-49 | VH 3-49 | 3-49RB | EVQLVESGGGLVQPGRSLRLSCTASGFTFGDYAMSWFRQAPGKGLEWVGFIRSKAYGGTTEYAASVKGRFTISRDDSKSIAYLQMNSLKTEDTAVYYCTR |
| IGHV3-53 | VH 3-53 | DP-42 | EVQLVESGGGLIQPGGSLRLSCAASGFTVSSNYMSWVRQAPGKGLEWVSVIYSGGSTYYADSVKGRFTISRDNSKNTLYLQMNSLRAEDTAVYYCAR |
| IGHV3-64 | VH 3-64 | DP-61 | EVQLVESGEGLVQPGGSLRLSCAASGFTFSSYAMHWVRQAPGKGLEYVSAISSNGGSTYYADSVKGRFTISRDNSKNTLYLQMGSLRAEDMAVYYCAR |
| IGHV3-66 | VH 3-66 | DP-86 | EVQLVESGGGLIQPGGSLRLSCAASGFTVSSNYMSWVRQAPGKGLEWVSVIYSCGSTYYADSVKGRFTISRDNSKNTLYLQMNSLRAEDTAVYYCAR |
| IGHV3-72 | VH 3-72 | DP-29 | EVQLVESGGGLVQPGGSLRLSCAASGFTFSDHYMDWVRQAPGKGLEWVGRTRNKANSYTTEYAASVKGRFTISRDDSKNSLYLQMNSLKTEDTAVYYCAR |
| IGHV3-73 | VH 3-73 | DA-11 | EVQLVESGGGLVQPGGSLKLSCAASGFTFSGSAMHWVRQASGKGLEWVGRIRSKANSYATAYAASVKGRFTISRDDSKNTAYLQMNSLKTEDTAVYYCTR |
| IGHV3-74 | VH 3-74 | DP-53 | EVQLVESGGGLVQPGGSLRLSCAASGFTFSSYWMHWVRQAPGKGLVWVSRINSDGSSTSYADSVKGRFTISRDNAKNTLYLQMNSLRAEDTAVYYCAR |

Figure 6C

| | | | |
|---|---|---|---|
| IGHV3-d | -- | -- | EVQLVESRGVLVQPGGSLRLSCAASGFTVSSNEMSWVRQAPGKGLEWVSSI SGGSTYYADSRKGRFTISRDNSKNTLHLQMNSLRAEDTAVYYCKK |
| IGHV4-4 | VH 4-4 | DP-70 | QVQLQESGPGLVKPSETLSLTCTVSGGSISSYYWSWIRQPAGKGLEWIGRIY TSGSTNYNPSLKSRVTMSVDTSKNQFSLKLSSVTAADTAVYYCAR |
| IGHV4-28 | VH 4-28 | DP-68 | QVQLQESGPGLVKPSDTLSLTCAVSGYSISSSNWWGWIRQPPGKGLEWIGYI YYSGSTYYNPSLKSRVTMSVDTSKNQFSLKLSSVTAVDTAVYYCAR |
| IGHV4-30-1 | -- | -- | QVQLQESGPGLVKPSQTLSLTCTVSGGSISSGGYYWSWIRQHPGKGLEWIG YIYYSGSTYYNPSLKSRVTISVDTSKNQFSLKLSSVTAADTAVYYCAR |
| IGHV4-30-2 | -- | DP-64 | QLQLQESGSGLVKPSQTLSLTCAVSGGSISSGGYSWSWIRQPPGKGLEWIG YIYHSGSTYYNPSLKSRVTISVDRSKNQFSLKLSSVTAADTAVYYCAR |
| IGHV4-30-4 | -- | DP-78 | QVQLQESGPGLVKPSQTLSLTCTVSGGSISSGDYYWSWIRQPPGKGLEWIG YIYYSGSTYYNPSLKSRVTISVDTSKNQFSLKLSSVTAADTAVYYCAR |
| IGHV4-31 | VH 4-31 | DP-65 | QVQLQESGPGLVKPSQTLSLTCTVSGGSISSGGYYWSWIRQHPGKGLEWIG YIYYSGSTYYNPSLKSRVTISVDTSKNQFSLKLSSVTAADTAVYYCAR |
| IGHV4-34 | VH 4-34 | DP-63 | QVQLQQWGAGLLKPSETLSLTCAVYGGSFSGYYWSWIRQPPGKGLEWIGEI NHSGSTNYNPSLKSRVTISVDTSKNQFSLKLSSVTAADTAVYYCARG |
| IGHV4-39 | VH 4-39 | DP-79 | QLQLQESGPGLVKPSETLSLTCTVSGGSISSSSYYWGWIRQPPGKGLEWIGS IYYSGSTYYNPSLKSRVTISVDTSKNQFSLKLSSVTAADTAVYYCAR |
| IGHV4-59 | VH 4-59 | DP-71 | QVQLQESGPGLVKPSETLSLTCTVSGGSISSYYWSWIRQPPGKGLEWIGYIY YSGSTNYNPSLKSRVTISVDTSKNQFSLKLSSVTAADTAVYYCAR |
| IGHV4-61 | VH 4-61 | DP-66 | QVQLQESGPGLVKPSETLSLTCTVSGGSVSSGGYYWSWIRQPPGKGLEWIG YIYYSGSTNYNPSLKSRVTISVDTSKNQFSLKLSSVTAADTAVYYCAR |
| IGHV4-b | -- | DP-67 | QVQLQESGPGLVKPSETLSLTCAVSGYSISSGYYWGWIRQPPGKGLEWIGSI YHSGSTYYNPSLKSRVTISVDTSKNQFSLKLSSVTAADTAVYYCAR |
| IGHV5-51 | VH 5-51 | DP-73 | EVQLVQSGAEVKKPGESLKISCKGSGYSFTSYWIGWVRQMPGKGLEWMGII YPGDSDTRYSPSFQGQVTISADKSISTAYLQWSSLKASDTAMYYCAR |
| IGHV5-a | -- | -- | EVQLVQSGAEVKKPGESLRISCKGSGYSFTSYWISWVRQMPGKGLEWMGRI DPSDSYTNYSPSFQGHVTISADKSISTAYLQWSSLKASDTAMYYCAR |
| IGHV6-1 | VH 6-1 | DP-74 | QVQLQQSGPGLVKPSQTLSLTCAISGDSVSSNSAAWNWIRQSPSRGLEWLG RTYYRSKWYNDYAVSVKSRITINPDTSKNQFSLQLNSVTPEDTAVYYCAR |
| IGHV7-4-1 | -- | DP-21 | QVQLVQSGSELKKPGASVKVSCKASGYTFTSYAMNWVRQAPGQGLEWMG WINTNTGNPTYAQGFTGRFVFSLDTSVSTAYLQICSLKAEDTAVYYCAR |
| IGHV7-81 | VH 7-81 | -- | QVQLVQSGHEVKQPGASVKVSCKASGYSFTTYGMNWVPQAPGQGLEWMG WFNTYTGNPTYAQGFTGRFVFSMDTSASTAYLQISSLKAEDMAMYYCAR |

51 functional 5 open reading frames

Figure 7A

| | Zachau | Protein sequence |
|---|---|---|
| IGKV1-5 | L12 | DIQMTQSPSTLSASVGDRVTITCRASQSISSWLAWYQQKPGKAPKLLIYDASSLESGVPSRFSGSGSGTEFTLTISSLQPDDFATYYCQQYNSYS |
| IGKV1-6 | L11 | AIQMTQSPSSLSASVGDRVTITCRASQGIRNDLGWYQQKPGKAPKLLIYAASSLQSGVPSRFSGSGSGTDFTLTISSLQPEDFATYYCLQDYNYP |
| IGKV1-8 | L9 | AIRMTQSPSSFSASTGDRVTITCRASQGISSYLAWYQQKPGKAPKLLIYAASTLQSGVPSRFSGSGSGTDFTLTISCLQSEDFATYYCQQYYSYP |
| IGKV1-9 | L8 | DIQLTQSPSFLSASVGDRVTITCRASQGISSYLAWYQQKPGKAPKLLIYAASTLQSGVPSRFSGSGSGTEFTLTISSLQPEDFATYYCQQLNSYP |
| IGKV1-12 | L5 | DIQMTQSPSSVSASVGDRVTITCRASQGISSWLAWYQQKPGKAPKLLIYAASSLQSGVPSRFSGSGSGTDFTLTISSLQPEDFATYYCQQANSFP |
| IGKV1-13 | L4/18a | AIQLTQSPSSLSASVGDRVTITCRASQGISSALAWYQQKPGKAPKLLIYDASSLESGVPSRFSGSGSGTDFTLTISSLQPEDFATYYCQQFNSYP |
| IGKV1-16 | L1 | DIQMTQSPSSLSASVGDRVTITCRASQGISNYLAWFQQKPGKAPKSLIYAASSLQSGVPSRFSGSGSGTDFTLTISSLQPEDFATYYCQQYNSYP |
| IGKV1-17 | A30 | DIQMTQSPSSLSASVGDRVTITCRASQGIRNDLGWYQQKPGKAPKRLIYAASSLQSGVPSRFSGSGSGTEFTLTISSLQPEDFATYYCLQHNSYP |
| IGKV1-27 | A20 | DIQMTQSPSSLSASVGDRVTITCRASQGISNYLAWYQQKPGKVPKLLIYAASTLQSGVPSRFSGSGSGTDFTLTISSLQPEDVATYYCQKYNSAP |
| IGKV1-33 | O18 | DIQMTQSPSSLSASVGDRVTITCQASQDISNYLNWYQQKPGKAPKLLIYDASNLETGVPSRFSGSGSGTDFTFTISSLQPEDIATYYCQQYDNLP |
| IGKV1-37 | O14 | DIQLTQSPSSLSASVGDRVTITCRVSQGISSYLNWYRQKPGKVPKLLIYSASNLQSGVPSRFSGSGSGTDFTLTISSLQPEDVATYYGQRTYNAPP |
| IGKV1-39 | O12 | DIQMTQSPSSLSASVGDRVTITCRASQSISSYLNWYQQKPGKAPKLLIYAASSLQSGVPSRFSGSGSGTDFTLTISSLQPEDFATYYCQQSYSTP |
| IGKV1D-08 | L24 | VIWMTQSPSLLSASTGDRVTISCRMSQGISSYLAWYQQKPGKAPELLIYAASTLQSGVPSRFSGSGSGTDFTLTISCLQSEDFATYYCQQYYSFP |
| IGKV1D-12 | L19 | DIQMTQSPSSVSASVGDRVTITCRASQGISSWLAWYQQKPGKAPKLLIYAASSLQSGVPSRFSGSGSGTDFTLTISSLQPEDFATYYCQQANSFP |
| IGKV1D-13 | L18 | AIQLTQSPSSLSASVGDRVTITCRASQGISSALAWYQQKPGKAPKLLIYDASSLESGVPSRFSGSGSGTDFTLTISSLQPEDFATYYCQQFNNYP |
| IGKV1D-16 | L15 | DIQMTQSPSSLSASVGDRVTITCRASQGISSWLAWYQQKPEKAPKSLIYAASSLQSGVPSRFSGSGSGTDFTLTISSLQPEDFATYYCQQYNSYP |
| IGKV1D-17 | L14 | NIQMTQSPSAMSASVGDRVTITCRARQGISNYLAWFQQKPGKVPKHLIYAASSLQSGVPSRFSGSGSGTEFTLTISSLQPEDFATYYCLQHNSYP |
| IGKV1D-33 | O8 | DIQMTQSPSSLSASVGDRVTITCQASQDISNYLNWYQQKPGKAPKLLIYDASNLETGVPSRFSGSGSGTDFTFTISSLQPEDIATYYCQQYDNLP |
| IGKV1D-37 | O4 | DIQLTQSPSSLSASVGDRVTITCRVSQGISSYLNWYRQKPGKVPKLLIYSASNLQSGVPSRFSGSGSGTDFTLTISSLQPEDVATYYGQRTYNAPP |

Figure 7B

| | | |
|---|---|---|
| IGKV1D-39 | O2 | DIQMTQSPSSLSASVGDRVTITCRASQSISSYLNWYQQKPGKAPKLLIYAASSL QSGVPSRFSGSGSGTDFTLTISSLQPEDFATYYCQQSYSTP |
| IGKV1D-42 | L22 | DIQMIQSPSFLSASVGDRVSIICWASEGISSNLAWYLQKPGKSPKLFLYDAKDL HPGVSSRFSGRGSGTDFTLTIISLKPEDFAAYYCKQDFSYPP |
| IGKV1D-43 | L23 | AIRMTQSPFSLSASVGDRVTITCWASQGISSYLAWYQQKPAKAPKLFIYYASSL QSGVPSRFSGSGSGTDYTLTISSLQPEDFATYYCQQYYSTP |
| IGKV2-24 | A23 | DIVMTQTPLSSPVTLGQPASISCRSSQSLVHSDGNTYLSWLQQRPGQPPRLLI YKISNRFSGVPDRFSGSGAGTDFTLKISRVEAEDVGVYYCMQATQFP |
| IGKV2-28 | A19 | DIVMTQSPLSLPVTPGEPASISCRSSQSLLHSNGYNYLDWYLQKPGQSPQLLI YLGSNRASGVPDRFSGSGSGTDFTLKISRVEAEDVGVYYCMQALQTP |
| IGKV2-29 | A18b | DIVMTQTPLSLSVTPGQPASISCKSSQSLLHSDGKTYLYWYLQKPGQSPQLLI YEVSSRFSGVPDRFSGSGSGTDFTLKISRVEAEDVGVYYCMQGIHLP |
| IGKV2-30 | A17 | DVVMTQSPLSLPVTLGQPASISCRSSQSLVYSDGNTYLNWFQQRPGQSPRR LIYKVSNRDSGVPDRFSGSGSGTDFTLKISRVEAEDVGVYYCMQGTHWP |
| IGKV2-40 | O11 | DIVMTQTPLSLPVTPGEPASISCRSSQSLLDSDDGNTYLDWYLQKPGQSPQLL IYTLSYRASGVPDRFSGSGSGTDFTLKISRVEAEDVGVYYCMQRIEFP |
| IGKV2D-24 | A7 | DIVMTQTPLSSPVTLGQPASISFRSSQSLVHSDGNTYLSWLQQRPGQPPRLLI YKVSNRFSGVPDRFSGSGAGTDFTLKISRVEAEDVGVYYCTQATQFP |
| IGKV2D-26 | A5 | EIVMTQTPLSLSITPGEQASISCRSSQSLLHSDGYTYLYWFLQKARPVSTLLIYE VSNRFSGVPDRFSGSGSGTDFTLKISRVEAEDFGVYYCMQDAQDPP |
| IGKV2D-28 | A3 | DIVMTQSPLSLPVTPGEPASISCRSSQSLLHSNGYNYLDWYLQKPGQSPQLLI YLGSNRASGVPDRFSGSGSGTDFTLKISRVEAEDVGVYYCMQALQTP |
| IGKV2D-29 | A2 | DIVMTQTPLSLSVTPGQPASISCKSSQSLLHSDGKTYLYWYLQKPGQPPQLLI YEVSNRFSGVPDRFSGSGSGTDFTLKISRVEAEDVGVYYCMQSIQLP |
| IGKV2D-30 | A1 | DVVMTQSPLSLPVTLGQPASISCRSSQSLVYSDGNTYLNWFQQRPGQSPRR LIYKVSNWDSGVPDRFSGSGSGTDFTLKISRVEAEDVGVYYCMQGTHWP |
| IGKV2D-40 | O1 | DIVMTQTPLSLPVTPGEPASISCRSSQSLLDSDDGNTYLDWYLQKPGQSPQLL IYTLSYRASGVPDRFSGSGSGTDFTLKISRVEAEDVGVYYCMQRIEFP |
| IGKV3-7 | L10 | EIVMTQSPPTLSLSPGERVTLSCRASQSVSSSYLTWYQQKPGQAPRLLIYGAS TRATSIPARFSGSGSGTDFTLTISSLQPEDFAVYYCQQDHNLPP |
| IGKV3-11 | L6 | EIVLTQSPATLSLSPGERATLSCRASQSVSSYLAWYQQKPGQAPRLLIYDASN RATGIPARFSGSGSGTDFTLTISSLEPEDFAVYYCQQRSNWP |
| IGKV3-15 | L2 | EIVMTQSPATLSVSPGERATLSCRASQSVSSNLAWYQQKPGQAPRLLIYGAS TRATGIPARFSGSGSGTEFTLTISSLQSEDFAVYYCQQYNNWP |

Figure 7C

| IGKV3-20 | A27 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSP |
|---|---|---|
| IGKV3D-07 | L25 | EIVMTQSPATLSLSPGERATLSCRASQSVSSSYLSWYQQKPGQAPRLLIYGASTRATGIPARFSGSGSGTDFTLTISSLQPEDFAVYYCQQDYNLP |
| IGKV3D-11 | L20 | EIVLTQSPATLSLSPGERATLSCRASQGVSSYLAWYQQKPGQAPRLLIYDASNRATGIPARFSGSGPGTDFTLTISSLEPEDFAVYYCQQRSNWH |
| IGKV3D-15 | L16 | EIVMTQSPATLSVSPGERATLSCRASQSVSSNLAWYQQKPGQAPRLLIYGASTRATGIPARFSGSGSGTEFTLTISSLQSEDFAVYYCQQYNNWP |
| IGKV3D-20 | A11 | EIVLTQSPATLSLSPGERATLSCGASQSVSSSYLAWYQQKPGLAPRLLIYDASSRATGIPDRFSGSGSGTDFTLTISRLEPEDFAVYYCQQYGSSP |
| IGKV4-1 | B3 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTP |
| IGKV5-2 | B2 | ETTLTQSPAFMSATPGDKVNISCKASQDIDDDMNWYQQKPGEAAIFIIQEATTLVPGIPPRFSGSGYGTDFTLTINNIESEDAAYYFCLQHDNFP |
| IGKV6-21 | A26 | EIVLTQSPDFQSVTPKEKVTITCRASQSIGSSLHWYQQKPDQSPKLLIKYASQSFSGVPSRFSGSGSGTDFTLTINSLEAEDAATYYCHQSSSLP |
| IGKV6D-21 | A10 | EIVLTQSPDFQSVTPKEKVTITCRASQSIGSSLHWYQQKPDQSPKLLIKYASQSFSGVPSRFSGSGSGTDFTLTINSLEAEDAATYYCHQSSSLP |
| IGKV6D-41 | A14 | DVVMTQSPAFLSVTPGEKVTITCQASEGIGNYLYWYQQKPDQAPKLLIKYASQSISGVPSRFSGSGSGTDFTFTISSLEAEDAATYYCQQGNKHP |

38 functional
8 open reading frames

Figure 8A

| | Kawasaki et al | Frippiat et al | Protein sequence |
|---|---|---|---|
| IGLV1-36 | VL 1-11 | 1a | QSVLTQPPSVSEAPRQRVTISCSGSSSNIGNNAVNWYQQLPGKAPKLLIYYDD LLPSGVSDRFSGSKSGTSASLAISGLQSEDEADYYCAAWDDSLNGP |
| IGLV1-40 | VL 1-13 | 1e | QSVLTQPPSVSGAPGQRVTISCTGSSSNIGAGYDVHWYQQLPGTAPKLLIYG NSNRPSGVPDRFSGSKSGTSASLAITGLQAEDEADYYCQSYDSSLSGS |
| IGLV1-44 | VL 1-16 | 1c | QSVLTQPPSASGTPGQRVTISCSGSSSNIGSNTVNWYQQLPGTAPKLLIYSNN QRPSGVPDRFSGSKSGTSASLAISGLQSEDEADYYCAAWDDSLNGP |
| IGLV1-47 | VL 1-17 | 1g | QSVLTQPPSASGTPGQRVTISCSGSSSNIGSNYVYWYQQLPGTAPKLLIYSNN QRPSGVPDRFSGSKSGTSASLAISGLRSEDEADYYCAAWDDSLSGP |
| IGLV1-50 | VL 1-18 | 1f | QSVLTQPPSVSGAPGQRVTISCTGSSSNIGAGYVVHWYQQLPGTAPKLLIYG NSNRPSGVPDQFSGSKSGTSASLAITGLQSEDEADYYCKAWDNSLNA |
| IGLV1-51 | VL 1-19 | 1b | QSVLTQPPSVSAAPGQKVTISCSGSSSNIGNNYVSWYQQLPGTAPKLLIYDNN KRPSGIPDRFSGSKSGTSATLGITGLQTGDEADYYCGTWDSSLSAG |
| IGLV2-08 | VL 1-2 | 2c | QSALTQPPSASGSPGQSVTISCTGTSSDVGGYNYVSWYQQHPGKAPKLMIY EVSKRPSGVPDRFSGSKSGNTASLTVSGLQAEDEADYYCSSYAGSNNF |
| IGLV2-11 | VL 1-3 | 2e | QSALTQPRSVSGSPGQSVTISCTGTSSDVGGYNYVSWYQQHPGKAPKLMIY DVSKRPSGVPDRFSGSKSGNTASLTISGLQAEDEADYYCCSYAGSYTF |
| IGLV2-14 | VL 1-4 | 2a2 | QSALTQPASVSGSPGQSITISCTGTSSDVGGYNYVSWYQQHPGKAPKLMIYE VSNRPSGVSNRFSGSKSGNTASLTISGLQAEDEADYYCSSYTSSSTL |
| IGLV2-18 | VL 1-5 | 2d | QSALTQPPSVSGSPGQSVTISCTGTSSDVGSYNRVSWYQQPPGTAPKLMIYE VSNRPSGVPDRFSGSKSGNTASLTISGLQAEDEADYYCSLYTSSSTF |
| IGLV2-23 | VL 1-7 | 2b2 | QSALTQPASVSGSPGQSITISCTGTSSDVGSYNLVSWYQQHPGKAPKLMIYE GSKRPSGVSNRFSGSKSGNTASLTISGLQAEDEADYYCCSYAGSSTF |
| IGLV2-33 | VL 1-9 | 2f | QSALTQPPFVSGAPGQSVTISCTGTSSDVGDYDHVFWYQKRLSTTSRLLIYN VNTRPSGISDLFSGSKSGNMASLTISGLKSEVEANYHCSLYSSSYTF |
| IGLV3-1 | VL 2-1 | 3r | SYELTQPPSVSVSPGQTASITCSGDKLGDKYACWYQQKPGQSPVLVIYQDSK RPSGIPERFSGSNSGNTATLTISGTQAMDEADYYCQAWDSSTA |
| IGLV3-9 | VL 2-6 | 3j | SYELTQPLSVSVALGQTARITCGGNNIGSKNVHWYQQKPGQAPVLVIYRDSN RPSGIPERFSGSNSGNTATLTISRAQAGDEADYYCQVWDSSTA |
| IGLV3-10 | VL 2-7 | 3p | SYELTQPPSVSVSPGQTARITCSGDALPKKYAYWYQQKSGQAPVLVIYEDSK RPSGIPERFSGSSSGTMATLTISGAQVEDEADYYCYSTDSSGNH |
| IGLV3-12 | VL 2-8 | 3i | SYELTQPHSVSVATAQMARITCGGNNIGSKAVHWYQQKPGQDPVLVIYSDSN RPSGIPERFSGSNPGNTATLTISRIEAGDEADYYCQVWDSSSDHP |
| IGLV3-16 | VL 2-11 | 3a | SYELTQPPSVSVSLGQMARITCSGEALPKKYAYWYQQKPGQFPVLVIYKDSE RPSGIPERFSGSSSGTIVTLTISGVQAEDEADYYCLSADSSGTYP |
| IGLV3-19 | VL 2-13 | 3l | SSELTQDPAVSVALGQTVRITCQGDSLRSYYASWYQQKPGQAPVLVIYGKNN RPSGIPDRFSGSSSGNTASLTITGAQAEDEADYYCNSRDSSGNHL |
| IGLV3-21 | VL 2-14 | 3h | SYVLTQPPSVSVAPGQTARITCGGNNIGSKSVHWYQQKPGQAPVLVVYDDS DRPSGIPERFSGSNSGNTATLTISRVEAGDEADYYCQVWDSSSDHP |
| IGLV3-22 | VL 2-15 | 3e | SYELTQLPSVSVSPGQTARITCSGDVLGENYADWYQQKPGQAPELVIYEDSE RYPGIPERFSGSTSGNTTTLTISRVLTEDEADYYCLSGDEDNP |
| IGLV3-25 | VL 2-17 | 3m | SYELTQPPSVSVSPGQTARITCSGDALPKQYAYWYQQKPGQAPVLVIYKDSE RPSGIPERFSGSSSGTTVTLTISGVQAEDEADYYCQSADSSGTYP |
| IGLV3-27 | VL 2-19 | -- | SYELTQPSSVSVSPGQTARITCSGDVLAKKYARWFQQKPGQAPVLVIYKDSE RPSGIPERFSGSSSGTTVTLTISGAQVEDEADYYCYSAADNNL |

Figure 8B

| IGLV3-32 | VL 2-23P | 3i1 | SSGPTQVPAVSVALGQMARITCQGDSMEGSYEHWYQQKPGQAPVLVIYDSS DRPSRIPERFSGSKSGNTTTLTITGAQAEDEADYYYQLIDNHA |
|---|---|---|---|
| IGLV4-3 | VL 5-1 | 4c | LPVLTQPPSASALLGASIKLTCTLSSEHSTYTIEWYQQRPGRSPQYIMKVKSD GSHSKGDGIPDRFMGSSSGADRYLTFSNLQSDDEAEYHCGESHTIDGQVG |
| IGLV4-60 | VL 5-4 | 4a | QPVLTQSSSASASLGSSVKLTCTLSSGHSSYIIAWHQQQPGKAPRYLMKLEG SGSYNKGSGVPDRFSGSSSGADRYLTISNLQFEDEADYYCETWDSNT |
| IGLV4-69 | VL 5-6 | 4b | QLVLTQSPSASASLGASVKLTCTLSSGHSSYAIAWHQQQPEKGPRYLMKLNS DGSHSKGDGIPDRFSGSSSGAERYLTISSLQSEDEADYYCQTWGTG |
| IGLV5-37 | VL 4-1 | 5e | QPVLTQPPSSSASPGESARLTCTLPSDINVGSYNIWYQQKPGSPPRYLLYYY SDSDKGQGSGVPSRFSGSKDASANTGILLISGLQSEDEADYYCMIWPSNAS |
| IGLV5-39 | -- | 5a | QPVLTQPTSLSASPGASARFTCTLRSGINVGTYRIYWYQQKPGSLPRYLLRYK SDSDKQQGSGVPSRFSGSKDASTNAGLLLISGLQSEDEADYYCAIWYSSTS |
| IGLV5-45 | VL 4-2 | 5c | QAVLTQPSSLSASPGASASLTCTLRSGINVGTYRIYWYQQKPGSPPQYLLRYK SDSDKQQGSGVPSRFSGSKDASANAGILLISGLQSEDEADYYCMIWHSSAS |
| IGLV5-48 | VL 4-3 | 5d | QPVLTQPTSLSASPGASARLTCTLRSGINLGSYRIFWYQQKPESPPRYLLSYY SDSSKHQGSGVPSRFSGSKDASSNAGILVISGLQSEDEADYYCMIWHSSAS |
| IGLV5-52 | VL 4-4 | 5b | QPVLTQPSSHSASSGASVRLTCMLSSGFSVGDFWIRWYQQKPGNPPRYLLY YHSDSNKGQGSGVPSRFSGSNDASANAGILRISGLQPEDEADYYCGTWHSN SKT |
| IGLV6-57 | VL 1-22 | 6a | NFMLTQPHSVSESPGKTVTISCTRSSGSIASNYVQWYQQRPGSSPTTVIYED NQRPSGVPDRFSGSIDSSSNSASLTISGLKTEDEADYYCQSYDSSN |
| IGLV7-43 | VL 3-2 | 7a | QTVVTQEPSLTVSPGGTVTLTCASSTGAVTSGYYPNWFQQKPGQAPRALIYS TSNKHSWTPARFSGSLLGGKAALTLSGVQPEDEAEYYCLLYYGGAQ |
| IGLV7-46 | VL 3-3 | 7b | QAVVTQEPSLTVSPGGTVTLTCGSSTGAVTSGHYPYWFQQKPGQAPRTLIYD TSNKHSWTPARFSGSLLGGKAALTLLGAQPEDEAEYYCLLSYSGAR |
| IGLV8-61 | VL 3-4 | 8a | QTVVTQEPSFSVSPGGTVTLTCGLSSGSVSTSYYPSWYQQTPGQAPRTLIYS TNTRSSGVPDRFSGSILGNKAALTITGAQADDESDYYCVLYMGSGIS |
| IGLV9-49 | VL 5-2 | 9a | QPVLTQPPSASASLGASVTLTCTLSSGYSNYKVDWYQQRPGKGPRFVMRVG TGGIVGSKGDGIPDRFSVLGSGLNRYLTIKNIQEEDESDYHCGADHGSGSNFV |
| IGLV10-54 | VL 1-20 | 10a | QAGLTQPPSVSKGLRQTATLTCTGNSNIVGNQGAAWLQQHQGHPPKLLSYR NNNRPSGISERFSASRSGNTASLTITGLQPEDEADYYCSALDSSLSA |
| IGLV11-55 | VL 4-6 | -- | RPVLTQPPSLSASPGATARLPCTLSSDLSVGGKNMFWYQQKPGSSPRLFLY HYSDSDKQLGPGVPSRVSGSKETSSNTAFLLISGLQPEDEADYYCQVYESSA N |

Figure 16

| No. | VH | VL | Purified fab expression mg/L | Purified Fab % monomer | Purified Fab Thermofluor | Purified IgG1 Expression mg/L | Purified IgG1 % monomer | Purified IgG1 Thermafluor | IgG1 Isoelectric point |
|---|---|---|---|---|---|---|---|---|---|
| 1 | VH_1_18 | VK_1_39 | 2,5 | 100 | 75.2 / 75.4 | 36 | 100 | 78,4 | 9,2 |
| 2 | VH_1_18 | VK_3_11 | 3 | 97 | 75,2 | | | | |
| 3 | VH_1_18 | VK_3_15 | 5 | 99 | 76,39 | 36,1 | 99 | 81,9 | 9,2 |
| 4 | VH_1_18 | VK_3_20 | 5 | 100 | 73.8 / 73.6 | 44 | 100 | 77 | 9 |
| 5 | VH_1_18 | VL_1-40 | | | | 59,1 | 90 | 83,6 | 8,9 |
| 6 | VH_1_18 | VL_1-47 | 6,5 | 98 | 74.1 / 74.3 | 52,9 | 98 | 83,9 | 9,3 |
| 7 | VH_1_18 | VL_2-23 | 4.0 / 5.0 / 4.5 | 98.0 / 99.0 / 97.0 | 73.8 / 71.0 | 45,9 | 93 | 80,4 | 9 |
| 8 | VH_1_18 | VL_3-1 | 2,5 | 97 | 75 | 60,8 | 96 | 84,5 | 8,2 |
| 9 | VH_1_46 | VK_1_09 | 2,5 | 95 | 73,1 | 42,8 | 100 | 77,6 | 8,9 |
| 10 | VH_1_46 | VK_3_15 | 3 | 100 | 74.5 / 74.3 | 60,9 | 100 | 76,5 | 8,9 |
| 11 | VH_1_46 | VL_1-40 | 6,5 | 99 | 73.9 / 73.4 | 50,7 | 93 | 80,5 | 8,2 |
| 12 | VH_1_46 | VL_1-51 | 4,5 | 100 | 73,56 | 65 | 100 | 79,5 | 8,6 |
| 13 | VH_1_46 | VL_2-23 | 7 | 100 | 72.9 / 72.7 | 49,6 | 98 | 78,5 | 8,6 |
| 14 | VH_1_46 | VL_3-1 | | | | 78,8 | 98 | 75,8 | 8,2 |
| 15 | VH_1_46 | VL_3-21 | 3 | 98 | 74,8 | 50,4 | 100 | 74,5 | 8,2 |
| 16 | VH_1_69*01 | VK_1_27 | 3,5 | 98 | 72,9 | | | | |
| 17 | VH_1_69*01 | VK_3_11 | 2,5 | 97 | | 22,6 | 100 | 77,8 | 8,2 |
| 18 | VH_1_69*01 | VL_1-40 | 4.5 / 6.5 | 90.0 / 99.0 | 73.8 / 72.7 | 34,7 | 95 | 81,7 | 8,2 |
| 19 | VH_1_69*01 | VL_1-51 | 7,5 | 99 | 73.3 / 72.9 | 53,9 | 99 | 77,9 | 8,6 |
| 20 | VH_1_69*01 | VL_3-1 | 2.0 / 3.0 | 99.0 / 96.0 | 74,4 | 36,4 | 99 | 79,6 | 7,4 |
| 21 | VH_1_69*01 | VL_3-21 | 4 | 98 | 73.3 / 73.1 | 34,5 | 98 | 76 | 8,2 |
| 22 | VH_3_07 | VK_1_12 | 6,5 | 100 | 74.0 / 74.1 | 57 | 100 | 77,6 | 8,9 |
| 23 | VH_3_07 | VK_1_16 | 7 | 98 | | 50 | 100 | 74 | 8,9 |
| 24 | VH_3_07 | VK_1_27 | 6 | 99 | 76.0 / 76.0 | 64 | 100 | 80 | 8,9 |
| 25 | VH_3_07 | VK_1_39 | 7 | 98 | 74.2 / 74.3 | 53,3 | 100 | 80 | 8,9 |
| 26 | VH_3_07 | VK_3_15 | 6 | 100 | 74.8 / 75.3 | 65,5 | 100 | 79 | 8,9 |
| 27 | VH_3_07 | VK_3_20 | | | | 32,7 | 100 | 78,4 | 8,7 |
| 28 | VH_3_07 | VL_1-47 | 9,5 | 99 | 72.0 / 71.3 | 56,7 | 99 | 79,4 | 9,1 |
| 29 | VH_3_07 | VL_1-51 | 8,5 | 97 | 72.0 / 71.3 | 63,3 | 100 | 79,9 | 8,7 |
| 30 | VH_3_07 | VL_2-23 | 3 | 94 | 72.5 / 72.2 | 43,3 | 90 | 81,4 | 8,7 |
| 31 | VH_3_07 | VL_3-1 | 1,5 | 94 | n.a. | 43,5 | 97 | n.a. | 7,6 |
| 32 | VH_3_11 | VK_1_05 | 4,5 | 98 | 70.0 / 70.1 | 56,4 | 100 | 74,3 | 8,6 |

Figure 17

| No. | VH | VL | Purified fab expression mg/L | Purified Fab % monomer | Purified Fab Thermofluor | Purified IgG1 expression mg/L | Purified IgG1 % monomer | Purified IgG1 Thermafluor | IgG1 Isoelectric point |
|---|---|---|---|---|---|---|---|---|---|
| 33 | VH_3_11 | VK_1_39 | 3,5 | 100 | 74.1 / 73.8 | 55,7 | 99 | 79 | 9 |
| 34 | VH_3_11 | VK_3_15 | 6,5 | 99 | 72 | 57,4 | 100 | 78,6 | 9,1 |
| 35 | VH_3_11 | VL_1-40 | 7 | 99 | 72 | 30 | 99 | 79,2 | 8,6 |
| 36 | VH_3_11 | VL_1-47 | 7,5 | 99 | 71.8 / 71.5 | 52,7 | 99 | 77,2 | 9,2 |
| 37 | VH_3_11 | VL_1-51 | 13 | 100 | 71.7 / 72.2 | 59,1 | 100 | 77 | 8,9 |
| 38 | VH_3_11 | VL_2-23 | 7 | 99 | 70.2 / 70.5 | 50 | 99 | 74,5 | 8,9 |
| 39 | VH_3_15 | VK_1_05 | 8,5 | 100 | 72.3 / 72.7 | 59,1 | 100 | 76 | 8,9 |
| 40 | VH_3_15 | VK_1_06 | 5 | 100 | 72,3 | 38 | 100 | 74,5 | 9,3 |
| 41 | VH_3_15 | VK_1_09 | 9,5 | 100 | 75.8 / 76.7 | 20 | 99 | 82 | 9,2 |
| 42 | VH_3_15 | VK_1_12 | 9 | 99 | 75.6 / 75.3 | 54,5 | 100 | 79,2 | 9,2 |
| 43 | VH_3_15 | VK_1_16 | 8,5 | 99 | 73.3 / 73.1 | 52,7 | 100 | 76,5 | 9,2 |
| 44 | VH_3_15 | VK_1_27 | 4,5 | 100 | 76,24 | 32 | 100 | 78,5 | 9,2 |
| 45 | VH_3_15 | VK_3_11 | 5,5 | 99 | 76 | 31,2 | 100 | 79,5 | 8,9 |
| 46 | VH_3_15 | VK_3_15 | 6 | 100 | 77 | 20 | 100 | 80 | 9,2 |
| 47 | VH_3_15 | VL_1-40 | 10,5 | 100 | 73.5 / 73.6 | 32 | 99 | 80,3 | 8,9 |
| 48 | VH_3_15 | VL_1-47 | 9 | 99 | 72.6 / 72.9 | 61,8 | 99 | 78 | 9,3 |
| 49 | VH_3_15 | VL_1-51 | 6 | 100 | 74,11 | 46 | 100 | 78,9 | 9,1 |
| 50 | VH_3_15 | VL_2-14 | 3.0 / 3.5 / 3.0 | 96.0 / 98.0 / 100 | 72.3 / 72.2 | 61 | 99 | 75,5 | 8,9 |
| 51 | VH_3_21 | VK_1_06 | 2 | 98 | 72.9 / 73.1 | 56 | 100 | 74,7 | 9,2 |
| 52 | VH_3_21 | VK_1_12 | 5,5 | 100 | 73,6 | 45,6 | 100 | 77,2 | 9,1 |
| 53 | VH_3_21 | VK_1_27 | 3 | 98 | 74.0 / 73.4 | 47,6 | 100 | 77,8 | 9 |
| 54 | VH_3_21 | VL_2-11 | 4 | 98 | 73.0 / 73.1 | 49,5 | 99 | 80 | 8,9 |
| 55 | VH_3_21 | VL_2-14 | 3.5 / 5.5 | 98.0 / 99.0 | 72.6 / 72.0 | 61 | 98 | 77 | 8,7 |
| 56 | VH_3_21 | VL_2-23 | 3,5 | 99 | 72.4 / 72.6 | 40 | 97 | 77,3 | 8,9 |
| 57 | VH_3_21 | VL_3-1 | 3.4 / 2.5 | 87.0 / 88.0 | 60,66 | 48 | 97 | 77,5 | 7,9 |
| 58 | VH_3_23 | VK_1_39 | 3 | 98 | 75,6 | 43,8 | 100 | 83,8 | 8,9 |
| 59 | VH_3_23 | VK_3_15 | 6 | 99 | 76,45 | 30 | 100 | 85 | 8,9 |
| 60 | VH_3_23 | VK_3_20 | 4,5 | 97 | 77,4 | 34,5 | 100 | 82 | 8,7 |
| 61 | VH_3_23 | VL_2-11 | 3 | 96 | 71,3 | 45,5 | 99 | 82,6 | 8,7 |
| 62 | VH_3_23 | VL_2-14 | 3,5 | 97 | 71,5 | 53,3 | 99 | 78 | 8,3 |
| 63 | VH_3_23 | VL_2-23 | 3,5 | 98 | 71.7 / 72.4 | 52,7 | 99 | 79 | 8,7 |
| 64 | VH_3_23 | VL_3-1 | 3 | 98 | 71,5 | 40 | 100 | 81 | 7,6 |

Figure 18

| No. | VH | VL | Purified fab expression mg/L | Purified Fab % monomer | Purified Fab Thermo-fluor | Purified IgG1 expression mg/L | Purified IgG1 % monomer | Purified IgG1 Thermafluor | IgG1 Isoelectric point |
|---|---|---|---|---|---|---|---|---|---|
| 65 | VH_3_23 | VL_3-21 | 5,5 | 97 | 72,05 | 34,5 | 100 | 79,1 | 8,3 |
| 66 | VH_3_30 | VK_3_15 | 7 | 98 | 71,3 | 27,8 | 100 | 80,7 | 9,2 |
| 67 | VH_3_30 | VK_3_20 | 3 | 97/100 | 72,5 | 31,7 | 100 | 81 | 9,1 |
| 68 | *VH_3_30* | *VL_2-23* | 3,5 | 98 | 72.0 / 72.2 | 45,7 | 96 | 80,5 | 9 |
| 69 | VH_3_30 | VL_3-1 | 2.4 / 1.0 | 94 | | 57,1 | 98 | 79,5 | 8,2 |
| 70 | VH_3_30 | VL_3-21 | 4,5 | 97 | 72.6 / 72.0 | 50 | 100 | 78 | 8,9 |
| 71 | VH_3_53 | VK_1_39 | 5,5 | 98 | 68,8 | 57,1 | 100 | 74,1 | 8,9 |
| 72 | VH_3_53 | VK_3_15 | 4,5 | 100 | 70,05 | 61 | 100 | 73,8 | 8,9 |
| 73 | VH_3_53 | VL_2-11 | 7,5 | 100 | 71 | 50 | 100 | 74,3 | 8,7 |
| 74 | VH_3_53 | VL_2-23 | 6 | 100 | 67,98 | 40 | 99 | 80,8 | 8,7 |
| 75 | *VH_3_53* | *VL_3-1* | 2,5 | 97 | 70,18 | 49,5 | 96 | 81,2 | 7,6 |
| 76 | VH_3_74 | VK_1_05 | 4 | 99 | 72,9 | 61,8 | 100 | 75,5 | 8,7 |
| 77 | VH_3_74 | VK_1_06 | 3,5 | 99 | 74,01 | 52,2 | 100 | 77 | 9,2 |
| 78 | VH_3_74 | VK_1_12 | 5,5 | 99 | 74,48 | 62 | 100 | 78,5 | 9,1 |
| 79 | VH_3_74 | VK_1_27 | 3,5 | 98 | 76,02 | 56 | 100 | 78,5 | 9,1 |
| 80 | VH_3_74 | VK_3_20 | 3,5 | 100 | 73 | 43,8 | 100 | 80,1 | 8,9 |
| 81 | VH_3_74 | VL_1-51 | 4,5 | 98 | 72,25 | 62,9 | 99 | 80,9 | 8,9 |
| 82 | *VH_3_74* | *VL_3-1* | 2.4 / 3.5 | 98.0 / 81.0 | 71,84 | 53,9 | 95 | 79 | 7,9 |
| 83 | VH_5_51 | VK_1_39 | 2,5 | 99 | 70,08 | 36,4 | 100 | 73,3 | 8,9 |
| 84 | VH_5_51 | VK_1_40 | 4 | 99 | 73,09 | 38,3 | 99 | 77,7 | 8,3 |
| 85 | VH_5_51 | VL_1-47 | 6 | 99 | 73,3 | 40 | 97 | 76,5 | 9 |
| 86 | VH_5_51 | VL_1-51 | 5,5 | 100 | 72,47 | 59 | 99 | 75,4 | 8,6 |
| 87 | VH_5_51 | VL_3-1 | 2 | 100 | | 34 | 97 | 76 | 7,6 |
| 88 | *VH_6_1* | VK_1_06 | 2 | 98 | 71,97 | 80 | 100 | n.a. | 9,3 |
| 89 | VH_6_1 | VK_1_09 | 7 | 99 | 76,4 | 66,7 | 100 | 80,3 | 9,2 |
| 90 | VH_6_1 | VK_1_27 | 7.5 / 5.0 | 100 / 80 | 76,13 | 84 | 99 | 80,2 | 9,2 |
| 91 | VH_6_1 | VK_3_15 | 6 | 100 | 75,75 | 38,3 | 100 | 76,4 | 9,2 |
| 92 | VH_6_1 | VK_3_20 | 8 | 100 | 72,69 | 70,5 | 100 | 77,5 | 9,1 |
| 93 | VH_6_1 | VL_1-47 | 7,5 | 100 | 70,28 | 38 | 98 | 73,9 | 9,3 |
| 94 | VH_6_1 | VL_1-51 | 8 | 100 | 73,6 | 62,9 | 99 | 76,9 | 9 |
| 95 | VH_6_1 | VL_3-1 | 2.3 / 3.0 | 97.0 / 98.0 | 70,9 | 26 | 97 | n.a. | 8,2 |

Figure 19

| No. | VH | VL | Tm before Acid | Tm after Acid | Change | Absorption Initial | Absorption 15 min Acid | Absorption 100 min Acid | Absorption neutralization |
|---|---|---|---|---|---|---|---|---|---|
| 1 | VH_1_18 | VK_1_39 |  | 79,2 |  | 0,041 | 0,061 | 0,05 | 0,042 |
| 2 | VH_1_18 | VK_3_11 |  |  |  |  |  |  |  |
| 3 | VH_1_18 | VK_3_15 | 81,9 | 81,9 | 0 | 0,036 | 0,054 | 0,042 | 0,038 |
| 4 | VH_1_18 | VK_3_20 |  | 77,7 |  | 0,037 | 0,043 | 0,042 | 0,037 |
| 5 | VH_1_18 | VL_1-40 | 83,7 | 84 | -0,3 | 0,036 | 0,051 | 0,039 | 0,038 |
| 6 | VH_1_18 | VL_1-47 | 84,2 | 84,2 | 0 | 0,036 | 0,051 | 0,04 | 0,038 |
| 7 | VH_1_18 | VL_2-23 | 80,9 | 80,7 | 0,2 | 0,036 | 0,049 | 0,04 | 0,039 |
| 8 | VH_1_18 | VL_3-1 | 84,9 | 84,7 | 0,2 | 0,036 | 0,049 | 0,04 | 0,038 |
| 9 | VH_1_46 | VK_1_09 | 78,2 | 78,1 | 0,1 | 0,036 | 0,053 | 0,045 | 0,042 |
| 10 | VH_1_46 | VK_3_15 | 77,4 | 77,6 | -0,2 | 0,036 | 0,045 | 0,041 | 0,037 |
| 11 | VH_1_46 | VL_1-40 | 80,6 | 80,7 | -0,1 | 0,036 | 0,045 | 0,04 | 0,039 |
| 12 | VH_1_46 | VL_1-51 | 79,4 | 79,3 | 0,1 | 0,036 | 0,04 | 0,039 | 0,038 |
| 13 | VH_1_46 | VL_2-23 | 78,7 | 78,6 | 0,1 | 0,037 | 0,057 | 0,041 | 0,038 |
| 14 | VH_1_46 | VL_3-1 | 76 | 75,9 | 0,1 | 0,043 | 0,062 | 0,067 | 0,096 |
| 15 | VH_1_46 | VL_3-21 | 74 | 74,2 | -0,2 | 0,039 | 0,044 | 0,042 | 0,043 |
| 16 | VH_1_69*01 | VK_1_27 |  |  |  |  |  |  |  |
| 17 | VH_1_69*01 | VK_3_11 | 77,6 | 78 | 0 | 0,037 | 0,048 | 0,039 | 0,038 |
| 18 | VH_1_69*01 | VL_1-40 | 81,7 | 81,7 | 0 | 0,039 | 0,05 | 0,048 | 0,042 |
| 19 | VH_1_69*01 | VL_1-51 | 78,2 | 78,1 | 0,1 | 0,037 | 0,045 | 0,042 | 0,04 |
| 20 | VH_1_69*01 | VL_3-1 | 79,2 | 79,1 | 0,1 | 0,041 | 0,047 | 0,046 | 0,048 |
| 21 | VH_1_69*01 | VL_3-21 | 78,4 | 76,4 | 2 | 0,04 | 0,06 | 0,045 | 0,038 |
| 22 | VH_3_07 | VK_1_12 | 77,8 | 78,2 | -0,4 | 0,036 | 0,047 | 0,041 | 0,037 |
| 23 | VH_3_07 | VK_1_16 |  | 74,4 |  | 0,036 | 0,046 | 0,043 | 0,038 |
| 24 | VH_3_07 | VK_1_27 | 80,2 | 80,4 | -0,2 | 0,039 | 0,041 | 0,04 | 0,04 |
| 25 | VH_3_07 | VK_1_39 | 80 | 80,2 | -0,2 | 0,037 | 0,038 | 0,038 | 0,039 |
| 26 | VH_3_07 | VK_3_15 | 79,5 | 79,7 | -0,2 | 0,037 | 0,038 | 0,037 | 0,038 |
| 27 | VH_3_07 | VK_3_20 | 78,5 | 78,9 | -0,4 | 0,038 | 0,042 | 0,043 | 0,041 |
| 28 | VH_3_07 | VL_1-47 | 78,8 | 79,1 | -0,3 | 0,037 | 0,039 | 0,037 | 0,037 |
| 29 | VH_3_07 | VL_1-51 | 79,8 | 79,8 | 0 | 0,039 | 0,041 | 0,041 | 0,04 |
| 30 | VH_3_07 | VL_2-23 | 81,2 | 81,2 | 0 | 0,043 | 0,049 | 0,043 | 0,041 |
| 31 | VH_3_07 | VL_3-1 | 81,2 | 81,2 | 0 | 0,036 | 0,042 | 0,037 | 0,038 |
| 32 | VH_3_11 | VK_1_05 | 74,5 | 75 | -0,5 | 0,036 | 0,037 | 0,037 | 0,036 |

Figure 20

| No. | VH | VL | Initial Radius [nm] | Initial % Poly-dispersity | Radius [nm] After acid | % Poly-dispersity After acid | Particle Staining before acid | Particle Staining after acid | Cumulative score |
|---|---|---|---|---|---|---|---|---|---|
| 1 | VH_1_18 | VK_1_39 | 5,7 | 4,8 | 5,4 | 9,1 | 1 | 3,00 | 1050 |
| 2 | VH_1_18 | VK_3_11 | | | | | | | |
| 3 | VH_1_18 | VK_3_15 | 5,2 | 4,1 | 5,3 | 7,2 | 1 | 2 | 1100 |
| 4 | VH_1_18 | VK_3_20 | 5,4 | 2,8 | 5,3 | 7,1 | 2 | 3 | 1450 |
| 5 | VH_1_18 | VL_1-40 | 5,6 | 5,7 | 5,7 | 7,8 | 1 | 2 | 1525 |
| 6 | VH_1_18 | VL_1-47 | 5,3 | 4,3 | 5,5 | 7,4 | 1 | 2 | 1450 |
| 7 | VH_1_18 | VL_2-23 | 5,4 | 2,7 | 5,6 | 9,5 | 1 | 1 | 1450 |
| 8 | VH_1_18 | VL_3-1 | 5,4 | 5,5 | 5,5 | 9,5 | 1 | 1 | 1600 |
| 9 | VH_1_46 | VK_1_09 | 5,1 | 2,2 | 5,3 | 6,8 | 1 | 1,5 | 1475 |
| 10 | VH_1_46 | VK_3_15 | 5,3 | 6,9 | 5,4 | 10,6 | 1 | 1 | 1550 |
| 11 | VH_1_46 | VL_1-40 | 5,6 | 8,4 | 5,4 | 8,5 | 1 | 1 | 1600 |
| 12 | VH_1_46 | VL_1-51 | 5,1 | 2,4 | 5,3 | 7,4 | 2,5 | 3 | 1500 |
| 13 | VH_1_46 | VL_2-23 | 5,2 | 2,1 | 5,2 | 5,3 | 2 | 1 | 1450 |
| 14 | VH_1_46 | VL_3-1 | 12,2 | 39,8 | 39 | mm | 2 | 4 | 400 |
| 15 | VH_1_46 | VL_3-21 | 9,3 | mm | 8,3 | mm | 1 | 3 | 875 |
| 16 | VH_1_69*01 | VK_1_27 | | | | | | | |
| 17 | VH_1_69*01 | VK_3_11 | 5,3 | 5,6 | 5,4 | 11,3 | 1 | 2 | 1525 |
| 18 | VH_1_69*01 | VL_1-40 | 7,1 | 10,6 | 7,8 | 16 | 3 | 2,5 | 1150 |
| 19 | VH_1_69*01 | VL_1-51 | 5,3 | 3,6 | 5,3 | 6,3 | 1 | 1 | 1575 |
| 20 | VH_1_69*01 | VL_3-1 | 7,3 | 26,2 | 33 | mm | 1 | 1 | 575 |
| 21 | VH_1_69*01 | VL_3-21 | 5,5 | 8,7 | 5,7 | 16,3 | 2 | 1 | 1025 |
| 22 | VH_3_07 | VK_1_12 | 5,1 | 2,6 | 5,2 | 5,6 | 1 | 1 | 1425 |
| 23 | VH_3_07 | VK_1_16 | 5,6 | 14,1 | 5,2 | 5,9 | 2,5 | 2,5 | 1575 |
| 24 | VH_3_07 | VK_1_27 | 5,1 | 2,2 | 5,3 | 9 | 1,5 | 1 | 1450 |
| 25 | VH_3_07 | VK_1_39 | 5,2 | 2,7 | 5,3 | 6,3 | 1 | 2 | 1450 |
| 26 | VH_3_07 | VK_3_15 | 5,1 | 2,5 | 5,3 | 6,8 | 2 | 3,5 | 1500 |
| 27 | VH_3_07 | VK_3_20 | 5,3 | 8,8 | 5,7 | 9,4 | 1 | 2,5 | E12 |
| 28 | VH_3_07 | VL_1-47 | 5,1 | 3,6 | 5,2 | 5,9 | 1 | 2 | 1700 |
| 29 | VH_3_07 | VL_1-51 | 5,2 | 4,5 | 5,1 | 4,9 | 1 | 1 | 1325 |
| 30 | VH_3_07 | VL_2-23 | 5,8 | 12,4 | 5,5 | 6,6 | 1 | 2 | 1600 |
| 31 | VH_3_07 | VL_3-1 | 5,3 | 4,1 | 5,4 | 7,3 | 1 | 1 | 1600 |
| 32 | VH_3_11 | VK_1_05 | 5,1 | 2,2 | 5,2 | 5,2 | 1 | 2 | 1150 |

Figure 21

| No. | VH | VL | Tm before Acid | Tm after Acid | Change | Absorption Inital | Absorption 15 min Acid | Absorption 100 min Acid | Absorption neutralization |
|---|---|---|---|---|---|---|---|---|---|
| 33 | VH_3_11 | VK_1_39 | 79 | 79,5 | -0,5 | 0,037 | 0,04 | 0,038 | 0,044 |
| 34 | VH_3_11 | VK_3_15 | 78,8 | 79 | -0,2 | 0,04 | 0,042 | 0,041 | 0,041 |
| 35 | VH_3_11 | VL_1-40 |  | 79,1 |  | 0,037 | 0,051 | 0,049 | 0,044 |
| 36 | VH_3_11 | VL_1-47 | 77,1 | 77,1 | 0 | 0,036 | 0,042 | 0,04 | 0,039 |
| 37 | VH_3_11 | VL_1-51 | 76,9 | 77 | -0,1 | 0,036 | 0,04 | 0,038 | 0,039 |
| 38 | VH_3_11 | VL_2-23 | 74,3 | 74,3 | 0 | 0,036 | 0,038 | 0,039 | 0,038 |
| 39 | VH_3_15 | VK_1_05 | 76,4 | 76,7 | -0,3 | 0,037 | 0,047 | 0,043 | 0,039 |
| 40 | VH_3_15 | VK_1_06 |  | 76,2 |  | 0,038 | 0,04 | 0,04 | 0,036 |
| 41 | VH_3_15 | VK_1_09 | 81,7 | 81,9 | -0,2 | 0,035 | 0,043 | 0,041 | 0,039 |
| 42 | VH_3_15 | VK_1_12 | 78,6 | 79,6 | -1 | 0,036 | 0,038 | 0,037 | 0,037 |
| 43 | VH_3_15 | VK_1_16 | 76,4 | 76,7 | -0,3 | 0,038 | 0,046 | 0,042 | 0,04 |
| 44 | VH_3_15 | VK_1_27 |  | 80,1 |  | 0,043 | 0,05 | 0,045 | 0,037 |
| 45 | VH_3_15 | VK_3_11 |  | 79,9 |  | 0,043 | 0,045 | 0,045 | 0,044 |
| 46 | VH_3_15 | VK_3_15 | 80,3 | 80,5 | -0,2 | 0,04 | 0,045 | 0,044 | 0,043 |
| 47 | VH_3_15 | VL_1-40 | 80,4 | 80,4 | 0 | 0,036 | 0,046 | 0,04 | 0,037 |
| 48 | VH_3_15 | VL_1-47 | 78,1 | 80,3 | -2,2 | 0,035 | 0,038 | 0,038 | 0,036 |
| 49 | VH_3_15 | VL_1-51 |  | 78,8 |  | 0,035 | 0,046 | 0,047 | 0,036 |
| 50 | VH_3_15 | VL_2-14 | 75,5 | 75,7 | -0,2 | 0,036 | 0,037 | 0,037 | 0,037 |
| 51 | VH_3_15 | VK_1_06 | 74,5 | 75,7 | -1,2 | 0,036 | 0,041 | 0,043 | 0,039 |
| 52 | VH_3_21 | VK_1_12 |  | 77,2 |  | 0,036 | 0,042 | 0,041 | 0,038 |
| 53 | VH_3_21 | VK_1_27 | 77,6 | 78,1 | -0,5 | 0,036 | 0,041 | 0,047 | 0,045 |
| 54 | VH_3_21 | VL_2-11 | 79,7 | 79,8 | -0,1 | 0,037 | 0,049 | 0,045 | 0,042 |
| 55 | VH_3_21 | VL_2-14 | 76,4 | 76,6 | -0,2 | 0,037 | 0,058 | 0,046 | 0,042 |
| 56 | VH_3_21 | VL_2-23 | 76,6 | 77 | -0,4 | 0,037 | 0,044 | 0,04 | 0,038 |
| 57 | VH_3_21 | VL_3-1 | 77,4 | 77,3 | 0,1 | 0,038 | 0,046 | 0,048 | 0,047 |
| 58 | VH_3_23 | VK_1_39 | 83,7 | 83,9 | -0,2 | 0,037 | 0,044 | 0,04 | 0,037 |
| 59 | VH_3_23 | VK_3_15 |  | 85 |  | 0,039 | 0,045 | 0,05 | 0,047 |
| 60 | VH_3_23 | VK_3_20 | 82,3 | 82,3 | 0 | 0,036 | 0,04 | 0,038 | 0,036 |
| 61 | VH_3_23 | VL_2-11 | 82,5 | 82,8 | -0,3 | 0,035 | 0,041 | 0,038 | 0,037 |
| 62 | VH_3_23 | VL_2-14 | 78,1 | 78,1 | 0 | 0,036 | 0,039 | 0,038 | 0,036 |
| 63 | VH_3_23 | VL_2-23 | 79 | 79 | 0 | 0,036 | 0,039 | 0,038 | 0,038 |
| 64 | VH_3_23 | VL_3-1 | 80,9 | 80,1 | 0,8 | 0,037 | 0,041 | 0,038 | 0,037 |

Figure 22

| No. | VH | VL | Initial Radius [nm] | Initial % Poly-dispersity | Radius [nm] After acid | % Poly-dispersity After acid | Particle Staining before acid | Particle Staining after acid | Cumulative score |
|---|---|---|---|---|---|---|---|---|---|
| 33 | VH_3_11 | VK_1_39 | 5,2 | 2,9 | 5,5 | 17,2 | 2 | 2 | 1075 |
| 34 | VH_3_11 | VK_3_15 | 5,2 | 5,6 | 5,2 | 5,7 | 1 | 2 | 1050 |
| 35 | VH_3_11 | VL_1-40 | 5,1 | 2,4 | 5,1 | 5,1 | 1 | 1 | 1550 |
| 36 | VH_3_11 | VL_1-47 | 5,2 | 6 | 5,2 | 7,4 | 1 | 3,5 | 1550 |
| 37 | VH_3_11 | VL_1-51 | 5,1 | 1,9 | 5,1 | 4,8 | 1 | 1 | 1675 |
| 38 | VH_3_11 | VL_2-23 | 5,1 | 2,4 | 5,1 | 8,7 | 1 | 1 | 1750 |
| 39 | VH_3_15 | VK_1_05 | 5,1 | 3 | 5,2 | 8,3 | 2 | 2 | 1575 |
| 40 | VH_3_15 | VK_1_06 | 5,1 | 2,3 | 5,2 | 3,8 | 1 | 2 | 1400 |
| 41 | VH_3_15 | VK_1_09 | 7 | 22 | 5,4 | 14,4 | 2,5 | 2 | 1175 |
| 42 | VH_3_15 | VK_1_12 | 5,1 | 2,2 | 5,2 | 4,6 | 2 | 2 | 1575 |
| 43 | VH_3_15 | VK_1_16 | 5,2 | 3,5 | 5,2 | 3,7 | 3 | 2 | 1025 |
| 44 | VH_3_15 | VK_1_27 | 5,1 | 3 | 5,3 | 9,2 | 1 | 2 | 1450 |
| 45 | VH_3_15 | VK_3_11 | 5,2 | 5,3 | 5,3 | 13,1 | 2 | 2 | 1225 |
| 46 | VH_3_15 | VK_3_15 | 5,4 | 17,7 | 5,5 | 16,4 | 1 | 2,5 | 1025 |
| 47 | VH_3_15 | VL_1-40 | 5,3 | 11,3 | 5,2 | 7,9 | 3 | 1 | 1000 |
| 48 | VH_3_15 | VL_1-47 | 5,1 | 4 | 5,2 | 5 | 1 | 2 | 1150 |
| 49 | VH_3_15 | VL_1-51 | 5,6 | 14,1 | 5,5 | 5,9 | 2 | 2 | 1275 |
| 50 | VH_3_15 | VL_2-14 | 5,5 | 20,7 | 5,5 | 13,1 | 1 | 1 | 1425 |
| 51 | VH_3_15 | VK_1_06 | 5,1 | 2 | 5,2 | 6 | 2 | 3 | 1300 |
| 52 | VH_3_21 | VK_1_12 | 5,2 | 3,6 | 5,7 | 16,8 | 3 | 2 | 1500 |
| 53 | VH_3_21 | VK_1_27 | 5,2 | 3,3 | 5,3 | 7,6 | 1 | 2 | 1475 |
| 54 | VH_3_21 | VL_2-11 | 5,1 | 2 | 5,2 | 6 | 2 | 2 | 1375 |
| 55 | VH_3_21 | VL_2-14 | 5,4 | 5,8 | 5,3 | 5 | 1 | 2 | 1525 |
| 56 | VH_3_21 | VL_2-23 | 5,3 | 4,7 | 5,2 | 4,8 | 1 | 1 | 1650 |
| 57 | VH_3_21 | VL_3-1 | 8 | mm | PD | mm | 1 | 2 | 675 |
| 58 | VH_3_23 | VK_1_39 | 5,3 | 6,3 | 5,2 | 5,3 | 2 | 2 | 1250 |
| 59 | VH_3_23 | VK_3_15 | 5,1 | 2,5 | 5,2 | 6 | 1 | 2 | 1375 |
| 60 | VH_3_23 | VK_3_20 | 5,2 | 4,4 | 5,2 | 6,2 | 1 | 2,5 | 1300 |
| 61 | VH_3_23 | VL_2-11 | 5,2 | 3,6 | 5,3 | 7,5 | 2 | 2 | 1375 |
| 62 | VH_3_23 | VL_2-14 | 5,1 | 3,2 | 5,2 | 5,1 | 2 | 2 | 1375 |
| 63 | VH_3_23 | VL_2-23 | 5,1 | 2,3 | 5,2 | 6,2 | 1 | 2 | 1325 |
| 64 | VH_3_23 | VL_3-1 | 5,2 | 6 | 5,3 | 5,9 | 1 | 2 | 1750 |

Figure 23

| No. | VH | VL | Tm before Acid | Tm after Acid | Change | Absorption Initial | Absorption 15 min Acid | Absorption 100 min Acid | Absorption neutralization |
|---|---|---|---|---|---|---|---|---|---|
| 65 | VH_3_23 | VL_3-21 | 79 | 79,2 | -0,2 | 0,036 | 0,041 | 0,038 | 0,037 |
| 66 | VH_3_30 | VK_3_15 | 81,1 | 81,2 | -0,1 | 0,037 | 0,039 | 0,038 | 0,037 |
| 67 | VH_3_30 | VK_3_20 | 80,9 | 81,2 | -0,3 | 0,037 | 0,043 | 0,043 | 0,044 |
| 68 | VH_3_30 | VL_2-23 | 80 | 80 | 0 | 0,036 | 0,041 | 0,039 | 0,037 |
| 69 | VH_3_30 | VL_3-1 | 79,7 | 79,6 | 0,1 | 0,039 | 0,046 | 0,049 | 0,054 |
| 70 | VH_3_30 | VL_3-21 | 78 | 78,2 | -0,2 | 0,039 | 0,043 | 0,042 | 0,041 |
| 71 | VH_3_53 | VK_1_39 | 73,8 | 74,5 | -0,7 | 0,042 | 0,047 | 0,045 | 0,044 |
| 72 | VH_3_53 | VK_3_15 | 73,6 | 74,1 | -0,5 | 0,037 | 0,041 | 0,039 | 0,038 |
| 73 | VH_3_53 | VL_2-11 | 73,6 | 73,8 | -0,2 | 0,036 | 0,038 | 0,043 | 0,037 |
| 74 | VH_3_53 | VL_2-23 | 69,6 | 69,6 | 0 | 0,036 | 0,042 | 0,039 | 0,037 |
| 75 | VH_3_53 | VL_3-1 | 72,6 | 73 | -0,4 | 0,036 | 0,043 | 0,038 | 0,039 |
| 76 | VH_3_74 | VK_1_05 | 75 | 75,6 | -0,6 | 0,036 | 0,043 | 0,039 | 0,04 |
| 77 | VH_3_74 | VK_1_06 | 77,8 | 77,9 | -0,1 | 0,037 | 0,039 | 0,038 | 0,037 |
| 78 | VH_3_74 | VK_1_12 | 79 | 79,8 | -0,8 | 0,038 | 0,04 | 0,039 | 0,038 |
| 79 | VH_3_74 | VK_1_27 | 78 | 78,3 | -0,3 | 0,037 | 0,049 | 0,041 | 0,038 |
| 80 | VH_3_74 | VK_3_20 | 80,3 | 80 | 0,3 | 0,036 | 0,039 | 0,038 | 0,037 |
| 81 | VH_3_74 | VL_1-51 | 80,7 | 80,5 | 0,2 | 0,036 | 0,041 | 0,038 | 0,038 |
| 82 | VH_3_74 | VL_3-1 | 78,8 | 78,6 | 0,2 | 0,039 | 0,045 | 0,043 | 0,04 |
| 83 | VH_3_74 | VK_1_39 | 73 | 73,6 | -0,6 | 0,037 | 0,04 | 0,039 | 0,041 |
| 84 | VH_5_51 | VL_1-40 | 77,6 | 77,8 | -0,2 | 0,036 | 0,041 | 0,038 | 0,038 |
| 85 | VH_5_51 | VL_1-47 | 76,4 | 76,7 | -0,3 | 0,035 | 0,04 | 0,04 | 0,037 |
| 86 | VH_5_51 | VL_1-51 | 75,7 | 75,6 | 0,1 | 0,036 | 0,047 | 0,042 | 0,04 |
| 87 | VH_5_51 | VL_3-1 | | 75,5 | | 0,037 | 0,038 | 0,037 | 0,04 |
| 88 | VH_6_1 | VK_1_06 | 73,6 | 73,3 | 0,3 | 0,038 | 0,04 | 0,04 | 0,037 |
| 89 | VH_6_1 | VK_1_09 | 80 | 80,3 | -0,3 | 0,037 | 0,04 | 0,039 | 0,039 |
| 90 | VH_6_1 | VK_1_27 | 80,2 | 80,4 | -0,2 | 0,04 | 0,046 | 0,045 | 0,042 |
| 91 | VH_6_1 | VK_3_15 | | 78,1 | | 0,036 | 0,038 | 0,038 | 0,038 |
| 92 | VH_6_1 | VK_3_20 | 77,2 | 77,4 | -0,2 | 0,036 | 0,038 | 0,038 | 0,038 |
| 93 | VH_6_1 | VL_1-47 | 73,6 | 73,8 | -0,2 | 0,046 | 0,081 | 0,078 | 0,094 |
| 94 | VH_6_1 | VL_1-51 | 76,6 | 76,6 | 0 | 0,036 | 0,039 | 0,037 | 0,038 |
| 95 | VH_6_1 | VL_3-1 | 69,4 | 69,9 | -0,5 | 0,047 | 0,075 | 0,072 | 0,113 |

Figure 24

| No. | VH | VL | Initial Radius [nm] | Initial % Poly-dispersity | Radius [nm] After acid | % Poly-dispersity After acid | Particle Staining before acid | Particle Staining after acid | Cumulative score |
|---|---|---|---|---|---|---|---|---|---|
| 65 | VH_3_23 | VL_3-21 | 5,4 | 6,2 | 5,4 | 5,7 | 2 | 1 | 1700 |
| 66 | VH_3_30 | VK_3_15 | 5,1 | 2,3 | 5,2 | 5,8 | 2 | 2 | 1575 |
| 67 | VH_3_30 | VK_3_20 | 5,3 | 5,9 | 5,3 | 7,7 | 2 | 2,5 | 1275 |
| 68 | VH_3_30 | VL_2-23 | 5,2 | 2,9 | 5,4 | 9 | 2 | 1 | 1725 |
| 69 | VH_3_30 | VL_3-1 | 13,9 | mm | 12 | mm | 2 | 2 | 525 |
| 70 | VH_3_30 | VL_3-21 | 5,1 | 2,8 | 5,2 | 4,6 | 2 | 2 | 1600 |
| 71 | VH_3_53 | VK_1_39 | 5,2 | 3,6 | 5,4 | 9,3 | 2 | 2 | 1375 |
| 72 | VH_3_53 | VK_3_15 | 5,2 | 4,2 | 5,2 | 6,3 | 1 | 1 | 1275 |
| 73 | VH_3_53 | VL_2-11 | 5,1 | 2,8 | 5,1 | 5,3 | 2 | 1 | 1275 |
| 74 | VH_3_53 | VL_2-23 | 5,1 | 2,4 | 5,3 | 6,2 | 2 | 1 | 1250 |
| 75 | VH_3_53 | VL_3-1 | 5,4 | 7 | 6,1 | 26,6 | 3 | 2,5 | 1475 |
| 76 | VH_3_74 | VK_1_05 | 5,1 | 2,2 | 5,2 | 5,7 | 2 | 1 | 1450 |
| 77 | VH_3_74 | VK_1_06 | 5,1 | 2 | 5,2 | 5,4 | 2,5 | 2 | 1725 |
| 78 | VH_3_74 | VK_1_12 | 5,1 | 2,1 | 5,3 | 6,7 | 2 | 1 | 1650 |
| 79 | VH_3_74 | VK_1_27 | 5,2 | 3,6 | 5,3 | 5,8 | 2 | 2 | 1525 |
| 80 | VH_3_74 | VK_3_20 | 5,1 | 2,4 | 5,6 | 18,9 | 2,5 | 2 | 1525 |
| 81 | VH_3_74 | VL_1-51 | 5,1 | 4,9 | 5,2 | 6,6 | 2 | 2 | 1325 |
| 82 | VH_3_74 | VL_3-1 | 5,3 | 3,2 | 5,5 | 8,6 | 2 | 2 | 1650 |
| 83 | VH_5_51 | VK_1_39 | 5,8 | 19,6 | 5,3 | 8,1 | 1,5 | 2 | 1650 |
| 84 | VH_5_51 | VL_1-40 | 5,5 | 13,6 | 5,3 | 6,7 | 2,5 | 2 | 1625 |
| 85 | VH_5_51 | VL_1-47 | 5,3 | 8 | 5,4 | 11,9 | 2 | 2 | 1575 |
| 86 | VH_5_51 | VL_1-51 | 5,1 | 2,7 | 5,2 | 6,2 | 1 | 2,5 | 1375 |
| 87 | VH_5_51 | VL_3-1 | 5,4 | 8,5 | 5,5 | 11,4 | 1,5 | 3 | 1300 |
| 88 | VH_6_1 | VK_1_06 | 5,2 | 2,5 | 5,2 | 4,2 | 2,5 | 1,5 | 1600 |
| 89 | VH_6_1 | VK_1_09 | 5,1 | 2,6 | 5,3 | 5,5 | 3 | 1 | 1450 |
| 90 | VH_6_1 | VK_1_27 | 5,3 | 4,3 | 5,5 | 8,4 | 2 | 1 | 1450 |
| 91 | VH_6_1 | VK_3_15 | 5,6 | 11,7 | 5,3 | 7,9 | 1 | 2 | 1075 |
| 92 | VH_6_1 | VK_3_20 | 5,2 | 5,1 | 5,2 | 5 | 2 | 2 | 1450 |
| 93 | VH_6_1 | VL_1-47 | 29,4 | mm | 100 | mm | 2,5 | 4 | 150 |
| 94 | VH_6_1 | VL_1-51 | 5 | 3,1 | 5,5 | 15,7 | 1 | 1 | 1725 |
| 95 | VH_6_1 | VL_3-1 | 30 | 33 | na | na | 2 | 4 | 375 |

Figure 25

Protein sequences — FRAMEWORK1 and HCDR1 (Kabat numbering)

| Kabat CDRs | FRAMEWORK1 | | | | | | | | | | | | | | | | | | | | | | | | | | | | | | HCDR1 | | | | | | |
|---|---|---|---|---|---|---|---|---|---|---|---|---|---|---|---|---|---|---|---|---|---|---|---|---|---|---|---|---|---|---|---|---|---|---|---|---|---|
| Kabat No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35a | 35b |
| VH1-18 | Q | V | Q | L | V | Q | S | G | A | E | V | K | K | P | G | A | S | V | K | V | S | C | K | A | S | G | Y | T | F | T | S | | | Y | G | I | S |
| VH1-46 | Q | V | Q | L | V | Q | S | G | A | E | V | K | K | P | G | A | S | V | K | V | S | C | K | A | S | G | Y | T | F | T | S | | | Y | Y | M | H |
| VH1-69*01 | Q | V | Q | L | V | Q | S | G | A | E | V | K | K | P | G | S | S | V | K | V | S | C | K | A | S | G | G | T | F | S | S | | | Y | A | I | S |
| VH3-07 | E | V | Q | L | V | E | S | G | G | G | L | V | Q | P | G | G | S | L | R | L | S | C | A | A | S | G | F | T | F | S | S | | | Y | W | M | S |
| VH3-11 | Q | V | Q | L | V | E | S | G | G | G | L | V | Q | P | G | G | S | L | R | L | S | C | A | A | S | G | F | T | F | S | S | | | Y | Y | M | S |
| VH3-15 | E | V | Q | L | V | E | S | G | G | G | V | V | Q | P | G | G | S | L | R | L | S | C | A | A | S | G | F | T | F | S | D | | | A | W | M | S |
| VH3-21 | E | V | Q | L | V | E | S | G | G | G | L | V | Q | P | G | G | S | L | R | L | S | C | A | A | S | G | F | T | F | S | N | | | Y | S | M | N |
| VH3-23 | E | V | Q | L | V | E | S | G | G | G | L | V | Q | P | G | R | S | L | R | L | S | C | A | A | S | G | F | T | F | S | S | | | Y | A | M | S |
| VH3-30 | Q | V | Q | L | V | E | S | G | G | G | V | V | Q | P | G | G | S | L | R | L | S | C | A | A | S | G | F | T | F | S | S | | | Y | A | M | H |
| VH3-53 | E | V | Q | L | V | E | S | G | G | G | L | I | Q | P | G | G | S | L | R | L | S | C | A | A | S | G | F | T | V | S | S | | . | Y | M | S |
| VH3-74 | E | V | Q | L | V | E | S | G | G | G | L | V | Q | P | G | G | S | L | R | L | S | C | A | A | S | G | F | T | F | S | S | | | Y | W | M | H |
| VH5-51 | E | V | Q | L | V | Q | S | G | A | E | V | K | K | P | G | E | S | L | K | I | S | C | K | G | S | G | Y | S | F | T | S | | | Y | W | I | G |
| VH6-01 | Q | V | Q | L | Q | Q | S | G | P | G | L | V | K | P | S | Q | T | L | S | L | T | C | A | I | S | G | D | S | V | S | S | N | S | A | A | W | N |

DNA sequences — FRAMEWORK1 and HCDR1 (Kabat numbering)

| Kabat No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35a | 35b |
|---|---|---|---|---|---|---|---|---|---|---|---|---|---|---|---|---|---|---|---|---|---|---|---|---|---|---|---|---|---|---|---|---|---|---|---|---|---|
| VH1-18 | CAG | GTG | CAG | CTG | GTG | CAG | AGC | GGT | GCC | GAA | GTG | AAA | AAA | CCA | GGC | GCC | AGC | GTG | AAA | GTT | AGC | TGC | AAA | GCC | AGC | GGC | TAT | ACC | TTT | ACC | AGC | | | TAT | GGC | ATT | AGC |
| VH1-46 | CAG | GTG | CAG | CTG | GTG | CAG | AGC | GGT | GCC | GAA | GTG | AAA | AAA | CCA | GGC | GCC | AGC | GTG | AAA | GTT | AGC | TGC | AAA | GCC | AGC | GGC | TAC | ACC | TTC | ACC | AGC | | | TAC | TAT | ATG | CAT |
| VH1-69*01 | CAG | GTG | CAG | CTG | GTG | CAG | AGC | GGT | GCC | GAA | GTG | AAA | AAA | CCA | GGC | AGT | AGC | GTG | AAA | GTG | AGC | TGC | AAA | GCC | AGC | GGC | GGT | ACC | TTT | AGC | AGC | | | TAT | GCC | ATT | AGC |
| VH3-07 | GAA | GTG | CAG | CTG | GTG | GAA | AGC | GGC | GGT | GGC | CTG | GTG | CAG | CCA | GGT | GGT | AGC | CTG | CGC | CTG | AGC | TGC | GCC | GCC | AGC | GGC | TTT | ACC | TTT | AGC | AGC | | | TAT | TGG | ATG | AGC |
| VH3-11 | GAA | GTG | CAG | CTG | GTG | GAA | AGC | GGC | GGT | GGC | CTG | GTG | CAG | CCA | GGT | GGT | AGC | CTG | CGC | CTG | AGC | TGC | GCC | GCC | AGC | GGC | TTT | ACC | TTT | AGC | AGC | | | TAC | TAC | ATG | AGC |
| VH3-15 | GAA | GTG | CAG | CTG | GTG | GAA | AGC | GGC | GGT | GGC | GTT | GTG | CAG | CCA | GGT | GGT | AGC | CTG | CGC | CTG | AGC | TGC | GCC | GCC | AGC | GGC | TTT | ACC | TTT | AGC | GAT | | | GCC | TGG | ATG | AGC |
| VH3-21 | GAA | GTG | CAG | CTG | GTG | GAA | AGC | GGC | GGT | GGC | CTG | GTG | CAG | CCA | GGT | GGT | AGC | CTG | CGC | CTG | AGC | TGC | GCC | GCC | AGC | GGC | TTT | ACC | TTT | AGC | AAC | | | TAT | AGC | ATG | AAC |
| VH3-23 | GAA | GTG | CAG | CTG | GTG | GAA | AGC | GGC | GGT | GGC | CTG | GTG | CAG | CCA | GGT | CGC | AGC | CTG | CGC | CTG | AGC | TGT | GCC | GCC | AGC | GGC | TTT | ACC | TTT | AGC | AGC | | | TAT | GCC | ATG | AGC |
| VH3-30 | CAG | GTG | CAG | CTG | GTG | GAA | AGC | GGC | GGT | GGC | GTT | GTG | CAG | CCA | GGT | GGT | AGC | CTG | CGC | CTG | AGC | TGT | GCC | GCC | AGC | GGC | TTT | ACC | TTT | AGC | AGC | | | TAT | GCC | ATG | CAT |
| VH3-53 | GAA | GTG | CAG | CTG | GTG | GAA | AGC | GGC | GGT | GGC | CTG | ATT | CAG | CCA | GGC | GGC | AGT | CTG | CGC | CTG | AGC | TGT | GCC | GCC | AGC | GGC | TTT | ACC | GTT | AGC | AGC | | | AAC | TAT | ATG | AGC |
| VH3-74 | GAA | GTG | CAG | CTG | GTG | GAA | AGC | GGC | GGT | GGC | CTG | GTG | CAG | CCG | GGC | GGC | AGC | CTG | CGC | CTG | AGC | TGC | GCC | GCC | AGC | GGC | TTT | ACC | TTT | ACC | AGC | | | TAT | TGG | ATG | CAT |
| VH5-51 | GAA | GTG | CAG | CTG | GTG | CAG | AGC | GGT | GCC | GAA | GTG | AAA | AAA | CCA | GGC | GAA | AGC | CTG | AAA | ATC | AGC | TGC | AAA | GGC | AGC | GGC | TAT | AGC | TTT | ACC | AGC | | | TAT | TGG | ATT | GGC |
| VH6-01 | CAG | GTG | CAG | CTG | CAA | CAG | AGC | GGC | CCA | GGC | CTG | GTT | AAA | CCG | AGC | CAG | ACC | CTG | AGC | CTG | ACC | TGC | GCC | ATT | AGC | GGC | GAT | AGC | GTT | AGC | AGC | AAC | AGC | GCC | GCC | TGG | AAC |

Figure 26

| Kabat CDRs | FRAMEWORK2 | | | | | | | | | | | | | HCDR2 | | | | | | | | | | | | | | | |
|---|---|---|---|---|---|---|---|---|---|---|---|---|---|---|---|---|---|---|---|---|---|---|---|---|---|---|---|---|---|
| Kabat No. | 36 | 37 | 38 | 39 | 40 | 41 | 42 | 43 | 44 | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 | 65 |
| VH1-18 | W | V | R | Q | A | P | G | Q | G | L | E | W | M | G | W | I | S | A | | | Y | N | G | N | T | N | Y | A | Q | K | L | Q | G |
| VH1-46 | W | V | R | Q | A | P | G | Q | G | L | E | W | M | G | I | I | N | P | | | S | G | G | S | T | S | Y | A | Q | K | F | Q | G |
| VH1-69*01 | W | V | R | Q | A | P | G | Q | G | L | E | W | M | G | G | I | I | P | | | I | F | G | T | A | S | Y | A | Q | K | F | Q | G |
| VH3-07 | W | V | R | Q | A | P | G | K | G | L | E | W | V | G | N | I | — | P | | | D | G | S | T | K | Y | Y | V | D | S | V | K | G |
| VH3-11 | W | V | R | Q | A | P | G | K | G | L | E | W | V | A | Y | I | K | Q | K | T | S | G | S | E | — | N | Y | A | D | S | V | K | G |
| VH3-15 | W | I | R | Q | A | P | G | K | G | L | E | W | V | S | Y | I | — | S | | | D | G | S | T | T | D | Y | A | A | P | V | V | G |
| VH3-21 | W | V | R | Q | A | P | G | K | G | L | E | W | V | S | R | I | K | S | | | D | S | G | T | T | Y | Y | A | D | S | V | K | G |
| VH3-23 | W | V | R | Q | A | P | G | K | G | L | E | W | V | S | S | I | S | S | | | S | S | G | S | T | Y | Y | A | D | S | V | K | G |
| VH3-30 | W | V | R | Q | A | P | G | K | G | L | E | W | V | A | A | I | S | G | | | S | G | G | S | T | S | Y | A | D | S | V | K | G |
| VH3-53 | W | V | R | Q | A | P | G | K | G | L | E | W | V | S | V | I | S | Y | | | D | G | S | N | K | Y | Y | A | D | S | V | K | G |
| VH3-74 | W | V | R | Q | A | P | G | K | G | L | V | W | V | S | R | I | N | S | | . | D | G | S | S | T | S | Y | A | D | S | V | K | G |
| VH5-51 | W | V | R | Q | M | P | G | K | G | L | E | W | M | G | R | I | — | P | | | G | D | S | D | T | R | Y | S | P | S | F | Q | G |
| VH6-01 | W | I | R | Q | S | P | S | R | G | L | E | W | L | G | R | T | Y | Y | R | | S | K | W | Y | N | D | Y | A | V | S | V | K | S |

| Kabat No. | 36 | 37 | 38 | 39 | 40 | 41 | 42 | 43 | 44 | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|---|---|---|---|---|---|---|---|---|---|---|---|
| VH1-18 | TGG | GTT | CGC | CAG | GCC | CCA | GGC | CAG | GGT | CTG | GAA | TGG | ATG | GGC | TGG | ATT | AGC | GCC | | | TAT | AAC | GGC | AAC | ACC | AAC | TAC | GCC | CAG | AAA | CTG | CAA | GGC |
| VH1-46 | TGG | GTT | CGC | CAG | GCC | CCA | GGC | CAG | GGT | CTG | GAA | TGG | ATG | GGC | ATT | ATT | AAC | CCG | | | AGC | GGC | GGC | AGC | ACC | AGC | TAT | GCA | CAG | AAA | TTT | CAG | GGC |
| VH1-69*01 | TGG | GTT | CGC | CAG | GCA | CCA | GGT | CAG | GGT | CTG | GAA | TGG | ATG | GGC | GGT | ATT | ATT | CCG | | | ATT | TTT | GGC | ACC | GCC | AGC | TAT | GCC | CAG | AAA | TTT | CAG | GGT |
| VH3-07 | TGG | GTT | CGC | CAG | GCC | CCA | GGC | AAA | GGC | CTG | GAA | TGG | GTG | GGC | AAC | ATC | — | CCG | | | GAT | GGC | AGC | ACC | AAA | TAC | TAT | GTG | GAT | AGC | GTG | AAA | GGC |
| VH3-11 | TGG | GTT | CGC | CAG | GCC | CCA | GGC | AAA | GGC | CTG | GAA | TGG | GTG | GCC | TAT | ATT | AAA | CAG | AAA | ACC | AGT | GGC | AGC | GAG | — | AAC | TAC | GCC | GAT | AGC | GTG | AAA | GGC |
| VH3-15 | TGG | ATT | CGC | CAG | GCC | CCA | GGC | AAA | GGC | CTG | GAA | TGG | GTG | AGC | TAT | ATT | AGC | AGC | | | GAT | GGC | AGC | ACC | ATC | GAT | TAT | GCC | GCC | CCA | GTG | AAA | GGC |
| VH3-21 | TGG | GTT | CGC | CAG | GCC | CCA | GGC | AAA | GGC | CTG | GAA | TGG | GTG | AGC | CGC | ATC | AGC | AGC | | | AGT | GGC | AGC | ACC | ACC | TAT | TAT | GCC | GAT | AGC | GTG | AAA | GGC |
| VH3-23 | TGG | GTT | CGC | CAG | GCC | CCA | GGC | AAA | GGC | CTG | GAA | TGG | GTG | AGC | AGC | ATT | AGC | AGC | | | AGC | GGT | GGC | AGC | ACC | TAT | TAT | GCC | GAT | AGC | GTG | AAA | GGC |
| VH3-30 | TGG | GTT | CGC | CAG | GCC | CCA | GGC | AAA | GGC | CTG | GAA | TGG | GTG | GCC | GCC | ATC | AGC | GGC | | | GCC | GGC | AGC | AAC | AAA | TAT | TAT | GCC | GAT | AGC | GTG | AAA | GGT |
| VH3-53 | TGG | GTT | CGC | CAG | GCC | CCA | GGC | AAA | GGC | CTG | GAA | TGG | GTG | AGC | GTG | ATT | AGC | TAT | | | GAT | GGC | AGC | AAC | AAA | TAT | TAT | GCC | GAT | AGC | GTG | AAA | GGC |
| VH3-74 | TGG | GTT | CGC | CAG | GCC | CCA | GGC | AAA | GGC | CTG | GTT | TGG | GTT | AGC | CGC | ATT | AAC | AGC | | | GAC | GGC | AGC | AGC | ACC | AGC | TAT | GCC | GAT | AGC | GTG | AAA | GGC |
| VH5-51 | TGG | GTT | CGC | CAG | ATG | CCG | GGC | AAA | GGC | CTG | GAA | TGG | ATG | GGC | CGC | ATT | TAT | CCG | | | GGC | GAT | AGC | GAT | ACC | CGC | TAT | AGC | CCG | AGC | TTT | CAG | GGC |
| VH6-01 | TGG | ATT | CGC | CAG | AGC | CCG | AGC | CGC | GGT | CTG | GAA | TGG | CTG | GGC | CGC | ACC | TAT | TAT | CGC | | AGC | AAA | TGG | TAC | AAC | GAT | TAC | GCC | GTT | AGC | GTG | AAA | AGC |

Figure 27

FRAMEWORK3

| Kabat CDRs | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Kabat No. | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
| VH1-18 | R | V | T | M | T | T | D | T | S | T | S | T | A | Y | M | E | L | R | S | L | R | S | D | D | T | A | V | Y | Y | C | A | R |
| VH1-46 | R | V | T | M | T | R | D | T | S | T | S | T | V | Y | M | E | L | S | S | L | R | S | E | D | T | A | V | Y | Y | C | A | R |
| VH1-69*01 | R | V | T | I | T | A | D | E | S | T | S | T | A | Y | M | E | L | S | S | L | R | S | E | D | T | A | V | Y | Y | C | A | R |
| VH3-07 | R | F | T | I | S | R | D | N | A | K | N | S | L | Y | L | Q | M | N | S | L | R | A | E | D | T | A | V | Y | Y | C | A | R |
| VH3-11 | R | F | T | I | S | R | D | N | A | K | N | S | L | Y | L | Q | M | N | S | L | R | A | E | D | T | A | V | Y | Y | C | A | R |
| VH3-15 | R | F | T | I | S | R | D | D | S | K | N | T | L | Y | L | Q | M | N | S | L | K | T | E | D | T | A | V | Y | Y | C | A | R |
| VH3-21 | R | F | T | I | S | R | D | N | A | K | N | S | L | Y | L | Q | M | N | S | L | R | A | E | D | T | A | V | Y | Y | C | A | R |
| VH3-23 | R | F | T | I | S | R | D | N | S | K | N | T | L | Y | L | Q | M | N | S | L | R | A | E | D | T | A | V | Y | Y | C | A | R |
| VH3-30 | R | F | T | I | S | R | D | N | S | K | N | T | L | Y | L | Q | M | N | S | L | R | A | E | D | T | A | V | Y | Y | C | A | R |
| VH3-53 | R | F | T | I | S | R | D | N | A | K | N | S | L | Y | L | Q | M | N | S | L | R | A | E | D | T | A | V | Y | Y | C | A | R |
| VH3-74 | R | F | T | I | S | R | D | N | A | K | N | S | L | Y | L | A | M | N | S | L | R | A | E | D | T | A | M | Y | Y | C | A | R |
| VH5-51 | Q | V | T | I | | A | D | K | S | I | S | Q | F | S | L | Q | W | S | S | L | K | P | S | D | T | A | V | Y | Y | C | A | R |
| VH6-01 | R | I | T | I | N | P | D | T | S | K | N | Q | F | S | L | Q | L | N | S | V | T | P | E | D | T | A | V | Y | Y | C | A | R |

| Kabat No. | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| VH1-18 | CG | GTG | ACC | ATG | ACC | ACC | GAT | ACC | AGC | ACC | AGC | ACC | GCC | TAT | ATG | GAA | CTG | CGC | TCC | CTG | CGC | AGC | GAC | GAT | ACC | GCC | GTG | TAT | TAT | TGC | GCG | CGT |
| VH1-46 | CG | CGTG | ACC | ATG | ACC | CGC | GAT | ACC | AGC | ACC | AGC | ACC | GTG | TAT | ATG | GAA | CTG | AGC | AGC | CTG | CGC | AGC | GAA | GAT | ACC | GCC | GTG | TAT | TAT | TGC | GCG | CGT |
| VH1-69*01 | CG | CGTG | ACC | ATT | ACC | GCA | GAT | GAA | AGC | ACC | AGC | ACC | GCC | TAT | ATG | GAA | CTG | AGC | AGC | CTG | CGC | AGC | GAA | GAT | ACC | GCA | GTG | TAT | TAT | TGC | GCG | CGG |
| VH3-07 | CG | CTTT | ACC | ATT | AGC | CGC | GAT | AAC | GCC | AAA | AAC | AGC | CTG | TAT | CTG | CAA | ATG | AAC | AGC | CTG | CGG | GCC | GAA | GAT | ACC | GCC | GTG | TAT | TAT | TGC | GCG | CGT |
| VH3-11 | CG | CTTT | ACC | ATT | AGC | CGC | GAT | AAC | GCC | AAA | AAC | AGC | CTG | TAT | CTG | CAA | ATG | AAC | AGC | CTG | CGG | GCC | GAA | GAT | ACC | GCC | GTG | TAT | TAT | TGC | GCG | CGT |
| VH3-15 | CG | CTTT | ACC | ATT | AGC | CGC | GAT | GAT | AGC | AAA | AAC | ACC | CTG | TAC | CTG | CAA | ATG | AAC | AGC | CTG | AAA | ACC | GAA | GAT | ACC | GCC | GTG | TAT | TAT | TGC | GCG | CGG |
| VH3-21 | CG | CTTT | ACC | ATT | AGC | CGC | GAT | AAC | AGC | AAA | AAC | ACC | CTG | TAT | CTG | CAA | ATG | AAC | AGC | CTG | CGG | GCC | GAA | GAT | ACC | GCC | GTG | TAT | TAT | TGC | GCG | CGT |
| VH3-23 | CG | CTTT | ACC | ATT | AGT | CGC | GAT | AAC | AGC | AAA | AAC | ACC | CTG | TAT | CTG | CAA | ATG | AAC | AGC | CTG | CGG | GCA | GAA | GAT | ACC | GCA | GTT | TAT | TAT | TGC | GCG | CGG |
| VH3-30 | CG | CTTT | ACC | ATT | AGC | CGC | GAT | AAC | AGC | AAA | AAC | ACC | CTG | TAT | CTG | CAA | ATG | AAC | AGC | CTG | CGG | GCC | GAA | GAT | ACC | GCC | GTG | TAT | TAT | TGC | GCG | CGT |
| VH3-53 | CG | CTTT | ACC | ATT | AGC | CGC | GAT | AAC | GCC | AAA | AAC | ACC | CTG | TAT | CTG | CAA | ATG | AAC | AGC | CTG | CGG | GCC | GAA | GAT | ACC | GCC | GTG | TAT | TAT | TGC | GCG | CGT |
| VH3-74 | CG | CTTT | ACC | ATT | AGC | CGC | GAT | AAC | GCC | AAA | AAC | ACC | CTG | TAT | CTG | CAA | TGG | AGC | AGC | CTG | AAA | GCC | AGC | GAT | ACC | GCC | ATG | TAT | TAT | TGC | GCG | CGT |
| VH5-51 | CA | GGTT | ACA | ATT | AGC | GCC | GAC | AAA | AGC | ATC | AGC | CAG | TTC | AGC | CTG | CAA | CTG | AGC | AGC | GTG | ACC | CCG | AGC | GAT | ACC | GCC | GTG | ATG | TAT | TGC | GCG | CGT |
| VH6-01 | CG | CATT | ACC | ATT | AAC | CCG | GAT | ACC | AGC | AAA | AAC | CAG | TTC | AGC | CTG | CAA | CTG | AAC | AGC | GTG | ACC | CCG | GAA | GAT | ACC | GCC | GTG | TAC | TAT | TGC | GCG | CGT |

Figure 28

| Kabat CDRs | FRAMEWORK1 | | | | | | | | | | | | | | | | | | | | | | | | | LCDR1 | | | | | | | | |
|---|---|---|---|---|---|---|---|---|---|---|---|---|---|---|---|---|---|---|---|---|---|---|---|---|---|---|---|---|---|---|---|---|---|---|
| Kabat No | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 27f | 28 | 29 | 30 | 31 | 32 | 33 | 34 |
| VK1-05 | D | I | Q | M | T | Q | S | P | S | T | L | S | A | S | V | G | D | R | V | T | I | T | C | R | A | S | Q | S | I | S | . | . | . | . | . | . | S | W | L | A |
| VK1-06 | A | I | Q | M | T | Q | S | P | S | S | L | S | A | S | V | G | D | R | V | T | I | T | C | R | A | S | Q | G | I | R | . | . | . | . | . | . | N | D | L | G |
| VK1-09 | D | I | Q | L | T | Q | S | P | S | F | L | S | A | S | V | G | D | R | V | T | I | T | C | R | A | S | Q | G | I | S | . | . | . | . | . | . | S | Y | L | A |
| VK1-12 | D | I | Q | M | T | Q | S | P | S | S | V | S | A | S | V | G | D | R | V | T | I | T | C | R | A | S | Q | G | I | S | . | . | . | . | . | . | S | W | L | A |
| VK1-16 | D | I | Q | M | T | Q | S | P | S | S | L | S | A | S | V | G | D | R | V | T | I | T | C | R | A | S | Q | G | I | S | . | . | . | . | . | . | N | Y | L | A |
| VK1-27 | D | I | Q | M | T | Q | S | P | S | S | L | S | A | S | V | G | D | R | V | T | I | T | C | R | A | S | Q | S | I | S | . | . | . | . | . | . | N | Y | L | A |
| VK1-39 | D | I | Q | M | T | Q | S | P | S | S | L | S | A | S | V | G | D | R | V | T | I | T | C | R | A | S | Q | S | I | S | . | . | . | . | . | . | S | Y | L | N |
| VK3-11 | E | I | V | L | T | Q | S | P | A | T | L | S | L | S | P | G | E | R | A | T | L | S | C | R | A | S | Q | S | V | S | . | . | . | . | . | . | S | Y | L | A |
| VK3-15 | E | I | V | M | T | Q | S | P | A | T | L | S | V | S | P | G | E | R | A | T | L | S | C | R | A | S | Q | S | V | S | . | . | . | . | . | . | S | N | L | A |
| VK3-20 | E | I | V | L | T | Q | S | P | G | T | L | S | L | S | P | G | E | R | A | T | L | S | C | R | A | S | Q | S | V | S | S | . | . | . | . | . | S | Y | L | A |

| Kabat No | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 27f | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|---|---|---|---|---|---|
| VK1-05 | GAT | ATT | CAG | ATG | ACC | CAG | AGC | CC.G | AGC | ACC | CTG | AGC | GCA | AGC | GTG | GGC | GAT | CGC | GTG | ACC | ATT | AC.C | TGC | CGC | GCC | AGT | CAG | AGC | ATT | AGC | | | | | | | AGC | TGG | CTG | GCC |
| VK1-06 | GCC | ATT | CAG | ATG | ACC | CAG | AGC | CC.G | AGC | AGC | CTG | AGC | GCA | AGC | GTG | GGC | GAT | CGC | GTG | ACC | ATT | AC.C | TGC | CGG | GCC | AGC | CAG | GGC | ATT | CGC | | | | | | | AAC | GAT | CTG | GGG |
| VK1-09 | GAT | ATT | CAG | CTG | ACC | CAG | AGC | CC.G | AGC | TTT | CTG | AGC | GCC | AGC | GTG | GGC | GAT | CGC | GTG | ACC | ATT | AC.C | TGC | CGG | GCC | AGC | CAG | GGC | ATT | CGC | | | | | | | AGC | TAT | CTG | GCC |
| VK1-12 | GAT | ATT | CAG | ATG | ACC | CAG | AGC | CC.G | AGC | AGC | GTT | AGC | GCC | AGC | GTG | GGC | GAT | CGC | GTG | ACC | ATT | AC.C | TGC | CGC | GCC | AGT | CAG | GGC | ATT | AGC | | | | | | | AGC | TGG | CTG | GCC |
| VK1-16 | GAT | ATT | CAG | ATG | ACC | CAG | AGC | CC.G | AGC | AGC | CTG | AGC | GCC | AGC | GTG | GGC | GAT | CGC | GTG | ACC | ATT | AC.C | TGC | CGG | GCC | AGC | CAG | GGC | ATT | AGC | | | | | | | AAC | TAT | CTG | GCC |
| VK1-27 | GAT | ATT | CAG | ATG | ACC | CAG | AGC | CC.G | AGC | AGC | CTG | AGC | GCA | AGC | GTG | GGT | GAT | CGC | GTG | ACC | ATT | AC.C | TGC | CGG | GCC | AGC | CAG | AGC | ATT | AGC | | | | | | | AAC | TAT | CTG | AAC |
| VK1-39 | GAT | ATT | CAG | ATG | ACC | CAG | AGC | CC.A | AGC | AGC | CTG | AGC | GCC | AGC | GTG | GGT | GAT | CGC | GTG | ACC | ATT | AC.C | TGC | CGC | GCC | AGC | CAG | AGC | ATT | AGC | | | | | | | AGC | TAT | CTG | GCC |
| VK3-11 | GAA | ATT | GTG | CTG | ACC | CAG | AGC | CC.G | GCC | ACC | CTG | AGC | CTG | AGC | CCA | GGC | GAA | CGC | GCC | ACC | CTG | AGC | TGT | CGC | GCA | AGC | CAG | AGC | GTG | AGC | | | | | | | AGC | TAT | CTG | GCC |
| VK3-15 | GAA | ATT | GTG | ATG | ACC | CAG | AGC | CC.G | GCC | ACC | CTG | AGC | GTT | AGC | CCA | GGC | GAA | CGC | GCC | ACC | CTG | AGC | TGT | CGC | GCA | AGC | CAG | AGC | GTG | AGC | | | | | | | AGC | AAC | CTG | GCC |
| VK3-20 | GAA | ATT | GTG | CTG | ACC | CAG | AGC | CC.G | GGC | ACC | CTG | AGC | CTG | AGC | CCA | GGC | GAA | CGC | GCC | ACC | CTG | AGC | TGT | CGC | GCA | AGC | CAG | AGC | GTT | AGC | AGC | | | | | | AGC | TAT | CTG | GCC |

Figure 29

| Kabat CDRs | | | | FRAMEWORK2 | | | | | | | | | | | LCDR2 | | | | | | |
|---|---|---|---|---|---|---|---|---|---|---|---|---|---|---|---|---|---|---|---|---|---|
| Kabat No | 35 | 36 | 37 | 38 | 39 | 40 | 41 | 42 | 43 | 44 | 45 | 46 | 47 | 48 | 49 | 50 | 51 | 52 | 53 | 54 | 55 | 56 |
| VK1-05 | W | Y | Q | Q | K | P | G | K | A | P | K | L | L | I | Y | D | A | S | S | L | E | S |
| VK1-06 | W | Y | Q | Q | K | P | G | K | A | P | K | L | L | I | Y | A | A | S | S | L | Q | S |
| VK1-09 | W | Y | Q | Q | K | P | G | K | A | P | K | L | L | I | Y | A | A | S | T | L | Q | S |
| VK1-12 | W | Y | Q | Q | K | P | G | K | A | P | K | L | L | I | Y | A | A | S | S | L | Q | S |
| VK1-16 | W | F | Q | Q | K | P | G | K | A | P | K | S | L | I | Y | A | A | S | S | L | Q | S |
| VK1-27 | W | Y | Q | Q | K | P | G | K | V | P | K | L | L | I | Y | A | A | S | T | L | Q | S |
| VK1-39 | W | Y | Q | Q | K | P | G | K | A | P | K | L | L | I | Y | A | A | S | S | L | Q | S |
| VK3-11 | W | Y | Q | Q | K | P | G | Q | A | P | R | L | L | I | Y | D | A | S | N | R | A | T |
| VK3-15 | W | Y | Q | Q | K | P | G | Q | A | P | R | L | L | I | Y | G | A | S | T | R | A | T |
| VK3-20 | W | Y | Q | Q | K | P | G | Q | A | P | R | L | L | I | Y | G | A | S | S | R | A | T |

| Kabat No | 35 | 36 | 37 | 38 | 39 | 40 | 41 | 42 | 43 | 44 | 45 | 46 | 47 | 48 | 49 | 50 | 51 | 52 | 53 | 54 | 55 | 56 |
|---|---|---|---|---|---|---|---|---|---|---|---|---|---|---|---|---|---|---|---|---|---|---|
| VK1-05 | TGG | TAT | CAG | CAG | AAA | CCG | GGC | AAA | GCC | CCG | AAA | CTG | CTG | ATC | TAT | GAT | GCC | AGC | AGC | CTG | GAA | AGC |
| VK1-06 | TGG | TAT | CAG | CAG | AAA | CCG | GGC | AAA | GCC | CCG | AAA | CTG | CTG | ATC | TAT | GCC | GCC | AGC | AGC | CTG | CAA | AGC |
| VK1-09 | TGG | TAT | CAG | CAG | AAA | CCG | GGC | AAA | GCC | CCG | AAA | CTG | CTG | ATC | TAT | GCC | GCC | AGC | ACC | CTG | CAA | AGC |
| VK1-12 | TGG | TAT | CAG | CAG | AAA | CCG | GGC | AAA | GCC | CCG | AAA | CTG | CTG | ATC | TAT | GCC | GCC | AGC | AGC | CTG | CAA | AGC |
| VK1-16 | TGG | TTT | CAG | CAG | AAA | CCG | GGC | AAA | GCC | CCG | AAA | AGC | CTG | ATC | TAT | GCC | GCC | AGC | AGC | CTG | CAA | AGC |
| VK1-27 | TGG | TAT | CAG | CAG | AAA | CCG | GGC | AAA | GTG | CCG | AAA | CTG | CTG | ATC | TAT | GCC | GCC | AGC | AGT | CTG | CAA | AGC |
| VK1-39 | TGG | TAT | CAG | CAG | AAA | CCA | GGC | AAA | GCC | CCA | AAA | CTG | CTG | ATT | TAT | GCC | GCA | AGC | ACC | CTG | CAA | AGC |
| VK3-11 | TGG | TAT | CAA | CAG | AAA | CCA | GGC | CAG | GCA | CCA | CGC | CTG | CTG | ATT | TAT | GAT | GCC | AGC | AAT | CGC | GCA | ACC |
| VK3-15 | TGG | TAT | CAG | CAG | AAA | CCG | GGT | CAG | GCC | CCG | CGC | CTG | CTG | ATC | TAT | GGT | GCC | AGC | ACC | CGC | GCC | ACC |
| VK3-20 | TGG | TAT | CAG | CAG | AAA | CCG | GGC | CAG | GCC | CCA | CGC | CTG | CTG | ATC | TAT | GGT | GCC | AGC | AGC | CGC | GCC | ACC |

Figure 30

FRAMEWORK3

| Kabat CDRs | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| Kabat No | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
| VK1-05 | G | V | P | S | R | F | S | G | S | G | S | G | T | E | F | T | L | T | I | S | S | L | Q | P | E | D | F | A | T | Y | Y | C |
| VK1-06 | G | V | P | S | R | F | S | G | S | G | S | G | T | D | F | T | L | T | I | S | S | L | Q | P | E | D | F | A | T | Y | Y | C |
| VK1-09 | G | V | P | S | R | F | S | G | S | G | S | G | T | E | F | T | L | T | I | S | S | L | Q | P | E | D | F | A | T | Y | Y | C |
| VK1-12 | G | V | P | S | R | F | S | G | S | G | S | G | T | D | F | T | L | T | I | S | S | L | Q | P | E | D | F | A | T | Y | Y | C |
| VK1-16 | G | V | P | S | R | F | S | G | S | G | S | G | T | D | F | T | L | T | I | S | S | L | Q | P | E | D | V | A | T | Y | Y | C |
| VK1-27 | G | V | P | S | R | F | S | G | S | G | S | G | T | D | F | T | L | T | I | S | S | L | Q | P | E | D | F | A | T | Y | Y | C |
| VK1-39 | G | V | P | S | R | F | S | G | S | G | S | G | T | D | F | T | L | T | I | S | S | L | Q | P | E | D | F | A | T | Y | Y | C |
| VK3-11 | G | I | P | A | R | F | S | G | S | G | S | G | T | D | F | T | L | T | I | S | S | L | E | P | E | D | F | A | V | Y | Y | C |
| VK3-15 | G | I | P | A | R | F | S | G | S | G | S | G | T | E | F | T | L | T | I | S | S | L | Q | S | E | D | F | A | V | Y | Y | C |
| VK3-20 | G | I | P | D | R | F | S | G | S | G | S | G | T | D | F | T | L | T | I | S | R | L | E | P | E | D | F | A | V | Y | Y | C |

| Kabat No | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|
| VK1-05 | GGC | GTG | CCG | AGC | CGC | TTT | AGC | GGC | AGC | GGT | AGC | GGC | ACC | GAG | TTC | ACC | CTG | ACC | ATT | AGC | AGC | CTG | CAA | CCG | GAA | GAC | TTT | GCC | ACC | TAT | TAT | TGC |
| VK1-06 | GGC | GTG | CCA | AGT | CGC | TTT | AGC | GGC | AGC | GGT | AGC | GGC | ACC | GAT | TTC | ACC | CTG | ACC | ATT | AGC | AGT | CTG | CAA | CCG | GAA | GAC | TTT | GCC | ACC | TAT | TAT | TGC |
| VK1-09 | GGC | GTG | CCA | AGC | CGC | TTT | AGC | GGC | AGC | GGT | AGC | GGC | ACC | GAG | TTC | ACC | CTG | ACC | ATT | AGC | AGC | CTG | CAA | CCG | GAA | GAC | TTT | GCC | ACC | TAT | TAT | TGC |
| VK1-12 | GGC | GTG | CCA | AGT | CGC | TTT | AGC | GGC | AGC | GGT | AGC | GGC | ACC | GAT | TTC | ACC | CTG | ACC | ATT | AGC | AGT | CTG | CAA | CCG | GAA | GAC | TTT | GCC | ACC | TAT | TAT | TGC |
| VK1-16 | GGC | GTG | CCA | AGT | CGC | TTT | AGC | GGC | AGC | GGT | AGC | GGC | ACC | GAT | TTC | ACC | CTG | ACC | ATT | AGC | AGC | CTG | CAA | CCG | GAA | GAC | GTG | GCC | ACC | TAT | TAT | TGC |
| VK1-27 | GGC | GTG | CCA | AGT | CGC | TTT | AGC | GGC | AGC | GGT | AGC | GGC | ACC | GAT | TTC | ACC | CTG | ACC | ATT | AGC | AGC | CTG | CAA | CCG | GAA | GAC | TTT | GCC | ACC | TAT | TAT | TGC |
| VK1-39 | GGT | GTG | CCG | AGC | CGC | TTT | AGC | GGC | AGC | GGT | AGC | GGC | ACC | GAT | TTT | ACC | CTG | ACC | ATT | AGC | AGC | CTG | CAA | CCG | GAA | GAC | TTT | GCC | ACC | TAT | TAT | TGC |
| VK3-11 | GGC | ATT | CCG | GCA | CGC | TTT | AGC | GGC | AGC | GGT | AGC | GGC | ACC | GAT | TTT | ACC | CTG | ACC | ATT | AGT | AGC | CTG | GAA | CCG | GAA | GAC | TTT | GCC | GTG | TAT | TAT | TGC |
| VK3-15 | GGC | ATT | CCA | GCA | CGC | TTT | AGC | GGC | AGC | GGT | AGC | GGC | ACC | GAG | TTC | ACC | CTG | ACC | ATT | AGC | AGC | CTG | CAA | AGC | GAA | GAC | TTT | GCC | GTG | TAT | TAT | TGC |
| VK3-20 | GGC | ATT | CCA | GAT | CGC | TTT | AGC | GGC | AGC | GGT | AGC | GGC | ACC | GAT | TTC | ACC | CTG | ACC | ATT | AGC | CGC | CTG | GAA | CCG | GAA | GAC | TTT | GCC | GTG | TAT | TAT | TGC |

| Kabat CDRs | FRAMEWORK2 | | | | | | | | | | | | | | | LCDR2 | | | | | | |
|---|---|---|---|---|---|---|---|---|---|---|---|---|---|---|---|---|---|---|---|---|---|---|
| Kabat No. | 35 | 36 | 37 | 38 | 39 | 40 | 41 | 42 | 43 | 44 | 45 | 46 | 47 | 48 | 49 | 50 | 51 | 52 | 53 | 54 | 55 | 56 |
| VL1-40 | W | Y | Q | Q | L | P | G | T | A | P | K | L | L | I | Y | G | N | S | N | R | P | S |
| VL1-47 | W | Y | Q | Q | L | P | G | T | A | P | K | L | L | I | Y | R | N | N | Q | R | P | S |
| VL1-51 | W | Y | Q | Q | L | P | G | T | A | P | K | L | L | I | Y | D | N | N | K | R | P | S |
| VL2-11 | W | Y | Q | Q | H | P | G | K | A | P | K | L | M | I | Y | D | V | S | K | R | P | S |
| VL2-14 | W | Y | Q | Q | H | P | G | K | A | P | K | L | M | I | Y | E | V | S | N | R | P | S |
| VL2-23 | W | Y | Q | Q | H | P | G | K | A | P | K | L | M | I | Y | E | G | S | K | R | P | S |
| VL3-1  | W | Y | Q | Q | K | P | G | Q | S | P | V | L | V | I | Y | Q | D | S | K | R | P | S |
| VL3-21 | W | Y | Q | Q | K | P | G | Q | A | P | V | L | V | I | Y | Y | D | S | D | R | P | S |

| Kabat No. | 35 | 36 | 37 | 38 | 39 | 40 | 41 | 42 | 43 | 44 | 45 | 46 | 47 | 48 | 49 | 50 | 51 | 52 | 53 | 54 | 55 | 56 |
|---|---|---|---|---|---|---|---|---|---|---|---|---|---|---|---|---|---|---|---|---|---|---|
| VL1-40 | T GG | TAT | C AG | CAG | CTG | CCA | GGC | AC C | GCA | CC G | AAA | CTG | CTG | ATT | TAT | GGC | AAC | AGC | AAT | CGC | CCA | AGC |
| VL1-47 | T GG | TAT | C AG | CAG | CTG | CCG | GGC | AC C | GCC | CC G | AAA | CTG | CTG | ATC | TAT | CGC | AAC | AAC | CAG | CGC | CCG | AGC |
| VL1-51 | T GG | TAT | C AG | CAG | CTG | CCG | GGC | AC C | GCC | CC G | AAA | CTG | CTG | ATC | TAT | GAT | AAC | AAC | AAA | CGC | CCG | AGC |
| VL2-11 | T GG | TAT | C AG | CAG | CAT | CCG | GGC | AA A | GCC | CC G | AAA | CTG | ATG | ATC | TAT | GAT | GTT | AGC | AAA | CGC | CCG | AGC |
| VL2-14 | T GG | TAT | C AG | CAG | CAT | CCG | GGC | AA A | GCC | CC G | AAA | CTG | ATG | ATC | TAT | GAA | GTT | AGC | AAC | CGC | CCG | AGC |
| VL2-23 | T GG | TAT | C AG | CAG | CAT | CCG | GGC | AA A | GCC | CC G | AAA | CTG | ATG | ATC | TAT | GAA | GGC | AGC | AAA | CGC | CCG | AGC |
| VL3-1  | T GG | TAT | C AG | CAG | AAA | CCG | GGC | CA G | AGC | CC G | GTG | CTG | GTT | ATC | TAT | CAG | GAT | AGC | AAA | CGC | CCG | AGC |
| VL3-21 | T GG | TAT | C AG | CAG | AAA | CCG | GGC | CA G | GCC | CC G | GTG | CTG | GTT | ATC | TAT | TAT | GAT | AGC | GAT | CGC | CCG | AGC |

Figure 33

FRAMEWORK3

| Kabat No. | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|
| VL1-40 | G | V | P | D | R | F | S | G | S | K | S | G | T | S | A | S | L | A | I | | G | L | Q | A | E | D | E | A | D | Y | Y | C |
| VL1-47 | G | V | P | D | R | F | S | G | S | K | S | G | T | S | A | S | L | A | I | | G | L | R | S | E | D | E | A | D | Y | Y | C |
| VL1-51 | G | I | P | D | R | F | S | G | S | K | S | G | T | S | A | T | L | G | I | | T | L | Q | T | E | D | E | A | D | Y | Y | C |
| VL2-11 | G | V | P | D | R | F | S | G | S | K | S | G | N | T | A | S | L | T | I | S | G | L | Q | A | E | D | E | A | D | Y | Y | C |
| VL2-14 | G | V | S | N | R | F | S | G | S | K | S | G | N | T | A | S | L | T | I | S | G | L | Q | A | E | D | E | A | D | Y | Y | C |
| VL2-23 | G | V | S | N | R | F | S | G | S | K | S | G | N | T | A | S | L | T | I | S | G | L | Q | A | E | D | E | A | D | Y | Y | C |
| VL3-1 | G | I | P | E | R | F | S | G | S | N | S | G | N | T | A | T | L | T | I | S | R | T | Q | A | E | D | E | A | D | Y | Y | C |
| VL3-21 | G | I | P | E | R | F | S | G | S | N | S | G | N | T | A | T | L | T | I | S | G | V | E | A | E | D | E | A | D | Y | Y | C |

| Kabat No. | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|
| VL1-40 | GGT | GTG | CCG | GAT | CGC | TTT | AGC | GGC | AGC | AAA | AGC | GGC | ACC | AGC | GCC | AGC | CTG | GCG | ATT | | ACC | GGT | CAA | GCC | GAA | GAC | GAA | GCC | GAT | TAT | TAC | TGC |
| VL1-47 | GGC | GTG | CCA | GAT | CGC | TTT | AGC | GGT | AGC | AAA | AGC | GGG | ACC | AGC | GCA | AGC | CTG | GCG | ATT | | AGC | GGC | CGC | AGC | GAA | GAC | GAA | GCC | GAT | TAT | TAC | TGC |
| VL1-51 | GGC | ATC | CCG | GAT | CGC | TTT | AGC | GGC | AGC | AAA | AGC | GGG | ACC | AGC | GCC | ACC | CTG | GGC | ATT | | ACC | GGC | CAA | ACC | GAA | GAC | GAA | GCC | GAT | TAT | TAC | TGC |
| VL2-11 | GGC | GTG | CCG | GAT | CGC | TTT | AGC | GGT | AGC | AAA | AGC | GGC | AAC | ACC | GCC | AGC | CTG | ACC | ATC | AGC | GGC | CTG | CAA | GCC | GAA | GAC | GAA | GCC | GAT | TAT | TAC | TGC |
| VL2-14 | GGC | GTT | AGC | AAT | CGC | TTT | AGC | GGG | AGC | AAA | AGC | GGG | AAC | ACC | GCC | AGC | CTG | ACC | ATT | AGC | GGC | CTG | CAA | GCC | GAA | GAC | GAA | GCC | GAT | TAT | TAC | TGC |
| VL2-23 | GGC | GTT | AGT | AAC | CGC | TTT | AGT | GGC | AGC | AAA | AGC | GGG | AAC | ACC | GCC | AGC | CTG | ACC | ATT | AGC | GGC | CTG | CAA | GCC | GAA | GAC | GAA | GCC | GAT | TAT | TAC | TGC |
| VL3-1 | GGC | ATT | CCA | GAA | CGC | TTT | AGC | GGC | AGC | AAC | AGC | GGG | AAC | ACC | GCC | ACC | CTG | ACC | ATT | AGC | CGC | ACC | CAG | GCC | GAA | GAC | GAA | GCC | GAT | TAT | TAC | TGC |
| VL3-21 | GGC | ATT | CCA | GAA | CGC | TTT | AGC | GGC | AGC | AAC | AGC | GGG | AAC | ACC | GCC | ACC | CTG | ACC | ATT | AGC | CGC | GTG | GAA | GCC | GAA | GAC | GAA | GCC | GAT | TAT | TAC | TGC |

Figure 34 Low Post Translational Modification VHs

Amino Acid Sequences

| Kabat CDRs | FRAMEWORK1 | | | | | | | | | | | | | | | | | | | | | | | | | | | | | | HCDR1 | | | | | | |
|---|---|---|---|---|---|---|---|---|---|---|---|---|---|---|---|---|---|---|---|---|---|---|---|---|---|---|---|---|---|---|---|---|---|---|---|---|---|
| Kabat No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35a | 35b |
| VH1-18 | Q | V | Q | L | V | Q | S | G | A | E | V | K | K | P | G | A | S | V | K | V | S | C | K | A | S | G | Y | T | F | T | S | | | Y | G | I | S |
| VH1-46 | Q | V | Q | L | V | Q | S | G | A | E | V | K | K | P | G | A | S | V | K | V | S | C | K | A | S | G | Y | T | F | T | S | | | Y | Y | I | H |
| VH1-69*01 | Q | V | Q | L | V | Q | S | G | A | E | V | K | K | P | G | S | S | V | K | V | S | C | K | A | S | G | Y | T | F | T | S | | | Y | A | I | S |
| VH3-07 | E | V | Q | L | V | E | S | G | G | G | L | V | Q | P | G | G | S | L | R | L | S | C | A | A | S | G | F | T | F | S | S | | | Y | W | I | S |
| VH3-11 | Q | V | Q | L | V | E | S | G | G | G | L | V | K | P | G | G | S | L | R | L | S | C | A | A | S | G | F | T | F | S | D | | | Y | Y | I | S |
| VH3-15 | E | V | Q | L | V | E | S | G | G | G | L | V | K | P | G | G | S | L | R | L | S | C | A | A | S | G | F | T | F | S | N | | | H | W | I | S |
| VH3-21 | E | V | Q | L | V | E | S | G | G | G | L | V | Q | P | G | G | S | L | R | L | S | C | A | A | S | G | F | T | F | S | S | | | Y | S | I | S |
| VH3-23 | E | V | Q | L | V | E | S | G | G | G | L | V | Q | P | G | G | S | L | R | L | S | C | A | A | S | G | F | T | F | S | S | | | Y | A | I | S |
| VH3-30 | Q | V | Q | L | V | E | S | G | G | G | L | V | Q | P | G | R | S | L | R | L | S | C | A | A | S | G | F | T | F | S | S | | | Y | A | I | H |
| VH3-53 | E | V | Q | L | V | E | S | G | G | G | L | V | Q | P | G | G | S | L | R | L | S | C | A | A | S | G | F | T | V | S | S | | | H | Y | I | S |
| VH3-74 | E | V | Q | L | V | E | S | G | G | G | L | V | K | P | G | G | S | L | R | L | S | C | A | A | S | G | F | T | F | S | S | | | Y | W | I | H |
| VH5-51 | E | V | Q | L | V | Q | S | G | A | E | V | K | K | P | G | E | S | L | K | I | S | C | K | G | S | G | Y | S | F | T | S | S | | Y | W | I | S |
| VH6-01 | Q | V | Q | L | Q | Q | S | G | P | G | L | V | K | P | S | Q | T | L | S | L | T | C | A | I | S | G | D | S | V | S | T | | | A | A | W | N |

Nucleotide Sequences

| Kabat No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35a | 35b |
|---|---|---|---|---|---|---|---|---|---|---|---|---|---|---|---|---|---|---|---|---|---|---|---|---|---|---|---|---|---|---|---|---|---|---|---|---|---|
| VH1-18 | CAG | GTG | CAG | CTG | GTG | CAG | AGC | GGT | GCC | GAA | GTG | AAA | AAA | CCA | GGC | GCC | AGC | GTG | AAA | GTT | AGC | TGC | AAA | GCC | AGC | GGC | TAT | ACC | TTT | ACC | AGC | | | TAT | GGC | ATT | AGC |
| VH1-46 | CAG | GTG | CAG | CTG | GTG | CAG | AGC | GGT | GCC | GAA | GTG | AAA | AAA | CCA | GGC | GCC | AGC | GTG | AAA | GTT | AGC | TGC | AAA | GCC | AGC | GGC | TAT | ACC | TTC | ACC | AGC | | | TAC | TAT | ATT | CAT |
| VH1-69*01 | CAG | GTG | CAG | CTG | GTG | CAG | AGC | GGT | GCC | GAA | GTG | AAA | AAA | CCA | GGC | AGC | AGC | GTG | AAA | GTG | AGC | TGC | AAA | GCC | AGC | GGC | TAT | ACC | TTT | ACC | AGC | | | TAT | GCC | ATT | AGC |
| VH3-07 | GAA | GTG | CAG | CTG | GTG | GAA | AGC | GGC | GGT | GGC | CTG | GTG | CAG | CCA | GGT | GGT | AGC | CTG | CGC | CTG | AGC | TGC | GCC | GCC | AGC | GGC | TTT | ACC | TTT | AGC | AGC | | | TAT | TGG | ATT | AGC |
| VH3-11 | CAG | GTG | CAG | CTG | GTG | GAA | AGC | GGC | GGT | GGC | CTG | GTG | AAA | CCA | GGT | GGT | AGC | CTG | CGC | CTG | AGC | TGC | GCC | GCC | AGC | GGC | TTT | ACC | TTT | AGC | GAT | | | TAT | TAC | ATT | AGC |
| VH3-15 | GAA | GTG | CAG | CTG | GTG | GAA | AGC | GGC | GGT | GGC | CTG | GTG | AAA | CCA | GGT | AGC | AGC | CTG | CGC | CTG | AGC | TGC | GCC | GCC | AGC | GGC | TTT | ACC | TTT | AGC | AAC | | | CAT | TGG | ATT | AGC |
| VH3-21 | GAA | GTG | CAG | CTG | GTG | GAA | AGC | GGC | GGT | GGC | CTG | GTG | CAG | CCA | GGT | GGT | AGC | CTG | CGC | CTG | AGC | TGC | GCC | GCC | AGC | GGC | TTT | ACC | TTT | AGC | AGC | | | TAT | AGC | ATT | AGC |
| VH3-23 | GAA | GTG | CAG | CTG | GTG | GAA | AGC | GGC | GGT | GGC | CTG | GTG | CAG | CCA | GGT | GGT | AGC | CTG | CGC | CTG | AGC | TGC | GCC | GCC | GCA | GGC | TTT | ACC | TTT | AGC | AGC | | | TAT | GCC | ATT | AGC |
| VH3-30 | GAA | GTG | CAG | CTG | GTG | GAA | AGC | GGC | GGT | GGC | CTG | GTG | CAG | CCA | GGT | CGC | AGC | CTG | CGC | CTG | AGC | TGT | GCC | GCC | AGC | GGC | TTT | ACC | GTT | AGC | AGC | | | TAT | GCC | ATT | CAT |
| VH3-53 | GAA | GTG | CAG | CTG | GTG | GAA | AGC | GGC | GGT | GGC | CTG | GTG | CAG | CCA | GGT | GGT | AGC | CTG | CGC | CTG | AGC | TGT | GCC | GCC | AGC | GGC | TTT | ACC | GTT | AGC | AGC | | | CAT | TAT | ATT | AGC |
| VH3-74 | GAA | GTG | CAG | CTG | GTG | GAA | AGC | GGC | GGT | GGC | CTG | GTG | AAA | CCG | GGC | GGT | AGC | CTG | CGC | ATC | AGC | TGC | GCC | GCC | AGC | GGC | TTT | ACC | TTT | AGC | AGC | | | TAT | TGG | ATT | CAT |
| VH5-51 | GAA | GTG | CAG | CTG | GTG | CAG | AGC | GGT | GCC | GAA | GTT | AAA | AAA | CCG | GGC | GAA | AGC | CTG | AAA | ATC | AGC | TGC | AAA | GGG | AGC | GGC | TAT | AGC | TTT | ACC | AGC | AGC | | TAT | TGG | ATT | AGC |
| VH6-01 | CAG | GTG | CAG | CTG | CAA | CAG | AGC | GGC | CCA | GGC | CTG | GTT | AAA | CCG | AGC | CAG | ACC | CTG | AGC | CTG | ACC | TGC | GCC | ATT | AGC | GGC | GAT | AGC | GTT | AGC | ACC | AGC | AGC | GCC | GCC | TGG | AAC |

Figure 35 Low Post Translational Modification VHs

| Kabat CDRs | | | | | FRAMEWORK2 | | | | | | | | | | | | HCDR2 | | | | | | | | | | | |
|---|---|---|---|---|---|---|---|---|---|---|---|---|---|---|---|---|---|---|---|---|---|---|---|---|---|---|---|---|
| Kabat No. | 36 | 37 | 38 | 39 | 40 | 41 | 42 | 43 | 44 | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 | 65 |
| VH1-18 | W | V | R | Q | A | P | G | Q | G | L | E | W | M | G | W | I | S | A | | | Y | G | N | T | N | Y | A | Q | K | L | Q | G |
| VH1-46 | W | V | R | Q | A | P | G | Q | G | L | E | W | M | G | I | I | N | P | | | S | G | G | S | T | S | Y | A | Q | K | F | Q | G |
| VH1-69*01 | W | V | R | Q | A | P | G | Q | G | L | E | W | M | G | G | I | I | P | | | I | F | G | T | A | N | Y | A | Q | K | F | Q | G |
| VH3-07 | W | V | R | Q | A | P | G | K | G | L | E | W | V | A | N | I | K | Q | | | S | G | S | E | T | Y | Y | V | E | S | V | K | G |
| VH3-11 | W | V | R | Q | A | P | G | K | G | L | E | W | V | S | Y | I | S | S | | K T | S | G | S | T | I | Y | A | E | S | V | K | G |
| VH3-15 | W | V | R | Q | A | P | G | K | G | L | E | W | V | G | R | I | K | S | | | Y | G | G | T | T | D | Y | A | E | P | V | K | G |
| VH3-21 | W | V | R | Q | A | P | G | K | G | L | E | W | V | S | S | I | S | S | | | S | S | S | Y | T | Y | A | E | S | V | K | G |
| VH3-23 | W | V | R | Q | A | P | G | K | G | L | E | W | V | S | A | I | S | G | | | S | G | G | S | T | Y | A | E | S | V | K | G |
| VH3-30 | W | V | R | Q | A | P | G | K | G | L | E | W | V | A | V | I | S | Y | | | S | G | S | N | K | Y | Y | A | E | S | V | K | G |
| VH3-53 | W | V | R | Q | A | P | G | K | G | L | E | W | V | S | V | I | Y | S | | | S | G | S | S | T | Y | Y | A | E | S | V | K | G |
| VH3-74 | W | V | R | Q | A | P | G | K | G | L | E | W | V | S | R | I | T | S | | | S | G | S | T | T | S | Y | A | E | S | V | K | G |
| VH5-51 | W | V | R | Q | M | P | G | K | G | L | E | W | M | G | I | I | Y | P | | R | G | I | T | Y | R | Y | S | P | S | F | Q | G |
| VH6-01 | W | I | R | Q | S | P | S | R | G | L | E | W | L | G | R | I | Y | Y | | | S | K | W | Y | N | D | Y | A | V | S | V | K | S |

| Kabat No. | 36 | 37 | 38 | 39 | 40 | 41 | 42 | 43 | 44 | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|---|---|---|---|---|---|---|---|---|---|---|---|
| VH1-18 | TGG | GTT | CGC | CAG | GCC | CCA | GGC | CAG | GGT | CTG | GAA | TGG | ATG | GGC | TGG | ATT | AGC | GCC | | | TAT | GGC | AAC | ACC | AAC | TAC | GCC | CAG | AAA | CTG | CAA | GGC |
| VH1-46 | TGG | GTT | CGC | CAG | GCC | CCA | GGC | CAG | GGT | CTG | GAA | TGG | ATG | GGC | ATT | ATT | AAC | CCG | | | AGC | GGC | GGC | AGC | ACC | AGC | TAT | GCA | CAG | AAA | TTT | CAG | GGC |
| VH1-69*01 | TGG | GTT | CGC | CAG | GCA | CCA | GGT | CAG | GGT | CTG | GAA | TGG | ATG | GGC | GGC | ATT | ATT | CCG | | | ATT | TTT | GGC | ACC | GCC | AAC | TAT | GCC | CAG | AAA | TTT | CAG | GGT |
| VH3-07 | TGG | GTT | CGC | CAG | GCC | CCA | GGC | AAA | GGC | CTG | GAA | TGG | GTG | GCG | AAC | ATC | AAA | CAG | | | AGC | GGC | AGC | GAG | ACC | TAT | TAT | GTG | GAG | AAA | GTG | AAA | GGC |
| VH3-11 | TGG | GTT | CGC | CAG | GCC | CCA | GGC | AAA | GGC | CTG | GAA | TGG | GTT | AGC | TAT | ATT | AGC | AGC | | AAA ACC | AGT | GGC | AGC | ACC | ACC | ATT | TAT | GCC | GAG | AGC | GTG | AAA | GGC |
| VH3-15 | TGG | GTT | CGC | CAG | GCC | CCA | GGC | AAA | GGC | CTG | GAA | TGG | GTT | GGC | CGC | ATC | AAA | AGC | | | TAT | GGC | GGC | ACC | ACC | GAT | TAT | GCC | GAG | CCA | GTG | AAA | GGC |
| VH3-21 | TGG | GTT | CGC | CAG | GCC | CCA | GGC | AAA | GGC | CTG | GAA | TGG | GTT | AGC | AGC | ATC | AGC | AGC | | | AGT | AGC | AGC | TAT | ACC | TAT | TAT | GCC | GAG | AGC | GTG | AAA | GGC |
| VH3-23 | TGG | GTG | CGC | CAA | GCA | CCA | GGC | AAA | GGC | CTG | GAA | TGG | GTG | AGC | GCC | ATT | AGC | GGC | | | AGC | GGT | GGC | AGC | AAC | ACC | TAT | GCC | GAG | AGC | GTG | AAA | GGT |
| VH3-30 | TGG | GTG | CGC | CAG | GCC | CCA | GGC | AAA | GGC | CTG | GAA | TGG | GTG | GCC | GTG | ATT | AGC | TAT | | | AGC | GGC | AGC | AAC | AAA | TAT | TAT | GCC | GAG | AGC | GTG | AAA | GGC |
| VH3-53 | TGG | GTG | CGC | CAG | GCC | CCA | GGC | AAA | GGC | CTG | GAA | TGG | GTG | AGC | GTG | ATC | TAT | AGC | | | AGC | GGC | AGC | AGC | ACC | TAT | TAT | GCC | GAG | AGC | GTG | AAA | GGC |
| VH3-74 | TGG | GTT | CGC | CAG | GCC | CCG | GGC | AAA | GGC | CTG | GTT | TGG | GTT | AGC | CGC | ATT | ACC | AGC | | | AGC | ACC | AGC | AGC | ACC | AGC | TAT | GCC | GAG | AGC | GTG | AAA | GGC |
| VH5-51 | TGG | GTT | CGC | CAG | ATG | CCG | GGC | AAA | GGC | CTG | GAA | TGG | ATG | GGC | ATT | ATC | TAT | CCG | | CGC | GGC | AAA | TGG | TAC | AAC | GAT | TAT | AGC | CCG | AGC | TTT | CAG | GGC |
| VH6-01 | TGG | ATT | CGC | CAG | AGC | CCG | AGC | CGC | GGT | CTG | GAA | TGG | CTG | GGC | CGC | ATT | TAT | TAT | | | AGC | AAA | TGG | TAC | AAC | GAT | TAC | GCC | GTT | AGC | GTG | AAA | AGC |

Figure 36 Low Post Translational Modification VHs

FRAMEWORK3

| Kabat No. | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| VH1-18 | R | V | T | M | T | T | D | T | S | T | S | T | A | Y | M | E | L | R | S | L | R | S | D | D | T | A | V | Y | Y | C | A | R |
| VH1-46 | R | V | T | M | T | R | D | T | S | T | S | T | V | Y | M | E | L | S | S | L | R | S | E | D | T | A | V | Y | Y | C | A | R |
| VH1-69*01 | R | V | T | I | T | A | D | E | S | T | S | T | A | Y | M | E | L | S | S | L | R | S | E | D | T | A | V | Y | Y | C | A | R |
| VH3-07 | R | F | T | I | S | R | D | N | A | K | N | S | L | Y | L | Q | M | N | S | L | R | A | E | D | T | A | V | Y | Y | C | A | R |
| VH3-11 | R | F | T | I | S | R | D | N | A | K | N | S | L | Y | L | Q | M | N | S | L | R | T | E | D | T | A | V | Y | Y | C | A | R |
| VH3-15 | R | F | T | I | S | R | D | N | S | K | N | T | L | Y | L | Q | M | N | S | L | K | A | E | D | T | A | V | Y | Y | C | A | R |
| VH3-21 | R | F | T | I | S | R | D | D | A | K | N | S | L | Y | L | Q | M | N | S | L | R | A | E | D | T | A | V | Y | Y | C | A | R |
| VH3-23 | R | F | T | I | S | R | D | N | S | K | N | T | L | Y | L | Q | M | N | S | L | R | A | E | D | T | A | V | Y | Y | C | A | R |
| VH3-30 | R | F | T | I | S | R | D | N | S | K | N | T | L | Y | L | Q | M | N | S | L | R | A | E | D | T | A | V | Y | Y | C | A | R |
| VH3-53 | R | F | T | I | S | R | D | N | A | K | N | S | L | Y | L | Q | M | N | S | L | R | A | E | D | T | A | V | Y | Y | C | A | R |
| VH3-74 | R | F | T | I | S | R | D | N | A | K | N | S | L | Y | L | Q | M | N | S | L | K | A | S | D | T | A | M | Y | Y | C | A | R |
| VH5-51 | Q | V | T | I | S | A | D | K | S | I | S | T | A | Y | L | Q | W | S | S | L | T | P | E | D | T | A | V | Y | Y | C | A | R |
| VH6-01 | R | I | T | I | N | P | D | T | S | K | N | Q | F | S | L | Q | L | N | S | V | T | P | E | D | T | A | V | Y | Y | C | A | R |

| Kabat No. | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| VH1-18 | CGC | GTG | ACC | ATG | ACC | ACC | GAT | AC C | AGC | AC C | AGC | ACC | GCC | TAT | ATG | GAA | CTG | CGC | AGC | CTG | CGC | AGC | GAC | GAT | ACC | GCC | GTG | TAT | TAT | TGC | GCG | CGT |
| VH1-46 | CGC | GTG | ACC | ATG | ACC | CGC | GAT | AC C | AGC | AC C | AGC | ACC | GTG | TAT | ATG | GAA | CTG | AGC | AGC | CTG | CGC | AGC | GAA | GAT | ACC | GCC | GTG | TAT | TAT | TGC | GCG | CGT |
| VH1-69*01 | CGC | GTG | ACC | ATT | ACC | GCA | GAT | GA A | AGC | AC C | AGC | ACC | GCC | TAT | ATG | GAA | CTG | AGC | AGC | CTG | CGC | AGC | GAA | GAT | ACC | GCA | GTG | TAT | TAT | TGC | GCG | CGG |
| VH3-07 | CGC | TTT | ACC | ATT | AGC | CGC | GAT | AA C | GCC | AA A | AAC | AGC | CTG | TAT | CTG | CAA | ATG | AAC | AGC | CTG | CGC | GCC | GAA | GAT | ACC | GCC | GTG | TAT | TAT | TGC | GCG | CGT |
| VH3-11 | CGC | TTT | ACC | ATT | AGC | CGC | GAT | AA C | GCC | AA A | AAC | AGC | CTG | TAT | CTG | CAA | ATG | AAC | AGC | CTG | CGC | ACC | GAA | GAT | ACC | GCC | GTG | TAT | TAT | TGC | GCG | CGT |
| VH3-15 | CGC | TTT | ACC | ATT | AGC | CGC | GAC | GA T | AGC | AA A | AAC | ACC | CTG | TAT | CTG | CAA | ATG | AAC | AGC | CTG | AAA | GCC | GAA | GAT | ACC | GCC | GTG | TAT | TAT | TGC | GCG | CGT |
| VH3-21 | CGC | TTT | ACC | ATT | AGC | CGC | GAT | AA C | GCC | AA A | AAC | AGC | CTG | TAT | CTG | CAA | ATG | AAC | AGC | CTG | CGG | GCC | GAA | GAT | ACC | GCC | GTG | TAT | TAT | TGC | GCG | CGT |
| VH3-23 | CGC | TTT | ACC | ATT | AGC | CGC | GAT | AA C | AGC | AA A | AAC | ACC | CTG | TAC | CTG | CAA | ATG | AAC | AGC | CTG | CGG | GCA | GAA | GAT | ACC | GCA | GTT | TAT | TAT | TGC | GCG | CGT |
| VH3-30 | CGC | TTT | ACC | ATT | AGT | CGC | GAT | AA C | AGC | AA A | AAC | ACC | CTG | TAC | CTG | CAA | ATG | AAC | AGC | CTG | CGG | GCC | GAA | GAT | ACC | GCC | GTG | TAT | TAT | TGC | GCG | CGT |
| VH3-53 | CGC | TTT | ACC | ATT | AGC | CGC | GAT | AA C | GCC | AA A | AAC | ACC | CTG | TAT | CTG | CAA | ATG | AAC | AGC | CTG | CGG | GCC | GAA | GAT | ACC | GCC | GTG | TAT | TAT | TGC | GCG | CGT |
| VH3-74 | CGC | TTT | ACC | ATT | AGC | CGC | GAT | AA C | GCC | AA A | AAC | AGC | CTG | TAT | CTG | CAA | ATG | TGG | AGC | CTG | AAA | GCC | AGC | GAT | ACC | GCC | ATG | TAT | TAT | TGC | GCG | CGT |
| VH5-51 | CA G | GTT | ACA | ATT | AGC | GCC | GAC | AA A | AGC | AT C | AGC | ACC | GCC | TAT | CTG | CAA | TGG | AGC | AGC | CTG | ACC | CCG | GAA | GAT | ACC | GCC | ACG | TAT | TAT | TGC | GCG | CGG |
| VH6-01 | CGC | ATT | ACC | ATT | AAC | CCG | GAT | AC C | AGC | AA A | AAC | CAG | TTC | AGC | CTG | CAA | CTG | AAC | AGC | GTG | ACC | CCG | GAA | GAT | ACC | GCC | GTG | TAC | TAT | TGC | GCG | CGT |

Figure 37

| VH | VL | Target | HCDR3 Length [aa] | LCDR3 Length [aa] | Fab Tm [°C] | Fab affinity [nM] | pI | IgG expression [mg/L] | IgG Tm [°C] | IgG SEC monomer [%] |
|---|---|---|---|---|---|---|---|---|---|---|
| VH3-23 | VK1-39 | DKK3 | 6 | 8 | 76,8 | nd | 9,2 | 28,5 | 81,8 | 97 |
| VH3-23 | VK1-39 | DKK3 | 7 | 8 | 73,4 | nd | 9,3 | 40,9 | 81,4 | 100 |
| VH3-23 | VK1-39 | DKK3 | 8 | 8 | 72,9 | nd | 9,1 | 36,4 | 77,0 | 98 |
| VH3-23 | VK1-39 | DKK3 | 8 | 8 | 74,0 | nd | 9,4 | 26,0 | 78,8 | 99 |
| VH3-23 | VK1-39 | DKK3 | 8 | 8 | 75,0 | nd | 9,4 | 20,5 | 79,0 | 99 |
| VH3-23 | VK1-39 | DKK3 | 6 | 8 | 76,3 | nd | 9,2 | 17,1 | 83,5 | 98 |
| VH3-23 | VK1-39 | DKK3 | 9 | 8 | 75,7 | nd | 9,2 | 32,0 | 81,6 | 97 |
| VH3-23 | VK1-39 | DKK3 | 8 | 8 | 72,2 | nd | 9,4 | 22,9 | 76,0 | 100 |
| VH3-23 | VL3-1 | DKK3 | 6 | 8 | 65,6 | nd | 8,9 | 19,0 | 70,5 | 96 |
| VH3-23 | VL3-1 | DKK3 | 7 | 9 | 63,6 | nd | 8,7 | 36,4 | 68,9 | 100 |
| VH3-23 | VL3-1 | DKK3 | 7 | 8 | 70,1 | nd | 7,9 | 29,1 | 69,1 | 97 |
| VH3-23 | VK1-39 | DKK3 | 11 | 8 | nd | nd | 9,4 | 26,7 | 79,5 | 100 |
| VH3-23 | VK1-39 | DKK3 | 6 | 8 | 74,5 | nd | 9,3 | 30,0 | 82,1 | 97 |
| VH3-23 | VK1-39 | DKK3 | 6 | 8 | 73,0 | nd | 9,1 | 22,0 | 77,3 | 96 |
| VH3-23 | VK1-39 | DKK3 | 11 | 8 | 74,0 | nd | 9,2 | 23,6 | 87,0 | 98 |
| VH3-23 | VL3-1 | DKK3 | 12 | 8 | nd | nd | 8,7 | 25,6 | 74,7 | 98 |
| VH3-23 | VL3-1 | DKK3 | 7 | 8 | 71,0 | nd | 8,7 | 45,5 | 76,9 | 97 |
| VH3-23 | VL3-1 | DKK3 | 5 | 8 | nd | nd | 8,7 | 32,0 | 68,7 | 97 |
| VH3-23 | VL3-1 | DKK3 | 7 | 8 | 65,0 | nd | 8,7 | 28,8 | 70,1 | 90 |
| VH3-23 | VL3-1 | DKK3 | 7 | 8 | 70,5 | nd | 8,9 | 31,1 | 74,1 | 99 |

Figure 38

| VH | VL | Target | HCDR3 Length [aa] | LCDR3 Length [aa] | Fab Tm [°C] | Fab affinity [nM] | pI | IgG expression [mg/L] | IgG Tm [°C] | IgG SEC monomer [%] |
|---|---|---|---|---|---|---|---|---|---|---|
| VH3-23 | VK1-39 | ErbB4/Her4 | 16 | 8 | 75,0 | nd | 8,7 | 31,8 | 85,4 | 99 |
| VH3-23 | VK1-39 | ErbB4/Her4 | 12 | 8 | 75,0 | nd | 9,0 | 36,4 | 82,0 | 100 |
| VH3-23 | VK1-39 | ErbB4/Her4 | 15 | 8 | 74,8 | 61 | 8,3 | 50,0 | 85,6 | 99 |
| VH3-23 | VK1-39 | ErbB4/Her4 | 13 | 8 | 68,4 | 22 | 9,2 | 17,5 | 77,4 | 99 |
| VH3-23 | VK1-39 | ErbB4/Her4 | 11 | 8 | 71,4 | 59 | 8,7 | 32,7 | 77,6 | 99 |
| VH3-23 | VK1-39 | ErbB4/Her4 | 15 | 8 | 69,0 | 14 | 9,1 | 28,5 | 74,1 | 100 |
| VH3-23 | VK1-39 | ErbB4/Her4 | 13 | 8 | 69,0 | 8,4 | 8,9 | 34,5 | 81,4 | 100 |
| VH3-23 | VK1-39 | ErbB4/Her4 | 16 | 8 | 73,3 | 20 | 8,9 | 25,3 | 83,2 | nsp |
| VH3-23 | VK1-39 | ErbB4/Her4 | 19 | 8 | 70,8 | 30 | 9,0 | 26,0 | 86,5 | 100 |
| VH3-23 | VK1-39 | ErbB4/Her4 | 17 | 8 | 76,7 | 14 | 8,7 | 35,0 | 78,6 | 99 |
| VH3-23 | VK1-39 | ErbB4/Her4 | 14 | 8 | 68,9 | 12 | 8,9 | 32,5 | 87,9 | 100 |
| VH3-23 | VK1-39 | ErbB4/Her4 | 19 | 8 | 74,5 | nd | 8,3 | 19,1 | 84,4 | 99 |
| VH3-23 | VL3-1 | ErbB4/Her4 | 17 | 8 | 77,5 | 2,1 | 7,4 | 41,8 | 74,3 | 99 |
| VH3-23 | VL3-1 | ErbB4/Her4 | 11 | 8 | 70,0 | nd | 7,4 | 36,1 | 76,0 | 98 |
| VH3-23 | VK1-39 | ErbB4/Her4 | 11 | 8 | 67,0 | 86 | 9,2 | 33,3 | 87,0 | 97 |
| VH3-23 | VL3-1 | ErbB4/Her4 | 15 | 8 | 69,1 | 1,2 | 8,3 | 42,0 | 69,6 | 99 |
| VH3-23 | VL3-1 | ErbB4/Her4 | 15 | 9 | 74,3 | nd | 7,6 | 26,0 | 69,1 | 98 |
| VH3-23 | VL3-1 | ErbB4/Her4 | 12 | 8 | 65,9 | 24 | 8,3 | 42,5 | 70,3 | 97 |
| VH3-23 | VL3-1 | ErbB4/Her4 | 18 | 10 | 69,0 | 13 | 8,7 | 31,1 | 72,6 | 99 |
| VH3-23 | VL3-1 | ErbB4/Her4 | 11 | 8 | 65,5 | 45 | 7,1 | 38,0 | 75,7 | 99 |
| VH3-23 | VL3-1 | ErbB4/Her4 | 12 | 10 | 69,9 | 55 | 7,6 | 29,4 | 79,0 | 97 |
| VH3-23 | VL3-1 | ErbB4/Her4 | 14 | 8 | 71,0 | 36 | 7,1 | 24,2 | 68,4 | 99 |
| VH3-23 | VL3-1 | ErbB4/Her4 | 15 | 8 | 71,0 | 48 | 8,0 | 26,9 | 73,4 | 99 |
| VH3-23 | VL3-1 | ErbB4/Her4 | 13 | 8 | 69,1 | 95 | 7,4 | 20,0 | 69,4 | 96 |

Figure 39

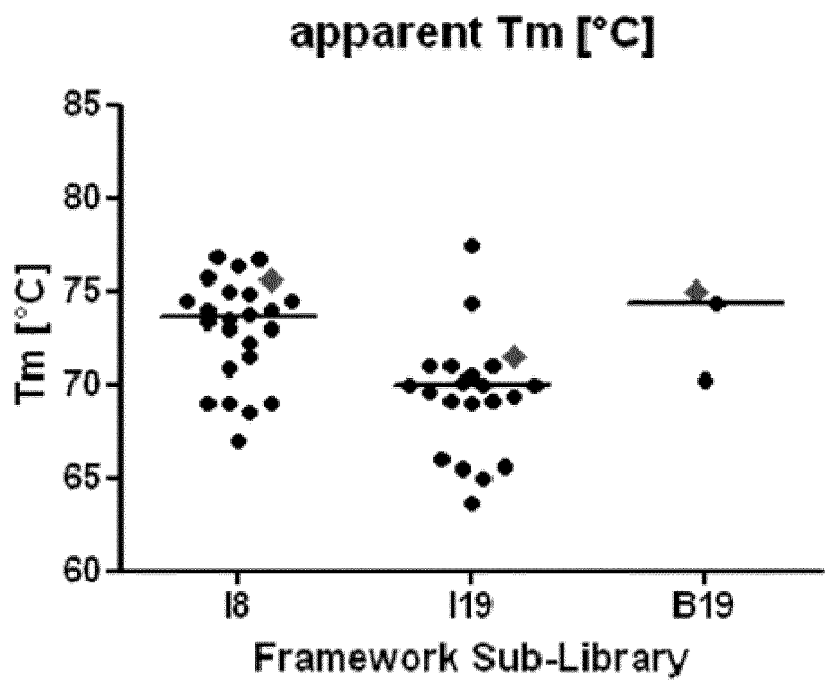

Key: Apparent midpoints of unfolding of selected Fabs as determined by Differential Scanning Fluorimetry (DSF) as described in Example 9.1.2. Each dot represents one unique Fab. Squares indicate the control Fabs as described in Example 9 with the constant CDR3s as described in Ewert S. et al.(2004), J. Mol. Biol. 325, p. 531ff. Bars indicate the Median.

I8 represents VH3-23/VK1-39

I19 represents VH3-23/VL3-1

B19 represents VH1-18/VL3-1

Figure 40

Heavy Chain Framework 4: JH4

| Kabat No. | 103 | 104 | 105 | 106 | 107 | 108 | 109 | 110 | 111 | 112 | 113 |
|---|---|---|---|---|---|---|---|---|---|---|---|
| FWR4 aa | W | G | Q | G | T | L | V | T | V | S | S |
| FWR4 nt | TGG | GGC | CAG | GGC | ACC | CTG | GTT | ACT | GTC | TCG | AGC |

OR

| Kabat No. | 103 | 104 | 105 | 106 | 107 | 108 | 109 | 110 | 111 | 112 | 113 |
|---|---|---|---|---|---|---|---|---|---|---|---|
| FWR4 aa | W | G | Q | G | T | L | V | T | V | S | S |
| FWR4 nt | TGG | GGC | CAG | GGC | ACC | CTG | GTT | ACT | GTC | TCG | AGC |

XhoI restriction site CTCGAG

Light Chain Kappa Framework 4: Jk1

|  | Kabat No. | 98 | 99 | 100 | 101 | 102 | 103 | 104 | 105 | 106 | 106A | 107 | 108 | 109 |
|---|---|---|---|---|---|---|---|---|---|---|---|---|---|---|
|  | FWR4 aa | F | G | Q | G | T | K | V | E | I |  | K | R | T |
| pJP_h_Igkappa vector | FWR4 nt | TTC | GGC | CAG | GGT | ACC | AAA | GTG | GAA | ATC |  | AAG | CGC | ACC |
| pJPx1 vector | FWR4 nt | TTC | GGC | CAG | GGT | ACC | AAA | GTT | GAA | ATT |  | AAA | CGC | ACC |
| or |  |  |  |  |  |  |  |  |  |  |  |  |  |  |
| pJPx1 vector | FWR4 nt | TTC | GGC | CAG | GGT | ACC | AAA | GTG | GAA | ATT |  | AAA | CGC | ACC |

KpnI/Acc65I restriction site GGTACC

Key: pJPx1 vector is an expression vector for Fab expression in E. coli
pJP_h_Igkappa vector is an expression vector for human kappa light chain expression in mammalian cells

Light Chain Lambda Framework 4: Jλ2/3

|  | Kabat No. | 98 | 99 | 100 | 101 | 102 | 103 | 104 | 105 | 106 | 106A | 107 | 108 |
|---|---|---|---|---|---|---|---|---|---|---|---|---|---|
|  | FWR4 aa | F | G | G | G | T | K | L | T | V | L | G | Q |
| pJP_h_Iglambda2 | FWR4 nt | TTT | GGC | GGC | GGT | ACC | AAG | CTG | ACC | GTG | CTC | GGC | CAG |
| pJPx1 | FWR4 nt | TTT | GGC | GGC | GGT | ACC | AAA | CTC | ACT | GTC | CTG | GGC | CAG |
| or |  |  |  |  |  |  |  |  |  |  |  |  |  |
| pJPx1 vector | FWR4 nt | TTT | GGC | GGC | GGT | ACC | AAA | CTG | ACC | GTG | CTG | GGC | CAG |

KpnI/Acc65I restriction site GGTACC

Key: pJPx1 vector is an expression vector for Fab expression in E. coli
pJP_h_Iglambda2 vector is an expression vector for human lambda light chain expression in mammalian cells

Figure 41A IgG1 Fc heavy

| IgG1 | 114 | 115 | 116 | 117 | 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 |
|---|---|---|---|---|---|---|---|---|---|---|---|---|---|---|---|---|---|---|---|---|---|---|---|---|---|---|---|---|---|
| pJP_h_IgIgG1f | | | | | | | | | | | | | | | | | | | | | | | | | | | | | |
| CH1 to CH3 | | | | | | | | | | | | | | | | CH1 | | | | | | | | | | | | | |
| | A | S | T | K | G | P | S | V | F | P | L | A | P | S | S | K | S | T | S | G | G | T | A | A | L | G | C | L | V |
| | GCG | TCG | ACC | AAA | GGC | CCC | AGC | GTG | TTC | CCT | CTG | GCC | CCC | AGC | AGC | AAG | AGC | ACC | TCT | GGC | GGA | ACA | GCC | GCC | CTG | GGC | TGC | CTG | GTC |

| 143 | 144 | 145 | 146 | 147 | 148 | 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | CH1 | | | | | | | | | | | |
| K | D | Y | F | P | E | P | V | T | V | S | W | N | S | G | A | L | T | S | G | V | H | T | F | P | A | V | L | Q | S | S | G | L | Y | S |
| AAG | GAC | TAC | TTC | CCC | GAG | CCC | GTG | ACC | GTG | TCC | TGG | AAC | TCT | GGC | GCC | CTG | ACC | AGC | GGC | GTG | CAC | ACC | TTT | CCA | GCC | GTC | CTG | CAG | AGC | AGC | GGC | CTG | TAC | AGC |

| 178 | 179 | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 | 211 |
|---|---|---|---|---|---|---|---|---|---|---|---|---|---|---|---|---|---|---|---|---|---|---|---|---|---|---|---|---|---|---|---|---|---|
| | | | | | | | | | | | | | | | | | | CH1 | | | | | | | | | | | | | | | |
| L | S | S | V | V | T | V | P | S | S | S | L | G | T | Q | T | Y | I | C | N | V | N | H | K | P | S | N | T | K | V | D | K | R | V |
| CTG | AGC | AGC | GTC | GTG | ACC | GTG | CCC | AGC | AGC | AGC | CTG | GGC | ACC | CAG | ACC | TAC | ATC | TGC | AAC | GTG | AAC | CAC | AAG | CCC | AGC | AAC | ACA | AAG | GTG | GAC | AAG | CGG | GTG |

| 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 | 241 | 242 | 243 | 244 | 245 |
|---|---|---|---|---|---|---|---|---|---|---|---|---|---|---|---|---|---|---|---|---|---|---|---|---|---|---|---|---|---|---|---|---|---|
| | | | | | | Hinge | | | | | | | | | | | | | | | | | CH2 | | | | | | | | | | |
| E | P | K | S | C | D | K | T | H | T | C | P | P | C | P | A | P | E | L | L | G | G | P | S | V | F | L | F | P | P | K | P | K | D |
| GAA | CCC | AAG | AGC | TGC | GAC | AAG | ACC | CAC | ACC | TGT | CCC | CCC | TGC | CCT | GCC | CCT | GAA | CTG | CTG | GGA | GGC | CCC | TCC | GTG | TTC | CTG | TTC | CCC | CCA | AAG | CCT | AAG | GAC |

| 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 | 269 | 270 | 271 | 272 | 273 | 274 | 275 | 276 | 277 | 278 | 279 | 280 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | CH2 | | | | | | | | | | | | | | | | | |
| T | L | M | I | S | R | T | P | E | V | T | C | V | V | V | D | V | S | H | E | D | P | E | V | K | F | N | W | Y | V | D | G | V | E | V |
| ACC | CTG | ATG | ATC | AGC | CGG | ACC | CCC | GAA | GTG | ACC | TGC | GTG | GTG | GTG | GAC | GTG | TCC | CAC | GAG | GAC | CCT | GAA | GTG | AAG | TTT | AAT | TGG | TAC | GTG | GAC | GGC | GTG | GAA | GTG |

The nucleic acid sequences shown have been codon optimized

Figure 41B IgG1 Fc heavy

CH2

| 281 | 282 | 283 | 284 | 285 | 286 | 287 | 288 | 289 | 290 | 291 | 292 | 293 | 294 | 295 | 296 | 297 | 298 | 299 | 300 | 301 | 302 | 303 | 304 | 305 | 306 | 307 | 308 | 309 | 310 | 311 | 312 | 313 | 314 | 315 |
|---|---|---|---|---|---|---|---|---|---|---|---|---|---|---|---|---|---|---|---|---|---|---|---|---|---|---|---|---|---|---|---|---|---|---|
| H | N | A | K | T | K | P | R | E | E | Q | Y | N | S | T | Y | R | V | V | S | V | L | T | V | L | H | Q | D | W | L | N | G | K | E | Y |
| CAC | AAC | GCC | AAG | ACC | AAG | CCC | AGA | GAG | GAA | CAG | TAC | AAC | AGC | ACC | TAC | CGG | GTG | GTG | TCC | GTG | CTG | ACC | GTG | CTG | CAC | CAG | GAC | TGG | CTG | AAC | GGC | AAA | GAG | TAC |

CH3

| 316 | 317 | 318 | 319 | 320 | 321 | 322 | 323 | 324 | 325 | 326 | 327 | 328 | 329 | 330 | 331 | 332 | 333 | 334 | 335 | 336 | 337 | 338 | 339 | 340 | 341 | 342 | 343 | 344 | 345 | 346 | 347 | 348 | 349 | 350 |
|---|---|---|---|---|---|---|---|---|---|---|---|---|---|---|---|---|---|---|---|---|---|---|---|---|---|---|---|---|---|---|---|---|---|---|
| K | C | K | V | S | N | K | A | L | P | A | P | I | E | K | T | I | S | K | A | K | G | Q | P | R | E | P | Q | V | Y | T | L | P | P | S |
| AAG | TGC | AAG | GTG | TCC | AAC | AAG | GCC | CTG | CCT | GCC | CCC | ATC | GAG | AAA | ACC | ATC | AGC | AAA | GCC | AAA | GGC | CAG | CCC | CGG | GAG | CCC | CAG | GTG | TAC | ACA | CTG | CCC | CCT | AGC |

| 351 | 352 | 353 | 354 | 355 | 356 | 357 | 358 | 359 | 360 | 361 | 362 | 363 | 364 | 365 | 366 | 367 | 368 | 369 | 370 | 371 | 372 | 373 | 374 | 375 | 376 | 377 | 378 | 379 | 380 | 381 | 382 | 383 | 384 | 385 |
|---|---|---|---|---|---|---|---|---|---|---|---|---|---|---|---|---|---|---|---|---|---|---|---|---|---|---|---|---|---|---|---|---|---|---|
| R | E | E | M | T | K | N | Q | V | S | L | T | C | L | V | K | G | F | Y | P | S | D | I | A | V | E | W | E | S | N | G | Q | P | E | N |
| CGG | GAA | GAG | ATG | ACC | AAG | AAC | CAG | GTG | TCC | CTG | ACC | TGC | CTC | GTG | AAG | GGC | TTC | TAC | CCC | AGC | GAC | ATT | GCC | GTG | GAA | TGG | GAG | AGC | AAC | GGC | CAG | CCC | GAG | AAC |

| 386 | 387 | 388 | 389 | 390 | 391 | 392 | 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 |
|---|---|---|---|---|---|---|---|---|---|---|---|---|---|---|---|---|---|---|---|---|---|---|---|---|---|---|---|---|---|---|---|---|---|---|
| N | Y | K | T | T | P | P | V | L | D | S | D | G | S | F | F | L | Y | S | K | L | T | V | D | K | S | R | W | Q | Q | G | N | V | F | S |
| AAC | TAC | AAG | ACC | ACC | CCT | CCC | GTG | CTG | GAC | AGC | GAC | GGC | TCA | TTC | TTC | CTG | TAC | AGC | AAG | CTG | ACC | GTG | GAC | AAG | AGC | CGG | TGG | CAG | CAG | GGC | AAC | GTG | TTC | AGC |

| 421 | 422 | 423 | 424 | 425 | 426 | 427 | 428 | 429 | 430 | 431 | 432 | 433 | 434 | 435 | 436 | 437 | 438 | 439 | 440 | 441 | 442 | 443 |
|---|---|---|---|---|---|---|---|---|---|---|---|---|---|---|---|---|---|---|---|---|---|---|
| C | S | V | M | H | E | A | L | H | N | H | Y | T | Q | K | S | L | S | L | S | P | G | K |
| TGC | TCC | GTG | ATG | CAC | GAG | GCC | CTG | CAC | AAC | CAC | TAC | ACC | CAG | AAG | TCC | CTG | AGC | CTG | AGC | CCC | GGC | AAG |

Figure 42 Fab Fc heavy

| Fab | | 114 | 115 | 116 | 117 | 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 |
|---|---|---|---|---|---|---|---|---|---|---|---|---|---|---|---|---|---|---|---|---|---|---|---|---|---|---|---|---|---|---|
| pJPx1 | | | | | | | | | | | | | | | | | | | | | | | | | | | | | | |
| CH1-Flag+HisTag | | A | S | T | K | G | P | S | V | F | P | L | A | P | S | S | K | S | T | S | G | G | T | A | A | L | G | C | L | V |
| | | GCG | TCG | ACC | AAA | GGC | CCG | AGC | GTG | TTT | CCG | CTG | GCC | CCG | AGC | AGC | AAA | AGC | ACC | AGC | GGC | GGC | ACC | GCC | GCA | CTG | GGC | TGC | CTG | GTG |

| 143 | 144 | 145 | 146 | 147 | 148 | 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 |
|---|---|---|---|---|---|---|---|---|---|---|---|---|---|---|---|---|---|---|---|---|---|---|---|---|---|---|---|---|---|---|---|---|---|---|
| CH1 | | | | | | | | | | | | | | | | | | | | | | | | | | | | | | | | | | |
| K | D | Y | F | P | E | P | V | T | V | S | W | N | S | G | A | L | T | S | G | V | H | T | F | P | A | V | L | Q | S | S | G | L | Y | S |
| AAA | GAT | TAT | TTC | CCG | GAA | CCA | GTG | ACC | GTG | AGC | TGG | AAC | AGC | GGT | GCC | CTG | ACC | AGC | GGC | GTG | CAT | ACC | TTT | CCG | GCG | GTG | CTG | CAA | AGC | AGC | GGC | CTG | TAT | AGC |

| 178 | 179 | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 | 211 |
|---|---|---|---|---|---|---|---|---|---|---|---|---|---|---|---|---|---|---|---|---|---|---|---|---|---|---|---|---|---|---|---|---|---|
| CH1 | | | | | | | | | | | | | | | | | | | | | | | | | | | | | | | | | |
| L | S | V | V | T | V | P | S | S | S | L | G | T | Q | T | Y | I | C | N | V | N | H | K | P | S | N | T | K | V | D | K | K | V |
| CTG | AGC | GTT | GTG | ACC | GTG | CCG | AGC | AGC | AGC | CTG | GGC | ACC | CAG | ACC | TAT | ATT | TGC | AAC | GTC | AAC | CAT | AAA | CCG | AGC | AAC | ACC | AAA | GTC | GAT | AAA | AAA | GTC |

| 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 |
|---|---|---|---|---|---|---|---|---|---|---|---|---|---|---|---|---|---|---|---|---|---|---|
| FLAG (M2) Tag | | | | | | | | | | | | | | | 6xHIS Tag | | | | | | | |
| E | P | K | S | E | F | D | Y | K | D | D | D | D | K | G | A | P | H | H | H | H | H | H |
| GAA | CCG | AAA | AGC | GAA | TTC | GAC | TAT | AAA | GAT | GAC | GAT | GAC | AAA | GGG | GCG | CCG | CAC | CAT | CAT | CAC | CAT | CAC |

The nucleic acid sequences shown have been codon optimized

Figure 43

IgG Fc kappa light

| IgG | pJP_h_lgkappa | V | A | A | P | S | V | F | I | F | P | P | S | D | E | Q | L | K | S | G | T | A | S | V | V | C | L |
|---|---|---|---|---|---|---|---|---|---|---|---|---|---|---|---|---|---|---|---|---|---|---|---|---|---|---|---|
| | Ckappa =IGKC | GTG | GCC | GCT | CCC | TCC | GTG | TTC | ATC | TTC | CCA | CCC | AGC | GAC | GAG | CAG | CTG | AAG | TCC | GGC | ACA | GCC | AGC | GTC | GTG | TGC | CTG |

| L | N | N | F | Y | P | R | E | A | K | V | Q | W | K | V | D | N | A | L | Q | S | G | N | S | Q | E | S | V | T | E | Q |
|---|---|---|---|---|---|---|---|---|---|---|---|---|---|---|---|---|---|---|---|---|---|---|---|---|---|---|---|---|---|---|
| CTG | AAC | AAC | TTC | TAC | CCC | CGC | GAG | GCC | AAA | GTG | CAG | TGG | AAG | GTG | GAC | AAC | GCC | CTC | CAG | AGC | GGC | AAC | AGC | CAG | GAA | AGC | GTC | ACC | GAG | CAG |

| D | S | K | D | S | T | Y | S | L | S | S | T | L | T | L | S | K | A | D | Y | E | K | H | K | V | Y | A | C | E | V | T |
|---|---|---|---|---|---|---|---|---|---|---|---|---|---|---|---|---|---|---|---|---|---|---|---|---|---|---|---|---|---|---|
| GAC | AGC | AAG | GAC | TCC | ACC | TAC | AGC | CTG | AGC | AGC | ACC | CTG | ACC | CTG | AGC | AAG | GCC | GAC | TAC | GAG | AAG | CAC | AAG | GTG | TAC | GCC | TGC | GAA | GTG | ACC |

| H | Q | G | L | S | S | P | V | T | K | S | F | N | R | G | E | C |
|---|---|---|---|---|---|---|---|---|---|---|---|---|---|---|---|---|
| CAC | CAG | GGC | CTG | TCC | AGC | CCC | GTG | ACC | AAG | AGC | TTC | AAC | CGG | GGC | GAG | TGC |

Fab Fc kappa light

| Fab | pJPx1 | V | A | A | P | S | V | F | I | F | P | P | S | D | E | Q | L | K | S | G | T | A | S | V | V | C | L |
|---|---|---|---|---|---|---|---|---|---|---|---|---|---|---|---|---|---|---|---|---|---|---|---|---|---|---|---|
| | Ckappa | GTG | GCA | GCA | CCG | AGC | GTG | TTT | ATC | TTT | CCG | CCG | AGC | GAT | GAA | CAG | CTG | AAA | AGC | GGC | ACC | GCC | AGC | GTT | GTT | TGC | CTG |

| L | N | N | F | Y | P | R | E | A | K | V | Q | W | K | V | D | N | A | L | Q | S | G | N | S | Q | E | S | V | T | E | Q |
|---|---|---|---|---|---|---|---|---|---|---|---|---|---|---|---|---|---|---|---|---|---|---|---|---|---|---|---|---|---|---|
| CTG | AAC | AAC | TTT | TAT | CCG | CGC | GAA | GCC | AAA | GTG | CAG | TGG | AAA | GTG | GAT | AAC | GCC | CTG | CAA | AGC | GGC | AAC | AGC | CAG | GAA | AGC | GTT | ACC | GAA | CAG |

| D | S | K | D | S | T | Y | S | L | S | S | T | L | T | L | S | K | A | D | Y | E | K | H | K | V | Y | A | C | E | V | T |
|---|---|---|---|---|---|---|---|---|---|---|---|---|---|---|---|---|---|---|---|---|---|---|---|---|---|---|---|---|---|---|
| GAT | AGC | AAA | GAT | AGC | ACC | TAC | AGC | CTG | AGC | AGC | ACC | CTG | ACC | CTG | AGC | AAA | GCC | GAT | TAT | GAA | AAA | CAT | AAA | GTG | TAT | GCC | TGC | GAA | GTG | ACC |

| H | Q | G | L | S | S | P | V | T | K | S | F | N | R | G | E | A |
|---|---|---|---|---|---|---|---|---|---|---|---|---|---|---|---|---|
| CAT | CAG | GGC | CTG | AGC | AGC | CCA | GTG | ACC | AAA | AGT | TTT | AAC | CGC | GGC | GAG | GCC |

Figure 44

IgG Fc lambda light

| IgG | pJP_h_Iglambda2 | P | K | A | A | P | S | V | T | L | F | P | P | S | S | E | E | L | Q | A | N | K | A | T | L | V | C |
|---|---|---|---|---|---|---|---|---|---|---|---|---|---|---|---|---|---|---|---|---|---|---|---|---|---|---|---|
| | Clambda2 | CCC | AAA | GCC | GCC | CCT | AGC | GTG | ACC | CTG | TTC | CCC | CCA | AGC | AGC | GAG | GAA | CTC | CAG | GCC | AAC | AAG | GCC | ACC | CTC | GTG | TGC |

| L | I | S | D | F | Y | P | G | A | V | T | V | A | W | K | A | D | S | S | P | V | K | A | G | V | E | T | T | T | P | S |
|---|---|---|---|---|---|---|---|---|---|---|---|---|---|---|---|---|---|---|---|---|---|---|---|---|---|---|---|---|---|---|
| CTG | ATC | AGC | GAC | TTC | TAC | CCT | GGC | GCC | GTG | ACC | GTG | GCC | TGG | AAG | GCC | GAT | AGC | AGC | CCT | GTG | AAG | GCC | GGC | GTG | GAA | ACC | ACC | ACC | CCC | AGC |

| K | Q | S | N | N | K | Y | A | A | S | S | Y | L | S | L | T | P | E | Q | W | K | S | H | R | S | Y | S | C | Q | V | T |
|---|---|---|---|---|---|---|---|---|---|---|---|---|---|---|---|---|---|---|---|---|---|---|---|---|---|---|---|---|---|---|
| AAG | CAG | AGC | AAC | AAC | AAA | TAC | GCC | GCC | AGC | AGC | TAC | CTG | AGC | CTG | ACC | CCC | GAG | CAG | TGG | AAG | TCC | CAC | AGA | TCC | TAC | AGC | TGC | CAG | GTC | ACA |

| H | E | G | S | T | V | E | K | T | V | A | P | T | E | C | S |
|---|---|---|---|---|---|---|---|---|---|---|---|---|---|---|---|
| CAC | GAG | GGC | AGC | ACC | GTG | GAA | AAG | ACC | GTG | GCC | CCC | ACC | GAG | TGC | AGC |

Fab Fc lambda light

| Fab | pJPx1 | P | K | A | A | P | S | V | T | L | F | P | P | S | S | E | E | L | Q | A | N | K | A | T | L | V | C |
|---|---|---|---|---|---|---|---|---|---|---|---|---|---|---|---|---|---|---|---|---|---|---|---|---|---|---|---|
| | Clambda2 | CCG | AAA | GCC | GCC | CCA | AGC | GTG | ACC | CTG | TTT | CCG | CCG | AGC | AGC | GAA | GAA | CTG | CAA | GCC | AAC | AAA | GCC | ACC | CTG | GTT | TGC |

| L | I | S | D | F | Y | P | G | A | V | T | V | A | W | K | A | D | S | S | P | V | K | A | G | V | E | T | T | T | P | S |
|---|---|---|---|---|---|---|---|---|---|---|---|---|---|---|---|---|---|---|---|---|---|---|---|---|---|---|---|---|---|---|
| CTG | ATC | AGC | GAT | TTT | TAT | CCG | GGT | GCC | GTG | ACC | GTG | GCC | TGG | AAA | GCC | GAT | AGC | AGC | CCG | GTG | AAA | GCC | GGC | GTG | GAA | ACC | ACC | ACC | CCG | AGC |

| K | Q | S | N | N | K | Y | A | A | S | S | Y | L | S | L | T | P | E | Q | W | K | S | H | R | S | Y | S | C | Q | V | T |
|---|---|---|---|---|---|---|---|---|---|---|---|---|---|---|---|---|---|---|---|---|---|---|---|---|---|---|---|---|---|---|
| AAA | CAG | AGC | AAC | AAC | AAA | TAT | GCC | GCC | AGC | AGC | TAT | CTG | AGC | CTG | ACC | CCG | GAA | CAG | TGG | AAA | AGC | CAT | CGC | AGC | TAT | AGT | TGT | CAA | GTG | ACC |

| H | E | G | S | T | V | E | K | T | V | A | P | T | E | A |
|---|---|---|---|---|---|---|---|---|---|---|---|---|---|---|
| CAT | GAA | GGC | AGC | ACC | GTG | GAA | AAA | ACC | GTG | GCC | CCG | ACC | GAG | GCC |

The nucleic acid sequences shown have been codon optimized

Key: pI values of selected IgGs as described in Example 9.2.4. Each dot represents one unique IgG. Squares indicate the control IgGs as described in Example 9 with the constant CDR3s as described in Ewert S. et al.(2004), J. Mol. Biol. 325, p. 531ff. Bars indicate the Median.

I8 represents VH3-23/VK1-39

I19 represents VH3-23/VL3-1

Key: Apparent midpoints of unfolding of selected IgGs as determined by Differential Scanning Fluorimetry (DSF) as described in Example 9.2.2. Each dot represents one unique IgG. Squares indicate the control IgGs as described in Example 9 with the constant CDR3s as described in Ewert S. et al.(2004), J. Mol. Biol. 325, p. 531ff. Bars indicate the Median.

I8 represents VH3-23/VK1-39

I19 represents VH3-23/VL3-1

Key: Expression yields of selected IgGs as determined by UV-spectrophotometry as described in Example 9.2.1. Each dot represents one unique IgG. Squares indicate the control IgGs as described in Example 9 with the constant CDR3s as described in Ewert S. et al.(2004), J. Mol. Biol. 325, p. 531ff. Bars indicate the Median.

I8 represents VH3-23/VK1-39

I19 represents VH3-23/VL3-1

Key: Monomer content of selected IgGs as determined by size exclusion chromatography (SEC) as described in Example 9.2.3. Each dot represents one unique IgG. Squares indicate the control IgGs as described in Example 9 with the constant CDR3s as described in Ewert S. et al.(2004), J. Mol. Biol. 325, p. 531ff. Bars indicate the Median.

I8 represents VH3-23/VK1-39

I19 represents VH3-23/VL3-1

Figure 49

| No. | Agitation VH | Agitation VL | Initial | after 45 min agitation at RT | after 1,5 h agitation at RT | After 2,5 H agitation at RT | After 3,5 h agitation at RT | After 24 h agitation at RT |
|---|---|---|---|---|---|---|---|---|
| 1 | VH_1_18 | VK_1_39 | 0,041 | 0,049 | 0,054 | 0,056 | 0,059 | 0,1 |
| 2 | VH_1_18 | VK_3_11 | | | | | | |
| 3 | VH_1_18 | VK_3_15 | 0,042 | 0,051 | 0,044 | 0,046 | 0,051 | 0,102 |
| 4 | VH_1_18 | VK_3_20 | 0,037 | 0,04 | 0,041 | 0,043 | 0,043 | 0,06 |
| 5 | VH_1_18 | VL_1-40 | 0,040 | 0,044 | 0,042 | 0,043 | 0,043 | 0,048 |
| 6 | VH_1_18 | VL_1-47 | 0,039 | 0,043 | 0,041 | 0,044 | 0,043 | 0,052 |
| 7 | VH_1_18 | VL_2-23 | 0,041 | 0,054 | 0,042 | 0,044 | 0,041 | 0,050 |
| 8 | VH_1_18 | VL_3-1 | 0,039 | 0,043 | 0,041 | 0,042 | 0,039 | 0,043 |
| 9 | VH_1_46 | VK_1_09 | 0,038 | 0,041 | 0,040 | 0,041 | 0,040 | 0,053 |
| 10 | VH_1_46 | VK_3_15 | 0,037 | 0,041 | 0,040 | 0,039 | 0,040 | 0,044 |
| 11 | VH_1_46 | VL_1-40 | 0,036 | 0,042 | 0,042 | 0,041 | 0,040 | 0,043 |
| 12 | VH_1_46 | VL_1-51 | 0,040 | 0,043 | 0,040 | 0,042 | 0,043 | 0,048 |
| 13 | VH_1_46 | VL_2-23 | 0,042 | 0,047 | 0,044 | 0,043 | 0,047 | 0,051 |
| 14 | VH_1_46 | VL_3-1 | 0,046 | 0,059 | 0,051 | 0,052 | 0,055 | 0,063 |
| 15 | VH_1_46 | VL_3-21 | 0,042 | 0,103 | 0,057 | 0,062 | 0,066 | 0,058 |
| 16 | VH_1_69*01 | VK_1_27 | | | | | | |
| 17 | VH_1_69*01 | VK_3_11 | 0,037 | 0,044 | 0,041 | 0,043 | 0,042 | 0,049 |
| 18 | VH_1_69*01 | VL_1-40 | 0,040 | 0,042 | 0,041 | 0,043 | 0,040 | 0,045 |
| 19 | VH_1_69*01 | VL_1-51 | 0,040 | 0,042 | 0,041 | 0,042 | 0,041 | 0,044 |
| 20 | VH_1_69*01 | VL_3-1 | 0,042 | 0,068 | 0,060 | 0,069 | 0,076 | 0,113 |
| 21 | VH_1_69*01 | VL_3-21 | 0,041 | 0,063 | 0,050 | 0,056 | 0,062 | 0,069 |
| 22 | VH_3_07 | VK_1_12 | 0,041 | 0,043 | 0,042 | 0,044 | 0,043 | 0,052 |
| 23 | VH_3_07 | VK_1_16 | 0,036 | 0,037 | 0,038 | 0,040 | 0,039 | 0,05 |
| 24 | VH_3_07 | VK_1_27 | 0,036 | 0,040 | 0,040 | 0,043 | 0,042 | 0,047 |
| 25 | VH_3_07 | VK_1_39 | 0,043 | 0,045 | 0,045 | 0,045 | 0,058 | 0,052 |
| 26 | VH_3_07 | VK_3_15 | 0,041 | 0,043 | 0,043 | 0,043 | 0,042 | 0,049 |
| 27 | VH_3_07 | VK_3_20 | 0,040 | 0,061 | 0,045 | 0,045 | 0,045 | 0,066 |
| 28 | VH_3_07 | VL_1-47 | 0,038 | 0,041 | 0,040 | 0,040 | 0,040 | 0,045 |
| 29 | VH_3_07 | VL_1-51 | 0,042 | 0,043 | 0,042 | 0,044 | 0,044 | 0,054 |
| 30 | VH_3_07 | VL_2-23 | 0,036 | 0,040 | 0,038 | 0,039 | 0,038 | 0,043 |
| 31 | VH_3_07 | VL_3-1 | 0,037 | 0,041 | 0,041 | 0,042 | 0,041 | 0,051 |
| 32 | VH_3_11 | VK_1_05 | 0,043 | 0,050 | 0,051 | 0,053 | 0,054 | 0,083 |

Figure 50

| No. | Agitation | | Tm after agitation stress | DLS | | Particle Staining | |
|---|---|---|---|---|---|---|---|
| | VH | VL | apparent Tm [°C] | Radius [nm] | % Poly-dispersity | IgGs before stress Categorized from 1-4 | IgGs Post stress categorized from 1-4 |
| 1 | VH_1_18 | VK_1_39 | 79,7 | 5,6 | 21,3 | | 4 |
| 2 | VH_1_18 | VK_3_11 | | | | | |
| 3 | VH_1_18 | VK_3_15 | 81,6 | 60 | 50 | 1,00 | 4,00 |
| 4 | VH_1_18 | VK_3_20 | 78 | 5,6 | 8,9 | | 4 |
| 5 | VH_1_18 | VL_1-40 | 83,9 | 6 | 16 | 1 | 3 |
| 6 | VH_1_18 | VL_1-47 | 84,0 | 6,1 | 21 | 1,00 | 2,5 |
| 7 | VH_1_18 | VL_2-23 | 80,4 | 5,9 | 22 | 1,00 | 3,0 |
| 8 | VH_1_18 | VL_3-1 | 84,7 | 5,5 | 8,5 | 1,00 | 3,0 |
| 9 | VH_1_46 | VK_1_09 | 77,8 | 6 | 23 | 1,00 | 3,5 |
| 10 | VH_1_46 | VK_3_15 | 77,4 | 6 | 36,4 | 1 | 3,5 |
| 11 | VH_1_46 | VL_1-40 | 80,7 | 5,9 | 19,5 | | 3,0 |
| 12 | VH_1_46 | VL_1-51 | 79,4 | 5,4 | 15,5 | 2,50 | 2,0 |
| 13 | VH_1_46 | VL_2-23 | 78,5 | 5,5 | 14,2 | 2,00 | 2,0 |
| 14 | VH_1_46 | VL_3-1 | 76,0 | 60 | 50 | 2,00 | 2,5 |
| 15 | VH_1_46 | VL_3-21 | 74,1 | 5,7 | 19,2 | 1,00 | 2,5 |
| 16 | VH_1_69*01 | VK_1_27 | | | | | |
| 17 | VH_1_69*01 | VK_3_11 | 77,8 | 5,8 | 22,6 | 1,00 | 3,0 |
| 18 | VH_1_69*01 | VL_1-40 | 81,6 | 7,3 | 13,2 | 3,00 | 2,5 |
| 19 | VH_1_69*01 | VL_1-51 | 78,1 | 5,3 | 4,1 | 1 | 2,5 |
| 20 | VH_1_69*01 | VL_3-1 | 79,5 | 60 | 50 | | 3,5 |
| 21 | VH_1_69*01 | VL_3-21 | 76,2 | 6 | 31,6 | 1 | 3,0 |
| 22 | VH_3_07 | VK_1_12 | 78,1 | 5,4 | 22,5 | 2,50 | 2,5 |
| 23 | VH_3_07 | VK_1_16 | 75,2 | 5,3 | 4,7 | | 2 |
| 24 | VH_3_07 | VK_1_27 | 80,2 | 6,2 | 50 | 1 | 1,5 |
| 25 | VH_3_07 | VK_1_39 | 80,0 | 5,3 | 7,1 | 1,00 | 2,5 |
| 26 | VH_3_07 | VK_3_15 | 79,2 | 5,9 | 29 | 2,00 | 3,5 |
| 27 | VH_3_07 | VK_3_20 | 78,3 | 60 | 50 | 1,00 | 2,0 |
| 28 | VH_3_07 | VL_1-47 | 78,8 | 5,5 | 19,3 | 1,00 | 3,0 |
| 29 | VH_3_07 | VL_1-51 | 79,7 | 60 | 50 | 1,00 | 2,5 |
| 30 | VH_3_07 | VL_2-23 | 81,2 | 5,8 | 18,7 | 1 | 3,0 |
| 31 | VH_3_07 | VL_3-1 | 80,9 | 5,7 | 23,8 | 1 | 3,5 |
| 32 | VH_3_11 | VK_1_05 | 74,8 | 60 | 50 | | |

Figure 51

| Agitation | | | Absorption at 320 nm | | | | | |
|---|---|---|---|---|---|---|---|---|
| No. | VH | VL | Initial | after 45 min agitation at RT | after 1,5 h agitation at RT | After 2,5 H agitation at RT | After 3,5 h agiitation at RT | After 24 h agitation at RT |
| 33 | VH_3_11 | VK_1_39 | 0,039 | 0,045 | 0,047 | 0,050 | 0,050 | 0,070 |
| 34 | VH_3_11 | VK_3_15 | 0,042 | 0,048 | 0,048 | 0,052 | 0,053 | 0,099 |
| 35 | VH_3_11 | VL_1-40 | 0,037 | 0,039 | 0,039 | 0,041 | 0,040 | 0,05 |
| 36 | VH_3_11 | VL_1-47 | 0,036 | 0,037 | 0,039 | 0,040 | 0,040 | 0,05 |
| 37 | VH_3_11 | VL_1-51 | 0,040 | 0,043 | 0,041 | 0,041 | 0,042 | 0,045 |
| 38 | VH_3_11 | VL_2-23 | 0,037 | 0,041 | 0,040 | 0,040 | 0,039 | 0,044 |
| 39 | VH_3_15 | VK_1_05 | 0,038 | 0,042 | 0,040 | 0,041 | 0,041 | 0,044 |
| 40 | VH_3_15 | VK_1_06 | 0,040 | 0,039 | 0,040 | 0,042 | 0,045 | 0,07 |
| 41 | VH_3_15 | VK_1_09 | 0,040 | 0,042 | 0,041 | 0,041 | 0,043 | 0,048 |
| 42 | VH_3_15 | VK_1_12 | 0,039 | 0,041 | 0,040 | 0,042 | 0,041 | 0,053 |
| 43 | VH_3_15 | VK_1_16 | 0,039 | 0,044 | 0,045 | 0,049 | 0,049 | 0,096 |
| 44 | VH_3_15 | VK_1_27 | 0,043 | 0,037 | 0,037 | 0,038 | 0,039 | 0,05 |
| 45 | VH_3_15 | VK_3_11 | 0,043 | 0,037 | 0,038 | 0,041 | 0,042 | 0,06 |
| 46 | VH_3_15 | VK_3_15 | 0,038 | 0,046 | 0,048 | 0,052 | 0,054 | 0,101 |
| 47 | VH_3_15 | VL_1-40 | 0,045 | 0,051 | 0,051 | 0,053 | 0,054 | 0,092 |
| 48 | VH_3_15 | VL_1-47 | 0,043 | 0,048 | 0,049 | 0,050 | 0,051 | 0,087 |
| 49 | VH_3_15 | VL_1-51 | 0,035 | 0,041 | 0,042 | 0,043 | 0,044 | 0,07 |
| 50 | VH_3_15 | VL_2-14 | 0,036 | 0,039 | 0,041 | 0,044 | 0,044 | 0,058 |
| 51 | VH_3_21 | VK_1_06 | 0,040 | 0,045 | 0,047 | 0,050 | 0,050 | 0,059 |
| 52 | VH_3_21 | VK_1_12 | 0,036 | 0,041 | 0,042 | 0,042 | 0,042 | 0,05 |
| 53 | VH_3_21 | VK_1_27 | 0,040 | 0,042 | 0,042 | 0,041 | 0,042 | 0,045 |
| 54 | VH_3_21 | VL_2-11 | 0,039 | 0,043 | 0,039 | 0,040 | 0,040 | 0,045 |
| 55 | VH_3_21 | VL_2-14 | 0,038 | 0,040 | 0,040 | 0,041 | 0,040 | 0,045 |
| 56 | VH_3_21 | VL_2-23 | 0,037 | 0,041 | 0,039 | 0,042 | 0,040 | 0,043 |
| 57 | VH_3_21 | VL_3-1 | 0,040 | 0,047 | 0,051 | 0,058 | 0,058 | 0,068 |
| 58 | VH_3_23 | VK_1_39 | 0,037 | 0,043 | 0,043 | 0,045 | 0,046 | 0,051 |
| 59 | VH_3_23 | VK_3_15 | 0,039 | 0,038 | 0,039 | 0,041 | 0,042 | 0,08 |
| 60 | VH_3_23 | VK_3_20 | 0,035 | 0,041 | 0,041 | 0,043 | 0,043 | 0,062 |
| 61 | VH_3_23 | VL_2-11 | 0,035 | 0,040 | 0,040 | 0,043 | 0,043 | 0,053 |
| 62 | VH_3_23 | VL_2-14 | 0,036 | 0,040 | 0,039 | 0,041 | 0,044 | 0,068 |
| 63 | VH_3_23 | VL_2-23 | 0,037 | 0,042 | 0,042 | 0,045 | 0,046 | 0,079 |
| 64 | VH_3_23 | VL_3-1 | 0,037 | 0,040 | 0,039 | 0,039 | 0,038 | 0,043 |

Figure 52

| No. | Agitation VH | VL | Tm after agitation stress apparent Tm [°C] | DLS Radius [nm] | DLS % Poly-dispersity | Particle Staining IgGs before stress Categorized from 1-4 | Particle Staining IgGs Post stress categorized from 1-4 |
|---|---|---|---|---|---|---|---|
| 33 | VH_3_11 | VK_1_39 | 79,2 | 60 | 50 | 2 | 3,5 |
| 34 | VH_3_11 | VK_3_15 | 79,0 | 60 | 50 | 1 | 3,5 |
| 35 | VH_3_11 | VL_1-40 | 80,5 | 5,1 | 3,1 | | 3,0 |
| 36 | VH_3_11 | VL_1-47 | 80,5 | 5,1 | 2,7 | | 4,0 |
| 37 | VH_3_11 | VL_1-51 | 77,1 | 5,4 | 9,9 | 1 | 2,0 |
| 38 | VH_3_11 | VL_2-23 | 74,1 | 5,6 | 22,4 | 1 | 2,5 |
| 39 | VH_3_15 | VK_1_05 | 76,0 | 6 | 24,9 | 2 | 2,0 |
| 40 | VH_3_15 | VK_1_06 | 79,0 | 25 | 50 | | 4,0 |
| 41 | VH_3_15 | VK_1_09 | 81,4 | 60 | 50 | 2,5 | 3,5 |
| 42 | VH_3_15 | VK_1_12 | 79,5 | 5,6 | 17,2 | 2 | 3,5 |
| 43 | VH_3_15 | VK_1_16 | 76,7 | 60 | 50 | 3 | 4,0 |
| 44 | VH_3_15 | VK_1_27 | 77,4 | 6,8 | 25 | | 3,0 |
| 45 | VH_3_15 | VK_3_11 | | 25 | 50 | | 3,0 |
| 46 | VH_3_15 | VK_3_15 | 80,3 | 291 | 23,7 | 1 | 4,0 |
| 47 | VH_3_15 | VL_1-40 | 80,7 | 60 | 50 | 3 | 3,5 |
| 48 | VH_3_15 | VL_1-47 | 77,8 | 60 | 50 | 1 | 3,5 |
| 49 | VH_3_15 | VL_1-51 | | 25 | 50 | | 2,5 |
| 50 | VH_3_15 | VL_2-14 | 75,5 | 60 | 50 | 2 | 3,0 |
| 51 | VH_3_15 | VK_1_06 | 75,5 | 6 | 23,8 | 1 | 2,5 |
| 52 | VH_3_21 | VK_1_12 | | 5,7 | 17,9 | | 2,0 |
| 53 | VH_3_21 | VK_1_27 | 77,6 | 5,5 | 16,9 | 1 | 2,5 |
| 54 | VH_3_21 | VL_2-11 | 79,7 | 6,4 | 31,6 | 2 | 2,5 |
| 55 | VH_3_21 | VL_2-14 | 76,4 | 6 | 24,7 | 1 | 3,0 |
| 56 | VH_3_21 | VL_2-23 | 76,9 | 6 | 25,2 | 1 | 2,5 |
| 57 | VH_3_21 | VL_3-1 | 77,4 | 6,4 | 44,4 | 1 | 3,0 |
| 58 | VH_3_23 | VK_1_39 | 83,4 | | 50,00 | 2 | 3,0 |
| 59 | VH_3_23 | VK_3_15 | | 5,9 | 27,6 | | 4 |
| 60 | VH_3_23 | VK_3_20 | 82,0 | 60,00 | 50,00 | 1 | 3,5 |
| 61 | VH_3_23 | VL_2-11 | 82,5 | 60,00 | 50,00 | 2 | 3,5 |
| 62 | VH_3_23 | VL_2-14 | 78,1 | 60,00 | 50,00 | 2 | 3,5 |
| 63 | VH_3_23 | VL_2-23 | 78,8 | 60,00 | 50,00 | 1 | 3,5 |
| 64 | VH_3_23 | VL_3-1 | 80,9 | 5,70 | 16,20 | 1 | 2,0 |

Figure 53

| No. | Agitation VH | VL | Initial | after 45 min agitation at RT | after 1,5 h agitation at RT | After 2,5 H agitation at RT | After 3,5 h agitiation at RT | After 24 h agitation at RT |
|---|---|---|---|---|---|---|---|---|
| | | | | | Absorption at 320 nm | | | |
| 65 | VH_3_23 | VL_3-21 | 0,040 | 0,041 | 0,040 | 0,041 | 0,043 | 0,045 |
| 66 | VH_3_30 | VK_3_15 | 0,038 | 0,044 | 0,040 | 0,040 | 0,041 | 0,046 |
| 67 | VH_3_30 | VK_3_20 | 0,040 | 0,044 | 0,041 | 0,043 | 0,046 | 0,050 |
| 68 | VH_3_30 | VL_2-23 | 0,037 | 0,040 | 0,039 | 0,039 | 0,039 | 0,043 |
| 69 | VH_3_30 | VL_3-1 | 0,042 | 0,065 | 0,080 | 0,093 | 0,098 | 0,183 |
| 70 | VH_3_30 | VL_3-21 | 0,036 | 0,039 | 0,039 | 0,039 | 0,038 | 0,052 |
| 71 | VH_3_53 | VK_1_39 | 0,036 | 0,040 | 0,041 | 0,042 | 0,041 | 0,047 |
| 72 | VH_3_53 | VK_3_15 | 0,036 | 0,042 | 0,043 | 0,046 | 0,048 | 0,085 |
| 73 | VH_3_53 | VL_2-11 | 0,037 | 0,044 | 0,043 | 0,045 | 0,049 | 0,074 |
| 74 | VH_3_53 | VL_2-23 | 0,035 | 0,042 | 0,043 | 0,047 | 0,047 | 0,082 |
| 75 | VH_3_53 | VL_3-1 | 0,036 | 0,039 | 0,038 | 0,041 | 0,040 | 0,047 |
| 76 | VH_3_74 | VK_1_05 | 0,037 | 0,041 | 0,039 | 0,040 | 0,040 | 0,049 |
| 77 | VH_3_74 | VK_1_06 | 0,035 | 0,039 | 0,038 | 0,038 | 0,038 | 0,043 |
| 78 | VH_3_74 | VK_1_12 | 0,039 | 0,044 | 0,042 | 0,041 | 0,040 | 0,045 |
| 79 | VH_3_74 | VK_1_27 | 0,038 | 0,044 | 0,041 | 0,043 | 0,041 | 0,047 |
| 80 | VH_3_74 | VK_3_20 | 0,036 | 0,038 | 0,038 | 0,040 | 0,039 | 0,044 |
| 81 | VH_3_74 | VL_1-51 | 0,037 | 0,039 | 0,039 | 0,040 | 0,041 | 0,067 |
| 82 | VH_3_74 | VL_3-1 | 0,036 | 0,039 | 0,038 | 0,040 | 0,039 | 0,045 |
| 83 | VH_3_74 | VK_1_39 | 0,036 | 0,039 | 0,037 | 0,037 | 0,038 | 0,038 |
| 84 | VH_5_51 | VL_1-40 | 0,036 | 0,041 | 0,038 | 0,040 | 0,039 | 0,042 |
| 85 | VH_5_51 | VL_1-47 | 0,035 | 0,041 | 0,039 | 0,041 | 0,041 | 0,047 |
| 86 | VH_5_51 | VL_1-51 | 0,037 | 0,044 | 0,043 | 0,045 | 0,046 | 0,059 |
| 87 | VH_5_51 | VL_3-1 | 0,036 | 0,041 | 0,042 | 0,044 | 0,046 | 0,08 |
| 88 | VH_6_1 | VK_1_06 | 0,037 | 0,042 | 0,040 | 0,040 | 0,039 | 0,045 |
| 89 | VH_6_1 | VK_1_09 | 0,039 | 0,061 | 0,042 | 0,043 | 0,040 | 0,046 |
| 90 | VH_6_1 | VK_1_27 | 0,039 | 0,060 | 0,042 | 0,042 | 0,044 | 0,067 |
| 91 | VH_6_1 | VK_3_15 | 0,04 | 0,045 | 0,049 | 0,056 | 0,054 | 0,11 |
| 92 | VH_6_1 | VK_3_20 | 0,038 | 0,044 | 0,039 | 0,039 | 0,043 | 0,052 |
| 93 | VH_6_1 | VL_1-47 | 0,048 | 0,058 | 0,061 | 0,067 | 0,072 | 0,164 |
| 94 | VH_6_1 | VL_1-51 | 0,036 | 0,042 | 0,039 | 0,039 | 0,038 | 0,043 |
| 95 | VH_6_1 | VL_3-1 | 0,048 | 0,056 | 0,051 | 0,053 | 0,052 | 0,061 |

Figure 54

| | Agitation | | Tm after agitation stress | DLS | | Particle Staining | |
|---|---|---|---|---|---|---|---|
| No. | VH | VL | apparent Tm [°C] | Radius [nm] | % Poly-dispersity | IgGs before stress Categorized from 1-4 | IgGs Post stress categorized from 1-4 |
| 65 | VH_3_23 | VL_3-21 | 79,0 | 5,30 | 10,60 | 2 | 2,0 |
| 66 | VH_3_30 | VK_3_15 | 80,9 | 5,70 | 24,60 | 2 | 2,5 |
| 67 | VH_3_30 | VK_3_20 | 80,9 | 6,70 | 50,00 | 2 | 3,0 |
| 68 | VH_3_30 | VL_2-23 | 80,2 | 5,90 | 23,70 | 2 | 2,5 |
| 69 | VH_3_30 | VL_3-1 | 79,5 | 94,00 | 50 | 2 | 4,0 |
| 70 | VH_3_30 | VL_3-21 | 77,8 | 5,70 | 21,60 | 2 | 3,0 |
| 71 | VH_3_53 | VK_1_39 | 74,1 | 5,90 | 24,60 | 1 | 3,0 |
| 72 | VH_3_53 | VK_3_15 | 73,8 | 60,00 | 50,00 | 2 | 3,5 |
| 73 | VH_3_53 | VL_2-11 | 73,8 | 60,00 | 50,00 | 2 | 3,0 |
| 74 | VH_3_53 | VL_2-23 | 69,6 | 60,00 | 50,00 | 2 | 3,5 |
| 75 | VH_3_53 | VL_3-1 | 73,1 | 5,40 | 12,00 | 3 | 2,5 |
| 76 | VH_3_74 | VK_1_05 | 75,5 | 6,10 | 42,20 | 2 | 2,5 |
| 77 | VH_3_74 | VK_1_06 | 77,8 | 5,50 | 18,10 | 2,5 | 2,0 |
| 78 | VH_3_74 | VK_1_12 | 79,3 | 5,30 | 12,60 | 2 | 2,0 |
| 79 | VH_3_74 | VK_1_27 | 78,1 | 5,50 | 15,70 | 2 | 2,0 |
| 80 | VH_3_74 | VK_3_20 | 79,7 | 60,00 | 50,00 | 2 | 2,5 |
| 81 | VH_3_74 | VL_1-51 | 80,7 | 60,00 | 50,00 | 2,5 | 3,0 |
| 82 | VH_3_74 | VL_3-1 | 79,0 | 5,50 | 15,60 | 2 | 2,5 |
| 83 | VH_3_74 | VK_1_39 | 73,6 | 5,30 | 10,50 | 1,5 | 3,0 |
| 84 | VH_5_51 | VL_1-40 | 77,6 | 5,70 | 23,10 | 2,5 | 2,5 |
| 85 | VH_5_51 | VL_1-47 | 76,4 | 5,80 | 21,80 | 2 | 3,0 |
| 86 | VH_5_51 | VL_1-51 | 75,7 | 5,60 | 22,70 | 1 | 2,5 |
| 87 | VH_5_51 | VL_3-1 | 77,1 | 7,4 | 24,4 | | 2,5 |
| 88 | VH_6_1 | VK_1_06 | 73,6 | 5,80 | 17,40 | 2,5 | 2,5 |
| 89 | VH_6_1 | VK_1_09 | 79,6 | 5,30 | 10,50 | 3 | 2,5 |
| 90 | VH_6_1 | VK_1_27 | 80,0 | 6,30 | 22,60 | 2 | 3,5 |
| 91 | VH_6_1 | VK_3_15 | 78,4 | 8,8 | 26,8 | | 4,0 |
| 92 | VH_6_1 | VK_3_20 | 77,1 | 60,00 | 50,00 | 2 | 3,0 |
| 93 | VH_6_1 | VL_1-47 | 73,6 | 60,00 | 44,6 | 2,5 | 3,0 |
| 94 | VH_6_1 | VL_1-51 | 76,7 | 5,70 | 22,80 | 1 | 2,5 |
| 95 | VH_6_1 | VL_3-1 | 69,6 | 40,00 | 50,00 | 2 | 2,0 |

Figure 55

| Cumulative Score Calculation | | | Score Absorption data acid treatment | | | | Score DLS Data before and after acid treatment | | | | Score Particle staining before and after acid | |
|---|---|---|---|---|---|---|---|---|---|---|---|---|
| No. | VH | VL | Initial | 15 min Acid treatment | 100 min Acid treatment | After neutralization | Initial Radius [nm] | Initial % Poly-dispersity | After acid treatment Radius [nm] | After acid treatment % Polydispersity | IgGs before Categorized from 1-4 | IgGs Post acid categorized from 1-4 |
| 1 | VH_1_18 | VK_1_39 | 75 | 0 | 25 | 75 | 100 | 100 | 100 | 100 | 100 | 25 |
| 2 | VH_1_18 | VK_3_11 | | | | | | | | | | |
| 3 | VH_1_18 | VK_3_15 | 100 | 25 | 75 | 100 | 100 | 100 | 100 | 100 | 100 | 75 |
| 4 | VH_1_18 | VK_3_20 | 100 | 75 | 75 | 100 | 100 | 100 | 100 | 100 | 75 | 25 |
| 5 | VH_1_18 | VL_1_40 | 100 | 25 | 100 | 100 | 100 | 100 | 100 | 100 | 100 | 75 |
| 6 | VH_1_18 | VL_1_47 | 100 | 25 | 75 | 100 | 100 | 100 | 100 | 100 | 100 | 75 |
| 7 | VH_1_18 | VL_2-23 | 100 | 25 | 75 | 100 | 100 | 100 | 100 | 100 | 100 | 100 |
| 8 | VH_1_18 | VL_3-1 | 100 | 25 | 75 | 100 | 100 | 100 | 100 | 100 | 100 | 100 |
| 9 | VH_1_46 | VK_1_09 | 100 | 25 | 25 | 75 | 100 | 100 | 100 | 100 | 100 | 100 |
| 10 | VH_1_46 | VK_3_15 | 100 | 25 | 75 | 100 | 100 | 100 | 100 | 100 | 100 | 100 |
| 11 | VH_1_46 | VL_1-40 | 100 | 25 | 75 | 100 | 100 | 100 | 100 | 100 | 100 | 25 |
| 12 | VH_1_46 | VL_1-51 | 100 | 75 | 100 | 100 | 100 | 100 | 100 | 100 | 25 | 75 |
| 13 | VH_1_46 | VL_2-23 | 100 | 25 | 75 | 100 | 100 | 100 | 100 | 100 | 75 | 0 |
| 14 | VH_1_46 | VL_3-1 | 75 | 0 | 0 | 0 | 50 | 50 | 25 | 0 | 75 | 25 |
| 15 | VH_1_46 | VL_3-21 | 100 | 75 | 75 | 75 | 50 | 50 | 50 | 0 | 100 | 25 |
| 16 | VH_1_69*01 | VK_1_27 | | | | | | | | | | |
| 17 | VH_1_69*01 | VK_3_11 | 100 | 25 | 100 | 100 | 100 | 100 | 100 | 100 | 100 | 75 |
| 18 | VH_1_69*01 | VL_1-40 | 100 | 25 | 25 | 75 | 50 | 50 | 50 | 75 | 25 | 25 |
| 19 | VH_1_69*01 | VL_1-51 | 100 | 25 | 75 | 75 | 100 | 100 | 100 | 100 | 100 | 100 |
| 20 | VH_1_69*01 | VL_3-1 | 75 | 25 | 25 | 25 | 50 | 50 | 75 | 0 | 100 | 25 |
| 21 | VH_1_69*01 | VL_3-21 | 75 | 0 | 0 | 100 | 100 | 100 | 100 | 75 | 100 | 100 |
| 22 | VH_3_07 | VK_1_12 | 100 | 25 | 75 | 100 | 100 | 100 | 100 | 100 | 100 | 25 |
| 23 | VH_3_07 | VK_1_16 | 100 | 25 | 75 | 100 | 100 | 100 | 100 | 100 | 25 | 100 |
| 24 | VH_3_07 | VK_1_27 | 100 | 75 | 75 | 75 | 100 | 100 | 100 | 100 | 100 | 75 |
| 25 | VH_3_07 | VK_1_39 | 100 | 100 | 100 | 100 | 100 | 100 | 100 | 100 | 100 | 0 |
| 26 | VH_3_07 | VK_3_15 | 100 | 100 | 100 | 100 | 100 | 100 | 100 | 75 | 75 | 25 |
| 27 | VH_3_07 | VK_3_20 | 100 | 75 | 75 | 75 | 100 | 100 | 100 | 0 | 100 | 75 |
| 28 | VH_3_07 | VL_1-47 | 100 | 100 | 100 | 100 | 100 | 100 | 100 | 100 | 100 | 100 |
| 29 | VH_3_07 | VL_1-51 | 100 | 75 | 75 | 100 | 100 | 100 | 100 | 100 | 100 | 75 |
| 30 | VH_3_07 | VL_2-23 | 75 | 25 | 75 | 75 | 100 | 100 | 100 | 100 | 100 | 100 |
| 31 | VH_3_07 | VL_3-1 | 100 | 75 | 100 | 100 | 100 | 100 | 100 | 100 | 100 | 100 |
| 32 | VH_3_11 | VK_1_05 | 100 | 100 | 100 | 100 | 100 | 100 | 100 | 100 | 100 | 75 |

Figure 56

| Cumulative Score Calculation | | | Score Absorption data during and after agitation | | | | | | Score DLS data after agitation | | Particle staining | Cumulative Score |
|---|---|---|---|---|---|---|---|---|---|---|---|---|
| No. | VH | VL | Inital | after 45 min agitation at RT | after 1,5 h agitation at RT | After 2,5 H agitation at RT | After 3,5 h agitiation n at RT | After 24 h agitation at RT | Radius [nm] | % Poly-dispersity | Particle staining after agitation | |
| 1 | VH_1_18 | VK_1_39 | 75 | 25 | 25 | 25 | 25 | 0 | 100 | 75 | 0 | 1050 |
| 2 | VH_1_18 | VK_3_11 | | | | | | | | | 0 | 1100 |
| 3 | VH_1_18 | VK_3_15 | 75 | 25 | 75 | 25 | 25 | 0 | 0 | 0 | 0 | 1450 |
| 4 | VH_1_18 | VK_3_20 | 100 | 75 | 75 | 75 | 75 | 25 | 100 | 100 | 25 | 1525 |
| 5 | VH_1_18 | VL_1-40 | 100 | 75 | 75 | 75 | 75 | 25 | 100 | 75 | 25 | 1450 |
| 6 | VH_1_18 | VL_1-47 | 100 | 25 | 75 | 75 | 75 | 25 | 50 | 75 | 25 | 1450 |
| 7 | VH_1_18 | VL_2-23 | 75 | 75 | 75 | 75 | 75 | 75 | 100 | 100 | 25 | 1600 |
| 8 | VH_1_18 | VL_3-1 | 100 | 75 | 75 | 75 | 75 | 25 | 100 | 75 | 0 | 1475 |
| 9 | VH_1_46 | VK_1_09 | 100 | 75 | 100 | 75 | 100 | 75 | 100 | 25 | 0 | 1550 |
| 10 | VH_1_46 | VK_3_15 | 100 | 75 | 100 | 100 | 75 | 75 | 100 | 75 | 25 | 1600 |
| 11 | VH_1_46 | VL_1-40 | 100 | 75 | 75 | 75 | 100 | 75 | 100 | 75 | 75 | 1500 |
| 12 | VH_1_46 | VL_1-51 | 100 | 75 | 75 | 75 | 75 | 25 | 100 | 100 | 75 | 1450 |
| 13 | VH_1_46 | VL_2-23 | 75 | 25 | 25 | 25 | 25 | 0 | 0 | 0 | 25 | 400 |
| 14 | VH_1_46 | VL_3-1 | 25 | 25 | 25 | 0 | 25 | 25 | 100 | 75 | 25 | 875 |
| 15 | VH_1_46 | VL_3-21 | 75 | 0 | 0 | 0 | 0 | 0 | | | | |
| 16 | VH_1_69*01 | VK_1_27 | | 75 | 75 | 75 | 75 | 25 | 100 | 75 | 25 | 1525 |
| 17 | VH_1_69*01 | VK_3_11 | 100 | 75 | 75 | 75 | 75 | 25 | 50 | 100 | 25 | 1150 |
| 18 | VH_1_69*01 | VL_1-40 | 100 | 75 | 75 | 75 | 75 | 75 | 100 | 100 | 25 | 1575 |
| 19 | VH_1_69*01 | VL_1-51 | 100 | 75 | 75 | 75 | 75 | 25 | | | 25 | 575 |
| 20 | VH_1_69*01 | VL_3-1 | 75 | 0 | 0 | 0 | 0 | 0 | 100 | 25 | 0 | 1025 |
| 21 | VH_1_69*01 | VL_3-21 | 75 | 0 | 25 | 25 | 0 | 0 | 100 | 75 | 25 | 1425 |
| 22 | VH_3_07 | VK_1_12 | 75 | 75 | 75 | 75 | 75 | 75 | 100 | 100 | 25 | 1575 |
| 23 | VH_3_07 | VK_1_16 | 100 | 100 | 100 | 100 | 100 | 25 | 50 | 0 | 75 | 1450 |
| 24 | VH_3_07 | VK_1_27 | 100 | 75 | 75 | 75 | 75 | 25 | 100 | 100 | 0 | 1450 |
| 25 | VH_3_07 | VK_1_39 | 75 | 25 | 25 | 25 | 25 | 25 | 100 | 100 | 100 | 1500 |
| 26 | VH_3_07 | VK_3_15 | 75 | 75 | 75 | 75 | 75 | 25 | 100 | 75 | 25 | 1500 |
| 27 | VH_3_07 | VK_3_20 | 100 | 0 | 0 | 0 | 25 | 0 | 0 | 0 | 0 | 1175 |
| 28 | VH_3_07 | VL_1_47 | 75 | 75 | 75 | 75 | 100 | 25 | 100 | 75 | 75 | 1700 |
| 29 | VH_3_07 | VL_1-51 | 75 | 75 | 75 | 75 | 75 | 25 | 0 | 0 | 25 | 1325 |
| 30 | VH_3_07 | VL_2-23 | 100 | 75 | 100 | 100 | 100 | 75 | 100 | 75 | 25 | 1600 |
| 31 | VH_3_07 | VL_3-1 | 100 | 75 | 75 | 75 | 75 | 25 | 100 | 75 | 25 | 1600 |
| 32 | VH_3_11 | VK_1_05 | 75 | 25 | 25 | 25 | 25 | 0 | 0 | 0 | 0 | 1150 |

Figure 57

| | Cumulative Score Calculation | | Score Absorption data acid treatment | | | | Score DLS Data before and after acid treatment | | | | Score Particle staining before and after acid treatment | |
|---|---|---|---|---|---|---|---|---|---|---|---|---|
| No. | VH | VL | Initial | 15 min Acid treatment | 100 min Acid treatment | After neutralization | Initial Radius [nm] | Initial % Poly-dispersity | After acid treatment Radius [nm] | After acid treatment % Polydispersity | IgGs before Categorized from 1-4 | IgGs Post acid categorized from 1-4 |
| 33 | VH_3_11 | VK_1_39 | 100 | 75 | 100 | 75 | 100 | 100 | 100 | 75 | 75 | 75 |
| 34 | VH_3_11 | VK_3_15 | 75 | 75 | 75 | 75 | 100 | 100 | 100 | 100 | 100 | 75 |
| 35 | VH_3_11 | VL_1_40 | 100 | 25 | 25 | 75 | 100 | 100 | 100 | 75 | 100 | 100 |
| 36 | VH_3_11 | VL_1-47 | 100 | 75 | 75 | 75 | 100 | 100 | 50 | 100 | 100 | 100 |
| 37 | VH_3_11 | VL_1-51 | 100 | 75 | 100 | 100 | 100 | 100 | 100 | 100 | 100 | 100 |
| 38 | VH_3_11 | VL_2-23 | 100 | 100 | 100 | 100 | 100 | 100 | 100 | 100 | 100 | 100 |
| 39 | VH_3_15 | VK_1_05 | 100 | 25 | 75 | 75 | 100 | 100 | 100 | 100 | 75 | 75 |
| 40 | VH_3_15 | VK_1_06 | 100 | 75 | 75 | 75 | 100 | 100 | 100 | 100 | 100 | 75 |
| 41 | VH_3_15 | VK_1_09 | 100 | 75 | 75 | 100 | 50 | 75 | 100 | 100 | 25 | 75 |
| 42 | VH_3_15 | VK_1_12 | 100 | 100 | 100 | 75 | 100 | 100 | 100 | 100 | 75 | 75 |
| 43 | VH_3_15 | VK_1_16 | 100 | 25 | 75 | 75 | 100 | 100 | 100 | 100 | 25 | 75 |
| 44 | VH_3_15 | VK_1_27 | 75 | 25 | 25 | 100 | 100 | 100 | 100 | 100 | 100 | 75 |
| 45 | VH_3_15 | VK_3_11 | 75 | 25 | 25 | 75 | 100 | 100 | 75 | 75 | 75 | 25 |
| 46 | VH_3_15 | VK_3_15 | 75 | 25 | 25 | 75 | 100 | 100 | 100 | 100 | 100 | 100 |
| 47 | VH_3_15 | VL_1-40 | 100 | 100 | 100 | 100 | 100 | 100 | 100 | 100 | 25 | 75 |
| 48 | VH_3_15 | VL_1-47 | 100 | 75 | 75 | 100 | 100 | 100 | 100 | 75 | 100 | 75 |
| 49 | VH_3_15 | VL_1-51 | 100 | 25 | 25 | 100 | 100 | 100 | 100 | 100 | 100 | 100 |
| 50 | VH_3_15 | VL_2-14 | 100 | 100 | 100 | 100 | 100 | 100 | 75 | 75 | 75 | 75 |
| 51 | VH_3_21 | VK_1_06 | 100 | 75 | 75 | 75 | 100 | 100 | 100 | 100 | 100 | 25 |
| 52 | VH_3_21 | VK_1_12 | 100 | 75 | 75 | 100 | 100 | 100 | 100 | 75 | 25 | 75 |
| 53 | VH_3_21 | VK_1_27 | 100 | 75 | 25 | 25 | 100 | 100 | 100 | 100 | 100 | 75 |
| 54 | VH_3_21 | VL_2-11 | 100 | 25 | 25 | 75 | 100 | 100 | 100 | 100 | 75 | 75 |
| 55 | VH_3_21 | VL_2-14 | 100 | 25 | 25 | 75 | 100 | 100 | 100 | 100 | 100 | 100 |
| 56 | VH_3_21 | VL_2-23 | 100 | 75 | 75 | 100 | 100 | 100 | 100 | 100 | 100 | 75 |
| 57 | VH_3_21 | VL_3-1 | 100 | 25 | 25 | 25 | 50 | 100 | 100 | 0 | 100 | 75 |
| 58 | VH_3_23 | VK_1_39 | 100 | 75 | 75 | 100 | 100 | 100 | 100 | 100 | 100 | 75 |
| 59 | VH_3_23 | VK_3_15 | 100 | 25 | 25 | 25 | 100 | 100 | 100 | 100 | 100 | 25 |
| 60 | VH_3_23 | VK_3_20 | 100 | 75 | 100 | 100 | 100 | 100 | 100 | 100 | 100 | 75 |
| 61 | VH_3_23 | VL_2-11 | 100 | 75 | 100 | 100 | 100 | 100 | 100 | 100 | 75 | 75 |
| 62 | VH_3_23 | VL_2-14 | 100 | 100 | 100 | 100 | 100 | 100 | 100 | 100 | 75 | 75 |
| 63 | VH_3_23 | VL_2-23 | 100 | 100 | 100 | 100 | 100 | 100 | 100 | 100 | 100 | 75 |
| 64 | VH_3_23 | VL_3-1 | 100 | 75 | 100 | 75 | 100 | 100 | 100 | 100 | 100 | 75 |

Figure 58

| Cumulative Score Calculation | | | Score Absorption data during and after agitation | | | | | | Score DLS data after agitation | | Particle staining | Cumulative Score |
|---|---|---|---|---|---|---|---|---|---|---|---|---|
| No. | VH | VL | Initial | after 45 min agitation at RT | after 1,5 h agitation at RT | After 2,5 H agitation at RT | After 3,5 h agitation at RT | After 24 h agitation at RT | Radius [nm] | % Poly-dispersity | Particle staining after agitation | |
| 33 | VH_3_11 | VK_1_39 | 100 | 25 | 25 | 25 | 25 | 0 | 0 | 0 | 0 | 1075 |
| 34 | VH_3_11 | VK_3_15 | 75 | 25 | 25 | 25 | 25 | 0 | 0 | 0 | 0 | 1050 |
| 35 | VH_3_11 | VL_1-40 | 100 | 100 | 100 | 75 | 100 | 25 | 100 | 100 | 25 | 1550 |
| 36 | VH_3_11 | VL_1-47 | 100 | 100 | 100 | 100 | 75 | 25 | 100 | 100 | 0 | 1550 |
| 37 | VH_3_11 | VL_1-51 | 100 | 75 | 75 | 75 | 75 | 75 | 100 | 100 | 75 | 1675 |
| 38 | VH_3_11 | VL_2-23 | 100 | 75 | 100 | 100 | 100 | 75 | 100 | 75 | 25 | 1750 |
| 39 | VH_3_15 | VK_1_05 | 100 | 75 | 75 | 75 | 75 | 75 | 100 | 75 | 75 | 1575 |
| 40 | VH_3_15 | VK_1_06 | 100 | 100 | 100 | 75 | 75 | 0 | 25 | 0 | 0 | 1400 |
| 41 | VH_3_15 | VK_1_09 | 75 | 75 | 75 | 75 | 75 | 25 | 0 | 0 | 0 | 1175 |
| 42 | VH_3_15 | VK_1_12 | 100 | 100 | 100 | 75 | 75 | 25 | 100 | 75 | 0 | 1575 |
| 43 | VH_3_15 | VK_1_16 | 100 | 75 | 75 | 25 | 25 | 0 | 0 | 0 | 0 | 1025 |
| 44 | VH_3_15 | VK_1_27 | 75 | 100 | 100 | 100 | 100 | 25 | 50 | 75 | 25 | 1450 |
| 45 | VH_3_15 | VK_3_11 | 75 | 100 | 100 | 75 | 75 | 0 | 25 | 0 | 25 | 1225 |
| 46 | VH_3_15 | VK_3_15 | 100 | 25 | 25 | 25 | 25 | 0 | 25 | 75 | 0 | 1025 |
| 47 | VL_1-40 | VL_1-40 | 75 | 25 | 25 | 25 | 25 | 0 | 0 | 0 | 0 | 1000 |
| 48 | VH_3_15 | VL_1-47 | 75 | 75 | 75 | 75 | 75 | 0 | 0 | 0 | 0 | 1150 |
| 49 | VH_3_15 | VL_1-51 | 100 | 75 | 75 | 75 | 75 | 0 | 25 | 0 | 25 | 1275 |
| 50 | VH_3_15 | VL_2-14 | 100 | 100 | 100 | 75 | 75 | 25 | 0 | 0 | 25 | 1425 |
| 51 | VH_3_21 | VK_1_06 | 100 | 25 | 25 | 25 | 25 | 25 | 100 | 75 | 25 | 1300 |
| 52 | VH_3_21 | VK_1_12 | 100 | 75 | 75 | 75 | 75 | 75 | 100 | 75 | 75 | 1500 |
| 53 | VH_3_21 | VK_1_27 | 100 | 75 | 100 | 75 | 75 | 75 | 100 | 75 | 25 | 1475 |
| 54 | VH_3_21 | VL_2-11 | 100 | 75 | 75 | 75 | 75 | 25 | 50 | 25 | 25 | 1375 |
| 55 | VH_3_21 | VL_2-14 | 100 | 100 | 100 | 75 | 75 | 0 | 100 | 75 | 25 | 1525 |
| 56 | VH_3_21 | VL_2-23 | 100 | 75 | 75 | 75 | 75 | 25 | 100 | 75 | 25 | 1650 |
| 57 | VH_3_21 | VL_3-1 | 100 | 25 | 25 | 25 | 25 | 0 | 50 | 0 | 25 | 675 |
| 58 | VH_3_23 | VK_1_39 | 100 | 75 | 75 | 75 | 75 | 25 | 0 | 0 | 25 | 1250 |
| 59 | VH_3_23 | VK_3_15 | 100 | 100 | 100 | 75 | 75 | 0 | 100 | 75 | 0 | 1375 |
| 60 | VH_3_23 | VK_3_20 | 100 | 75 | 75 | 75 | 75 | 0 | 0 | 0 | 0 | 1300 |
| 61 | VH_3_23 | VL_2-11 | 100 | 100 | 75 | 75 | 75 | 25 | 0 | 0 | 0 | 1375 |
| 62 | VH_3_23 | VL_2-14 | 100 | 75 | 100 | 75 | 75 | 0 | 0 | 0 | 0 | 1375 |
| 63 | VH_3_23 | VL_2-23 | 100 | 75 | 75 | 75 | 25 | 0 | 0 | 0 | 0 | 1325 |
| 64 | VH_3_23 | VL_3-1 | 100 | 75 | 100 | 100 | 100 | 75 | 100 | 75 | 75 | 1750 |

Figure 59

| Cumulative Score Calculation | | | Score Absorption data acid treatment | | | | Score DLS Data before and after acid treatment | | | | Score Particle staining before and after acid treatment | |
|---|---|---|---|---|---|---|---|---|---|---|---|---|
| No. | VH | VL | Initial | 15 min Acid treatment | 100 min Acid treatment | After neutralization | Initial Radius [nm] | Initial % Poly-dispersity | After acid treatment Radius [nm] | After acid treatment % Polydispersity | IgGs before Categorized from 1-4 | IgGs Post acid categorized from 1-4 |
| 65 | VH_3_23 | VL_3-21 | 100 | 75 | 100 | 100 | 100 | 100 | 100 | 100 | 75 | 100 |
| 66 | VH_3_30 | VK_3_15 | 100 | 100 | 100 | 100 | 100 | 100 | 100 | 100 | 75 | 75 |
| 67 | VH_3_30 | VK_3_20 | 100 | 75 | 75 | 75 | 100 | 100 | 100 | 100 | 75 | 25 |
| 68 | VH_3_30 | VL_2-23 | 100 | 75 | 100 | 100 | 100 | 100 | 100 | 100 | 75 | 100 |
| 69 | VH_3_30 | VL_3-1 | 100 | 25 | 25 | 25 | 50 | 50 | 50 | 0 | 75 | 75 |
| 70 | VH_3_30 | VL_3-21 | 100 | 75 | 75 | 75 | 100 | 100 | 100 | 100 | 75 | 75 |
| 71 | VH_3_53 | VK_1_39 | 75 | 25 | 25 | 25 | 100 | 100 | 100 | 100 | 75 | 75 |
| 72 | VH_3_53 | VK_3_15 | 100 | 75 | 100 | 100 | 100 | 100 | 100 | 100 | 100 | 100 |
| 73 | VH_3_53 | VL_2-11 | 100 | 100 | 75 | 75 | 100 | 100 | 100 | 100 | 75 | 75 |
| 74 | VH_3_53 | VL_2-23 | 100 | 75 | 100 | 100 | 100 | 100 | 100 | 100 | 75 | 100 |
| 75 | VH_3_53 | VL_3-1 | 100 | 75 | 100 | 100 | 100 | 100 | 100 | 75 | 25 | 25 |
| 76 | VH_3_74 | VK_1_05 | 100 | 75 | 75 | 75 | 100 | 100 | 100 | 100 | 75 | 100 |
| 77 | VH_3_74 | VK_1_06 | 100 | 100 | 100 | 100 | 100 | 100 | 100 | 100 | 25 | 75 |
| 78 | VH_3_74 | VK_1_12 | 100 | 75 | 100 | 100 | 100 | 100 | 100 | 100 | 75 | 100 |
| 79 | VH_3_74 | VK_1_27 | 100 | 25 | 25 | 25 | 100 | 100 | 100 | 75 | 75 | 75 |
| 80 | VH_3_74 | VK_3_20 | 100 | 100 | 100 | 100 | 100 | 100 | 100 | 100 | 75 | 75 |
| 81 | VH_3_74 | VL_1-51 | 100 | 75 | 75 | 75 | 100 | 100 | 100 | 100 | 75 | 75 |
| 82 | VH_3_74 | VL_3-1 | 100 | 75 | 100 | 100 | 100 | 100 | 100 | 100 | 75 | 75 |
| 83 | VH_5_51 | VL_1_39 | 100 | 25 | 75 | 75 | 100 | 100 | 75 | 100 | 100 | 75 |
| 84 | VH_5_51 | VL_1-40 | 100 | 75 | 100 | 100 | 100 | 100 | 100 | 100 | 25 | 75 |
| 85 | VH_5_51 | VL_1-47 | 100 | 25 | 25 | 25 | 100 | 100 | 100 | 100 | 75 | 25 |
| 86 | VH_5_51 | VL_1-51 | 100 | 75 | 75 | 75 | 100 | 100 | 100 | 75 | 100 | 25 |
| 87 | VH_5_51 | VL_3-1 | 100 | 25 | 25 | 25 | 100 | 100 | 100 | 100 | 100 | 25 |
| 88 | VH_6_1 | VK_1_06 | 100 | 100 | 100 | 100 | 100 | 100 | 100 | 100 | 25 | 100 |
| 89 | VH_6_1 | VK_1_09 | 100 | 75 | 75 | 75 | 100 | 100 | 100 | 100 | 25 | 100 |
| 90 | VH_6_1 | VK_1_27 | 100 | 100 | 100 | 100 | 100 | 100 | 100 | 100 | 75 | 100 |
| 91 | VH_6_1 | VK_3_15 | 75 | 25 | 25 | 25 | 100 | 100 | 100 | 100 | 100 | 100 |
| 92 | VH_6_1 | VK_3_20 | 100 | 100 | 100 | 100 | 100 | 100 | 100 | 100 | 75 | 75 |
| 93 | VH_6_1 | VL_1-47 | 25 | 0 | 0 | 0 | 0 | 0 | 0 | 0 | 25 | 0 |
| 94 | VH_6_1 | VL_1-51 | 100 | 100 | 100 | 100 | 25 | 100 | 100 | 75 | 100 | 100 |
| 95 | VH_6_1 | VL_3-1 | 25 | 0 | 0 | 0 | 0 | 25 | 25 | 0 | 75 | 0 |

Figure 60

| Cumulative Score Calculation | | | Score Absorption data during and after agitation | | | | | | Score DLS data after agitation | | | Particle staining | Cumulative Score |
|---|---|---|---|---|---|---|---|---|---|---|---|---|---|
| No. | VH | VL | Inital | after 45 min agitation at RT | after 1,5 h agitation at RT | After 2,5 H agitation at RT | After 3,5 h agitiation at RT | After 24 h agitation at RT | Radius [nm] | % Poly-dispersity | | Particle staining after agitation | |
| 65 | VH_3_23 | VL_3-21 | 100 | 75 | 75 | 75 | 75 | 75 | 100 | 100 | | 75 | 1700 |
| 66 | VH_3_30 | VK_3_15 | 100 | 75 | 75 | 75 | 75 | 25 | 100 | 75 | | 25 | 1575 |
| 67 | VH_3_30 | VK_3_20 | 100 | 75 | 75 | 75 | 25 | 25 | 50 | 0 | | 25 | 1275 |
| 68 | VH_3_30 | VL_2-23 | 100 | 100 | 100 | 100 | 100 | 75 | 100 | 75 | | 25 | 1725 |
| 69 | VH_3_30 | VL_3-1 | 75 | 0 | 0 | 0 | 0 | 0 | 25 | 0 | | 0 | 525 |
| 70 | VH_3_30 | VL_3-21 | 100 | 100 | 100 | 100 | 100 | 25 | 100 | 75 | | 25 | 1600 |
| 71 | VH_3_53 | VK_1_39 | 100 | 75 | 75 | 75 | 75 | 25 | 100 | 75 | | 25 | 1375 |
| 72 | VH_3_53 | VK_3_15 | 100 | 75 | 75 | 25 | 25 | 0 | 0 | 0 | | 0 | 1275 |
| 73 | VH_3_53 | VL_2-11 | 100 | 75 | 75 | 25 | 25 | 0 | 0 | 0 | | 25 | 1275 |
| 74 | VH_3_53 | VL_2-23 | 100 | 75 | 75 | 75 | 75 | 0 | 0 | 0 | | 0 | 1250 |
| 75 | VH_3_53 | VL_3-1 | 100 | 100 | 100 | 75 | 100 | 25 | 100 | 100 | | 25 | 1475 |
| 76 | VH_3_74 | VK_1_05 | 100 | 75 | 75 | 75 | 75 | 25 | 50 | 0 | | 25 | 1450 |
| 77 | VH_3_74 | VK_1_06 | 100 | 100 | 100 | 100 | 100 | 75 | 100 | 75 | | 75 | 1725 |
| 78 | VH_3_74 | VK_1_12 | 100 | 75 | 75 | 75 | 75 | 25 | 100 | 100 | | 75 | 1650 |
| 79 | VH_3_74 | VK_1_27 | 100 | 100 | 100 | 100 | 100 | 25 | 100 | 75 | | 75 | 1525 |
| 80 | VH_3_74 | VK_3_20 | 100 | 100 | 100 | 100 | 100 | 75 | 0 | 0 | | 25 | 1525 |
| 81 | VH_3_74 | VL_1-51 | 100 | 100 | 100 | 75 | 75 | 0 | 0 | 0 | | 25 | 1325 |
| 82 | VH_3_74 | VL_3-1 | 100 | 100 | 100 | 100 | 100 | 75 | 100 | 75 | | 25 | 1650 |
| 83 | VH_5_51 | VK_1_39 | 100 | 100 | 100 | 100 | 100 | 100 | 100 | 100 | | 25 | 1650 |
| 84 | VH_5_51 | VL_1_40 | 100 | 75 | 75 | 75 | 75 | 75 | 100 | 75 | | 25 | 1625 |
| 85 | VH_5_51 | VL_1_47 | 100 | 75 | 75 | 75 | 75 | 25 | 100 | 75 | | 25 | 1575 |
| 86 | VH_5_51 | VL_1-51 | 100 | 75 | 25 | 25 | 25 | 0 | 100 | 75 | | 25 | 1375 |
| 87 | VH_5_51 | VL_3-1 | 100 | 75 | 100 | 75 | 75 | 0 | 50 | 75 | | 25 | 1300 |
| 88 | VH_6_1 | VK_1_06 | 100 | 75 | 75 | 75 | 75 | 25 | 100 | 75 | | 25 | 1600 |
| 89 | VH_6_1 | VK_1_09 | 100 | 0 | 75 | 75 | 75 | 25 | 100 | 100 | | 25 | 1450 |
| 90 | VH_6_1 | VK_1_27 | 100 | 25 | 75 | 75 | 75 | 0 | 50 | 75 | | 0 | 1450 |
| 91 | VH_6_1 | VK_3_15 | 75 | 25 | 25 | 25 | 25 | 0 | 50 | 0 | | 0 | 1075 |
| 92 | VH_6_1 | VK_3_20 | 100 | 75 | 100 | 100 | 75 | 25 | 0 | 0 | | 25 | 1450 |
| 93 | VH_6_1 | VL_1_47 | 25 | 25 | 0 | 0 | 0 | 0 | 0 | 0 | | 25 | 150 |
| 94 | VH_6_1 | VL_1-51 | 100 | 75 | 100 | 100 | 100 | 75 | 100 | 75 | | 25 | 1725 |
| 95 | VH_6_1 | VL_3-1 | 25 | 25 | 25 | 25 | 25 | 0 | 25 | 0 | | 75 | 375 |

Figure 61 A

| Germline protein pair composition | Target | Antigen Immobilization | Blocking | # clones screened | ELISA hits per 368 | | # clones sequenced | # unique antibodies |
|---|---|---|---|---|---|---|---|---|
| | | | | | >10X Background | 5-10X Background | | |
| VH3-23 K1-39 | FZD4-Fc | Fc capture | Milk powder and Fc blocking | 368 | 149 | 0 | 85 | 19 |
| VH1-69 L1-51<br>VH3-07 L1-51<br>VH3-15 L1-51<br>VH5-51 L1-51<br>VH6-1 L1-51 | GFP | Epoxy M450 beads | Chemiblocker | 368 | 132 | 24 | 34 | 21 |
| VH3-23 K1-39<br>VH3-74 K1-06 | GFP | Epoxy M450 beads | Chemiblocker | 368 | 6 | 11 | 10 | 7 |
| VH1-69 L1-51<br>VH3-07 L1-51<br>VH3-15 L1-51<br>VH5-51 L1-51<br>VH6-1 L1-51 | HER4-Fc | Epoxy M450 beads | Chemiblocker + 50 µg/ml irrelevant Fc fusion protein | 368 | 223 | 31 | 25 | 21 |
| VH3-23 K1-39<br>VH3-74 K1-06 | HER4-Fc | Epoxy M450 beads | Chemiblocker + 50 µg/ml irrelevant Fc fusion protein | 368 | 69 | 38 | 27 | 8 |
| VH1-69 L1-51<br>VH3-07 L1-51<br>VH3-15 L1-51<br>VH5-51 L1-51<br>VH6-1 L1-51 | FZD4-Fc | Epoxy M450 beads | Chemiblocker + 50 µg/ml irrelevant Fc fusion protein | 368 | 64 | 19 | 24 | 15 |
| VH3-23 K1-39<br>VH3-74 K1-06 | FZD4-Fc | Epoxy M450 beads | Chemiblocker + 50 µg/ml irrelevant Fc fusion protein | 368 | 97 | 44 | 42 | 28 |
| VH1-18 VK3-20<br>VH3-07 VK1-12<br>VH3-15 VK1-05<br>VH3-15 VK1-06<br>VH3-15 VK1-12<br>VH3-21 VK1-12 | GFP | Epoxy M450 beads | Chemiblocker | 368 | 5 | 2 | 7 | 4 |

Figure 61 B

| Germline protein pair composition | Target | Antigen immobilization | Blocking | # clones screened | ELISA hits per 368 | | # clones sequenced | # unique antibodies |
|---|---|---|---|---|---|---|---|---|
| | | | | | >10X Background | 5-10X Background | | |
| VH3-23 VL3-1 | GFP | Epoxy M450 beads | Chemiblocker | 368 | 10 | 16 | 26 | 17 |
| VH1-18 VK3-20<br>VH3-07 VK1-12<br>VH3-15 VK1-05<br>VH3-15 VK1-06<br>VH3-15 VK1-12<br>VH3-21 VK1-12 | HER4-Fc | Epoxy M450 beads | Chemiblocker + irrelevant Fc fusion protein | 368 | 168 | 14 | 61 | 20 |
| VH1-18 VK3-20<br>VH3-07 VK1-12<br>VH3-15 VK1-05<br>VH3-15 VK1-06<br>VH3-15 VK1-12<br>VH3-21 VK1-12 | FZD4-Fc | Epoxy M450 beads | Chemiblocker + irrelevant Fc fusion protein | 368 | 161 | 30 | 93 | 27 |
| VH3-11 VL1-47<br>VH3-23 VL2-23<br>VH3-53 VL2-11<br>VH5-51 VL1-40<br>VH3-23 VL3-1 | GFP | Epoxy M450 beads | Chemiblocker | 368 | 36 | 16 | 52 | 43 |
| VH1-46 VK3-15<br>VH3-07 VK1-27 | GFP | Epoxy M450 beads | Chemiblocker | 368 | 36 | 9 | 36 | 14 |
| VH3-11 VL1-47<br>VH3-23 VL2-23<br>VH3-53 VL2-11<br>VH5-51 VL1-40<br>VH3-23 VL3-1 | HER4-Fc | Epoxy M450 beads | Chemiblocker + irrelevant Fc fusion protein | 368 | 141 | 38 | 96 | 26 |
| VH1-46 VK3-15<br>VH3-07 VK1-27 | HER4-Fc | Epoxy M450 beads | Chemiblocker + irrelevant Fc fusion protein | 368 | 12 | 98 | 40 | 1 |
| VH3-11 VL1-47<br>VH3-23 VL2-23<br>VH3-53 VL2-11<br>VH5-51 VL1-40<br>VH3-23 VL3-1 | FZD4-Fc | Epoxy M450 beads | Chemiblocker + 50 µg/ml irrelevant Fc fusion protein | 368 | 77 | 21 | 88 | 27 |

Figure 61C

| Germline protein pair composition | Target | Antigen immobilization | Blocking | # clones screened | ELISA hits per 368 >10X Background | ELISA hits per 368 5-10X Background | # clones sequenced | # unique antibodies |
|---|---|---|---|---|---|---|---|---|
| VH5-51 VK1-39<br>VH3-74 VK1-12<br>VH3-15 VK3-11<br>VH3-74 VK3-20<br>VH6-1 VK3-20<br>VH1-18 VK3-20 | HER4-Fc | Epoxy M450 beads | Chemiblocker + irrelevant Fc fusion protein | 368 | 12 | 5 | 11 | 8 |
| VH5-51 VK1-39<br>VH3-74 VK1-12<br>VH3-15 VK3-11<br>VH3-74 VK3-20<br>VH6-1 VK3-20<br>VH1-18 VK3-20 | FZD4-Fc | Epoxy M450 beads | Chemiblocker + irrelevant Fc fusion protein | 368 | 15 | 1 | 9 | 8 |
| VH3-23 VK3-15<br>VH3-53 VK3-15<br>VH3-07 VK3-15<br>VH6-01 VK1-09<br>VH3-15 VK1-27<br>VH3-74 VK1-05<br>VH3-07 VK1-12 | HER4-Fc | Epoxy M450 beads | Chemiblocker + irrelevant Fc fusion protein | 368 | 5 | 2 | 6 | 5 |

Figure 61D

| Germline protein pair composition | Target | Antigen immobilization | Blocking | # clones screened | ELISA hits per 368 | | # clones sequenced | # unique antibodies |
|---|---|---|---|---|---|---|---|---|
| | | | | | >10X Background | 5-10X Background | | |
| VH3-11 VL1-40<br>VH3-07 VL1-47<br>VH1-46 VL1-51<br>VH3-11 VL1-51<br>VH3-11 VL2-23<br>VH5-51 VL1-51 | GFP | Epoxy M450 beads | Chemiblocker | 368 | 14 | 1 | 6 | 4 |
| VH3-11 VL1-40<br>VH3-07 VL1-47<br>VH1-46 VL1-51<br>VH3-11 VL1-51<br>VH3-11 VL2-23<br>VH5-51 VL1-51 | HER4-Fc | Epoxy M450 beads | Chemiblocker + irrelevant Fc fusion protein | 368 | 13 | 3 | 8 | 4 |
| VH3-11 VL1-40<br>VH3-07 VL1-47<br>VH1-46 VL1-51<br>VH3-11 VL1-51<br>VH3-11 VL2-23<br>VH5-51 VL1-51 | FZD4-Fc | Epoxy M450 beads | Chemiblocker + irrelevant Fc fusion protein | 368 | 4 | 0 | 2 | 2 |

Figure 62A

| VH | VL | Target | HCDR3 Kabat Length [aa] | LCDR3 SAS Length [aa] | pI | expression [mg/L] | Tm [°C] | SEC monomer [%] |
|---|---|---|---|---|---|---|---|---|
| VH3-23 | VK1-39 | rhErbB4/HER4-Fc | 10 | 8 | 8,7 | 27,3 | 81,8 | 99 |
| VH3-23 | VK1-39 | rhErbB4/HER4-Fc | 8 | 8 | 9,4 | 3,5 | 79,1 | na |
| VH3-23 | VK1-39 | rhErbB4/HER4-Fc | 12 | 8 | 9,2 | 22,0 | 77,8 | 99 |
| VH3-23 | VK1-39 | rhErbB4/HER4-Fc | 14 | 8 | 8,7 | 26,0 | 86,1 | 99 |
| VH3-23 | VK1-39 | rhErbB4/HER4-Fc | 10 | 8 | 9,3 | 13,8 | 81,2 | 98 |
| VH1-69 | VL1-51 | rhErbB4/HER4-Fc | 9 | 9 | 9,2 | 37,6 | 75,5 | 87 |
| VH1-69 | VL1-51 | rhErbB4/HER4-Fc | 8 | 10 | 8,9 | 36,0 | 69,8 | 97 |
| VH1-69 | VL1-51 | rhErbB4/HER4-Fc | 9 | 11 | 9,1 | 26,4 | 75,0 | 89 |
| VH1-69 | VL1-51 | rhErbB4/HER4-Fc | 9 | 11 | 8,6 | 33,5 | 68,9 | 95 |
| VH1-69 | VL1-51 | rhErbB4/HER4-Fc | 9 | 10 | 9,1 | 18,0 | 75,0 | 92 |
| VH3-23 | VK1-39 | rhFZD4-Fc | 11 | 8 | 9,2 | 15,4 | 86,3 | 98 |
| VH3-23 | VK1-39 | rhFZD4-Fc | 10 | 8 | 9,1 | 18,9 | 78,5 | 100 |
| VH3-23 | VK1-39 | rhFZD4-Fc | 11 | 8 | 9,1 | 1,0 | 79,6 | na |
| VH3-23 | VK1-39 | rhFZD4-Fc | 8 | 8 | 9,1 | 13,8 | 81,9 | 99 |
| VH3-23 | VK1-39 | rhFZD4-Fc | 10 | 8 | 9,2 | 21,6 | 81,8 | 100 |
| VH3-23 | VK1-39 | rhFZD4-Fc | 10 | 8 | 8,9 | 14,7 | 78,1 | 100 |
| VH3-23 | VK1-39 | rhFZD4-Fc | 10 | 8 | 9,1 | 17,6 | 78,9 | 100 |
| VH3-23 | VK1-39 | rhFZD4-Fc | 10 | 8 | 9,2 | 11,4 | 82,1 | 100 |
| VH3-23 | VK1-39 | eGFP | 10 | 8 | 9,2 | 1,6 | 76,7 | na |
| VH3-23 | VK1-39 | eGFP | 10 | 8 | 8,7 | 7,0 | 83,7 | na |
| VH3-23 | VK1-39 | eGFP | 14 | 11 | 9,2 | 17,2 | 81,8 | 99 |
| VH3-23 | VK1-39 | eGFP | 15 | 11 | 9,0 | 13,2 | 81,8 | 100 |
| VH3-23 | VK1-39 | eGFP | 15 | 11 | 9,0 | 17,5 | 81,0 | 97 |
| VH5-51 | VL1-51 | eGFP | 15 | 11 | 9,3 | 38,2 | 67,0 | 98 |
| VH5-51 | VL1-51 | eGFP | 15 | 11 | 9,2 | 34,0 | 67,3 | 98 |
| VH5-51 | VL1-51 | eGFP | 16 | 11 | 9,0 | 30,5 | 76,7 | 93 |
| VH5-51 | VL1-51 | eGFP | 17 | 11 | 9,0 | 21,8 | 63,0 | 95 |
| VH5-51 | VL1-51 | eGFP | 15 | 12 | 9,2 | 9,0 | 71,7 | na |

Figure 62B

| VH | VL | Target | HCDR3 Kabat Length [aa] | LCDR3 SAS Length [aa] | pI | expression [mg/L] | Tm [°C] | SEC monomer [%] |
|---|---|---|---|---|---|---|---|---|
| VH1-46 | VK3-15 | eGFP | 12 | 9 | 9,3 | 10,5 | 68,9 | 96 |
| VH1-46 | VK3-15 | eGFP | 11 | 9 | 9,4 | 4 | 75,2 | 100 |
| VH1-46 | VK3-15 | eGFP | 11 | 9 | 9,4 | 10,5 | 79,4 | 74/78 |
| VH3-15 | VK1-05 | rhErbB4/HER4-Fc | 10 | 8 | 9,2 | 48,3 | 80,4 | 100 |
| VH3-21 | VK1-12 | rhErbB4/HER4-Fc | 14 | 8 | 9,4 | 30,5 | 73,6 | 100 |
| VH3-21 | VK1-12 | rhErbB4/HER4-Fc | 15 | 8 | 9,4 | 13,8 | 73,6 | 96/95 |
| VH3-21 | VK1-12 | rhErbB4/HER4-Fc | 11 | 8 | 9,2 | 20 | nsp | 100 |
| VH5-51 | VL1-40 | rhErbB4/HER4-Fc | 10 | 10 | 9 | 27,6 | 66 | 91/93 |
| VH5-51 | VL1-40 | rhErbB4/HER4-Fc | 10 | 10 | 8,7 | 35,2 | 73,2 | 94/95 |
| VH3-21 | VK1-12 | rhFZD4-Fc | 12 | 8 | 9,4 | 31,3 | 79,5 | 99 |
| VH3-21 | VK1-12 | rhFZD4-Fc | 10 | 8 | 9,1 | 21,9 | 76,2 | 100 |
| VH3-23 | VL3-1 | rhFZD4-Fc | 12 | 10 | 8,9 | 4,4 | nsp | 85 |
| VH3-23 | VL3-1 | rhFZD4-Fc | 13 | 10 | 8,9 | 14,7 | 66,2 | 85/91 |
| VH3-23 | VL3-1 | rhFZD4-Fc | 13 | 10 | 8,7 | 40,8 | 75,5 | 93/97 |
| VH1-69 | VL1-51 | rhErbB4/HER4-Fc | 7 | 11 | 8,9 | 20,7 | 69,2 | 93/93 |
| VH1-69 | VL1-51 | rhErbB4/HER4-Fc | 9 | 11 | 9,1 | 28,6 | 69,6 | 91/91 |
| VH1-69 | VL1-51 | rhErbB4/HER4-Fc | 9 | 11 | 9,1 | 33 | 76,1 | 95/96 |
| VH1-69 | VL1-51 | rhErbB4/HER4-Fc | 10 | 11 | 8,9 | 34,5 | 74 | 88/90 |

Figure 62C

| VH | VL | Target | HCDR3 Kabat Length [aa] | LCDR3 SAS Length [aa] | pI | expression [mg/L] | Tm [°C] | SEC monomer [%] |
|---|---|---|---|---|---|---|---|---|
| VH1-69 | VL1-51 | rhErbB4/HER4-Fc | 9 | 10 | 8,9 | 29,9 | 76,2 | 88/90 |
| VH1-69-low | VL1-51 | rhErbB4/HER4-Fc | 7 | 11 | 9,1 | 34 | 71 | 98 |
| VH1-69-low | VL1-51 | rhErbB4/HER4-Fc | 10 | 10 | 8,9 | 61,8 | 77,5 | 95 |
| VH1-69-low | VL1-51 | rhErbB4/HER4-Fc | 9 | 10 | 9,1 | 40 | 79 | 93 |
| VH1-69-low | VL1-51 | rhErbB4/HER4-Fc | 7 | 10 | 9,2 | 37,8 | 78,9 | 97/98 |
| VH3-23 | VL1-47 | eGFP | 9 | 11 | 9,4 | 46,1 | 67,8 | 100 |
| VH3-23 | VL1-47 | eGFP | 9 | 9 | 9,5 | 39,8 | 66,5 | 100 |
| VH3-23 | VL1-47 | eGFP | 9 | 11 | 9,4 | 4,1 | 70,4 | 97 |
| VH3-23 | VL1-47 | eGFP | 6 | 11 | 9,5 | 52,2 | 68,5 | 94/96 |
| VH3-53 | VL2-11 | rhErbB4/HER4-Fc | 14 | 9 | 9,2 | 12,7 | 75,1 | 100 |
| VH3-53 | VL2-11 | rhErbB4/HER4-Fc | 7 | 10 | 9,4 | 37,8 | 73,6 | 96 |
| VH3-53 | VL2-11 | rhErbB4/HER4-Fc | 10 | 10 | 9,2 | 48,3 | 75,6 | 98/99 |
| VH3-07 | VK1-27 | rhErbB4/HER4-Fc | 10 | 8 | 9 | 25,5 | 82,9 | 100 |
| VH3-53 | VL2-11 | rhFZD4-Fc | 11 | 9 | 9,1 | 56 | 70,7 | 98 |

VH1-69-low means the low PTM VHs shown in Figures 34-36

SEQUENCE LISTING

```
<160> NUMBER OF SEQ ID NOS: 316

<210> SEQ ID NO 1
<211> LENGTH: 11
<212> TYPE: PRT
<213> ORGANISM: Homo sapiens

<400> SEQUENCE: 1

Trp Gly Gly Asp Gly Phe Tyr Ala Met Asp Tyr
1               5                   10

<210> SEQ ID NO 2
<211> LENGTH: 9
<212> TYPE: PRT
<213> ORGANISM: Homo sapiens

<400> SEQUENCE: 2

Gln Gln His Tyr Thr Thr Pro Pro Thr
1               5

<210> SEQ ID NO 3
<211> LENGTH: 11
<212> TYPE: PRT
<213> ORGANISM: Homo sapiens

<400> SEQUENCE: 3

Gln Ser Tyr Asp Ser Ser Leu Ser Gly Val Val
1               5                   10

<210> SEQ ID NO 4
<211> LENGTH: 15
<212> TYPE: PRT
<213> ORGANISM: Homo sapiens

<400> SEQUENCE: 4

Tyr Phe Asp Tyr Trp Gly Gln Gly Thr Leu Val Thr Val Ser Ser
1               5                   10                  15
```

-continued

```
<210> SEQ ID NO 5
<211> LENGTH: 12
<212> TYPE: PRT
<213> ORGANISM: Homo sapiens

<400> SEQUENCE: 5

Trp Thr Phe Gly Gln Gly Thr Lys Val Glu Ile Lys
1               5                   10

<210> SEQ ID NO 6
<211> LENGTH: 12
<212> TYPE: PRT
<213> ORGANISM: Homo sapiens

<400> SEQUENCE: 6

Val Val Phe Gly Gly Gly Thr Lys Leu Thr Val Leu
1               5                   10

<210> SEQ ID NO 7
<211> LENGTH: 63
<212> TYPE: DNA
<213> ORGANISM: Escherichia coli
<220> FEATURE:
<221> NAME/KEY: CDS
<222> LOCATION: (1)..(63)

<400> SEQUENCE: 7 atg aaa cag agc acc att gcc ctg gcc ctg ctg ccg ctg ctg ttt acc     48
Met Lys Gln Ser Thr Ile Ala Leu Ala Leu Leu Pro Leu Leu Phe Thr
1               5                   10                  15 cca gtg acc aaa gcc                                                 63
Pro Val Thr Lys Ala
            20

<210> SEQ ID NO 8
<211> LENGTH: 21
<212> TYPE: PRT
<213> ORGANISM: Escherichia coli

<400> SEQUENCE: 8

Met Lys Gln Ser Thr Ile Ala Leu Ala Leu Leu Pro Leu Leu Phe Thr
1               5                   10                  15

Pro Val Thr Lys Ala
            20

<210> SEQ ID NO 9
<211> LENGTH: 63
<212> TYPE: DNA
<213> ORGANISM: Escherichia coli
<220> FEATURE:
<221> NAME/KEY: CDS
<222> LOCATION: (1)..(63)

<400> SEQUENCE: 9 atg aaa cag agc acc att gcc ctg gcc ctg ctg ccg ctg ctg ttt acc     48
Met Lys Gln Ser Thr Ile Ala Leu Ala Leu Leu Pro Leu Leu Phe Thr
1               5                   10                  15 cca gtg gtg cta gcc                                                 63
Pro Val Val Leu Ala
            20

<210> SEQ ID NO 10
<211> LENGTH: 21
<212> TYPE: PRT
```

```
<213> ORGANISM: Escherichia coli

<400> SEQUENCE: 10

Met Lys Gln Ser Thr Ile Ala Leu Ala Leu Leu Pro Leu Leu Phe Thr
1               5                   10                  15

Pro Val Val Leu Ala
            20

<210> SEQ ID NO 11
<211> LENGTH: 63
<212> TYPE: DNA
<213> ORGANISM: Escherichia coli
<220> FEATURE:
<221> NAME/KEY: CDS
<222> LOCATION: (1)..(63)

<400> SEQUENCE: 11 atg aaa aaa acc gcc att gcc att gcc gtg gcc ctg gca ggc ttt gcc      48
Met Lys Lys Thr Ala Ile Ala Ile Ala Val Ala Leu Ala Gly Phe Ala
1               5                   10                  15 acc gtg gcg cag gcc                                                  63
Thr Val Ala Gln Ala
            20

<210> SEQ ID NO 12
<211> LENGTH: 21
<212> TYPE: PRT
<213> ORGANISM: Escherichia coli

<400> SEQUENCE: 12

Met Lys Lys Thr Ala Ile Ala Ile Ala Val Ala Leu Ala Gly Phe Ala
1               5                   10                  15

Thr Val Ala Gln Ala
            20

<210> SEQ ID NO 13
<211> LENGTH: 63
<212> TYPE: DNA
<213> ORGANISM: Escherichia coli
<220> FEATURE:
<221> NAME/KEY: CDS
<222> LOCATION: (1)..(63)

<400> SEQUENCE: 13 atg aaa aaa acc gcc att gcc att gcc gtg gcc ctg gca ggc ttt gcc      48
Met Lys Lys Thr Ala Ile Ala Ile Ala Val Ala Leu Ala Gly Phe Ala
1               5                   10                  15 acc gtg gca tat gcc                                                  63
Thr Val Ala Tyr Ala
            20

<210> SEQ ID NO 14
<211> LENGTH: 21
<212> TYPE: PRT
<213> ORGANISM: Escherichia coli

<400> SEQUENCE: 14

Met Lys Lys Thr Ala Ile Ala Ile Ala Val Ala Leu Ala Gly Phe Ala
1               5                   10                  15

Thr Val Ala Tyr Ala
            20

<210> SEQ ID NO 15
<211> LENGTH: 63
```

<212> TYPE: DNA
<213> ORGANISM: Escherichia coli

<400> SEQUENCE: 15
atgaaaaaaa ccgccattgc cattgccgtg gccctggcag gctttgccac cgtggcatat    60
gcg                                                                  63

<210> SEQ ID NO 16
<211> LENGTH: 57
<212> TYPE: DNA
<213> ORGANISM: Homo sapiens
<220> FEATURE:
<221> NAME/KEY: CDS
<222> LOCATION: (1)..(57)

<400> SEQUENCE: 16 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtc ctg tcc                                                          57
Val Leu Ser <210> SEQ ID NO 17
<211> LENGTH: 19
<212> TYPE: PRT
<213> ORGANISM: Homo sapiens

<400> SEQUENCE: 17

Met Lys His Leu Trp Phe Phe Leu Leu Leu Val Ala Ala Pro Arg Trp
1               5                   10                  15

Val Leu Ser

<210> SEQ ID NO 18
<211> LENGTH: 57
<212> TYPE: DNA
<213> ORGANISM: Homo sapiens
<220> FEATURE:
<221> NAME/KEY: CDS
<222> LOCATION: (1)..(57)

<400> SEQUENCE: 18 atg aag cac ctg tgg ttc ttt ctg ctg ctg gtg gcc gct ccc cgg tgg    48
Met Lys His Leu Trp Phe Phe Leu Leu Leu Val Ala Ala Pro Arg Trp
1               5                   10                  15 gtg cta gcc                                                          57
Val Leu Ala <210> SEQ ID NO 19
<211> LENGTH: 19
<212> TYPE: PRT
<213> ORGANISM: Homo sapiens

<400> SEQUENCE: 19

Met Lys His Leu Trp Phe Phe Leu Leu Leu Val Ala Ala Pro Arg Trp
1               5                   10                  15

Val Leu Ala

<210> SEQ ID NO 20
<211> LENGTH: 60
<212> TYPE: DNA
<213> ORGANISM: Homo sapiens
<220> FEATURE:
<221> NAME/KEY: CDS
<222> LOCATION: (1)..(60)

<400> SEQUENCE: 20

```
atg gtg ttg cag acc cag gtc ttc att tct ctg ttg ctc tgg atc tct        48
Met Val Leu Gln Thr Gln Val Phe Ile Ser Leu Leu Leu Trp Ile Ser
1               5                   10                  15 ggt gcc tac ggg                                                         60
Gly Ala Tyr Gly
            20
```

<210> SEQ ID NO 21
<211> LENGTH: 20
<212> TYPE: PRT
<213> ORGANISM: Homo sapiens

<400> SEQUENCE: 21

```
Met Val Leu Gln Thr Gln Val Phe Ile Ser Leu Leu Leu Trp Ile Ser
1               5                   10                  15

Gly Ala Tyr Gly
            20
```

<210> SEQ ID NO 22
<211> LENGTH: 60
<212> TYPE: DNA
<213> ORGANISM: Homo sapiens
<220> FEATURE:
<221> NAME/KEY: CDS
<222> LOCATION: (1)..(60)

<400> SEQUENCE: 22

```
atg gtg ctc cag acc cag gtg ttc atc agc ctg ctg ctg tgg atc agc        48
Met Val Leu Gln Thr Gln Val Phe Ile Ser Leu Leu Leu Trp Ile Ser
1               5                   10                  15 ggc gca tat gcg                                                         60
Gly Ala Tyr Ala
            20
```

<210> SEQ ID NO 23
<211> LENGTH: 20
<212> TYPE: PRT
<213> ORGANISM: Homo sapiens

<400> SEQUENCE: 23

```
Met Val Leu Gln Thr Gln Val Phe Ile Ser Leu Leu Leu Trp Ile Ser
1               5                   10                  15

Gly Ala Tyr Ala
            20
```

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
acaggtgccc actcccaggt gcag                                              24
```

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 25
aaggtgtcca gtgtgargtg cag                                           23

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccagatggg tcctgtccca ggtgcag                                       27

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caaggagtct gttccgaggt gcag                                          24

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gggaattctc acaggagacg a                                             21

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggaaggtgtg cacgccgctg gtc                                           23

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgcaaccgg tgtacattcc caggtgcagc tggtgcag                           38

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 31
ctgcaaccgg tgtacattcc gaggtgcagc tggtgcag                              38

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctgcaaccgg tgtacattct gaggtgcagc tggtggag                              38

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctgcaaccgg tgtacattct gaggtgcagc tgttggag                              38

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctgcaaccgg tgtacattcc caggtgcagc tgcaggag                              38

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctgcaaccgg tgtacattcc caggtgcagc tacagcagtg                            40

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgcgaagtcg acgctgagga gacggtgacc ag                                    32

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
```
tgcgaagtcg acgctgaaga gacggtgacc attg    34

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tgcgaagtcg acgctgagga gacggtgacc gtg    33

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gttcggggaa gtagtccttg ac    22

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atgaggstcc cygctcagct gctgg    25

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctcttcctcc tgctactctg gctcccag    28

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atttctctgt tgctctggat ctctg    25

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
gtttctcgta gtctgctttg ctca                                          24
```

```
<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atgacccagw ctccabycwc cctg                                          24
```

```
<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtgctgtcct tgctgtcctg ct                                            22
```

```
<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggtcctgggc ccagtctgtg ctg                                           23
```

```
<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggtcctgggc ccagtctgcc ctg                                           23
```

```
<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gctctgtgac ctcctatgag ctg                                           23
```

```
<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggtctctctc scagcytgtg ctg                                           23
```

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gttcttgggc caattttatg ctg                                              23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggtccaattc ycaggctgtg gtg                                              23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gagtggattc tcagactgtg gtg                                              23

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
caccagtgtg gccttgttgg cttg                                             24

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctgctaccgg ttcctgggcc cagtctgtgc tgackcag                              38

<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctgctaccgg ttcctgggcc cagtctgccc tgactcag                              38

<210> SEQ ID NO 56
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ctgctaccgg ttctgtgacc tcctatgagc tgacwcag                        38

<210> SEQ ID NO 57
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ctgctaccgg ttctctctcs cagcytgtgc tgactca                         37

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctgctaccgg ttcttgggcc aattttatgc tgactcag                        38

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctgctaccgg ttccaattcy cagrctgtgg tgacycag                        38

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctcctcactc gagggyggga acagagtg                                   28

<210> SEQ ID NO 61
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Asn Ile Tyr Ser Asp Gly Ser Asn Thr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Met Tyr Arg Trp Pro Phe His Tyr Phe Asp Tyr Trp
            100                 105                 110

Gly Gln Gly Thr Leu Val Thr Val Ser Ser
        115                 120

<210> SEQ ID NO 62
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Lys Tyr Val
            20                  25                  30

Ser Trp Tyr Gln Gln Lys Pro Gly Gln Ala Pro Val Val Val Ile Tyr
        35                  40                  45

Gly Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Asp Ser Ser Tyr Phe Val
                85                  90                  95

Phe Gly Gly Gly Thr Lys Leu Thr Val Leu Gly Gln
            100                 105

<210> SEQ ID NO 63
<211> LENGTH: 98
<212> TYPE: PRT
<213> ORGANISM: Homo sapiens

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 64
<211> LENGTH: 98
<212> TYPE: PRT
<213> ORGANISM: Homo sapiens

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ser Asn Ala Gly Asn Gly Asn Thr Lys Tyr Ser Gln Glu Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg

<210> SEQ ID NO 65
<211> LENGTH: 99
<212> TYPE: PRT
<213> ORGANISM: Homo sapiens

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly

<210> SEQ ID NO 66
<211> LENGTH: 98
<212> TYPE: PRT
<213> ORGANISM: Homo sapiens

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr

```
                65                  70                  75                  80
Met Glu Leu Arg Ser Leu Arg Ser Asp Asp Thr Ala Val Tyr Tyr Cys
                    85                  90                  95

Ala Arg

<210> SEQ ID NO 67
<211> LENGTH: 98
<212> TYPE: PRT
<213> ORGANISM: Homo sapiens

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                    85                  90                  95

Ala Thr

<210> SEQ ID NO 68
<211> LENGTH: 98
<212> TYPE: PRT
<213> ORGANISM: Homo sapiens

<400> SEQUENCE: 68

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
                20                  25                  30

Tyr Leu His Trp Val Arg Gln Ala Pro Gly Gln Ala Leu Glu Trp Met
            35                  40                  45

Gly Trp Ile Thr Pro Phe Asn Gly Asn Thr Asn Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                    85                  90                  95

Ala Arg

<210> SEQ ID NO 69
<211> LENGTH: 98
<212> TYPE: PRT
<213> ORGANISM: Homo sapiens

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45
```

-continued

Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 70
<211> LENGTH: 98
<212> TYPE: PRT
<213> ORGANISM: Homo sapiens

<400> SEQUENCE: 70

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Met Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala

<210> SEQ ID NO 71
<211> LENGTH: 98
<212> TYPE: PRT
<213> ORGANISM: Homo sapiens

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 72
<211> LENGTH: 98
<212> TYPE: PRT
<213> ORGANISM: Homo sapiens

<400> SEQUENCE: 72

Gln Val Gln Leu Val Gln Ser Gly Ala Glu Val Lys Lys Pro Gly Ser
1               5                   10                  15

-continued

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 73
<211> LENGTH: 86
<212> TYPE: PRT
<213> ORGANISM: Homo sapiens

<400> SEQUENCE: 73

Lys Ser Gly Ala Ser Val Lys Val Ser Cys Ser Phe Ser Gly Phe Thr
1               5                   10                  15

Ile Thr Ser Tyr Gly Ile His Trp Val Gln Gln Ser Pro Gly Gln Gly
            20                  25                  30

Leu Glu Trp Met Gly Trp Ile Asn Pro Gly Asn Gly Ser Pro Ser Tyr
        35                  40                  45

Ala Lys Lys Phe Gln Gly Arg Phe Thr Met Thr Arg Asp Met Ser Thr
50                  55                  60

Thr Thr Ala Tyr Thr Asp Leu Ser Ser Leu Thr Ser Glu Asp Met Ala
65                  70                  75                  80

Val Tyr Tyr Tyr Ala Arg
                85

<210> SEQ ID NO 74
<211> LENGTH: 98
<212> TYPE: PRT
<213> ORGANISM: Homo sapiens

<400> SEQUENCE: 74

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 75
<211> LENGTH: 100
<212> TYPE: PRT
<213> ORGANISM: Homo sapiens

<400> SEQUENCE: 75

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 76
<211> LENGTH: 100
<212> TYPE: PRT
<213> ORGANISM: Homo sapiens

<400> SEQUENCE: 76

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
            35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 77
<211> LENGTH: 100
<212> TYPE: PRT
<213> ORGANISM: Homo sapiens

<400> SEQUENCE: 77

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Cys Val Ser Trp Ile Arg Gln Pro Pro Gly Lys Ala Leu Glu
            35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100
```

-continued

<210> SEQ ID NO 78
<211> LENGTH: 98
<212> TYPE: PRT
<213> ORGANISM: Homo sapiens

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 79
<211> LENGTH: 99
<212> TYPE: PRT
<213> ORGANISM: Homo sapiens

<400> SEQUENCE: 79

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 80
<211> LENGTH: 98
<212> TYPE: PRT
<213> ORGANISM: Homo sapiens

<400> SEQUENCE: 80

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

-continued

Leu Gln Met Asn Ser Leu Arg Ala Glu Asp Thr Ala Val Tyr Tyr Cys
                    85                  90                  95

Ala Arg

<210> SEQ ID NO 81
<211> LENGTH: 97
<212> TYPE: PRT
<213> ORGANISM: Homo sapiens

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Asp Thr Ala Val Tyr Tyr Cys Ala
                85                  90                  95

Arg

<210> SEQ ID NO 82
<211> LENGTH: 100
<212> TYPE: PRT
<213> ORGANISM: Homo sapiens

<400> SEQUENCE: 82

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 83
<211> LENGTH: 98
<212> TYPE: PRT
<213> ORGANISM: Homo sapiens

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Ala Arg Lys Ala Pro Gly Lys Gly Leu Glu Trp Val
        35                  40                  45

```
Ser Gly Val Ser Trp Asn Gly Ser Arg Thr His Tyr Val Asp Ser Val
    50                  55                  60

Lys Arg Arg Phe Ile Ile Ser Arg Asp Asn Ser Arg Asn Ser Leu Tyr
65                  70                  75                  80

Leu Gln Lys Asn Arg Arg Ala Glu Asp Met Ala Val Tyr Tyr Cys
                85                  90                  95

Val Arg

<210> SEQ ID NO 84
<211> LENGTH: 98
<212> TYPE: PRT
<213> ORGANISM: Homo sapiens

<400> SEQUENCE: 84

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Gly Ile Asn Trp Asn Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 85
<211> LENGTH: 98
<212> TYPE: PRT
<213> ORGANISM: Homo sapiens

<400> SEQUENCE: 85

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 86
<211> LENGTH: 98
<212> TYPE: PRT
<213> ORGANISM: Homo sapiens

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys

<210> SEQ ID NO 87
<211> LENGTH: 98
<212> TYPE: PRT
<213> ORGANISM: Homo sapiens

<400> SEQUENCE: 87

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg

<210> SEQ ID NO 88
<211> LENGTH: 98
<212> TYPE: PRT
<213> ORGANISM: Homo sapiens

<400> SEQUENCE: 88

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg

<210> SEQ ID NO 89
<211> LENGTH: 98
<212> TYPE: PRT
<213> ORGANISM: Homo sapiens

<400> SEQUENCE: 89
```

-continued

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 90
<211> LENGTH: 98
<212> TYPE: PRT
<213> ORGANISM: Homo sapiens

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 91
<211> LENGTH: 98
<212> TYPE: PRT
<213> ORGANISM: Homo sapiens

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val His Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Thr Leu Tyr
65                  70                  75                  80

Leu Gln Thr Asn Ser Leu Arg Ala Glu Asp Thr Ala Val Tyr Tyr Cys
                85                  90                  95

Val Arg

<210> SEQ ID NO 92

```
<211> LENGTH: 97
<212> TYPE: PRT
<213> ORGANISM: Homo sapiens

<400> SEQUENCE: 92

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Val Ser Ser Asn
            20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
50                  55                  60

Arg Phe Thr Ile Ser Arg Asp Asn Ser Lys Thr Leu Tyr Leu Gln
65                  70                  75                  80

Met Asn Asn Leu Arg Ala Glu Gly Thr Ala Ala Tyr Tyr Cys Ala Arg
                85                  90                  95

Tyr

<210> SEQ ID NO 93
<211> LENGTH: 99
<212> TYPE: PRT
<213> ORGANISM: Homo sapiens

<400> SEQUENCE: 93

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp

<210> SEQ ID NO 94
<211> LENGTH: 98
<212> TYPE: PRT
<213> ORGANISM: Homo sapiens

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95
```

Ala Arg

<210> SEQ ID NO 95
<211> LENGTH: 100
<212> TYPE: PRT
<213> ORGANISM: Homo sapiens

<400> SEQUENCE: 95

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 96
<211> LENGTH: 97
<212> TYPE: PRT
<213> ORGANISM: Homo sapiens

<400> SEQUENCE: 96

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 97
<211> LENGTH: 98
<212> TYPE: PRT
<213> ORGANISM: Homo sapiens

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

-continued

```
Lys Gly Arg Phe Thr Ile Ser Arg Asp Asn Ser Lys Asn Thr Leu Tyr
 65                  70                  75                  80

Leu Gln Met Gly Ser Leu Arg Ala Glu Asp Met Ala Val Tyr Tyr Cys
             85                  90                  95

Ala Arg

<210> SEQ ID NO 98
<211> LENGTH: 97
<212> TYPE: PRT
<213> ORGANISM: Homo sapiens

<400> SEQUENCE: 98

Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Lys Gly Leu Glu Trp Val
         35                  40                  45

Ser Val Ile Tyr Ser Cys Gly Ser Thr Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg

<210> SEQ ID NO 99
<211> LENGTH: 100
<212> TYPE: PRT
<213> ORGANISM: Homo sapiens

<400> SEQUENCE: 99

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp His
             20                  25                  30

Tyr Met Asp Trp Val Arg Gln Ala Pro Gly Lys Gly Leu Glu Trp Val
         35                  40                  45

Gly Arg Thr Arg Asn Lys Ala Asn Ser Tyr Thr Thr Glu Tyr Ala Ala
     50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
             85                  90                  95

Tyr Cys Ala Arg
            100

<210> SEQ ID NO 100
<211> LENGTH: 100
<212> TYPE: PRT
<213> ORGANISM: Homo sapiens

<400> SEQUENCE: 100

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Thr Phe Ser Gly Ser
             20                  25                  30
```

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
            85                  90                  95

Tyr Cys Thr Arg
            100

<210> SEQ ID NO 101
<211> LENGTH: 98
<212> TYPE: PRT
<213> ORGANISM: Homo sapiens

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
            35                  40                  45

Ser Arg Ile Asn Ser Asp Gly Ser Ser Thr Ser Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg

<210> SEQ ID NO 102
<211> LENGTH: 96
<212> TYPE: PRT
<213> ORGANISM: Homo sapiens

<400> SEQUENCE: 102

Glu Val Gln Leu Val Glu Ser Arg Gly Val Leu Val Gln Pro Gly Gly
1               5                   10                  15

Ser Leu Arg Leu Ser Cys Ala Ala Ser Gly Phe Thr Val Ser Ser Asn
            20                  25                  30

Glu Met Ser Trp Val Arg Gln Ala Pro Gly Lys Gly Leu Glu Trp Val
            35                  40                  45

Ser Ser Ile Ser Gly Gly Ser Thr Tyr Tyr Ala Asp Ser Arg Lys Gly
50                  55                  60

Arg Phe Thr Ile Ser Arg Asp Asn Ser Lys Asn Thr Leu His Leu Gln
65                  70                  75                  80

Met Asn Ser Leu Arg Ala Glu Asp Thr Ala Val Tyr Tyr Cys Lys Lys
            85                  90                  95

<210> SEQ ID NO 103
<211> LENGTH: 97
<212> TYPE: PRT
<213> ORGANISM: Homo sapiens

<400> SEQUENCE: 103

Gln Val Gln Leu Gln Glu Ser Gly Pro Gly Leu Val Lys Pro Ser Glu

-continued

```
               1               5                  10                 15
            Thr Leu Ser Leu Thr Cys Thr Val Ser Gly Gly Ser Ile Ser Ser Tyr
                            20                 25                 30

Tyr Trp Ser Trp Ile Arg Gln Pro Ala Gly Lys Gly Leu Glu Trp Ile
                            35                 40                 45

Gly Arg Ile Tyr Thr Ser Gly Ser Thr Asn Tyr Asn Pro Ser Leu Lys
                            50                 55                 60

Ser Arg Val Thr Met Ser Val Asp Thr Ser Lys Asn Gln Phe Ser Leu
            65                          70                 75                 80

Lys Leu Ser Ser Val Thr Ala Ala Asp Thr Ala Val Tyr Tyr Cys Ala
                            85                 90                 95

Arg

<210> SEQ ID NO 104
<211> LENGTH: 98
<212> TYPE: PRT
<213> ORGANISM: Homo sapiens

<400> SEQUENCE: 104

Gln Val Gln Leu Gln Glu Ser Gly Pro Gly Leu Val Lys Pro Ser Asp
            1               5                  10                 15

Thr Leu Ser Leu Thr Cys Ala Val Ser Gly Tyr Ser Ile Ser Ser Ser
                            20                 25                 30

Asn Trp Trp Gly Trp Ile Arg Gln Pro Pro Gly Lys Gly Leu Glu Trp
                            35                 40                 45

Ile Gly Tyr Ile Tyr Tyr Ser Gly Ser Thr Tyr Tyr Asn Pro Ser Leu
                            50                 55                 60

Lys Ser Arg Val Thr Met Ser Val Asp Thr Ser Lys Asn Gln Phe Ser
            65                          70                 75                 80

Leu Lys Leu Ser Ser Val Thr Ala Val Asp Thr Ala Val Tyr Tyr Cys
                            85                 90                 95

Ala Arg

<210> SEQ ID NO 105
<211> LENGTH: 99
<212> TYPE: PRT
<213> ORGANISM: Homo sapiens

<400> SEQUENCE: 105

Gln Val Gln Leu Gln Glu Ser Gly Pro Gly Leu Val Lys Pro Ser Gln
            1               5                  10                 15

Thr Leu Ser Leu Thr Cys Thr Val Ser Gly Gly Ser Ile Ser Ser Gly
                            20                 25                 30

Gly Tyr Tyr Trp Ser Trp Ile Arg Gln His Pro Gly Lys Gly Leu Glu
                            35                 40                 45

Trp Ile Gly Tyr Ile Tyr Tyr Ser Gly Ser Thr Tyr Tyr Asn Pro Ser
            50                          55                 60

Leu Lys Ser Arg Val Thr Ile Ser Val Asp Thr Ser Lys Asn Gln Phe
            65                          70                 75                 80

Ser Leu Lys Leu Ser Ser Val Thr Ala Ala Asp Thr Ala Val Tyr Tyr
                            85                 90                 95

Cys Ala Arg

<210> SEQ ID NO 106
<211> LENGTH: 99
<212> TYPE: PRT
```

<213> ORGANISM: Homo sapiens

<400> SEQUENCE: 106

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 107
<211> LENGTH: 99
<212> TYPE: PRT
<213> ORGANISM: Homo sapiens

<400> SEQUENCE: 107

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 108
<211> LENGTH: 99
<212> TYPE: PRT
<213> ORGANISM: Homo sapiens

<400> SEQUENCE: 108

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 109
<211> LENGTH: 98
<212> TYPE: PRT
<213> ORGANISM: Homo sapiens

<400> SEQUENCE: 109

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly
```

<210> SEQ ID NO 110
<211> LENGTH: 99
<212> TYPE: PRT
<213> ORGANISM: Homo sapiens

<400> SEQUENCE: 110

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg
```

<210> SEQ ID NO 111
<211> LENGTH: 97
<212> TYPE: PRT
<213> ORGANISM: Homo sapiens

<400> SEQUENCE: 111

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95
Arg

<210> SEQ ID NO 112
<211> LENGTH: 99
<212> TYPE: PRT
<213> ORGANISM: Homo sapiens

<400> SEQUENCE: 112

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Gly Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 113
<211> LENGTH: 98
<212> TYPE: PRT
<213> ORGANISM: Homo sapiens

<400> SEQUENCE: 113

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 114
<211> LENGTH: 98
<212> TYPE: PRT
<213> ORGANISM: Homo sapiens

<400> SEQUENCE: 114

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45
```

```
Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 115
<211> LENGTH: 98
<212> TYPE: PRT
<213> ORGANISM: Homo sapiens

<400> SEQUENCE: 115

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Thr Ser Tyr
                 20                  25                  30

Trp Ile Ser Trp Val Arg Gln Met Pro Gly Lys Gly Leu Glu Trp Met
             35                  40                  45

Gly Arg Ile Asp Pro Ser Asp Ser Tyr Thr Asn Tyr Ser Pro Ser Phe
        50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 116
<211> LENGTH: 101
<212> TYPE: PRT
<213> ORGANISM: Homo sapiens

<400> SEQUENCE: 116

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
                 20                  25                  30

Ser Ala Ala Trp Asn Trp Ile Arg Gln Ser Pro Ser Arg Gly Leu Glu
             35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg
            100

<210> SEQ ID NO 117
<211> LENGTH: 98
<212> TYPE: PRT
<213> ORGANISM: Homo sapiens

<400> SEQUENCE: 117

Gln Val Gln Leu Val Gln Ser Gly Ser Glu Leu Lys Lys Pro Gly Ala
 1               5                  10                  15
```

```
Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
            85                  90                  95

Ala Arg

<210> SEQ ID NO 118
<211> LENGTH: 98
<212> TYPE: PRT
<213> ORGANISM: Homo sapiens

<400> SEQUENCE: 118

Gln Val Gln Leu Val Gln Ser Gly His Glu Val Lys Gln Pro Gly Ala
 1               5                  10                  15

Ser Val Lys Val Ser Cys Lys Ala Ser Gly Tyr Ser Phe Thr Thr Tyr
            20                  25                  30

Gly Met Asn Trp Val Pro Gln Ala Pro Gly Gln Gly Leu Glu Trp Met
            35                  40                  45

Gly Trp Phe Asn Thr Tyr Thr Gly Asn Pro Thr Tyr Ala Gln Gly Phe
 50                  55                  60

Thr Gly Arg Phe Val Phe Ser Met Asp Thr Ser Ala Ser Thr Ala Tyr
 65                  70                  75                  80

Leu Gln Ile Ser Ser Leu Lys Ala Glu Asp Met Ala Met Tyr Tyr Cys
            85                  90                  95

Ala Arg

<210> SEQ ID NO 119
<211> LENGTH: 95
<212> TYPE: PRT
<213> ORGANISM: Homo sapiens

<400> SEQUENCE: 119

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser
            85                  90                  95

<210> SEQ ID NO 120
<211> LENGTH: 95
<212> TYPE: PRT
<213> ORGANISM: Homo sapiens

<400> SEQUENCE: 120
```

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
                85                  90                  95

<210> SEQ ID NO 121
<211> LENGTH: 95
<212> TYPE: PRT
<213> ORGANISM: Homo sapiens

<400> SEQUENCE: 121

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95

<210> SEQ ID NO 122
<211> LENGTH: 95
<212> TYPE: PRT
<213> ORGANISM: Homo sapiens

<400> SEQUENCE: 122

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95

<210> SEQ ID NO 123
<211> LENGTH: 95
<212> TYPE: PRT
<213> ORGANISM: Homo sapiens

<400> SEQUENCE: 123

Asp Ile Gln Met Thr Gln Ser Pro Ser Ser Val Ser Ala Ser Val Gly

```
                1               5                    10                   15
Asp Arg Val Thr Ile Thr Cys Arg Ala Ser Gln Gly Ile Ser Ser Trp
                        20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                      80

Glu Asp Phe Ala Thr Tyr Tyr Cys Gln Gln Ala Asn Ser Phe Pro
                85                  90                  95
```

<210> SEQ ID NO 124
<211> LENGTH: 95
<212> TYPE: PRT
<213> ORGANISM: Homo sapiens

<400> SEQUENCE: 124

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                    20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                      80

Glu Asp Phe Ala Thr Tyr Tyr Cys Gln Gln Phe Asn Ser Tyr Pro
                85                  90                  95
```

<210> SEQ ID NO 125
<211> LENGTH: 95
<212> TYPE: PRT
<213> ORGANISM: Homo sapiens

<400> SEQUENCE: 125

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                    20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                      80

Glu Asp Phe Ala Thr Tyr Tyr Cys Gln Gln Tyr Asn Ser Tyr Pro
                85                  90                  95
```

<210> SEQ ID NO 126
<211> LENGTH: 95
<212> TYPE: PRT
<213> ORGANISM: Homo sapiens

<400> SEQUENCE: 126

```
Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95
```

<210> SEQ ID NO 127
<211> LENGTH: 95
<212> TYPE: PRT
<213> ORGANISM: Homo sapiens

<400> SEQUENCE: 127

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95
```

<210> SEQ ID NO 128
<211> LENGTH: 95
<212> TYPE: PRT
<213> ORGANISM: Homo sapiens

<400> SEQUENCE: 128

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95
```

<210> SEQ ID NO 129
<211> LENGTH: 96
<212> TYPE: PRT
<213> ORGANISM: Homo sapiens

<400> SEQUENCE: 129

```
Asp Ile Gln Leu Thr Gln Ser Pro Ser Ser Leu Ser Ala Ser Val Gly
1               5                   10                  15
```

```
Asp Arg Val Thr Ile Thr Cys Arg Val Ser Gln Gly Ile Ser Ser Tyr
                20                  25                  30

Leu Asn Trp Tyr Arg Gln Lys Pro Gly Lys Val Pro Lys Leu Leu Ile
             35                  40                  45

Tyr Ser Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Gly Gln Arg Thr Tyr Asn Ala Pro Pro
                 85                  90                  95

<210> SEQ ID NO 130
<211> LENGTH: 95
<212> TYPE: PRT
<213> ORGANISM: Homo sapiens

<400> SEQUENCE: 130

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                 85                  90                  95

<210> SEQ ID NO 131
<211> LENGTH: 95
<212> TYPE: PRT
<213> ORGANISM: Homo sapiens

<400> SEQUENCE: 131

Val Ile Trp Met Thr Gln Ser Pro Ser Leu Leu Ser Ala Ser Thr Gly
 1               5                   10                  15

Asp Arg Val Thr Ile Ser Cys Arg Met Ser Gln Gly Ile Ser Ser Tyr
                20                  25                  30

Leu Ala Trp Tyr Gln Gln Lys Pro Gly Lys Ala Pro Glu Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Tyr Ser Phe Pro
                 85                  90                  95

<210> SEQ ID NO 132
<211> LENGTH: 95
<212> TYPE: PRT
<213> ORGANISM: Homo sapiens

<400> SEQUENCE: 132

Asp Ile Gln Met Thr Gln Ser Pro Ser Val Ser Ala Ser Val Gly
 1               5                   10                  15

Asp Arg Val Thr Ile Thr Cys Arg Ala Ser Gln Gly Ile Ser Ser Trp
```

```
                    20                  25                  30

Leu Ala Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                    85                  90                  95

<210> SEQ ID NO 133
<211> LENGTH: 95
<212> TYPE: PRT
<213> ORGANISM: Homo sapiens

<400> SEQUENCE: 133

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
                35                  40                  45

Tyr Asp Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro
                    85                  90                  95

<210> SEQ ID NO 134
<211> LENGTH: 95
<212> TYPE: PRT
<213> ORGANISM: Homo sapiens

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                    85                  90                  95

<210> SEQ ID NO 135
<211> LENGTH: 95
<212> TYPE: PRT
<213> ORGANISM: Homo sapiens

<400> SEQUENCE: 135

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile Ser Asn Tyr
                20                  25                  30
```

```
Leu Ala Trp Phe Gln Gln Lys Pro Gly Lys Val Pro Lys His Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 136
<211> LENGTH: 95
<212> TYPE: PRT
<213> ORGANISM: Homo sapiens

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 137
<211> LENGTH: 96
<212> TYPE: PRT
<213> ORGANISM: Homo sapiens

<400> SEQUENCE: 137

Asp Ile Gln Leu Thr Gln Ser Pro Ser Ser Leu Ser Ala Ser Val Gly
1               5                   10                  15

Asp Arg Val Thr Ile Thr Cys Arg Val Ser Gln Gly Ile Ser Ser Tyr
            20                  25                  30

Leu Asn Trp Tyr Arg Gln Lys Pro Gly Lys Val Pro Lys Leu Leu Ile
            35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Arg Thr Tyr Asn Ala Pro Pro
                85                  90                  95

<210> SEQ ID NO 138
<211> LENGTH: 95
<212> TYPE: PRT
<213> ORGANISM: Homo sapiens

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                 85                  90                  95
```

<210> SEQ ID NO 139
<211> LENGTH: 96
<212> TYPE: PRT
<213> ORGANISM: Homo sapiens

<400> SEQUENCE: 139

```
Asp Ile Gln Met Ile Gln Ser Pro Ser Phe Leu Ser Ala Ser Val Gly
 1               5                  10                  15

Asp Arg Val Ser Ile Ile Cys Trp Ala Ser Glu Gly Ile Ser Ser Asn
                 20                  25                  30

Leu Ala Trp Tyr Leu Gln Lys Pro Gly Lys Ser Pro Lys Leu Phe Leu
         35                  40                  45

Tyr Asp Ala Lys Asp Leu His Pro Gly Val Ser Ser Arg Phe Ser Gly
 50                      55                  60

Arg Gly Ser Gly Thr Asp Phe Thr Leu Thr Ile Ile Ser Leu Lys Pro
 65                  70                  75                  80

Glu Asp Phe Ala Ala Tyr Tyr Cys Lys Gln Asp Phe Ser Tyr Pro Pro
                 85                  90                  95
```

<210> SEQ ID NO 140
<211> LENGTH: 95
<212> TYPE: PRT
<213> ORGANISM: Homo sapiens

<400> SEQUENCE: 140

```
Ala Ile Arg Met Thr Gln Ser Pro Phe Ser Leu Ser Ala Ser Val Gly
 1               5                  10                  15

Asp Arg Val Thr Ile Thr Cys Trp Ala Ser Gln Gly Ile Ser Ser Tyr
                 20                  25                  30

Leu Ala Trp Tyr Gln Gln Lys Pro Ala Lys Ala Pro Lys Leu Phe Ile
         35                  40                  45

Tyr Tyr Ala Ser Ser Leu Gln Ser Gly Val Pro Ser Arg Phe Ser Gly
 50                      55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Tyr Ser Thr Pro
                 85                  90                  95
```

<210> SEQ ID NO 141
<211> LENGTH: 100
<212> TYPE: PRT
<213> ORGANISM: Homo sapiens

<400> SEQUENCE: 141

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
                 20                  25                  30

Asp Gly Asn Thr Tyr Leu Ser Trp Leu Gln Gln Arg Pro Gly Gln Pro
```

```
                35                  40                  45
Pro Arg Leu Leu Ile Tyr Lys Ile Ser Asn Arg Phe Ser Gly Val Pro
        50                  55                  60
Asp Arg Phe Ser Gly Ser Gly Ala Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Thr Gln Phe Pro
            100

<210> SEQ ID NO 142
<211> LENGTH: 100
<212> TYPE: PRT
<213> ORGANISM: Homo sapiens

<400> SEQUENCE: 142

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
                20                  25                  30
Asn Gly Tyr Asn Tyr Leu Asp Trp Tyr Leu Gln Lys Pro Gly Gln Ser
            35                  40                  45
Pro Gln Leu Leu Ile Tyr Leu Gly Ser Asn Arg Ala Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro
            100

<210> SEQ ID NO 143
<211> LENGTH: 100
<212> TYPE: PRT
<213> ORGANISM: Homo sapiens

<400> SEQUENCE: 143

Asp Ile Val Met Thr Gln Thr Pro Leu Ser Leu Ser Val Thr Pro Gly
1               5                   10                  15
Gln Pro Ala Ser Ile Ser Cys Lys Ser Ser Gln Ser Leu Leu His Ser
                20                  25                  30
Asp Gly Lys Thr Tyr Leu Tyr Trp Tyr Leu Gln Lys Pro Gly Gln Ser
            35                  40                  45
Pro Gln Leu Leu Ile Tyr Glu Val Ser Ser Arg Phe Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Gly
                85                  90                  95
Ile His Leu Pro
            100

<210> SEQ ID NO 144
<211> LENGTH: 100
<212> TYPE: PRT
<213> ORGANISM: Homo sapiens

<400> SEQUENCE: 144
```

```
Asp Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100
```

<210> SEQ ID NO 145
<211> LENGTH: 101
<212> TYPE: PRT
<213> ORGANISM: Homo sapiens

<400> SEQUENCE: 145

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100
```

<210> SEQ ID NO 146
<211> LENGTH: 100
<212> TYPE: PRT
<213> ORGANISM: Homo sapiens

<400> SEQUENCE: 146

```
Asp Ile Val Met Thr Gln Thr Pro Leu Ser Ser Pro Val Thr Leu Gly
1               5                   10                  15

Gln Pro Ala Ser Ile Ser Phe Arg Ser Ser Gln Ser Leu Val His Ser
            20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro
            100
```

<210> SEQ ID NO 147
<211> LENGTH: 101
<212> TYPE: PRT
<213> ORGANISM: Homo sapiens

<400> SEQUENCE: 147

Glu Ile Val Met Thr Gln Thr Pro Leu Ser Leu Ser Ile Thr Pro Gly
1               5                   10                  15

Glu Gln Ala Ser Ile Ser Cys Arg Ser Ser Gln Ser Leu Leu His Ser
            20                  25                  30

Asp Gly Tyr Thr Tyr Leu Tyr Trp Phe Leu Gln Lys Ala Arg Pro Val
        35                  40                  45

Ser Thr Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Asp
                85                  90                  95

Ala Gln Asp Pro Pro
            100

<210> SEQ ID NO 148
<211> LENGTH: 100
<212> TYPE: PRT
<213> ORGANISM: Homo sapiens

<400> SEQUENCE: 148

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 149
<211> LENGTH: 100
<212> TYPE: PRT
<213> ORGANISM: Homo sapiens

<400> SEQUENCE: 149

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Ile Gln Leu Pro
            100

<210> SEQ ID NO 150
<211> LENGTH: 100
<212> TYPE: PRT
<213> ORGANISM: Homo sapiens

<400> SEQUENCE: 150

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
                 20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro
            100

<210> SEQ ID NO 151
<211> LENGTH: 101
<212> TYPE: PRT
<213> ORGANISM: Homo sapiens

<400> SEQUENCE: 151

Asp Ile Val Met Thr Gln Thr Pro Leu Ser Leu Pro Val Thr Pro Gly
  1               5                  10                  15

Glu Pro Ala Ser Ile Ser Cys Arg Ser Ser Gln Ser Leu Leu Asp Ser
                 20                  25                  30

Asp Asp Gly Asn Thr Tyr Leu Asp Trp Tyr Leu Gln Lys Pro Gly Gln
             35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Ile Glu Phe Pro
            100

<210> SEQ ID NO 152
<211> LENGTH: 97
<212> TYPE: PRT
<213> ORGANISM: Homo sapiens

<400> SEQUENCE: 152

Glu Ile Val Met Thr Gln Ser Pro Pro Thr Leu Ser Leu Ser Pro Gly
  1               5                  10                  15

Glu Arg Val Thr Leu Ser Cys Arg Ala Ser Gln Ser Val Ser Ser Ser
```

```
            20                  25                  30
Tyr Leu Thr Trp Tyr Gln Gln Lys Pro Gly Gln Ala Pro Arg Leu Leu
        35                  40                  45

Ile Tyr Gly Ala Ser Thr Arg Ala Thr Ser Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp His Asn Leu Pro
                85                  90                  95

Pro
```

<210> SEQ ID NO 153
<211> LENGTH: 95
<212> TYPE: PRT
<213> ORGANISM: Homo sapiens

<400> SEQUENCE: 153

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 154
<211> LENGTH: 95
<212> TYPE: PRT
<213> ORGANISM: Homo sapiens

<400> SEQUENCE: 154

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 155
<211> LENGTH: 96
<212> TYPE: PRT
<213> ORGANISM: Homo sapiens

<400> SEQUENCE: 155

```
Glu Ile Val Leu Thr Gln Ser Pro Gly Thr Leu Ser Leu Ser Pro Gly
1               5                   10                  15
```

-continued

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 156
<211> LENGTH: 96
<212> TYPE: PRT
<213> ORGANISM: Homo sapiens

<400> SEQUENCE: 156

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 157
<211> LENGTH: 95
<212> TYPE: PRT
<213> ORGANISM: Homo sapiens

<400> SEQUENCE: 157

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 158
<211> LENGTH: 95
<212> TYPE: PRT
<213> ORGANISM: Homo sapiens

<400> SEQUENCE: 158

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn

-continued

```
                20                  25                  30
Leu Ala Trp Tyr Gln Gln Lys Pro Gly Gln Ala Pro Arg Leu Leu Ile
            35                  40                  45
Tyr Gly Ala Ser Thr Arg Ala Thr Gly Ile Pro Ala Arg Phe Ser Gly
        50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro
                85                  90                  95
```

<210> SEQ ID NO 159
<211> LENGTH: 96
<212> TYPE: PRT
<213> ORGANISM: Homo sapiens

<400> SEQUENCE: 159

```
Glu Ile Val Leu Thr Gln Ser Pro Ala Thr Leu Ser Leu Ser Pro Gly
1               5                   10                  15
Glu Arg Ala Thr Leu Ser Cys Gly Ala Ser Gln Ser Val Ser Ser Ser
                20                  25                  30
Tyr Leu Ala Trp Tyr Gln Gln Lys Pro Gly Leu Ala Pro Arg Leu Leu
            35                  40                  45
Ile Tyr Asp Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
```

<210> SEQ ID NO 160
<211> LENGTH: 101
<212> TYPE: PRT
<213> ORGANISM: Homo sapiens

<400> SEQUENCE: 160

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
                20                  25                  30
Ser Asn Asn Lys Asn Tyr Leu Ala Trp Tyr Gln Gln Lys Pro Gly Gln
            35                  40                  45
Pro Pro Lys Leu Leu Ile Tyr Trp Ala Ser Thr Arg Glu Ser Gly Val
        50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Thr Pro
            100
```

<210> SEQ ID NO 161
<211> LENGTH: 95
<212> TYPE: PRT
<213> ORGANISM: Homo sapiens

<400> SEQUENCE: 161

```
Glu Thr Thr Leu Thr Gln Ser Pro Ala Phe Met Ser Ala Thr Pro Gly
1               5                   10                  15
```

```
Asp Lys Val Asn Ile Ser Cys Lys Ala Ser Gln Asp Ile Asp Asp
            20                  25                  30

Met Asn Trp Tyr Gln Gln Lys Pro Gly Glu Ala Ala Ile Phe Ile Ile
         35                  40                  45

Gln Glu Ala Thr Thr Leu Val Pro Gly Ile Pro Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro
                 85                  90                  95

<210> SEQ ID NO 162
<211> LENGTH: 95
<212> TYPE: PRT
<213> ORGANISM: Homo sapiens

<400> SEQUENCE: 162

Glu Ile Val Leu Thr Gln Ser Pro Asp Phe Gln Ser Val Thr Pro Lys
  1               5                  10                  15

Glu Lys Val Thr Ile Thr Cys Arg Ala Ser Gln Ser Ile Gly Ser Ser
             20                  25                  30

Leu His Trp Tyr Gln Gln Lys Pro Asp Gln Ser Pro Lys Leu Leu Ile
          35                  40                  45

Lys Tyr Ala Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro
                 85                  90                  95

<210> SEQ ID NO 163
<211> LENGTH: 95
<212> TYPE: PRT
<213> ORGANISM: Homo sapiens

<400> SEQUENCE: 163

Glu Ile Val Leu Thr Gln Ser Pro Asp Phe Gln Ser Val Thr Pro Lys
  1               5                  10                  15

Glu Lys Val Thr Ile Thr Cys Arg Ala Ser Gln Ser Ile Gly Ser Ser
             20                  25                  30

Leu His Trp Tyr Gln Gln Lys Pro Asp Gln Ser Pro Lys Leu Leu Ile
          35                  40                  45

Lys Tyr Ala Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro
                 85                  90                  95

<210> SEQ ID NO 164
<211> LENGTH: 95
<212> TYPE: PRT
<213> ORGANISM: Homo sapiens

<400> SEQUENCE: 164

Asp Val Val Met Thr Gln Ser Pro Ala Phe Leu Ser Val Thr Pro Gly
  1               5                  10                  15
```

-continued

```
Glu Lys Val Thr Ile Thr Cys Gln Ala Ser Glu Gly Ile Gly Asn Tyr
             20                  25                  30

Leu Tyr Trp Tyr Gln Gln Lys Pro Asp Gln Ala Pro Lys Leu Leu Ile
         35                  40                  45

Lys Tyr Ala Ser Gln Ser Ile Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gln Gln Gly Asn Lys His Pro
                 85                  90                  95
```

<210> SEQ ID NO 165
<211> LENGTH: 99
<212> TYPE: PRT
<213> ORGANISM: Homo sapiens

<400> SEQUENCE: 165

```
Gln Ser Val Leu Thr Gln Pro Pro Ser Val Ser Glu Ala Pro Arg Gln
 1               5                  10                  15

Arg Val Thr Ile Ser Cys Ser Gly Ser Ser Asn Ile Gly Asn Asn
             20                  25                  30

Ala Val Asn Trp Tyr Gln Gln Leu Pro Gly Lys Ala Pro Lys Leu Leu
         35                  40                  45

Ile Tyr Tyr Asp Asp Leu Leu Pro Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro
```

<210> SEQ ID NO 166
<211> LENGTH: 100
<212> TYPE: PRT
<213> ORGANISM: Homo sapiens

<400> SEQUENCE: 166

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser
            100
```

<210> SEQ ID NO 167
<211> LENGTH: 99
<212> TYPE: PRT
<213> ORGANISM: Homo sapiens

<400> SEQUENCE: 167

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro

<210> SEQ ID NO 168
<211> LENGTH: 99
<212> TYPE: PRT
<213> ORGANISM: Homo sapiens

<400> SEQUENCE: 168

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro

<210> SEQ ID NO 169
<211> LENGTH: 99
<212> TYPE: PRT
<213> ORGANISM: Homo sapiens

<400> SEQUENCE: 169

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Gln Phe
        50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Lys Ala Trp Asp Asn Ser
                85                  90                  95

Leu Asn Ala

<210> SEQ ID NO 170

```
<211> LENGTH: 99
<212> TYPE: PRT
<213> ORGANISM: Homo sapiens

<400> SEQUENCE: 170

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly

<210> SEQ ID NO 171
<211> LENGTH: 99
<212> TYPE: PRT
<213> ORGANISM: Homo sapiens

<400> SEQUENCE: 171

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe

<210> SEQ ID NO 172
<211> LENGTH: 99
<212> TYPE: PRT
<213> ORGANISM: Homo sapiens

<400> SEQUENCE: 172

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95
```

Tyr Thr Phe

<210> SEQ ID NO 173
<211> LENGTH: 99
<212> TYPE: PRT
<213> ORGANISM: Homo sapiens

<400> SEQUENCE: 173

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 174
<211> LENGTH: 99
<212> TYPE: PRT
<213> ORGANISM: Homo sapiens

<400> SEQUENCE: 174

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Arg Val Ser Trp Tyr Gln Gln Pro Pro Gly Thr Ala Pro Lys Leu
        35                  40                  45

Met Ile Tyr Glu Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Leu Tyr Thr Ser Ser
                85                  90                  95

Ser Thr Phe

<210> SEQ ID NO 175
<211> LENGTH: 99
<212> TYPE: PRT
<213> ORGANISM: Homo sapiens

<400> SEQUENCE: 175

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Thr Phe

<210> SEQ ID NO 176
<211> LENGTH: 99
<212> TYPE: PRT
<213> ORGANISM: Homo sapiens

<400> SEQUENCE: 176

Gln Ser Ala Leu Thr Gln Pro Pro Phe Val Ser Gly Ala Pro Gly Gln
  1               5                  10                  15

Ser Val Thr Ile Ser Cys Thr Gly Thr Ser Ser Asp Val Gly Asp Tyr
                 20                  25                  30

Asp His Val Phe Trp Tyr Gln Lys Arg Leu Ser Thr Thr Ser Arg Leu
             35                  40                  45

Leu Ile Tyr Asn Val Asn Thr Arg Pro Ser Gly Ile Ser Asp Leu Phe
         50                  55                  60

Ser Gly Ser Lys Ser Gly Asn Met Ala Ser Leu Thr Ile Ser Gly Leu
 65                  70                  75                  80

Lys Ser Glu Val Glu Ala Asn Tyr His Cys Ser Leu Tyr Ser Ser Ser
                 85                  90                  95

Tyr Thr Phe

<210> SEQ ID NO 177
<211> LENGTH: 95
<212> TYPE: PRT
<213> ORGANISM: Homo sapiens

<400> SEQUENCE: 177

Ser Tyr Glu Leu Thr Gln Pro Pro Ser Val Ser Val Ser Pro Gly Gln
  1               5                  10                  15

Thr Ala Ser Ile Thr Cys Ser Gly Asp Lys Leu Gly Asp Lys Tyr Ala
                 20                  25                  30

Cys Trp Tyr Gln Gln Lys Pro Gly Gln Ser Pro Val Leu Val Ile Tyr
             35                  40                  45

Gln Asp Ser Lys Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala
                 85                  90                  95

<210> SEQ ID NO 178
<211> LENGTH: 95
<212> TYPE: PRT
<213> ORGANISM: Homo sapiens

<400> SEQUENCE: 178

Ser Tyr Glu Leu Thr Gln Pro Leu Ser Val Ser Val Ala Leu Gly Gln
  1               5                  10                  15

Thr Ala Arg Ile Thr Cys Gly Gly Asn Asn Ile Gly Ser Lys Asn Val
                 20                  25                  30

His Trp Tyr Gln Gln Lys Pro Gly Gln Ala Pro Val Leu Val Ile Tyr
             35                  40                  45
```

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala
                85                  90                  95

<210> SEQ ID NO 179
<211> LENGTH: 96
<212> TYPE: PRT
<213> ORGANISM: Homo sapiens

<400> SEQUENCE: 179

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
                20                  25                  30

Tyr Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

<210> SEQ ID NO 180
<211> LENGTH: 97
<212> TYPE: PRT
<213> ORGANISM: Homo sapiens

<400> SEQUENCE: 180

Ser Tyr Glu Leu Thr Gln Pro His Ser Val Ser Val Ala Thr Ala Gln
1               5                   10                  15

Met Ala Arg Ile Thr Cys Gly Gly Asn Asn Ile Gly Ser Lys Ala Val
                20                  25                  30

His Trp Tyr Gln Gln Lys Pro Gly Gln Asp Pro Val Leu Val Ile Tyr
            35                  40                  45

Ser Asp Ser Asn Arg Pro Ser Gly Ile Pro Glu Arg Phe Ser Gly Ser
    50                  55                  60

Asn Pro Gly Asn Thr Ala Thr Leu Thr Ile Ser Arg Ile Glu Ala Gly
65                  70                  75                  80

Asp Glu Ala Asp Tyr Tyr Cys Gln Val Trp Asp Ser Ser Ser Asp His
                85                  90                  95

Pro

<210> SEQ ID NO 181
<211> LENGTH: 97
<212> TYPE: PRT
<213> ORGANISM: Homo sapiens

<400> SEQUENCE: 181

Ser Tyr Glu Leu Thr Gln Pro Pro Ser Val Ser Val Ser Leu Gly Gln
1               5                   10                  15

Met Ala Arg Ile Thr Cys Ser Gly Glu Ala Leu Pro Lys Lys Tyr Ala
                20                  25                  30

Tyr Trp Tyr Gln Gln Lys Pro Gly Gln Phe Pro Val Leu Val Ile Tyr
            35                  40                  45

```
Lys Asp Ser Glu Arg Pro Ser Gly Ile Pro Glu Arg Phe Ser Gly Ser
        50                  55                  60

Ser Ser Gly Thr Ile Val Thr Leu Thr Ile Ser Gly Val Gln Ala Glu
65                  70                  75                  80

Asp Glu Ala Asp Tyr Tyr Cys Leu Ser Ala Asp Ser Ser Gly Thr Tyr
                85                  90                  95

Pro
```

<210> SEQ ID NO 182
<211> LENGTH: 97
<212> TYPE: PRT
<213> ORGANISM: Homo sapiens

<400> SEQUENCE: 182

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu
```

<210> SEQ ID NO 183
<211> LENGTH: 97
<212> TYPE: PRT
<213> ORGANISM: Homo sapiens

<400> SEQUENCE: 183

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Pro
```

<210> SEQ ID NO 184
<211> LENGTH: 95
<212> TYPE: PRT
<213> ORGANISM: Homo sapiens

<400> SEQUENCE: 184

```
Ser Tyr Glu Leu Thr Gln Leu Pro Ser Val Ser Val Pro Gly Gln
1               5                   10                  15
```

-continued

Thr Ala Arg Ile Thr Cys Ser Gly Asp Val Leu Gly Glu Asn Tyr Ala
            20                  25                  30

Asp Trp Tyr Gln Gln Lys Pro Gly Gln Ala Pro Glu Leu Val Ile Tyr
        35                  40                  45

Glu Asp Ser Glu Arg Tyr Pro Gly Ile Pro Glu Arg Phe Ser Gly Ser
50                  55                  60

Thr Ser Gly Asn Thr Thr Thr Leu Thr Ile Ser Arg Val Leu Thr Glu
65                  70                  75                  80

Asp Glu Ala Asp Tyr Tyr Cys Leu Ser Gly Asp Glu Asp Asn Pro
                85                  90                  95

<210> SEQ ID NO 185
<211> LENGTH: 97
<212> TYPE: PRT
<213> ORGANISM: Homo sapiens

<400> SEQUENCE: 185

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Pro

<210> SEQ ID NO 186
<211> LENGTH: 95
<212> TYPE: PRT
<213> ORGANISM: Homo sapiens

<400> SEQUENCE: 186

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn Leu
                85                  90                  95

<210> SEQ ID NO 187
<211> LENGTH: 94
<212> TYPE: PRT
<213> ORGANISM: Homo sapiens

<400> SEQUENCE: 187

Ser Ser Gly Pro Thr Gln Val Pro Ala Val Ser Val Ala Leu Gly Gln
1               5                   10                  15

```
Met Ala Arg Ile Thr Cys Gln Gly Asp Ser Met Glu Gly Ser Tyr Glu
             20                  25                  30

His Trp Tyr Gln Gln Lys Pro Gly Gln Ala Pro Val Leu Val Ile Tyr
         35                  40                  45

Asp Ser Ser Asp Arg Pro Ser Arg Ile Pro Glu Arg Phe Ser Gly Ser
 50                  55                  60

Lys Ser Gly Asn Thr Thr Thr Leu Thr Ile Thr Gly Ala Gln Ala Glu
 65                  70                  75                  80

Asp Glu Ala Asp Tyr Tyr Tyr Gln Leu Ile Asp Asn His Ala
                 85                  90
```

<210> SEQ ID NO 188
<211> LENGTH: 103
<212> TYPE: PRT
<213> ORGANISM: Homo sapiens

<400> SEQUENCE: 188

```
Leu Pro Val Leu Thr Gln Pro Pro Ser Ala Ser Ala Leu Leu Gly Ala
 1               5                  10                  15

Ser Ile Lys Leu Thr Cys Thr Leu Ser Ser Glu His Ser Thr Tyr Thr
             20                  25                  30

Ile Glu Trp Tyr Gln Gln Arg Pro Gly Arg Ser Pro Gln Tyr Ile Met
         35                  40                  45

Lys Val Lys Ser Asp Gly Ser His Ser Lys Gly Asp Gly Ile Pro Asp
 50                  55                  60

Arg Phe Met Gly Ser Ser Ser Gly Ala Asp Arg Tyr Leu Thr Phe Ser
 65                  70                  75                  80

Asn Leu Gln Ser Asp Asp Glu Ala Glu Tyr His Cys Gly Glu Ser His
                 85                  90                  95

Thr Ile Asp Gly Gln Val Gly
            100
```

<210> SEQ ID NO 189
<211> LENGTH: 99
<212> TYPE: PRT
<213> ORGANISM: Homo sapiens

<400> SEQUENCE: 189

```
Gln Pro Val Leu Thr Gln Ser Ser Ser Ala Ser Ala Ser Leu Gly Ser
 1               5                  10                  15

Ser Val Lys Leu Thr Cys Thr Leu Ser Ser Gly His Ser Ser Tyr Ile
             20                  25                  30

Ile Ala Trp His Gln Gln Gln Pro Gly Lys Ala Pro Arg Tyr Leu Met
         35                  40                  45

Lys Leu Glu Gly Ser Gly Ser Tyr Asn Lys Gly Ser Gly Val Pro Asp
 50                  55                  60

Arg Phe Ser Gly Ser Ser Ser Gly Ala Asp Arg Tyr Leu Thr Ile Ser
 65                  70                  75                  80

Asn Leu Gln Phe Glu Asp Glu Ala Asp Tyr Tyr Cys Glu Thr Trp Asp
                 85                  90                  95

Ser Asn Thr
```

<210> SEQ ID NO 190
<211> LENGTH: 98
<212> TYPE: PRT
<213> ORGANISM: Homo sapiens

```
<400> SEQUENCE: 190

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
        35                  40                  45

Lys Leu Asn Ser Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Thr Gly

<210> SEQ ID NO 191
<211> LENGTH: 104
<212> TYPE: PRT
<213> ORGANISM: Homo sapiens

<400> SEQUENCE: 191

Gln Pro Val Leu Thr Gln Pro Pro Ser Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gly Gln Gly Ser Gly Val
    50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Ala Asp Tyr Tyr Cys
                85                  90                  95

Met Ile Trp Pro Ser Asn Ala Ser
                100

<210> SEQ ID NO 192
<211> LENGTH: 104
<212> TYPE: PRT
<213> ORGANISM: Homo sapiens

<400> SEQUENCE: 192

Gln Pro Val Leu Thr Gln Pro Thr Ser Leu Ser Ala Ser Pro Gly Ala
1               5                   10                  15

Ser Ala Arg Phe Thr Cys Thr Leu Arg Ser Gly Ile Asn Val Gly Thr
            20                  25                  30

Tyr Arg Ile Tyr Trp Tyr Gln Gln Lys Pro Gly Ser Leu Pro Arg Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Thr Asn Ala Gly Leu
65                  70                  75                  80

Leu Leu Ile Ser Gly Leu Gln Ser Glu Asp Glu Ala Asp Tyr Tyr Cys
                85                  90                  95

Ala Ile Trp Tyr Ser Ser Thr Ser
                100
```

<210> SEQ ID NO 193
<211> LENGTH: 104
<212> TYPE: PRT
<213> ORGANISM: Homo sapiens

<400> SEQUENCE: 193

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100

<210> SEQ ID NO 194
<211> LENGTH: 104
<212> TYPE: PRT
<213> ORGANISM: Homo sapiens

<400> SEQUENCE: 194

Gln Pro Val Leu Thr Gln Pro Thr Ser Leu Ser Ala Ser Pro Gly Ala
1               5                   10                  15

Ser Ala Arg Leu Thr Cys Thr Leu Arg Ser Gly Ile Asn Leu Gly Ser
            20                  25                  30

Tyr Arg Ile Phe Trp Tyr Gln Gln Lys Pro Glu Ser Pro Arg Tyr
        35                  40                  45

Leu Leu Ser Tyr Tyr Ser Asp Ser Ser Lys His Gln Gly Ser Gly Val
    50                  55                  60

Pro Ser Arg Phe Ser Gly Ser Lys Asp Ala Ser Ser Asn Ala Gly Ile
65                  70                  75                  80

Leu Val Ile Ser Gly Leu Gln Ser Glu Asp Glu Ala Asp Tyr Tyr Cys
                85                  90                  95

Met Ile Trp His Ser Ser Ala Ser
            100

<210> SEQ ID NO 195
<211> LENGTH: 105
<212> TYPE: PRT
<213> ORGANISM: Homo sapiens

<400> SEQUENCE: 195

Gln Pro Val Leu Thr Gln Pro Ser Ser His Ser Ala Ser Ser Gly Ala
1               5                   10                  15

Ser Val Arg Leu Thr Cys Met Leu Ser Ser Gly Phe Ser Val Gly Asp
            20                  25                  30

Phe Trp Ile Arg Trp Tyr Gln Gln Lys Pro Gly Asn Pro Pro Arg Tyr
        35                  40                  45

Leu Leu Tyr Tyr His Ser Asp Ser Asn Lys Gly Gln Gly Ser Gly Val
    50                  55                  60

```
Pro Ser Arg Phe Ser Gly Asn Asp Ala Ser Ala Asn Ala Gly Ile
 65                  70                  75                  80

Leu Arg Ile Ser Gly Leu Gln Pro Glu Asp Glu Ala Asp Tyr Tyr Cys
                 85                  90                  95

Gly Thr Trp His Ser Asn Ser Lys Thr
            100                 105

<210> SEQ ID NO 196
<211> LENGTH: 98
<212> TYPE: PRT
<213> ORGANISM: Homo sapiens

<400> SEQUENCE: 196

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn

<210> SEQ ID NO 197
<211> LENGTH: 98
<212> TYPE: PRT
<213> ORGANISM: Homo sapiens

<400> SEQUENCE: 197

Gln Thr Val Val Thr Gln Glu Pro Ser Leu Thr Val Ser Pro Gly Gly
 1               5                  10                  15

Thr Val Thr Leu Thr Cys Ala Ser Ser Thr Gly Ala Val Thr Ser Gly
                20                  25                  30

Tyr Tyr Pro Asn Trp Phe Gln Gln Lys Pro Gly Gln Ala Pro Arg Ala
            35                  40                  45

Leu Ile Tyr Ser Thr Ser Asn Lys His Ser Trp Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Leu Leu Tyr Tyr Gly Gly
                 85                  90                  95

Ala Gln

<210> SEQ ID NO 198
<211> LENGTH: 98
<212> TYPE: PRT
<213> ORGANISM: Homo sapiens

<400> SEQUENCE: 198

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
                20                  25                  30
```

-continued

His Tyr Pro Tyr Trp Phe Gln Gln Lys Pro Gly Gln Ala Pro Arg Thr
              35                  40                  45

Leu Ile Tyr Asp Thr Ser Asn Lys His Ser Trp Thr Pro Ala Arg Phe
 50                  55                  60

Ser Gly Ser Leu Leu Gly Gly Lys Ala Ala Leu Thr Leu Leu Gly Ala
 65                  70                  75                  80

Gln Pro Glu Asp Glu Ala Glu Tyr Tyr Cys Leu Leu Ser Tyr Ser Gly
                 85                  90                  95

Ala Arg

<210> SEQ ID NO 199
<211> LENGTH: 99
<212> TYPE: PRT
<213> ORGANISM: Homo sapiens

<400> SEQUENCE: 199

Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Ser
                20                  25                  30

Tyr Tyr Pro Ser Trp Tyr Gln Gln Thr Pro Gly Gln Ala Pro Arg Thr
              35                  40                  45

Leu Ile Tyr Ser Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Ser
                 85                  90                  95

Gly Ile Ser

<210> SEQ ID NO 200
<211> LENGTH: 104
<212> TYPE: PRT
<213> ORGANISM: Homo sapiens

<400> SEQUENCE: 200

Gln Pro Val Leu Thr Gln Pro Pro Ser Ala Ser Ala Ser Leu Gly Ala
 1               5                  10                  15

Ser Val Thr Leu Thr Cys Thr Leu Ser Ser Gly Tyr Ser Asn Tyr Lys
                20                  25                  30

Val Asp Trp Tyr Gln Gln Arg Pro Gly Lys Gly Pro Arg Phe Val Met
              35                  40                  45

Arg Val Gly Thr Gly Gly Ile Val Gly Ser Lys Gly Asp Gly Ile Pro
 50                  55                  60

Asp Arg Phe Ser Val Leu Gly Ser Gly Leu Asn Arg Tyr Leu Thr Ile
 65                  70                  75                  80

Lys Asn Ile Gln Glu Glu Asp Glu Ser Asp Tyr His Cys Gly Ala Asp
                 85                  90                  95

His Gly Ser Gly Ser Asn Phe Val
             100

<210> SEQ ID NO 201
<211> LENGTH: 98
<212> TYPE: PRT
<213> ORGANISM: Homo sapiens

<400> SEQUENCE: 201

```
Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Ile Val Gly Asn Gln
                20                  25                  30

Gly Ala Ala Trp Leu Gln Gln His Gln Gly His Pro Pro Lys Leu Leu
            35                  40                  45

Ser Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Leu Asp Ser Ser Leu
                85                  90                  95

Ser Ala

<210> SEQ ID NO 202
<211> LENGTH: 104
<212> TYPE: PRT
<213> ORGANISM: Homo sapiens

<400> SEQUENCE: 202

Arg Pro Val Leu Thr Gln Pro Pro Ser Leu Ser Ala Ser Pro Gly Ala
1               5                   10                  15

Thr Ala Arg Leu Pro Cys Thr Leu Ser Ser Asp Leu Ser Val Gly Gly
                20                  25                  30

Lys Asn Met Phe Trp Tyr Gln Gln Lys Pro Gly Ser Ser Pro Arg Leu
            35                  40                  45

Phe Leu Tyr His Tyr Ser Asp Ser Asp Lys Gln Leu Gly Pro Gly Val
    50                  55                  60

Pro Ser Arg Val Ser Gly Ser Lys Glu Thr Ser Ser Asn Thr Ala Phe
65                  70                  75                  80

Leu Leu Ile Ser Gly Leu Gln Pro Glu Asp Glu Ala Asp Tyr Tyr Cys
                85                  90                  95

Gln Val Tyr Glu Ser Ser Ala Asn
            100

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 203

His His His His His His
1               5

<210> SEQ ID NO 204
<211> LENGTH: 98
<212> TYPE: PRT
<213> ORGANISM: Homo sapiens

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45
```

-continued

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 205
<211> LENGTH: 98
<212> TYPE: PRT
<213> ORGANISM: Homo sapiens

<400> SEQUENCE: 205

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 206
<211> LENGTH: 98
<212> TYPE: PRT
<213> ORGANISM: Homo sapiens

<400> SEQUENCE: 206

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 207
<211> LENGTH: 98
<212> TYPE: PRT
<213> ORGANISM: Homo sapiens

<400> SEQUENCE: 207

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 208
<211> LENGTH: 98
<212> TYPE: PRT
<213> ORGANISM: Homo sapiens

<400> SEQUENCE: 208

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 209
<211> LENGTH: 100
<212> TYPE: PRT
<213> ORGANISM: Homo sapiens

<400> SEQUENCE: 209

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 210
<211> LENGTH: 98
<212> TYPE: PRT
<213> ORGANISM: Homo sapiens
```

<400> SEQUENCE: 210

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 211
<211> LENGTH: 98
<212> TYPE: PRT
<213> ORGANISM: Homo sapiens

<400> SEQUENCE: 211

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 212
<211> LENGTH: 98
<212> TYPE: PRT
<213> ORGANISM: Homo sapiens

<400> SEQUENCE: 212

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

```
<210> SEQ ID NO 213
<211> LENGTH: 97
<212> TYPE: PRT
<213> ORGANISM: Homo sapiens

<400> SEQUENCE: 213

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 214
<211> LENGTH: 98
<212> TYPE: PRT
<213> ORGANISM: Homo sapiens

<400> SEQUENCE: 214

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 215
<211> LENGTH: 98
<212> TYPE: PRT
<213> ORGANISM: Homo sapiens

<400> SEQUENCE: 215

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

Leu Gln Trp Ser Ser Leu Lys Ala Ser Asp Thr Ala Met Tyr Tyr Cys
                85                  90                  95

Ala Arg

<210> SEQ ID NO 216
<211> LENGTH: 101
<212> TYPE: PRT
<213> ORGANISM: Homo sapiens

<400> SEQUENCE: 216

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100

<210> SEQ ID NO 217
<211> LENGTH: 294
<212> TYPE: DNA
<213> ORGANISM: Homo sapiens

<400> SEQUENCE: 217
caggtgcagc tggtgcagag cggtgccgaa gtgaaaaaac caggcgccag cgtgaaagtt     60
agctgcaaag ccagcggcta cctttacc agctatggca ttagctgggt tcgccaggcc    120
ccaggccagg gtctggaatg gatgggctgg attagcgcct ataacggcaa caccaactac    180
gcccagaaac tgcaaggccg cgtgaccatg accaccgata ccagcaccag caccgcctat    240
atggaactgc gctccctgcg cagcgacgat accgccgtgt attattgcgc gcgt           294

<210> SEQ ID NO 218
<211> LENGTH: 294
<212> TYPE: DNA
<213> ORGANISM: Homo sapiens

<400> SEQUENCE: 218
caggtgcagc tggtgcagag cggtgccgaa gtgaaaaaac caggcgccag cgtgaaagtt     60
agctgcaaag ccagcggcta taccttcacc agctactata tgcattgggt tcgccaggcc    120
ccaggccagg gtctggaatg gatgggcatt attaacccga gcggcggcag caccagctat    180
gcacagaaat ttcagggccg cgtgaccatg acccgcgata ccagcaccag caccgtgtat    240
atggaactga gcagcctgcg cagcgaagat accgccgtgt attattgcgc gcgt           294

<210> SEQ ID NO 219
<211> LENGTH: 294
<212> TYPE: DNA
<213> ORGANISM: Homo sapiens

<400> SEQUENCE: 219
caggtgcagc tggtgcagag cggtgccgaa gtgaaaaaac caggcagcag cgtgaaagtg     60

```
agctgtaaag ccagcggtgg cacctttagc agctatgcca ttagctgggt tcgccaggca    120
ccaggtcagg gtctggaatg gatgggtggc attattccga ttttttggcac cgccaactat    180 gcccagaaat tcagggtcg cgtgaccatt accgcagatg aaagcaccag caccgcctat    240
atggaactga gcagcctgcg cagcgaagat accgcagtgt attattgcgc gcgg          294

<210> SEQ ID NO 220
<211> LENGTH: 294
<212> TYPE: DNA
<213> ORGANISM: Homo sapiens

<400> SEQUENCE: 220
gaagtgcagc tggtggaaag cggcggtggc ctggtgcagc aggtggtag cctgcgcctg     60 agctgcgccg ccagcggctt tacctttagc agctattgga tgagctgggt tcgccaggcc    120
ccaggcaaag gcctggaatg ggtggcgaac atcaaacagg atggcagcga gaaatactat   180
gtggatagcg tgaaaggccg ctttaccatt agccgcgata cgccaaaaaa cagcctgtat   240
ctgcaaatga acagcctgcg ggccgaagat accgccgtgt attattgcgc gcgt         294

<210> SEQ ID NO 221
<211> LENGTH: 294
<212> TYPE: DNA
<213> ORGANISM: Homo sapiens

<400> SEQUENCE: 221
caggtgcagc tggtggaaag cggcggtggc ctggtgaaac caggcggtag cctgcgcctg    60
agctgcgccg ccagcggctt tacctttagc gattactaca tgagctggat tcgccaggcc   120
ccaggcaaag gcctggaatg ggttagctat attagcagca gtggcagcac catctattac    180
gccgatagcg tgaaaggccg ctttaccatt agccgcgata cgccaaaaaa cagcctgtat   240
ctgcaaatga acagcctgcg ggccgaagat accgccgtgt attattgcgc gcgt         294

<210> SEQ ID NO 222
<211> LENGTH: 300
<212> TYPE: DNA
<213> ORGANISM: Homo sapiens

<400> SEQUENCE: 222
gaagtgcagc tggtggaaag cggcggtggc ctggtgaaac caggcggtag cctgcgcctg    60
agctgcgccg ccagcggctt tacctttagc aacgcctgga tgagctgggt tcgccaggcc   120
ccaggcaaag gcctggaatg ggttggccgc atcaaaagca aaaccgatgg cggcaccacc    180
gattatgccg ccccagtgaa aggccgcttt accattagcc gcgacgatag caaaaacacc    240
ctgtacctgc aaatgaacag cctgaaaacc gaagataccg ccgtgtatta ttgcgcgcgt   300

<210> SEQ ID NO 223
<211> LENGTH: 294
<212> TYPE: DNA
<213> ORGANISM: Homo sapiens

<400> SEQUENCE: 223
gaagtgcagc tggtggaaag cggcggtggc ctggtgaaac caggcggtag cctgcgcctg    60
agctgcgccg ccagcggctt tacctttagc agctatagca tgaactgggt tcgccaggcc   120
ccaggcaaag gcctggaatg ggttagcagc atcagcagca gtagcagcta tatctattac    180
gccgatagcg tgaaaggccg ctttaccatt agccgcgata cgccaaaaaa cagcctgtat   240
```

```
ctgcaaatga acagcctgcg ggccgaagat accgccgtgt attattgcgc gcgt        294
```

<210> SEQ ID NO 224
<211> LENGTH: 294
<212> TYPE: DNA
<213> ORGANISM: Homo sapiens

<400> SEQUENCE: 224

```
gaagtgcagc tgctggaaag cggtggcggt ctggtgcagc caggtggtag cctgcgcctg    60
agctgtgccg caagcggctt tacctttagc agctatgcca tgagctgggt gcgccaagca   120
ccaggcaaag gcctggaatg ggtgagcgcc attagcggca gcgtggcag cacctattat    180
gccgatagcg tgaaaggtcg ctttaccatt agtcgcgata cagcaaaaa caccctgtat    240
ctgcaaatga cagcctgcg ggcagaagat accgcagttt attattgcgc gcgg         294
```

<210> SEQ ID NO 225
<211> LENGTH: 294
<212> TYPE: DNA
<213> ORGANISM: Homo sapiens

<400> SEQUENCE: 225

```
caggtgcagc tggtggaaag cggcggtggc gttgtgcagc caggtcgcag tctgcgcctg    60
agctgtgccg ccagcggctt tacctttagc agctatgcca tgcattgggt tcgccaggcc   120
ccaggcaaag gcctggaatg ggtggccgtg attagctatg atggcagcaa caaatattac   180
gccgatagcg tgaaaggccg ctttaccatt agccgcgata cagcaaaaa caccctgtac    240
ctgcaaatga cagcctgcg ggccgaagat accgccgtgt attattgcgc gcgt         294
```

<210> SEQ ID NO 226
<211> LENGTH: 291
<212> TYPE: DNA
<213> ORGANISM: Homo sapiens

<400> SEQUENCE: 226

```
gaagtgcagc tggtggaaag cggcggtggc ctgattcagc caggcggtag cctgcgcctg    60
agctgtgccg ccagcggctt taccgttagc agcaactata tgagctgggt tcgccaggcc   120
ccaggcaaag gcctggaatg ggttagcgtg atctatagcg gcggcagcac ctattatgcc   180
gatagcgtga aggccgctt taccattagc cgcgataaca gcaaaaacac cctgtacctg    240
caaatgaaca gcctgcgggc cgaagatacc gccgtgtatt attgcgcgcg t            291
```

<210> SEQ ID NO 227
<211> LENGTH: 294
<212> TYPE: DNA
<213> ORGANISM: Homo sapiens

<400> SEQUENCE: 227

```
gaagtgcagc tggtggaaag cggcggtggc ctggtgcagc caggtggtag cctgcgcctg    60
agctgcgccg ccagcggctt tacctttagc agctattgga tgcattgggt tcgccaggcc   120
ccaggcaaag gcctggtttg ggttagccgc attaacagcg acggcagcag caccagctat   180
gccgatagcg tgaaaggccg ctttaccatt agccgcgata cgccaaaaa caccctgtat    240
ctgcaaatga cagcctgcg ggccgaagat accgccgtgt attattgcgc gcgt         294
```

<210> SEQ ID NO 228
<211> LENGTH: 294
<212> TYPE: DNA
<213> ORGANISM: Homo sapiens

<400> SEQUENCE: 228

```
gaagtgcagc tggtgcagag cggtgccgaa gtgaaaaaac cgggcgaaag cctgaaaatc    60
agctgcaaag cagcggcta tagctttacc agctattgga ttggctgggt cgccagatg    120
ccgggcaaag gcctggaatg gatgggcatt atctatccgg gcgatagcga tacccgctat   180
agcccgagct ttcagggcca ggttacaatt agcgccgaca aaagcatcag caccgcctat   240
ctgcaatgga gcagcctgaa agccagcgat accgccatgt attattgcgc gcgt         294
```

<210> SEQ ID NO 229
<211> LENGTH: 303
<212> TYPE: DNA
<213> ORGANISM: Homo sapiens

<400> SEQUENCE: 229

```
caggtgcagc tgcaacagag cggcccaggc ctggttaaac cgagccagac cctgagcctg    60
acctgcgcca ttagcggcga tagcgttagc agcaacagcg ccgcctggaa ctggattcgc   120
cagagcccga gccgcggtct ggaatggctg gccgcacct attatcgcag caatggtac    180
aacgattacg ccgttagcgt gaaaagccgc attaccatta accggatac agcaaaaac    240
cagttcagcc tgcaactgaa cagcgtgacc ccggaagata ccgccgtgta ttactgcgcg   300
cgt                                                                 303
```

<210> SEQ ID NO 230
<211> LENGTH: 88
<212> TYPE: PRT
<213> ORGANISM: Homo sapiens

<400> SEQUENCE: 230

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys
                85
```

<210> SEQ ID NO 231
<211> LENGTH: 88
<212> TYPE: PRT
<213> ORGANISM: Homo sapiens

<400> SEQUENCE: 231

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 232
<211> LENGTH: 88
<212> TYPE: PRT
<213> ORGANISM: Homo sapiens

<400> SEQUENCE: 232

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys
                85

<210> SEQ ID NO 233
<211> LENGTH: 88
<212> TYPE: PRT
<213> ORGANISM: Homo sapiens

<400> SEQUENCE: 233

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 234
<211> LENGTH: 88
<212> TYPE: PRT
<213> ORGANISM: Homo sapiens

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
              65                  70                  75                  80
Glu Asp Phe Ala Thr Tyr Tyr Cys
                85

<210> SEQ ID NO 235
<211> LENGTH: 88
<212> TYPE: PRT
<213> ORGANISM: Homo sapiens

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys
                85

<210> SEQ ID NO 236
<211> LENGTH: 88
<212> TYPE: PRT
<213> ORGANISM: Homo sapiens

<400> SEQUENCE: 236

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 237
<211> LENGTH: 88
<212> TYPE: PRT
<213> ORGANISM: Homo sapiens

<400> SEQUENCE: 237

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys
            85

<210> SEQ ID NO 238
<211> LENGTH: 88
<212> TYPE: PRT
<213> ORGANISM: Homo sapiens

<400> SEQUENCE: 238

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys
            85

<210> SEQ ID NO 239
<211> LENGTH: 89
<212> TYPE: PRT
<213> ORGANISM: Homo sapiens

<400> SEQUENCE: 239

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys
            85

<210> SEQ ID NO 240
<211> LENGTH: 264
<212> TYPE: DNA
<213> ORGANISM: Homo sapiens

<400> SEQUENCE: 240
gatattcaga tgacccagag cccgagcacc ctgagcgcaa gcgtgggcga tcgcgtgacc      60
attacctgcc gcgccagtca gagcattagc agctggctgg cctggtatca gcagaaaccg     120
ggcaaagccc cgaaactgct gatctatgat gccagcagcc tggaaagcgg cgtgccgagc     180
cgctttagcg gcagcggtag cggcaccgag ttcaccctga ccattagcag cctgcaaccg     240
gaagactttg ccacctatta ttgc                                            264

<210> SEQ ID NO 241
<211> LENGTH: 264
<212> TYPE: DNA
<213> ORGANISM: Homo sapiens

<400> SEQUENCE: 241

```
gccattcaga tgacccagag cccgagcagc ctgagcgcaa gcgtgggcga tcgcgtgacc        60
attacctgcc gcgccagcca gggcattcgc aacgatctgg gctggtatca gcagaaaccg       120
ggcaaagccc cgaaactgct gatctatgcc gccagcagcc tgcaaagcgg cgtgccaagt       180
cgctttagcg gcagcggtag cggcaccgat ttcaccctga ccattagcag tctgcaaccg       240
gaagactttg ccacctatta ttgc                                              264
```

<210> SEQ ID NO 242
<211> LENGTH: 264
<212> TYPE: DNA
<213> ORGANISM: Homo sapiens

<400> SEQUENCE: 242

```
gatattcagc tgacccagag cccgagcttt ctgagcgcca gcgtgggcga tcgcgtgacc        60
attacctgcc gcgccagcca gggcattagc agctatctgg cctggtatca gcagaaaccg       120
ggcaaagccc cgaaactgct gatctatgcc gccagcaccc tgcaaagcgg cgtgccaagc       180
cgctttagcg gcagcggtag cggcaccgag ttcaccctga ccattagcag cctgcaaccg       240
gaagactttg ccacctatta ttgc                                              264
```

<210> SEQ ID NO 243
<211> LENGTH: 264
<212> TYPE: DNA
<213> ORGANISM: Homo sapiens

<400> SEQUENCE: 243

```
gatattcaga tgacccagag cccgagcagc gttagcgcca gcgtgggcga tcgcgtgacc        60
attacctgcc gcgccagtca gggcattagc agctggctgg cctggtatca gcagaaaccg       120
ggcaaagccc cgaaactgct gatctatgcc gccagcagcc tgcaaagcgg cgtgccaagt       180
cgctttagcg gcagcggtag cggcaccgat ttcaccctga ccattagcag tctgcaaccg       240
gaagactttg ccacctatta ttgc                                              264
```

<210> SEQ ID NO 244
<211> LENGTH: 264
<212> TYPE: DNA
<213> ORGANISM: Homo sapiens

<400> SEQUENCE: 244

```
gatattcaga tgacccagag cccgagcagc ctgagcgcaa gcgtgggcga tcgcgtgacc        60
attacctgcc gcgccagcca gggcattagc aactatctgg catggtttca gcagaaaccg       120
ggcaaagccc cgaaaagcct gatctatgcc gccagcagtc tgcaaagcgg cgtgccaagt       180
cgctttagcg gcagcggtag cggcaccgat ttcaccctga ccattagcag cctgcaaccg       240
gaagactttg ccacctatta ttgc                                              264
```

<210> SEQ ID NO 245
<211> LENGTH: 264
<212> TYPE: DNA
<213> ORGANISM: Homo sapiens

<400> SEQUENCE: 245

```
gatattcaga tgacccagag cccgagcagc ctgagcgcaa gcgtgggcga tcgcgtgacc        60
attacctgcc gcgccagcca gggcattagc aactatctgg cctggtatca gcagaaaccg       120
```

```
ggcaaagtgc cgaaactgct gatctatgcc gccagcaccc tgcaaagcgg cgtgccaagt      180
cgctttagcg gcagcggtag cggcaccgat ttcaccctga ccattagcag cctgcaaccg      240
gaagacgtgg cgacctatta ttgc                                            264
```

<210> SEQ ID NO 246
<211> LENGTH: 264
<212> TYPE: DNA
<213> ORGANISM: Homo sapiens

<400> SEQUENCE: 246

```
gatattcaga tgacccagag cccgagcagc ctgagcgcca gcgtgggtga tcgcgtgacc      60
attacctgtc gcgcaagcca gagcattagc agctatctga actggtatca gcagaaacca     120
ggcaaagccc caaaactgct gatttatgcc gcaagcagcc tgcaaagcgg tgtgccgagc     180
cgctttagcg gcagcggtag cggcaccgat tttaccctga ccattagtag cctgcaaccg     240
gaagactttg ccacctatta ttgc                                            264
```

<210> SEQ ID NO 247
<211> LENGTH: 264
<212> TYPE: DNA
<213> ORGANISM: Homo sapiens

<400> SEQUENCE: 247

```
gaaattgtgc tgacccagag cccagccacc ctgagcctga gcccaggtga acgcgcaacc      60
ctgagctgtc gcgcaagcca gagcgtgagc agctatctgg cctggtatca acagaaacca     120
ggccaggcac cacgcctgct gatttatgat gccagcaatc gcgcaaccgg cattccggca     180
cgctttagcg gcagcggtag cggcaccgat tttaccctga ccattagcag cctggaaccg     240
gaagactttg ccgtgtatta ttgc                                            264
```

<210> SEQ ID NO 248
<211> LENGTH: 264
<212> TYPE: DNA
<213> ORGANISM: Homo sapiens

<400> SEQUENCE: 248

```
gaaattgtga tgacccagag cccggccacc ctgagcgtta gcccaggcga acgcgcaacc      60
ctgagctgtc gcgccagtca gagcgttagc agcaacctgg cctggtatca gcagaaaccg     120
ggtcaggccc cacgcctgct gatctatggt gccagcaccc gcgccaccgg cattccagca     180
cgctttagcg gcagcggtag cggcaccgag ttcaccctga ccattagcag cctgcaaagc     240
gaagactttg ccgtgtatta ttgc                                            264
```

<210> SEQ ID NO 249
<211> LENGTH: 267
<212> TYPE: DNA
<213> ORGANISM: Homo sapiens

<400> SEQUENCE: 249

```
gaaattgtgc tgacccagag cccgggcacc ctgagcctga gcccaggcga acgcgcaacc      60
ctgagctgtc gcgccagtca gagcgttagc agcagctatc tggcctggta tcagcagaaa     120
ccgggccagg ccccacgcct gctgatctat ggtgccagca gccgcgccac cggcattcca     180
gatcgcttta gcggcagcgg tagcggcacc gatttcaccc tgaccattag ccgcctggaa     240
ccggaagact ttgccgtgta ttattgc                                         267
```

```
<210> SEQ ID NO 250
<211> LENGTH: 90
<212> TYPE: PRT
<213> ORGANISM: Homo sapiens

<400> SEQUENCE: 250

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys
                85                  90

<210> SEQ ID NO 251
<211> LENGTH: 89
<212> TYPE: PRT
<213> ORGANISM: Homo sapiens

<400> SEQUENCE: 251

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys
                85

<210> SEQ ID NO 252
<211> LENGTH: 89
<212> TYPE: PRT
<213> ORGANISM: Homo sapiens

<400> SEQUENCE: 252

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Glu Asp Glu Ala Asp Tyr Tyr Cys
                85

<210> SEQ ID NO 253
```

```
<211> LENGTH: 90
<212> TYPE: PRT
<213> ORGANISM: Homo sapiens

<400> SEQUENCE: 253

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys
                85                  90

<210> SEQ ID NO 254
<211> LENGTH: 90
<212> TYPE: PRT
<213> ORGANISM: Homo sapiens

<400> SEQUENCE: 254

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys
                85                  90

<210> SEQ ID NO 255
<211> LENGTH: 90
<212> TYPE: PRT
<213> ORGANISM: Homo sapiens

<400> SEQUENCE: 255

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys
                85                  90

<210> SEQ ID NO 256
<211> LENGTH: 87
```

-continued

```
<212> TYPE: PRT
<213> ORGANISM: Homo sapiens

<400> SEQUENCE: 256

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys
                85

<210> SEQ ID NO 257
<211> LENGTH: 87
<212> TYPE: PRT
<213> ORGANISM: Homo sapiens

<400> SEQUENCE: 257

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys
                85

<210> SEQ ID NO 258
<211> LENGTH: 270
<212> TYPE: DNA
<213> ORGANISM: Homo sapiens

<400> SEQUENCE: 258
cagagcgtgc tgacccagcc accaagcgtg agcggtgcac caggtcagcg cgtgaccatt    60
agctgcaccg gcagcagcag caacattggc gcaggctatg atgtgcattg gtatcagcag   120
ctgccaggca ccgcaccgaa actgctgatt tatggcaaca gcaatcgccc aagcggtgtg   180
ccggatcgct ttagcggcag caaaagcggc accagcgcca gcctggcgat taccggtctg   240
caagccgaag acgaagccga ttattactgc                                    270

<210> SEQ ID NO 259
<211> LENGTH: 267
<212> TYPE: DNA
<213> ORGANISM: Homo sapiens

<400> SEQUENCE: 259
cagagcgtgc tgacccagcc accaagcgca agcggcaccc aggccagcg cgtgaccatt    60 agctgtagcg gcagcagcag caacattggc agcaactatg tgtactggta tcagcagctg   120
```
ccgggcaccg ccccgaaact gctgatctat cgcaacaacc agcgcccgag cggcgtgcca    180
gatcgcttta gcggtagcaa aagcggcacc agcgcaagcc tggcgattag cggcctgcgc    240
agcgaagacg aagccgatta ttactgc                                        267

<210> SEQ ID NO 260
<211> LENGTH: 267
<212> TYPE: DNA
<213> ORGANISM: Homo sapiens

<400> SEQUENCE: 260
cagagcgtgc tgacccagcc gccgagcgtt agcgccgcac caggccagaa agtgaccatt    60
agctgtagcg gcagcagcag caacatcggc aacaactacg ttagctggta tcagcagctg    120
ccgggcaccg ccccgaaact gctgatctat gataacaaca acgcccgag cggcatcccg     180 gatcgcttta gcggtagcaa aagcggcacc agcgccaccc tgggcattac cggcctgcaa    240
accgaagacg aagccgatta ttactgc                                        267

<210> SEQ ID NO 261
<211> LENGTH: 270
<212> TYPE: DNA
<213> ORGANISM: Homo sapiens

<400> SEQUENCE: 261
cagagcgccc tgacccagcc acgcagcgtt agcggtagcc caggccagag cgtgaccatt    60
agctgcaccg gcaccagcag cgacgtgggc ggctataact acgttagctg gtatcagcag    120
catccgggca aagccccgaa actgatgatc tatgatgtta gcaaacgccc gagcggcgtg    180
ccggatcgct ttagcggcag caaaagcggc aacaccgcca gcctgaccat cagcggcctg    240
caagccgaag acgaagccga ttattactgc                                     270

<210> SEQ ID NO 262
<211> LENGTH: 270
<212> TYPE: DNA
<213> ORGANISM: Homo sapiens

<400> SEQUENCE: 262
cagagcgccc tgacccagcc agccagcgtt agcggtagcc caggccagag cattaccatt    60
agctgcaccg gcaccagcag cgacgtgggc ggctataact acgttagctg gtatcagcag    120
catccgggca aagccccgaa actgatgatc tatgaagtta gcaaccgccc gagcggcgtt    180
agcaatcgct ttagcggcag caaaagcggc aacaccgcca gcctgaccat tagcggcctg    240
caagccgaag acgaagccga ttattactgc                                     270

<210> SEQ ID NO 263
<211> LENGTH: 270
<212> TYPE: DNA
<213> ORGANISM: Homo sapiens

<400> SEQUENCE: 263
cagagcgccc tgacccagcc agccagcgtt agcggtagcc caggccagag cattaccatt    60
agctgcaccg gcaccagcag cgacgtgggc agctataacc tggttagctg gtatcagcag    120
catccgggca aagccccgaa actgatgatc tatgaaggca gcaaacgccc gagcggcgtt    180
agcaaccgct ttagtggcag caaaagcggc aacaccgcca gcctgaccat tagcggcctg    240
caagccgaag acgaagccga ttattactgc                                     270

<210> SEQ ID NO 264
<211> LENGTH: 261
<212> TYPE: DNA
<213> ORGANISM: Homo sapiens

<400> SEQUENCE: 264

```
agctatgaac tgacccagcc gccgagcgtt agcgttagcc caggccagac cgccagcatt      60
acctgtagcg gcgacaaact gggcgacaaa tacgcctact ggtatcagca gaaaccgggc     120
cagagcccgg tgctggttat ctatcaggat agcaaacgcc cgagcggcat tccgaacgc      180
tttagcggca gcaacagcgg caacaccgcc accctgacca ttagcggcac ccaggccgaa     240
gacgaagccg attattactg c                                               261
```

<210> SEQ ID NO 265
<211> LENGTH: 261
<212> TYPE: DNA
<213> ORGANISM: Homo sapiens

<400> SEQUENCE: 265

```
agctatgtgc tgacccagcc gccgagcgtt agcgtggccc caggcaaaac cgcccgcatt      60
acctgcggcg gcaacaacat tggcagcaaa agcgtgcact ggtatcagca gaaaccgggc     120
caggccccgg tgctggttat ctattatgat agcgatcgcc cgagcggcat tccgaacgc      180
tttagcggca gcaacagcgg caacaccgcc accctgacca ttagccgcgt ggaagccgaa     240
gacgaagccg attattactg c                                               261
```

<210> SEQ ID NO 266
<211> LENGTH: 98
<212> TYPE: PRT
<213> ORGANISM: Homo sapiens

<400> SEQUENCE: 266

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Gly Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg
```

<210> SEQ ID NO 267
<211> LENGTH: 98
<212> TYPE: PRT
<213> ORGANISM: Homo sapiens

<400> SEQUENCE: 267

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Ile His Trp Val Arg Gln Ala Pro Gly Gln Gly Leu Glu Trp Met
        35                  40                  45
```

-continued

Gly Ile Ile Asn Pro Ser Gly Gly Ser Thr Ser Tyr Ala Gln Lys Phe
                50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 268
<211> LENGTH: 98
<212> TYPE: PRT
<213> ORGANISM: Homo sapiens

<400> SEQUENCE: 268

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Ala Ile Ser Trp Val Arg Gln Ala Pro Gly Gln Gly Leu Glu Trp Met
                35                  40                  45

Gly Gly Ile Ile Pro Ile Phe Gly Thr Ala Asn Tyr Ala Gln Lys Phe
                50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 269
<211> LENGTH: 98
<212> TYPE: PRT
<213> ORGANISM: Homo sapiens

<400> SEQUENCE: 269

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Ile Ser Trp Val Arg Gln Ala Pro Gly Lys Gly Leu Glu Trp Val
                35                  40                  45

Ala Asn Ile Lys Gln Ser Gly Ser Glu Thr Tyr Tyr Val Glu Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 270
<211> LENGTH: 98
<212> TYPE: PRT
<213> ORGANISM: Homo sapiens

<400> SEQUENCE: 270

Gln Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Asp His
            20                  25                  30

Tyr Ile Ser Trp Ile Arg Gln Ala Pro Gly Lys Gly Leu Glu Trp Val
        35                  40                  45

Ser Tyr Ile Ser Ser Ser Gly Ser Thr Thr Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 271
<211> LENGTH: 100
<212> TYPE: PRT
<213> ORGANISM: Homo sapiens

<400> SEQUENCE: 271

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Gly Arg Ile Lys Ser Lys Thr Tyr Gly Gly Thr Thr Asp Tyr Ala Glu
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 272
<211> LENGTH: 98
<212> TYPE: PRT
<213> ORGANISM: Homo sapiens

<400> SEQUENCE: 272

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Ile Asn Trp Val Arg Gln Ala Pro Gly Lys Gly Leu Glu Trp Val
        35                  40                  45

Ser Ser Ile Ser Ser Ser Ser Ser Tyr Thr Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 273
<211> LENGTH: 98
<212> TYPE: PRT
<213> ORGANISM: Homo sapiens
```

-continued

<400> SEQUENCE: 273

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 274
<211> LENGTH: 98
<212> TYPE: PRT
<213> ORGANISM: Homo sapiens

<400> SEQUENCE: 274

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Ala Val Ile Ser Tyr Ser Gly Ser Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 275
<211> LENGTH: 97
<212> TYPE: PRT
<213> ORGANISM: Homo sapiens

<400> SEQUENCE: 275

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser His
            20                  25                  30

Tyr Ile Ser Trp Val Arg Gln Ala Pro Gly Lys Gly Leu Glu Trp Val
        35                  40                  45

Ser Val Ile Tyr Ser Gly Gly Ser Thr Tyr Tyr Ala Glu Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

```
<210> SEQ ID NO 276
<211> LENGTH: 98
<212> TYPE: PRT
<213> ORGANISM: Homo sapiens

<400> SEQUENCE: 276

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Val Trp Val
        35                  40                  45

Ser Arg Ile Thr Ser Ser Gly Ser Ser Thr Ser Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 277
<211> LENGTH: 98
<212> TYPE: PRT
<213> ORGANISM: Homo sapiens

<400> SEQUENCE: 277

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Tyr Pro Gly Thr Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 278
<211> LENGTH: 101
<212> TYPE: PRT
<213> ORGANISM: Homo sapiens

<400> SEQUENCE: 278

Gln Val Gln Leu Gln Gln Ser Gly Pro Gly Leu Val Lys Pro Ser Gln
1               5                   10                  15

Thr Leu Ser Leu Thr Cys Ala Ile Ser Gly Gly Ser Val Ser Thr Ser
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80
```

Gln Phe Ser Leu Gln Leu Asn Ser Val Thr Pro Glu Asp Thr Ala Val
            85                  90                  95

Tyr Tyr Cys Ala Arg
        100

<210> SEQ ID NO 279
<211> LENGTH: 294
<212> TYPE: DNA
<213> ORGANISM: Homo sapiens

<400> SEQUENCE: 279
caggtgcagc tggtgcagag cggtgccgaa gtgaaaaaac caggcgccag cgtgaaagtt     60
agctgcaaag ccagcggcta taccttacc agctatggca ttagctgggt tcgccaggcc    120
ccaggccagg gtctggaatg gatgggctgg attagcgcct atggcggcaa caccaactac    180
gcccagaaac tgcaaggccg cgtgaccatg accaccgata ccagcaccag caccgcctat    240
atggaactgc gctccctgcg cagcgacgat accgccgtgt attattgcgc gcgt          294

<210> SEQ ID NO 280
<211> LENGTH: 294
<212> TYPE: DNA
<213> ORGANISM: Homo sapiens

<400> SEQUENCE: 280
caggtgcagc tggtgcagag cggtgccgaa gtgaaaaaac caggcgccag cgtgaaagtt     60
agctgcaaag ccagcggcta taccttcacc agctactata ttcattgggt tcgccaggcc    120
ccaggccagg gtctggaatg gatgggcatt attaacccga gcggcggcag caccagctat    180
gcacagaaat tcagggccg cgtgaccatg acccgcgata ccagcaccag caccgtgtat    240
atggaactga gcagcctgcg cagcgaagat accgccgtgt attattgcgc gcgt          294

<210> SEQ ID NO 281
<211> LENGTH: 294
<212> TYPE: DNA
<213> ORGANISM: Homo sapiens

<400> SEQUENCE: 281
caggtgcagc tggtgcagag cggtgccgaa gtgaaaaaac caggcagcag cgtgaaagtg     60
agctgtaaag ccagcggtta taccttagc agctatgcca ttagctgggt tcgccaggca    120
ccaggtcagg gtctggaatg gatgggtggc attattccga tttttggcac cgccaactat    180
gcccagaaat ttcagggtcg cgtgaccatt accgcagatg aaagcaccag caccgcctat    240
atggaactga gcagcctgcg cagcgaagat accgcagtgt attattgcgc gcgk          294

<210> SEQ ID NO 282
<211> LENGTH: 294
<212> TYPE: DNA
<213> ORGANISM: Homo sapiens

<400> SEQUENCE: 282
gaagtgcagc tggtggaaag cggcggtggc ctggtgcagc caggtggtag cctgcgcctg     60
agctgcgccg ccagcggctt taccttagc agctattgga ttagctgggt tcgccaggcc    120
ccaggcaaag gcctggaatg ggtggcgaac atcaaacaga gcggcagcga gacctactat    180
gtggagagcg tgaaaggccg ctttaccatt agccgcgata cgccaaaaa cagcctgtat    240 ctgcaaatga acagcctgcg ggccgaagat accgccgtgt attattgcgc gcgt          294

<210> SEQ ID NO 283
<211> LENGTH: 294
<212> TYPE: DNA
<213> ORGANISM: Homo sapiens

<400> SEQUENCE: 283
caggtgcagc tggtggaaag cggcggtggc ctggtgaaac caggcggtag cctgcgcctg      60
agctgcgccg ccagcggctt tacctttagc gatcattaca ttagctggat tcgccaggcc     120
ccaggcaaag gcctggaatg ggttagctat attagcagca gtggcagcac cacctattac     180
gccgagagcg tgaaaggccg ctttaccatt agccgcgata cgccaaaaa cagcctgtat      240 ctgcaaatga acagcctgcg ggccgaagat accgccgtgt attattgcgc gcgt           294

<210> SEQ ID NO 284
<211> LENGTH: 300
<212> TYPE: DNA
<213> ORGANISM: Homo sapiens

<400> SEQUENCE: 284
gaagtgcagc tggtggaaag cggcggtggc ctggtgaaac caggcggtag cctgcgcctg      60
agctgcgccg ccagcggctt tacctttagc aactattgga ttagctgggt tcgccaggcc     120
ccaggcaaag gcctggaatg ggttggccgc atcaaaagca aaacctatgg cggcaccacc     180
gattatgccg agccagtgaa aggccgcttt accattagcc gcgacgatag caaaaacacc     240
ctgtacctgc aaatgaacag cctgaaaacc gaagataccg ccgtgtatta ttgcgcgcgt    300

<210> SEQ ID NO 285
<211> LENGTH: 294
<212> TYPE: DNA
<213> ORGANISM: Homo sapiens

<400> SEQUENCE: 285
gaagtgcagc tggtggaaag cggcggtggc ctggtgaaac caggcggtag cctgcgcctg      60
agctgcgccg ccagcggctt tacctttagc agctatagca ttaactgggt tcgccaggcc     120
ccaggcaaag gcctggaatg ggttagcagc atcagcagca gtagcagcta tacctattac     180
gccgagagcg tgaaaggccg ctttaccatt agccgcgata cgccaaaaa cagcctgtat      240 ctgcaaatga acagcctgcg ggccgaagat accgccgtgt attattgcgc gcgt           294

<210> SEQ ID NO 286
<211> LENGTH: 294
<212> TYPE: DNA
<213> ORGANISM: Homo sapiens

<400> SEQUENCE: 286
gaagtgcagc tgctggaaag cggtggcggt ctggtgcagc caggtggtag cctgcgcctg      60
agctgtgccg caagcggctt tacctttagc agctatgcca ttagctgggt gcgccaagca     120
ccaggcaaag gcctggaatg ggtgagcgcc attagcggca gcgtggcag cacctattat      180 gccgagagcg tgaaaggtcg ctttaccatt agtcgcgata cagcaaaaa caccctgtat      240 ctgcaaatga acagcctgcg ggcagaagat accgcagttt attattgcgc gcgk           294

<210> SEQ ID NO 287
<211> LENGTH: 294
<212> TYPE: DNA
<213> ORGANISM: Homo sapiens

<400> SEQUENCE: 287

```
caggtgcagc tggtggaaag cggcggtggc gttgtgcagc aggtcgcag tctgcgcctg      60 agctgtgccg ccagcggctt taccttagc agctatgcca ttcattgggt tcgccaggcc     120
ccaggcaaag gcctggaatg ggtggccgtg attagctata gcggcagcaa caaatattac    180
gccgagagcg tgaaaggccg ctttaccatt agccgcgata cagcaaaaa cacccctgtac   240 ctgcaaatga acagcctgcg ggccgaagat accgccgtgt attattgcgc gcgt          294
```

<210> SEQ ID NO 288
<211> LENGTH: 291
<212> TYPE: DNA
<213> ORGANISM: Homo sapiens

<400> SEQUENCE: 288

```
gaagtgcagc tggtggaaag cggcggtggc ctgattcagc caggcggtag cctgcgcctg    60
agctgtgccg ccagcggctt taccgttagc agccattata ttagctgggt tcgccaggcc    120
ccaggcaaag gcctggaatg ggttagcgtg atctatagcg cggcagcac ctattatgcc    180 gagagcgtga aaggccgctt taccattagc cgcgataaca gcaaaaacac cctgtacctg   240
caaatgaaca gcctgcgggc cgaagatacc gccgtgtatt attgcgcgcg t              291
```

<210> SEQ ID NO 289
<211> LENGTH: 294
<212> TYPE: DNA
<213> ORGANISM: Homo sapiens

<400> SEQUENCE: 289

```
gaagtgcagc tggtggaaag cggcggtggc ctggtgcagc caggtggtag cctgcgcctg    60
agctgcgccg ccagcggctt tacctttagc agctattgga ttcattgggt tcgccaggcc    120
ccaggcaaag gcctggtttg ggttagccgc attaccagca gcggcagcag caccagctat   180
gccgagagcg tgaaaggccg ctttaccatt agccgcgata cgccaaaaa cacccctgtat    240 ctgcaaatga acagcctgcg ggccgaagat accgccgtgt attattgcgc gcgt          294
```

<210> SEQ ID NO 290
<211> LENGTH: 294
<212> TYPE: DNA
<213> ORGANISM: Homo sapiens

<400> SEQUENCE: 290

```
gaagtgcagc tggtgcagag cggtgccgaa gtgaaaaaac cgggcgaaag cctgaaaatc   60
agctgcaaag gcagcggcta tagctttacc agctattgga ttagctgggt tcgccagatg   120
ccgggcaaag gcctggaatg gatgggcatt atctatccgg gcaccagcta taccgctat    180 agcccgagct ttcagggcca ggttacaatt agcgccgaca aaagcatcag caccgcctat   240
ctgcaatgga gcagcctgaa agccagcgat accgccatgt attattgcgc gcgt          294
```

<210> SEQ ID NO 291
<211> LENGTH: 303
<212> TYPE: DNA
<213> ORGANISM: Homo sapiens

<400> SEQUENCE: 291

```
caggtgcagc tgcaacagag cggcccaggc ctggttaaac cgagccagac cctgagcctg    60
acctgcgcca ttagcggcgg cagcgttagc accagcagcg ccgcctggaa ctggattcgc   120
cagagcccga gccgcggtct ggaatggctg ggccgcattt attatcgcag caaatggtac   180
aacgattacg ccgttagcgt gaaaagccgc attaccatta acccggatac cagcaaaaac   240
```
cagttcagcc tgcaactgaa cagcgtgacc ccggaagata ccgccgtgta ttactgcgcg    300
cgt                                                                  303

<210> SEQ ID NO 292
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 292 tgg ggc cag ggc acc ctg gtt act gtc tcg agc                           33
Trp Gly Gln Gly Thr Leu Val Thr Val Ser Ser
1               5                   10

<210> SEQ ID NO 293
<211> LENGTH: 11
<212> TYPE: PRT
<213> ORGANISM: Homo sapiens

<400> SEQUENCE: 293

Trp Gly Gln Gly Thr Leu Val Thr Val Ser Ser
1               5                   10

<210> SEQ ID NO 294
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 294 tgg ggc cag ggc acc ctg gtt act gtc tcg agc                           33
Trp Gly Gln Gly Thr Leu Val Thr Val Ser Ser
1               5                   10

<210> SEQ ID NO 295
<211> LENGTH: 11
<212> TYPE: PRT
<213> ORGANISM: Homo sapiens

<400> SEQUENCE: 295

Trp Gly Gln Gly Thr Leu Val Thr Val Ser Ser
1               5                   10

<210> SEQ ID NO 296
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 296 ttc ggc cag ggt acc aaa gtg gaa atc aag cgc acc                       36
Phe Gly Gln Gly Thr Lys Val Glu Ile Lys Arg Thr
1               5                   10

<210> SEQ ID NO 297
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 297

Phe Gly Gln Gly Thr Lys Val Glu Ile Lys Arg Thr
1               5                   10

<210> SEQ ID NO 298
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
ttcggccagg gtaccaaagt tgaaattaaa cgcacc                              36

<210> SEQ ID NO 299
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 299 ttc ggc cag cgt acc aaa gtg gaa att aaa cgc acc                     36
Phe Gly Gln Gly Thr Lys Val Glu Ile Lys Arg Thr
1               5                   10

<210> SEQ ID NO 300
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 300 ttt ggc ggc ggt acc aag ctg acc gtg ctc ggc cag                     36
Phe Gly Gly Gly Thr Lys Leu Thr Val Leu Gly Gln
1               5                   10

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Phe Gly Gly Gly Thr Lys Leu Thr Val Leu Gly Gln
1               5                   10

<210> SEQ ID NO 302
<211> LENGTH: 36
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 302
tttggcggcg gtaccaaact cactgtgctg ggccag                             36

<210> SEQ ID NO 303
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
tttggcggcg gtaccaaact cactgtcctg ggccag                             36

<210> SEQ ID NO 304
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(990)

<400> SEQUENCE: 304

```
gcg tcg acc aaa ggc ccc agc gtg ttc cct ctg gcc ccc agc agc aag        48
Ala Ser Thr Lys Gly Pro Ser Val Phe Pro Leu Ala Pro Ser Ser Lys
1               5                   10                  15 agc acc tct ggc gga aca gcc gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gag ccc gtg acc gtg tcc tgg aac tct ggc gcc ctg acc agc       144
Phe Pro Glu Pro Val Thr Val Ser Trp Asn Ser Gly Ala Leu Thr Ser
        35                  40                  45 ggc gtg cac acc ttt cca gcc gtg ctc cag agc agc ggc ctg tac agc       192
Gly Val His Thr Phe Pro Ala Val Leu Gln Ser Ser Gly Leu Tyr Ser
    50                  55                  60 ctg agc agc gtc gtg acc gtg ccc agc agc agc ctg ggc acc cag acc       240
Leu Ser Ser Val Val Thr Val Pro Ser Ser Ser Leu Gly Thr Gln Thr
65                  70                  75                  80 tac atc tgc aac gtg aac cac aag ccc agc aac aca aag gtg gac aag       288
Tyr Ile Cys Asn Val Asn His Lys Pro Ser Asn Thr Lys Val Asp Lys
                85                  90                  95 cgg gtg gaa ccc aag agc tgc gac aag acc cac acc tgt ccc ccc tgc       336
Arg Val Glu Pro Lys Ser Cys Asp Lys Thr His Thr Cys Pro Pro Cys
            100                 105                 110 cct gcc cct gaa ctg ctg gga ggc ccc tcc gtg ttc ctg ttc ccc cca       384
Pro Ala Pro Glu Leu Leu Gly Gly Pro Ser Val Phe Leu Phe Pro Pro
        115                 120                 125 aag cct aag gac acc ctg atg atc agc cgg acc ccc gaa gtg acc tgc       432
Lys Pro Lys Asp Thr Leu Met Ile Ser Arg Thr Pro Glu Val Thr Cys
    130                 135                 140 gtg gtg gtg gac gtg tcc cac gag gac cct gaa gtg aag ttt aat tgg       480
Val Val Val Asp Val Ser His Glu Asp Pro Glu Val Lys Phe Asn Trp
145                 150                 155                 160 tac gtg gac ggc gtg gaa gtg cac aac gcc aag acc aag ccc aga gag       528
Tyr Val Asp Gly Val Glu Val His Asn Ala Lys Thr Lys Pro Arg Glu
                165                 170                 175 gaa cag tac aac agc acc tac cgg gtg gtg tcc gtg ctg acc gtg ctg       576
Glu Gln Tyr Asn Ser Thr Tyr Arg Val Val Ser Val Leu Thr Val Leu
```

```
Glu Gln Tyr Asn Ser Thr Tyr Arg Val Val Ser Val Leu Thr Val Leu
            180                 185                 190 cac cag gac tgg ctg aac ggc aaa gag tac aag tgc aag gtg tcc aac      624
His Gln Asp Trp Leu Asn Gly Lys Glu Tyr Lys Cys Lys Val Ser Asn
            195                 200                 205 aag gcc ctg cct gcc ccc atc gag aaa acc atc agc aag gcc aaa ggc      672
Lys Ala Leu Pro Ala Pro Ile Glu Lys Thr Ile Ser Lys Ala Lys Gly
210                 215                 220 cag ccc cgc gag ccc cag gtg tac aca ctg ccc cct agc cgg gaa gag      720
Gln Pro Arg Glu Pro Gln Val Tyr Thr Leu Pro Pro Ser Arg Glu Glu
225                 230                 235                 240 atg acc aag aac cag gtg tcc ctg acc tgc ctc gtg aag ggc ttc tac      768
Met Thr Lys Asn Gln Val Ser Leu Thr Cys Leu Val Lys Gly Phe Tyr
            245                 250                 255 ccc agc gac att gcc gtg gaa tgg gag agc aac ggc cag ccc gag aac      816
Pro Ser Asp Ile Ala Val Glu Trp Glu Ser Asn Gly Gln Pro Glu Asn
            260                 265                 270 aac tac aag acc acc ccc cct gtg ctg gac agc gac ggc tca ttc ttc      864
Asn Tyr Lys Thr Thr Pro Pro Val Leu Asp Ser Asp Gly Ser Phe Phe
            275                 280                 285 ctg tac agc aag ctg acc gtg gac aag agc cgg tgg cag cag ggc aac      912
Leu Tyr Ser Lys Leu Thr Val Asp Lys Ser Arg Trp Gln Gln Gly Asn
290                 295                 300 gtg ttc agc tgc tcc gtg atg cac gag gcc ctg cac aac cac tac acc      960
Val Phe Ser Cys Ser Val Met His Glu Ala Leu His Asn His Tyr Thr
305                 310                 315                 320 cag aag tcc ctg agc ctg agc ccc ggc aag                              990
Gln Lys Ser Leu Ser Leu Ser Pro Gly Lys
            325                 330

<210> SEQ ID NO 305
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
    195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 306
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 306 gcg tcg acc aaa ggc ccg agc gtg ttt ccg ctg gcc ccg agc agc aaa      48
Ala Ser Thr Lys Gly Pro Ser Val Phe Pro Leu Ala Pro Ser Ser Lys
1               5                   10                  15 agc acc agc ggc ggc acc gcc gca ctg ggc tgc ctg gtg aaa gat tat      96
Ser Thr Ser Gly Gly Thr Ala Ala Leu Gly Cys Leu Val Lys Asp Tyr
                20                  25                  30 ttc ccg gaa cca gtg acc gtg agc tgg aac agc ggt gcc ctg acc agc     144
Phe Pro Glu Pro Val Thr Val Ser Trp Asn Ser Gly Ala Leu Thr Ser
            35                  40                  45 ggc gtg cat acc ttt ccg gcg gtg ctg caa agc agc ggc ctg tat agc     192
Gly Val His Thr Phe Pro Ala Val Leu Gln Ser Ser Gly Leu Tyr Ser
        50                  55                  60 ctg agc agc gtt gtg acc gtg ccg agc agc agc ctg ggc acc cag acc     240
Leu Ser Ser Val Val Thr Val Pro Ser Ser Ser Leu Gly Thr Gln Thr
65                  70                  75                  80 tat att tgc aac gtc aac cat aaa ccg agc aac acc aaa gtc gat aaa     288
Tyr Ile Cys Asn Val Asn His Lys Pro Ser Asn Thr Lys Val Asp Lys
                85                  90                  95 aaa gtc gaa ccg aaa agc gaa ttc gac tat aaa gat gac gat gac aaa     336
Lys Val Glu Pro Lys Ser Glu Phe Asp Tyr Lys Asp Asp Asp Asp Lys
                100                 105                 110 ggg gcg ccg cac cat cat cac cat cac                                 363
Gly Ala Pro His His His His His His
            115                 120
```

<210> SEQ ID NO 307
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Glu Phe Asp Tyr Lys Asp Asp Asp Lys
            100                 105                 110

Gly Ala Pro His His His His His His
            115                 120

<210> SEQ ID NO 308
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(315)

<400> SEQUENCE: 308 gtg gcc gct ccc tcc gtg ttc atc ttc cca ccc agc gac gag cag ctg      48
Val Ala Ala Pro Ser Val Phe Ile Phe Pro Pro Ser Asp Glu Gln Leu
1               5                   10                  15 aag tcc ggc aca gcc agc gtc gtg tgc ctg ctg aac aac ttc tac ccc      96
Lys Ser Gly Thr Ala Ser Val Val Cys Leu Leu Asn Asn Phe Tyr Pro
            20                  25                  30 cgc gag gcc aaa gtg cag tgg aag gtg gac aac gcc ctc cag agc ggc     144
Arg Glu Ala Lys Val Gln Trp Lys Val Asp Asn Ala Leu Gln Ser Gly
        35                  40                  45 aac agc cag gaa agc gtc acc gag cag gac agc aag gac tcc acc tac     192
Asn Ser Gln Glu Ser Val Thr Glu Gln Asp Ser Lys Asp Ser Thr Tyr
    50                  55                  60 agc ctg agc agc acc ctg acc ctg agc aag gcc gac tac gag aag cac     240
Ser Leu Ser Ser Thr Leu Thr Leu Ser Lys Ala Asp Tyr Glu Lys His
65                  70                  75                  80 aag gtg tac gcc tgc gaa gtg acc cac cag ggc ctg tcc agc ccc gtg     288
Lys Val Tyr Ala Cys Glu Val Thr His Gln Gly Leu Ser Ser Pro Val
                85                  90                  95 acc aag agc ttc aac cgg ggc gag tgc                                 315
Thr Lys Ser Phe Asn Arg Gly Glu Cys
            100                 105

<210> SEQ ID NO 309
<211> LENGTH: 105
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 309

```
Val Ala Ala Pro Ser Val Phe Ile Phe Pro Pro Ser Asp Glu Gln Leu
1               5                   10                  15
Lys Ser Gly Thr Ala Ser Val Val Cys Leu Leu Asn Asn Phe Tyr Pro
            20                  25                  30
Arg Glu Ala Lys Val Gln Trp Lys Val Asp Asn Ala Leu Gln Ser Gly
        35                  40                  45
Asn Ser Gln Glu Ser Val Thr Glu Gln Asp Ser Lys Asp Ser Thr Tyr
    50                  55                  60
Ser Leu Ser Ser Thr Leu Thr Leu Ser Lys Ala Asp Tyr Glu Lys His
65                  70                  75                  80
Lys Val Tyr Ala Cys Glu Val Thr His Gln Gly Leu Ser Ser Pro Val
                85                  90                  95
Thr Lys Ser Phe Asn Arg Gly Glu Cys
            100                 105
```

<210> SEQ ID NO 310
<211> LENGTH: 315
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(315)

<400> SEQUENCE: 310

```
gtg gcc gca ccg agc gtg ttt atc ttt ccg ccg agc gat gaa cag ctg      48
Val Ala Ala Pro Ser Val Phe Ile Phe Pro Pro Ser Asp Glu Gln Leu
1               5                   10                  15 aaa agc ggc acc gcc agc gtg gtg tgc ctg ctg aac aac ttt tat ccg      96
Lys Ser Gly Thr Ala Ser Val Val Cys Leu Leu Asn Asn Phe Tyr Pro
            20                  25                  30 cgc gaa gcc aaa gtg cag tgg aaa gtg gat aac gcc ctg caa agc ggc     144
Arg Glu Ala Lys Val Gln Trp Lys Val Asp Asn Ala Leu Gln Ser Gly
        35                  40                  45 aac agc cag gaa agc gtt acc gaa cag gat agc aaa gat agc acc tac     192
Asn Ser Gln Glu Ser Val Thr Glu Gln Asp Ser Lys Asp Ser Thr Tyr
    50                  55                  60 agc ctg agc agc acc ctg acc ctg agc aaa gcc gat tat gaa aaa cat     240
Ser Leu Ser Ser Thr Leu Thr Leu Ser Lys Ala Asp Tyr Glu Lys His
65                  70                  75                  80 aaa gtg tat gcc tgc gaa gtg acc cat cag ggc ctg agc agc cca gtg     288
Lys Val Tyr Ala Cys Glu Val Thr His Gln Gly Leu Ser Ser Pro Val
                85                  90                  95 acc aaa agt ttt aac cgc ggc gag gcc                                 315
Thr Lys Ser Phe Asn Arg Gly Glu Ala
            100                 105
```

<210> SEQ ID NO 311
<211> LENGTH: 105
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 311

Val Ala Ala Pro Ser Val Phe Ile Phe Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Ala
            100                 105

<210> SEQ ID NO 312
<211> LENGTH: 312
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: CDS
<222> LOCATION: (1)..(312)

<400> SEQUENCE: 312 ccc aaa gcc gcc cct agc gtg acc ctg ttc ccc cca agc agc gag gaa      48
Pro Lys Ala Ala Pro Ser Val Thr Leu Phe Pro Pro Ser Ser Glu Glu
1               5                   10                  15 ctc cag gcc aac aag gcc acc ctc gtg tgc ctg atc agc gac ttc tac      96
Leu Gln Ala Asn Lys Ala Thr Leu Val Cys Leu Ile Ser Asp Phe Tyr
            20                  25                  30 cct ggc gcc gtg acc gtg gcc tgg aag gcc gat agc agc cct gtg aag     144
Pro Gly Ala Val Thr Val Ala Trp Lys Ala Asp Ser Ser Pro Val Lys
        35                  40                  45 gcc ggc gtg gaa acc acc acc ccc agc aag cag agc aac aac aaa tac     192
Ala Gly Val Glu Thr Thr Thr Pro Ser Lys Gln Ser Asn Asn Lys Tyr
    50                  55                  60 gcc gcc agc agc tac ctg agc ctg acc ccc gag cag tgg aag tcc cac     240
Ala Ala Ser Ser Tyr Leu Ser Leu Thr Pro Glu Gln Trp Lys Ser His
65                  70                  75                  80 aga tcc tac agc tgc cag gtc aca cac gag ggc agc acc gtg gaa aag     288
Arg Ser Tyr Ser Cys Gln Val Thr His Glu Gly Ser Thr Val Glu Lys
                85                  90                  95 acc gtg gcc ccc acc gag tgc agc                                     312
Thr Val Ala Pro Thr Glu Cys Ser
            100

<210> SEQ ID NO 313
<211> LENGTH: 104
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 313

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 314
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(309)

<400> SEQUENCE: 314 ccg aaa gcc gcc cca agc gtg acc ctg ttt ccg ccg agc agc gaa gaa      48
Pro Lys Ala Ala Pro Ser Val Thr Leu Phe Pro Pro Ser Ser Glu Glu
1               5                   10                  15 ctg caa gcc aac aaa gcc acc ctg gtt tgc ctg atc agc gat ttt tat      96
Leu Gln Ala Asn Lys Ala Thr Leu Val Cys Leu Ile Ser Asp Phe Tyr
            20                  25                  30 ccg ggt gcc gtg acc gtg gcc tgg aaa gcc gat agc agc ccg gtg aaa     144
Pro Gly Ala Val Thr Val Ala Trp Lys Ala Asp Ser Ser Pro Val Lys
        35                  40                  45 gcc ggc gtg gaa acc acc acc ccg agc aaa cag agc aac aac aaa tat     192
Ala Gly Val Glu Thr Thr Thr Pro Ser Lys Gln Ser Asn Asn Lys Tyr
    50                  55                  60 gcc gcc agc agc tat ctg agc ctg acc ccg gaa cag tgg aaa agc cat     240
Ala Ala Ser Ser Tyr Leu Ser Leu Thr Pro Glu Gln Trp Lys Ser His
65                  70                  75                  80 cgc agc tat agt tgt caa gtg acc cat gaa ggc agc acc gtg gaa aaa     288
Arg Ser Tyr Ser Cys Gln Val Thr His Glu Gly Ser Thr Val Glu Lys
                85                  90                  95 acc gtg gcc ccg acc gag gcc                                          309
Thr Val Ala Pro Thr Glu Ala
            100

<210> SEQ ID NO 315
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

```
Pro Gly Ala Val Thr Val Ala Trp Lys Ala Asp Ser Ser Pro Val Lys
            35                  40                  45

Ala Gly Val Glu Thr Thr Thr Pro Ser Lys Gln Ser Asn Asn Lys Tyr
 50                  55                  60

Ala Ala Ser Ser Tyr Leu Ser Leu Thr Pro Glu Gln Trp Lys Ser His
 65                  70                  75                  80

Arg Ser Tyr Ser Cys Gln Val Thr His Glu Gly Ser Thr Val Glu Lys
                 85                  90                  95

Thr Val Ala Pro Thr Glu Ala
            100

<210> SEQ ID NO 316
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Met Ser Gly Ser His His His His His His Gly Thr Met Val Ser Lys
 1               5                  10                  15

Gly Glu Glu Leu Phe Thr Gly Val Val Pro Ile Leu Val Glu Leu Asp
             20                  25                  30

Gly Asp Val Asn Gly His Lys Phe Ser Val Ser Gly Glu Gly Glu Gly
         35                  40                  45

Asp Ala Thr Tyr Gly Lys Leu Thr Leu Lys Phe Ile Cys Thr Thr Gly
 50                  55                  60

Lys Leu Pro Val Pro Trp Pro Thr Leu Val Thr Thr Leu Thr Tyr Gly
 65                  70                  75                  80

Val Gln Cys Phe Ser Arg Tyr Pro Asp His Met Lys Gln His Asp Phe
                 85                  90                  95

Phe Lys Ser Ala Met Pro Glu Gly Tyr Val Gln Glu Arg Thr Ile Phe
            100                 105                 110

Phe Lys Asp Asp Gly Asn Tyr Lys Thr Arg Ala Glu Val Lys Phe Glu
        115                 120                 125

Gly Asp Thr Leu Val Asn Arg Ile Glu Leu Lys Gly Ile Asp Phe Lys
    130                 135                 140

Glu Asp Gly Asn Ile Leu Gly His Lys Leu Glu Tyr Asn Tyr Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Met Val Leu Leu Glu Phe Val Thr Ala Ala
225                 230                 235                 240

Gly Ile Thr Leu Gly Met Asp Glu Leu Tyr Lys Asp Ile
                245                 250
```

COLLECTION AND METHODS FOR ITS USE

CROSS-REFERENCE TO RELATED APPLICATIONS

This application is a divisional of U.S. application Ser. No. 13/884,975 filed on May 13, 2013, which is a national stage entry of PCT/EP2011/070473 filed on Nov. 18, 2011 and claims the benefit of U.S. provisional application Ser. No. 61/494,452 filed Jun. 8, 2011, and U.S. provisional application Ser. No. 61/415,367 filed Nov. 19, 2010, which are each incorporated by reference in their entireties.

SEQUENCE LISTING

The instant application contains a Sequence Listing which has been submitted in ASCII format via EFS-Web and is hereby incorporated by reference in its entirety. Said ASCII copy, created on Feb. 15, 2011, is named MS130US.txt and is 229, 568 bytes in size.

BACKGROUND

Advances in pharmaceutical development, especially in the field of therapeutic antibodies, are rapidly enabling and/or improving the treatment of many diseases. These advances, by reaching novel target spaces and providing novel mechanisms of action are increasingly improving the quality of lives of patients even with the most severe and challenging diseases. One challenge for the health care system in general and patients in particular is that the costs of new drugs, enabled by of these pharmaceutical advances, are also rapidly increasing. The high costs are a result of the investments required for the development of pharmaceuticals, especially of antibodies, which currently exceed one billion dollars per marketed product. The high risk of failure in development and very long developmental timelines make these investments inevitable. It may take over fifteen years from the time of identification of a potential therapeutic antibody until it reaches the market and can benefit patients. Each stage of development, from identification, pre-clinical, clinical to market entry is riddled with challenges and risks. Pharmaceutical companies are constantly working to reduce developmental costs by reducing timelines and risks of failure in order to get the most effective medicines into the hands of patients quickly.

The following disclosure provides a valuable advance which allows for faster identification of the optimal therapeutic antibodies for the treatment of any disease. Therapeutic antibody candidates must fulfill a number of development criteria in order to make it to the market, such as, long term stability, low aggregation propensity and high expression yields. The disclosed advance increases the probability and speed of identifying an antibody that can fulfill all of the rigorous development criteria right from the start. The resultant antibody will be less expensive to produce and will be effective and safe in the treatment of numerous diseases.

A well known method of identifying therapeutic antibodies is through the use of phage display technology. Phage display utilizes virus-like particles that are grown in bacteria to display antibodies. One benefit of this technology is that the libraries used are massive, with up to $1 \times 10^{11}$ antibodies, which can quickly be tested for binding to any target relevant for any disease. See, for example, Knappik et al., (2000), "Fully synthetic human combinatorial antibody libraries (HuCAL) based on modular consensus frameworks and CDRs randomized with trinucleotides," *J. Mol. Biol.* 11; 296(1):57-86, and U.S. Pat. No. 6,300,064, both of which are incorporated by reference in their entireties. The benefit of working with such large numbers is that the output of a screening against a target may result in hundreds of antibodies that bind to the therapeutic target, all of which could be therapeutically relevant. A problem, though, is that often only a few of these antibodies are developable, meaning that they can meet all of the rigorous criteria required in order to make it to the market.

In order for a new phage display collection to shorten the identification timelines and reduce the inherent risks, the collection should comprise antibodies having the properties which are necessary for selection and clinical development and which will result in safe and effective treatment in patients. Such properties include: 1) high phage display rates, so that each and every antibody of the collection can be tested against the target of interest; 2) high expression levels in both Fab and IgG1 formats, so that the antibody or fragment can be reproduced efficiently with the needed quantity; 3) high thermal stability in both Fab and IgG1 formats, to ensure structural and functional integrity of the molecules delivered to patients; 4) high stability in serum in both Fab and IgG1 formats, so that the antibody shows increased half-life and prolonged activity; 5) high monomeric content (% monomer) as determined by size exclusion chromatography (SEC) in both Fab and IgG1 formats as this signifies a low aggregation propensity; 6) high isoelectric point (pI) in IgG1 format; 7) high thermal stability in Fab and IgG1 formats before and after exposure to acid; 8) low turbidity in Fab or IgG1 formats before and after exposure to acid; 9) stable molecular radius and % polydispersity before and after exposure to acid; 10) low risk of immunogenicity, thereby increasing safety, and/or 11) high diversity, so that one collection can be used to identify many antibodies against any therapeutic target.

A collection, which in essential ways imitates the human immune system, should be highly valuable, or even the optimal solution. The human immune system is composed of antibodies encoded by germline genes. Antibodies, in part, comprise of a variable heavy chain and variable light chains. There are approximately 50 variable heavy chain germline genes and approximately 50 variable light chain germline genes, combined providing about 2,500 combinations of different variable heavy and light chain pairs. In humans, all 2500 of these combinations are believed to be produced. It has been found, though, that certain variable heavy chains, variable light chains and/or variable heavy and light chain combinations (pairs) are present at a higher level than others. It was hypothesized that there must be some reason that some are present more than others, and if so, that the highly present germline genes may have favorable functional properties. Therefore, one way of providing a collection of antibodies having favorable functional properties is to generate a collection comprising the abundant variable heavy chain, variable light chain, and/or variable heavy chain and variable light chain pairs present in the human immune repertoire.

In addition, the germline gene sequences present in humans are thought to have very low immunogenicity, for obvious reasons, therefore these sequences can be imitated in recombinant antibodies in order to lower the risk of immunogenicity.

Approaches to evaluate the variable heavy and light chain germline gene pairings prevalent in the human immune repertoire have been undertaken. See de Wildt et al., Analysis of heavy and light chain pairings indicates that receptor editing shapes the human antibody repertoire, J Mol. Biol. 22; 285(3):895-901 (January 1999), which is incorporated by reference in its entirety. Wildt et al. took blood samples from human donors, sorted the IgG+ B cells, which had undergone somatic hypermutation, PCR amplified the cDNAs, sequenced each cDNA, and aligned each sequence to the known human variable domain germline genes. Wildt et al. observed that only a few germline genes dominated the immune repertoire and that the frequent heavy and light chain gene segments are often paired.

Attempts at maintaining the heavy and light chain variable domain pairings of individual B cells have also been undertaken. For example, libraries of variable domain "cognate pairs" have been disclosed. See Meijer et al., Isolation of human antibody repertoires with preservation of the natural heavy and light chain pairing, J Mol. Biol., 358(3): 764-72 (May 5, 2006); and WO2005042774, which are both incorporated by reference in their entirety. Libraries according to the techniques described in Meijer et al. have been generated from individual B cells from an immunized host. Generally, the B cells are sorted by FACS so that CD38$^{HI}$ B cells, which represent somatically hypermutated cells, are selected, their cDNAs are PCR amplified, and the antibody gene products are inserted into Fab vectors for selection. Such cognate pair libraries are not without their limitations. For example, the hosts providing the B cells typically are immunized; and the B cell populations sorted have been hypermutated, therefore, the resulting libraries are biased towards a particular immunogen.

Additionally, attempts at utilizing prominent variable heavy chain or variable light chains for collection generation have been undertaken. For example, in Shi et al., "De Novo Selection of High-Affinity Antibodies from Synthetic Fab Libraries Displayed on Phage as pIX Fusion Proteins; J Mol. Biol., 397(2):385-96 (Mar. 26, 2010) and the respective patent application WO2009085462; and WO2006014498, which are incorporated by reference in their entireties. There, variable heavy chain or variable light chain germline protein sequences were incorporated into libraries based upon their frequency of use in the human immune repertoire.

Additional attempts have also been undertaken, which incorporate a specific germline pair into a collection. For example, WO1999020749, which is incorporated by reference in its entirety, describes a collection where its members comprise heavy chains having the canonical structure of a hypervariable loop encoded by the human germline heavy chain gene segment DP-47 (IGHV3-23) and/or framework regions encoded by the germline gene, and/or light chains having the canonical structure of a hypervariable loop encoded by the human germline light chain gene segment O2/O12 (IGKV1-39/1D-39) and/or framework regions encoded by the germline gene.

Additional approaches have generated libraries directly from or derived from B cells. For example, Glanville et al., Precise Determination of the Diversity of a Combinatorial Antibody Library Gives Insight into the Human Immunoglobulin Repertoire, Proc Natl Acad Sci 1; 106(48):20216-21 (December 2009), which is incorporated by reference in its entirety, which describes an antibody collection built from the diversity of 654 human donor Immunoglobulin M (IgM) repertoires. Specifically, the heavy and light chain V-gene cDNAs from 654 human donors were separately PCR amplified (separating the variable heavy and light chain pair) and the heavy and light chain domains were then randomly re-associated. WO2003052416, which is incorporated by reference in its entirety, also describes the isolation of B cells from a host exhibiting a pronounced response to a pathogen of interest, resulting from either an infection by a micro-organism or treatment with a vaccine. In WO2003052416, the cDNA encoding the CDR3 region of the variable regions was sequenced and antibody fragments comprising the dominant CDR3s were designed. WO2009100896, which is incorporated by reference in its entirety, describes the isolation of B cells from an immunized host, where the cDNAs encoding the variable heavy and light chain regions were sequenced and the abundance of the unpaired variable heavy and variable light chain sequences was determined. In WO2009100896, libraries were synthesized comprising the randomly recombined variable heavy and variable light chains, wherein the antibodies were specific for one immunogen. A summary of these and additional approaches is found in Fuh et al., Synthetic antibodies as therapeutics, Expert Opin Biol Ther., 7(1):73-87 (January 2007), which is incorporated by reference in its entirety.

There is, therefore, a high need for a collection of antibodies or fragments thereof that incorporate the variable heavy and variable light chain gene pairs present in the human immune repertoire that have favorable biophysical properties relevant to development, while at the same time excluding the pairs that exist in nature, but do not have such biophysical properties. These and other needs are satisfied by the present invention.

SUMMARY

The present disclosure provides a valuable solution to the problem of efficiently identifying antibodies or antibody fragments against any antigen that are developable and safe and effective in patients. In its most general sense, the inventors began with the idea that an antibody collection that imitates the human immune system in essential ways may be advantageous. On one level, the inventors decided to imitate the human immune system by incorporating the optimal germline gene sequences, or portions thereof, from the human immune repertoire into antibodies. As such, in some embodiments, the antibodies of the collection comprise portions, for example, framework regions that are germline in sequence. Using the germline sequences should dramatically decrease the risk of immunogenicity of recombinant antibodies for therapeutic use in patients.

In addition, the inventors worked from their hypothesis that the variable heavy chain and variable light chain germline gene pairs abundant in the human immune repertoire likely have favorable biophysical properties that would lead to more efficient clinical development and increase the safety and efficacy of the resulting antibodies in patients. As background, each B cell encodes one antibody, and each antibody comprises a variable heavy chain and variable light chain. Each of the variable heavy chain and variable light chains of an antibody can be aligned with germline sequences in order to determine the origin of the antibody, meaning from which germline gene the variable heavy chain and variable light chain are encoded. Therefore, for each antibody the variable heavy chain and variable light chain comprise a germline gene or germline protein pair, for example, VH3-23 paired with VK1-5.

In order to prove the hypothesis that the prominent germline gene pairs likely have favorable biophysical properties, the first step was to identify the variable heavy chain and variable light chain germline gene pairs prominent in the human immune repertoire. This was done by extensively searching publically available literature and by sampling B cells from a human host. As a next step, this data was pooled, analyzed and the variable heavy chain and variable light chain germline pairs present in the human immune repertoire were ranked in terms of their prevalence. From this data it was clear that certain variable heavy chain and variable light chain germline gene pairs were present more frequently than others in the human immune repertoire.

As a next step, it had to be determined which germline protein pairs were to be tested for the functional properties relevant to development, as there are ~2500 pairs in the human immune repertoire, it is not preferred to test each one. One way would be to test the variable heavy chain and variable light chain germline protein pairs that occur most prominently in the human immune repertoire, for example, see Table 6. One could, for example, select the top four hundred pairs for testing, or select the variable heavy chain and variable light chain germline gene pairs present at or above a certain threshold number. This approach would require the synthesis and testing of a very large number of variable heavy chain and variable light chain germline protein pair sequences; therefore, such an approach may not be very efficient.

As an alternative approach, the inventors selected a subset of the variable heavy chain and variable light chain germline pairs that are representative of, accurately reproduce, or cover the majority of the prominent pairs of the human immune repertoire. This approach was based, in part, upon the observation that a small number of variable heavy, variable κ light chain, and variable λ light chain germline genes (unpaired) are dominant in the human immune repertoire. Wildt et al. at 895-896 describes this phenomenon. Wildt et al. also states that the frequent heavy and light chain gene segments are often paired, and observed that half of the pairings sampled corresponded to only five germline pairs. Therefore, a small number of the prominent heavy and light chain germline genes (unpaired) can be combined to generate a group of heavy and light chain pairs that are representative of the human immune repertoire.

This approach was undertaken in the following way. The data showing the linked VH/VL pairs, see, e.g., Table 6, and the data identifying the presence of the unlinked VH or VL chains, see, e.g. Example 3 and Table 5, was analyzed to determine the variable heavy chain, variable κ light chain, and variable λ light chain germline genes (unpaired) that are prominent in the human immune repertoire.

As a next step the prominent variable heavy chain, variable κ light chain, and variable λ light chain germline protein sequences (unpaired) were evaluated to determine their biophysical properties relevant to development, see Example 4. The variable heavy chain, variable κ light chain, and variable λ light chain germline protein sequences were evaluated in silico for the following properties: (i) CDR length, (ii) isoelectric point (pI) (a preferred isoelectric point is 7.5 or above as this is should provide stability in a neutral or slightly acidic formulation buffer), (iii) potential sites for potential post translational modification sites (PTM's) (specifically, N-linked glycosylation sites (N×S or N×T) or chemical modifications such as Asp cleavage (often at a DP or DQ), (iv) Asp isomerization (DS, DG), (v) deamidation (NS, NG) which can occur in vivo (in serum) or upon storage in formulation buffer and lead to loss of antigen binding), (vi) the presence of Methionines in the CDRs (might be prone to oxidization when exposed to solvent), (vii) the presence of unpaired Cysteines (will form disulfide bonds with any other unpaired cysteine, thus leading to crosslinking of proteins and/or lower expression levels), (viii) deviations from germline, (ix) the presence of possible T-cell epitopes, and (x) theoretical aggregation propensity.

As a next step the variable heavy chain, variable κ light chain, and variable λ light chain germline protein sequences having favorable in silico biophysical characteristics were combined to form variable heavy chain and variable light chain pairs. As shown in Table 5, and FIGS. 2-3, generally, the top 20 VH, top 8 Vλ and top 12 Vκ were selected for synthesis, combination and subsequent functional analysis. The germline gene sequences were synthesized and then combined in order to generate 400 germline protein pairs (20VH×20VL) that are representative of, accurately reproduce, or cover the majority of the prominent pairs from the human immune repertoire as shown in Table 6. This was done by synthesizing the variable heavy and light chain germline genes, combining them into pairs, expressing the pairs as protein (germline protein pairs) and testing each to identify their biophysical properties. The following properties were tested: (i) relative display rate on phage in the Fab format, (ii) relative expression level in the Fab format, e.g., in *E. coli*; (iii) thermal stability in the Fab format; (iv) stability in bovine or mouse serum in the Fab format; (v) relative expression level in the IgG1 format; and (vi) stability in bovine serum in the IgG1 format.

The testing of the 400 germline protein pairs for display, expression, thermal and serum stability acted as a preliminary filter to remove the germline protein pairs that, although they exist in nature, do not have biophysical properties thought to be favorable for therapeutic development. The goal was to select a sub-group of germline protein pairs having favorable developability characteristics, while at the same time maintaining a high level of diversity within a collection so that the collection can be used to identify developable candidates against any antigen. Table 12 shows ~60 bold and underlined germline protein pairs which met the thresholds of an embodiment of the disclosure. Table 12 was previously disclosed in WO2010/136598 (MorphoSys AG), which claims the benefit of 61/182,350, and 61/299,401, which are all incorporated by reference in their entireties.

Of the 400 germline protein pairs tested (results shown in Table 12), 95 were selected for further testing. Of the 95 germline protein pairs selected for further testing, some were chosen because they met the previous criteria, and it was desirable to further test them. Others were chosen, despite not meeting certain thresholds, so that these pairs could be re-evaluated. The 95 germline protein pairs shown in FIGS. 16-24 were synthesized, expressed, purified and then tested in both Fab and IgG1 formats for the following a) purified Fab expression in mg/L, b) purified Fab monomeric content (% monomer), c) purified Fab thermal stability, d) purified IgG1 expression in mg/L, e) purified IgG1 monomeric content (% monomer), f) purified IgG1 thermal stability, g) IgG1 isoelectric point and h) IgG1 stress testing with exposure to acid, including differential scanning fluorometry (DSF), absorption, dynamic light scattering and particle staining.

In an embodiment, the following germline protein pairs (54) were identified as having superior functional activity related to developability (data shown in FIGS. 16-24):
VH1-18 (SEQ ID NO: 204)/VK1-39 (SEQ ID NO: 236);
VH1-18 (SEQ ID NO: 204)/VK3-15 (SEQ ID NO: 238);
VH1-18 (SEQ ID NO: 204)/VK3-20 (SEQ ID NO: 239);
VH1-46 (SEQ ID NO: 205)/VK3-15 (SEQ ID NO: 238);
VH1-46 (SEQ ID NO: 205)/VL1-51 (SEQ ID NO: 252);
VH1-46 (SEQ ID NO: 205)/VL3-21 (SEQ ID NO: 257);
VH1-69*01 (SEQ ID NO: 206)/VL1-51 (SEQ ID NO: 252);
VH3-07 (SEQ ID NO: 207)/VK1-12 (SEQ ID NO: 233);
VH3-07 (SEQ ID NO: 207)/VK1-16 (SEQ ID NO: 234);

VH3-07 (SEQ ID NO: 207)/VK1-27 (SEQ ID NO: 235);
VH3-07 (SEQ ID NO: 207)/VK1-39 (SEQ ID NO: 236);
VH3-07 (SEQ ID NO: 207)/VK3-15 (SEQ ID NO: 238);
VH3-07 (SEQ ID NO: 207)/VL1-47 (SEQ ID NO: 251);
VH3-07 (SEQ ID NO: 207)/VL1-51 (SEQ ID NO: 252);
VH3-11 (SEQ ID NO: 208)/VK1-05 (SEQ ID NO: 230);
VH3-11 (SEQ ID NO: 208)/VK1-39 (SEQ ID NO: 236);
VH3-11 (SEQ ID NO: 208)/VK3-15 (SEQ ID NO: 238);
VH3-11 (SEQ ID NO: 208)/VL1-40 (SEQ ID NO: 250);
VH3-11 (SEQ ID NO: 208)/VL1-47 (SEQ ID NO: 251);
VH3-11 (SEQ ID NO: 208)/VL1-51 (SEQ ID NO: 252);
VH3-11 (SEQ ID NO: 208)/VL2-23 (SEQ ID NO: 255);
VH3-15 (SEQ ID NO: 209)/VK1-05 (SEQ ID NO: 230);
VH3-15 (SEQ ID NO: 209)/VK1-06 (SEQ ID NO: 231);
VH3-15 (SEQ ID NO: 209)/VK1-12 (SEQ ID NO: 233);
VH3-15 (SEQ ID NO: 209)/VK1-16 (SEQ ID NO: 234);
VH3-15 (SEQ ID NO: 209)/VK1-27 (SEQ ID NO: 235);
VH3-15 (SEQ ID NO: 209)/VK3-11 (SEQ ID NO: 237);
VH3-15 (SEQ ID NO: 209)/VL1-40 (SEQ ID NO: 250);
VH3-15 (SEQ ID NO: 209)/VL1-47 (SEQ ID NO: 251);
VH3-15 (SEQ ID NO: 209)/VL1-51 (SEQ ID NO: 252);
VH3-15 (SEQ ID NO: 209)/VL2-14 (SEQ ID NO: 254);
VH3-21 (SEQ ID NO: 210)/VK1-12 (SEQ ID NO: 233);
VH3-21 (SEQ ID NO: 210)/VK1-27 (SEQ ID NO: 235);
VH3-21 (SEQ ID NO: 210)/VL2-11 (SEQ ID NO: 253);
VH3-23 (SEQ ID NO: 211)/VK1-39 (SEQ ID NO: 236);
VH3-23 (SEQ ID NO: 211)/VK3-15 (SEQ ID NO: 238);
VH3-23 (SEQ ID NO: 211)/VL2-23 (SEQ ID NO: 255);
VH3-23 (SEQ ID NO: 211)/VL3-1 (SEQ ID NO: 256);
VH3-30 (SEQ ID NO: 212)/VK3-20 (SEQ ID NO: 239);
VH3-53 (SEQ ID NO: 213)/VK3-15 (SEQ ID NO: 238);
VH3-53 (SEQ ID NO: 213)/VL2-11 (SEQ ID NO: 253);
VH3-74 (SEQ ID NO: 214)/VK1-05 (SEQ ID NO: 230);
VH3-74 (SEQ ID NO: 214)/VK1-06 (SEQ ID NO: 231);
VH3-74 (SEQ ID NO: 214)/VK1-12 (SEQ ID NO: 233);
VH3-74 (SEQ ID NO: 214)/VK1-27 (SEQ ID NO: 235);
VH3-74 (SEQ ID NO: 214)/VK3-20 (SEQ ID NO: 239);
VH3-74 (SEQ ID NO: 214)/VL1-51 (SEQ ID NO: 252);
VH5-51 (SEQ ID NO: 215)/VK1-39 (SEQ ID NO: 236);
VH5-51 (SEQ ID NO: 215)/VL1-40 (SEQ ID NO: 250);
VH5-51 (SEQ ID NO: 215)/VL1-51 (SEQ ID NO: 252);
VH6-1 (SEQ ID NO: 216)/VK1-09 (SEQ ID NO: 232);
VH6-1 (SEQ ID NO: 216)/VK3-15 (SEQ ID NO: 238);
VH6-1 (SEQ ID NO: 216)/VK3-20 (SEQ ID NO: 239) and
VH6-1 (SEQ ID NO: 216)/VL1-51 (SEQ ID NO: 252).
Specifically, in this embodiment, the germline protein pairs (54) had values at or above the following thresholds for each criteria: a) purified Fab expression yield (as described in Example 9.1.1) of at least 2.5 mg/L; b) purified IgG1 expression yield (as described in Example 9.2.1) of at least 30.0 mg/L; c) thermal stability of purified Fab (as described in Example 9.1.2) of at least 70° C.; d) thermal stability of purified IgG1 (as described in Example 9.2.2) of at least 73° C.; e) monomeric content of purified Fab (as described in Example 9.1.3) of at least 98%; and f) monomeric content of purified IgG1 (as described in Example 9.2.3) of at least 99%. Therefore, collections comprising any number of these variable heavy chain and variable light chain pairs could be used to identify developable antibodies or fragments thereof against any antigen.

As compared to Table 32 of WO2010/136598, Table 32 shows only 21 of the 54 pairs as having certain different functional properties.

Embodiments of the present disclosure include collections comprising a subset of the germline protein pairs above (36 of the 54) having superior functional activity related to developability. In one embodiment, a collection comprises synthetic antibodies or functional fragments thereof, wherein the antibodies or functional fragments comprise variable heavy chain and variable light chain pairs, wherein the framework regions of the variable heavy chain and variable light chain pairs comprise germline protein sequences of the variable heavy chain and variable light chain pairs VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In this embodiment, the subset (36) germline protein pairs was selected from the 54 germline protein pairs based upon the stress testing data. The stress testing data was identified using the methods described in Examples 9.2.5 (a-d), data shown in FIGS. 19-24, Example 9.2.6 (a-d), data shown in FIGS. 19-54 and Example 9.2.7, scoring shown in FIGS. 55-60. The stress testing evaluated the 95 germline protein pairs in IgG1 format in order to determine their ability to withstand exposure to acid and agitation with glass beads. An antibody's ability to withstand exposure to acid is an increasingly important factor, as a virus inactivation step is standard during the downstream processing (DSP) of Chemistry, Manufacturing and Control (CMC). The ability of antibodies or antibody fragments to resist sheer forces is a helpful criterion as filtration steps cannot be avoided during processing and sheer forces occur during administration via syringe needles or plastic tubes.

The above subset collection, (36) germline protein pairs of an embodiment, were selected as they have additional superior functional properties relevant to developability as they showed stronger resistance to acid and agitation stress than the other pairs of the 54. The 36 germline protein pairs selected in this embodiment, had values at or above the following thresholds for each criteria: a) purified Fab expression yield (as described in Example 9.1.1) of at least 2.5 mg/L; b) purified IgG1 expression yield (as described in Example 9.2.1) of at least 30.0 mg/L; c) thermal stability of purified Fab (as described in Example 9.1.2) of at least 70° C.; d) thermal stability of purified IgG1 (as described in Example 9.2.2) of at least 73° C.; e) monomeric content of purified Fab (as described in Example 9.1.3) of at least 98%; f) monomeric content of purified IgG1 (as described in Example 9.2.3) of at least 99% and g) stress testing cumulative score (as described in Example 9.2.7) of at least 1225.

As compared to Table 32 of WO2010/136598, Table 32 shows only 14 of the 36 pairs as having certain different functional properties. Additionally, WO2010/136598 does not disclose the specific combination of the 36 pairs.

In another embodiment, the thresholds for each criterion were selected as follows: a) purified Fab expression yield (as described in Example 9.1.1) of at least 2.5 mg/L; b) purified IgG1 expression yield (as described in Example 9.2.1) of at least 30.0 mg/L; c) thermal stability of purified Fab (as described in Example 9.1.2) of at least 70° C.; d) thermal stability of purified IgG1 (as described in Example 9.2.2) of at least 73° C.; e) monomeric content of purified Fab (as described in Example 9.1.3) of at least 99%; f) monomeric content of purified IgG1 (as described in Example 9.2.3) of at least 99%; g) isoelectric point of purified IgG1 (as described in Example 9.2.4) of at least 8.3; and h) stress testing cumulative score (as described in Example 9.2.7) of at least 1225. In this embodiment, a collection comprises (33 pairs): VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK3-15 (SEQ ID NO: 238); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

As compared to Table 32 of WO2010/136598, Table 32 shows only 14 of the 33 pairs as having certain different functional properties. Additionally, WO2010/136598 does not disclose the specific combination of the 33 pairs.

In a further embodiment, pairs were added to a collection even though the pairs themselves did not meet all of the thresholds within each criteria, but were added to the collections in order to enhance diversity. In an embodiment, a collection further comprises: VH3-23 (SEQ ID NO: 211)/VK1-39 (SEQ ID NO: 236); VH3-23 (SEQ ID NO: 211)/VL2-23 (SEQ ID NO: 255); and VH3-23 (SEQ ID NO: 211)/VL3-1 (SEQ ID NO: 256). In this embodiment, a collection comprises (36 pairs): VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

Such collections overcome many of the problems of the prior art. For example, collections derived from B cells include VH/VL pairs that do not have favorable biophysical properties, as the VH and VL pairings present in such a collection are identical to the pairings present in the sample of B cells. If a large enough sample of B cells is taken, each of the approximately 50 VH and 50 VL class pairing combinations (2500) will be present. The extensive testing of VH and VL pairs in the present disclosure shows that many of the VH and VL germline gene pairs (germline protein pairs) that exist in nature fail to have properties that would allow for developability in the clinic. Therefore, such B cell libraries comprise many VH and VL pairs that are likely not developable. Therefore, it may be desirable to generate libraries of large diversity comprising the VH and VL pairs having advantageous functional properties, but with a B cell collection approach, this is not possible.

For example, an aspect of the present disclosure is a collection of antibodies or functional fragments comprising the variable heavy and light chain germline protein pairs having advantageous properties that enhance developability, but excluding variable heavy and light chain germline gene pairs not having such properties, even if they are prominently expressed in the human immune repertoire. In this way, the collection was designed to exclude the variable heavy and light chain combinations or pairs that occur in nature (out of the 2,500 pairs) which fail to have advantageous functional properties. For example, VH4-34 is frequently occurring in the human immune repertoire as shown in Table 5, but it is also known that antibodies derived from this heavy chain germline gene can be B cell cytotoxic, therefore, antibodies derived from this gene could be excluded from a collection design. See Bhat et al., Rapid cytotoxicity of human B lymphocytes induced by VH4-34 (VH4.21) gene-encoded monoclonal antibodies, Clin Exp Immunol., 105(1):183-90 (July 1996).

DESCRIPTION OF THE DRAWINGS

FIG. 2 shows the 20 VH germline genes selected for synthesis, combination and functional characterization, as described in detail in Example 4. The figure also shows the results of the in silico analysis of each germline gene, where pI represents isoelectric point, PTMs are potential post translational modification sites in the complementarity determining regions, as described herein, N×S/T are N-linked glycosylation sites, and Met in CDR are methionines.

FIG. 3 shows the 8 Vλ and 12 Vκ germline genes selected for synthesis, combination and functional characterization, as described in detail in Example 4. The figure also shows the results of the in silico analysis of each germline gene, where pI represents isoelectric point, PTMs are potential post translational modification sites in the complementarity determining regions, as described herein, N×S/T are N-linked glycosylation sites, and Met in CDR are methionines. Here, VL means Vλ.

FIG. 4 shows the VH/Vκ pairs of the pooled data from Examples 2.1 and Example 2.2. The numerical entries represent the number of each VH/Vκ germline gene pair from an individual B cell identified in the pooled data. The Y axis shows the VH germline genes ranked from top (most prevalent) VH3-23 to bottom (less prevalent) VH3-20 in terms of frequency of expression in the pooled data. The X axis shows the Vκ germline genes ranked from left (most prevalent) IGKV3-20 to right (less prevalent) IGKV1D-17 in terms of frequency of expression in the pooled data. The number 1358 is the number of B cells sampled.

FIG. 5 shows the VH/Vλ pairs of the pooled data from Examples 2.1 and Example 2.2. The numerical entries represent the number of each VH/Vλ germline gene pair from an individual B cell identified in the pooled data. The Y axis shows the VH germline genes ranked from top (most prevalent) VH3-23 to bottom (less prevalent) VH3-20 in terms of frequency of expression in the pooled data. The X axis shows the Vλ germline genes ranked from left (most prevalent) IGLV2-14 to right (less prevalent) IGLV4-60 in terms of frequency of expression in the pooled data. The number 779 is the number of B cells sampled.

FIGS. 6A-C show the amino acid sequences encoded by the VH germline genes (SEQ ID NOS 63-118, respectively, in order of appearance), as described in Tomlinson et al., (1992), "The Repertoire of Human Germline Vh Sequences Reveals about Fifty Groups of Vh Segments with Different Hypervariable Loop" J. Mol. Biol. 227, 776-798; Matsuda et al. (1998), "The complete nucleotide sequence of the human immunoglobulin heavy chain variable region locus" Exp Med 188(11):2151-62; and LeFranc M P (2001) "Nomenclature of the human immunoglobulin heavy (IGH) genes." Exp Clin Immunogenet. 18(2):100-16.

FIGS. 7A-C show the amino acid sequences encoded by the Vκ germline genes (SEQ ID NOS 119-164, respectively, in order of appearance), as described in Schäble and Zachau (1993), "The variable genes of the human immunoglobulin kappa locus," Biol. Chem. Hoppe Seyler. 374(11):1001-22; Brensing-Küppers et al. (1997), "The human immunoglobulin kappa locus on yeast artificial chromosomes (YACs)" Gene. 191(2):173-81; Kawasaki et al. (2001), "Evolutionary dynamics of the human immunoglobulin kappa locus and the germline repertoire of the Vkappa genes" Eur J Immunol 31(4):1017-28; and Lefranc M P (2001) "Nomenclature of the human immunoglobulin kappa (IGK) genes" Exp Clin Immunogenet., 18, 161-174.

FIGS. 8A-B show the amino acid sequences encoded by the Vλ germline genes (SEQ ID NOS 165-202, respectively, in order of appearance), as described in Kawasaki et al., (1997) "One-Megabase Sequence Analysis of the Human immunoglobulin lambda Gene Locus" Genome Research 7(3):250-61; Frippiat et al., (1995) "Organization of the human immunoglobulin lambda light-chain locus on chromosome 22q11.2" Hum. Mol. Genet., 4, 983-991; and LeFranc M P (2001) "Nomenclature of the human immunoglobulin lambda (IGL) genes. Exp Clin Immunogenet.; 18:242-254.

FIG. 16 of the 95 germline protein pairs further tested as described in Example 9, this figure shows the purified Fab expression yield in mg/L (culture), purified Fab monomeric content (% monomer), purified Fab thermal stability in ° C., purified IgG1 expression yield in mg/L (cell culture), purified IgG1 monomeric content (% monomer), purified IgG1 thermal stability in ° C. (the transition shown is that of the variable domains, the transition of the Fc domains is not shown) and IgG1 isoelectric point of the tested germline protein pairs numbers 1-32. The data was determined using the methods described in Example 9.1.1-9.1.3 and 9.2.1-9.2.4. Here, VL means Vλ.

FIG. 17 of the 95 germline protein pairs further tested as described in Example 9, this figure shows the purified Fab expression yield in mg/L (culture), purified Fab monomeric content (% monomer), purified Fab thermal stability in ° C., purified IgG1 expression yield in mg/L (cell culture), purified IgG1 monomeric content (% monomer), purified IgG1 thermal stability in ° C. (the transition shown is that of the variable domains, the transition of the Fc domains is not shown) and IgG1 isoelectric point of the tested germline protein pairs numbers 33-64. The data was determined using the methods described in Example 9.1.1-9.1.3 and 9.2.1-9.2.4. Here, VL means Vλ.

FIG. 18 of the 95 germline protein pairs further tested as described in Example 9, this figure shows the purified Fab expression yield in mg (purified Fab)/L (culture), purified Fab monomeric content (% monomer), purified Fab thermal stability in ° C., purified IgG1 expression yield in mg (purified IgG1)/L (cell culture), purified IgG1 monomeric content (% monomer), purified IgG1 thermal stability in ° C. (the transition shown is that of the variable domains, the transition of the Fc domains is not shown) and IgG1 isoelectric point of the tested germline protein pairs numbers 65-95. The data was determined using the methods described in Example 9.1.1-9.1.3 and 9.2.1-9.2.4. Here, VL means Vλ.

FIG. 19 of the 95 germline protein pairs further tested as described in Example 9, this figure shows the thermal stability in ° C. (apparent Tm) before and after acid exposure (the apparent Tm given corresponds to the unfolding of the variable domains, the unfolding midpoint of the Fc domains is not shown) as determined using differential scanning fluorometry as described in Example 9.2.5(a), the relative change in turbidity based upon the UV absorption before and during acid exposure and after neutralization as described in Example 9.2.5(b). The data shown is of the tested germline protein pairs numbers 1-32. Here, VL means Vλ.

FIG. 20 of the 95 germline protein pairs further tested as described in Example 9, this figure shows the particle radius (nm) before and after acid exposure and the polydispersity before and after acid exposure as described in Example 9.2.5(c), the particle staining before and after acid as described in Example 9.2.5(d), and the cumulative score as described in Example 9.2.7. The data shown is of the tested germline protein pairs numbers 1-32. Here, VL means Vλ.

FIG. 21 of the 95 germline protein pairs further tested as described in Example 9, this figure shows the thermal stability in ° C. (apparent Tm) before and after acid exposure (the apparent Tm given corresponds to the unfolding of the variable domains, the unfolding midpoint of the Fc domains is not shown) as determined using differential scanning fluorometry as described in Example 9.2.5(a), the relative change in turbidity based upon the UV absorption before and during acid exposure and after neutralization as described in Example 9.2.5(b). The data shown is of the tested germline protein pairs numbers 33-64. Here, VL means Vλ.

FIG. 22 of the 95 germline protein pairs further tested as described in Example 9, this figure shows the particle radius (nm) before and after acid exposure and the polydispersity before and after acid exposure as described in Example 9.2.5(c), the particle staining before and after acid as described in Example 9.2.5(d), and the cumulative score as described in Example 9.2.7. The data shown is of the tested germline protein pairs numbers 33-64. Here, VL means Vλ.

FIG. 23 of the 95 germline protein pairs further tested as described in Example 9, this figure shows the thermal stability in ° C. (apparent Tm) before and after acid exposure (the apparent Tm given corresponds to the unfolding of the variable domains, the unfolding midpoint of the Fc domains is not shown) as determined using differential scanning fluorometry as described in Example 9.2.5(a), the relative change in turbidity based upon the UV absorption before and during acid exposure and after neutralization as described in Example 9.2.5(b). The data shown is of the tested germline protein pairs numbers 65-95. Here, VL means Vλ.

FIG. 24 of the 95 germline protein pairs further tested as described in Example 9, this figure shows the particle radius (nm) before and after acid exposure and the polydispersity before and after acid exposure as described in Example 9.2.5(c), the particle staining before and after acid as described in Example 9.2.5(d), and the cumulative score as described in Example 9.2.7. The data shown is of the tested germline protein pairs numbers 65-95. Here, VL means Vλ.

FIG. 25 shows the VH germline protein (SEQ ID NOS 204-216, respectively, in order of appearance) and DNA sequences (SEQ ID NOS 217-229, respectively, in order of appearance) of the Framework 1 and HCDR1 regions of certain variable heavy chains. The amino acid sequences are germline protein sequences, as defined herein. The DNA sequences have been codon optimized by GeneArt for *E. coli* expression avoiding rare human codons. The germline genes shown are the same as those shown in FIG. 6, but only include the VH germline genes selected for embodiments of the collection.

FIG. 26 shows the VH germline protein (SEQ ID NOS 204-216 (continued), respectively, in order of appearance) and DNA sequences (SEQ ID NOS 217-229 (continued), respectively, in order of appearance) of the Framework 2 and HCDR2 regions of certain variable heavy chains. The amino acid sequences are germline protein sequences, as defined herein. The DNA sequences have been codon optimized by GeneArt for *E. coli* expression avoiding rare human codons. The germline genes shown are the same as those shown in FIG. 6, but only include the VH germline genes selected for embodiments of the collection.

FIG. 27 shows the VH germline protein (SEQ ID NOS 204-216 (continued), respectively, in order of appearance) and DNA sequences (SEQ ID NOS 217-229 (continued), respectively, in order of appearance) of the Framework 3 region of certain variable heavy chains. The amino acid sequences are germline protein sequences, as defined herein. The DNA sequences have been codon optimized by GeneArt for *E. coli* expression avoiding rare human codons. The germline genes shown are the same as those shown in FIG. 6, but only include the VH germline genes selected for embodiments of the collection.

FIG. 28 shows the Vκ germline protein (SEQ ID NOS 230-239, respectively, in order of appearance) and DNA sequences (SEQ ID NOS 240-249, respectively, in order of appearance) of the Framework 1 and LCDR1 regions of certain variable light chains. The amino acid sequences are germline protein sequences, as defined herein. The DNA sequences have been codon optimized by GeneArt for *E. coli* expression avoiding rare human codons. The germline genes shown are the same as those shown in FIG. 7, but only include the Vκ germline genes selected for embodiments of the collection.

FIG. 29 shows the Vκ germline protein (SEQ ID NOS 230-239 (continued), respectively, in order of appearance) and DNA sequences (SEQ ID NOS 240-249 (continued), respectively, in order of appearance) of the Framework 2 and LCDR2 regions of certain variable light chains. The amino acid sequences are germline protein sequences, as defined herein. The DNA sequences have been codon optimized by GeneArt for *E. coli* expression avoiding rare human codons. The germline genes shown are the same as those shown in FIG. 7, but only include the Vκ germline genes selected for embodiments of the collection.

FIG. 30 shows the Vκ germline protein (SEQ ID NOS 230-239 (continued), respectively, in order of appearance) and DNA sequences (SEQ ID NOS 240-249 (continued), respectively, in order of appearance) of the Framework 3 region of certain variable light chains. The amino acid sequences are germline protein sequences, as defined herein. The DNA sequences have been codon optimized by GeneArt for *E. coli* expression avoiding rare human codons. The germline genes shown are the same as those shown in FIG.

Figure 1:
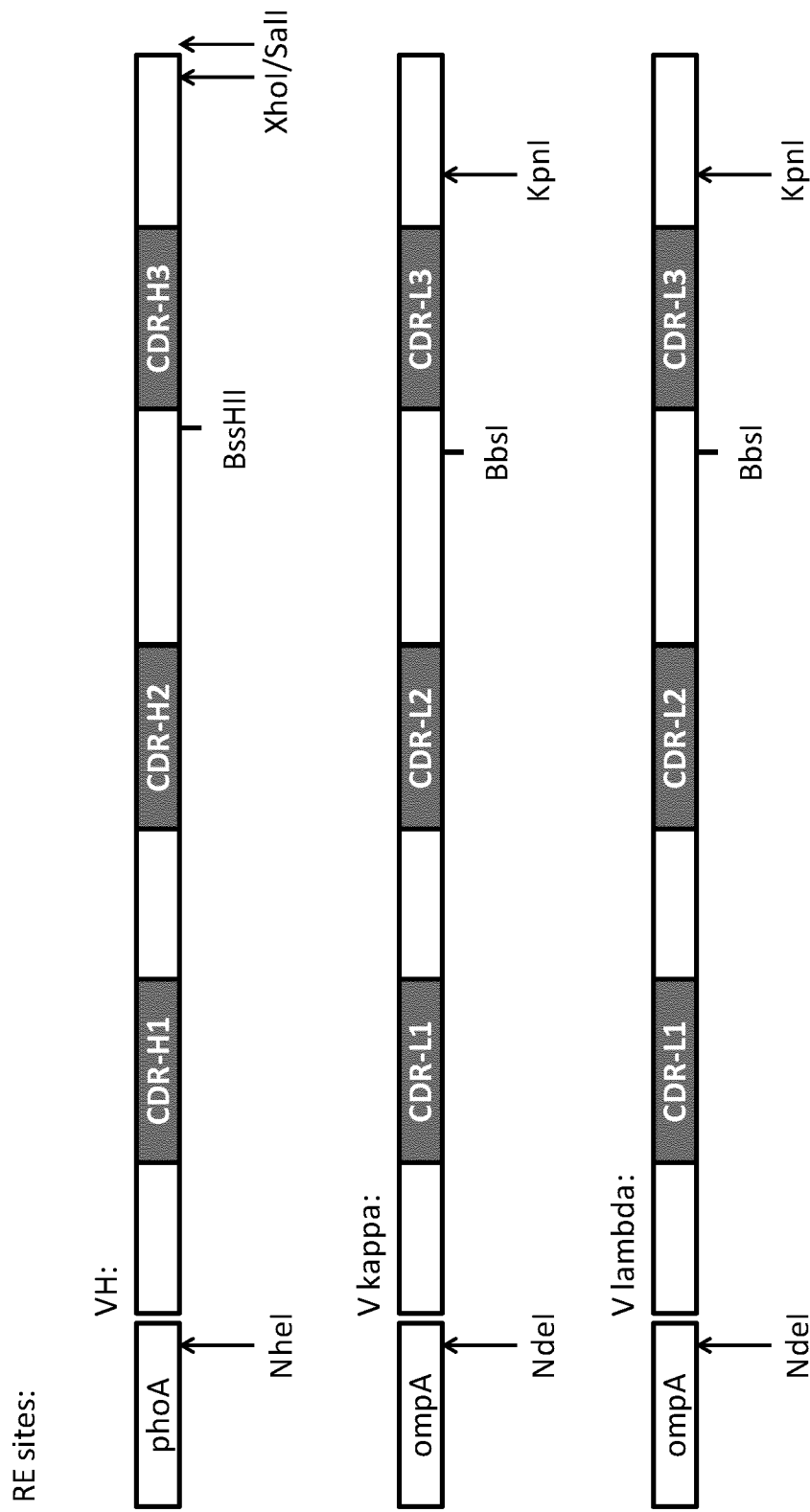
FIG. 1 shows the restriction sites selected for incorporation into the C-terminus of the phoA and ompA E. coli signal sequences, as described in detail in Example 1, and includes the restriction sites around CDR 3 and their respective orientations. This figure, while displaying the E. coli signal sequences, also represents the C-terminal restriction sites selected for incorporation in the human heavy chain and kappa chain leader sequences for use in IgG1 expression, as also described in detail in Example 1.

7, but only include the Vκ germline genes selected for embodiments of the collection.

Figure 31:
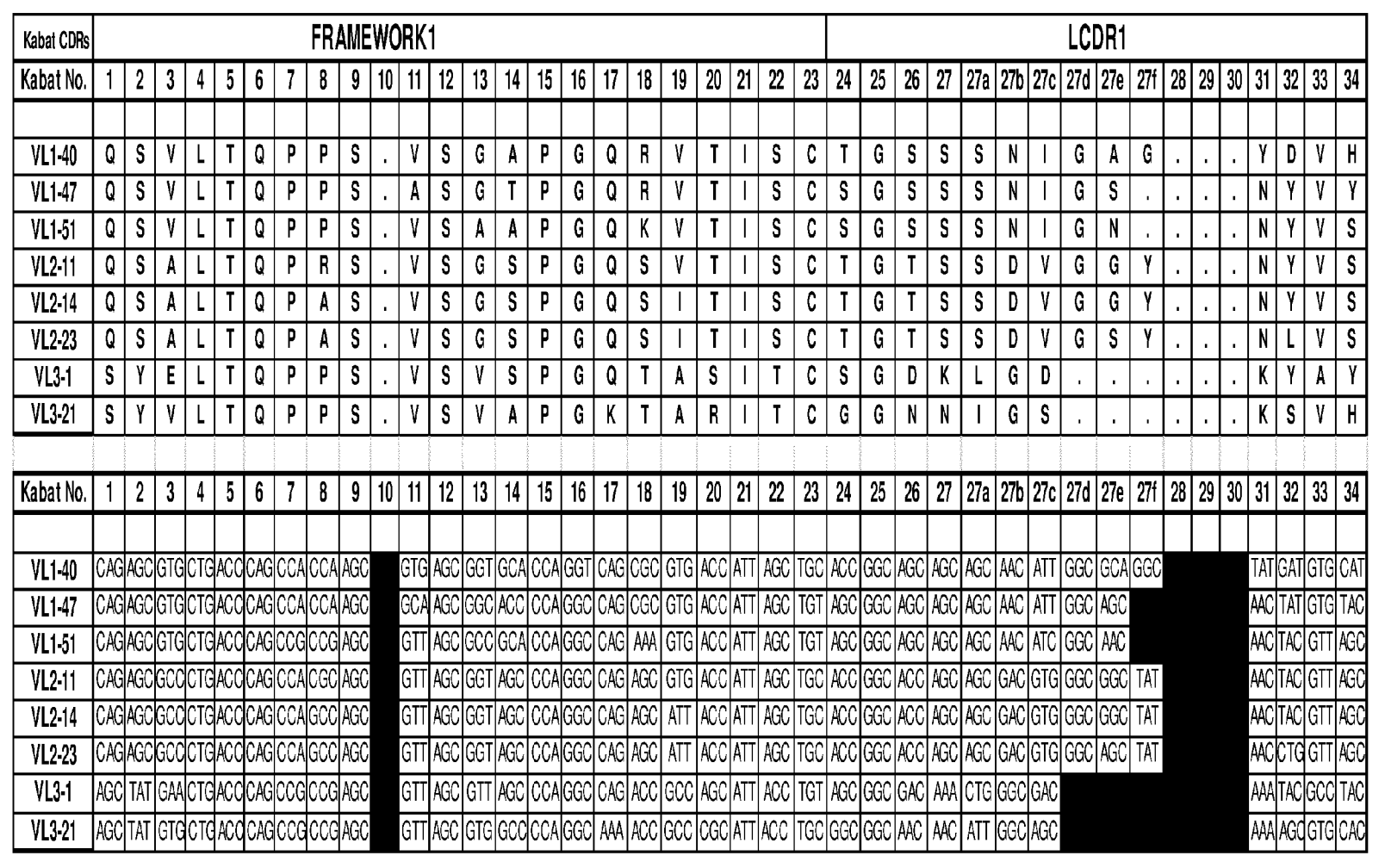

FIG. 31 shows the Vλ germline protein (SEQ ID NOS 250-257, respectively, in order of appearance) and DNA sequences (SEQ ID NOS 258-265, respectively, in order of appearance) of the Framework 1 and LCDR1 regions of certain variable light chains. The amino acid sequences are germline protein sequences, as defined herein. The DNA sequences have been codon optimized by GeneArt for *E. coli* expression avoiding rare human codons. The germline genes shown are the same as those shown in FIG. 8, but only include the Vλ germline genes selected for embodiments of the collection. Here, VL means Vλ.

FIG. 32 shows the Vλ germline protein (SEQ ID NOS 250-257 (continued), respectively, in order of appearance) and DNA sequences (SEQ ID NOS 258-265 (continued), respectively, in order of appearance) of the Framework 2 and LCDR2 regions of certain variable light chains. The amino acid sequences are germline protein sequences, as defined herein. The DNA sequences have been codon optimized by GeneArt for *E. coli* expression avoiding rare human codons. The germline genes shown are the same as those shown in FIG. 8, but only include the Vλ germline genes selected for embodiments of the collection. Here, VL means Vλ.

FIG. 33 shows the Vλ germline protein (SEQ ID NOS 250-257 (continued), respectively, in order of appearance) and DNA sequences (SEQ ID NOS 258-265 (continued), respectively, in order of appearance) of the Framework 3 region of certain variable light chains. The amino acid sequences are germline protein sequences, as defined herein. The DNA sequences have been codon optimized by GeneArt for *E. coli* expression avoiding rare human codons. The germline genes shown are the same as those shown in FIG. 8, but only include the Vλ germline genes selected for embodiments of the collection. Here, VL means Vλ.

FIG. 34 shows the VH germline protein (SEQ ID NOS 266-278, respectively, in order of appearance) and DNA sequences (SEQ ID NOS 279-291, respectively, in order of appearance) of the Framework 1 and HCDR1 regions of certain variable heavy chains. The amino acid sequences have been modified within HCDR1 to remove potential post translational modification sites (PTMs). The DNA sequences have been codon optimized by GeneArt for *E. coli* expression avoiding rare human codons. The amino acids that have been modified in HCDR1 are underlined and the corresponding DNA encoding each position is bold and underlined.

FIG. 35 shows the VH germline protein (SEQ ID NOS 266-278 (continued), respectively, in order of appearance) and DNA sequences (SEQ ID NOS 279-291 (continued), respectively, in order of appearance) of the Framework 2 and HCDR2 regions of certain variable heavy chains. The amino acid sequences have been modified within HCDR2 to remove potential post translational modification sites (PTMs). The DNA sequences have been codon optimized by GeneArt for *E. coli* expression avoiding rare human codons. The amino acids that have been modified in HCDR2 are underlined and the corresponding DNA encoding each position is bold and underlined.

FIG. 36 shows the VH germline protein (SEQ ID NOS 266-278 (continued), respectively, in order of appearance) and DNA sequences (SEQ ID NOS 279-291 (continued), respectively, in order of appearance) of the Framework 3 region of certain variable heavy chains. The amino acid sequences are germline as no potential post translation modification sites were removed within the framework regions. The DNA sequences have been codon optimized by GeneArt for *E. coli* expression avoiding rare human codons. VH1-69*01 and VH3-23 may also have nucleotides CGT at position 94.

FIG. 37 shows representative antibodies or antibody fragments specific for Dkk3 identified from the sub-collections VH3-23/VK1-39, and VH3-23/VL3-1, as described in Example 11. The figure shows the sub-collection from which each antibody or fragment was identified, the antigen, the length of the CDR-H3 and CDR-L3, the Fab thermal stability and affinity, the IgG1 pI, expression yield (mg/L), thermal stability and monomeric content (% monomer) determined by SEC. Here, VL means Vλ.

FIG. 38 shows representative antibodies or antibody fragments specific for ErbB4/Her4_Fc identified from the sub-collections VH3-23/VK1-39, and VH3-23/VL3-1, as described in Example 11. The figure shows the sub-collection from which each antibody or fragment was identified, the antigen, the length of the CDR-H3 and CDR-L3, the Fab thermal stability and affinity, the IgG1 pI, expression yield (mg/L), thermal stability and monomeric content (% monomer) determined by SEC. Here, VL means Vλ.

FIG. 39 shows apparent temperature melting points of selected Fabs as determined by Differential Scannning Fluorimetry (DSF) as described in Example 9.1.2. Each dot represents one unique Fab. Squares indicate the control Fabs as described in Example 9. Bars indicate the Median. The control represents the antibody tested for functional properties in Example 9, comprising germline FR regions and CDR1 and 2 of the respective germline protein pair, and the CDR3 from Ewert et al. The selected Fabs were generated in Example 11, and differ in sequence from the control antibody only in the CDR3. The close clustering here, shows that the output of the collection, meaning antibodies or fragments selected against DKK3 or ErbB4/Her4_Fc antigen, maintain the superior functional properties of the members of the collection design.

FIG. 40 shows the amino acid sequences (SEQ ID NOS 293, 295, 297 and 301, respectively, in order of appearance) and codon optimized nucleic acid sequences (SEQ ID NOS 292, 294, 296, 298, 299, 300, 302 and 303, respectively, in order of appearance) encoding the FR4 regions of collections of the invention.

FIGS. 41A and B show the amino acid sequence (SEQ ID NO: 305) and codon optimized nucleic acid sequence (SEQ ID NO: 304) encoding the IgG1f heavy chain constant domain of collections of the invention. The nucleic acid sequences shown have been codon optimized.

FIG. 42 shows the amino acid sequence (SEQ ID NO: 307) and codon optimized nucleic acid sequences (SEQ ID NO: 306) encoding the Fab heavy chain constant domain of collections of the invention.

FIG. 43 shows the amino acid sequences (SEQ ID NOS 309 and 311, respectively, in order of appearance) and codon optimized nucleic acid sequences (SEQ ID NOS 308 and 310, respectively, in order of appearance) encoding the IgG1f and Fab kappa light chain constant domains of collections of the invention. The nucleic acid sequences shown have been codon optimized.

FIG. 44 shows the amino acid sequences (SEQ ID NOS 313 and 315, respectively, in order of appearance) and codon optimized nucleic acid sequences (SEQ ID NOS 312 and 314, respectively, in order of appearance) encoding the IgG1f and Fab lambda light chain constant domains of collections of the invention.

Figure 45:
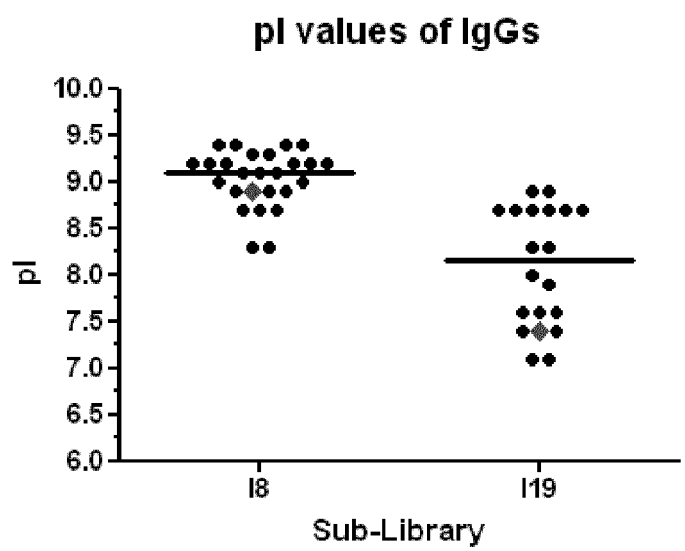

FIG. 45 shows isoelectric point (pI) values of selected IgGs as described in Example 9.2.4. Each dot represents one unique IgG. Squares indicate the control IgGs as described in Example 9. Bars indicate the Median. The control represents the antibody tested for functional properties in Example 9, comprising germline FR regions and CDR1 and 2 of the respective germline protein pair, and the CDR3 from Ewert et al. The selected IgGs were generated in Example 11, and differ in sequence from the control antibody only in the CDR3. The close clustering here, shows that the output of the collection, meaning antibodies or fragments selected against DKK3 or ErbB4/Her4_Fc antigen, maintain the superior functional properties of the members of the collection design.

Figure 46:
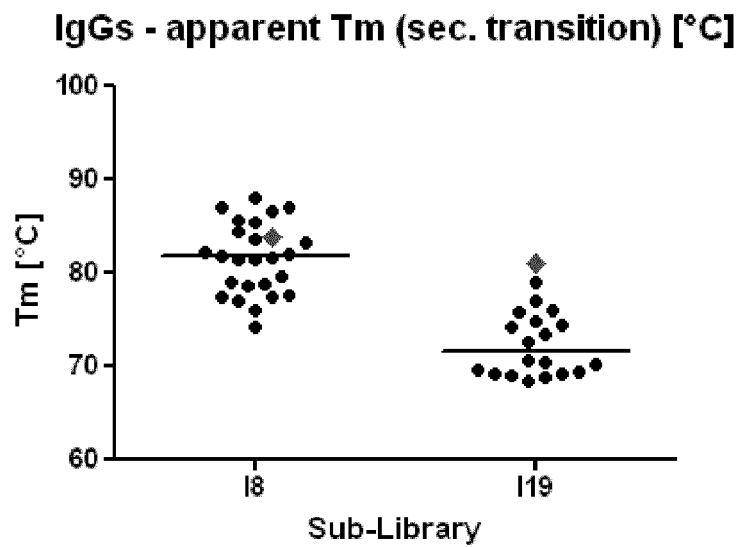

FIG. 46 shows apparent midpoints of unfolding of selected IgGs as determined by Differential Scanning Fluorimetry (DSF) as described in Example 9.2.2. Each dot represents one unique IgG. Squares indicate the control IgGs as described in Example 9. Bars indicate the Median. The control represents the antibody tested for functional properties in Example 9, comprising germline FR regions and CDR1 and 2 of the respective germline protein pair, and the CDR3 from Ewert et al. The selected IgGs were generated in Example 11, and differ in sequence from the control antibody only in the CDR3. The close clustering here, shows that the output of the collection, meaning antibodies or fragments selected against DKK3 or ErbB4/Her4_Fc antigen, maintain the superior functional properties of the members of the collection design.

Figure 47:
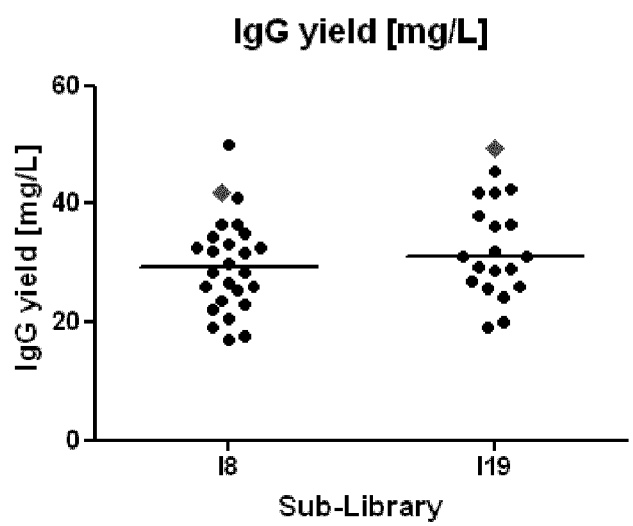

FIG. 47 shows expression yields of selected IgGs as determined by UV-spectrophotometry as described in Example 9.2.1. Each dot represents one unique IgG. Squares indicate the control IgGs as described in Example 9. Bars indicate the Median. The control represents the antibody tested for functional properties in Example 9, comprising germline FR regions and CDR1 and 2 of the respective germline protein pair, and the CDR3 from Ewert et al. The selected IgGs were generated in Example 11, and differ in sequence from the control antibody only in the CDR3. The close clustering here, shows that the output of the collection, meaning antibodies or fragments selected against DKK3 or ErbB4/Her4_Fc antigen, maintain the superior functional properties of the members of the collection design.

Figure 48:
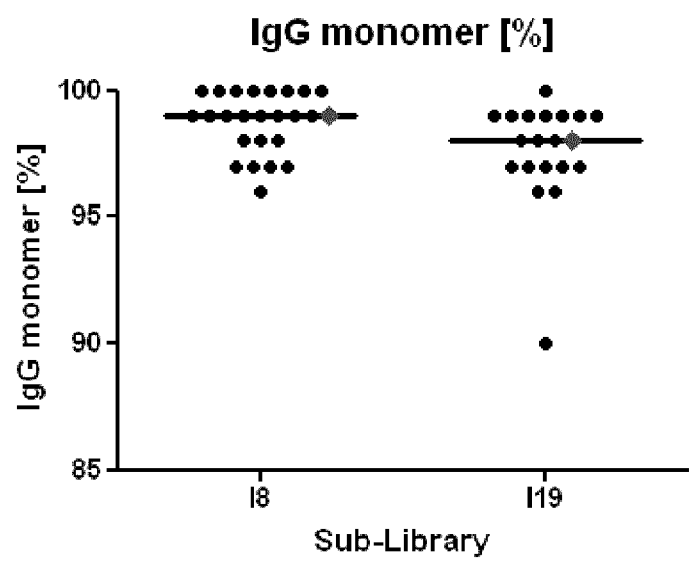

FIG. 48 shows monomeric content of selected IgGs as determined by size exclusion chromatography (SEC) as described in Example 9.2.3. Each dot represents one unique IgG. Squares indicate the control IgGs as described in Example 9. Bars indicate the Median. The control represents the antibody tested for functional properties in Example 9, comprising germline FR regions and CDR1 and 2 of the respective germline protein pair, and the CDR3 from Ewert et al. The selected IgGs were generated in Example 11, and differ in sequence from the control antibody only in the CDR3. The close clustering here, shows that the output of the collection, meaning antibodies or fragments selected against DKK3 or ErbB4/Her4_Fc antigen, maintain the superior functional properties of the members of the collection design. Here, VL means Vλ.

FIG. 49 of the 95 germline protein pairs further tested as described in Example 9, this figure shows the relative change in turbidity based upon the UV absorption before and during agitation with glass beads as described in Example 9.2.6(a). The data shown is of the tested germline protein pairs numbers 1-32. Here, VL means Vλ.

FIG. 50 of the 95 germline protein pairs further tested as described in Example 9, this figure shows the thermal stability in ° C. (apparent Tm) after agitation with glass beads (the apparent Tm given corresponds to the unfolding of the variable domains, the unfolding midpoint of the Fc domains is not shown) as determined using differential scanning fluorometry as described in Example 9.2.6(b) shows the particle radius (nm) after agitation with glass beads, the polydispersity after agitation with glass beads as described in Example 9.2.6(c), and the particle staining before and after agitation with glass beads as described in Example 9.2.6(d). The data shown is of the tested germline protein pairs numbers 1-32. Here, VL means Vλ.

FIG. 51 of the 95 germline protein pairs further tested as described in Example 9, this figure shows the relative change in turbidity based upon the UV absorption before and during stress testing as described in Example 9.2.6(a). The data shown is of the tested germline protein pairs numbers 33-64. Here, VL means Vλ.

FIG. 52 of the 95 germline protein pairs further tested as described in Example 9, this figure shows the thermal stability in ° C. (apparent Tm) after agitation with glass beads (the apparent Tm given corresponds to the unfolding of the variable domains, the unfolding midpoint of the Fc domains is not shown) as determined using differential scanning fluorometry as described in Example 9.2.6(b) shows the particle radius (nm) after agitation with glass beads, the polydispersity after agitation with glass beads as described in Example 9.2.6(c), and the particle staining before and after agitation with glass beads as described in Example 9.2.6(d). The data shown is of the tested germline protein pairs numbers 33-64. Here, VL means Vλ.

FIG. 53 of the 95 germline protein pairs further tested as described in Example 9, this figure shows the relative change in turbidity based upon the UV absorption before and during stress testing as described in Example 9.2.6(a). The data shown is of the tested germline protein pairs numbers 65-95. Here, VL means Vλ.

FIG. 54 of the 95 germline protein pairs further tested as described in Example 9, this figure shows the thermal stability in ° C. (apparent Tm) after agitation with glass beads (the apparent Tm given corresponds to the unfolding of the variable domains, the unfolding midpoint of the Fc domains is not shown) as determined using differential scanning fluorometry as described in Example 9.2.6(b) shows the particle radius (nm) after agitation with glass beads, the polydispersity after agitation with glass beads as described in Example 9.2.6(c), and the particle staining before and after agitation with glass beads as described in Example 9.2.6(d). The data shown is of the tested germline protein pairs numbers 65-95. Here, VL means Vλ.

FIG. 55 as described in Example 9.2.7 for each of the stress testing experiments done in Examples 9.2.5-9.2.6, exact values were identified, and for each exact value a corresponding score was provided. This figure shows the score, whether 0, 25, 75, or 100 given to each value for the experiments completed in Example 9.2.5, acid testing. The scores shown are of the tested germline protein pairs numbers 1-32. Here, VL means Vλ.

FIG. 56 as described in Example 9.2.7 for each of the stress testing experiments done in Examples 9.2.5-9.2.6, exact values were identified, and for each exact value a corresponding score was provided. This figure shows the score, whether 0, 25, 75, or 100 given to each value for the experiments completed in Example 9.2.6, agitation with glass beads. In addition, this figure shows the cumulative score, which was calculated by adding together the scores from the tests done in Examples 9.2.5-9.2.6. The scores shown are of the tested germline protein pairs numbers 1-32. Here, VL means Vλ.

FIG. 57 as described in Example 9.2.7 for each of the stress testing experiments done in Examples 9.2.5-9.2.6, exact values were identified, and for each exact value a corresponding score was provided. This figure shows the score, whether 0, 25, 75, or 100 given to each value for the experiments completed in Example 9.2.5, acid testing. The scores shown are of the tested germline protein pairs numbers 33-64. Here, VL means Vλ.

FIG. 58 as described in Example 9.2.7 for each of the stress testing experiments done in Examples 9.2.5-9.2.6, exact values were identified, and for each exact value a corresponding score was provided. This figure shows the score, whether 0, 25, 75, or 100 given to each value for the experiments completed in Example 9.2.6, agitation with glass beads. In addition, this figure shows the cumulative score, which was calculated by adding together the scores from the tests done in Examples 9.2.5-9.2.6. The scores shown are of the tested germline protein pairs numbers 33-64. Here, VL means Vλ.

FIG. 59 as described in Example 9.2.7 for each of the stress testing experiments done in Examples 9.2.5-9.2.6, exact values were identified, and for each exact value a corresponding score was provided. This figure shows the score, whether 0, 25, 75, or 100 given to each value for the experiments completed in Example 9.2.5, acid testing. The scores shown are of the tested germline protein pairs numbers 65-95. Here, VL means Vλ.

FIG. 60 as described in Example 9.2.7 for each of the stress testing experiments done in Examples 9.2.5-9.2.6, exact values were identified, and for each exact value a corresponding score was provided. This figure shows the score, whether 0, 25, 75, or 100 given to each value for the experiments completed in Example 9.2.6, agitation with glass beads. In addition, this figure shows the cumulative score, which was calculated by adding together the scores from the tests done in Examples 9.2.5-9.2.6. The scores shown are of the tested germline protein pairs numbers 65-95. Here, VL means Vλ.

FIGS. 61A-D germline protein pairs of embodiments of the invention were displayed on phage and selected against Frizzled-4 Fc, GFP or erbB4/Her4_Fc fusion. This figure shows the sub-collections used, the antigen selected against, the number of clones screened, ELISA positive hits, and number of unique antibodies. Here, VL means Vλ.

FIGS. 62A-C shows IgGs from sub-collections selected against rhErbB4/Her4_Fc fusion, rhFZD-4 Fc fusion and eGFP, as described in Example 11. The figures show the sub-collection from which each antibody was identified, the antigen, the length of the CDR-H3 and CDR-L3, the IgG1 pI, IgG1 expression yield (mg/L), IgG1 thermal stability and monomeric content (% monomer) determined by SEC. Here, VL means Vλ.

DETAILED DESCRIPTION

Definitions

To facilitate understanding of the invention, the following definitions and illustrations are provided.

"Database or readable medium" as used herein, refers to any format for storing sequence data and thus any collection of information, such as a database file, a lookup table, an Excel spreadsheet or the like. In certain embodiments the database is stored in electronic form, such as a computer readable memory device. This includes media such as a server, a client, a hard disk, a CD, a DVD, a personal digital assistant such as a Palm Pilot, a tape, a zip disk, the computer's internal ROM (read-only-memory) or the internet or worldwide web. Other media for the storage of files accessible by a computer will be obvious to one skilled in the art.

"In silico" refers to manipulations, analysis, or designs performed on a computer, but may also be likewise performed on paper or mentally.

The term "antibody" as used herein includes whole antibodies. An antibody may be polyclonal, affinity-purified polyclonal, monoclonal, human, murine or rodent, chimeric, camelid or humanized antibodies. An antibody may belong to any of the antibody classes, such as IgG, IgG1, IgG2, IgG3, IgG4, IgA (including human subclasses IgA1 and IgA2), IgD, IgE, or IgM. An "antibody" is a protein comprising at least two heavy (H) chains and two light (L) chains inter-connected by disulfide bonds.

The term antibody "fragment" or "functional fragment" as used herein includes any antigen binding fragment, such as Fab, F(ab')2, Fab', Fv, scFv, single chains which include an Fc portion, nanobodies and other antibody like structures having scaffolds other than variable framework regions. The term "functional fragment" includes, but is not limited to any portion of an antibody, that retains the ability to bind to an antigen of interest.

As used herein, the term "affinity" refers to the strength of interaction between antibody and antigen at antigenic sites. Within each antigenic site, the variable region of the antibody interacts through non-covalent forces with an antigen at numerous sites; the more interactions, the stronger the affinity. As used herein, the term "high affinity" for an antibody or functional fragment thereof, such as an IgG antibody, refers to an antibody having a KD of $10^{-8}$ M or less, $10^{-9}$ M or less, or $10^{-10}$ M or less, or $10^{-11}$ M or less, or $10^{-12}$ M or less for a target antigen. However, "high affinity" binding can vary for other antibody isotypes. For example, "high affinity" binding for an IgM isotype refers to an antibody having a KD of $10^{-7}$ M or less, or $10^{-8}$ M or less.

The term "Kassoc" or "Ka", as used herein, is intended to refer to the association rate constant of a particular antibody-antigen interaction, whereas the term "Kdis" or "Kd," as used herein, is intended to refer to the dissociation rate constant of a particular antibody-antigen interaction. The term "KD", as used herein, is intended to refer to the equilibrium dissociation constant, which is obtained from the ratio of Kd to Ka (i.e. Kd/Ka) and is expressed as a molar concentration (M). KD values for antibodies can be determined using methods well established in the art. A method for determining the KD of an antibody is by using surface plasmon resonance, or using a biosensor system such as a Biacore® system.

The term "chimeric antibody" is an antibody molecule in which (a) the constant region, or a portion thereof, is altered, replaced or exchanged so that the antigen binding site (variable region) is linked to a constant region of a different or altered class, effector function and/or species.

The term "isotype" refers to the antibody class (e.g., IgM, IgE, IgG such as IgG1 IgG2 or IgG4) that is provided by the heavy chain constant region genes. Isotype also includes modified versions of one of these classes, where modifications have been made to alter the Fc function, for example, to enhance or reduce effector functions or binding to Fc receptors.

The term "germline" means the nucleic acid sequence encoding antibodies or functional fragments thereof that are passed down from parent to offspring.

The term "germline protein sequence" or "germline amino acid sequence" means a) the amino acid sequence of a variable region of antibody or functional fragment thereof encoded by a germline gene; b) the amino acid sequence encoded by a modified nucleic acid sequence encoding a variable region of antibody or functional fragment thereof having the same amino acid sequence as a variable region of an antibody or functional fragment thereof encoded by a germline gene, wherein the nucleic acid sequence is modified by, for example, by codon optimization, the addition of desired restriction sites, optimized GC content, the removal of undesired mRNA splice sites or the removal of mRNA instability motifs, or c) an amino acid sequence encoded by a germline gene, but with minor mutations in the amino acid sequence, such as, for the purpose of removing of an undesired cysteine, or introduction of desired restriction site, e.g. BbsI, or that result from errors in synthesis, amplification or cloning. Examples of "germline protein sequences" or "germline amino acid sequences" are shown in FIGS. 6-8 and 25-33. Additionally, "germline protein sequence" or "germline amino acid sequence" include the constructs as prepared in Example 5, which comprise a) for VH: leader sequence (modified phoA incorporating a NheI RE site as shown in Table 1); germline FR1, CDR1, FR2, CDR2 and FR3 (incorporating a BssHII RE site (GCGCGC) as shown in FIG. 1); CDR-H3 (WGGDG-FYAMDY) (SEQ ID NO: 1) of the 4D5 antibody as used in Ewert S. et al., J. Mol. Biol. (2003) 325, 531-553; and the JH4 FR4 (incorporating a XhoI RE site (CTCGAG) as shown in FIG. 1);

b) for Vk: leader sequence (ompA incorporating the NdeI RE site as shown in Table 2); germline FR1, CDR1, FR2, CDR2 and FR3 (incorporating a BbsI RE site (GAAGAC) as shown in FIG. 1), kappa-like CDR-L3 (QQHYTTPPT) (SEQ ID NO: 2) according to Ewert S. et al., J. Mol. Biol. (2003) 325, 531-553; and the Jk1 FR4 (incorporating a KpnI/Acc65I RE site (GGTACC) as shown in FIG. 1); and c) for Vλ: leader sequence (ompA incorporating the NdeI RE site as shown in Table 2); germline FR1, CDR1, FR2, CDR2 and FR3 (incorporating a BbsI RE site (GAAGAC) as shown in FIG. 1), lambda-like CDR-L3 (QSYDSSLS-GVV) (SEQ ID NO: 3) according to Ewert S. et al., J. Mol. Biol. (2003) 325, 531-553; and the JI2/3 FR4 (incorporating a KpnI/Acc65I RE site (GGTACC) as shown in FIG. 1).

The "germline protein sequences" or "germline amino acid sequences" of antibodies encoded by the germline genes are disclosed in the following publications, for VH: Tomlinson et al., (1992), "The Repertoire of Human Germline Vh Sequences Reveals about Fifty Groups of Vh Segments with Different Hypervariable Loop" J. Mol. Biol. 227, 776-798; Matsuda et al. (1998), "The complete nucleotide sequence of the human immunoglobulin heavy chain variable region locus" J Exp Med 188(11):2151-62; and LeFranc M P (2001) "Nomenclature of the human immunoglobulin heavy (IGH) genes." Exp Clin Immunogenet. 18(2):100-16; for Vλ: Kawasaki et al., (1997) "One-Megabase Sequence Analysis of the Human immunoglobulin lambda Gene Locus" Genome Research 7(3):250-61; Frippiat et al., (1995) "Organization of the human immunoglobulin lambda light-chain locus on chromosome 22q11.2" Hum. Mol. Genet., 4, 983-991; and LeFranc M P (2001) "Nomenclature of the human immunoglobulin lambda (IGL) genes. Exp Clin Immunogenet.; 18:242-254; and for Vκ: Schäble and Zachau (1993), "The variable genes of the human immunoglobulin kappa locus," Biol. Chem. Hoppe Seyler. 374(11):1001-22; Brensing-Küppers et al. (1997), "The human immunoglobulin kappa locus on yeast artificial chromosomes (YACs)" Gene. 191(2):173-81; Kawasaki et al. (2001), "Evolutionary dynamics of the human immunoglobulin kappa locus and the germline repertoire of the Vkappa genes" Eur J Immunol 31(4):1017-28; and Lefranc M P (2001) "Nomenclature of the human immunoglobulin kappa (IGK) genes" Exp Clin Immunogenet., 18, 161-174, which are all hereby incorporated by reference in their entireties.

In parts of the specification, e.g. FIG. 5, the nomenclature of the variable domain germline genes used within the present application are IMGT, as described in the LeFranc et al. publications cited in the previous paragraph. Regarding nomenclature, "VH" and "IGHV" mean heavy chain variable domain, wherein the numbering of the genes is IMGT; "VL", "Vλ" and "IGLV" mean lambda light chain variable domain, wherein the numbering of the genes is IMGT and "Vκ," "VK" and "IGKV" mean kappa light chain variable domain, wherein the numbering of the genes is IMGT. Alternatively, "VL" can be used to mean variable light chain, including Vκ and Vλ.

The term "germline gene sequence" means a) the nucleic acid sequence of a germline gene encoding a variable region of an antibody or functional fragment thereof, or b) a modified nucleic acid sequence encoding a variable region of an antibody or functional fragment thereof having the same amino acid sequence as a variable region of an antibody encoded by a germline gene, wherein the nucleic acid sequence is modified by, for example, codon optimization, the addition of desired restriction sites, optimized GC content, the removal of undesired splice sites or the removal of mRNA instability motifs.

The term "germline gene pair(s)" means the pair of nucleic acid sequences, and their corresponding germline gene, encoding a variable heavy chain and a variable light chain of an antibody or functional fragment thereof. For example, a germline gene pair could be VH3-23/Vκ1-5, where the antibody encoded by VH3-23/Vκ1-5 comprises a variable heavy chain, or a portion thereof, encoded by germline gene VH3-23 and a variable light chain, or portion thereof, encoded by germline gene Vκ1-5.

The term "germline protein pair" means an antibody or functional fragment thereof, wherein the variable heavy chain, or portion thereof, and the variable light chain, or portion thereof, a) are each encoded by a specific germline gene, or b) are each encoded by a modified nucleic acid sequence encoding a variable region of an antibody or functional fragment thereof having the same amino acid sequence as a variable region of an antibody encoded by the specific germline gene, wherein the nucleic acid sequence is modified by, for example, by codon optimization, the addition of desired restriction sites, optimized GC content, the removal of undesired mRNA splice sites or the removal of mRNA instability motifs, or c) each comprise an amino acid sequence encoded by a germline gene, but with point mutations in the amino acid sequence, such as, for the purpose of removing of an undesired cysteine, or introduction of desired restriction sites, e.g. BbsI, or that result from errors in synthesis, amplification or cloning. For example, a germline protein pair could be the antibody or functional fragment encoded by VH3-23/Vκ1-5, where the antibody comprises a variable heavy chain, or a portion thereof, encoded by germline gene VH3-23 and a variable light chain, or portion thereof, encoded by germline gene Vκ1-5. A "germline protein pair" includes the constructs as prepared in Example 5, which comprise a) for VH: leader sequence (modified phoA incorporating a NheI RE site as shown in Table 1); germline FR1, CDR1, FR2, CDR2 and FR3 (incorporating a BssHII RE site (GCGCGC) as shown in FIG. 1); CDR-H3 (WGGDG-FYAMDY) (SEQ ID NO: 1) of the 4D5 antibody as used in Ewert S. et al., J. Mol. Biol. (2003) 325, 531-553; and the JH4 FR4 (incorporating a XhoI RE site (CTCGAG) as shown in FIG. 1);

b) for Vk: leader sequence (ompA incorporating the NdeI RE site as shown in Table 2); germline FR1, CDR1, FR2, CDR2 and FR3 (incorporating a BbsI RE site (GAAGAC) as shown in FIG. 1), kappa-like CDR-L3 (QQHYTTPPT) (SEQ ID NO: 2) according to Ewert S. et al., J. Mol. Biol. (2003) 325, 531-553; and the Jk1 FR4 (incorporating a KpnI/Acc65I RE site (GGTACC) as shown in FIG. 1); and c) for Vλ: leader sequence (ompA incorporating the NdeI RE site as shown in Table 2); germline FR1, CDR1, FR2, CDR2 and FR3 (incorporating a BbsI RE site (GAAGAC) as shown in FIG. 1), lambda-like CDR-L3 (QSYDSSLS-GVV) (SEQ ID NO: 3) according to Ewert S. et al., J. Mol. Biol. (2003) 325, 531-553; and the Jl2/3 FR4 (incorporating a KpnI/Acc65I RE site (GGTACC) as shown in FIG. 1).

The term "variable heavy chain and variable light chain pair" or "VH/VL pair" means the combination of one variable heavy chain and one variable light chain. An antibody and functional fragment, e.g. a Fab, comprises at least one variable heavy chain bound to a variable light chain, which form the antigen binding region. An example, of a variable heavy chain and variable light chain pair is the antibody or functional fragment, or portion thereof, comprising germline amino acid sequences from VH3-23/Vκ1-5, or encoded by the germline genes VH3-23/Vκ1-5, where the antibody comprises a variable heavy chain, or a portion thereof, comprising germline amino acid sequences from VH3-23, or encoded by germline gene VH3-23 and a variable light chain, or portion thereof, comprising germline amino acid sequences from Vκ1-5, or encoded by germline gene Vκ1-5.

The term "substantially all" means at least 90%. For example, substantially all of the antibodies or functional fragments comprise variable heavy chain and variable light chain framework regions comprising germline amino acid sequences of a germline protein pair having certain properties, means that at least 90% of the antibodies or fragments comprise, variable heavy chain and variable light chain framework regions comprising germline amino acid sequences of a germline protein pair having such properties.

The sequences of the JH4 for variable heavy chain, Jκ1 for variable κ light chain, and Jλ2/3 for variable λ light chain regions are described in the following publications: Scaviner et al., (1999), "Protein displays of the human immunoglobulin heavy, kappa and lambda variable and joining regions" Exp Clin Immunogenet. 16(4):234-40; for JH: Ravetch et al., (1981), "Structure of the human immunoglobulin mu locus: characterization of embryonic and rearranged J and D genes." Cell 27 (3 pt 2): 583-91; for JK: Hieter et al. (1982), "Evolution of human immunoglobulin kappa J region genes." J Biol Chem 257(3):1516-22; for JL: Kawasaki et al., (1997) "One-Megabase Sequence Analysis of the Human immunoglobulin lambda Gene Locus" Genome Research 7(3):250-61, which are all incorporated by reference herein in their entireties. The JH4 amino acid sequence is (YFDYWGQGTLVTVSS) (SEQ ID NO: 4); the Jκ1 amino acid sequence is (WTFGQGTKVEIK) (SEQ ID NO: 5); and the Jλ2/3 amino acid sequence is (VVFGGGT-KLTVL) (SEQ ID NO: 6).

The term "variable domain/region/(VH or VL)" means the region of an immunoglobulin that comprises one or more Ig domains substantially encoded by any of the VL (including Vk and Vλ), VH, JL (including Jk and Jλ), and JH nucleic acids that make up the light chain (including κ and λ) and heavy chain immunoglobulin genetic loci respectively. A light or heavy chain variable region (VL and VH) is made up of a "framework" or "FR" region interspersed by three hypervariable regions referred to as "complementarity determining regions" or "CDRs." The extent of the framework region and CDRs have been defined using at least the following conventions: see Kabat, 1991, J. Immunol., 147, 915-920; Chothia & Lesk, 1987, J. Mol. Biol. 196: 901-917; Chothia et al., 1989, Nature 342: 877-883; Al-Lazikani et al., 1997, J. Mol. Biol. 273: 927-948); see also http://www.bioc.uzh.ch/antibody/Numbering/NumFrame.html (which shows the well known numbering conventions of antibody amino acids and the location of the CDRs and framework regions), and that used in FIGS. 25-36.

The term "framework region" means the part of the variable domain which serves as a scaffold for the antigen binding loops. Examples of the framework regions include FR1, FR2, FR3, and FR4 of either the variable heavy or variable light chains.

The term "complementarity determining region" or "CDR" means an antibody's antigen binding loops. Each of the two variable domains of an antibody Fv fragment contains three CDRs. The complementarity determining regions include CDR1, CDR2, and CDR3 of either the variable heavy or variable light chains.

The term "human immune repertoire" means a repertoire of the nucleic acids isolated from B cells from the immune system of a human. A repertoire may be that of an individual, or a population, and may come from naïve B cells and/or antigen experienced B cells. The present invention is amenable to the determination of an immune repertoire from a single individual, provided sufficient B-cells are obtained. Preferably, the immune repertoire is obtained from multiple individuals to avoid sample biases. An example of a human immune repertoire is described in Examples 2-3.

An "antigen" and "immunogen" are defined as any molecule that is bound specifically by an antibody.

The term "specific for an antigen/immunogen" means the specific association between an antibody and a corresponding molecule. Specificity can be determined by the methods described in Example 11, such as ELISA and/or Biacore.

"CDR diversification" or "diversified CDR" is obtained by varying the amino acid composition within a CDR. A diversified CDR can be found in a collection of antibodies or fragments having one or more identical framework regions, e.g. germline framework regions, wherein the antibodies or fragments have CDR3s comprising different amino acid sequences. Diversified CDRs can be achieved by any methods known to one of skill in the art, including the methods described by the following: WO9708320, U.S. Pat. No. 6,300,064, which is incorporated by reference in its entirety; WO2008053275, U.S. Ser. No. 12/158,181, which is incorporated by reference in its entirety; WO07056441, U.S. 60/806,602, which is incorporated by reference in its entirety; WO2009036379, U.S. 60/993,785, which is incorporated by reference in its entirety; WO2009114815, Ser. No. 12/922,153, which is incorporated by reference in its entirety; WO020617071, U.S. Ser. No. 12/762,051, which is incorporated by reference in its entirety. CDRs are generally known to be the immunogen binding regions, therefore having collections comprising members representing a large diversity within the CDRs, especially CDR3, increases the possibility that a collection will comprise antibodies or fragments thereof having specificity, and optimal properties for any immunogen.

The term "variant" means an antibody or fragment having a different amino acid sequence than another antibody or fragment. The term "variant" includes antibodies or fragments that are essentially identical in sequence in the framework regions, but have different amino acid sequences in a CDR region, e.g. CDR3. Variants of a variable heavy chain and variable light chain pair, have essentially the same amino acid sequence within the framework regions, but have different amino acid sequences within the CDR3 region.

The term "synthesis" or "synthesized" means gene synthesis, where nucleic acid sequences are synthesized into physical DNA, comprising polynucleotides. Standard DNA synthesis comprises single nucleotide synthesis, where single-stranded oligo-nucleotides are generated and then the overlapping oligonucleotides are ligated using a PCR-like assembly. Companies, such as, Sloning (Puchheim, Germany), Geneart (Regensburg, Germany), DNA2.0 (Menlo Park, Calif. USA), Entelechon (Regensburg, Germany), and Genscript (Piscataway, N.J. USA) provide gene synthesis technology. Sloning, for example, utilizes a set of pre-made double stranded triplet nucleotides.

The term "synthetic" describes a molecule that is made outside of the human body by synthesis or synthesized, e.g. DNA. The term "synthetic" also describes a protein, e.g. antibody or fragment that is translated from a synthetic DNA molecule.

The term "collection" or "library" means at least two members. The term "member" includes, but is not limited to nucleic acids encoding antibodies or fragments thereof or the antibodies or fragments thereof themselves.

The term "nucleic acid" is used herein interchangeably with the term "polynucleotide" or "DNA" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985; and Rossolini et al., *Mol. Cell. Probes* 8:91-98, 1994).

As used herein, the term, "codon optimized" or "codon optimization" means that a nucleotide sequence has been altered so that it includes codons that are preferred in a certain production system, e.g. cell or organism. The optimized nucleotide sequence is engineered to retain the amino acid sequence originally encoded by the starting nucleotide sequence. In addition the nucleotide sequence may be designed to be completely or as much as possible devoid of inhibitory motifs, mRNA splice sites, mRNA instability motifs and undesired restriction sites. It can also be optimized for GC content, desired restriction sites and other parameters. Sequences may be optimized for expression in different hosts, including bacterial or eukaryotic cells, specifically mammalian cells. The amino acid sequences encoded by optimized nucleotide sequences may also be referred to as optimized.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "polypeptide" and "protein" are used interchangeably herein to refer to a polymer of amino acid residues.

The terms "identical" in the context of two or more nucleic acids or polypeptide sequences, refer to two or more sequences or subsequences that are the same.

The term "vector" refers to a polynucleotide molecule capable of transporting another polynucleotide to which it has been linked. Preferred vectors are those capable of autonomous replication and/or expression of nucleic acids to which they are linked. Vectors capable of directing the expression of nucleic acids to which they are operatively linked are referred to herein as "expression vectors." One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. Vectors may be compatible with prokaryotic or eukaryotic cells. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Figure 14:
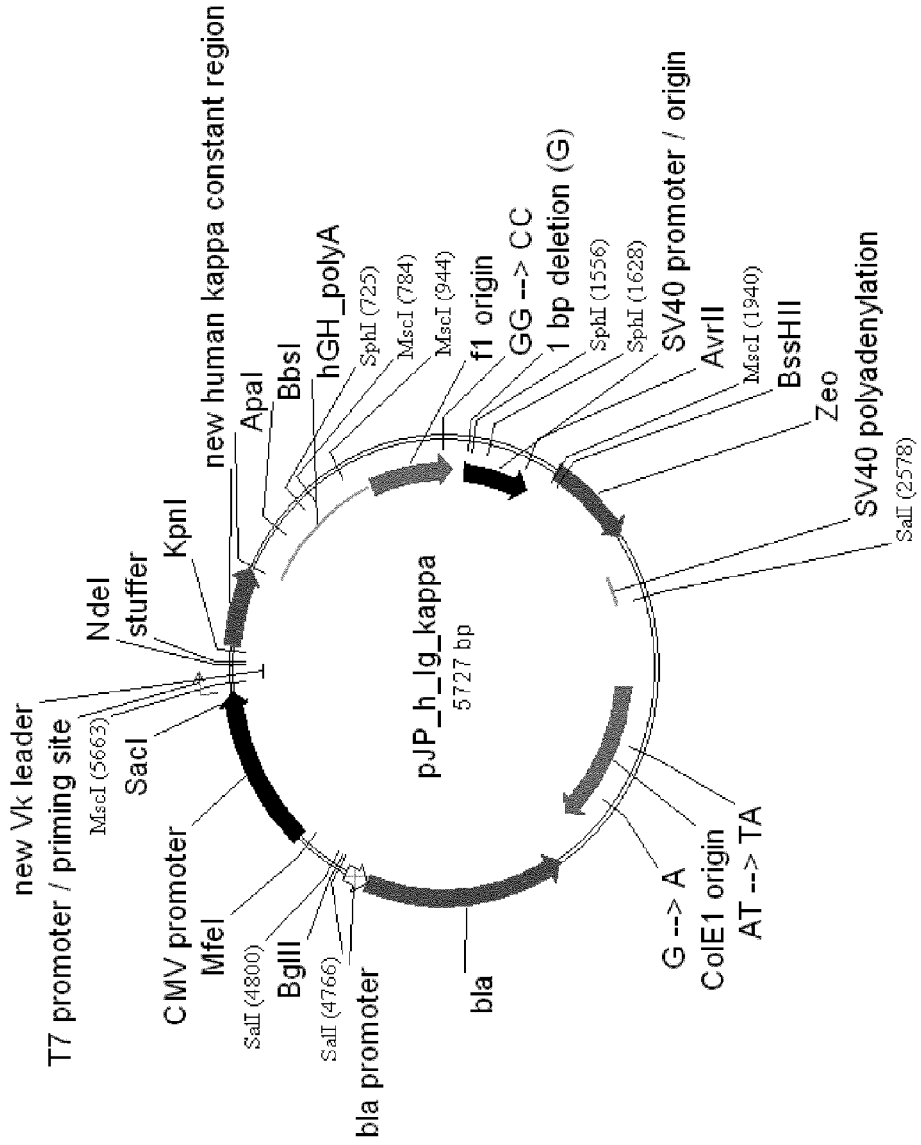
FIG. 14 shows the pJP_h_Ig_kappa variable κ light chain IgG expression vector.
Figure 15:
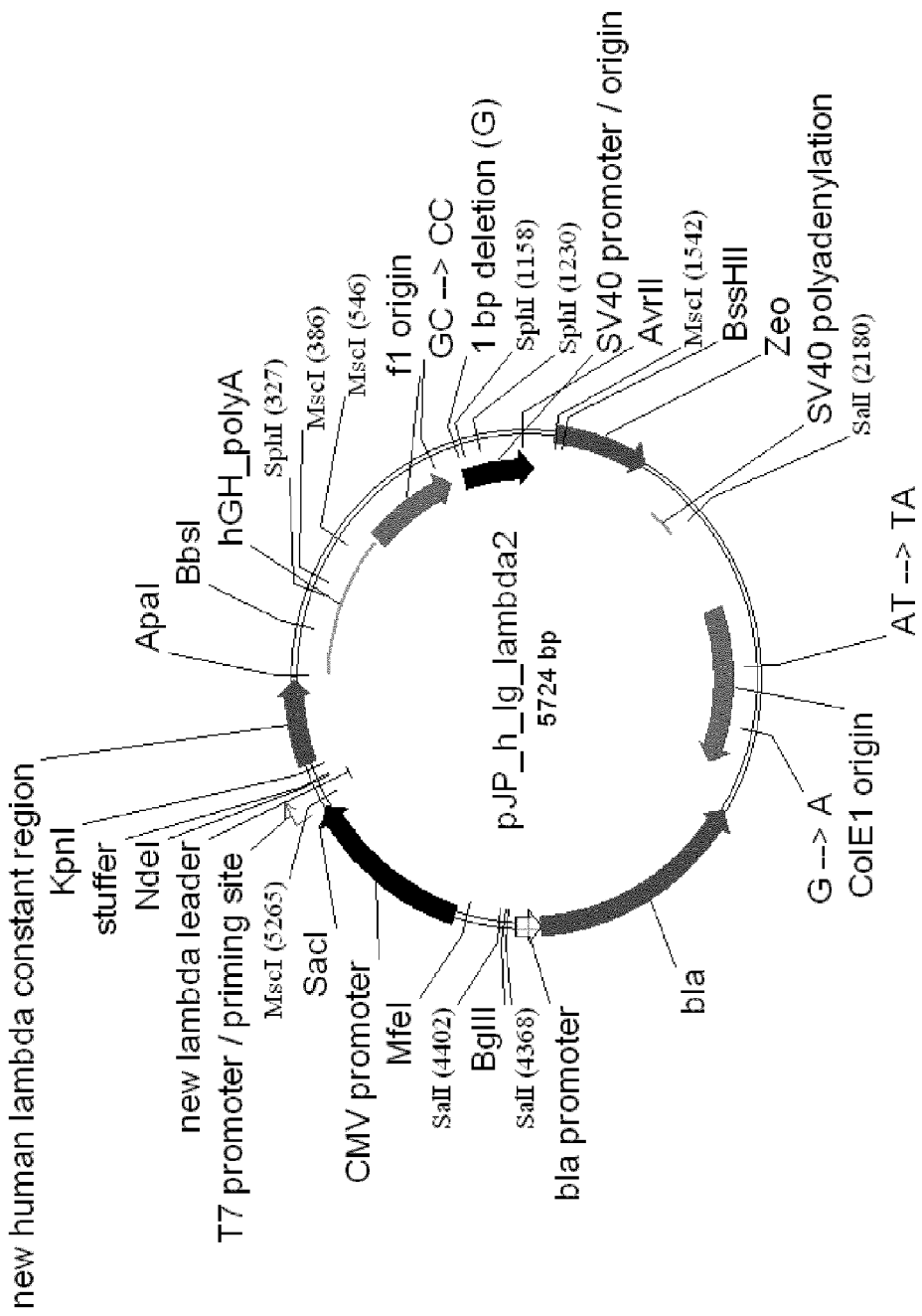
FIG. 15 shows the pJP_h_Ig_lambda2 variable λ light chain IgG expression vector.

Vectors typically include a prokaryotic replicon which may include a prokaryotic promoter capable of directing the expression (transcription and translation) of the VH- and/or VL-coding homologs in a bacterial host cell, such as *Escherichia coli* transformed therewith. Additionally, vectors include IgG expression vectors for use in mammalian cells, e.g. see FIGS. 13-15. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment.

Examples of such vector plasmids include pUC8, pUC9, pBR322, and pBR329, pPL and pKK223, available commercially.

A "display vector" includes a DNA sequence having the ability to direct replication and maintenance of the recombinant DNA molecule extra chromosomally in a host cell, such as a bacterial host cell, transformed therewith. Such DNA sequences are well known in the art. Display vectors can for example be phage vectors or phagemid vectors originating from the class of fd, M13, or fl filamentous bacteriophage. Such vectors are capable of facilitating the display of a protein including, for example, a binding protein or a fragment thereof, on the surface of a filamentous bacteriophage. Display vectors suitable for display on phage, ribosomes, DNA, bacterial cells or eukaryotic cells, for example yeast or mammalian cells are also known in the art, for example, as are viral vectors or vectors encoding chimeric proteins.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Typical host cells are prokaryotic (such as bacterial, including but not limited to *E. coli*) or eukaryotic (which includes yeast, mammalian cells, and more). Bacterial cells are preferred prokaryotic host cells and typically are a strain of *Escherichia coli* (*E. coli*) such as, for example, the *E. coli* strain DH5 available from Bethesda Research Laboratories, Inc., Bethesda, Md. Preferred eukaryotic host cells include yeast and mammalian cells including murine and rodents, preferably vertebrate cells such as those from a mouse, rat, monkey or human cell line, for example HKB11 cells, PERC.6 cells, or CHO cells.

The introduction of vectors into host cells may be accomplished by a number of transformation or transfection methods known to those skilled in the art, including calcium phosphate precipitation, electroporation, microinjection, liposome fusion, RBC ghost fusion, protoplast fusion, viral infection and the like. The production of monoclonal full-length antibodies, Fab fragments, Fv fragments and scFv fragments is well known.

Transformation of appropriate cell hosts with a recombinant DNA molecule is accomplished by methods that typically depend on the type of vector and cells used. With regard to transformation of prokaryotic host cells, see, for example, Cohen et al., Proceedings National Academy of Science, USA, Vol. 69, P. 2110 (1972); and Maniatis et al., Molecular Cloning, a Laboratory Manual, Cold spring Harbor Laboratory, Cold Spring Harbor, N.Y. (1982). With regard to the transformation of vertebrate cells with retroviral vectors containing rDNAs, see for example, Sorge et al., Mol. Cell. Biol., 4:1730-1737 (1984); Graham et al., Virol., 52:456 (1973); and Wigler et al., Proceedings National Academy of Sciences, USA, Vol. 76, P. 1373-1376 (1979).

eGFP (enhanced green fluorescent protein) has the following amino acid sequence:

MSGSHHHHHHGTMVSKGEELFTGVVPILVELDG-DVNGHKFSVSGEGEGDATYGKLT LKFICTTGKLPVP-WPTLVTTLTYGVQCFSRYPDHMKQHDFFKSAMP-EGYVQERTIFF KDDGNYKTRAEVKFEGDTLVNRI-ELKGIDFKEDGNILGHKLEYNYNSHNVYIMADK QKNGIKVNFKIRHNIEDGSVQLADHYQQNTPIGDG-PVLLPDNHYLSTQSALSKDPNEK RDHMV-LLEFVTAAGITLGMDELYK<u>*DI*</u>. (SEQ ID NO: 317) The amino acids underlined and in italics represent the His tag, and those only underlined represent the addition of a restriction enzyme recognition sequence.

Collections of Antibodies or Fragments Thereof

The present disclosure enables collections of antibodies or functional fragments thereof and the nucleic acids encoding such antibodies or fragments that can be used in the identification of therapeutic antibodies against any target, where the antibodies or fragments are clinically developable, safe and effective in patients. As background, the inventors assumed that the variable heavy chain and variable light chain germline gene pairs abundant in the human immune repertoire (such as, VH3-23/VK1-5) likely have favorable biophysical properties that would lead to more efficient development and increase the safety and efficacy of the resulting antibodies in patients. Such favorable biophysical properties could include: a) high relative display rate in Fab format; b) high relative Fab expression yield; c) temperature stability in both Fab and IgG format; d) bovine/mouse serum stability of both Fab and IgG format; e) high IgG1 expression yield; e) SEC monomeric content (% monomer) in both Fab and IgG format; and/or f) high IgG1 isoelectric point (pI).

Each B cell encodes one antibody, and each antibody comprises a variable heavy chain and variable light chain. Each of the variable heavy chain and variable light chains of an antibody can be aligned with a germline gene sequence (or germline protein sequence) in order to determine the origin of the antibody, meaning from which germline gene the variable heavy chain and variable light chain were derived. Therefore, for each antibody, it can be said, that the variable heavy chain and variable light chain comprise a germline gene pair, or germline protein pair, for example, VH3-23 paired with VK1-5.

In order to prove the hypothesis that the germline protein pairs abundant in the human immune repertoire likely have favorable biophysical properties, the first step was to identify the variable heavy chain and variable light chain germline gene pairs (germline protein pairs) present in the human immune repertoire. In some aspects the data is obtained from publically available literature or databases and from the sampling of B cells.

The following articles were identified and analyzed in detail: Wardemann H. et al. (2003) Science 301, 1374-1377 and any supporting tables; Yurasov S. et al. (2005) J. Exp. Med. 201, 703-712 and any supporting tables; Tsuiji M. et al. (2006) J. Exp. Med. 203, 393-401 and any supporting tables; Yurasov S. et al. (2006) J. Exp. Med. 203, 2255-2262 and any supporting tables, Tiller T. et al. (2007) Immunity 26, 205-213 and any supporting tables, and Mietzner B. et al. (2008) PNAS 105, 9727-9732 and any supporting tables, all of which are incorporated by reference in their entireties.

Alternatively, databases, such as NCBI, can be searched using Ig-Blast. As of 2005 the database contained at least 25,000 rearranged human antibody sequences in FASTA format. Of the 22,500 entries, 13,235 represented VH sequences, 1,506 represented Vκ and 2,259 represented Vλ.

Generally, in the relevant publically available literature and databases, the following methods were followed: B cells were isolated from human donors, the B cells were sorted in order to determine their stage of development or differentiation, cDNAs were generated and amplified representing the DNA encoding the antibody from each B cell, the cDNAs were sequenced, cDNAs encoding the variable heavy chain and variable light chains were aligned to the known germline gene sequences, and the germline gene pair from each B cell was determined.

In some embodiments the data was obtained from the sampling and isolation of human B cells, which comprised a method similar to that used in the literature. In these aspects the method of producing a collection of synthetic antibodies or functional fragments thereof comprises the step of obtaining data comprising the variable heavy chain and variable light chain germline gene pairs present in the human immune repertoire; wherein the obtaining step further comprises the steps of aa) isolating human B cells from a sample; ab) generating cDNA from the B cells; ac) PCR amplifying the cDNA from the B cells; ad) sequencing the PCR products; and ae) identifying the germline genes of the PCR products. Both sets of data provided the variable heavy chain and variable light chain germline gene pairs that are present in the human immune repertoire.

Using antibody sequence data, one of skill in the art, can identify the germline families and/or genes of each VH, Vκ and Vλ variable domain. Using this approach, the prominence of each VH and VL germline family and/or gene, and/or the germline family and/or gene of each VH and VL domain pair can readily be determined by one of skill in the art.

The raw data obtained from literature and from B cells was pooled, analyzed and the variable heavy chain and variable light chain germline gene pairs present in the human immune repertoire were ranked in terms of number of each. From this data it was clear that certain variable heavy chain and variable light chain germline gene pairs are present more frequently than others in the human immune repertoire. These prominent pairs were expected to have superior biophysical properties.

As a next step, it had to be determined which germline protein pairs were to be tested for functional properties relevant to developability, as there are ~2500 pairs in the human immune repertoire. One way would be to test the variable heavy chain and variable light chain germline protein pairs that occur most prominently in the human immune repertoire, for example see Table 6. One could, for example, select the top four hundred pairs for testing, or select the variable heavy chain and variable light chain germline protein pairs present above a certain threshold number. This approach, however, would require the synthesis and testing of a large number of variable heavy chain and variable light chain germline protein pair sequences; therefore, such an approach would not be very efficient.

As an alternative approach, the inventors selected a subset of the variable heavy chain and variable light chain germline pairs that are representative of, accurately reproduce, or cover the majority of the prominent pairs from the human immune repertoire. This approach was based, in part, upon the observation that a small number of variable heavy, variable κ light chain, and variable λ light chain germline genes are dominant in the human immune repertoire. Wildt et al. at 895-896 describes this phenomenon. Wildt et al. also states that the frequently expressed heavy and light chain gene segments are often paired, and observed that half of the pairings sampled correspond to only five germline pairs. Therefore, a small number of the prominent heavy and light chain germline genes (unpaired) can be combined to generate a group of pairs that are representative of the human immune repertoire.

Therefore, the raw data was analyzed to determine the variable heavy chain, variable κ light chain, and variable λ light chain (unpaired) germline genes prominent in the human immune repertoire. The prominent variable heavy chain, variable κ light chain, and variable λ light chain germline protein sequences were then evaluated to determine their biophysical properties relevant to development. The variable heavy chain, variable κ light chain, and variable λ light chain germline protein sequences were evaluated in silico for the following properties: CDR length, isoelectric point (pI) the preferred isoelectric point is 7.5 or above as this is should provide stability in a standard pH 5.5 to pH 7 formulation buffer, sites of potential post translational modification sites in the complementarity determining regions (PTM's) (specifically, N-linked glycosylation sites (NxS or NxT) or chemical modifications such as Asp cleavage (often at a DP), Asp isomerization (DS, DG), deamidation (NS, NG) which can occur in vivo (in serum) or upon storage in formulation buffer and lead to loss of antibody binding), the presence of Methionines in the CDRs (can be oxidized when exposed to solvent), the presence of unpaired Cysteines (will form disulfide bonds with any other unpaired cysteine, thus leading to crosslinking of proteins and/or lower expression levels), deviations from germline, the presence of potential T-cell epitopes, and theoretical aggregation propensity.

As shown in Tables 5, and FIGS. 2 and 3, generally, the top 20 VH, top 8 Vλ and top 12 Vκ were selected for synthesis, combination and subsequent functional analysis. The germline gene sequences were synthesized and then combined in order to generate 400 germline protein pairs that are representative of the germline gene pairs found in the immune repertoire, wherein each of the variable regions has favorable biophysical properties as identified in silico. The 400 VH/VL germline protein pairs were tested for the following properties: a) relative display after phage production and phage ELISA in Fab format; b) relative Fab expression yield after Fab production in *E. coli*, *E. coli* cell lysis and ELISA detection of produced Fab; c) temperature stability of Fab after Fab production in *E. coli*, *E. coli* cell lysis and ELISA detection of non-denatured Fab after incubation at increased temperatures; d) bovine/mouse serum stability of Fab from *E. coli* lysates by ELISA detection of non-denatured Fab after incubation in bovine/mouse serum; e) relative human IgG1 expression yield levels after IgG1 production in mammalian cells and ELISA detection of secreted IgG1 from cell culture supernatants; and f) bovine serum stability of human IgG1 by ELISA detection of non-denatured Fab after incubation in bovine/mouse serum.

Of the 400 germline protein pairs tested (results shown in Table 12), 95 were selected for further testing. After synthesis, expression and purification, the 95 germline protein pairs shown in FIGS. 16-24 were tested in both Fab and IgG1 formats for the following a) purified Fab expression yield in mg/L, b) purified Fab monomeric content (% monomer), c) purified Fab thermal stability, d) purified IgG1 expression yield in mg/L, e) purified IgG1 monomeric content (% monomer), f) purified IgG1 thermal stability, g) IgG1 isoelectric point and h) IgG1 stress testing with exposure to acid, including differential scanning fluorometry (DSF), absorption, dynamic light scattering and particle staining. The results are shown in FIGS. 16-24.

In an embodiment, the following thresholds were set i) an expression yield in Fab format of at least 2.5 mg/L; ii) thermal stability at 70° C. or above in Fab format; iii) monomeric content (% monomer) in Fab format of at least 98% as determined by SEC; iv) an expression yield in IgG1 format of at least 30 mg/L; v) thermal stability at 73° C. or above in IgG1 format; and vii) monomeric content (% monomer) in IgG1 format of at least 99% as determined by SEC. Therefore, in an embodiment, a collection comprises synthetic antibodies or functional fragments thereof or synthetic nucleic acids encoding such antibodies or functional fragments, wherein the antibodies or functional fragments comprise variable heavy chain and variable light chain framework regions comprising germline protein sequences of a germline protein pair, wherein said germline protein pairs comprise the following properties:
  i) an expression yield in Fab format of at least 2.5 mg/L;
  ii) thermal stability at 70° C. or above in Fab format;
  iii) monomeric content (% monomer) in Fab format of at least 98% as determined by SEC;
  iv) an expression yield in IgG1 format of at least 30 mg/L;
  v) thermal stability at 73° C. or above in IgG1 format; and
  vi) monomeric content (% monomer) in IgG1 format of at least 99% as determined by SEC.

In additional embodiments, a collection comprises synthetic antibodies or functional fragments thereof or synthetic nucleic acids encoding such antibodies or functional fragments, wherein substantially all, or at least 50%, or at least 60%, or at least 70%, or at least 80%, or at least 90%, or at least 95%, or each of the antibodies or functional fragments comprise variable heavy chain and variable light chain framework regions comprising germline protein sequences of a germline protein pair, wherein said germline protein pairs comprise the following properties:
  i) an expression yield in Fab format of at least 2.5 mg/L;
  ii) thermal stability at 70° C. or above in Fab format;
  iii) monomeric content (% monomer) in Fab format of at least 98% as determined by SEC;
  iv) an expression yield in IgG1 format of at least 30 mg/L;
  v) thermal stability at 73° C. or above in IgG1 format; and
  vi) monomeric content (% monomer) in IgG1 format of at least 99% as determined by SEC.

In additional embodiments, a collection comprises synthetic antibodies or functional fragments thereof or synthetic nucleic acids encoding such antibodies or functional fragments, wherein the antibodies or functional fragments consists of or consists essentially of variable heavy chain and variable light chain framework regions comprising germline protein sequences of a germline protein pair, wherein said germline protein pairs comprise the following properties:
  i) an expression yield in Fab format of at least 2.5 mg/L;
  ii) thermal stability at 70° C. or above in Fab format;
  iii) monomeric content (% monomer) in Fab format of at least 98% as determined by SEC;
  iv) an expression yield in IgG1 format of at least 30 mg/L;
  v) thermal stability at 73° C. or above in IgG1 format; and
  vii) monomeric content (% monomer) in IgG1 format of at least 99% as determined by SEC.

In certain embodiments,
  i) the expression yield in Fab format was determined by UV-spectrophotometry using an extinction coefficient of 1.538 mL/mg and measuring absorbance at 280 nm.
In certain embodiments,
  ii) the thermal stability in Fab format was determined by differential scanning fluorometry using PBS buffer.
In certain embodiments,
  iii) the monomeric content (% monomer) in Fab format was determined by size exclusion chromatography using a Superdex75 HR10/30 column and Gibco D-PBS buffer at pH 7.4.

In certain embodiments,
  iv) the expression yield in IgG1 format was determined by UV-spectrophotometry using an extinction coefficient of 1.369 mL/mg and measuring absorbance at 280 nm.
In certain embodiments,
  v) the thermal stability in IgG1 format was determined by differential scanning fluorometry using PBS buffer.
In certain embodiments,
  vi) the monomeric content (% monomer) in IgG1 format was determined by size exclusion chromatography using a Tosoh TSK-Gel G3000SWxl column and Gibco D-PBS buffer at pH 7.4.

UV-spectrophotometry may be performed using the Nanadrop system (peqlab, Erlangen, Germany). Differential scanning fluorometry may be performed using the iCycler iQ5 Thermal Cycler (Biorad). Differential scanning fluorometry may be performed using Gibco D-PBS, pH 7.4 (Invitrogen, Paisley, USA). Size exclusion chromatography may be performed using the ÄKTA Purifier System (GE Healthcare).

The following germline protein pairs (54) were at or above the following thresholds using the method described above: i) an expression yield in Fab format of at least 2.5 mg/L; ii) thermal stability at 70° C. or above in Fab format; iii) monomeric content (% monomer) in Fab format of at least 98% as determined by SEC; iv) an expression yield in IgG1 format of at least 30 mg/L; v) thermal stability at 73° C. or above in IgG1 format; and vii) monomeric content (% monomer) in IgG1 format of at least 99% as determined by SEC, therefore, have superior functional activity related to developability, (data shown in FIGS. 16-24): VH1-18 (SEQ ID NO: 204)/VK1-39 (SEQ ID NO: 236); VH1-18 (SEQ ID NO: 204)/VK3-15 (SEQ ID NO: 238); VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-46 (SEQ ID NO: 205)/VL3-21 (SEQ ID NO: 257); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-16 (SEQ ID NO: 234); VH3-07 (SEQ ID NO: 207)/VK1-27 (SEQ ID NO: 235); VH3-07 (SEQ ID NO: 207)/VK1-39 (SEQ ID NO: 236); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VK1-05 (SEQ ID NO: 230); VH3-11 (SEQ ID NO: 208)/VK1-39 (SEQ ID NO: 236); VH3-11 (SEQ ID NO: 208)/VK3-15 (SEQ ID NO: 238); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-16 (SEQ ID NO: 234); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-40 (SEQ ID NO: 250); VH3-15 (SEQ ID NO: 209)/VL1-47 (SEQ ID NO: 251); VH3-15 (SEQ ID NO: 209)/VL1-51 (SEQ ID NO: 252); VH3-15 (SEQ ID NO: 209)/VL2-14 (SEQ ID NO: 254); VH3-21 (SEQ ID NO: 210)/VK1-12 (SEQ ID NO: 233); VH3-21 (SEQ ID NO: 210)/VK1-27 (SEQ ID NO: 235); VH3-21 (SEQ ID NO: 210)/VL2-11 (SEQ ID NO: 253); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ NO: 211)/VL3-1 (SEQ ID NO: 256); VH3-30 (SEQ ID NO: 212)/VK3-20 (SEQ ID NO: 239); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK1-27 (SEQ ID NO: 235); VH3-74 (SEQ ID NO: 214)/VK3-20 (SEQ ID NO: 239); VH3-74 (SEQ ID NO: 214)/VL1-51 (SEQ ID NO: 252); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-15 (SEQ ID NO: 238); VH6-1 (SEQ ID NO: 216)/VK3-20 (SEQ ID NO: 239) and VH6-1 (SEQ ID NO: 216)/VL1-51 (SEQ ID NO: 252). Therefore, collections comprising any number of these germline protein pairs could be used to identify developable antibodies or fragments thereof against any antigen.

In an aspect, a collection comprises synthetic antibodies or functional fragments thereof or synthetic nucleic acids encoding such antibodies or functional fragments, wherein the antibodies or functional fragments comprise variable heavy chain and variable light chain pairs, wherein the framework regions of the variable heavy chain and variable light chain pairs comprise germline protein sequences of specific variable heavy chain and variable light chain pairs, for example, VH1-18/VK1-39. This means that the collection comprises antibodies or fragments wherein the framework regions of the antibodies or fragments comprise the germline protein sequences of VH1-18/VK1-39, where the variable heavy chain framework regions comprise the germline protein sequences of VH1-18 and the variable light chain framework regions comprise the germline protein sequences of VK1-39. A large number of germline protein pairs were tested, as constructs (as described in Examples 5 and 9), for their functional properties related to development. A number of constructs tested showed superior functional properties related to developability. The inventors believe that there is a high correlation between the input (antibody collection used for selection against an antigen) and output (antibodies identified from the collection as specific for the antigen) regarding the tested functional properties. Therefore, the collections of the invention comprise antibodies or fragments that comprise, in part, the same amino acid sequences as the constructs tested, for example, the framework regions and/or complementarity determining regions. Since, in an aspect, the collections comprise the amino acid sequences, or the nucleic acids encoding them, of the tested constructs it is believed that the collections comprise antibodies or fragments having the same superior functional properties related to developpabiltiy as the constructs tested. Therefore, it is expected that the antibodies or fragments subsequently selected from the collections against an antigen will also have the same superior functional properties relevant to developability. This hypothesis is supported by the experiments and data described in Example 11, see FIGS. 37-39, 45-48 and 62.

In some embodiments, a collection comprises synthetic antibodies or functional fragments thereof or synthetic nucleic acids encoding such antibodies or functional fragments, wherein the antibodies or functional fragments comprise variable heavy chain and variable light chain pairs, wherein the framework regions of the variable heavy chain and variable light chain pairs comprise germline protein sequences selected from two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more, thirty four or more, thirty five or more, or thirty six or more, thirty seven or more, thirty eight or more, thirty nine or more, forty or more, forty one or more, or forty two or more, or forty three or more, or forty four or more, or forty five or more, or forty six or more, or forty seven or more, or forty eight or more, or forty nine or more, or fifty or more, or fifty one or more, or fifty two or more, or fifty three or more, or fifty four variable heavy chain and variable light chain pairs of VH1-18 (SEQ ID NO: 204)/VK1-39 (SEQ ID NO: 236); VH1-18 (SEQ ID NO: 204)/VK3-15 (SEQ ID NO: 238); VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-46 (SEQ ID NO: 205)/VL3-21 (SEQ ID NO: 257); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-16 (SEQ ID NO: 234); VH3-07 (SEQ ID NO: 207)/VK1-27 (SEQ ID NO: 235); VH3-07 (SEQ ID NO: 207)/VK1-39 (SEQ ID NO: 236); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VK1-05 (SEQ ID NO: 230); VH3-11 (SEQ ID NO: 208)/VK1-39 (SEQ ID NO: 236); VH3-11 (SEQ ID NO: 208)/VK3-15 (SEQ ID NO: 238); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-16 (SEQ ID NO: 234); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-40 (SEQ ID NO: 250); VH3-15 (SEQ ID NO: 209)/VL1-47 (SEQ ID NO: 251); VH3-15 (SEQ ID NO: 209)/VL1-51 (SEQ ID NO: 252); VH3-15 (SEQ ID NO: 209)/VL2-14 (SEQ ID NO: 254); VH3-21 (SEQ ID NO: 210)/VK1-12 (SEQ ID NO: 233); VH3-21 (SEQ ID NO: 210)/VK1-27 (SEQ ID NO: 235); VH3-21 (SEQ ID NO: 210)/VL2-11 (SEQ ID NO: 253); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-30 (SEQ ID NO: 212)/VK3-20 (SEQ ID NO: 239); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK1-27 (SEQ ID NO: 235); VH3-74 (SEQ ID NO: 214)/VK3-20 (SEQ ID NO: 239); VH3-74 (SEQ ID NO: 214)/VL1-51 (SEQ ID NO: 252); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO:

252); VH6-1 (SEQ ID NO: 216)/VK1-09 (SEQ ID NO: 232); VH6-1 (SEQ ID NO: 216)/VK3-15 (SEQ ID NO: 238); VH6-1 (SEQ ID NO: 216)/VK3-20 (SEQ ID NO: 239) and VH6-1 (SEQ ID NO: 216)/VL1-51 (SEQ ID NO: 252).

In an embodiment, a collection comprises synthetic antibodies or functional fragments thereof or synthetic nucleic acids encoding such antibodies or functional fragments, wherein substantially all, or at least 50%, or at least 60%, or at least 70%, or at least 80%, or at least 90% or at least 95% or each of the antibodies or functional fragments comprise variable heavy chain and variable light chain pairs, wherein the framework regions of the variable heavy chain and variable light chain pairs comprise germline protein sequences selected from the variable heavy chain and variable light chain pairs VH1-18 (SEQ ID NO: 204)/VK1-39 (SEQ ID NO: 236); VH1-18 (SEQ ID NO: 204)/VK3-15 (SEQ ID NO: 238); VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-46 (SEQ ID NO: 205)/VL3-21 (SEQ ID NO: 257); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-16 (SEQ ID NO: 234); VH3-07 (SEQ ID NO: 207)/VK1-27 (SEQ ID NO: 235); VH3-07 (SEQ ID NO: 207)/VK1-39 (SEQ ID NO: 236); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VK1-05 (SEQ ID NO: 230); VH3-11 (SEQ ID NO: 208)/VK1-39 (SEQ ID NO: 236); VH3-11 (SEQ ID NO: 208)/VK3-15 (SEQ ID NO: 238); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-16 (SEQ ID NO: 234); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-40 (SEQ ID NO: 250); VH3-15 (SEQ ID NO: 209)/VL1-47 (SEQ ID NO: 251); VH3-15 (SEQ ID NO: 209)/VL1-51 (SEQ ID NO: 252); VH3-15 (SEQ ID NO: 209)/VL2-14 (SEQ ID NO: 254); VH3-21 (SEQ ID NO: 210)/VK1-12 (SEQ ID NO: 233); VH3-21 (SEQ ID NO: 210)/VK1-27 (SEQ ID NO: 235); VH3-21 (SEQ ID NO: 210)/VL2-11 (SEQ ID NO: 253); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-30 (SEQ ID NO: 212)/VK3-20 (SEQ ID NO: 239); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK1-27 (SEQ ID NO: 235); VH3-74 (SEQ ID NO: 214)/VK3-20 (SEQ ID NO: 239); VH3-74 (SEQ ID NO: 214)/VL1-51 (SEQ ID NO: 252); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-15 (SEQ ID NO: 238); VH6-1 (SEQ ID NO: 216)/VK3-20 (SEQ ID NO: 239) and VH6-1 (SEQ ID NO: 216)/VL1-51 (SEQ ID NO: 252).

An embodiment comprises a collection of synthetic antibodies or functional fragments thereof or synthetic nucleic acids encoding such antibodies or functional fragments, wherein the antibodies or functional fragments comprise variable heavy chain and variable light chain pairs, wherein the framework regions of the variable heavy chain and variable light chain pairs comprise germline protein sequences of the, consisting of or consisting essentially of the variable heavy chain and variable light chain pairs VH1-18 (SEQ ID NO: 204)/VK1-39 (SEQ ID NO: 236); VH1-18 (SEQ ID NO: 204)/VK3-15 (SEQ ID NO: 238); VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-46 (SEQ ID NO: 205)/VL3-21 (SEQ ID NO: 257); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-16 (SEQ ID NO: 234); VH3-07 (SEQ ID NO: 207)/VK1-27 (SEQ ID NO: 235); VH3-07 (SEQ ID NO: 207)/VK1-39 (SEQ ID NO: 236); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VK1-05 (SEQ ID NO: 230); VH3-11 (SEQ ID NO: 208)/VK1-39 (SEQ ID NO: 236); VH3-11 (SEQ ID NO: 208)/VK3-15 (SEQ ID NO: 238); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-16 (SEQ ID NO: 234); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-40 (SEQ ID NO: 250); VH3-15 (SEQ ID NO: 209)/VL1-47 (SEQ ID NO: 251); VH3-15 (SEQ ID NO: 209)/VL1-51 (SEQ ID NO: 252); VH3-15 (SEQ ID NO: 209)/VL2-14 (SEQ ID NO: 254); VH3-21 (SEQ ID NO: 210)/VK1-12 (SEQ ID NO: 233); VH3-21 (SEQ ID NO: 210)/VK1-27 (SEQ ID NO: 235); VH3-21 (SEQ ID NO: 210)/VL2-11 (SEQ ID NO: 253); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-30 (SEQ ID NO: 212)/VK3-20 (SEQ ID NO: 239); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK1-27 (SEQ ID NO: 235); VH3-74 (SEQ ID NO: 214)/VK3-20 (SEQ ID NO: 239); VH3-74 (SEQ ID NO: 214)/VL1-51 (SEQ ID NO: 252); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-15 (SEQ ID NO: 238); VH6-1 (SEQ ID NO: 216)/VK3-20 (SEQ ID NO: 239) and VH6-1 (SEQ ID NO: 216)/VL1-51 (SEQ ID NO: 252).

In embodiments comprising the 54 pairs or a subset thereof, additional pairs may be selected to be added to the collection, wherein each germline protein pair added comprises the following properties:
i) an expression yield in Fab format of at least 2.5 mg/l as determined by UV-spectrophotometry using an extinction coefficient of 1.538 mL/mg and measuring absorbance at 280 nm,
ii) thermal stability at 70° C. or above in Fab format as determined by differential scanning fluorometry using PBS buffer,
iii) monomeric content (% monomer) in Fab format of at least 98% as determined by size exclusion chromatography using a Superdex75 HR10/30 column and Gibco D-PBS buffer at pH 7.4,
iv) an expression yield in IgG1 format of at least 30 mg/l as determined by UV-spectrophotometry using an extinction coefficient of 1.369 mL/mg and measuring absorbance at 280 nm,
v) thermal stability at 73° C. or above in IgG1 format as determined by differential scanning fluorometry using PBS buffer, and
vi) the monomeric content (% monomer) in IgG1 format of at least 99% as determined by size exclusion chromatography using a Tosoh TSK-Gel G3000SWxl column and Gibco D-PBS buffer at pH 7.4.

UV-spectrophotometry may be performed using the Nanadrop system (peqlab, Erlangen, Germany). Differential scanning fluorometry may be performed using the iCycler iQ5 Thermal Cycler (Biorad). Differential scanning fluorometry may be performed using Gibco D-PBS, pH 7.4 (Invitrogen, Paisley, USA). Size exclusion chromatography may be performed using the ÄKTA Purifier System (GE Healthcare).

Embodiments of the present disclosure comprise subsets of the germline protein pairs (54) above having superior functional activity related to developability. In an embodiment, a subset of germline protein pairs (36 out of 54) were selected based upon a comparison of the stress testing data identified using the methods described in Examples 9.2.5 (a-d), data shown in FIGS. 19-24, Example 9.2.6 (a-d), data shown in FIGS. 49-54 and Example 9.2.7, scoring shown in FIGS. 55-60. The stress testing methods evaluated the 95 germline protein pairs in IgG1 format in order to determine their ability to withstand exposure to acid and agitation with glass beads. The 36 germline protein pairs, of an embodiment, were selected as they have additional superior functional properties relevant to developability as they showed strong resistance to acid and agitation stress. The 36 germline protein pairs selected in an embodiment, fulfilled all of the threshold functional activities of the 54, and, in addition, scored at or above 1225 in the stress testing cumulative score (as described in Example 9.2.7), which rated the germline protein pairs according to the following characteristics: absorption at 320 nm before and after acid exposure, radius and % polydispersity before and after acid exposure, particle staining before and after acid exposure, absorption at 320 nm before and after agitation with glass beads, radius and % polydispersity after agitation with glass beads, and particle staining after agitation with glass beads. The 36 germline protein pairs selected in this embodiment, had values at or above the following thresholds for each criteria: a) purified Fab expression yield (as described in Example 9.1.1) of at least 2.5 mg/L; b) purified IgG1 expression yield (as described in Example 9.2.1) of at least 30.0 mg/L; c) thermal stability of purified Fab (as described in Example 9.1.2) of at least 70° C.; d) thermal stability of purified IgG1 (as described in Example 9.2.2) of at least 73° C.; e) monomeric content of purified Fab (as described in Example 9.1.3) of at least 98%; f) monomeric content of purified IgG1 (as described in Example 9.2.3) of at least 99% and g) stress testing cumulative score (as described in Example 9.2.7) of at least 1225.

Therefore, in an embodiment, a collection comprises synthetic antibodies or functional fragments thereof or synthetic nucleic acids encoding such antibodies or functional fragments, wherein the antibodies or functional fragments comprise variable heavy chain and variable light chain pairs, wherein the framework regions of the variable heavy chain and variable light chain pairs comprise germline protein sequences of the variable heavy chain and variable light chain pairs VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In embodiments comprising the 36 pairs or a subset thereof, additional pairs may be selected to be added to the collection, wherein each germline protein pair added comprises the following properties:
i) an expression yield in Fab format of at least 2.5 mg/l as determined by UV-spectrophotometry using an extinction coefficient of 1.538 mL/mg and measuring absorbance at 280 nm,
ii) thermal stability at 70° C. or above in Fab format as determined by differential scanning fluorometry using PBS buffer,
iii) monomeric content (% monomer) in Fab format of at least 98% as determined by size exclusion chromatography using a Superdex75 HR10/30 column and Gibco D-PBS buffer at pH 7.4, iv) an expression yield in IgG1 format of at least 30 mg/l as determined by UV-spectrophotometry using an extinction coefficient of 1.369 mL/mg and measuring absorbance at 280 nm,
v) thermal stability at 73° C. or above in IgG1 format as determined by differential scanning fluorometry using PBS buffer, and
vi) the monomeric content (% monomer) in IgG1 format of at least 99% as determined by size exclusion chromatography using a Tosoh TSK-Gel G3000SWxl column and Gibco D-PBS buffer at pH 7.4.

UV-spectrophotometry may be performed using the Nanadrop system (peqlab, Erlangen, Germany). Differential scanning fluorometry may be performed using the iCycler iQ5 Thermal Cycler (Biorad). Differential scanning fluorometry may be performed using Gibco D-PBS, pH 7.4 (Invitrogen, Paisley, USA). Size exclusion chromatography may be performed using the ÄKTA Purifier System (GE Healthcare).

In embodiments, a collection of synthetic antibodies or functional fragments thereof or synthetic nucleic acids encoding such antibodies or functional fragments, wherein substantially all, or at least 50%, or at least 60%, or at least 70%, or at least 80%, or at least 90% or at least 95% or each of the antibodies or functional fragments comprise variable heavy chain and variable light chain pairs, wherein the framework regions of the variable heavy chain and variable light chain pairs comprise germline protein sequences selected from the variable heavy chain and variable light chain pairs VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In other embodiments, a collection comprises synthetic antibodies or functional fragments thereof or synthetic nucleic acids encoding such antibodies or functional fragments, wherein the antibodies or functional fragments comprise variable heavy chain and variable light chain pairs, wherein the framework regions of the variable heavy chain and variable light chain pairs comprise germline protein sequences selected from two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more, thirty four or more, thirty five or more, or thirty six of the following variable heavy chain and variable light chain pairs VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In an embodiment, a collection comprises synthetic antibodies or functional fragments thereof or synthetic nucleic acids encoding such antibodies or functional fragments, wherein the antibodies or functional fragments comprise variable heavy chain and variable light chain pairs, wherein the framework regions of the variable heavy chain and variable light chain pairs comprise germline protein sequences of, consisting of or consisting essentially of the following variable heavy chain and variable light chain pairs VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233);

VH3-07 (SEQ ID NO: 207)/VK1-27 (SEQ ID NO: 235);
VH3-07 (SEQ ID NO: 207)/VK3-15 (SEQ ID NO: 238);
VH3-07 (SEQ ID NO: 207)/VL1-47 (SEQ ID NO: 251);
VH3-07 (SEQ ID NO: 207)/VL1-51 (SEQ ID NO: 252);
VH3-11 (SEQ ID NO: 208)/VL1-40 (SEQ ID NO: 250);
VH3-11 (SEQ ID NO: 208)/VL1-47 (SEQ ID NO: 251);
VH3-11 (SEQ ID NO: 208)/VL1-51 (SEQ ID NO: 252);
VH3-11 (SEQ ID NO: 208)/VL2-23 (SEQ ID NO: 255);
VH3-15 (SEQ ID NO: 209)/VK1-05 (SEQ ID NO: 230);
VH3-15 (SEQ ID NO: 209)/VK1-06 (SEQ ID NO: 231);
VH3-15 (SEQ ID NO: 209)/VK1-12 (SEQ ID NO: 233);
VH3-15 (SEQ ID NO: 209)/VK1-27 (SEQ ID NO: 235);
VH3-15 (SEQ ID NO: 209)/VK3-11 (SEQ ID NO: 237);
VH3-15 (SEQ ID NO: 209)/VL1-51 (SEQ ID NO: 252);
VH3-21 (SEQ ID NO: 210)/VK1-12 (SEQ ID NO: 233);
VH3-23 (SEQ ID NO: 211)/VK1-39 (SEQ ID NO: 236);
VH3-23 (SEQ ID NO: 211)/VK3-15 (SEQ ID NO: 238);
VH3-23 (SEQ ID NO: 211)/VL2-23 (SEQ ID NO: 255);
VH3-23 (SEQ ID NO: 211)/VL3-1 (SEQ ID NO: 256);
VH3-53 (SEQ ID NO: 213)/VK3-15 (SEQ ID NO: 238);
VH3-53 (SEQ ID NO: 213)/VL2-11 (SEQ ID NO: 253);
VH3-74 (SEQ ID NO: 214)/VK1-05 (SEQ ID NO: 230);
VH3-74 (SEQ ID NO: 214)/VK1-06 (SEQ ID NO: 231);
VH3-74 (SEQ ID NO: 214)/VK1-12 (SEQ ID NO: 233);
VH3-74 (SEQ ID NO: 214)/VK3-20 (SEQ ID NO: 239);
VH5-51 (SEQ ID NO: 215)/VK1-39 (SEQ ID NO: 236);
VH5-51 (SEQ ID NO: 215)/VL1-40 (SEQ ID NO: 250);
VH5-51 (SEQ ID NO: 215)/VL1-51 (SEQ ID NO: 252);
VH6-1 (SEQ ID NO: 216)/VK1-09 (SEQ ID NO: 232);
VH6-1 (SEQ ID NO: 216)/VK3-20 (SEQ ID NO: 239) and
VH6-1 (SEQ ID NO: 216)/VL1-51 (SEQ ID NO: 252).

In another embodiment, the thresholds for each criterion were selected as follows: a) purified Fab expression yield (as described in Example 9.1.1) of at least 2.5 mg/L; b) purified IgG1 expression yield (as described in Example 9.2.1) of at least 30.0 mg/L; c) thermal stability of purified Fab (as described in Example 9.1.2) of at least 70° C.; d) thermal stability of purified IgG1 (as described in Example 9.2.2) of at least 73° C.; e) monomeric content of purified Fab (as described in Example 9.1.3) of at least 99%; f) monomeric content of purified IgG1 (as described in Example 9.2.3) of at least 99%; g) isoelectric point of purified IgG1 (as described in Example 9.2.4) of at least 8.3; and h) stress testing cumulative score (as described in Example 9.2.7) of at least 1225.

Therefore, in an embodiment, a collection comprises synthetic antibodies or functional fragments thereof or synthetic nucleic acids encoding such antibodies or functional fragments, wherein the antibodies or functional fragments comprise variable heavy chain and variable light chain framework regions comprising germline protein sequences of a germline protein pair, wherein said germline protein pairs comprise the following properties:
 i) an expression yield in Fab format of at least 2.5 mg/L;
 ii) thermal stability at 70° C. or above in Fab format;
 iii) monomeric content (% monomer) in Fab format of at least 99% as determined by SEC;
 iv) an expression yield in IgG1 format of at least 30 mg/L;
 v) thermal stability at 73° C. or above in IgG1 format;
 vi) monomeric content (% monomer) in IgG1 format of at least 99% as determined by SEC, and
 vii) an isoelectric point in IgG1 format of at least 8.3.

In certain embodiments,
 i) the expression yield in Fab format was determined by UV-spectrophotometry using an extinction coefficient of 1.538 mL/mg and measuring absorbance at 280 nm.

In certain embodiments,
 ii) the thermal stability in Fab format was determined by differential scanning fluorometry using PBS buffer.

In certain embodiments,
 iii) the monomeric content (% monomer) in Fab format was determined by size exclusion chromatography using a Superdex75 HR10/30 column and Gibco D-PBS buffer at pH 7.4.

In certain embodiments,
 iv) the expression yield in IgG1 format was determined by UV-spectrophotometry using an extinction coefficient of 1.369 mL/mg and measuring absorbance at 280 nm.

In certain embodiments,
 v) the thermal stability in IgG1 format was determined by differential scanning fluorometry using PBS buffer.

In certain embodiments,
 vi) the monomeric content (% monomer) in IgG1 format was determined by size exclusion chromatography using a Tosoh TSK-Gel G3000SWxl column and Gibco D-PBS buffer at pH 7.4.

UV-spectrophotometry may be performed using the Nanadrop system (peqlab, Erlangen, Germany). Differential scanning fluorometry may be performed using the iCycler iQ5 Thermal Cycler (Biorad). Differential scanning fluorometry may be performed using Gibco D-PBS, pH 7.4 (Invitrogen, Paisley, USA). Size exclusion chromatography may be performed using the ÄKTA Purifier System (GE Healthcare).

In additional embodiments, a collection comprises synthetic antibodies or functional fragments thereof or synthetic nucleic acids encoding such antibodies or functional fragments, wherein substantially all, or at least 50%, or at least 60%, or at least 70%, or at least 80%, or at least 90%, or at least 95% or each of the antibodies or functional fragments comprise variable heavy chain and variable light chain framework regions comprising germline protein sequences of a germline protein pair, wherein said germline protein pairs comprise the following properties:
 i) an expression yield in Fab format of at least 2.5 mg/L;
 ii) thermal stability at 70° C. or above in Fab format;
 iii) monomeric content (% monomer) in Fab format of at least 99% as determined by SEC;
 iv) an expression yield in IgG1 format of at least 30 mg/L;
 v) thermal stability at 73° C. or above in IgG1 format;
 vi) monomeric content (% monomer) in IgG1 format of at least 99% as determined by SEC, and
 vii) an isoelectric point in IgG1 format of at least 8.3.

In additional embodiments, a collection comprises synthetic antibodies or functional fragments thereof or synthetic nucleic acids encoding such antibodies or functional fragments, wherein the antibodies or functional fragments consists of or consists essentially of variable heavy chain and variable light chain framework regions comprising germline protein sequences of a germline protein pair, wherein said germline protein pairs comprise the following properties:
 i) an expression yield in Fab format of at least 2.5 mg/L;
 ii) thermal stability at 70° C. or above in Fab format;
 iii) monomeric content (% monomer) in Fab format of at least 99% as determined by SEC;
 iv) an expression yield in IgG1 format of at least 30 mg/L;
 v) thermal stability at 73° C. or above in IgG1 format;
 vi) monomeric content (% monomer) in IgG1 format of at least 99% as determined by SEC, and
 vii) an isoelectric point in IgG1 format of at least 8.3.

The following germline protein pairs (33) were at or above the following thresholds: a) purified Fab expression yield (as described in Example 9.1.1) of at least 2.5 mg/L;

b) purified IgG1 expression yield (as described in Example 9.2.1) of at least 30.0 mg/L; c) thermal stability of purified Fab (as described in Example 9.1.2) of at least 70° C.; d) thermal stability of purified IgG1 (as described in Example 9.2.2) of at least 73° C.; e) monomeric content of purified Fab (as described in Example 9.1.3) of at least 99%; f) monomeric content of purified IgG1 (as described in Example 9.2.3) of at least 99%; g) isoelectric point of purified IgG1 (as described in Example 9.2.4) of at least 8.3; and h) stress testing cumulative score (as described in Example 9.2.7) of at least 1225, therefore, have superior functional activity related to developability: VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK3-15 (SEQ ID NO: 238); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

Therefore, in an embodiment, a collection comprises synthetic antibodies or functional fragments thereof or synthetic nucleic acids encoding such antibodies or functional fragments, wherein the antibodies or functional fragments comprise variable heavy chain and variable light chain pairs, wherein the framework regions of the variable heavy chain and variable light chain pairs comprise germline protein sequences of the variable heavy chain and variable light chain pairs VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK3-15 (SEQ ID NO: 238); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In embodiments comprising the 33 pairs or a subset thereof, additional pairs may be selected to be added to the collection, wherein each germline protein pair added comprises the following properties:
  i) an expression yield in Fab format of at least 2.5 mg/l as determined by UV-spectrophotometry using an extinction coefficient of 1.538 mL/mg and measuring absorbance at 280 nm,
  ii) thermal stability at 70° C. or above in Fab format as determined by differential scanning fluorometry using PBS buffer,
  iii) monomeric content (% monomer) in Fab format of at least 99% as determined by size exclusion chromatography using a Superdex75 HR10/30 column and Gibco D-PBS buffer at pH 7.4,
  iv) an expression yield in IgG1 format of at least 30 mg/l as determined by UV-spectrophotometry using an extinction coefficient of 1.369 mL/mg and measuring absorbance at 280 nm,
  v) thermal stability at 73° C. or above in IgG1 format as determined by differential scanning fluorometry using PBS buffer, and
  vi) the monomeric content (% monomer) in IgG1 format of at least 99% as determined by size exclusion chromatography using a Tosoh TSK-Gel G3000SWxl column and Gibco D-PBS buffer at pH 7.4.

UV-spectrophotometry may be performed using the Nanadrop system (peqlab, Erlangen, Germany). Differential scanning fluorometry may be performed using the iCycler iQ5 Thermal Cycler (Biorad). Differential scanning fluorometry may be performed using Gibco D-PBS, pH 7.4 (Invitrogen, Paisley, USA). Size exclusion chromatography may be performed using the ÄKTA Purifier System (GE Healthcare).

In embodiments comprising the 33 pairs or a subset thereof, additional pairs may be selected to be added to the collection, wherein each germline protein pair added further comprises the following property:
  vii) an isoelectric point in IgG1 format of at least 8.3.

In a further embodiment, pairs are added to a collection even though the pairs themselves did not meet all of the thresholds within each criteria, but were added to the collections in order to enhance diversity. In an embodiment the collection of 33 germline protein pairs further comprises: VH3-23 (SEQ ID NO: 211)/VK1-39 (SEQ ID NO: 236); VH3-23 (SEQ ID NO: 211)/VL2-23 (SEQ ID NO: 255); and VH3-23 (SEQ ID NO: 211)/VL3-1 (SEQ ID NO: 256). In this embodiment, the collection comprises (36 pairs): VH1-

18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In embodiments, collections comprising any number of these germline protein pairs or synthetic nucleic acids encoding such antibodies or functional fragments could be used to identify developable antibodies or fragments thereof against any antigen.

In some embodiments, a collection comprises synthetic antibodies or functional fragments thereof or synthetic nucleic acids encoding such antibodies or functional fragments, wherein the antibodies or functional fragments comprise variable heavy chain and variable light chain pairs, wherein the framework regions of the variable heavy chain and variable light chain pairs comprise germline protein sequences selected from two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more variable heavy chain and variable light chain pairs selected from the group consisting of VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK3-15 (SEQ ID NO: 238); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09

In an embodiment, a collection comprises synthetic antibodies or functional fragments thereof or synthetic nucleic acids encoding such antibodies or functional fragments, wherein substantially all, or at least 50%, or at least 60%, or at least 70%, or at least 80%, or at least 90% or at least 95% or each of the antibodies or functional fragments comprise variable heavy chain and variable light chain pairs, wherein the framework regions of the variable heavy chain and variable light chain pairs comprise germline protein sequences selected from the variable heavy chain and variable light chain pairs VH1-18 (SEQ ID NO: 204)/VK3-20

(SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

An embodiment comprises a collection of synthetic antibodies or functional fragments thereof or synthetic nucleic acids encoding such antibodies or functional fragments, wherein the antibodies or functional fragments comprise variable heavy chain and variable light chain pairs, wherein the framework regions of the variable heavy chain and variable light chain pairs comprise germline protein sequences of, consisting of or consisting essentially of the variable heavy chain and variable light chain pairs VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK3-15 (SEQ ID NO: 238); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

An additional aspect to the present invention is the ability of the collections to be useful in identifying antibodies or functional fragments thereof against any immunogen. Therefore, in some embodiments, the collections comprise variable heavy chain framework regions and variable light chain framework regions comprising germline protein sequences of at least two different germline protein pairs; at least three different germline protein pairs; at least four different germline protein pairs; at least five different germline protein pairs; at least six different germline protein pairs; at least seven different germline protein pairs; at least eight different germline protein pairs; at least nine different germline protein pairs; at least ten different germline protein pairs; at least eleven different germline protein pairs; at least twelve different germline protein pairs; at least thirteen different germline protein pairs; at least fourteen different germline protein pairs; at least fifteen different germline protein pairs; at least sixteen different germline protein pairs; at least seventeen different germline protein pairs; at least eighteen different germline protein pairs; at least nineteen different germline protein pairs; at least twenty different germline protein pairs; at least 21 different germline protein pairs; at least 22 different germline protein pairs; at least 23 different germline protein pairs; at least 24 different germline protein pairs; at least 25 different germline protein pairs; at least 26 different germline protein pairs; at least 27 different germline protein pairs; at least 28 different variable heavy chain germline protein; at least 29 different germline protein pairs sequences; at least 30 different germline protein pairs; at least 31 different germline protein pairs; at least 32 different germline protein pairs; at least 33 different germline protein pairs; at least 34 different germline protein pairs; at least 35 different germline protein pairs; at least 36 different germline protein pairs; at least 37 different germline protein pairs; at least 38 different germline protein pairs; at least 39 different germline protein pairs; at least 40 different germline protein pairs; at least 41 different germline protein pairs; at least 42 different germline protein pairs; at least 43 different germline protein pairs; at least 44 different germline protein pairs; at least 45 different germline protein pairs; at least 46 different germline protein pairs; at least 47 different germline protein pairs; at least 48 different germline protein pairs; at least 49 different germline protein pairs; at least 50 different germline protein pairs; at least 51 different germline protein pairs; at least 52 different germline protein pairs; at least 53 different germline protein pairs; at least 54 different germline protein pairs.

As a low potential for immunogenicity in humans is a goal for therapeutic antibodies, in an aspect, the collections comprise framework regions comprising germline protein sequences or nucleic acids encoding them. In addition, in order to maintain a low risk of immunogenicity, complementarity determining regions may be used comprising germline protein sequences. In an embodiment, the collections comprise synthetic antibodies or functional fragments thereof or synthetic nucleic acids encoding such antibodies or functional fragments comprising one or more complementarity determining regions comprising germline protein sequences from the respective variable heavy chain and variable light chain pairs, wherein the amino acid and nucleic acid sequences of the complementarity determining regions of the variable heavy chains and variable light chains are depicted in FIGS. 25-33. More specifically, in an embodiment, a collection comprises antibodies or functional fragments thereof or synthetic nucleic acids encoding such antibodies or functional fragments comprising CDR1 regions comprising germline protein sequences from the respective variable heavy chain and/or variable light chain pairs, wherein the amino acid and nucleic acid sequences of the CDR1 region of the variable heavy chains and variable light chains are depicted in FIGS. 25, 28, and 31, and the corresponding SEQ ID NOs: 204-265. In an embodiment, a collection comprises antibodies or functional fragments thereof or synthetic nucleic acids encoding such antibodies or functional fragments comprising HCDR1 regions comprising germline protein sequences from the respective variable heavy chain and variable light chain pairs, wherein the amino acid and nucleic acid sequences of the HCDR1 region of the variable heavy chains and variable light chains are depicted in FIG. 25 and the corresponding SEQ ID NOs: 204-229. In an embodiment, a collection comprises antibodies or functional fragments thereof or synthetic nucleic acids encoding such antibodies or functional fragments comprising LCDR1 regions comprising germline protein sequences from the respective variable heavy chain and variable light chain pairs, wherein the amino acid and nucleic acid sequences of the LCDR1 region of the variable heavy chains and variable light chains are depicted in FIGS. 28 and 31 and the corresponding SEQ ID NOs: 230-265. In an additional embodiment, a collection comprises antibodies or functional fragments thereof or synthetic nucleic acids encoding such antibodies or functional fragments comprising CDR2 regions comprising germline protein sequences from the respective variable heavy chain and variable light chain pairs, wherein the amino acid and nucleic acid sequences of the CDR2 region of the variable heavy chains and variable light chains are depicted in FIGS. 26, 29, and 32, and the corresponding SEQ ID NOs: 204-265. In an additional embodiment, a collection comprises antibodies or functional fragments thereof or synthetic nucleic acids encoding such antibodies or functional fragments comprising HCDR2 regions comprising germline protein sequences from the respective variable heavy chain and variable light chain pairs, wherein the amino acid and nucleic acid sequences of the HCDR2 region of the variable heavy chains and variable light chains are depicted in FIG. 26 and the corresponding SEQ ID NOs: 204-229. In an additional embodiment, a collection comprises antibodies or functional fragments thereof or synthetic nucleic acids encoding such antibodies or functional fragments comprising LCDR2 regions comprising germline protein sequences from the respective variable heavy chain and variable light chain pairs, wherein the amino and nucleic acid sequences of the LCDR2 region of the variable heavy chains and variable light chains are depicted in FIGS. 29 and 32 and the corresponding SEQ ID NOs: 230-265.

An aspect of the disclosure includes modifying germline complementarity determining regions to remove potential post translational modification sites (PTMs). Examples of variable heavy chain complementarity determining regions modified to remove PTMs are shown in FIGS. 34-36. In an aspect, a collection comprises antibodies or functional fragments thereof or synthetic nucleic acids encoding such antibodies or functional fragments comprising one or more complementarity determining regions comprising amino acid modifications that remove potential post translational modification sites. In an embodiment, a collection comprises antibodies or functional fragments thereof or synthetic nucleic acids encoding such antibodies or functional fragments comprising one or more complementarity determining regions comprising the complementarity determining region sequences or nucleic acid sequences encoding the same depicted in FIGS. 34-36 from the respective variable heavy chain. In a further embodiment, a collection comprises antibodies or functional fragments thereof or synthetic nucleic acids encoding such antibodies or functional fragments comprising HCDR1 regions comprising the HCDR1 or nucleic acids encoding the same depicted in FIGS. 34-36 from the respective variable heavy chain. The amino acid sequences of the low PTM HCDR1s are depicted in SEQ ID NOs: 266-278. The nucleic acid sequences of the low PTM HCDR1s are depicted in SEQ ID NOs: 279-291. In a further embodiment, a collection comprises antibodies or functional fragments thereof or synthetic nucleic acids encoding such antibodies or functional fragments comprising HCDR2 regions comprising the HCDR2 regions or nucleic acids encoding the same depicted in FIGS. 34-36 from the respective variable heavy chain. The amino acid sequences of the low PTM HCDR2s are depicted in SEQ ID NOs: 266-278. The nucleic acid sequences of the low PTM HCDR2s are depicted in SEQ ID NOs: 279-291.

An aspect of the disclosure includes utilizing germline FR4 sequences in the collections. In an embodiment, a collection comprises antibodies or functional fragments thereof or synthetic nucleic acids encoding such antibodies or functional fragments comprising a FR4 region selected from the group consisting of: JH4 (SEQ ID NO:293), Jκ1 (SEQ ID NO:297), and Jλ2/3 (SEQ ID NO:301). In an embodiment, a collection comprises antibodies or functional fragments thereof or synthetic nucleic acids encoding such antibodies or functional fragments comprising a germline JH4 FR4 region, whose amino acid or nucleic acid sequence is depicted in FIG. 40. The JH4 FR4 amino acid sequence is depicted in (SEQ ID NO:293) and (SEQ ID NO:295). The JH4 FR4 nucleic acid sequence is depicted in (SEQ ID NO:292) and (SEQ ID NO:294). In an embodiment, a collection comprises antibodies or functional fragments thereof or synthetic nucleic acids encoding such antibodies or functional fragments comprising a germline Jκ1 FR4 region, whose amino acid or nucleic acid sequence is depicted in FIG. 40. The Jκ1 FR4 amino acid sequence is depicted in (SEQ ID NO:297). The Jκ1 FR4 nucleic acid sequence is depicted in (SEQ ID NO:296), (SEQ ID NO:298) and (SEQ ID NO:299). In an embodiment, a collection comprises antibodies or functional fragments thereof or synthetic nucleic acids encoding such antibodies or functional fragments comprising a germline Jλ2/3 FR4 region, whose amino acid or nucleic acid sequence is depicted in FIG. 40. The Jλ2/3 FR4 amino acid sequence is depicted in (SEQ ID NO:301). The Jλ2/3 FR4 nucleic acid sequence is depicted in (SEQ ID NO:300), (SEQ ID NO:302) and (SEQ ID NO:303).

In an aspect, in order to enhance the ability of identifying antibodies or fragment thereof against any antigen, collections comprise a diversified CDR3 region. In an embodiment, a collection comprises antibodies or functional fragments thereof or synthetic nucleic acids encoding such antibodies or functional fragments comprising a diversified HCDR3 region. In an embodiment, a collection comprises antibodies or functional fragments thereof or synthetic nucleic acids encoding such antibodies or functional fragments comprising a diversified LCDR3 region.

In another aspect, in order to enhance the ability of identifying antibodies or fragments thereof against any antigen, collections comprise at least $1 \times 10^4$ antibodies or functional fragments thereof or synthetic nucleic acids encoding such antibodies or functional fragments, at least $1 \times 10^5$ antibodies or functional fragments thereof or synthetic nucleic acids encoding such antibodies or functional fragments, at least $1 \times 10^6$ antibodies or functional fragments thereof or synthetic nucleic acids encoding such antibodies or functional fragments, at least $1 \times 10^7$ antibodies or functional fragments thereof or synthetic nucleic acids encoding such antibodies or functional fragments, at least $1 \times 10^8$ antibodies or functional fragments thereof or synthetic nucleic acids encoding such antibodies or functional fragments, at least $1 \times 10^9$ antibodies or functional fragments thereof or synthetic nucleic acids encoding such antibodies or functional fragments, at least $1 \times 10^{10}$ antibodies or functional fragments thereof or synthetic nucleic acids encoding such antibodies or functional fragments, or at least $1 \times 10^{11}$ antibodies or functional fragments thereof or synthetic nucleic acids encoding such antibodies or functional fragments.

In an embodiment the collections comprise antibodies or synthetic nucleic acids encoding such antibodies selected from the group consisting of human IgG1, IgG2, IgG3, IgG4, IgA, IgE, IgM and IgD. In an embodiment the collections comprise antibody fragments or synthetic nucleic acids encoding such fragments selected from the group consisting of Fab, F(ab')2, Fab', Fv, and scFv.

In embodiments, the IgG heavy chain constant domains of the antibodies of the collections comprise the amino acid sequences shown in FIGS. 41A-B (SEQ ID NO: 305). In other embodiments, the nucleic acids encoding the IgG heavy chain constant domains of the antibodies of the collection comprise the nucleic acid sequences shown in FIGS. 41A-B (SEQ ID NO: 304). In embodiments, the Fab heavy chain constant domains of the antibody fragments of the collections comprise the amino acid sequences shown in FIG. 42 (SEQ ID NO: 307). In other embodiments, the nucleic acids encoding the Fab heavy chain constant domains of the antibodies of the collection comprise the nucleic acid sequences shown in FIG. 42 (SEQ ID NO: 306). In embodiments, the IgG (SEQ ID NO: 309) and/or Fab (SEQ ID NO: 311) kappa light chain constant domains of the antibodies or antibody fragments of the collections comprise the amino acid sequences shown in FIG. 43. In other embodiments, the nucleic acids encoding the IgG (SEQ ID NO: 308) and/or Fab (SEQ ID NO: 310) kappa light chain constant domains of the antibodies or antibody fragments of the collections comprise the nucleic acid sequences shown in FIG. 43. In embodiments, the IgG (SEQ ID NO: 313) and/or Fab (SEQ ID NO: 315) lambda light chain constant domains of the antibodies or antibody fragments of the collections comprise the amino acid sequences shown in FIG. 44. In other embodiments, the nucleic acids encoding the IgG (SEQ ID NO: 312) and/or Fab (SEQ ID NO: 314) lambda light chain constant domains of the antibodies or antibody fragments of the collections comprise the nucleic acid sequences shown in FIG. 44.

An aspect comprises, a vector comprising the collections of nucleic acids described herein. In an embodiment, the vector comprises a display vector. In an embodiment, the vector comprises a phagemid vector, yeast display or mammalian display vector. An aspect is a recombinant host cell comprising the nucleic acids described herein, or a vector described herein. In an embodiment, the recombinant host is prokaryotic or eukaryotic. In embodiment, the recombinant host cell of is *E. coli*, mammalian or yeast.

Methods of Making

An aspect comprises methods of producing the collections described herein.

An aspect comprises, a method of producing a collection of synthetic antibodies or functional fragments thereof or synthetic nucleic acids encoding such antibodies or functional fragments, comprising a) identifying the variable heavy chain and variable light chain germline gene pairs present in the human immune repertoire;

b) testing the variable heavy chain and variable light chain germline protein pairs identified in step a) for the following properties:
  i) an expression yield in Fab format of at least 2.5 mg/L;
  ii) thermal stability at 70° C. or above in Fab format;
  iii) monomeric content (% monomer) in Fab format of at least 98% as determined by SEC;
  iv) an expression yield in IgG1 format of at least 30 mg/L;
  v) thermal stability at 73° C. or above in IgG1 format; and
  vii) monomeric content (% monomer) in IgG1 format of at least 99% as determined by SEC; and c) generating a collection, wherein substantially all, or at least 50%, or at least 60%, or at least 70%, or at least 80%, or at least 90% or at least 95% of each of the, or the antibodies or functional fragments thereof comprise variable heavy chain and variable light chain pairs, wherein the framework regions of the variable heavy chain and variable light chain pairs comprise germline protein sequences of the germline protein pairs fulfilling the properties of step b).

In certain embodiments of the method,
  i) the expression yield in Fab format was determined by UV-spectrophotometry using an extinction coefficient of 1.538 mL/mg and measuring absorbance at 280 nm.
In certain embodiments,
  ii) the thermal stability in Fab format was determined by differential scanning fluorometry using PBS buffer.
In certain embodiments,
  iii) the monomeric content (% monomer) in Fab format was determined by size exclusion chromatography using a Superdex75 HR10/30 column and Gibco D-PBS buffer at pH 7.4.
In certain embodiments,
  iv) the expression yield in IgG1 format was determined by UV-spectrophotometry using an extinction coefficient of 1.369 mL/mg and measuring absorbance at 280 nm.
In certain embodiments,
  v) the thermal stability in IgG1 format was determined by differential scanning fluorometry using PBS buffer.
In certain embodiments,
  vi) the monomeric content (% monomer) in IgG1 format was determined by size exclusion chromatography using a Tosoh TSK-Gel G3000SWxl column and Gibco D-PBS buffer at pH 7.4.

UV-spectrophotometry may be performed using the Nanadrop system (peqlab, Erlangen, Germany). Differential scanning fluorometry may be performed using the iCycler iQ5 Thermal Cycler (Biorad). Differential scanning fluorometry may be performed using Gibco D-PBS, pH 7.4 (Invitrogen, Paisley, USA). Size exclusion chromatography may be performed using the ÄKTA Purifier System (GE Healthcare).

In an embodiment, step a) further comprises the steps
  aa) isolating human B cells from a sample;
  ab) generating cDNAs from the B cells;
  ac) PCR amplifying the cDNAs from the B cells;
  ad) sequencing the PCR products;
  ae) identifying the germline genes of each PCR product.

The DNA encoding antibodies and fragments thereof from each B cell are isolated, and amplified e.g., the heavy and light chain are physically isolated in a PCR reaction. The DNA is preferably sequenced. The DNA sequenced may be cDNA generated from B cell mRNA. mRNA extraction from eukaryotic cells, such as B cells, is a well know technological procedure. Numerous protocols exist and commercial kits are available. Such as the PolyATtract® mRNA Isolation System (Promega, Madison, Wis., USA) or various RNeasy and Oligotex DirectmRNA kits (both from Qiagen, Hilden, Germany). Many of these techniques make use of the polyA tail of the eukaryotic mRNA, e.g. via affinity purification to oligo (dT) matrices, such as oligo (dT) cellulose.

cDNA can be selectively amplified from the isolated mRNA via reverse transcription using specific primers, followed by conventional PCR. Specific primers are used to amplify variable heavy and light chain domain nucleic acids. See Cancer Surv. 1997; 30:21-44, J. Clin. Pathol. 1994; 47:493-6, J. Clin. Pathol. 1990; 43:888-90 or Mol. Pathol. 2002 April; 55(2): 98-101. The DNA coding for both the variable and light chain domains from one B cell are maintained together so that the variable domain heavy and light chain class pairing can be identified. Techniques for the isolation of nucleic acids encoding variable domain pairings from individual B cells are well known in the art. See for example, WO01/92291; WO92/15678; WO93/03151, WO2005/042774; Mullinax R L et al., 1992 Biotechniques 12:6 864-868; Chapal, N. et al. 1997 Biotechniques 23, 518-524, Embleton M J et al., 1992 Nucleic Acids Res. 20:15, 3831-3837; Coronella, J. A. et al. 2000 Nucleic Acids Res. 28:20, E85; Thirion S et al., 1996 European Journal of Cancer Prevention 5:6 507-511; and Wang, X et al. 2000 J. Immunol. Methods 20, 217-225.

Preferably, the DNA from each of the B cells is sequenced. Various companies exist which are able to sequence entire genomes, such as Helicos BioSciences Corporation (Cambridge, Mass., USA). With its True Single Molecule Sequencing™ technology, Helicos is able to directly sequence single molecules of DNA or RNA at high speed and efficiency. Other companies able to perform similar sequence endeavors include Illumina (San Diego, Calif., USA; Solexa system) and Roche (Basel, CH; 454 system). No cloning steps are required prior to sequencing.

In another aspect, the disclosure enables methods of identifying the germline family of the heavy and light chain variable domain pairs present in the immune repertoire. All antibodies or fragments thereof can be traced back to their germline family using methods known to one of skill in the art. By analyzing the sequence of a nucleic acid encoding an antibody or fragment thereof, the germline family of both the VH and VL can be determined by methods known to one of skill in the art. For example, Wildt et. al, (1999) sampled B cells from 3 patients and identified 365 VH and VL class pairings. The RNA from each B cell was used for cDNA synthesis and the cDNA encoding the VH and VL regions was PCR amplified and sequenced. As shown in FIG. 1 of Wildt, certain VH and VLs classes paired more frequently than others, for example, VH3-8 with Vκ3-1, Vκ3-19, Vκ4-1, Vλ2-3, or Vλ1-2, and VH3-9 with Vκ3-1, Vκ3-3 or Vλ1-5.

In an embodiment, step b) further comprises the steps ba) synthesizing DNA encoding antibodies or functional fragments thereof comprising variable heavy chain and variable light chain germline protein pairs representing the pairs present in the human immune repertoire;

bb) expressing the germline protein pairs synthesized in ba); and bc) testing the germline protein pairs of bb) for each of the properties.

In an aspect of the method, the nucleic acids encoding collections of antibodies or fragments thereof of the invention are synthesized and expressed in collections that may be used for selection against an antigen. In this embodiment the method comprises step c), wherein step c) comprises the steps ca) synthesizing nucleic acids encoding the antibodies or functional fragments thereof; cb) cloning the nucleic acids into a vector; cc) expressing the antibodies or functional fragments thereof.

In another embodiment of the method, the antibodies or functional fragments comprise variable heavy chain and variable light chain pairs, wherein the framework regions of the variable heavy chain and variable light chain pairs comprise the germline protein sequences from the variable heavy chain and variable light chain pairs of VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In another embodiment of the method, the antibodies or functional fragments comprise variable heavy chain and variable light chain pairs, wherein the framework regions of the variable heavy chain and variable light chain pairs comprise germline protein sequences comprising two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more, thirty four or more, thirty five or more, or thirty six or more, thirty seven or more, thirty eight or more, thirty nine or more, forty or more, forty one or more, or forty two or more, or forty three or more, or forty four or more, or forty five or more, or forty six or more, or forty seven or more, or forty eight or more, or forty nine or more, or fifty or more, or fifty one or more, or fifty two or more, or fifty three or more, or fifty four variable heavy chain and variable light chain pairs selected from the group consisting of VH1-18 (SEQ ID NO: 204)/VK1-39 (SEQ ID NO: 236); VH1-18 (SEQ ID NO: 204)/VK3-15 (SEQ ID NO: 238); VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-46 (SEQ ID NO: 205)/VL3-21 (SEQ ID NO: 257); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-16 (SEQ ID NO: 234); VH3-07 (SEQ ID NO: 207)/VK1-27 (SEQ ID NO: 235); VH3-07 (SEQ ID NO: 207)/VK1-39 (SEQ ID NO: 236); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VK1-05 (SEQ ID NO: 230); VH3-11 (SEQ ID NO: 208)/VK1-39 (SEQ ID NO: 236); VH3-11 (SEQ ID NO: 208)/VK3-15 (SEQ ID NO: 238); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-16 (SEQ ID NO: 234); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-40 (SEQ ID NO: 250); VH3-15 (SEQ ID NO: 209)/VL1-47 (SEQ ID NO: 251); VH3-15 (SEQ ID NO: 209)/VL1-51 (SEQ ID NO: 252); VH3-15 (SEQ ID NO: 209)/VL2-14 (SEQ ID NO: 254); VH3-21 (SEQ ID NO: 210)/VK1-12 (SEQ ID NO: 233); VH3-21 (SEQ ID NO: 210)/VK1-27 (SEQ ID NO: 235); VH3-21 (SEQ ID NO: 210)/VL2-11 (SEQ ID NO: 253); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-30 (SEQ ID NO: 212)/VK3-20 (SEQ ID NO: 239); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK1-27 (SEQ ID NO: 235); VH3-74 (SEQ ID NO: 214)/VK3-20 (SEQ ID NO: 239); VH3-74 (SEQ ID NO: 214)/VL1-51 (SEQ ID NO: 252); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-15 (SEQ ID NO: 238); VH6-1 (SEQ ID NO: 216)/VK3-20 (SEQ ID NO: 239) and VH6-1 (SEQ ID NO: 216)/VL1-51 (SEQ ID NO: 252).

In further embodiments of the method, substantially all, or at least 50%, or at least 60%, or at least 70%, or at least 80%, or at least 90% or at least 95% or each of the, or the antibodies or functional fragments comprises variable heavy chain and variable light chain framework regions comprising germline protein sequences of a germline protein pair, wherein said germline protein pair comprises the following properties:
  i) an expression yield in Fab format of at least 2.5 mg/L;
  ii) thermal stability at 70° C. or above in Fab format;
  iii) monomeric content (% monomer) in Fab format of at least 99% as determined by SEC;
  iv) an expression yield in IgG1 format of at least 30 mg/L;
  v) thermal stability at 73° C. or above in IgG1 format; and
  vii) monomeric content (% monomer) in IgG1 format of at least 99% as determined by SEC
  viii) an isoelectric point in IgG1 format of at least 8.3.

In this embodiment of the method, the antibodies or functional fragments comprise variable heavy chain and variable light chain pairs, wherein the framework regions of the variable heavy chain and variable light chain pairs comprise the germline protein sequences from the variable heavy chain and variable light chain pairs of VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK3-15 (SEQ ID NO: 238); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In a further embodiment of the method, the antibodies or functional fragments comprise variable heavy chain and variable light chain pairs, wherein the framework regions of the variable heavy chain and variable light chain pairs further comprise the germline protein sequences from the variable heavy chain and variable light chain pairs of VH3-23 (SEQ ID NO: 211)/VK1-39 (SEQ ID NO: 236); VH3-23 (SEQ ID NO: 211)/VL2-23 (SEQ ID NO: 255); and VH3-23 (SEQ ID NO: 211)/VL3-1 (SEQ ID NO: 256). In this embodiment of the method, the collection comprises (36 pairs): VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO:

236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

Methods of Using

An aspect comprises methods of using the collections described herein to identify antibodies or fragments specific for an antigen.

An aspect of the disclosure comprises a method of identifying an antibody or antibody fragment specific for an antigen, comprising:

(a) contacting the antigen with a collection of antibodies or functional fragments thereof, wherein substantially all, or at least 50%, or at least 60%, or at least 70%, or at least 80%, or at least 90% or at least 95% or each of the, or the antibodies or functional fragments of the collection comprise variable heavy chain and variable light chain pairs, wherein the framework regions of the variable heavy chain and variable light chain pairs comprise germline protein sequences of germline protein pairs comprising the following properties:

i) an expression yield in Fab format of at least 2.5 mg/L;
ii) thermal stability at 70° C. or above in Fab format;
iii) monomeric content (% monomer) in Fab format of at least 98% as determined by SEC;
iv) an expression yield in IgG1 format of at least 30 mg/L;
v) thermal stability at 73° C. or above in IgG1 format; and
vii) monomeric content (% monomer) in IgG1 format of at least 99% as determined by SEC, and (b) selecting one or more antibodies or antibody fragments that bind to said antigen.

In certain embodiments,
i) the expression yield in Fab format was determined by UV-spectrophotometry using an extinction coefficient of 1.538 mL/mg and measuring absorbance at 280 nm.

In certain embodiments,
ii) the thermal stability in Fab format was determined by differential scanning fluorometry using PBS buffer.

In certain embodiments,
iii) the monomeric content (% monomer) in Fab format was determined by size exclusion chromatography using a Superdex75 HR10/30 column and Gibco D-PBS buffer at pH 7.4.

In certain embodiments,
iv) the expression yield in IgG1 format was determined by UV-spectrophotometry using an extinction coefficient of 1.369 mL/mg and measuring absorbance at 280 nm.

In certain embodiments,
v) the thermal stability in IgG1 format was determined by differential scanning fluorometry using PBS buffer.

In certain embodiments,
vi) the monomeric content (% monomer) in IgG1 format was determined by size exclusion chromatography using a Tosoh TSK-Gel G3000SWxl column and Gibco D-PBS buffer at pH 7.4.

UV-spectrophotometry may be performed using the Nanadrop system (peqlab, Erlangen, Germany). Differential scanning fluorometry may be performed using the iCycler iQ5 Thermal Cycler (Biorad). Differential scanning fluorometry may be performed using Gibco D-PBS, pH 7.4 (Invitrogen, Paisley, USA). Size exclusion chromatography may be performed using the ÄKTA Purifier System (GE Healthcare).

In an embodiment of the method the framework regions of the variable heavy chain and variable light chain pairs comprise germline protein sequences from VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In an embodiment of the method the antibodies or functional fragments thereof comprise two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more, thirty four or more, thirty five or more, or thirty six or more, thirty seven or more, thirty eight or more, thirty nine or more, forty or more, forty one or more, or forty two or more, or forty three or more, or forty four or more, or forty five or more, or forty six or more, or forty seven or more, or forty eight or more, or forty nine or more, or fifty or more, or fifty one or more, or fifty two or more, or fifty three or more, or fifty four variable heavy chain and variable light chain pairs selected from the group consisting of variable heavy chain and variable light chain pairs selected from VH1-18 (SEQ ID NO: 204)/VK1-39 (SEQ ID NO: 236);

VH1-18 (SEQ ID NO: 204)/VK3-15 (SEQ ID NO: 238);
VH1-18 (SEQ ID NO: 204)/VK3-20 (SEQ ID NO: 239);
VH1-46 (SEQ ID NO: 205)/VK3-15 (SEQ ID NO: 238);
VH1-46 (SEQ ID NO: 205)/VL1-51 (SEQ ID NO: 252);
VH1-46 (SEQ ID NO: 205)/VL3-21 (SEQ ID NO: 257);
VH1-69*01 (SEQ ID NO: 206)/VL1-51 (SEQ ID NO: 252);
VH3-07 (SEQ ID NO: 207)/VK1-12 (SEQ ID NO: 233);
VH3-07 (SEQ ID NO: 207)/VK1-16 (SEQ ID NO: 234);
VH3-07 (SEQ ID NO: 207)/VK1-27 (SEQ ID NO: 235);
VH3-07 (SEQ ID NO: 207)/VK1-39 (SEQ ID NO: 236);
VH3-07 (SEQ ID NO: 207)/VK3-15 (SEQ ID NO: 238);
VH3-07 (SEQ ID NO: 207)/VL1-47 (SEQ ID NO: 251);
VH3-07 (SEQ ID NO: 207)/VL1-51 (SEQ ID NO: 252);
VH3-11 (SEQ ID NO: 208)/VK1-05 (SEQ ID NO: 230);
VH3-11 (SEQ ID NO: 208)/VK1-39 (SEQ ID NO: 236);
VH3-11 (SEQ ID NO: 208)/VK3-15 (SEQ ID NO: 238);
VH3-11 (SEQ ID NO: 208)/VL1-40 (SEQ ID NO: 250);
VH3-11 (SEQ ID NO: 208)/VL1-47 (SEQ ID NO: 251);
VH3-11 (SEQ ID NO: 208)/VL1-51 (SEQ ID NO: 252);
VH3-11 (SEQ ID NO: 208)/VL2-23 (SEQ ID NO: 255);
VH3-15 (SEQ ID NO: 209)/VK1-05 (SEQ ID NO: 230);
VH3-15 (SEQ ID NO: 209)/VK1-06 (SEQ ID NO: 231);
VH3-15 (SEQ ID NO: 209)/VK1-12 (SEQ ID NO: 233);
VH3-15 (SEQ ID NO: 209)/VK1-16 (SEQ ID NO: 234);
VH3-15 (SEQ ID NO: 209)/VK1-27 (SEQ ID NO: 235);
VH3-15 (SEQ ID NO: 209)/VK3-11 (SEQ ID NO: 237);
VH3-15 (SEQ ID NO: 209)/VL1-40 (SEQ ID NO: 250);
VH3-15 (SEQ ID NO: 209)/VL1-47 (SEQ ID NO: 251);
VH3-15 (SEQ ID NO: 209)/VL1-51 (SEQ ID NO: 252);
VH3-15 (SEQ ID NO: 209)/VL2-14 (SEQ ID NO: 254);
VH3-21 (SEQ ID NO: 210)/VK1-12 (SEQ ID NO: 233);
VH3-21 (SEQ ID NO: 210)/VK1-27 (SEQ ID NO: 235);
VH3-21 (SEQ ID NO: 210)/VL2-11 (SEQ ID NO: 253);
VH3-23 (SEQ ID NO: 211)/VK1-39 (SEQ ID NO: 236);
VH3-23 (SEQ ID NO: 211)/VK3-15 (SEQ ID NO: 238);
VH3-23 (SEQ ID NO: 211)/VL2-23 (SEQ ID NO: 255);
VH3-23 (SEQ ID NO: 211)/VL3-1 (SEQ ID NO: 256);
VH3-30 (SEQ ID NO: 212)/VK3-20 (SEQ ID NO: 239);
VH3-53 (SEQ ID NO: 213)/VK3-15 (SEQ ID NO: 238);
VH3-53 (SEQ ID NO: 213)/VL2-11 (SEQ ID NO: 253);
VH3-74 (SEQ ID NO: 214)/VK1-05 (SEQ ID NO: 230);
VH3-74 (SEQ ID NO: 214)/VK1-06 (SEQ ID NO: 231);
VH3-74 (SEQ ID NO: 214)/VK1-12 (SEQ ID NO: 233);
VH3-74 (SEQ ID NO: 214)/VK1-27 (SEQ ID NO: 235);
VH3-74 (SEQ ID NO: 214)/VK3-20 (SEQ ID NO: 239);
VH3-74 (SEQ ID NO: 214)/VL1-51 (SEQ ID NO: 252);
VH5-51 (SEQ ID NO: 215)/VK1-39 (SEQ ID NO: 236);
VH5-51 (SEQ ID NO: 215)/VL1-40 (SEQ ID NO: 250);
VH5-51 (SEQ ID NO: 215)/VL1-51 (SEQ ID NO: 252);
VH6-1 (SEQ ID NO: 216)/VK1-09 (SEQ ID NO: 232);
VH6-1 (SEQ ID NO: 216)/VK3-15 (SEQ ID NO: 238);
VH6-1 (SEQ ID NO: 216)/VK3-20 (SEQ ID NO: 239) and
VH6-1 (SEQ ID NO: 216)/VL1-51 (SEQ ID NO: 252).

In embodiment of the method, substantially all, or at least 50%, or at least 60%, or at least 70%, or at least 80%, or at least 90% or at least 95% or each of the, or the antibodies or functional fragments comprises variable heavy chain and variable light chain framework regions comprising germline protein sequences of a germline protein pair, wherein said germline protein pair comprises the following properties:

i) an expression yield in Fab format of at least 2.5 mg/L;
ii) thermal stability at 70° C. or above in Fab format;
iii) monomeric content (% monomer) in Fab format of at least 99% as determined by SEC;
iv) an expression yield in IgG1 format of at least 30 mg/L;
v) thermal stability at 73° C. or above in IgG1 format;
vii) monomeric content (% monomer) in IgG1 format of at least 99% as determined by SEC; and
viii) an isoelectric point in IgG1 format of at least 8.3.

In this embodiment of the method the framework regions of the variable heavy chain and variable light chain pairs comprise germline protein sequences from VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK3-15 (SEQ ID NO: 238); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In a further embodiment of the method the framework regions of the variable heavy chain and variable light chain pairs comprise germline protein sequences further selected from the variable heavy chain and variable light chain pairs VH3-23 (SEQ ID NO: 211)/VK1-39 (SEQ ID NO: 236); VH3-23 (SEQ ID NO: 211)/VL2-23 (SEQ ID NO: 255); and VH3-23 (SEQ ID NO: 211)/VL3-1 (SEQ ID NO: 256). In this embodiment, a collection comprises (36 pairs): VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07

(SEQ ID NO: 207)/VL1-51 (SEQ ID NO: 252); VH3-11
(SEQ ID NO: 208)/VL1-40 (SEQ ID NO: 250); VH3-11
(SEQ ID NO: 208)/VL1-47 (SEQ ID NO: 251); VH3-11
(SEQ ID NO: 208)/VL1-51 (SEQ ID NO: 252); VH3-11
(SEQ ID NO: 208)/VL2-23 (SEQ ID NO: 255); VH3-15
(SEQ ID NO: 209)/VK1-05 (SEQ ID NO: 230); VH3-15
(SEQ ID NO: 209)/VK1-06 (SEQ ID NO: 231); VH3-15
(SEQ ID NO: 209)/VK1-12 (SEQ ID NO: 233); VH3-15
(SEQ ID NO: 209)/VK1-27 (SEQ ID NO: 235); VH3-15
(SEQ ID NO: 209)/VK3-11 (SEQ ID NO: 237); VH3-15
(SEQ ID NO: 209)/VL1-51 (SEQ ID NO: 252); VH3-21
(SEQ ID NO: 210)/VK1-12 (SEQ ID NO: 233); VH3-23
(SEQ ID NO: 211)/VK1-39 (SEQ ID NO: 236); VH3-23
(SEQ ID NO: 211)/VK3-15 (SEQ ID NO: 238); VH3-23
(SEQ ID NO: 211)/VL2-23 (SEQ ID NO: 255); VH3-23
(SEQ ID NO: 211)/VL3-1 (SEQ ID NO: 256); VH3-53
(SEQ ID NO: 213)/VK3-15 (SEQ ID NO: 238); VH3-53
(SEQ ID NO: 213)/VL2-11 (SEQ ID NO: 253); VH3-74
(SEQ ID NO: 214)/VK1-05 (SEQ ID NO: 230); VH3-74
(SEQ ID NO: 214)/VK1-06 (SEQ ID NO: 231); VH3-74
(SEQ ID NO: 214)/VK1-12 (SEQ ID NO: 233); VH3-74
(SEQ ID NO: 214)/VK3-20 (SEQ ID NO: 239); VH5-51
(SEQ ID NO: 215)/VK1-39 (SEQ ID NO: 236); VH5-51
(SEQ ID NO: 215)/VL1-40 (SEQ ID NO: 250); VH5-51
(SEQ ID NO: 215)/VL1-51 (SEQ ID NO: 252); VH6-1
(SEQ ID NO: 216)/VK1-09 (SEQ ID NO: 232); VH6-1
(SEQ ID NO: 216)/VK3-20 (SEQ ID NO: 239) and VH6-1
(SEQ ID NO: 216)/VL1-51 (SEQ ID NO: 252).

Aspects of the Methods

In further aspects of the methods disclosed herein, the collections comprise synthetic antibodies or functional fragments thereof or synthetic nucleic acids encoding such antibodies or functional fragments comprising one or more complementarity determining regions comprising germline protein sequences from the respective variable heavy chain and variable light chain pairs, wherein the amino acid sequences of the complementarity determining regions of the variable heavy chains and variable light chains are depicted in FIGS. 25-33. More specifically, in an embodiment of the method, a collection comprises antibodies or functional fragments thereof or synthetic nucleic acids encoding such antibodies or functional fragments comprising CDR1 regions comprising germline protein sequences from the respective variable heavy chain and/or variable light chain pairs, wherein the amino acid and nucleic acid sequences of the CDR1 region of the variable heavy chains and variable light chains are depicted in FIGS. 25, 28 and 31 and the corresponding SEQ ID NOs: 204-265. In an embodiment of the method, a collection comprises antibodies or functional fragments thereof or synthetic nucleic acids encoding such antibodies or functional fragments comprising HCDR1 regions comprising germline protein sequences from the respective variable heavy chain and variable light chain pairs, wherein the amino acid and nucleic acid sequences of the HCDR1 region of the variable heavy chains and variable light chains are depicted in FIG. 25 and the corresponding SEQ ID NOs: 204-229. In an embodiment of the method, a collection comprises antibodies or functional fragments thereof or synthetic nucleic acids encoding such antibodies or functional fragments comprising LCDR1 regions comprising germline protein sequences from the respective variable heavy chain and variable light chain pairs, wherein the amino acid and nucleic acid sequences of the LCDR1 region of the variable heavy chains and variable light chains are depicted in FIGS. 28 and 31 and the corresponding SEQ ID NOs: 230-265. In an additional embodiment of the method, a collection comprises antibodies or functional fragments thereof or synthetic nucleic acids encoding such antibodies or functional fragments comprising CDR2 regions comprising germline protein sequences from the respective variable heavy chain and variable light chain pairs, wherein the amino acid and nucleic acid sequences of the CDR2 region of the variable heavy chains and variable light chains are depicted in FIGS. 26, 29 and 32 and the corresponding SEQ ID NOs:204-265. In an additional embodiment of the method, a collection comprises antibodies or functional fragments thereof or synthetic nucleic acids encoding such antibodies or functional fragments comprising HCDR2 regions comprising germline protein sequences from the respective variable heavy chain and variable light chain pairs, wherein the amino acid and nucleic acid sequences of the HCDR2 region of the variable heavy chains and variable light chains are depicted in FIG. 26 and the corresponding SEQ ID NOs: 204-229. In an additional embodiment of the method, a collection comprises antibodies or functional fragments thereof or synthetic nucleic acids encoding such antibodies or functional fragments comprising LCDR2 regions comprising germline protein sequences from the respective variable heavy chain and variable light chain pairs, wherein the amino acid and nucleic acid sequences of the LCDR2 region of the variable heavy chains and variable light chains are depicted in FIGS. 29 and 32 and the corresponding SEQ ID NOs: 230-265.

In embodiments of the method, a collection comprises antibodies or functional fragments thereof or synthetic nucleic acids encoding such antibodies or functional fragments comprising one or more complementarity determining regions comprising amino acid modifications that remove potential post translational modification sites. In an embodiment of the method, a collection comprises antibodies or functional fragments thereof or synthetic nucleic acids encoding such antibodies or functional fragments comprising one or more complementarity determining regions comprising the complementarity determining region sequences or nucleic acid sequences encoding the same depicted in FIGS. 34-36 from the respective variable heavy chain. In a further embodiment of the method, a collection comprises antibodies or functional fragments thereof or synthetic nucleic acids encoding such antibodies or functional fragments comprising HCDR1 regions comprising the HCDR1 or nucleic acids encoding the same depicted in FIGS. 34-36 from the respective variable heavy chain. The amino acid sequences of the low PTM HCDR1s are depicted in SEQ ID NOs: 266-278. The nucleic acid sequences of the low PTM HCDR1s are depicted in SEQ ID NOs: 279-291. In a further embodiment of the method, a collection comprises antibodies or functional fragments thereof or synthetic nucleic acids encoding such antibodies or functional fragments comprising HCDR2 regions comprising the HCDR2 regions or nucleic acids encoding the same depicted in FIGS. 34-36 from the respective variable heavy chain. The amino acid sequences of the low PTM HCDR2s are depicted in SEQ ID NOs: 266-278. The nucleic acid sequences of the low PTM HCDR2s are depicted in SEQ ID NOs: 279-291.

In an embodiment of the method, a collection comprises antibodies or functional fragments thereof or synthetic nucleic acids encoding such antibodies or functional fragments comprising a FR4 region selected from the group consisting of: JH4 (SEQ ID NO:293), Jκ1 (SEQ ID NO:297), and Jλ2/3 (SEQ ID NO:301). In an embodiment of the method, a collection comprises antibodies or functional fragments thereof or synthetic nucleic acids encoding such antibodies or functional fragments comprising a germline JH4 FR4 region, whose amino acid or nucleic acid sequence is depicted in FIG. 40. The JH4 FR4 amino acid sequence is depicted in (SEQ ID NO:293) and (SEQ ID NO:295). The JH4 FR4 nucleic acid sequence is depicted in (SEQ ID NO:292) and (SEQ ID NO:294). In an embodiment of the method, a collection comprises antibodies or functional fragments thereof or synthetic nucleic acids encoding such antibodies or functional fragments comprising a germline Jk1 FR4 region, whose amino acid or nucleic acid sequence is depicted in FIG. 40. The Jk1 FR4 amino acid sequence is depicted in (SEQ ID NO:297). The Jk1 FR4 nucleic acid sequence is depicted in (SEQ ID NO:296), (SEQ ID NO:298) and (SEQ ID NO:299). In an embodiment of the method, a collection comprises antibodies or functional fragments thereof or synthetic nucleic acids encoding such antibodies or functional fragments comprising a germline Jλ2/3 FR4 region, whose amino acid or nucleic acid sequence is depicted in FIG. 40. The Jλ2/3 FR4 amino acid sequence is depicted in (SEQ ID NO:301). The Jλ2/3 FR4 nucleic acid sequence is depicted in (SEQ ID NO:300), (SEQ ID NO:302) and (SEQ ID NO:303).

In an aspect, in order to enhance the ability of identifying antibodies or fragment thereof against any antigen, collections comprise a diversified CDR3 region. In an embodiment of the method, a collection comprises antibodies or functional fragments thereof or synthetic nucleic acids encoding such antibodies or functional fragments comprising a diversified HCDR3 region. In an embodiment of the method, a collection comprises antibodies or functional fragments thereof or synthetic nucleic acids encoding such antibodies or functional fragments comprising a diversified LCDR3 region.

In another aspect, in order to enhance the ability of identifying antibodies or fragments thereof against any antigen, collections of the method comprise at least $1 \times 10^4$ antibodies or functional fragments thereof or synthetic nucleic acids encoding such antibodies or functional fragments, at least $1 \times 10^5$ antibodies or functional fragments thereof or synthetic nucleic acids encoding such antibodies or functional fragments, at least $1 \times 10^6$ antibodies or functional fragments thereof or synthetic nucleic acids encoding such antibodies or functional fragments, at least $1 \times 10^7$ antibodies or functional fragments thereof or synthetic nucleic acids encoding such antibodies or functional fragments, at least $1 \times 10^8$ antibodies or functional fragments thereof or synthetic nucleic acids encoding such antibodies or functional fragments, at least $1 \times 10^9$ antibodies or functional fragments thereof or synthetic nucleic acids encoding such antibodies or functional fragments, at least $1 \times 10^{10}$ antibodies or functional fragments thereof or synthetic nucleic acids encoding such antibodies or functional fragments, or at least $1 \times 10^{11}$ antibodies or functional fragments thereof or synthetic nucleic acids encoding such antibodies or functional fragments.

In an embodiment of the method the collections comprise antibodies or synthetic nucleic acids encoding such antibodies selected from the group consisting of human IgG1, IgG2, IgG3, IgG4, IgA, IgE, IgM and IgD. In an embodiment of the method the collections comprise antibody fragments or synthetic nucleic acids encoding such fragments selected from the group consisting of Fab, F(ab')2, Fab', Fv, and scFv.

In embodiments of the method, the IgG heavy chain constant domains of the antibodies of the collections comprise the amino acid sequences shown in FIGS. 41A-B (SEQ ID NO: 305). In other embodiments of the method, the nucleic acids encoding the IgG heavy chain constant domains of the antibodies of the collection comprise the nucleic acid sequences shown in FIGS. 41A-B (SEQ ID NO: 304). In embodiments, the Fab heavy chain constant domains of the antibody fragments of the collections comprise the amino acid sequences shown in FIG. 42 (SEQ ID NO: 307). In other embodiments of the method, the nucleic acids encoding the Fab heavy chain constant domains of the antibodies of the collection comprise the nucleic acid sequences shown in FIG. 42 (SEQ ID NO: 306). In embodiments of the method, the IgG (SEQ ID NO: 309) and/or Fab (SEQ ID NO: 311) kappa light chain constant domains of the antibodies or antibody fragments of the collections comprise the amino acid sequences shown in FIG. 43. In other embodiments of the method, the nucleic acids encoding the IgG (SEQ ID NO: 308) and/or Fab (SEQ ID NO: 310) kappa light chain constant domains of the antibodies or antibody fragments of the collections comprise the nucleic acid sequences shown in FIG. 43. In embodiments of the method, the IgG (SEQ ID NO: 313) and/or Fab (SEQ ID NO: 315) lambda light chain constant domains of the antibodies or antibody fragments of the collections comprise the amino acid sequences shown in FIG. 44. In other embodiments of the method, the nucleic acids encoding the IgG (SEQ ID NO: 312) and/or Fab (SEQ ID NO: 314) lambda light chain constant domains of the antibodies or antibody fragments of the collections comprise the nucleic acid sequences shown in FIG. 44.

Antibodies of the Invention

In another aspect, the disclosure provides a synthetic antibody or functional fragment thereof or a synthetic nucleic acid encoding such antibody or functional fragments, wherein the antibody or functional fragment comprises a variable heavy chain and variable light chain pair, wherein the framework regions of the variable heavy chain and variable light chain pair comprises germline protein sequences selected from the variable heavy chain and variable light chain pairs VH1-18 (SEQ ID NO: 204)/VK1-39 (SEQ ID NO: 236); VH1-18 (SEQ ID NO: 204)/VK3-15 (SEQ ID NO: 238); VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-46 (SEQ ID NO: 205)/VL3-21 (SEQ ID NO: 257); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-16 (SEQ ID NO: 234); VH3-07 (SEQ ID NO: 207)/VK1-27 (SEQ ID NO: 235); VH3-07 (SEQ ID NO: 207)/VK1-39 (SEQ ID NO: 236); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VK1-05 (SEQ ID NO: 230); VH3-11 (SEQ ID NO: 208)/VK1-39 (SEQ ID NO: 236); VH3-11 (SEQ ID NO: 208)/VK3-15 (SEQ ID NO: 238); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-16 (SEQ ID NO: 234); VH3-15 (SEQ ID NO: 209)/VK1-27

(SEQ ID NO: 235); VH3-15 (SEQ ID NO: 209)/VK3-11 (SEQ ID NO: 237); VH3-15 (SEQ ID NO: 209)/VL1-40 (SEQ ID NO: 250); VH3-15 (SEQ ID NO: 209)/VL1-47 (SEQ ID NO: 251); VH3-15 (SEQ ID NO: 209)/VL1-51 (SEQ ID NO: 252); VH3-15 (SEQ ID NO: 209)/VL2-14 (SEQ ID NO: 254); VH3-21 (SEQ ID NO: 210)/VK1-12 (SEQ ID NO: 233); VH3-21 (SEQ ID NO: 210)/VK1-27 (SEQ ID NO: 235); VH3-21 (SEQ ID NO: 210)/VL2-11 (SEQ ID NO: 253); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-30 (SEQ ID NO: 212)/VK3-20 (SEQ ID NO: 239); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK1-27 (SEQ ID NO: 235); VH3-74 (SEQ ID NO: 214)/VK3-20 (SEQ ID NO: 239); VH3-74 (SEQ ID NO: 214)/VL1-51 (SEQ ID NO: 252); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-15 (SEQ ID NO: 238); VH6-1 (SEQ ID NO: 216)/VK3-20 (SEQ ID NO: 239) and VH6-1 (SEQ ID NO: 216)/VL1-51 (SEQ ID NO: 252).

In an embodiment, the synthetic antibody or functional fragment thereof or synthetic nucleic acid encoding such antibody or functional fragment thereof comprises one or more complementarity determining regions comprising germline protein sequences from the respective variable heavy chain and variable light chain pair, wherein the amino acid sequence of the complementarity determining region of the variable heavy chain and variable light chain are depicted in FIGS. 25-33. More specifically, in an embodiment, the synthetic antibody or functional fragment thereof or synthetic nucleic acid encoding such antibody or functional fragment thereof comprises a CDR1 region comprising germline protein sequences from the respective variable heavy chain and/or variable light chain pair, wherein the amino acid sequence of the CDR1 region of the variable heavy chains and variable light chains are depicted in FIGS. 25, 28, and 31, and the corresponding SEQ ID NOs: 204-265. In an embodiment, the synthetic antibody or functional fragment thereof or synthetic nucleic acid encoding such antibody or functional fragment thereof comprises an HCDR1 region comprising germline protein sequences from the respective variable heavy chain and variable light chain pair, wherein the amino acid sequences of the HCDR1 region of the variable heavy chain and variable light chain are depicted in FIG. 25 and the corresponding SEQ ID NOs: 204-229. In an embodiment, the synthetic antibody or functional fragment thereof or synthetic nucleic acid encoding such antibody or functional fragment thereof comprises an LCDR1 region comprising germline protein sequences from the respective variable heavy chain and variable light chain pair, wherein the amino acid sequences of the LCDR1 region of the variable heavy chains and variable light chain are depicted in FIGS. 28 and 31 and the corresponding SEQ ID NOs: 230-265. In an additional embodiment, the synthetic antibody or functional fragment thereof or synthetic nucleic acid encoding such antibody or functional fragment thereof comprises a CDR2 region comprising germline protein sequences from the respective variable heavy chain and variable light chain pair, wherein the amino acid sequences of the CDR2 region of the variable heavy chain and variable light chain are depicted in FIGS. 26, 29, and 32, and the corresponding SEQ ID NOs: 204-265. In an additional embodiment, the synthetic antibody or functional fragment thereof or synthetic nucleic acid encoding such antibody or functional fragment thereof comprises an HCDR2 region comprising germline protein sequences from the respective variable heavy chain and variable light chain pair, wherein the amino acid sequences of the HCDR2 region of the variable heavy chain and variable light chain are depicted in FIG. 26 and the corresponding SEQ ID NOs: 204-229. In an additional embodiment, the synthetic antibody or functional fragment thereof or synthetic nucleic acid encoding such antibody or functional fragment thereof comprises an LCDR2 region comprising germline protein sequences from the respective variable heavy chain and variable light chain pair, wherein the amino acid sequences of the LCDR2 region of the variable heavy chain and variable light chain are depicted in FIGS. 29 and 32 and the corresponding SEQ ID NOs: 230-265.

An aspect of the disclosure includes modifying germline complementarity determining regions to remove potential post translational modification sites (PTMs). Examples of variable heavy chain complementarity determining regions modified to remove PTMs are shown in FIGS. 34-36. In an aspect, the synthetic antibody or functional fragment thereof or synthetic nucleic acid encoding such antibody or functional fragment thereof comprises one or more complementarity determining regions comprising amino acid modifications that remove potential post translational modification sites. In an embodiment, the synthetic antibody or functional fragment thereof or synthetic nucleic acid encoding such antibody or functional fragment thereof comprises one or more complementarity determining regions comprising the complementarity determining region sequences or nucleic acid sequences encoding the same depicted in FIGS. 34-36 from the respective variable heavy chain. In a further embodiment, the synthetic antibody or functional fragment thereof or synthetic nucleic acid encoding such antibody or functional fragment thereof comprises an HCDR1 region comprising the HCDR1 or nucleic acids encoding the same depicted in FIGS. 34-36 from the respective variable heavy chain. The amino acid sequences of the low PTM HCDR1s are depicted in SEQ ID NOs: 266-278. The nucleic acid sequences of the low PTM HCDR1s are depicted in SEQ ID NOs: 279-291. In a further embodiment, the synthetic antibody or functional fragment thereof or synthetic nucleic acid encoding such antibody or functional fragment thereof comprises an HCDR2 region comprising the HCDR2 region or nucleic acids encoding the same depicted in FIGS. 34-36 from the respective variable heavy chain. The amino acid sequences of the low PTM HCDR2s are depicted in SEQ ID NOs: 266-278. The nucleic acid sequences of the low PTM HCDR2s are depicted in SEQ ID NOs: 279-291.

An aspect of the disclosure includes utilizing germline FR4 sequences. In an embodiment, the synthetic antibody or functional fragment thereof or synthetic nucleic acid encoding such antibody or functional fragment thereof comprises a FR4 region selected from the group consisting of: JH4 (SEQ ID NO:293), Jκ1 (SEQ ID NO:297), and Jλ2/3 (SEQ ID NO:301). In an embodiment, the synthetic antibody or functional fragment thereof or synthetic nucleic acid encoding such antibody or functional fragment thereof comprises a germline JH4 FR4 region, whose amino acid or nucleic acid sequence is depicted in FIG. 40. The JH4 FR4 amino acid sequence is depicted in (SEQ ID NO:293) and (SEQ ID NO:295). The JH4 FR4 nucleic acid sequence is depicted in (SEQ ID NO:292) and (SEQ ID NO:294). In an embodiment, the synthetic antibody or functional fragment thereof or synthetic nucleic acid encoding such antibody or functional fragment thereof comprises a germline Jk1 FR4 region, whose amino acid or nucleic acid sequence is depicted in FIG. 40. The Jk1 FR4 amino acid sequence is depicted in (SEQ ID NO:297). The Jk1 FR4 nucleic acid sequence is depicted in (SEQ ID NO:296), (SEQ ID NO:298) and (SEQ ID NO:299). In an embodiment, the synthetic antibody or functional fragment thereof or synthetic nucleic acid encoding such antibody or functional fragment thereof comprises a germline Jλ2/3 FR4 region, whose amino acid or nucleic acid sequence is depicted in FIG. 40. The Jλ2/3 FR4 amino acid sequence is depicted in (SEQ ID NO:301). The Jλ2/3 FR4 nucleic acid sequence is depicted in (SEQ ID NO:300), (SEQ ID NO:302) and (SEQ ID NO:303).

In an embodiment the synthetic antibody or synthetic nucleic acid encoding such antibody is selected from the group consisting of human IgG1, IgG2, IgG3, IgG4, IgA, IgE, IgM and IgD. In an embodiment the synthetic antibody fragment or synthetic nucleic acid encoding such antibody fragment is selected from the group consisting of Fab, F(ab')2, Fab', Fv, and scFv.

In embodiments, the IgG heavy chain constant domain of the antibody comprises the amino acid sequences shown in FIGS. 41A-B (SEQ ID NO: 305). In other embodiments, the nucleic acids encoding the IgG heavy chain constant domains of the antibody comprises the nucleic acid sequences shown in FIGS. 41A-B (SEQ ID NO: 304). In embodiments, the Fab heavy chain constant domain of the antibody fragments comprises the amino acid sequences shown in FIG. 42 (SEQ ID NO: 307). In other embodiments, the nucleic acids encoding the Fab heavy chain constant domain of the antibody fragment comprises the nucleic acid sequences shown in FIG. 42 (SEQ ID NO: 306). In embodiments, the IgG (SEQ ID NO: 309) and/or Fab (SEQ ID NO: 311) kappa light chain constant domains of the antibodies or antibody fragments comprise the amino acid sequences shown in FIG. 43. In other embodiments, the nucleic acids encoding the IgG (SEQ ID NO: 308) and/or Fab (SEQ ID NO: 310) kappa light chain constant domains of the antibodies or antibody fragments comprise the nucleic acid sequences shown in FIG. 43. In embodiments, the IgG (SEQ ID NO: 313) and/or Fab (SEQ ID NO: 315) lambda light chain constant domains of the antibodies or antibody fragments comprise the amino acid sequences shown in FIG. 44. In other embodiments, the nucleic acids encoding the IgG (SEQ ID NO: 312) and/or Fab (SEQ ID NO: 314) lambda light chain constant domains of the antibodies or antibody fragments comprise the nucleic acid sequences shown in FIG. 44.

EXAMPLES

Example 1

Generation of Restriction Sites in the C-Terminus of a Prokaryotic Signal Sequence and Human Leader Sequence, Providing for Fully Germline FR1 Regions In one aspect, the present disclosure describes collections of antibodies or fragments thereof comprising framework regions comprising germline protein sequences, specifically FR1. It is expected that having germline sequences shall lower the immunogenicity risk of the antibodies when administered in humans. Compatible restriction sites, however, must be used in order to enable standard cloning of the nucleic acids encoding the collections of antibodies into display and/or expression vectors so that the antibodies can be screened against immunogens. In the past, restriction sites utilized for cloning were often located within the framework regions, thus modifying the nucleic acid and/or amino acid sequence away from germline. In order to ensure that at least the framework 1 (FR1) region of each of the antibodies of the present disclosure maintain a germline protein sequence, there should not be any restriction sites within FR1 which would lead to deviations from the germline amino acid sequence. Therefore, an aspect of the present disclosure is the incorporation of an identical or at least compatible restriction site within the C-terminus of prokaryotic signal sequences and human leader sequences, specifically within the three C-terminal residues. Additionally, a prokaryotic signal sequence and human leader sequence comprising an identical or compatible restriction site must be functional and allow for good display and expression yield of the antibodies or fragments thereof in both prokaryotic and mammalian expression systems.

FIG. 1 shows the selected restriction sites and their corresponding positions. The NheI (VLA) restriction site was selected for incorporation into the prokaryotic heavy chain signal sequences (phoA). The nucleic acid and amino acid sequences of the wildtype phoA signal sequence and the NheI (VLA) phoA signal sequence are shown in Table 1.

TABLE 1

```
Wildtype E. coli phoA signal sequence (C-terminal amino acid
sequence from position -3 to -1 is TKA without restriction site):
M   K   Q   S   T   I   A   L   A   L   L   P   L   L   F   T   P   V   T   K   A
ATGAAACAGAGCACCATTGCCCTGGCCCTGCTGCCGCTGCTGTTTACCCCAGTGACCAAA
GCC
(SEQ ID NOS 8 and 7, respectively, in order of appearance)

PhoA wild type C-terminus
T   K   A
ACC AAA GCC

Modified E. coli phoA signal sequence with C-terminal VLA and
NheI restriction site (=GCTAGC):
M   K   Q   S   T   I   A   L   A   L   L   P   L   L   F   T   P   V   V   L   A
ATGAAACAGAGCACCATTGCCCTGGCCCTGCTGCCGCTGCTGTTTACCCCAGTGGTGCTA
GCC
(SEQ ID NOS 10 and 9, respectively, in order of appearance)
```

The NdeI (AYA) restriction site was selected for incorporation into the prokaryotic kappa and lambda signal sequences (ompA). The nucleic acid and amino acid sequences of the wildtype ompA signal sequence and the modified NdeI (AYA) ompA signal sequence are shown in Table 2.

TABLE 2

Wildtype *E. coli* ompA signal sequence (C-terminal amino acid sequence from position -3 to -1 is AQA without restriction site):
M  K  K  T  A  I  A  I  A  V  A  L  A  G  F  A  T  V  A  Q  A
ATGAAAAAAACCGCCATTGCCATTGCCGTGGCCCTGGCAGGCTTTGCCACCGTGGCGCAG
GCC
(SEQ ID NOS 12 and 11, respectively, in order of appearance)

OmpA wild type C-terminus
A   Q   A
GCG CAG GCC

Modified *E. coli* ompA signal sequence with C-terminal AYA and NdeI restriction site (=CATATG):
M  K  K  T  A  I  A  I  A  V  A  L  A  G  F  A  T  V  A  Y  A
ATGAAAAAAACCGCCATTGCCATTGCCGTGGCCCTGGCAGGCTTTGCCACCGTGGCATAT
GCC Alternatively the DNA sequence includes:
ATGAAAAAAACCGCCATTGCCATTGCCGTGGCCCTGGCAGGCTTTGCCACCGTGGCATAT
GCG
(SEQ ID NOS 14, 13 and 15 respectively, in order of appearance)

In order to allow an easy switch from *E. coli* expressed Fab to mammalian expressed IgG formats, the human leader sequences for the IgG light chain (human kappa leader) and IgG heavy chain (human heavy chain leader) were generated to contain the same restriction sites as the C-termini of the ompA (NdeI (AYA)) and phoA (NheI (VLA)) signal sequences. The wildtype and modified human heavy chain leader and human kappa leader sequences are shown in Table 3.

TABLE 3

| Heavy chain leader |
| --- |
| A)<br>Wildtype human heavy chain leader (C-terminal amino acid sequence from position -3 to -1 is VLS without restriction site):<br>M  K  H  L  W  F  F  L  L  L  V  A  A  P  R  W  V  L  S<br>ATGAAACACCTGTGGTTCTTCCTCCTGCTGGTGGCAGCTCCCAGATGGGTCCTGTCC<br>(SEQ ID NOS 17 and 16, respectively, in order of appearance)<br><br>Wild type Heavy chain leader C-terminus<br>V   L   S<br>GTC CTG TCC<br><br>B)<br>Modified human heavy chain leader with C-terminal VLA and NheI restriction site (=GCTAGC):<br>M  K  H  L  W  F  F  L  L  L  V  A  A  P  R  W  V  L  A<br>ATGAAGCACCTGTGGTTCTTTCTGCTGCTGGTGGCCGCTCCCCGGTGGGTGCTAGCC<br>(SEQ ID NOS 19 and 18, respectively, in order of appearance)<br><br>C)<br>Wildtype human kappa leader (C-terminal amino acid sequence from position -3 to -1 is AYG without restriction site):<br>M  V  L  Q  T  Q  V  F  I  S  L  L  L  W  I  S  G  A  Y  G<br>ATGGTGTTGCAGACCCAGGTCTTCATTTCTCTGTTGCTCTGGATCTCTGGTGCCTACGGG<br>(SEQ ID NOS 21 and 20, respectively, in order of appearance)<br><br>Kappa leader C-terminus<br>A   Y   G<br>GCC TAC GGG<br><br>D)<br>Modified human kappa leader with C-terminal AYA and NdeI restriction site (=CATATG):<br>M  V  L  Q  T  Q  V  F  I  S  L  L  L  W  I  S  G  A  Y  A<br>ATGGTGCTCCAGACCCAGGTGTTCATCAGCCTGCTGCTGTGGATCAGCGGCGCATATGCG<br>(SEQ ID NOS 23 and 22, respectively, in order of appearance) |

The selected modified prokaryotic signal sequences and human leader sequences (a) result in high yields of Fab and IgG protein according to the vector system used, (b) provide full compatibility for switching antibody formats, vectors and expression systems between prokaryotic and mammalian systems and (c) are located in the signal/leader sequences thereby maintaining the full germline sequences of FR1.

Example 2

Identification of the Most Abundant VH/VL Pairs in the Human Repertoire

In its most general sense, the inventors began with the idea that an antibody collection that imitates the human immune system in essential ways may be advantageous. The inventors worked from their hypothesis that the variable heavy chain and variable light chain germline gene pairs abundantly expressed in the human immune repertoire likely have favorable biophysical properties that would lead to more efficient clinical development and increase the safety and efficacy of the resulting antibodies in patients. In order to prove this hypothesis, the first step was to identify the variable heavy chain and variable light chain germline gene pairs prominently expressed in the human immune repertoire.

Example 2.1

Determination of VH/VL Pair Germline Gene Usage

In order to identify the predominantly expressed VH/VL germline gene pairs from the human immune repertoire, publically available data was analyzed and human B cells were sampled. As a first step, publically available data was reviewed to identify articles describing the VH/VL germline gene pairs isolated from human B cells. As mentioned, many publically available databases provide antibody sequences, however, many provide only the sequences of either variable domain, VH or VL, but seldom provide the linkage of VH/VL germline gene pairs. The following articles were identified and analyzed in detail: Wardemann H. et al. (2003) Science 301, 1374-1377 and any supporting tables; Yurasov S. et al. (2005) J. Exp. Med. 201, 703-712 and any supporting tables; Tsuiji M. et al. (2006) J. Exp. Med. 203, 393-401 and any supporting tables; Yurasov S. et al. (2006) J. Exp. Med. 203, 2255-2262 and any supporting tables, Tiller T. et al. (2007) Immunity 26, 205-213 and any supporting tables, and Mietzner B. et al. (2008) PNAS 105, 9727-9732 and any supporting tables, all of which are incorporated by reference in their entireties. Additional VH/VL pair data was identified from a sample of human B cells, as described below.

Example 2.2

Determination of VH/VL Pair Gene Usage from a Human Sample

In order to obtain additional VH/VL germline gene pair usage data, PBMCs were isolated from a human host. The PBMCs were sorted, the cDNAs of the B cells were amplified using PCR, the DNA from the B cells was sequenced and then the sequences were blasted with IgBLAST (NCBI) to identify the VH/VL germline gene pairs from each B cell.

General methods of isolating and sorting human PBMCs from venous blood and mononuclear cells from bone marrow are described in Tiller et al., J Immunol Methods, 2008 Jan. 1; 329(1-2):112-24, which is incorporated by reference in its entirety. The PBMCs were isolated and then single sorted according to the cell surface marker of the phenotype of interest. Ig gene transcripts of the single sorted mature naïve (mn) B cells and antibody secreting cells (asc) were then PCR amplified for determination of the VH/VL germline gene pairings. General methods of PCR amplifying cDNA of B cells and the primers useful for the same are also described in Tiller et. al. 2008 (citation above). The specific primers used are shown in Table 4.

TABLE 4

(SEQ ID NOS 24-60, respectively, in order of appearance):

for μ or γ heavy chain PCR:

HC 1st PCR

| | | | |
|---|---|---|---|
| 5' | L-VH 1 | ACAGGTGCCCACTCCCAGGTGCAG | 24 |
| 5' | L-VH 3 | AAGGTGTCCAGTGTGARGTGCAG | 23 |
| 5' | L-VH 4/6 | CCCAGATGGGTCCTGTCCCAGGTGCAG | 27 |
| 5' | L-VH 5 | CAAGGAGTCTGTTCCGAGGTGCAG | 24 |
| 3' | Cμ CH1 (m u) | GGGAATTCTCACAGGAGACGA | 21 |
| 3' | Cg CH1 (gamma) | GGAAGGTGTGCACGCCGCTGGTC | 23 |

HC 2nd PCR

| | | | |
|---|---|---|---|
| 5' | AgeI VH1 | CTGCAACCGGTGTACATTCCCAGGTGCAGCTGGTGCAG | 38 |
| 5' | AgeI VH1/5 | CTGCAACCGGTGTACATTCCGAGGTGCAGCTGGTGCAG | 38 |
| 5' | AgeI VH3 | CTGCAACCGGTGTACATTCTGAGGTGCAGCTGGTGGAG | 38 |
| 5' | AgeI VH3-23 | CTGCAACCGGTGTACATTCTGAGGTGCAGCTGTTGGAG | 38 |
| 5' | AgeI VH4 | CTGCAACCGGTGTACATTCCCAGGTGCAGCTGCAGGAG | 38 |
| 5' | AgeI VH 4-34 | CTGCAACCGGTGTACATTCCCAGGTGCAGCTACAGCAGTG | 40 |
| 3' | SalI JH 1/2/4/5 | TGCGAAGTCGACGCTGAGGAGACGGTGACCAG | 32 |
| 3' | SalI JH 3 | TGCGAAGTCGACGCTGAAGAGACGGTGACCATTG | 34 |
| 3' | SalI JH 6 | TGCGAAGTCGACGCTGAGGAGACGGTGACCGTG | 33 |
| 3' | IgG (internal) | GTTCGGGGAAGTAGTCCTTGAC | 22 |

TABLE 4-continued (SEQ ID NOS 24-60, respectively, in order of appearance):

for kappa light chain PCR:

k LC 1st PCR

| | | |
|---|---|---|
| 5' L-Vk 1/2 | ATGAGGSTCCCYGCTCAGCTGCTGG | 25 |
| 5' L-Vk 3 | CTCTTCCTCCTGCTACTCTGGCTCCCAG | 28 |
| 5' L-Vk 4 | ATTTCTCTGTTGCTCTGGATCTCTG | 25 |
| 3' Ck 543 | GTTTCTCGTAGTCTGCTTTGCTCA | 24 | k LC 2nd PCR

| | | |
|---|---|---|
| 5' Pan Vk | ATGACCCAGWCTCCABYCWCCCTG | 24 |
| 3' Ck 494 | GTGCTGTCCTTGCTGTCCTGCT | 22 | for lambda light chain PCR:

(LC 1st PCR

| | | |
|---|---|---|
| 5' L-Vl 1 | GGTCCTGGGCCCAGTCTGTGCTG | 23 |
| 5' L-Vl 2 | GGTCCTGGGCCCAGTCTGCCCTG | 23 |
| 5' L-Vl 3 | GCTCTGTGACCTCCTATGAGCTG | 23 |
| 5' L-Vl 4/5 | GGTCTCTCTCSCAGCYTGTGCTG | 23 |
| 5' L-Vl 6 | GTTCTTGGGCCAATTTTATGCTG | 23 |
| 5' L-Vl 7 | GGTCCAATTCYCAGGCTGTGGTG | 23 |
| 5' L-Vl 8 | GAGTGGATTCTCAGACTGTGGTG | 23 |
| 3' Cl | CACCAGTGTGGCCTTGTTGGCTTG | 24 |

(LC 2nd PCR

| | | |
|---|---|---|
| 5'AgeI Vl 1 | CTGCTACCGGTTCCTGGGCCCAGTCTGTGCTGACKCAG | 38 |
| 5'AgeI Vl 2 | CTGCTACCGGTTCCTGGGCCCAGTCTGCCCTGACTCAG | 38 |
| 5'AgeI Vl 3 | CTGCTACCGGTTCTGTGACCTCCTATGAGCTGACWCAG | 38 |
| 5'AgeI Vl 4/5 | CTGCTACCGGTTCTCTCTCSCAGCYTGTGCTGACTCA | 37 |
| 5'AgeI Vl 6 | CTGCTACCGGTTCTTGGGCCAATTTTATGCTGACTCAG | 38 |
| 5'AgeI Vl 7/8 | CTGCTACCGGTTCCAATTCYCAGRCTGTGGTGACYCAG | 38 |
| 3'XhoI Cl | CTCCTCACTCGAGGGYGGGAACAGAGTG | 28 | cDNAs of the single sorted mature naïve (mn) B cells and antibody secreting cells (asc) were synthesized. Nested PCR was conducted, where human IgH, Igk and IgL V gene transcripts were PCR amplified independently. The sequencing results were blasted with IgBLAST (NCBI) to identify the respective VH, VK, and VL germline genes.

Example 2.3

VH/VL Germline Gene Pairs Identified in the Human Immune Repertoire

The VH/VL germline gene pair data identified from the publically available literature as described in Example 2.1 was pooled with the data identified from a human sample as described in Example 2.2. The pooled data was analyzed and is shown as a ranking in Table 6, i.e. the ranking of the percentage/proportion (%) of the VH/VL germline gene pairs identified in the human immune repertoire.

Example 3

Determining the VH and VL Germline Gene Usage

A review of Table 6 shows that a small number of VH/VL pairs are dominant in the human immune repertoire as compared to the total number of germline genes. Wildt et al. at 895-896 described this phenomenon. Wildt et al. also described that the frequently expressed heavy and light chain gene segments are often paired, and observed that half of the pairings sampled corresponded to only five VH/VL germline gene pairs.

Additionally, the pooled data and additional references were evaluated to identify the VH, Vκ, and Vλ germline genes that are independently expressed (not as pairs) in the human immune repertoire. The additional literature references, which include unpaired VH and/or VL germline gene expression, were Brezinschek H. P. et al. (1997) J. Clin. Invest. 99, 2488, Demaison C. et al. (1995) Immunogenetics 42, 342, and Foster S. J. et al. (1997) J. Clin. Invest. 99, 1614, which are both incorporated by reference in their entireties. The data from Examples 2.1 and 2.2 and additional references were pooled and ranked to determine the VH, Vκ, and Vλ germline genes most prominently expressed in the human immune repertoire. The ranking is shown in Table 5.

In comparing Table 5, showing the unlinked VH, Vλ and Vκ germline gene prevalence in the human immune repertoire and Table 6, showing the linked VH/VL pair germline gene prevalence within the human immune repertoire, it was apparent that many of the VH, Vλ and Vκ germline genes that are highly represented when evaluated independent of linkage or pairing were also highly represented in the VH/VL pairings.

This observation is confirmed by the plots shown in FIGS. 4-5, which show the VH/VL germline gene pairs of the human immune repertoire. The figures show the actual number of each VH/VL germline gene pair identified from the pooled data, plotted on a matrix, where the Y axis includes the ranking of the VH germline genes, and the X axis includes the ranking of the VL germline genes.

Example 4

Selecting the VH/VL Germline Gene Pairings for Further Evaluation of their Biophysical Properties As a next step, it had to be determined which germline protein pairs were to be tested, as there are ~2500 pairs in the human immune repertoire and the inventors goal was to identify which of the germline protein pairs comprise favorable biophysical properties which would aid in selection and development. One way would be to test the variable heavy chain and variable light chain germline protein pairs that occur most prominently in the human immune repertoire, for example see Table 6. One could, for example, select the top four hundred pairs for testing, or select the variable heavy chain and variable light chain germline protein pairs present above a certain threshold number. This approach would require the synthesis and testing of a large number of different variable heavy chain and variable light chain germline protein pair sequences; therefore, such an approach may not be very efficient.

As an alternative approach, the inventors selected a subset of the variable heavy chain and variable light chain germline pairs that are representative of, accurately reproduce, or cover the majority of the prominent pairs from the human immune repertoire. This approach was based, in part, upon the above observation that a small number of variable heavy, variable κ light chain, and variable λ light chain germline genes (unpaired) are dominant in the human immune repertoire. Therefore, a small number of the prominent heavy and light chain germline genes (unpaired) can be combined to generate a group of VH/VL pairs that are representative of the human immune repertoire.

This approach was undertaken in the following way. In Example 3, the variable heavy chain, variable κ light chain, and variable λ light chain germline gene expression was determined. As a next step, an in silico analysis was completed of the prominent VH, Vλ and Vκ germline genes, where at least the following factors were evaluated: CDR length, isoelectric point (pI) (the preferred isoelectric point is 7.5 or above as this is should provide stability in a standard pH 5.5 to pH 7 formulation buffer), potential post translational modification sites (PTM's) (specifically, N-linked glycosylation sites (NxS or NxT) or chemical modifications such as Asp cleavage (often at a DP or DQ), Asp isomerization (DS, DG), deamidation (NS, NG) which can occur in vivo (in serum) or upon storage in formulation buffer and lead to loss of antibody binding), the presence of Methionines in the CDRs (can be oxidized when exposed to solvent), the presence of unpaired cysteines (will form disulfide bonds with any other unpaired cysteine, thus leading to crosslinking of proteins and/or lower expression yield), deviations from germline, the presence of possible T-cell epitopes, and theoretical aggregation propensity. Selected data from the in silico analysis is shown in FIGS. 2-3.

Based upon the in silico analysis of the most prominent VH, Vλ and Vκ germline genes, a subset of these were selected for synthesis, combination and subsequent functional testing. This subset is shown in FIGS. 2-3. When comparing Table 5 and FIGS. 2-3, it is clear that not all of the most prominent VH, Vλ and Vκ germline genes were selected for further testing. Of the most prominent VH germline genes, shown in Table 5, IGHV4-34, IGHV4-59, and IGHV3-9 were not selected. Instead, see in FIGS. 2-3, IGHV3-74, IGHV3-73, and IGHV6-1 were selected. In total, 20 VH germline genes were selected. Of the most prominent Vκ germline genes, shown in Table 5, IGKV4-1, IGKV2-28/2D-28, IGKV1-33/1D-33, and IGKV1-8 were not selected. In total, 12 Vκ germline genes were selected. Of the most prominent Vλ germline genes shown in Table 5, IGLV1-44 was not selected. In total, 8 Vλ germline genes were selected.

Table 5 shows the ranking of the VH, Vκ, and Vλ germline gene usage from the human immune repertoire and bolds and underlines the germline genes that were selected for further functional testing.

TABLE 5

| | VH n = 2463 | | | Vκ n = 1656 | | | Vλ n = 780 | |
|---|---|---|---|---|---|---|---|---|
| 1 | IGHV3-23 | 10.6 | 1 | IGKV3-20 | 16.2 | 1 | IGLV2-14 | 18.1 |
| 2 | IGHV3-30 | 8.0 | 2 | IGKV1-39/1D-39 | 14.2 | 2 | IGLV1-40 | 11.3 |
| 3 | IGHV4-39 | 7.6 | 3 | IGKV1-5 | 11.2 | 3 | IGLV1-44 | 11.3 |
| 4 | IGHV4-34 | 6.8 | 4 | IGKV3-15 | 11.1 | 4 | IGLV1-51 | 10.0 |
| 5 | IGHV4-59 | 5.8 | 5 | IGKV4-1 | 8.5 | 5 | IGLV2-23 | 8.1 |
| 6 | IGHV1-69 | 5.3 | 6 | IGKV3-11 | 7.6 | 6 | IGLV3-21 | 8.1 |
| 7 | IGHV5-51 | 4.6 | 7 | IGKV2-28/2D-28 | 6.0 | 7 | IGLV1-47 | 6.5 |
| 8 | IGHV3-7 | 4.5 | 8 | IGKV1-33/1D-33 | 4.6 | 8 | IGLV3-1 | 5.3 |
| 9 | IGHV1-18 | 4.1 | 9 | IGKV2-30 | 2.6 | 9 | IGLV2-11 | 5.1 |
| 10 | IGHV3-48 | 4.0 | 10 | IGKV1-9 | 2.4 | 10 | IGLV2-8 | 4.5 |
| 11 | IGHV3-15 | 3.3 | 11 | IGKV1-17 | 2.4 | 11 | IGLV6-57 | 1.7 |
| 12 | IGHV3-21 | 3.3 | 12 | IGKV1-27 | 2.2 | 12 | IGLV3-25 | 1.5 |
| 13 | IGHV1-2 | 3.2 | 13 | IGKV1-8 | 1.9 | 13 | IGLV7-46 | 1.5 |
| 14 | IGHV3-33 | 3.0 | 14 | IGKV1-16 | 1.3 | 14 | IGLV1-36 | 1.2 |
| 15 | IGHV4-31 | 3.0 | 15 | IGKV1-6 | 1.1 | 15 | IGLV7-43 | 1.2 |
| 16 | IGHV3-53 | 2.7 | 16 | IGKV1-12 | 1.1 | 16 | IGLV9-49 | 1.2 |
| 17 | IGHV3-11 | 2.6 | 17 | IGKV2D-29 | 1.0 | 17 | IGLV4-69 | 1.0 |
| 18 | IGHV3-9 | 2.2 | 18 | IGKV1-13 | 0.7 | 18 | IGLV2-18 | 0.6 |
| 19 | IGHV4-4 | 2.1 | 19 | IGKV1D-8 | 0.5 | 19 | IGLV3-10 | 0.5 |
| 20 | IGHV1-46 | 2.1 | 20 | IGKV2-24 | 0.5 | 20 | IGLV3-27 | 0.5 |
| 21 | IGHV3-74 | 1.6 | 21 | IGKV5-2 | 0.4 | 21 | IGLV3-9 | 0.3 |
| 22 | IGHV1-24 | 1.1 | 22 | IGKV1D-12 | 0.3 | 22 | IGLV3-12 | 0.1 |
| 23 | IGHV4-61 | 1.1 | 23 | IGKV2-40/2D-40 | 0.3 | 23 | IGLV3-19 | 0.1 |
| 24 | IGHV1-8 | 1.1 | 24 | IGKV3D-20 | 0.3 | 24 | IGLV3-22 | 0.1 |
| 25 | IGHV1-3 | 1.0 | 25 | IGKV1D-43 | 0.2 | 25 | IGLV4-60 | 0.1 |
| 26 | IGHV3-49 | 1.0 | 26 | IGKV2D-30 | 0.2 | 26 | IGLV8-61 | 0.1 |
| 27 | IGHV3-43 | 0.6 | 27 | IGKV3D-11 | 0.2 | 27 | IGLV3-16 | 0.0 |
| 28 | IGHV4-28 | 0.6 | 28 | IGKV3D-15 | 0.2 | 28 | IGLV4-3 | 0.0 |

TABLE 5-continued

| | VH n = 2463 | | | Vκ n = 1656 | | | Vλ n = 780 | |
|---|---|---|---|---|---|---|---|---|
| 29 | IGHV3-64 | 0.5 | 29 | IGKV2-29 | 0.2 | 29 | IGLV5-37 | 0.0 |
| 30 | IGHV7-81 | 0.5 | 30 | IGKV1D-16 | 0.1 | 30 | IGLV5-39 | 0.0 |
| 31 | IGHV3-13 | 0.4 | 31 | IGKV1D-17 | 0.1 | 31 | IGLV5-45 | 0.0 |
| 32 | IGHV3-72 | 0.4 | 32 | IGKV3D-7 | 0.1 | 32 | IGLV5-52 | 0.0 |
| 33 | IGHV1-58 | 0.3 | 33 | IGKV6-21/6D-21 | 0.1 | 33 | IGLV10-54 | 0.0 |
| 34 | IGHV3-73 | 0.3 | 34 | IGKV6D-41 | 0.1 | | | |
| 35 | IGHV3-66 | 0.2 | 35 | IGKV1D-13 | 0.0 | | | |
| 36 | IGHV7-4.1 | 0.2 | | | | | | |
| 37 | IGHV2-5 | 0.1 | | | | | | |
| 38 | IGHV4-30.2 | 0.1 | | | | | | |
| 39 | IGHV3-20 | 0.1 | | | | | | |
| 40 | IGHV6-1 | 0.0 | | | | | | |
| 41 | IGHV1-e | 0.0 | | | | | | |
| 42 | IGHV1-f | 0.0 | | | | | | |
| 43 | IGHV1-45 | 0.0 | | | | | | |
| 44 | IGHV2-26 | 0.0 | | | | | | |
| 45 | IGHV2-70 | 0.0 | | | | | | |
| 46 | IGHV3-d | 0.0 | | | | | | |
| 47 | IGHV4-b | 0.0 | | | | | | |
| 48 | IGHV4-30.4 | 0.0 | | | | | | |
| 49 | IGHV5-a | 0.0 | | | | | | |

Example 4.1

Recombination of Abundant VH, Vκ, and Vλ Germline Genes to Yield Representation of VH/VL Most Prominent Pairs in the Human Immune Repertoire As a next step, the 20 VH, 12 Vκ and 8 Vλ selected VH, Vκ, and Vλ germline genes were synthesized and combined to generate 400 VH/VL germline gene pairs, which pairs were subsequently tested for their biophysical properties. Table 6 shows that the 400 VH/VL germline gene pairs generated for functional testing do, in fact, accurately reproduce or cover the majority of the prominent VH/VL germline gene pairs in the human immune repertoire. Table 6 shows the ranking of the VH/VL pairs expressed in the human immune repertoire, wherein the 400 VH/VL pairs that were tested are bolded and underlined.

TABLE 6

The 400 VH/VL germline gene pairs functionally tested are representative of the VH/VL germline gene pairs identified in the human immune repertoire

| pos | V heavy | V light | % |
|---|---|---|---|
| 1 | IGHV3-23 | IGKV1-5 | 1.26 |
| 2 | IGHV4-34 | IGKV3-20 | 1.17 |
| 3 | IGHV3-23 | IGKV3-20 | 1.12 |
| 4 | IGHV4-39 | IGKV3-15 | 1.03 |
| 5 | IGHV3-23 | IGKV3-15 | 0.94 |
| 6 | IGHV4-59 | IGKV1-39/1D-39 | 0.89 |
| 7 | IGHV4-39 | IGKV1-39/1D-39 | 0.84 |
| | IGHV4-34 | IGKV1-39/1D-39 | 0.84 |
| 8 | IGHV4-59 | IGKV3-20 | 0.70 |
| | IGHV1-18 | IGKV3-20 | 0.70 |
| 9 | IGHV3-30 | IGKV3-20 | 0.66 |
| | IGHV4-39 | IGKV1-5 | 0.66 |
| | IGHV1-69 | IGKV1-39/1D-39 | 0.66 |
| | IGHV5-51 | IGLV 1-40 | 0.66 |
| 10 | IGHV3-23 | IGKV4-1 | 0.61 |
| | IGHV4-39 | IGKV3-20 | 0.61 |
| | IGHV4-39 | IGLV 2-14 | 0.61 |
| | IGHV4-39 | IGLV 3-21 | 0.61 |
| 11 | IGHV3-23 | IGKV1-39/1D-39 | 0.56 |
| | IGHV3-30 | IGKV1-39/1D-39 | 0.56 |
| | IGHV3-30 | IGKV3-11 | 0.56 |

TABLE 6-continued

The 400 VH/VL germline gene pairs functionally tested are representative of the VH/VL germline gene pairs identified in the human immune repertoire

| pos | V heavy | V light | % |
|---|---|---|---|
| | IGHV1-69 | IGKV3-20 | 0.56 |
| | IGHV3-48 | IGKV3-20 | 0.56 |
| | IGHV1-2 | IGKV3-20 | 0.56 |
| 12 | IGHV3-30 | IGKV4-1 | 0.51 |
| | IGHV5-51 | IGLV 2-14 | 0.51 |
| 13 | IGHV4-59 | IGKV4-1 | 0.47 |
| | IGHV5-51 | IGKV3-20 | 0.47 |
| | IGHV3-7 | IGKV1-39/1D-39 | 0.47 |
| | IGHV3-7 | IGKV1-5 | 0.47 |
| | IGHV3-15 | IGKV3-20 | 0.47 |
| | IGHV4-39 | IGLV 2-14 | 0.47 |
| | IGHV4-39 | IGLV 2-8 | 0.47 |
| | IGHV4-34 | IGLV 2-14 | 0.47 |
| 14 | IGHV3-23 | IGKV3-11 | 0.42 |
| | IGHV3-30 | IGKV1-5 | 0.42 |
| | IGHV3-30 | IGKV3-15 | 0.42 |
| | IGHV4-34 | IGKV1-5 | 0.42 |
| | IGHV3-21 | IGKV1-5 | 0.42 |
| | IGHV3-21 | IGKV3-15 | 0.42 |
| | IGHV3-30 | IGLV 1-51 | 0.42 |
| | IGHV4-34 | IGLV 1-51 | 0.42 |
| | IGHV3-21 | IGLV 1-51 | 0.42 |
| | IGHV3-53 | IGLV 1-44 | 0.42 |
| 15 | IGHV4-59 | IGKV3-15 | 0.37 |
| | IGHV4-34 | IGKV3-15 | 0.37 |
| | IGHV5-51 | IGKV4-1 | 0.37 |
| | IGHV1-69 | IGKV4-1 | 0.37 |
| | IGHV1-69 | IGKV3-11 | 0.37 |
| | IGHV3-7 | IGKV3-15 | 0.37 |
| | IGHV1-18 | IGKV1-39/1D-39 | 0.37 |
| | IGHV3-48 | IGKV1-39/1D-39 | 0.37 |
| | IGHV3-33 | IGKV3-15 | 0.37 |
| | IGHV3-53 | IGKV1-5 | 0.37 |
| | IGHV4-59 | IGLV 1-40 | 0.37 |
| | IGHV1-69 | IGLV 2-14 | 0.37 |
| | IGHV1-69 | IGLV 1-44 | 0.37 |
| | IGHV4-31 | IGLV 2-14 | 0.37 |
| | IGHV1-2 | IGLV 2-14 | 0.37 |
| 16 | IGHV3-23 | IGKV2-28/2D-28 | 0.33 |
| | IGHV3-30 | IGKV1-9 | 0.33 |
| | IGHV4-34 | IGKV4-1 | 0.33 |
| | IGHV5-51 | IGKV1-39/1D-39 | 0.33 |
| | IGHV5-51 | IGKV3-15 | 0.33 |
| | IGHV1-69 | IGKV3-15 | 0.33 |

TABLE 6-continued

The 400 VH/VL germline gene pairs functionally tested are representative of the VH/VL germline gene pairs identified in the human immune repertoire

| pos | V heavy | V light | % |
|---|---|---|---|
|  | IGHV1-18 | IGKV1-33/1D-33 | 0.33 |
|  | IGHV3-48 | IGKV3-11 | 0.33 |
|  | IGHV3-21 | IGKV1-39/1D-39 | 0.33 |
|  | IGHV4-31 | IGKV3-20 | 0.33 |
|  | IGHV4-31 | IGKV3-11 | 0.33 |
|  | IGHV3-30 | IGLV 2-14 | 0.33 |
|  | IGHV4-39 | IGLV 1-44 | 0.33 |
|  | IGHV1-69 | IGLV 1-40 | 0.33 |
|  | IGHV3-9 | IGLV 2-23 | 0.33 |
| 17 | IGHV3-23 | IGKV1-33/1D-33 | 0.28 |
|  | IGHV4-39 | IGKV3-11 | 0.28 |
|  | IGHV4-34 | IGKV3-11 | 0.28 |
|  | IGHV4-34 | IGKV2-28/2D-28 | 0.28 |
|  | IGHV5-51 | IGKV3-11 | 0.28 |
|  | IGHV5-51 | IGKV1-13 | 0.28 |
|  | IGHV3-7 | IGKV3-20 | 0.28 |
|  | IGHV3-48 | IGKV3-15 | 0.28 |
|  | IGHV3-48 | IGKV4-1 | 0.28 |
|  | IGHV3-48 | IGKV1-33/1D-33 | 0.28 |
|  | IGHV3-15 | IGKV1-39/1D-39 | 0.28 |
|  | IGHV3-15 | IGKV1-5 | 0.28 |
|  | IGHV1-2 | IGKV1-39/1D-39 | 0.28 |
|  | IGHV3-33 | IGKV3-20 | 0.28 |
|  | IGHV3-33 | IGKV1-39/1D-39 | 0.28 |
|  | IGHV3-33 | IGKV4-1 | 0.28 |
|  | IGHV3-53 | IGKV3-15 | 0.28 |
|  | IGHV3-11 | IGKV1-5 | 0.28 |
|  | IGHV4-4 | IGKV3-20 | 0.28 |
|  | IGHV1-46 | IGKV3-20 | 0.28 |
|  | IGHV3-23 | IGLV 1-40 | 0.28 |
|  | IGHV3-23 | IGLV 3-21 | 0.28 |
|  | IGHV4-39 | IGLV 1-40 | 0.28 |
|  | IGHV4-34 | IGLV 1-40 | 0.28 |
|  | IGHV4-34 | IGLV 1-47 | 0.28 |
|  | IGHV3-48 | IGLV 2-14 | 0.28 |
|  | IGHV3-48 | IGLV 1-47 | 0.28 |
|  | IGHV1-2 | IGLV 1-40 | 0.28 |
|  | IGHV3-9 | IGLV 2-14 | 0.28 |
|  | IGHV4-4 | IGLV 1-44 | 0.28 |
| 18 | IGHV3-23 | IGKV1-17 | 0.23 |
|  | IGHV4-39 | IGKV4-1 | 0.23 |
|  | IGHV4-39 | IGKV2-28/2D-28 | 0.23 |
|  | IGHV1-69 | IGKV1-5 | 0.23 |
|  | IGHV3-7 | IGKV4-1 | 0.23 |
|  | IGHV1-18 | IGKV1-5 | 0.23 |
|  | IGHV1-18 | IGKV2-28/2D-28 | 0.23 |
|  | IGHV3-21 | IGKV3-20 | 0.23 |
|  | IGHV3-33 | IGKV1-5 | 0.23 |
|  | IGHV3-53 | IGKV1-39/1D-39 | 0.23 |
|  | IGHV3-53 | IGKV1-33/1D-33 | 0.23 |
|  | IGHV3-11 | IGKV1-39/1D-39 | 0.23 |
|  | IGHV3-11 | IGKV3-15 | 0.23 |
|  | IGHV4-4 | IGKV1-39/1D-39 | 0.23 |
|  | IGHV1-46 | IGKV1-39/1D-39 | 0.23 |
|  | IGHV4-61 | IGKV4-1 | 0.23 |
|  | IGHV3-23 | IGLV 1-44 | 0.23 |
|  | IGHV3-23 | IGLV 2-11 | 0.23 |
|  | IGHV3-23 | IGLV 3-1 | 0.23 |
|  | IGHV3-30 | IGLV 1-40 | 0.23 |
|  | IGHV4-39 | IGLV 1-51 | 0.23 |
|  | IGHV4-39 | IGLV 2-23 | 0.23 |
|  | IGHV4-59 | IGLV 3-1 | 0.23 |
|  | IGHV5-51 | IGLV 1-44 | 0.23 |
|  | IGHV1-69 | IGLV 1-51 | 0.23 |
|  | IGHV1-69 | IGLV 2-11 | 0.23 |
|  | IGHV1-18 | IGLV 2-14 | 0.23 |
|  | IGHV1-18 | IGLV 1-40 | 0.23 |
|  | IGHV3-21 | IGLV 2-14 | 0.23 |
|  | IGHV1-2 | IGLV 1-44 | 0.23 |
| 19 | IGHV3-23 | IGKV1-27 | 0.19 |
|  | IGHV3-23 | IGKV1-8 | 0.19 |
|  | IGHV3-30 | IGKV2-28/2D-28 | 0.19 |
|  | IGHV4-39 | IGKV1-33/1D-33 | 0.19 |
|  | IGHV4-39 | IGKV1-27 | 0.19 |
|  | IGHV4-59 | IGKV3-11 | 0.19 |
|  | IGHV5-51 | IGKV1-5 | 0.19 |
|  | IGHV5-51 | IGKV2-28/2D-28 | 0.19 |
|  | IGHV3-7 | IGKV3-11 | 0.19 |
|  | IGHV3-7 | IGKV2-30 | 0.19 |
|  | IGHV1-18 | IGKV3-15 | 0.19 |
|  | IGHV1-18 | IGKV3-11 | 0.19 |
|  | IGHV3-21 | IGKV4-1 | 0.19 |
|  | IGHV3-15 | IGKV3-15 | 0.19 |
|  | IGHV3-15 | IGKV4-1 | 0.19 |
|  | IGHV3-15 | IGKV1-33/1D-33 | 0.19 |
|  | IGHV4-31 | IGKV1-39/1D-39 | 0.19 |
|  | IGHV4-31 | IGKV1-5 | 0.19 |
|  | IGHV4-31 | IGKV3-15 | 0.19 |
|  | IGHV4-31 | IGKV2-28/2D-28 | 0.19 |
|  | IGHV3-33 | IGKV2-28/2D-28 | 0.19 |
|  | IGHV3-53 | IGKV4-1 | 0.19 |
|  | IGHV3-53 | IGKV3-11 | 0.19 |
|  | IGHV3-74 | IGKV3-20 | 0.19 |
|  | IGHV4-4 | IGKV1-5 | 0.19 |
|  | IGHV1-46 | IGKV1-9 | 0.19 |
|  | IGHV1-8 | IGKV3-15 | 0.19 |
|  | IGHV1-24 | IGKV3-11 | 0.19 |
|  | IGHV1-3 | IGKV1-39/1D-39 | 0.19 |
|  | IGHV3-49 | IGKV1-39/1D-39 | 0.19 |
|  | IGHV3-23 | IGLV 2-23 | 0.19 |
|  | IGHV3-30 | IGLV 1-44 | 0.19 |
|  | IGHV4-59 | IGLV 2-14 | 0.19 |
|  | IGHV4-59 | IGLV 1-44 | 0.19 |
|  | IGHV4-59 | IGLV 1-51 | 0.19 |
|  | IGHV4-34 | IGLV 2-8 | 0.19 |
|  | IGHV5-51 | IGLV 1-47 | 0.19 |
|  | IGHV1-69 | IGLV 2-8 | 0.19 |
|  | IGHV3-7 | IGLV 1-40 | 0.19 |
|  | IGHV3-15 | IGLV 1-44 | 0.19 |
|  | IGHV4-31 | IGLV 2-23 | 0.19 |
|  | IGHV3-33 | IGLV 2-14 | 0.19 |
|  | IGHV3-33 | IGLV 1-47 | 0.19 |
|  | IGHV3-33 | IGLV 2-23 | 0.19 |
|  | IGHV3-33 | IGLV 3-21 | 0.19 |
|  | IGHV3-9 | IGLV 1-44 | 0.19 |
|  | IGHV4-4 | IGLV 2-14 | 0.19 |
|  | IGHV1-46 | IGLV 1-51 | 0.19 |
|  | IGHV4-61 | IGLV 1-44 | 0.19 |
|  | IGHV1-8 | IGLV 2-14 | 0.19 |
|  | IGHV4-28 | IGLV 2-23 | 0.19 |
| 20 | IGHV3-23 | IGKV1-9 | 0.14 |
|  | IGHV3-23 | IGKV1-16 | 0.14 |
|  | IGHV4-39 | IGKV1-6 | 0.14 |
|  | IGHV4-59 | IGKV1-5 | 0.14 |
|  | IGHV4-59 | IGKV1-27 | 0.14 |
|  | IGHV4-34 | IGKV1-33/1D-33 | 0.14 |
|  | IGHV5-51 | IGKV1-33/1D-33 | 0.14 |
|  | IGHV1-69 | IGKV2-28/2D-28 | 0.14 |
|  | IGHV1-69 | IGKV1-33/1D-33 | 0.14 |
|  | IGHV3-7 | IGKV2-28/2D-28 | 0.14 |
|  | IGHV3-7 | IGKV1-8 | 0.14 |
|  | IGHV3-48 | IGKV2-28/2D-28 | 0.14 |
|  | IGHV3-48 | IGKV1-8 | 0.14 |
|  | IGHV3-15 | IGKV3-11 | 0.14 |
|  | IGHV3-15 | IGKV2-28/2D-28 | 0.14 |
|  | IGHV3-15 | IGKV1-9 | 0.14 |
|  | IGHV4-31 | IGKV1-33/1D-33 | 0.14 |
|  | IGHV1-2 | IGKV1-5 | 0.14 |
|  | IGHV1-2 | IGKV4-1 | 0.14 |
|  | IGHV3-11 | IGKV3-20 | 0.14 |
|  | IGHV3-11 | IGKV3-11 | 0.14 |
|  | IGHV3-11 | IGKV2-28/2D-28 | 0.14 |
|  | IGHV3-9 | IGKV1-39/1D-39 | 0.14 |
|  | IGHV3-9 | IGKV1-5 | 0.14 |
|  | IGHV3-9 | IGKV4-1 | 0.14 |
|  | IGHV3-9 | IGKV2D-29 | 0.14 |
|  | IGHV3-74 | IGKV1-39/1D-39 | 0.14 |
|  | IGHV3-74 | IGKV1-5 | 0.14 |

TABLE 6-continued

The 400 VH/VL germline gene pairs functionally tested are representative of the VH/VL germline gene pairs identified in the human immune repertoire

| pos | V heavy | V light | % |
|---|---|---|---|
| | IGHV3-74 | IGKV3-15 | 0.14 |
| | IGHV3-74 | IGKV4-1 | 0.14 |
| | IGHV4-4 | IGKV3-15 | 0.14 |
| | IGHV4-4 | IGKV4-1 | 0.14 |
| | IGHV4-4 | IGKV3-11 | 0.14 |
| | IGHV1-46 | IGKV1-5 | 0.14 |
| | IGHV1-46 | IGKV3-15 | 0.14 |
| | IGHV4-61 | IGKV1-39/1D-39 | 0.14 |
| | IGHV1-24 | IGKV1-39/1D-39 | 0.14 |
| | IGHV1-24 | IGKV3-15 | 0.14 |
| | IGHV1-3 | IGKV3-15 | 0.14 |
| | IGHV3-49 | IGKV1-17 | 0.14 |
| | IGHV3-43 | IGKV1-5 | 0.14 |
| | IGHV7-81 | IGKV3-20 | 0.14 |
| | IGHV3-13 | IGKV1-39/1D-39 | 0.14 |
| | IGHV3-23 | IGLV 1-51 | 0.14 |
| | IGHV3-30 | IGLV 3-21 | 0.14 |
| | IGHV3-30 | IGLV 3-1 | 0.14 |
| | IGHV4-39 | IGLV 1-47 | 0.14 |
| | IGHV4-39 | IGLV 2-18 | 0.14 |
| | IGHV4-59 | IGLV 1-47 | 0.14 |
| | IGHV5-51 | IGLV 2-23 | 0.14 |
| | IGHV5-51 | IGLV 3-21 | 0.14 |
| | IGHV1-69 | IGLV 2-23 | 0.14 |
| | IGHV3-7 | IGLV 1-44 | 0.14 |
| | IGHV3-7 | IGLV 1-51 | 0.14 |
| | IGHV3-7 | IGLV 1-47 | 0.14 |
| | IGHV3-7 | IGLV 3-21 | 0.14 |
| | IGHV1-18 | IGLV 1-44 | 0.14 |
| | IGHV1-18 | IGLV 1-51 | 0.14 |
| | IGHV3-48 | IGLV 3-1 | 0.14 |
| | IGHV3-21 | IGLV 1-47 | 0.14 |
| | IGHV3-15 | IGLV 7-46 | 0.14 |
| | IGHV4-31 | IGLV 1-40 | 0.14 |
| | IGHV4-31 | IGLV 1-51 | 0.14 |
| | IGHV4-31 | IGLV 1-47 | 0.14 |
| | IGHV1-2 | IGLV 1-51 | 0.14 |
| | IGHV1-2 | IGLV 2-23 | 0.14 |
| | IGHV1-2 | IGLV 3-1 | 0.14 |
| | IGHV3-11 | IGLV 2-14 | 0.14 |
| | IGHV3-11 | IGLV 1-44 | 0.14 |
| | IGHV3-11 | IGLV 2-11 | 0.14 |
| | IGHV3-11 | IGLV 3-1 | 0.14 |
| | IGHV3-9 | IGLV 1-47 | 0.14 |
| | IGHV3-9 | IGLV 2-11 | 0.14 |
| | IGHV3-74 | IGLV 2-23 | 0.14 |
| | IGHV3-74 | IGLV 3-21 | 0.14 |
| | IGHV4-4 | IGLV 1-40 | 0.14 |
| | IGHV1-46 | IGLV 2-14 | 0.14 |
| | IGHV1-46 | IGLV 1-44 | 0.14 |
| | IGHV4-61 | IGLV 2-14 | 0.14 |
| 21 | IGHV3-23 | IGKV2D-29 | 0.09 |
| | IGHV3-23 | IGKV2-29 | 0.09 |
| | IGHV3-23 | IGKV2-40/2D-40 | 0.09 |
| | IGHV3-30 | IGKV1-33/1D-33 | 0.09 |
| | IGHV3-30 | IGKV2-30 | 0.09 |
| | IGHV3-30 | IGKV1-8 | 0.09 |
| | IGHV3-30 | IGKV1-6 | 0.09 |
| | IGHV3-30 | IGKV2-24 | 0.09 |
| | IGHV3-30 | IGKV1D-8 | 0.09 |
| | IGHV4-39 | IGKV2-30 | 0.09 |
| | IGHV4-59 | IGKV1-33/1D-33 | 0.09 |
| | IGHV4-59 | IGKV1-12 | 0.09 |
| | IGHV4-34 | IGKV1-9 | 0.09 |
| | IGHV4-34 | IGKV1-17 | 0.09 |
| | IGHV4-34 | IGKV1-16 | 0.09 |
| | IGHV5-51 | IGKV2-30 | 0.09 |
| | IGHV1-69 | IGKV1-27 | 0.09 |
| | IGHV1-69 | IGKV1-8 | 0.09 |
| | IGHV1-69 | IGKV3D-15 | 0.09 |
| | IGHV3-7 | IGKV1-9 | 0.09 |
| | IGHV3-7 | IGKV1-17 | 0.09 |
| | IGHV3-7 | IGKV1-27 | 0.09 |
| | IGHV3-7 | IGKV1-13 | 0.09 |
| | IGHV1-18 | IGKV4-1 | 0.09 |
| | IGHV1-18 | IGKV2-30 | 0.09 |
| | IGHV3-48 | IGKV1-9 | 0.09 |
| | IGHV3-48 | IGKV1-17 | 0.09 |
| | IGHV3-48 | IGKV1-16 | 0.09 |
| | IGHV3-21 | IGKV3-11 | 0.09 |
| | IGHV3-21 | IGKV2-28/2D-28 | 0.09 |
| | IGHV3-21 | IGKV1-27 | 0.09 |
| | IGHV3-21 | IGKV1-8 | 0.09 |
| | IGHV3-21 | IGKV1-6 | 0.09 |
| | IGHV4-31 | IGKV4-1 | 0.09 |
| | IGHV4-31 | IGKV1-17 | 0.09 |
| | IGHV4-31 | IGKV1-27 | 0.09 |
| | IGHV1-2 | IGKV3-15 | 0.09 |
| | IGHV1-2 | IGKV2-28/2D-28 | 0.09 |
| | IGHV1-2 | IGKV1-27 | 0.09 |
| | IGHV3-33 | IGKV3-11 | 0.09 |
| | IGHV3-33 | IGKV1-33/1D-33 | 0.09 |
| | IGHV3-33 | IGKV1-9 | 0.09 |
| | IGHV3-53 | IGKV3-20 | 0.09 |
| | IGHV3-53 | IGKV1-27 | 0.09 |
| | IGHV3-53 | IGKV1-8 | 0.09 |
| | IGHV3-11 | IGKV4-1 | 0.09 |
| | IGHV3-11 | IGKV1-6 | 0.09 |
| | IGHV3-9 | IGKV3-15 | 0.09 |
| | IGHV3-9 | IGKV3-11 | 0.09 |
| | IGHV3-9 | IGKV1-16 | 0.09 |
| | IGHV3-74 | IGKV3-11 | 0.09 |
| | IGHV3-74 | IGKV2-30 | 0.09 |
| | IGHV4-4 | IGKV2-28/2D-28 | 0.09 |
| | IGHV4-4 | IGKV2D-29 | 0.09 |
| | IGHV1-46 | IGKV3-11 | 0.09 |
| | IGHV1-46 | IGKV1-27 | 0.09 |
| | IGHV1-46 | IGKV1-16 | 0.09 |
| | IGHV4-61 | IGKV3-15 | 0.09 |
| | IGHV1-8 | IGKV3-20 | 0.09 |
| | IGHV1-8 | IGKV4-1 | 0.09 |
| | IGHV1-24 | IGKV2-28/2D-28 | 0.09 |
| | IGHV1-24 | IGKV2-30 | 0.09 |
| | IGHV1-3 | IGKV3-20 | 0.09 |
| | IGHV3-49 | IGKV3-20 | 0.09 |
| | IGHV3-49 | IGKV1-5 | 0.09 |
| | IGHV3-43 | IGKV3-11 | 0.09 |
| | IGHV3-64 | IGKV1-5 | 0.09 |
| | IGHV3-64 | IGKV3-11 | 0.09 |
| | IGHV7-81 | IGKV1-39/1D-39 | 0.09 |
| | IGHV3-13 | IGKV4-1 | 0.09 |
| | IGHV3-72 | IGKV1-5 | 0.09 |
| | IGHV3-72 | IGKV3-15 | 0.09 |
| | IGHV1-58 | IGKV3-20 | 0.09 |
| | IGHV3-66 | IGKV1-39/1D-39 | 0.09 |
| | IGHV3-23 | IGLV 1-36 | 0.09 |
| | IGHV3-30 | IGLV 2-23 | 0.09 |
| | IGHV3-30 | IGLV 2-11 | 0.09 |
| | IGHV3-30 | IGLV 9-49 | 0.09 |
| | IGHV3-30 | IGLV 3-10 | 0.09 |
| | IGHV4-39 | IGLV 3-1 | 0.09 |
| | IGHV4-39 | IGLV 6-57 | 0.09 |
| | IGHV4-59 | IGLV 2-23 | 0.09 |
| | IGHV4-59 | IGLV 3-21 | 0.09 |
| | IGHV4-59 | IGLV 2-11 | 0.09 |
| | IGHV4-34 | IGLV 1-44 | 0.09 |
| | IGHV4-34 | IGLV 2-23 | 0.09 |
| | IGHV4-34 | IGLV 3-21 | 0.09 |
| | IGHV4-34 | IGLV 3-25 | 0.09 |
| | IGHV5-51 | IGLV 1-36 | 0.09 |
| | IGHV5-51 | IGLV 3-25 | 0.09 |
| | IGHV1-69 | IGLV 1-47 | 0.09 |
| | IGHV1-69 | IGLV 3-21 | 0.09 |
| | IGHV1-69 | IGLV 3-1 | 0.09 |
| | IGHV3-7 | IGLV 2-14 | 0.09 |
| | IGHV1-18 | IGLV 2-8 | 0.09 |
| | IGHV1-18 | IGLV 6-57 | 0.09 |
| | IGHV3-48 | IGLV 2-11 | 0.09 |

TABLE 6-continued

The 400 VH/VL germline gene pairs functionally tested are representative of the VH/VL germline gene pairs identified in the human immune repertoire

| pos | V heavy | V light | % |
|---|---|---|---|
| | IGHV3-21 | IGLV 1-40 | 0.09 |
| | IGHV3-21 | IGLV 1-44 | 0.09 |
| | IGHV3-21 | IGLV 3-21 | 0.09 |
| | IGHV3-21 | IGLV 2-11 | 0.09 |
| | IGHV3-21 | IGLV 4-69 | 0.09 |
| | IGHV3-15 | IGLV 1-40 | 0.09 |
| | IGHV3-15 | IGLV 1-51 | 0.09 |
| | IGHV3-15 | IGLV 3-1 | 0.09 |
| | IGHV3-15 | IGLV 2-8 | 0.09 |
| | IGHV3-15 | IGLV 7-43 | 0.09 |
| | IGHV4-31 | IGLV 3-21 | 0.09 |
| | IGHV1-2 | IGLV 2-8 | 0.09 |
| | IGHV1-2 | IGLV 7-46 | 0.09 |
| | IGHV3-33 | IGLV 6-57 | 0.09 |
| | IGHV3-53 | IGLV 2-14 | 0.09 |
| | IGHV3-11 | IGLV 2-23 | 0.09 |
| | IGHV3-11 | IGLV 3-21 | 0.09 |
| | IGHV3-11 | IGLV 4-69 | 0.09 |
| | IGHV3-9 | IGLV 3-21 | 0.09 |
| | IGHV3-9 | IGLV 2-8 | 0.09 |
| | IGHV3-74 | IGLV 2-14 | 0.09 |
| | IGHV4-4 | IGLV 1-51 | 0.09 |
| | IGHV4-4 | IGLV 2-23 | 0.09 |
| | IGHV4-4 | IGLV 2-8 | 0.09 |
| | IGHV1-46 | IGLV 2-11 | 0.09 |
| | IGHV4-61 | IGLV 2-11 | 0.09 |
| | IGHV1-8 | IGLV 1-47 | 0.09 |
| | IGHV1-24 | IGLV 2-23 | 0.09 |
| | IGHV1-3 | IGLV 2-14 | 0.09 |
| | IGHV1-3 | IGLV 2-23 | 0.09 |
| | IGHV1-3 | IGLV 3-1 | 0.09 |
| | IGHV3-49 | IGLV 3-21 | 0.09 |
| | IGHV4-28 | IGLV 1-44 | 0.09 |
| | IGHV4-28 | IGLV 1-51 | 0.09 |
| | IGHV4-28 | IGLV 1-36 | 0.09 |
| | IGHV3-43 | IGLV 1-51 | 0.09 |
| | IGHV3-64 | IGLV 3-21 | 0.09 |
| | IGHV7-81 | IGLV 2-14 | 0.09 |
| | IGHV7-81 | IGLV 3-21 | 0.09 |
| 22 | IGHV3-23 | IGKV2-30 | 0.05 |
| | IGHV3-23 | IGKV1-12 | 0.05 |
| | IGHV3-23 | IGKV3D-20 | 0.05 |
| | IGHV3-23 | IGKV1D-12 | 0.05 |
| | IGHV3-23 | IGKV1D-13 | 0.05 |
| | IGHV3-30 | IGKV1-17 | 0.05 |
| | IGHV3-30 | IGKV1-27 | 0.05 |
| | IGHV3-30 | IGKV1-16 | 0.05 |
| | IGHV3-30 | IGKV2D-29 | 0.05 |
| | IGHV3-30 | IGKV1-13 | 0.05 |
| | IGHV3-30 | IGKV5-2 | 0.05 |
| | IGHV3-30 | IGKV2D-30 | 0.05 |
| | IGHV4-39 | IGKV1-17 | 0.05 |
| | IGHV4-39 | IGKV3D-15 | 0.05 |
| | IGHV4-59 | IGKV2-30 | 0.05 |
| | IGHV4-59 | IGKV1-17 | 0.05 |
| | IGHV4-59 | IGKV1-8 | 0.05 |
| | IGHV4-59 | IGKV1-16 | 0.05 |
| | IGHV4-59 | IGKV1D-43 | 0.05 |
| | IGHV4-59 | IGKV2D-30 | 0.05 |
| | IGHV4-59 | IGKV1D-17 | 0.05 |
| | IGHV4-34 | IGKV1-27 | 0.05 |
| | IGHV4-34 | IGKV1-8 | 0.05 |
| | IGHV4-34 | IGKV1-12 | 0.05 |
| | IGHV5-51 | IGKV1-9 | 0.05 |
| | IGHV5-51 | IGKV1-17 | 0.05 |
| | IGHV5-51 | IGKV1-27 | 0.05 |
| | IGHV5-51 | IGKV1-12 | 0.05 |
| | IGHV1-69 | IGKV2-30 | 0.05 |
| | IGHV1-69 | IGKV1-16 | 0.05 |
| | IGHV1-69 | IGKV1-6 | 0.05 |
| | IGHV1-69 | IGKV2D-29 | 0.05 |
| | IGHV1-69 | IGKV2D-30 | 0.05 |
| | IGHV1-69 | IGKV1D-16 | 0.05 |
| | IGHV3-7 | IGKV1-6 | 0.05 |
| | IGHV3-7 | IGKV1D-8 | 0.05 |
| | IGHV3-7 | IGKV1D-17 | 0.05 |
| | IGHV1-18 | IGKV1-17 | 0.05 |
| | IGHV1-18 | IGKV1-8 | 0.05 |
| | IGHV1-18 | IGKV1-16 | 0.05 |
| | IGHV1-18 | IGKV1-12 | 0.05 |
| | IGHV1-18 | IGKV1-13 | 0.05 |
| | IGHV1-18 | IGKV2-40/2D-40 | 0.05 |
| | IGHV3-48 | IGKV1-5 | 0.05 |
| | IGHV3-48 | IGKV1-27 | 0.05 |
| | IGHV3-48 | IGKV1-6 | 0.05 |
| | IGHV3-48 | IGKV2D-29 | 0.05 |
| | IGHV3-48 | IGKV3D-20 | 0.05 |
| | IGHV3-48 | IGKV1D-12 | 0.05 |
| | IGHV3-21 | IGKV2D-29 | 0.05 |
| | IGHV3-15 | IGKV2-30 | 0.05 |
| | IGHV3-15 | IGKV1-27 | 0.05 |
| | IGHV3-15 | IGKV2D-29 | 0.05 |
| | IGHV3-15 | IGKV1-13 | 0.05 |
| | IGHV3-15 | IGKV1D-43 | 0.05 |
| | IGHV4-31 | IGKV1-6 | 0.05 |
| | IGHV4-31 | IGKV2-29 | 0.05 |
| | IGHV4-31 | IGKV2-40/2D-40 | 0.05 |
| | IGHV1-2 | IGKV1-33/1D-33 | 0.05 |
| | IGHV1-2 | IGKV2-30 | 0.05 |
| | IGHV1-2 | IGKV1-8 | 0.05 |
| | IGHV1-2 | IGKV1-6 | 0.05 |
| | IGHV3-33 | IGKV1-17 | 0.05 |
| | IGHV3-33 | IGKV1-8 | 0.05 |
| | IGHV3-33 | IGKV1-16 | 0.05 |
| | IGHV3-33 | IGKV2-24 | 0.05 |
| | IGHV3-53 | IGKV2-28/2D-28 | 0.05 |
| | IGHV3-53 | IGKV1-9 | 0.05 |
| | IGHV3-53 | IGKV1-17 | 0.05 |
| | IGHV3-53 | IGKV1-12 | 0.05 |
| | IGHV3-53 | IGKV2-29 | 0.05 |
| | IGHV3-53 | IGKV1D-16 | 0.05 |
| | IGHV3-11 | IGKV1-33/1D-33 | 0.05 |
| | IGHV3-11 | IGKV1-9 | 0.05 |
| | IGHV3-11 | IGKV1-17 | 0.05 |
| | IGHV3-11 | IGKV1-12 | 0.05 |
| | IGHV3-11 | IGKV1D-8 | 0.05 |
| | IGHV3-9 | IGKV3-20 | 0.05 |
| | IGHV3-9 | IGKV2-28/2D-28 | 0.05 |
| | IGHV3-9 | IGKV1-17 | 0.05 |
| | IGHV3-9 | IGKV1-27 | 0.05 |
| | IGHV3-9 | IGKV1-8 | 0.05 |
| | IGHV3-9 | IGKV1-12 | 0.05 |
| | IGHV3-9 | IGKV1D-8 | 0.05 |
| | IGHV4-4 | IGKV1-17 | 0.05 |
| | IGHV4-4 | IGKV1-27 | 0.05 |
| | IGHV4-4 | IGKV1-6 | 0.05 |
| | IGHV4-4 | IGKV1D-8 | 0.05 |
| | IGHV1-46 | IGKV4-1 | 0.05 |
| | IGHV1-46 | IGKV1-33/1D-33 | 0.05 |
| | IGHV1-46 | IGKV1-8 | 0.05 |
| | IGHV4-61 | IGKV3-11 | 0.05 |
| | IGHV4-61 | IGKV2-28/2D-28 | 0.05 |
| | IGHV4-61 | IGKV1-16 | 0.05 |
| | IGHV4-61 | IGKV1-12 | 0.05 |
| | IGHV4-61 | IGKV1-13 | 0.05 |
| | IGHV1-8 | IGKV1-39/1D-39 | 0.05 |
| | IGHV1-8 | IGKV1-5 | 0.05 |
| | IGHV1-8 | IGKV3-11 | 0.05 |
| | IGHV1-8 | IGKV2-28/2D-28 | 0.05 |
| | IGHV1-8 | IGKV1-33/1D-33 | 0.05 |
| | IGHV1-8 | IGKV1-9 | 0.05 |
| | IGHV1-8 | IGKV2-29 | 0.05 |
| | IGHV1-24 | IGKV3-20 | 0.05 |
| | IGHV1-24 | IGKV4-1 | 0.05 |
| | IGHV1-24 | IGKV1-33/1D-33 | 0.05 |
| | IGHV1-24 | IGKV2-24 | 0.05 |
| | IGHV1-24 | IGKV2-40/2D-40 | 0.05 |
| | IGHV1-3 | IGKV1-5 | 0.05 |

TABLE 6-continued

The 400 VH/VL germline gene pairs functionally tested are representative of the VH/VL germline gene pairs identified in the human immune repertoire

| pos | V heavy | V light | % |
|---|---|---|---|
| | IGHV1-3 | IGKV1-33/1D-33 | 0.05 |
| | IGHV1-3 | IGKV2-30 | 0.05 |
| | IGHV1-3 | IGKV1-6 | 0.05 |
| | IGHV1-3 | IGKV2D-29 | 0.05 |
| | IGHV3-49 | IGKV3-15 | 0.05 |
| | IGHV3-49 | IGKV3-11 | 0.05 |
| | IGHV3-49 | IGKV2-28/2D-28 | 0.05 |
| | IGHV4-28 | IGKV3-20 | 0.05 |
| | IGHV4-28 | IGKV1-39/1D-39 | 0.05 |
| | IGHV3-43 | IGKV3-15 | 0.05 |
| | IGHV3-43 | IGKV4-1 | 0.05 |
| | IGHV3-43 | IGKV2-28/2D-28 | 0.05 |
| | IGHV3-43 | IGKV1-33/1D-33 | 0.05 |
| | IGHV3-64 | IGKV3-15 | 0.05 |
| | IGHV3-64 | IGKV1-9 | 0.05 |
| | IGHV3-64 | IGKV2D-29 | 0.05 |
| | IGHV7-81 | IGKV1-5 | 0.05 |
| | IGHV7-81 | IGKV4-1 | 0.05 |
| | IGHV7-81 | IGKV2-28/2D-28 | 0.05 |
| | IGHV3-13 | IGKV1-5 | 0.05 |
| | IGHV3-13 | IGKV1-33/1D-33 | 0.05 |
| | IGHV3-13 | IGKV1-9 | 0.05 |
| | IGHV3-13 | IGKV2-30 | 0.05 |
| | IGHV3-72 | IGKV3-20 | 0.05 |
| | IGHV3-72 | IGKV1-9 | 0.05 |
| | IGHV3-72 | IGKV1-17 | 0.05 |
| | IGHV3-72 | IGKV1-16 | 0.05 |
| | IGHV3-73 | IGKV2-28/2D-28 | 0.05 |
| | IGHV3-73 | IGKV1-9 | 0.05 |
| | IGHV1-58 | IGKV1-5 | 0.05 |
| | IGHV1-58 | IGKV4-1 | 0.05 |
| | IGHV1-58 | IGKV3-11 | 0.05 |
| | IGHV4-30.2 | IGKV1-39/1D-39 | 0.05 |
| | IGHV4-30.2 | IGKV4-1 | 0.05 |
| | IGHV7-4.1 | IGKV1-39/1D-39 | 0.05 |
| | IGHV7-4.1 | IGKV1-5 | 0.05 |
| | IGHV3-20 | IGKV1-39/1D-39 | 0.05 |
| | IGHV3-23 | IGLV 1-47 | 0.05 |
| | IGHV3-23 | IGLV 2-8 | 0.05 |
| | IGHV3-23 | IGLV 7-43 | 0.05 |
| | IGHV3-23 | IGLV 2-18 | 0.05 |
| | IGHV3-23 | IGLV 3-19 | 0.05 |
| | IGHV3-30 | IGLV 1-47 | 0.05 |
| | IGHV3-30 | IGLV 2-8 | 0.05 |
| | IGHV3-30 | IGLV 6-57 | 0.05 |
| | IGHV3-30 | IGLV 3-27 | 0.05 |
| | IGHV4-39 | IGLV 7-46 | 0.05 |
| | IGHV4-39 | IGLV 3-9 | 0.05 |
| | IGHV4-59 | IGLV 2-8 | 0.05 |
| | IGHV4-59 | IGLV 6-57 | 0.05 |
| | IGHV4-59 | IGLV 3-12 | 0.05 |
| | IGHV4-34 | IGLV 2-11 | 0.05 |
| | IGHV4-34 | IGLV 1-36 | 0.05 |
| | IGHV4-34 | IGLV 7-43 | 0.05 |
| | IGHV4-34 | IGLV 9-49 | 0.05 |
| | IGHV5-51 | IGLV 7-43 | 0.05 |
| | IGHV1-69 | IGLV 6-57 | 0.05 |
| | IGHV1-69 | IGLV 3-25 | 0.05 |
| | IGHV1-69 | IGLV 3-10 | 0.05 |
| | IGHV3-7 | IGLV 2-23 | 0.05 |
| | IGHV3-7 | IGLV 3-1 | 0.05 |
| | IGHV3-7 | IGLV 2-8 | 0.05 |
| | IGHV3-7 | IGLV 7-46 | 0.05 |
| | IGHV3-7 | IGLV 3-27 | 0.05 |
| | IGHV1-18 | IGLV 2-23 | 0.05 |
| | IGHV1-18 | IGLV 2-11 | 0.05 |
| | IGHV1-18 | IGLV 1-36 | 0.05 |
| | IGHV1-18 | IGLV 3-25 | 0.05 |
| | IGHV1-18 | IGLV 3-10 | 0.05 |
| | IGHV3-48 | IGLV 1-40 | 0.05 |
| | IGHV3-48 | IGLV 1-44 | 0.05 |
| | IGHV3-48 | IGLV 1-51 | 0.05 |
| | IGHV3-48 | IGLV 2-23 | 0.05 |
| | IGHV3-48 | IGLV 3-21 | 0.05 |
| | IGHV3-48 | IGLV 3-25 | 0.05 |
| | IGHV3-48 | IGLV 7-46 | 0.05 |
| | IGHV3-48 | IGLV 9-49 | 0.05 |
| | IGHV3-21 | IGLV 2-23 | 0.05 |
| | IGHV3-21 | IGLV 3-1 | 0.05 |
| | IGHV3-21 | IGLV 2-8 | 0.05 |
| | IGHV3-21 | IGLV 6-57 | 0.05 |
| | IGHV3-21 | IGLV 3-25 | 0.05 |
| | IGHV3-21 | IGLV 7-46 | 0.05 |
| | IGHV3-15 | IGLV 2-14 | 0.05 |
| | IGHV3-15 | IGLV 1-47 | 0.05 |
| | IGHV3-15 | IGLV 2-23 | 0.05 |
| | IGHV3-15 | IGLV 3-21 | 0.05 |
| | IGHV3-15 | IGLV 6-57 | 0.05 |
| | IGHV3-15 | IGLV 3-25 | 0.05 |
| | IGHV3-15 | IGLV 2-18 | 0.05 |
| | IGHV3-15 | IGLV 3-22 | 0.05 |
| | IGHV4-31 | IGLV 1-44 | 0.05 |
| | IGHV4-31 | IGLV 2-11 | 0.05 |
| | IGHV4-31 | IGLV 3-1 | 0.05 |
| | IGHV4-31 | IGLV 4-69 | 0.05 |
| | IGHV4-31 | IGLV 7-43 | 0.05 |
| | IGHV1-2 | IGLV 3-21 | 0.05 |
| | IGHV1-2 | IGLV 2-11 | 0.05 |
| | IGHV1-2 | IGLV 3-27 | 0.05 |
| | IGHV3-33 | IGLV 1-40 | 0.05 |
| | IGHV3-33 | IGLV 1-44 | 0.05 |
| | IGHV3-33 | IGLV 1-51 | 0.05 |
| | IGHV3-33 | IGLV 2-11 | 0.05 |
| | IGHV3-33 | IGLV 3-1 | 0.05 |
| | IGHV3-33 | IGLV 4-69 | 0.05 |
| | IGHV3-33 | IGLV 3-27 | 0.05 |
| | IGHV3-33 | IGLV 9-49 | 0.05 |
| | IGHV3-33 | IGLV 3-9 | 0.05 |
| | IGHV3-53 | IGLV 1-51 | 0.05 |
| | IGHV3-53 | IGLV 1-47 | 0.05 |
| | IGHV3-53 | IGLV 2-23 | 0.05 |
| | IGHV3-53 | IGLV 2-11 | 0.05 |
| | IGHV3-53 | IGLV 3-1 | 0.05 |
| | IGHV3-53 | IGLV 2-8 | 0.05 |
| | IGHV3-53 | IGLV 7-46 | 0.05 |
| | IGHV3-11 | IGLV 1-40 | 0.05 |
| | IGHV3-11 | IGLV 1-51 | 0.05 |
| | IGHV3-11 | IGLV 1-47 | 0.05 |
| | IGHV3-11 | IGLV 2-8 | 0.05 |
| | IGHV3-11 | IGLV 3-25 | 0.05 |
| | IGHV3-11 | IGLV 7-46 | 0.05 |
| | IGHV3-11 | IGLV 9-49 | 0.05 |
| | IGHV3-11 | IGLV 8-61 | 0.05 |
| | IGHV3-9 | IGLV 1-40 | 0.05 |
| | IGHV3-9 | IGLV 1-51 | 0.05 |
| | IGHV3-9 | IGLV 4-69 | 0.05 |
| | IGHV3-9 | IGLV 4-60 | 0.05 |
| | IGHV3-74 | IGLV 1-47 | 0.05 |
| | IGHV3-74 | IGLV 2-11 | 0.05 |
| | IGHV3-74 | IGLV 3-1 | 0.05 |
| | IGHV3-74 | IGLV 2-8 | 0.05 |
| | IGHV3-74 | IGLV 7-43 | 0.05 |
| | IGHV3-74 | IGLV 7-46 | 0.05 |
| | IGHV4-4 | IGLV 2-11 | 0.05 |
| | IGHV4-4 | IGLV 3-1 | 0.05 |
| | IGHV4-4 | IGLV 3-25 | 0.05 |
| | IGHV4-4 | IGLV 9-49 | 0.05 |
| | IGHV1-46 | IGLV 1-40 | 0.05 |
| | IGHV1-46 | IGLV 1-47 | 0.05 |
| | IGHV1-46 | IGLV 2-23 | 0.05 |
| | IGHV1-46 | IGLV 3-21 | 0.05 |
| | IGHV1-46 | IGLV 6-57 | 0.05 |
| | IGHV4-61 | IGLV 2-23 | 0.05 |
| | IGHV4-61 | IGLV 3-21 | 0.05 |
| | IGHV4-61 | IGLV 3-1 | 0.05 |
| | IGHV4-61 | IGLV 7-43 | 0.05 |
| | IGHV1-8 | IGLV 1-51 | 0.05 |
| | IGHV1-8 | IGLV 2-11 | 0.05 |

TABLE 6-continued

The 400 VH/VL germline gene pairs functionally tested are representative of the VH/VL germline gene pairs identified in the human immune repertoire

| pos | V heavy | V light | % |
|---|---|---|---|
| | IGHV1-8 | IGLV 2-8 | 0.05 |
| | IGHV1-8 | IGLV 9-49 | 0.05 |
| | IGHV1-24 | IGLV 2-14 | 0.05 |
| | IGHV1-24 | IGLV 1-40 | 0.05 |
| | IGHV1-24 | IGLV 1-44 | 0.05 |
| | IGHV1-24 | IGLV 3-21 | 0.05 |
| | IGHV1-24 | IGLV 2-11 | 0.05 |
| | IGHV1-3 | IGLV 1-40 | 0.05 |
| | IGHV3-49 | IGLV 2-14 | 0.05 |
| | IGHV3-49 | IGLV 1-40 | 0.05 |
| | IGHV3-49 | IGLV 2-23 | 0.05 |
| | IGHV3-49 | IGLV 2-8 | 0.05 |
| | IGHV4-28 | IGLV 2-14 | 0.05 |
| | IGHV3-43 | IGLV 2-14 | 0.05 |
| | IGHV3-43 | IGLV 2-11 | 0.05 |
| | IGHV3-43 | IGLV 3-1 | 0.05 |
| | IGHV3-43 | IGLV 1-36 | 0.05 |
| | IGHV3-43 | IGLV 9-49 | 0.05 |
| | IGHV3-64 | IGLV 2-14 | 0.05 |
| | IGHV3-64 | IGLV 7-43 | 0.05 |
| | IGHV7-81 | IGLV 1-40 | 0.05 |
| | IGHV3-13 | IGLV 1-40 | 0.05 |
| | IGHV3-13 | IGLV 1-47 | 0.05 |
| | IGHV3-72 | IGLV 1-51 | 0.05 |
| | IGHV3-72 | IGLV 4-69 | 0.05 |
| | IGHV3-73 | IGLV 1-40 | 0.05 |
| | IGHV3-73 | IGLV 1-51 | 0.05 |
| | IGHV3-73 | IGLV 1-47 | 0.05 |
| | IGHV3-73 | IGLV 2-11 | 0.05 |
| | IGHV3-73 | IGLV 6-57 | 0.05 |
| | IGHV1-58 | IGLV 2-14 | 0.05 |
| | IGHV3-66 | IGLV 1-44 | 0.05 |
| | IGHV3-66 | IGLV 1-47 | 0.05 |
| | IGHV3-66 | IGLV 3-25 | 0.05 |
| | IGHV4-30.2 | IGLV 3-21 | 0.05 |
| | IGHV7-4.1 | IGLV 1-51 | 0.05 |
| | IGHV3-20 | IGLV 2-14 | 0.05 |

"pos": represents the position of relative ranking of the VH/VL pairs as determined by the percentage (%) of each VH/VL pair from the total pooled data.
N = 2137 B cells

Example 5

Generation of Germline Genes for Functional Analysis

As a next step, the VH, Vλ, and Vκ germline genes selected for combination and subsequent testing, as shown in Table 5, were sent to Geneart (Regensburg, Germany) for codon optimization respective to E. coli expression (neutral to mammalian expression with no rare human codons), gene optimization to remove potential inhibitory or splice motifs and synthesis.

The germline protein sequences of each of the VH, Vλ, and Vκ germline genes are shown in FIGS. 6-8. Each germline gene sequence was synthesized as follows:

a) for VH: leader sequence (modified phoA signal sequence incorporating a NheI restriction site as shown in Table 1); germline FR1, CDR1, FR2, CDR2 and FR3 (incorporating a BssHII restriction site (GCGCGC) as shown in FIG. 1); CDR-H3 (WGGDGFYAMDY) (SEQ ID NO: 1) of the 4D5 antibody as used in Ewert S. et al., J. Mol. Biol. (2003) 325, 531-553; and the JH4 FR4 (incorporating a XhoI (CTCGAG) restriction site as shown in FIG. 1);

b) for Vk: leader sequence (modified ompA signal sequence incorporating the NdeI restriction site as shown in Table 2); germline FR1, CDR1, FR2, CDR2 and FR3 (incorporating a BbsI restriction site (GAAGAC) as shown in FIG. 1), kappa-like CDR-L3 (QQHYTTPPT) (SEQ ID NO: 2) according to Ewert S. et al., J. Mol. Biol. (2003) 325, 531-553; and the Jk1 FR4 (incorporating a KpnI/Acc65I RE site (GGTACC) as shown in FIG. 1);

c) for Vλ: leader sequence (modified ompA signal sequence incorporating the NdeI restriction site as shown in Table 2); germline FR1, CDR1, FR2, CDR2 and FR3 (incorporating a BbsI restriction site (GAAGAC) as shown in FIG. 1), lambda-like CDR-L3 (QSYDSSLSGVV) (SEQ ID NO: 3) according to Ewert S. et al., J. Mol. Biol. (2003) 325, 531-553; and the JI2/3 FR4 (incorporating a KpnI/Acc65I RE site (GGTACC) as shown in FIG. 1).

Example 6

Functional Testing of Germline Protein Pairs Representative of the Human Immune Repertoire The 400 Germline protein pairs were then inserted into phage display, E. Coli and mammalian expression vectors either in Fab or human IgG1 format and then tested for the following properties: a) relative display after phage production and phage ELISA in Fab format; b) relative Fab expression yield after Fab production in E. coli, E. coli cell lysis and ELISA detection of produced Fab; c) temperature stability of Fab after Fab production in E. coli, E. coli cell lysis and ELISA detection of non-denatured Fab after incubation at increased temperatures; d) bovine/mouse serum stability of Fab from E. coli lysates by ELISA detection of non-denatured Fab after incubation in bovine/mouse serum; e) relative human IgG1 expression yield after IgG1 production in mammalian cells and ELISA detection of secreted IgG1 from cell culture supernatants; and f) bovine serum stability of human IgG1 by ELISA detection of non-denatured IgG after incubation in bovine/mouse serum.

Example 6.1

Generation of Fab Pool Displayed on Phage for Functional Characterization

Figure 9:
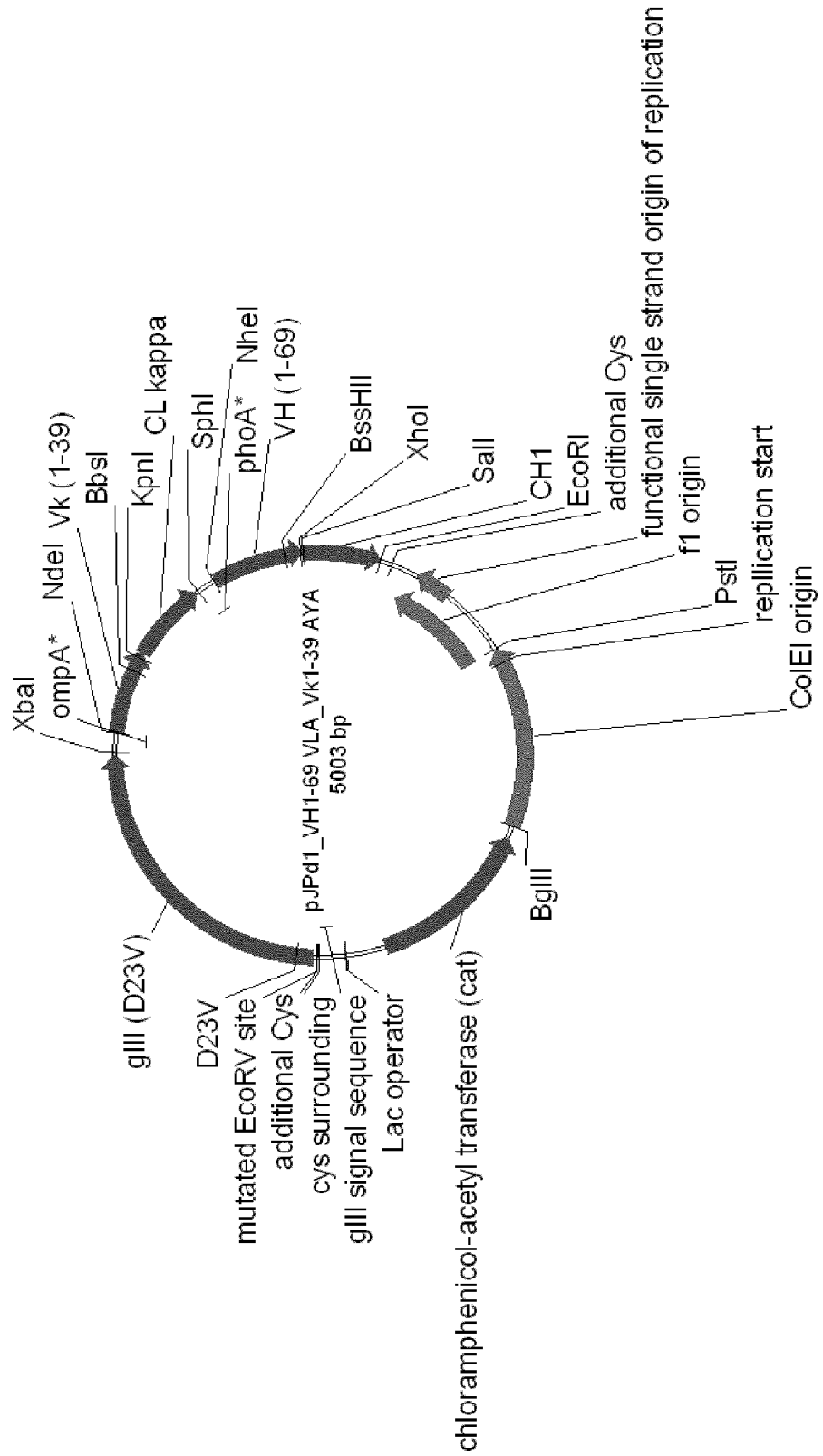
FIG. 9 shows the pJPd1 Fab tricistronic phage display vector.

The antibody or antibody fragments synthesized in Example 5, shown in Table 5, were cloned into the tricistronic Fab display vector pJPd1 (FIG. 9) for functional testing. Fab pools were generated that contained combinations of each of the master genes, the 20 VH, combined with the 8 Vλ and 12 Vκ, yielding the 400 combinations shown in Table 6.

Figure 12:
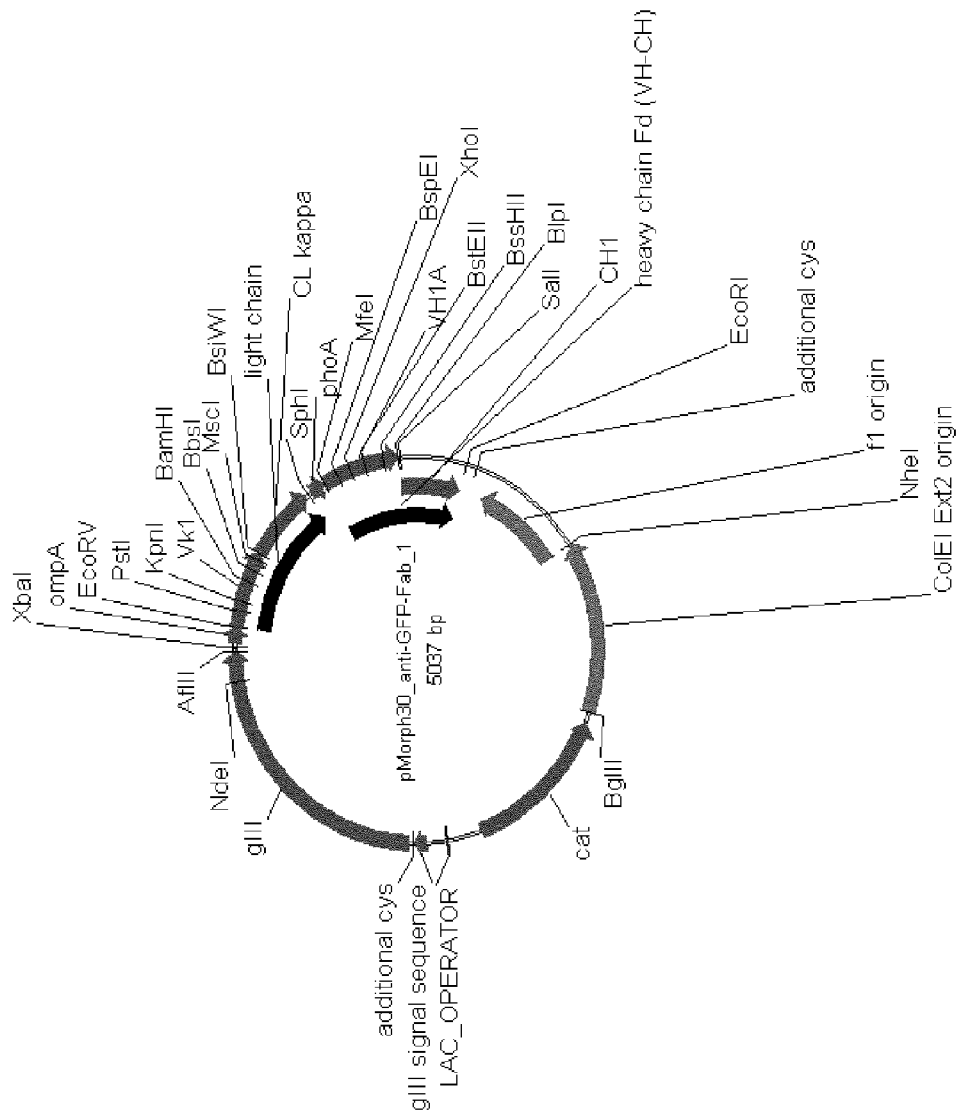
FIG. 12 shows the pMORPH30 Fab display vector.

Phage comprising the above gene pairs were produced in a small scale using 96 well plates. A master plate was generated by filling each of the wells with 2xYT/CAM/TET/Gluc medium and inoculating with clones from the 400 VH/VL combinations wherein pMORPH30_Vk3-11_AQA/VH3-23_TKA or pMORPH30_Vk3-11_AYA/VH3-23_VLA (pMORPH30 is shown in FIG. 12) were used as a control. The plates were incubated overnight at 37° C. while shaking. The master plates were stored in a final concentration of 15% glycerol, and frozen at −80° C.

Additional 96 well plates were produced for phage production using 2xYT/CAM/TET/Gluc as medium and inoculated with clones from the master plates described above. The plates were incubated at 37° C. for ~2-4 h while shaking at 400 rpm, until an OD600 nm of ~0.5 was reached.

The plates were infected with 5 μl helper phage per well (Hyperphage; PROGEN; 1×1012 pfu/ml). The plates were incubated at 37° C. for 45 min without shaking and then for 60 min while shaking at 400 rpm. The bacteria were spun down at 2200 g for 5 min at 4° C.

The helper phage containing supernatants were discarded and the infected *E. coli* pellets were re-suspended with 2xYT/Cam/TET/Kan/IPTG without glucose. The re-suspended pellets were transferred into a new 96 deep well plate pre-filled with 2xYT/Cm/TET/Kan/IPTG. The plates were incubated overnight at 22° C., while shaking. The phage containing supernatants were harvested by spinning down and discarding *E. coli* cells and debris.

Example 6.2

Evaluation of Fab Phage Display Ranking Using ELISA

The phage supernatants prepared as described in Example 6.1 were used for Fab phage display ranking in phage ELISAs. Display of the Fab fragments was evaluated in a phage ELISA using two different capture antibodies:
(1) The anti-M13 antibody (Amersham #27-9420-01) was used for capture of phage particles via the major coat protein g8p; therefore, phage titer can be determined.
(2) An anti-Fd antibody (The Binding Site #PC075) was used, which binds to the displayed Fab; therefore, only phage displaying Fabs comprising the master genes, are captured.

The respective capture antibodies were immobilized on black 96-well Maxisorp™ plates by dispensing 100 µl antibody solution at a concentration of 7.5 µg/ml for the anti-M13 antibody and a 1.0 µg/ml concentration for the anti-Fd antibody into different wells, sealing the plate with laminated foil and incubating overnight at 4° C. The next day, the plates were washed twice with TBST, and each well was blocked with 300 µl CTBST for 1 h at room temperature.

Both the phage supernatants and reference samples were transferred for detection as follows. The blocked ELISA plates were washed twice with TBST. 100 µl of appropriately diluted phage supernatants in CTBST was transferred from the dilution plates to the coated ELISA plates, incubated for 1-2 h at room temperature, and washed 5x with TBST. 100 µl/well of anti-M13 peroxidase conjugate (Amersham) diluted 1:5000 in CTBST was added, and incubated for 1-2 h at room temperature. The Quanta Blu (Pierce) working solution was prepared by mixing 1 part (e.g. 0.5 ml) peroxide solution with 9 parts (e.g. 4.5 ml) substrate solution and equilibrating it to room temperature for at least 30 min. The ELISA plates were washed 5x with TBST, 100 µl/well of the Quanta Blu working solution was added. The fluorescence was measured after an incubation time of ~2 min (excitation: 320 nm, emission: 430 nm) and subsequently at intervals of 5 min.

The evaluation of the ELISA data was completed as follows: calibration curves were created by using a HuCAL GOLD reference phage preparation (VH3 kappa+lambda) and the titers of the phage supernatants and controls were calculated. For each sample, the titer on anti-Fd was divided by the titer on anti-M13 (anti-pVIII), the resulting ratio is the relative display rate. Table 12 shows the relative display rates for most of the 400 Germline protein pairs.

Example 6.3

Figure 10:
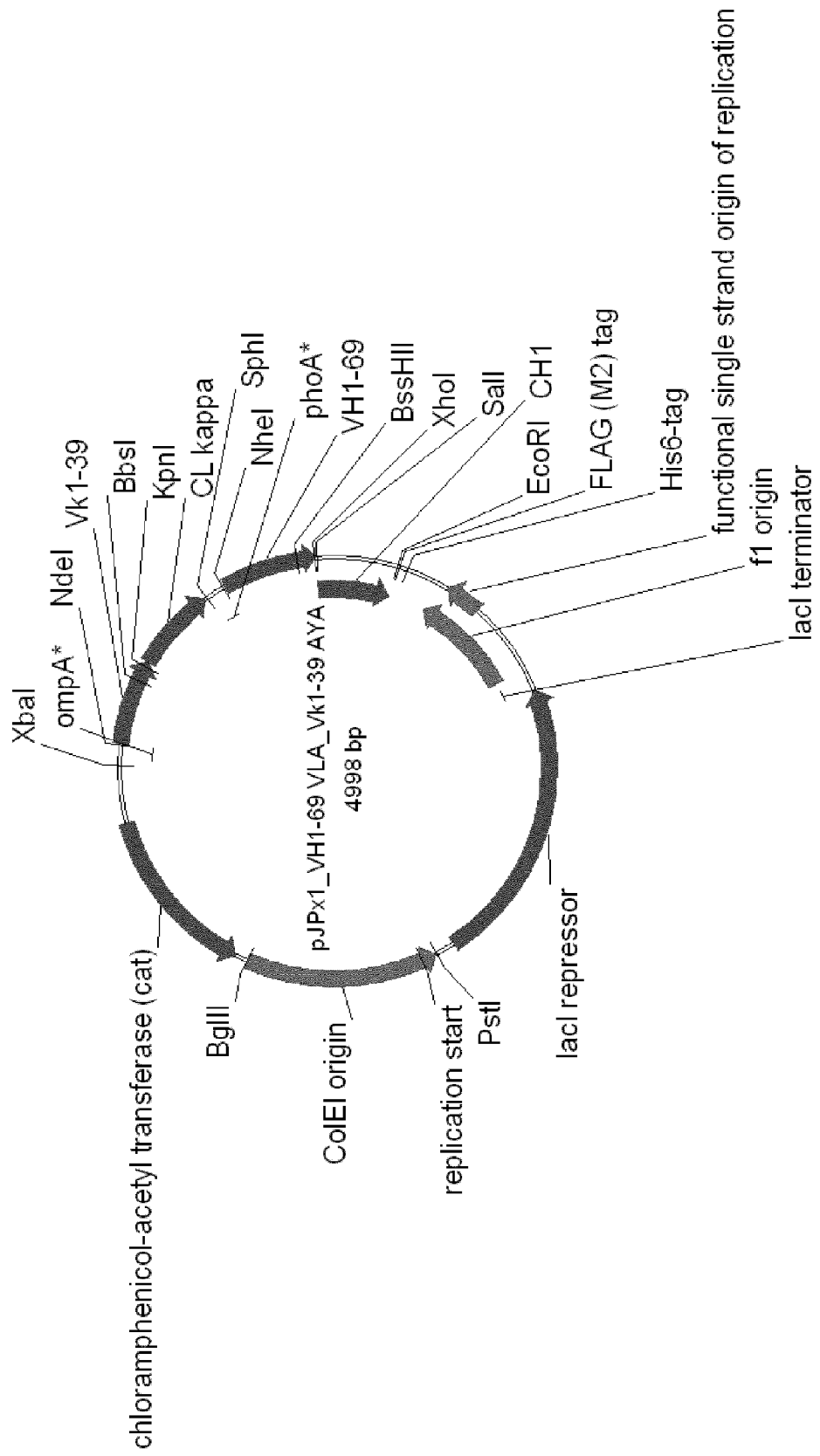
FIG. 10 shows the pJPx1 Fab expression vector.

Screening ELISA of 400 VH/VL Combinations to Determine the Fab Expression Yield in *E. coli* Lysates Masterplates (MP) were inoculated by picking clones transformed by pools of VH/VL combinations in the Fab expression vector pJPx1 (shown in FIG. 10) into 2YT/Cam/1% Gluc medium per well. These plates were incubated at 37° C. over night while shaking. Expression plates (EP) were inoculated with 2.5 µl of the cultures from MPs into 2YT/Cam/0.1% Glucose per well. Controls (see Table 8) were inoculated from glycerol stocks. These plates were incubated for 6 hours at 37° C. and shaking, then Fab expression was induced by adding IPTG and incubated at 22° C. over night while shaking. *E. coli* cell lysates were produced by adding boric/acid/EDTA/lysozyme-buffer to the EPs (1 h incubation at 22° C., shaking), and bacterial lysates were subsequently blocked with 12.5% MPBST, shaking at least for 30 min at room temperature. *E. coli* lysates from expression plates were diluted appropriately in 0.5% MPBS and used in the following assay.

Table 7 shows the unlabeled coating antibodies and AP-labeled detection antibodies which were used.

TABLE 7

|  | MOR Name | Label | Host | Antibody | Company | Number | Concentration | Dilution | Lot |
| --- | --- | --- | --- | --- | --- | --- | --- | --- | --- |
| Coating Ab | 15 | unlabeled | sheep | anti-Human IgG (Fd) | Binding Site | pc075 | 12.1 mg/ml | 1:1000 | 236366, Exp 2009/10 |
| detection Ab | AP27 | AP | mouse | anti-FlagM2 | Sigma | A9469 | 1.1 mg/ml | 1:5000 | 048K6143, new lot |

Table 8 describes the controls used.

TABLE 8

| # | Construct name |
| --- | --- |
| 3 | pMx11_FH VH1-69 VLA_Vl1-40 AYA |
| 5 | pMx11_FH VH3-23 VLA_Vk3-11 AYA |
| empty | pMx9_APStuffer_FHClone1 |
| BEL | (not containing Fab molecules!) |

The screening ELISA comprised the following steps: Coating 384 wells of a MaxiSorp plate with anti-human IgG Fd specific antibodies diluted in PBS, and incubating over night at 4° C. The next day, the plates were washed 2x with PBST and blocked by adding (5% Milkpowder in PBS) to each well and incubating for 1-2 h at RT, while shaking. Then the plates were washed again with PBST, and pre-blocked *E. coli*-lysates, diluted in 0.5% MPBS, were added and incubated for 1 h while shaking at RT. Also the controls #3 and #5, were added. The plates were then washed with PBST and the AP-labeled detection antibody was diluted in 0.5% MPBS. The diluted detection antibody was added and then incubated for 1 h at RT while shaking gently. The signal was identified by the following: washing the wells with TBST and adding 20 µl of AttoPhos (1:5 diluted in ddH2O), and reading at 5 min and 7-8 min using Tecan (infiniTe F200), program PrimeScreen.

Figure 11:
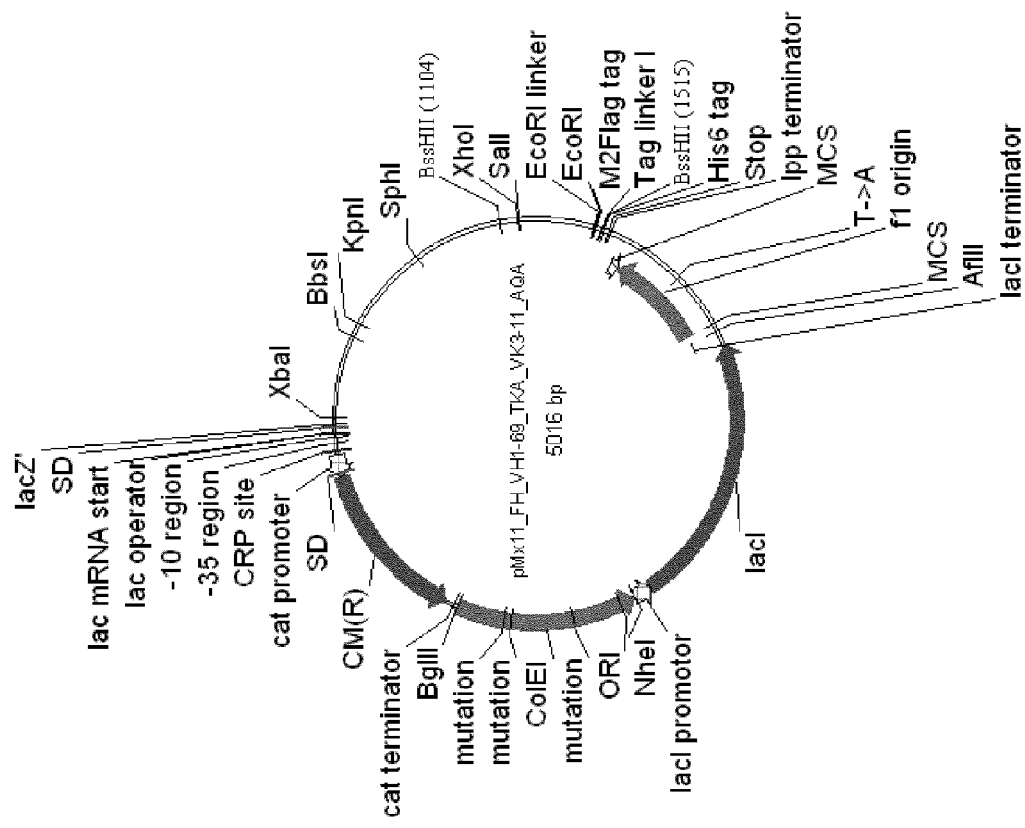
FIG. 11 shows the pMx11 (pMORPHX11) Fab expression vector.

Relative Fab expression yields are calculated by dividing the ELISA signal of the respective VH/VL pair through the ELISA signal of the reference Fab pMx11_FH VH1-69 VLA_VI1-40 AYA. Thereby equally high ELISA signals result in a relative Fab expression yield of 1. The reference Fab is expressed in a pMORPHX11 plasmids (shown in FIG. 11) comprising a) the modified phoA heavy chain signal sequence comprising the C-terminal NheI restriction site; b) the modified ompA light chain signal sequence comprising the C-terminal NdeI restriction site; c) the variable heavy germline protein sequences of the VH1-69*01 germline gene as shown in FIG. 6A, d) the variable light germline protein sequences of the IGLV1-40 germline gene as shown in FIG. 8A; e) incorporating the CDR-H3 (WGGDGFYAMDY) (SEQ ID NO: 1) of the hu4D5-8 antibody, and the JH4 germline protein sequence for heavy chain FR4; f) incorporating the CDR-L3 region (QSYDSSLSGVV) (SEQ ID NO: 3) and the JI2/3 germline protein sequence for light chain FR4. The hu4D5-8 is described in Carter P. et al. (1992) "Humanization of an anti-p185Her2 antibody for human cancer therapy" Proc. Natl. Acad. Sci. USA 89, 4285-4289) and Ewert S. et al., J. Mol. Biol. (2003) 325, 531-553. All genes were generated at Geneart (Regensburg, Germany). The results are shown in Table 12.

Example 6.4

Screening ELISA of 400 VH/VL Combinations to Determine the Temperature Stability of Fab in BEL Lysates Expression plates were generated as in Example 6.3. Diluted E. coli lysates from expression plates were incubated at different temperatures for 45 minutes and used in the following assay. Table 9 shows the unlabeled coating antibodies and AP-labeled detection antibodies which were used.

incubated for 1-2 h at RT while shaking. Then the diluted E. coli lysates from the expression plates were distributed into four 96 well PCR-plates (each about 40 µl) and exposed to different temperatures (4° C. (on ice), 60° C., 70° C., 80° C. and then on ice) in a PCR-Cycler, each temperature for 45 min. The blocked 384 well plates were washed with PBST, then the pre-incubated Fab lysates, were added to the plates. The plates were then incubated 1 h at RT while shaking. The plates were washed with PBST, the AP-labeled detection antibodies were diluted in 0.5% MPBS. 20 µl/well of the diluted detection antibodies were added and incubated for 1 h at RT while shaking gently. The signal was identified by the following: washing the wells with TBST and adding AttoPhos (1:5 diluted in ddH2O) to all wells. The signal was read at different timepoints (5 min to 10 min) using Tecan (infiniTe F200), program PimeScreen. The results are shown in Table 12.

Example 6.5

Screening ELISA of 400 VH/VL Combinations to Determine the Serum Stability of Fab in E. coli Lysates Expression plates were generated as in Example 6.3. The Fab containing E. coli lysates were diluted and incubated in bovine and mouse serum using the following steps: E. coli lysates from the expression plates were diluted in 50% serum (total volume of 100 µl), 1:1000 Cam was added to prevent growth of bacteria, and the lysates were split into two 96 well plates and both plates were frozen. The first

TABLE 9

| | MOR Name | Label | Host | Antibody | Company | Number | Concentration | Dilution | Lot |
|---|---|---|---|---|---|---|---|---|---|
| coating Ab | 57 | unlabeled | Mouse | monoclonal Anti poly Histidine Antibody IgG1 (anti 6x-Histidine); polypeptides containing a polyhistidine tag | R&D Systems | MAB050 | 500 µg/ml | 1:250 | AEJ1708111 |
| detection Ab | AP30 | AP | goat | anti-human kappa light chains | Sigma | A3813 | 2.3 mg/ml | 1:2300 | 018K6069 |
| detection Ab | AP5 | AP | goat | anti-human lambda light chains | Sigma | A2904 | 0.8 mg/ml | 1:800 | 096K6030 |

The screening ELISA comprised the following steps: 384 wells of a MaxiSorp plate were coated with coating antibody (see table above) diluted in PBS. The plates were incubated over night at 4° C. The next day, the plates were washed with PBST and blocked by adding 5% MPBS to each well and plate was thawed and incubated at 37° C. for 12-13 days. The second plate was stored at −80° C. until performing the ELISA (0 days incubation at 37° C.). Table 10 shows the unlabeled coating antibodies and AP-labeled detection antibodies which were used.

TABLE 10

| | MOR Name | Label | Host | Antibody | Company | Number | Concentration | Dilution | Lot |
|---|---|---|---|---|---|---|---|---|---|
| coating Ab | 36 | Fab | Goat | anti-Human IgG (H + L) | Jackson Immuno Research | 109-006-088 | 1.3 mg/ml | 1:1000 | 80299 |
| detection Ab | AP30 | AP | goat | anti-human kappa light chains | Sigma | A3813 | 2.3 mg/ml | 1:2300 | 018K6069 |
| detection Ab | AP5 | AP | Goat | anti-Human lambda-light chain; bound + free | Sigma | A2904 | 0.8 mg/ml | 1:800 | 096K6030 |

On day 11 or 12, the 384 wells of a MaxiSorp plate were coated with 20 µl coating antibody diluted in PBS. The plates were incubated over night at 4° C. The following day, the plates were washed with PBST and blocked by adding 5% MPBS to each well and incubating for 1-2 h at RT while shaking. Then the blocked 384 well plates were washed with PBST. *E. coli* lysates in serum from the −80° C. and 37° C. samples were transferred to the coated ELISA plates and incubated for 1 hour at RT while shaking. The plates were washed with PBST, and the AP-labeled detection antibodies were diluted in 0.5% MPBS. AP-labeled detection antibody was added and the plate was incubated for 1 h at RT while shaking. The signal was identified by the following: washing the wells with TBST and adding AttoPhos (1:5 diluted in ddH2O) to all wells. The signal was read at different timepoints (5 min to 10 min) using Tecan (infiniTe F200), program PrimeScreen. The results of the bovine serum stability testing are shown in FIG. 19. The results of the mouse serum stability testing are shown in Table 12.

Example 7

Generation of Human IgG1 for Evaluation of Biophysical Properties

Figure 13:
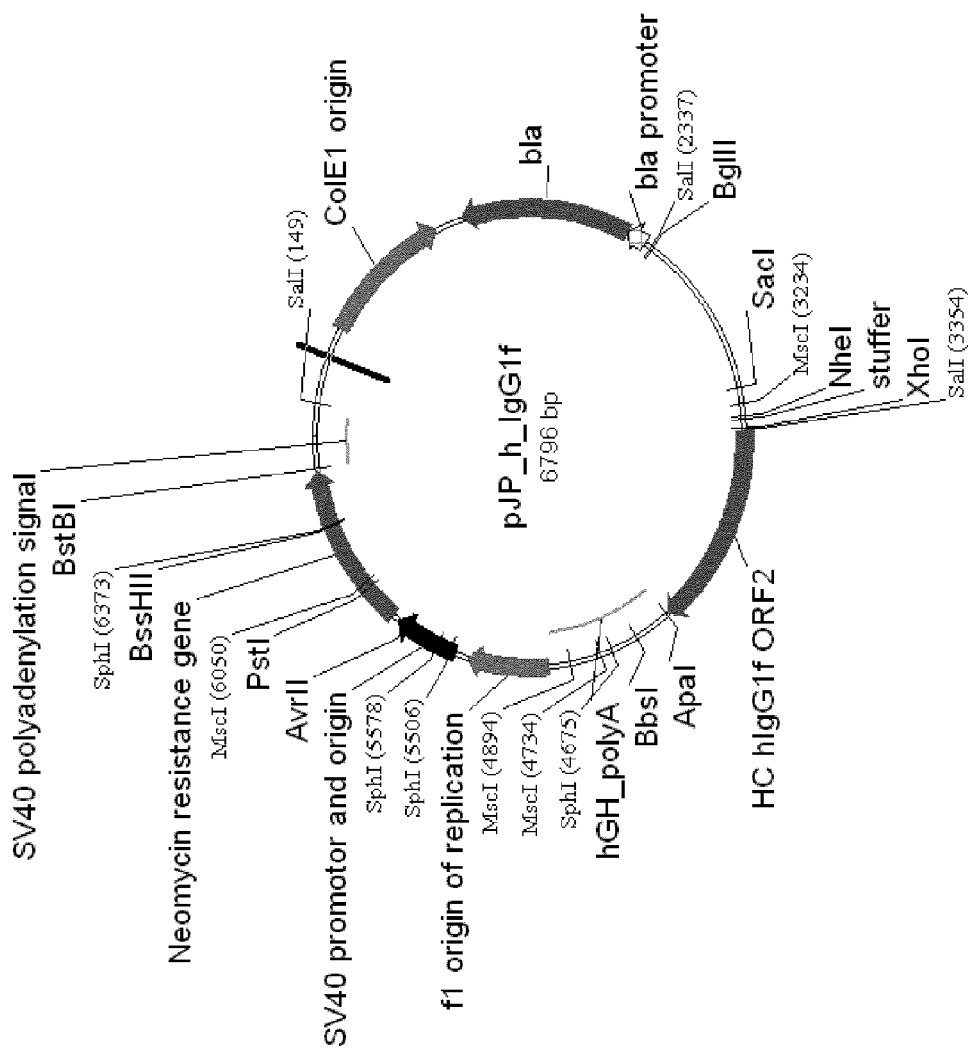
FIG. 13 shows the pJP_h_IgG1f variable heavy chain IgG1 expression vector.

For generation of the 400 IgG1 germline protein pairs, the 20 variable region heavy chain genes were sub-cloned into the human IgG1 expression vector pJP_hIgG1f shown in FIG. 13. In parallel the 12 variable region kappa genes were sub-cloned into the mammalian kappa light chain expression vector pJP_hIgkappa shown in FIG. 14 and the 8 variable region lambda genes were sub-cloned into the mammalian lambda light chain expression vector pJP_hIglambda2 shown in FIG. 15.

By co-transfection of each, a heavy chain and a light chain expression plasmid for all 400 VH/VL pairs can be produced separately by only cloning 40 expression constructs. Thus HEK.EBNA cells were co-transfected with all 20 heavy chain constructs and all 20 of the light chain expression constructs. Human IgG1 was harvested or detected several days post transfection from the cell culture supernatants.

Example 7.1

IgG1 Expression Ranking

One of the criteria for the selection of the VH/VL pairings to be included in a collection is the level of expression of the 400 different VH/VL pairings in the IgG1 format. The expression level of each VH/VL pairing in human IgG1 format was assessed by sandwich ELISA. Therefore, HEK.EBNA cells were transfected with all 400 VH/VL combinations in human IgG1 format and expressed in small scale. The cell culture supernatants were harvested after few days and IgG levels assessed.

The following procedure was performed. 384-well MaxiSorp™ plates were coated with Fcγ-pan R10Z8E9 mouse anti-human IgG at 2.5 µg/ml in PBS. The plates were incubated overnight at 4° C. The plates were washed with PBST. The plates were blocked with 5% BSA or 1× Chemiblocker in PBST and incubated for 1 h at room temperature while shaking and again washed with PBST. The IgG expression supernatants were diluted in 2.5% BSA-PBST and the diluted samples were added to the blocked and washed ELISA plate. The following controls were used: empty supernatant and supernatants with a low expressing antibody, moderate expressing antibody and a high expressing antibody. The plates were incubated for 2 h at room temperature while shaking. The plates were then washed with TBST. Appropriately diluted Fcγ-pan R10Z8E9 mouse anti-human IgG Biotin conjugate in 1% BSA-TBST was added. The plates were incubated for 1 h at room temperature. The plates were washed with TBST. Streptavidin-AP diluted 1:2000 in 0.5% BSA-TBST was added and the plates were incubated for 1 h at room temperature while shaking. The plates were washed with TBST. AttoPhos™ fluorescence substrate (prepared according to manufacturer's instructions) diluted in TBST directly before use was added. After 5 and 10 min, the fluorescence was measured via Tecan microplate reader.

Relative IgG1 expression yields were calculated by dividing the ELISA signal of the respective VH/VL pair through the ELISA signal of the reference IgG1 MOR03080 (shown in Table 11). Thereby equally high ELISA signals result in a relative IgG1 expression yield level of 1.

TABLE 11

The amino acid sequence of MOR03080 is as follows:

03080 Variable heavy chain with CDRs in bold:
(1) QVQLVESGGGLVQPGGSLRLSCAASGFTFSSYGMHWVRQAPGK
    GLEWVSN

(51) IYSDGSNTFY ADSVKGRFTISRDNSKNTLYLQMNSLRAEDTAVYY
     CARNM

(101) YRWPFHYFFDYWGQGTLVTVSS (SEQ ID NO: 61)

03080 Variable light chain with CDRs in bold
(1) DIELTQPPSV SVAPGQTARISCSGDNIGNKYVSWYQQKPGQAPVV
    VIYGD

(51) NNRPSGIPERFSGSNSGNTATLTISGTQAEDEADYYC**SSYDSSYF
     V**FGGG (101) TKLTVLGQ (SEQ ID NO: 62)

The results are shown in Table 12. The sequences of the Fc portion are shown in FIGS. 48, 50-51.

Example 7.2

IgG1 Serum Stability Ranking

One of the criteria for the selection of the variable heavy and variable light chain pairings to be included in a collection is the serum stability of the 400 different variable heavy and variable light chain pairings in IgG1 format. Serum stability of each IgG antibody supernatant was assessed by incubation in 50% mouse serum for 14 days and subsequent sandwich ELISA with mouse anti-human IgG (CH2) clone R10Z8E9. Again all 400 VH/VL combinations in human IgG1 format were transfected into HEK.EBNA cells and expressed in small scale. The cell culture supernatants were harvested after few days and the IgGs in the supernatant tested for serum stability.

The following procedure was performed. 384-well MaxiSorp™ plate were coated with Fcγ-pan R10Z8E9 mouse anti-human IgG at 2.5 µg/ml in PBS. The plates were incubated overnight at 4° C. The plates were washed with PBST and then blocked with 5% BSA-PBST or 1× Chemiblocker for 1 h at room temperature while shaking. The plates were washed with PBST. The IgG1 containing cell culture supernatants were diluted a) in 2.5% BSA-PBST and b) in 50% mouse serum and incubated at 37° C. for at least 14 days and these samples were added to the blocked and washed ELISA plate. The following controls were used: empty supernatant and supernatants a low expressing antibody, a moderate expressing antibody, and a high expressing antibody. The plates were incubated for 2 h at room temperature while shaking. The plates were washed with TBST.

Fcγ-pan R10Z8E9 mouse anti-human IgG Biotin conjugate diluted to 0.8 μg/ml in 1% BSA-TBST was added. The plates were incubated for 1 h at room temperature. The plates were washed with TBST. Streptavidin-AP diluted 1:2000 in 0.5% BSA-TBST was added. The plates were incubated for 1 h at room temperature while shaking. The plates were washed with TBST. AttoPhos™ fluorescence substrate (prepared according to manufacturer's instructions) diluted 1:5 in TBST directly before use was added. After 5 and 10 min, the fluorescence was measured via Tecan microplate reader. The results are shown in Table 12.

Example 8

Selection of the VH/VL Pairs with Favorable Bio-Physical Properties for Incorporation into Collection Once the 400 germline protein pairs were tested for the following properties: a) relative display after phage production and phage ELISA in Fab format; b) relative Fab expression yield after Fab production in *E. coli*, *E. coli* cell lysis and ELISA detection of produced Fab; c) temperature stability of Fab after Fab production in *E. coli*, *E. coli* cell lysis and ELISA detection of non-denatured Fab after incubation at increased temperatures; d) bovine/mouse serum stability of Fab from *E. coli* lysates by ELISA detection of non-denatured Fab after incubation in bovine/mouse serum; e) relative human IgG1 expression yield after IgG1 production in mammalian cells and ELISA detection of secreted IgG1 from cell culture supernatants; and f) bovine serum stability of human IgG1 by ELISA detection of non-denatured IgG1 after incubation in bovine/mouse serum; then the next step was to select which VH/VL germline pairs were to be incorporated into the collection. The results of the functional testing for each VH/VL germline protein pairs are shown Table 12.

TABLE 12

Compilation of functional data for each of the 400 Germline protein pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 1 | hVH_1_2 | hVK_1_05 | 0.1 | 0.0 | bg | U | S | 10 | 0.0 | bg |
| 2 | hVH_1_2 | hVK_1_06 | 0.1 | 0.2 | 60 | S | S | 42 | 0.0 | bg |
| 3 | hVH_1_2 | hVK_1_09 | 0.0 | 0.0 | bg | U | S | 11 | 0.0 | bg |
| 4 | hVH_1_2 | hVK_1_12 | 0.0 | 0.0 | bg | S | S | 20 | 0.0 | bg |
| 5 | hVH_1_2 | hVK_1_16 | 0.1 | 0.0 | bg | S | S | 20 | 0.0 | bg |
| 6 | hVH_1_2 | hVK_1_17 | 0.0 | 0.0 | bg | S | S | 21 | 0.0 | bg |
| 7 | hVH_1_2 | hVK_1_27 | 0.0 | 0.1 | bg | S | S | 22 | 0.0 | bg |
| 8 | hVH_1_2 | hVK_1_39 | 0.0 | 0.0 | bg | S | S | 21 | 0.0 | bg |
| 9 | hVH_1_2 | hVK_2_30 | | 0.0 | bg | S | S | 20 | 0.0 | bg |
| 10 | hVH_1_2 | hVK_3_11 | 0.0 | 0.0 | bg | S | S | 20 | 0.0 | bg |
| 11 | hVH_1_2 | hVK_3_15 | 0.0 | 0.0 | bg | U | S | 10 | 0.0 | bg |
| 12 | hVH_1_2 | hVK_3_20 | | 0.0 | bg | S | S | 21 | 0.0 | bg |
| 13 | hVH_1_2 | hVL_1-40 | | | | | | 0 | 0.3 | bg |
| 14 | hVH_1_2 | hVL_1-47 | 0.0 | 0.0 | 4 | U | U | 2 | 0.0 | bg |
| 15 | hVH_1_2 | hVL_1-51 | 0.0 | 0.0 | 4 | U | U | 0 | 0.4 | bg |
| 16 | hVH_1_2 | hVL_2-11 | 0.1 | 0.0 | 4 | S | S | 22 | 0.3 | bg |
| 17 | hVH_1_2 | hVL_2-14 | 0.1 | 0.0 | 4 | U | U | 0 | 0.1 | bg |
| 18 | hVH_1_2 | hVL_2-23 | 0.0 | 0.0 | 4 | U | U | 0 | 0.0 | bg |
| 19 | hVH_1_2 | hVL_3-1 | 0.4 | 0.0 | 4 | U | U | 1 | 0.0 | bg |
| 20 | hVH_1_2 | hVL_3-21 | 0.0 | 0.0 | 4 | U | U | 0 | 0.0 | bg |
| 21 | hVH_1_18 | hVK_1_05 | 2.0 | 0.4 | 60 | S | S | 54 | 0.4 | S |
| 22 | hVH_1_18 | hVK_1_06 | 0.6 | 0.5 | 60 | S | S | 56 | 0.2 | S |
| 23 | hVH_1_18 | hVK_1_09 | | | | | | 0 | 0.1 | S |
| 24 | hVH_1_18 | hVK_1_12 | 1.6 | 0.5 | 60 | S | S | 56 | 0.1 | bg |
| 25 | hVH_1_18 | hVK_1_16 | 2.0 | | | | | 3 | 0.2 | S |
| 26 | hVH_1_18 | hVK_1_17 | | 0.5 | | S | S | 38 | 0.3 | S |
| 27 | hVH_1_18 | hVK_1_27 | 1.2 | 0.4 | 70 | S | S | 62 | 0.5 | S |
| 28 | hVH_1_18 | hVK_1_39 | 3.7 | 0.3 | 60 | S | S | 53 | 0.1 | S |
| 29 | hVH_1_18 | hVK_2_30 | 1.9 | 0.5 | 60 | S | S | 56 | 0.0 | S |
| 30 | hVH_1_18 | hVK_3_11 | | 0.6 | 60 | S | S | 56 | 0.0 | S |
| 31 | hVH_1_18 | hVK_3_15 | 2.6 | 0.5 | 70 | S | S | 67 | 0.3 | S |
| 32 | hVH_1_18 | hVK_3_20 | 2.2 | 0.9 | 60 | S | S | 72 | 0.0 | S |
| 33 | hVH_1_18 | hVL_1-40 | 2.4 | | | | | 4 | 0.5 | S |
| 34 | hVH_1_18 | hVL_1-47 | | 0.8 | 60 | S | S | 66 | 0.4 | U |
| 35 | hVH_1_18 | hVL_1-51 | | | | | | 0 | 0.5 | S |
| 36 | hVH_1_18 | hVL_2-11 | 1.9 | | | | | 3 | 0.5 | U |
| 37 | hVH_1_18 | hVL_2-14 | 2.5 | 0.6 | 60 | S | S | 64 | 0.5 | U |
| 38 | hVH_1_18 | hVL_2-23 | 4.3 | 0.7 | 60 | S | S | 70 | 0.4 | S |
| 39 | hVH_1_18 | hVL_3-1 | 4.4 | 0.6 | 60 | S | S | 65 | 0.2 | U |
| 40 | hVH_1_18 | hVL_3-21 | 3.4 | 0.6 | 60 | S | S | 64 | 0.2 | S |
| 41 | hVH_1_46 | hVK_1_05 | | 0.4 | 60 | S | S | 51 | 0.9 | S |
| 42 | hVH_1_46 | hVK_1_06 | | | | | | 0 | 0.9 | S |
| 43 | hVH_1_46 | hVK_1_09 | 3.0 | 0.6 | 60 | S | S | 63 | 0.4 | S |
| 44 | hVH_1_46 | hVK_1_12 | | 0.5 | 60 | S | S | 55 | 0.2 | S |
| 45 | hVH_1_46 | hVK_1_16 | 1.3 | 0.6 | 60 | S | S | 61 | 0.3 | S |
| 46 | hVH_1_46 | hVK_1_17 | 1.3 | | | | | 2 | 0.5 | S |
| 47 | hVH_1_46 | hVK_1_27 | | | | | | 0 | 0.6 | S |
| 48 | hVH_1_46 | hVK_1_39 | 2.5 | 0.4 | 60 | S | S | 55 | 0.5 | S |
| 49 | hVH_1_46 | hVK_2_30 | | 0.2 | 4 | U | S | 16 | 0.0 | S |

TABLE 12-continued

Compilation of functional data for each of the 400 Germline protein pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 50 | hVH_1_46 | hVK_3_11 | | | | | | 0 | 0.1 | S |
| 51 | hVH_1_46 | hVK_3_15 | 3.0 | 0.7 | 60 | S | S | 68 | 0.4 | S |
| 52 | hVH_1_46 | hVK_3_20 | | | | | | 0 | 0.1 | S |
| 53 | hVH_1_46 | hVL_1-40 | | 1.0 | 60 | S | S | 73 | 0.9 | S |
| 54 | hVH_1_46 | hVL_1-47 | | | | | | 0 | 0.6 | U |
| 55 | hVH_1_46 | hVL_1-51 | 5.7 | | | | | 10 | 0.3 | S |
| 56 | hVH_1_46 | hVL_2-11 | 1.6 | | | | | 3 | 0.3 | S |
| 57 | hVH_1_46 | hVL_2-14 | | | | | | 0 | 0.3 | U |
| 58 | hVH_1_46 | hVL_2-23 | 2.7 | 1.0 | 60 | S | S | 79 | 0.3 | S |
| 59 | hVH_1_46 | hVL_3-1 | 4.3 | | | | | 7 | 0.4 | S |
| 60 | hVH_1_46 | hVL_3-21 | 5.2 | | | | | 9 | 0.3 | S |
| 61 | **hVH_1_69*01 | hVK_1_05 | 2.1 | 0.5 | 60 | S | S | 59 | 0.9 | S** |
| 62 | hVH_1_69*01 | hVK_1_06 | 2.9 | | | | | 5 | 0.5 | S |
| 63 | hVH_1_69*01 | hVK_1_09 | | 0.3 | 60 | S | U | 37 | 0.4 | S |
| 64 | hVH_1_69*01 | hVK_1_12 | 2.1 | 0.4 | 60 | S | S | 53 | 0.3 | S |
| 65 | hVH_1_69*01 | hVK_1_16 | 1.2 | | | | | 2 | 0.4 | S |
| 66 | hVH_1_69*01 | hVK_1_17 | 0.9 | 0.3 | 4 | S | S | 31 | 0.3 | S |
| 67 | hVH_1_69*01 | hVK_1_27 | 0.2 | 0.3 | 70 | S | S | 56 | 0.4 | S |
| 68 | hVH_1_69*01 | hVK_1_39 | 3.5 | 0.1 | 4 | S | S | 31 | 0.4 | U |
| 69 | hVH_1_69*01 | hVK_2_30 | | | | | | 0 | 0.0 | S |
| 70 | hVH_1_69*01 | hVK_3_11 | | 0.7 | 60 | S | S | 60 | 0.0 | S |
| 71 | hVH_1_69*01 | hVK_3_15 | 1.6 | 0.5 | 70 | S | S | 66 | 0.5 | S |
| 72 | hVH_1_69*01 | hVK_3_20 | | 0.5 | 60 | S | S | 54 | 0.0 | S |
| 73 | hVH_1_69*01 | hVL_1-40 | | 1.0 | 60 | S | S | 72 | 0.2 | S |
| 74 | hVH_1_69*01 | hVL_1-47 | | | | | | 0 | 0.2 | U |
| 75 | hVH_1_69*01 | hVL_1-51 | | 0.8 | 60 | S | S | 64 | 0.3 | S |
| 76 | hVH_1_69*01 | hVL_2-11 | 0.8 | 0.7 | 60 | S | S | 65 | 0.2 | S |
| 77 | hVH_1_69*01 | hVL_2-14 | | 0.8 | 60 | S | S | 64 | 0.3 | U |
| 78 | hVH_1_69*01 | hVL_2-23 | 1.8 | | | | | 3 | 0.3 | S |
| 79 | hVH_1_69*01 | hVL_3-1 | 3.4 | 0.7 | | | | 52 | 0.2 | S |
| 80 | hVH_1_69*01 | hVL_3-21 | 4.6 | 0.7 | 60 | S | S | 71 | 0.1 | S |
| 81 | hVH_3_07 | hVK_1_05 | | 0.7 | 60 | S | S | 63 | 0.9 | U |
| 82 | hVH_3_07 | hVK_1_06 | | 0.9 | 60 | S | S | 69 | 1.3 | S |
| 83 | hVH_3_07 | hVK_1_09 | 6.7 | 0.4 | 60 | S | S | 50 | 1.5 | S |
| 84 | hVH_3_07 | hVK_1_12 | 10.6 | 0.9 | 70 | S | S | 97 | 0.9 | S |
| 85 | hVH_3_07 | hVK_1_16 | 7.0 | | | | | 12 | 1.5 | S |
| 86 | hVH_3_07 | hVK_1_17 | 10.5 | 0.5 | 4 | S | S | 40 | 0.9 | S |
| 87 | hVH_3_07 | hVK_1_27 | 14.5 | 0.5 | 70 | S | S | 87 | 1.8 | S |
| 88 | hVH_3_07 | hVK_1_39 | 27.3 | 0.3 | 60 | U | S | 85 | 1.2 | S |
| 89 | hVH_3_07 | hVK_2_30 | 13.0 | | | | | 0 | 0.3 | S |
| 90 | hVH_3_07 | hVK_3_11 | | | | | | 0 | 0.4 | S |
| 91 | hVH_3_07 | hVK_3_15 | 14.5 | 0.7 | 70 | S | S | 95 | 1.8 | S |
| 92 | hVH_3_07 | hVK_3_20 | | | | | | 0 | 0.4 | S |
| 93 | hVH_3_07 | hVL_1-40 | 8.2 | | | | | 14 | 0.3 | S |
| 94 | hVH_3_07 | hVL_1-47 | 6.3 | 1.2 | 60 | S | S | 90 | 0.8 | U |
| 95 | hVH_3_07 | hVL_1-51 | | 1.0 | 60 | S | S | 74 | 0.9 | S |
| 96 | hVH_3_07 | hVL_2-11 | | | | | | 0 | 1.2 | S |
| 97 | hVH_3_07 | hVL_2-14 | 11.3 | | | | | 19 | 0.8 | U |
| 98 | hVH_3_07 | hVL_2-23 | 6.9 | 0.8 | 60 | S | S | 76 | 0.7 | S |
| 99 | hVH_3_07 | hVL_3-1 | 5.0 | 0.5 | 60 | S | S | 64 | 1.2 | S |
| 100 | hVH_3_07 | hVL_3-21 | | 0.7 | 60 | S | S | 61 | 0.3 | S |
| 101 | hVH_3_11 | hVK_1_05 | 5.5 | 0.5 | 60 | S | S | 65 | 0.5 | S |
| 102 | hVH_3_11 | hVK_1_06 | 4.3 | 0.6 | 60 | S | S | 64 | 1.4 | S |
| 103 | hVH_3_11 | hVK_1_09 | 6.7 | | | | | 0 | 0.9 | S |
| 104 | hVH_3_11 | hVK_1_12 | 8.2 | 0.6 | 60 | S | S | 73 | 0.9 | S |
| 105 | hVH_3_11 | hVK_1_16 | 10.3 | 0.6 | 60 | S | U | 61 | 1.2 | S |
| 106 | hVH_3_11 | hVK_1_17 | | | | | | 0 | 0.9 | S |
| 107 | hVH_3_11 | hVK_1_27 | 6.0 | | | | | 0 | 1.7 | S |
| 108 | hVH_3_11 | hVK_1_39 | 29.0 | | | | | 50 | 1.8 | S |
| 109 | hVH_3_11 | hVK_2_30 | | 0.4 | 4 | S | S | 34 | 1.1 | U |
| 110 | hVH_3_11 | hVK_3_11 | 0.0 | | | | | 0 | 0.6 | S |
| 111 | hVH_3_11 | hVK_3_15 | 4.6 | 0.7 | 60 | S | S | 68 | 1.6 | S |
| 112 | hVH_3_11 | hVK_3_20 | | | | | | 0 | 0.2 | S |
| 113 | hVH_3_11 | hVL_1-40 | 12.4 | | | | | 21 | 0.3 | S |
| 114 | hVH_3_11 | hVL_1-47 | 8.1 | 0.8 | 60 | S | S | 80 | 1.3 | U |
| 115 | hVH_3_11 | hVL_1-51 | | 1.1 | 60 | S | S | 77 | 1.9 | S |
| 116 | hVH_3_11 | hVL_2-11 | 8.4 | | | | | 14 | 1.1 | S |
| 117 | hVH_3_11 | hVL_2-14 | 6.4 | 0.9 | 60 | S | S | 81 | 0.4 | U |
| 118 | hVH_3_11 | hVL_2-23 | 8.9 | 1.0 | 60 | S | S | 88 | 0.4 | S |
| 119 | hVH_3_11 | hVL_3-1 | | 0.5 | 60 | S | S | 53 | 1.6 | S |
| 120 | hVH_3_11 | hVL_3-21 | 9.8 | | | | | 17 | 0.3 | S |
| 121 | hVH_3_15 | hVK_1_05 | 8.1 | 0.5 | 60 | S | S | 68 | 0.4 | S |
| 122 | hVH_3_15 | hVK_1_06 | 11.7 | 0.6 | 60 | S | S | 79 | 0.8 | S |

TABLE 12-continued

Compilation of functional data for each of the 400 Germline protein pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 123 | hVH_3_15 | hVK_1_09 | 10.0 | 0.5 | 70 | S | S | 80 | 0.9 | S |
| 124 | hVH_3_15 | hVK_1_12 | 11.5 | 0.7 | 70 | S | S | 90 | 0.7 | S |
| 125 | hVH_3_15 | hVK_1_16 | 14.5 | 0.7 | 60 | S | S | 86 | 1.5 | S |
| 126 | hVH_3_15 | hVK_1_17 | 6.4 | 0.6 | 4 | U | U | 30 | 0.8 | S |
| 127 | hVH_3_15 | hVK_1_27 | 7.8 | 0.5 | 70 | S | S | 77 | 1.7 | S |
| 128 | hVH_3_15 | hVK_1_39 | 14.2 | 0.4 | 60 | S | S | 76 | 1.8 | S |
| 129 | hVH_3_15 | hVK_2_30 |  | 0.3 | 4 | S | U | 23 | 0.6 | S |
| 130 | hVH_3_15 | hVK_3_11 | 19.4 |  |  |  |  | 33 | 0.8 | S |
| 131 | hVH_3_15 | hVK_3_15 | 12.1 | 0.6 | 70 | S | S | 70 | 1.9 | S |
| 132 | hVH_3_15 | hVK_3_20 | 8.9 |  |  |  |  | 0 | 0.5 | S |
| 133 | hVH_3_15 | hVL_1-40 | 16.7 | 0.9 | 60 | S | S | 98 | 0.1 | S |
| 134 | hVH_3_15 | hVL_1-47 | 13.0 | 1.2 | 60 | S | S | 102 | 0.2 | U |
| 135 | hVH_3_15 | hVL_1-51 | 11.0 | 1.1 | 60 | S | S | 94 | 0.9 | S |
| 136 | hVH_3_15 | hVL_2-11 | 10.5 | 0.9 | 60 | S | S | 88 | 0.8 | S |
| 137 | hVH_3_15 | hVL_2-14 | 9.7 | 0.8 | 60 | S | S | 83 | 0.9 | U |
| 138 | hVH_3_15 | hVL_2-23 | 10.1 |  |  |  |  | 17 | 0.4 | S |
| 139 | hVH_3_15 | hVL_3-1 | 9.4 | 0.3 | 4 | S | S | 46 | 1.0 | S |
| 140 | hVH_3_15 | hVL_3-21 | 9.2 | 0.8 |  | S | S | 65 | 0.2 | S |
| 141 | hVH_3_21 | hVK_1_05 | 10.0 |  |  |  |  | 17 | 0.8 | S |
| 142 | hVH_3_21 | hVK_1_06 | 16.1 | 1.0 | 60 | S | S | 99 | 0.9 | S |
| 143 | hVH_3_21 | hVK_1_09 |  |  |  |  |  | 0 | 0.4 | S |
| 144 | hVH_3_21 | hVK_1_12 | 11.3 | 0.6 | 60 | S | S | 77 | 0.5 | S |
| 145 | hVH_3_21 | hVK_1_16 |  | 0.9 | 60 | S | S | 68 | 0.0 | S |
| 146 | hVH_3_21 | hVK_1_17 | 5.0 |  |  |  |  | 9 | 0.0 | S |
| 147 | hVH_3_21 | hVK_1_27 | 8.7 | 0.6 | 60 | S | S | 78 | 0.5 | S |
| 148 | hVH_3_21 | hVK_1_39 | 11.6 | 0.5 | 60 | S | S | 54 | 0.8 | S |
| 149 | hVH_3_21 | hVK_2_30 |  | 0.6 | 4 | S | S | 44 | 0.1 | U |
| 150 | hVH_3_21 | hVK_3_11 |  |  |  |  |  | 0 | 0.2 | S |
| 151 | hVH_3_21 | hVK_3_15 |  | 0.8 | 60 | S | S | 65 | 0.3 | S |
| 152 | hVH_3_21 | hVK_3_20 |  |  |  |  |  | 0 | 0.5 | S |
| 153 | hVH_3_21 | hVL_1-40 |  | 1.0 | 60 | S | S | 72 | 0.5 | S |
| 154 | hVH_3_21 | hVL_1-47 | 0.0 | 1.2 | 60 | S | S | 81 | 0.3 | S |
| 155 | hVH_3_21 | hVL_1-51 |  |  |  |  |  | 0 | 0.9 | S |
| 156 | hVH_3_21 | hVL_2-11 |  | 0.9 | 60 | S | S | 68 | 0.7 | S |
| 157 | hVH_3_21 | hVL_2-14 | 6.5 | 0.9 | 60 | S | S | 81 | 1.2 | S |
| 158 | hVH_3_21 | hVL_2-23 | 8.8 | 1.0 | 60 | S | S | 90 | 0.9 | S |
| 159 | hVH_3_21 | hVL_3-1 |  | 0.7 | 60 | S | S | 60 | 0.4 | S |
| 160 | hVH_3_21 | hVL_3-21 | 11.8 | 0.9 | 60 | S | S | 88 | 0.1 | S |
| 161 | hVH_3_23 | hVK_1_05 |  | 0.8 | 60 | S | S | 64 | 0.2 | S |
| 162 | hVH_3_23 | hVK_1_06 |  | 0.7 | 60 | S | S | 61 | 0.2 | S |
| 163 | hVH_3_23 | hVK_1_09 | 6.1 | 0.8 | 70 | S | S | 86 | 0.1 | S |
| 164 | hVH_3_23 | hVK_1_12 |  | 0.9 | 60 | S | S | 68 | 0.1 | S |
| 165 | hVH_3_23 | hVK_1_16 | 8.4 | 0.6 | 60 | S | S | 72 | 0.2 | S |
| 166 | hVH_3_23 | hVK_1_17 |  | 0.6 | 4 | S | U | 31 | 0.1 | S |
| 167 | hVH_3_23 | hVK_1_27 | 17.1 |  |  |  |  | 29 | 0.2 | S |
| 168 | hVH_3_23 | hVK_1_39 | 10.8 |  |  |  |  | 19 | 0.3 | S |
| 169 | hVH_3_23 | hVK_2_30 | 4.1 | 0.3 | 4 | S | S | 39 | 0.0 | bg |
| 170 | hVH_3_23 | hVK_3_11 |  |  |  |  |  | 0 | 0.0 | bg |
| 171 | hVH_3_23 | hVK_3_15 |  | 0.7 | 70 | S | S | 73 | 0.4 | S |
| 172 | hVH_3_23 | hVK_3_20 | 13.3 |  |  |  |  | 0 | 0.2 | S |
| 173 | hVH_3_23 | hVL_1-40 |  |  |  |  |  | 0 | 0.1 | S |
| 174 | hVH_3_23 | hVL_1-47 |  |  |  |  |  | 0 | 0.1 | S |
| 175 | hVH_3_23 | hVL_1-51 | 10.2 | 1.1 | 60 | S | S | 94 | 0.2 | S |
| 176 | hVH_3_23 | hVL_2-11 | 13.6 |  |  |  |  | 23 | 0.1 | S |
| 177 | hVH_3_23 | hVL_2-14 | 9.1 |  |  |  |  | 16 | 0.3 | S |
| 178 | hVH_3_23 | hVL_2-23 | 7.4 | 0.9 | 60 | S | S | 82 | 0.3 | S |
| 179 | hVH_3_23 | hVL_3-1 | 4.6 | 0.4 | 60 | S | S | 60 | 0.1 | S |
| 180 | hVH_3_23 | hVL_3-21 | 7.4 | 0.8 | 60 | S | S | 78 | 0.1 | S |
| 181 | hVH_3_30 | hVK_1_05 |  |  |  |  |  | 0 | 0.7 | S |
| 182 | hVH_3_30 | hVK_1_06 |  | 1.0 | 60 | S | S | 75 | 0.6 | S |
| 183 | hVH_3_30 | hVK_1_09 |  |  |  |  |  | 0 | 0.3 | S |
| 184 | hVH_3_30 | hVK_1_12 | 5.4 | 0.8 | 60 | S | S | 73 | 0.3 | S |
| 185 | hVH_3_30 | hVK_1_16 |  | 0.9 | 60 | S | S | 69 | 0.4 | S |
| 186 | hVH_3_30 | hVK_1_17 |  |  |  |  |  | 0 | 0.5 | S |
| 187 | hVH_3_30 | hVK_1_27 | 9.1 | 0.4 | 60 | S | U | 38 | 0.5 | S |
| 188 | hVH_3_30 | hVK_1_39 | 13.1 | 0.0 | bg | U | U | 19 | 1.0 | S |
| 189 | hVH_3_30 | hVK_2_30 |  | 0.4 | 4 | S | U | 23 | 0.1 | bg |
| 190 | hVH_3_30 | hVK_3_11 |  | 0.4 | 60 | S | S | 50 | 0.1 | S |
| 191 | hVH_3_30 | hVK_3_15 |  | 0.7 | 60 | S | S | 61 | 0.9 | S |
| 192 | hVH_3_30 | hVK_3_20 |  | 0.7 | 60 | S | S | 63 | 0.4 | S |
| 193 | hVH_3_30 | hVL_1-40 |  |  |  |  |  | 0 | 0.8 | S |
| 194 | hVH_3_30 | hVL_1-47 |  | 1.1 | 60 | S | S | 78 | 0.3 | S |
| 195 | hVH_3_30 | hVL_1-51 |  |  |  |  |  | 0 | 0.4 | S |

TABLE 12-continued

Compilation of functional data for each of the 400 Germline protein pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 196 | hVH_3_30 | hVL_2-11 | | 0.7 | 60 | S | S | 62 | 0.4 | S |
| 197 | hVH_3_30 | hVL_2-14 | | 0.8 | 60 | S | S | 66 | 1.0 | S |
| 198 | hVH_3_30 | hVL_2-23 | 9.5 | 1.0 | 60 | S | S | 89 | 0.5 | S |
| 199 | hVH_3_30 | hVL_3-1 | 8.8 | 0.6 | 60 | S | S | 73 | 0.5 | S |
| 200 | hVH_3_30 | hVL_3-21 | 16.6 | 0.8 | 60 | S | S | 93 | 0.2 | S |
| 201 | hVH_3_33 | hVK_1_05 | | 0.3 | 60 | S | S | 46 | 0.0 | S |
| 202 | hVH_3_33 | hVK_1_06 | | | | | | 0 | 0.6 | S |
| 203 | hVH_3_33 | hVK_1_09 | | 0.7 | 60 | S | S | 60 | 0.2 | S |
| 204 | hVH_3_33 | hVK_1_12 | | 0.2 | 60 | S | U | 34 | 0.2 | S |
| 205 | hVH_3_33 | hVK_1_16 | | | | | | 0 | 0.4 | S |
| 206 | hVH_3_33 | hVK_1_17 | | | | | | 0 | 0.5 | S |
| 207 | hVH_3_33 | hVK_1_27 | | 0.6 | 60 | S | S | 57 | 0.2 | S |
| 208 | hVH_3_33 | hVK_1_39 | | | | | | 0 | 0.8 | S |
| 209 | hVH_3_33 | hVK_2_30 | | | | | | 0 | 0.3 | S |
| 210 | hVH_3_33 | hVK_3_11 | | | | | | 0 | 0.6 | S |
| 211 | hVH_3_33 | hVK_3_15 | 12.3 | 0.6 | 60 | S | S | 77 | 0.9 | S |
| 212 | hVH_3_33 | hVK_3_20 | | 1.0 | 60 | S | S | 72 | 0.3 | S |
| 213 | hVH_3_33 | hVL_1-40 | | | | | | 0 | 1.0 | S |
| 214 | hVH_3_33 | hVL_1-47 | | 1.1 | 60 | S | S | 77 | 0.4 | S |
| 215 | hVH_3_33 | hVL_1-51 | | | | | | 0 | 0.6 | S |
| 216 | hVH_3_33 | hVL_2-11 | | 0.5 | 60 | S | S | 54 | 0.5 | S |
| 217 | hVH_3_33 | hVL_2-14 | | 0.9 | 4 | S | S | 53 | 0.9 | S |
| 218 | hVH_3_33 | hVL_2-23 | 17.1 | 0.5 | 60 | S | S | 82 | 0.5 | S |
| 219 | hVH_3_33 | hVL_3-1 | | 0.2 | 60 | S | S | 44 | 0.7 | S |
| 220 | hVH_3_33 | hVL_3-21 | | 0.8 | 60 | S | S | 67 | 0.5 | S |
| 221 | hVH_3_48 | hVK_1_05 | | | | | | 0 | 0.6 | S |
| 222 | hVH_3_48 | hVK_1_06 | | | | | | 0 | 0.7 | S |
| 223 | hVH_3_48 | hVK_1_09 | | | | | | 0 | 0.2 | S |
| 224 | hVH_3_48 | hVK_1_12 | | | | | | 0 | 0.3 | S |
| 225 | hVH_3_48 | hVK_1_16 | 8.7 | | | | | 15 | 0.5 | S |
| 226 | hVH_3_48 | hVK_1_17 | | | | | | 0 | 0.5 | S |
| 227 | hVH_3_48 | hVK_1_27 | 8.9 | 0.7 | 60 | S | S | 74 | 0.9 | S |
| 228 | hVH_3_48 | hVK_1_39 | | | | | | 0 | 0.5 | S |
| 229 | hVH_3_48 | hVK_2_30 | | | | | | 0 | 0.3 | S |
| 230 | hVH_3_48 | hVK_3_11 | | | | | | 0 | 0.7 | S |
| 231 | hVH_3_48 | hVK_3_15 | 12.1 | | | | | 21 | 0.3 | S |
| 232 | hVH_3_48 | hVK_3_20 | | 0.8 | 60 | S | S | 65 | 0.4 | S |
| 233 | hVH_3_48 | hVL_1-40 | | 0.8 | | S | S | 51 | 0.6 | S |
| 234 | hVH_3_48 | hVL_1-47 | 10.3 | | | | | 18 | 0.4 | S |
| 235 | hVH_3_48 | hVL_1-51 | | 1.2 | 60 | S | S | 80 | 0.7 | S |
| 236 | hVH_3_48 | hVL_2-11 | | | | | | 0 | 0.6 | S |
| 237 | hVH_3_48 | hVL_2-14 | | | | | | 0 | 0.6 | S |
| 238 | hVH_3_48 | hVL_2-23 | 9.3 | | | | | 16 | 0.5 | S |
| 239 | hVH_3_48 | hVL_3-1 | 6.0 | 0.8 | | S | S | 61 | 0.5 | S |
| 240 | hVH_3_48 | hVL_3-21 | | | | | | 0 | 0.3 | S |
| 241 | hVH_3_53 | hVK_1_05 | 11.1 | 0.7 | 4 | U | S | 60 | 0.8 | S |
| 242 | hVH_3_53 | hVK_1_06 | | 0.7 | 60 | S | S | 63 | 0.7 | S |
| 243 | hVH_3_53 | hVK_1_09 | 8.3 | 0.9 | 60 | S | S | 83 | 0.4 | S |
| 244 | hVH_3_53 | hVK_1_12 | 14.8 | 0.7 | 60 | S | S | 60 | 0.2 | S |
| 245 | hVH_3_53 | hVK_1_16 | 10.7 | 0.0 | bg | bg | U | 20 | 0.3 | S |
| 246 | hVH_3_53 | hVK_1_17 | 2.9 | 0.5 | 4 | S | S | 42 | 0.5 | S |
| 247 | hVH_3_53 | hVK_1_27 | 6.9 | 0.4 | 60 | S | S | 62 | 0.2 | S |
| 248 | hVH_3_53 | hVK_1_39 | | 0.6 | 60 | S | S | 56 | 0.2 | S |
| 249 | hVH_3_53 | hVK_2_30 | 1.3 | 0.3 | 4 | S | S | 32 | 0.0 | bg |
| 250 | hVH_3_53 | hVK_3_11 | | 0.8 | 60 | S | S | 64 | 0.3 | S |
| 251 | hVH_3_53 | hVK_3_15 | 9.6 | 0.7 | 60 | S | S | 63 | 0.5 | S |
| 252 | hVH_3_53 | hVK_3_20 | | 0.3 | 4 | S | S | 32 | 0.3 | S |
| 253 | hVH_3_53 | hVL_1-40 | | 1.1 | 4 | S | S | 60 | 1.1 | S |
| 254 | hVH_3_53 | hVL_1-47 | | 1.1 | 60 | S | S | 79 | 0.2 | S |
| 255 | hVH_3_53 | hVL_1-51 | 6.4 | 1.3 | 60 | S | S | 96 | 0.4 | S |
| 256 | hVH_3_53 | hVL_2-11 | 7.2 | 0.8 | 60 | S | S | 78 | 0.3 | S |
| 257 | hVH_3_53 | hVL_2-14 | | 1.0 | 60 | S | S | 75 | 0.8 | S |
| 258 | hVH_3_53 | hVL_2-23 | 6.3 | 1.1 | 60 | S | S | 86 | 0.6 | S |
| 259 | hVH_3_53 | hVL_3-1 | 5.1 | 0.6 | 60 | S | S | 67 | 0.5 | S |
| 260 | hVH_3_53 | hVL_3-21 | | 0.8 | 60 | S | S | 66 | 0.5 | S |
| 261 | hVH_3_73 | hVK_1_05 | 0.4 | 0.2 | 60 | S | S | 45 | 1.1 | S |
| 262 | hVH_3_73 | hVK_1_06 | 0.3 | 0.2 | 60 | S | S | 45 | 1.0 | S |
| 263 | hVH_3_73 | hVK_1_09 | 0.3 | 0.1 | 60 | S | S | 39 | 0.9 | S |
| 264 | hVH_3_73 | hVK_1_12 | 0.3 | 0.1 | 60 | S | S | 38 | 0.5 | S |
| 265 | hVH_3_73 | hVK_1_16 | 0.3 | 0.2 | 60 | S | S | 44 | 1.1 | S |
| 266 | hVH_3_73 | hVK_1_17 | 0.1 | | | | | 0 | 1.0 | S |
| 267 | hVH_3_73 | hVK_1_27 | 3.6 | 0.1 | 4 | S | S | 24 | 0.9 | S |
| 268 | hVH_3_73 | hVK_1_39 | 0.2 | 0.2 | 4 | S | S | 27 | 0.8 | S |

TABLE 12-continued

Compilation of functional data for each of the 400 Germline protein pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 269 | hVH_3_73 | hVK_2_30 | | 0.1 | bg | S | S | 22 | 0.3 | S |
| 270 | hVH_3_73 | hVK_3_11 | 0.5 | | | | | 0 | 0.2 | S |
| 271 | hVH_3_73 | hVK_3_15 | 0.2 | 0.1 | 60 | S | S | 39 | 0.1 | S |
| 272 | hVH_3_73 | hVK_3_20 | | | | | | 0 | 1.1 | S |
| 273 | hVH_3_73 | hVL_1-40 | | 0.1 | 60 | S | S | 40 | 1.2 | S |
| 274 | hVH_3_73 | hVL_1-47 | 0.0 | 0.3 | 4 | S | S | 31 | 0.8 | S |
| 275 | hVH_3_73 | hVL_1-51 | 0.3 | 0.2 | 60 | S | S | 44 | 0.7 | S |
| 276 | hVH_3_73 | hVL_2-11 | 0.2 | 0.2 | 4 | S | S | 26 | 0.8 | S |
| 277 | hVH_3_73 | hVL_2-14 | | | | | | 0 | 0.4 | S |
| 278 | hVH_3_73 | hVL_2-23 | 0.8 | | | | | 1 | 0.1 | S |
| 279 | hVH_3_73 | hVL_3-1 | 0.0 | 0.1 | 60 | S | S | 39 | 1.0 | S |
| 280 | hVH_3_73 | hVL_3-21 | 0.4 | 0.2 | 60 | S | S | 43 | 1.1 | S |
| 281 | hVH_3_74 | hVK_1_05 | 6.4 | | | | | 11 | 0.6 | S |
| 282 | hVH_3_74 | hVK_1_06 | 9.5 | 0.9 | 60 | S | S | 86 | 1.0 | S |
| 283 | hVH_3_74 | hVK_1_09 | 8.7 | 0.6 | 60 | S | S | 74 | 0.5 | S |
| 284 | hVH_3_74 | hVK_1_12 | 8.4 | 0.6 | 60 | S | S | 74 | 0.0 | S |
| 285 | hVH_3_74 | hVK_1_16 | 8.0 | | | | | 11 | 0.8 | S |
| 286 | hVH_3_74 | hVK_1_17 | | 0.6 | 60 | S | S | 58 | 0.2 | S |
| 287 | hVH_3_74 | hVK_1_27 | 5.0 | 0.6 | 70 | S | S | 77 | 1.1 | S |
| 288 | hVH_3_74 | hVK_1_39 | 8.7 | | | | | 15 | 0.3 | S |
| 289 | hVH_3_74 | hVK_2_30 | | 0.4 | | S | S | 37 | 0.7 | S |
| 290 | hVH_3_74 | hVK_3_11 | | | | | | 0 | 0.1 | S |
| 291 | hVH_3_74 | hVK_3_15 | 10.0 | 0.8 | 70 | S | S | 94 | 1.0 | S |
| 292 | hVH_3_74 | hVK_3_20 | | 0.7 | 60 | S | S | 62 | 0.6 | S |
| 293 | hVH_3_74 | hVL_1-40 | 8.8 | 0.4 | 4 | S | S | 51 | 1.3 | S |
| 294 | hVH_3_74 | hVL_1-47 | 3.2 | 1.2 | | S | S | 72 | 0.6 | S |
| 295 | hVH_3_74 | hVL_1-51 | 7.1 | 1.1 | 60 | S | S | 91 | 1.2 | S |
| 296 | hVH_3_74 | hVL_2-11 | | 0.6 | 60 | S | S | 59 | 0.8 | S |
| 297 | hVH_3_74 | hVL_2-14 | 4.7 | | | | | 8 | 0.6 | S |
| 298 | hVH_3_74 | hVL_2-23 | | | | | | 0 | 1.0 | S |
| 299 | hVH_3_74 | hVL_3-1 | 7.0 | 0.6 | 60 | S | S | 70 | 0.3 | S |
| 300 | hVH_3_74 | hVL_3-21 | 1.8 | 0.6 | 60 | S | S | 60 | 0.3 | S |
| 301 | hVH_4_04*03 | hVK_1_05 | | 0.8 | 60 | S | S | 67 | 0.6 | S |
| 302 | hVH_4_04*03 | hVK_1_06 | | 0.8 | 60 | S | S | 64 | 1.1 | S |
| 303 | hVH_4_04*03 | hVK_1_09 | 4.5 | 0.1 | bg | S | S | 30 | 0.6 | S |
| 304 | hVH_4_04*03 | hVK_1_12 | | 0.7 | 60 | S | S | 61 | 0.8 | S |
| 305 | hVH_4_04*03 | hVK_1_16 | 3.2 | 0.2 | 60 | S | S | 48 | 0.4 | S |
| 306 | hVH_4_04*03 | hVK_1_17 | | 0.4 | 4 | S | S | 34 | 0.8 | S |
| 307 | hVH_4_04*03 | hVK_1_27 | | 0.4 | 60 | S | S | 48 | 0.9 | S |
| 308 | hVH_4_04*03 | hVK_1_39 | | 0.2 | bg | S | S | 26 | 1.0 | S |
| 309 | hVH_4_04*03 | hVK_2_30 | 0.3 | 0.5 | 4 | S | S | 38 | 0.2 | U |
| 310 | hVH_4_04*03 | hVK_3_11 | | 0.6 | bg | S | S | 43 | 0.3 | S |
| 311 | hVH_4_04*03 | hVK_3_15 | | 0.6 | 60 | S | S | 58 | 1.1 | S |
| 312 | hVH_4_04*03 | hVK_3_20 | | 1.1 | 60 | S | U | 65 | 1.1 | S |
| 313 | hVH_4_04*03 | hVL_1-40 | | 1.0 | 60 | S | S | 75 | 0.9 | S |
| 314 | hVH_4_04*03 | hVL_1-47 | 8.3 | | | | | 14 | 0.4 | S |
| 315 | hVH_4_04*03 | hVL_1-51 | | 0.9 | 60 | S | S | 71 | 0.6 | S |
| 316 | hVH_4_04*03 | hVL_2-11 | | 1.0 | 60 | S | S | 73 | 0.7 | S |
| 317 | hVH_4_04*03 | hVL_2-14 | | 0.7 | 60 | S | S | 63 | 0.4 | S |
| 318 | **hVH_4_04*03 | hVL_2-23 | 2.7 | 1.0 | 60 | S | S | 77 | 0.7 | S** |
| 319 | **hVH_4_04*03 | hVL_3-1 | 2.2 | 0.6 | 60 | S | S | 63 | 1.3 | S** |
| 320 | **hVH_4_04*03 | hVL_3-21 | 5.2 | 0.7 | 60 | S | S | 69 | 0.5 | S** |
| 321 | hVH_4_31 | hVK_1_05 | | 0.0 | bg | S | S | 21 | 0.0 | bg |
| 322 | hVH_4_31 | hVK_1_06 | | | | | | 0 | 0.2 | bg |
| 323 | hVH_4_31 | hVK_1_09 | | 0.1 | 4 | S | S | 23 | 0.6 | S |
| 324 | hVH_4_31 | hVK_1_12 | | 0.1 | 60 | S | S | 37 | 0.4 | S |
| 325 | hVH_4_31 | hVK_1_16 | | 0.0 | bg | S | S | 20 | 0.0 | bg |
| 326 | hVH_4_31 | hVK_1_17 | | 0.0 | bg | U | bg | 1 | 0.2 | bg |
| 327 | hVH_4_31 | hVK_1_27 | | 0.0 | bg | S | S | 20 | 0.0 | bg |
| 328 | hVH_4_31 | hVK_1_39 | | 0.8 | 60 | S | S | 65 | 0.5 | S |
| 329 | hVH_4_31 | hVK_2_30 | | 0.0 | bg | S | S | 20 | 0.0 | bg |
| 330 | hVH_4_31 | hVK_3_11 | | | | | | 0 | 0.0 | bg |
| 331 | hVH_4_31 | hVK_3_15 | | 0.1 | bg | S | S | 24 | 0.1 | S |
| 332 | hVH_4_31 | hVK_3_20 | | | | | | 0 | 0.4 | S |
| 333 | hVH_4_31 | hVL_1-40 | 0.0 | 0.6 | 60 | S | S | 57 | 0.8 | S |
| 334 | hVH_4_31 | hVL_1-47 | 0.0 | 0.7 | 60 | S | S | 62 | 0.1 | S |
| 335 | hVH_4_31 | hVL_1-51 | | 0.9 | 60 | S | S | 70 | 0.3 | S |
| 336 | hVH_4_31 | hVL_2-11 | | 0.5 | 60 | S | S | 55 | 0.2 | S |
| 337 | hVH_4_31 | hVL_2-14 | 0.0 | | | | | 0 | 0.5 | S |
| 338 | hVH_4_31 | hVL_2-23 | | 0.0 | 60 | S | S | 37 | 0.3 | S |
| 339 | hVH_4_31 | hVL_3-1 | 1.4 | 0.3 | 60 | S | S | 50 | 1.3 | S |
| 340 | hVH_4_31 | hVL_3-21 | | 0.4 | 60 | S | S | 50 | 0.4 | bg |
| 341 | hVH_4_39 | hVK_1_05 | 0.0 | 0.3 | 60 | S | S | 45 | 0.3 | S |

TABLE 12-continued

Compilation of functional data for each of the 400 Germline protein pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 342 | hVH_4_39 | hVK_1_06 | 1.6 | | | | | 3 | 0.8 | S |
| 343 | hVH_4_39 | hVK_1_09 | | 0.5 | 4 | S | S | 37 | 0.7 | S |
| 344 | hVH_4_39 | hVK_1_12 | | | | | | 0 | 0.9 | S |
| 345 | hVH_4_39 | hVK_1_16 | | | | | | 0 | 0.5 | S |
| 346 | hVH_4_39 | hVK_1_17 | 0.7 | 0.3 | 4 | S | S | 33 | 1.0 | S |
| 347 | hVH_4_39 | hVK_1_27 | | | | | | 0 | 0.4 | S |
| 348 | hVH_4_39 | hVK_1_39 | 2.1 | 0.3 | 60 | S | S | 48 | 1.2 | S |
| 349 | hVH_4_39 | hVK_2_30 | | 0.2 | 4 | S | S | 27 | 0.2 | S |
| 350 | hVH_4_39 | hVK_3_11 | | 0.3 | 60 | S | S | 48 | 0.2 | S |
| 351 | hVH_4_39 | hVK_3_15 | | 0.6 | 70 | S | S | 68 | 1.0 | S |
| 352 | hVH_4_39 | hVK_3_20 | | 0.6 | 60 | S | S | 49 | 1.2 | S |
| 353 | hVH_4_39 | hVL_1-40 | 0.6 | 0.9 | 70 | S | S | 81 | 1.1 | S |
| 354 | hVH_4_39 | hVL_1-47 | | 0.7 | 70 | S | S | 72 | 0.3 | S |
| 355 | hVH_4_39 | hVL_1-51 | | 0.8 | 60 | S | S | 65 | 0.5 | S |
| 356 | hVH_4_39 | hVL_2-11 | | | | | | 0 | 0.3 | S |
| 357 | hVH_4_39 | hVL_2-14 | 2.0 | 0.6 | 60 | S | S | 63 | 0.5 | S |
| 358 | hVH_4_39 | hVL_2-23 | 0.9 | 0.7 | 60 | S | S | 62 | 0.4 | S |
| 359 | hVH_4_39 | hVL_3-1 | 3.6 | 0.5 | 60 | S | S | 59 | 0.9 | S |
| 360 | hVH_4_39 | hVL_3-21 | | 0.6 | 60 | S | S | 57 | 0.6 | S |
| 361 | hVH_5_51 | hVK_1_05 | | 0.5 | 60 | S | S | 52 | 0.4 | S |
| 362 | hVH_5_51 | hVK_1_06 | | 0.5 | 60 | S | S | 54 | 0.9 | S |
| 363 | hVH_5_51 | hVK_1_09 | 2.6 | 0.5 | 60 | S | S | 57 | 0.5 | S |
| 364 | hVH_5_51 | hVK_1_12 | 1.8 | | | | | 3 | 0.8 | S |
| 365 | hVH_5_51 | hVK_1_16 | 1.3 | | | | | 2 | 0.5 | S |
| 366 | hVH_5_51 | hVK_1_17 | | 0.3 | 4 | S | S | 32 | 0.6 | S |
| 367 | hVH_5_51 | hVK_1_27 | 0.4 | 0.2 | 60 | S | S | 43 | 1.0 | S |
| 368 | hVH_5_51 | hVK_1_39 | 3.7 | 0.3 | 60 | S | S | 51 | 1.2 | S |
| 369 | hVH_5_51 | hVK_2_30 | 0.9 | 0.2 | 4 | S | | 19 | 0.7 | S |
| 370 | hVH_5_51 | hVK_3_11 | | 1.0 | 60 | S | | 62 | 0.6 | S |
| 371 | hVH_5_51 | hVK_3_15 | 1.9 | | | | | 3 | 1.2 | S |
| 372 | hVH_5_51 | hVK_3_20 | | | | | | 0 | 1.1 | S |
| 373 | hVH_5_51 | hVL_1-40 | | 1.0 | 60 | S | S | 72 | 1.3 | S |
| 374 | hVH_5_51 | hVL_1-47 | | 1.0 | 60 | S | S | 73 | 0.8 | S |
| 375 | hVH_5_51 | hVL_1-51 | | 1.1 | 60 | S | S | 77 | 0.5 | S |
| 376 | hVH_5_51 | hVL_2-11 | 0.0 | 0.7 | 60 | S | S | 63 | 0.3 | S |
| 377 | hVH_5_51 | hVL_2-14 | 2.1 | | | | | 4 | 0.8 | S |
| 378 | hVH_5_51 | hVL_2-23 | 3.0 | 1.0 | 60 | S | S | 79 | 0.7 | S |
| 379 | hVH_5_51 | hVL_3-1 | 3.8 | 0.7 | 60 | S | S | 67 | 1.3 | S |
| 380 | hVH_5_51 | hVL_3-21 | | | | | | 0 | 0.7 | S |
| 381 | hVH_6_1 | hVK_1_05 | | 0.7 | 60 | S | S | 62 | 0.0 | S |
| 382 | hVH_6_1 | hVK_1_06 | 3.3 | 0.6 | 60 | S | S | 64 | 1.2 | S |
| 383 | hVH_6_1 | hVK_1_09 | 5.9 | | | | | 10 | 1.3 | S |
| 384 | hVH_6_1 | hVK_1_12 | 1.5 | 0.0 | bg | U | S | 13 | 1.1 | S |
| 385 | hVH_6_1 | hVK_1_16 | | | | | | 0 | 1.4 | S |
| 386 | hVH_6_1 | hVK_1_17 | | 0.5 | 60 | S | S | 54 | 1.3 | S |
| 387 | hVH_6_1 | hVK_1_27 | | 0.5 | 70 | S | S | 63 | 1.2 | S |
| 388 | hVH_6_1 | hVK_1_39 | | 0.3 | 60 | S | S | 45 | 1.1 | S |
| 389 | hVH_6_1 | hVK_2_30 | | 0.3 | 4 | S | S | 32 | 0.3 | S |
| 390 | hVH_6_1 | hVK_3_11 | | | | | | 0 | 0.9 | S |
| 391 | hVH_6_1 | hVK_3_15 | | 0.7 | 70 | S | S | 70 | 1.3 | S |
| 392 | hVH_6_1 | hVK_3_20 | | 0.9 | 60 | S | S | 70 | 1.3 | S |
| 393 | hVH_6_1 | hVL_1-40 | 7.2 | | | | | 12 | 1.4 | S |
| 394 | hVH_6_1 | hVL_1-47 | | 1.1 | 60 | S | S | 75 | 0.2 | S |
| 395 | hVH_6_1 | hVL_1-51 | | 1.1 | 60 | S | S | 75 | 0.5 | S |
| 396 | hVH_6_1 | hVL_2-11 | 1.0 | 1.0 | 60 | S | S | 73 | 0.2 | S |
| 397 | hVH_6_1 | hVL_2-14 | | | | | | 0 | 0.4 | S |
| 398 | hVH_6_1 | hVL_2-23 | 2.1 | 0.8 | 60 | S | S | 69 | 0.4 | S |
| 399 | hVH_6_1 | hVL_3-1 | | 0.5 | 60 | S | S | 55 | 1.4 | S |
| 400 | hVH_6_1 | hVL_3-21 | 0.4 | 0.8 | 60 | S | S | 66 | 0.5 | S |

Table 12 Key:
For relative Fab display, relative Fab expression and relative IgG1 expression, the values illustrate the levels as compared to a control. Higher numbers indicate higher levels.
For Fab thermostability, the numbers 60 and 70 indicate VH/VL pairs which are stable for 45 minutes at 60° C. or 70° C. at the tested conditions. The number 4 indicates temperature instable pairs and bg (background) indicates low expression levels.
For Fab stability in mouse serum, Fab stability in bovine serum and IgG1 stability in bovine serum, S stands for stable, U for unstable, and bg for background, at the tested conditions.

As described in the previous examples, the predominant VH and VL germline genes and the predominant VH/VL germline gene pairs were identified from the human immune repertoire, then the predominant VH and VL germline protein sequences were analysed in silico in order to identify and select variable heavy chain and variable light chain germline protein sequences having favorable biophysical properties. As shown in Table 5, and FIGS. 2-3, generally, the top 20VH, top 8Vλ and top 12 Vκ were selected for synthesis, combination and subsequent functional analysis.

The germline gene sequences were synthesized and then combined in order to generate 400 germline protein pairs that are representative of the abundant germline gene pairs expressed in the human immune repertoire. The 400 VH/VL germline protein pairs were tested for the following properties: a) relative display after phage production and phage ELISA in Fab format; b) relative Fab expression yield after Fab production in *E. coli*, *E. coli* cell lysis and ELISA detection of produced Fab; c) temperature stability of Fab after Fab production in *E. coli*, *E. coli* cell lysis and ELISA detection of non-denatured Fab after incubation at increased temperatures; d) bovine/mouse serum stability of Fab from *E. coli* lysates by ELISA detection of non-denatured Fab after incubation in bovine/mouse serum; e) relative human IgG1 expression yield after IgG1 production in mammalian cells and ELISA detection of secreted IgG1 from cell culture supernatants; and f) bovine serum stability of human IgG1 by ELISA detection of non-denatured IgG1 after incubation in bovine/mouse serum.

Using the data provided in Table 12, one of skill in the art could readily identify the germline protein pairs having favorable biophysical properties.

Generally, the germline protein pairs having a threshold value in each functional property were selected for incorporation in the collections. For example, in some embodiments, the germline protein pairs comprising all of the following properties were selected for incorporation into a collection: i) a relative display rate in Fab format comprising a value within the top 75% of Fabs sampled; ii) an expression yield in Fab format of at least 0.4 as compared to Fab VH1-69 VLA_VI1-40 AYA; iii) thermal stability at 60° C. or more for at least 45 minutes in Fab format; iv) stability in bovine or mouse serum in Fab format for greater than ten days at 37° C.; v) an expression yield in IgG format of at least 0.4 as compared to MOR03080; and vi) stability in serum in IgG format for fourteen days at 37° C. Table 32 shows in bold and underline the germline protein pairs comprising all of these functional properties.

As described above, however, germline protein pairs having one or more of the functional properties may be selected for incorporation into collections. Here, an aggregate ranking of the 400 germline protein pairs tested was created, so that each germline protein pair could be ranked against the other giving weight to each of the functional properties tested. This allowed the inventors to select one or more germline protein pairs having one or more or all of the listed functional properties. In some embodiments, the collections comprise all of the germline protein pairs having the above characteristics. In some embodiments, the collection comprises the germline protein pairs having the highest aggregate score of the 400 pairs tested. In some embodiments, the germline protein pairs having aggregate scores within the top 10%, top 20%, or top 30% of the 400 pairs tested were selected for incorporation into collections.

Example 9

Further Testing of ~100 VH/VL Pairs

Of the 400 germline protein pairs tested above (results shown in Table 12), 95 were selected for further testing. The previous testing of the 400 germline protein pairs for display, expression yield, thermal and serum stability acted as a preliminary filter to remove the germline protein pairs that do not have characteristics thought to be favorable for therapeutic development. The goal was to select a sub-group of germline protein pairs having favorable developability characteristics, while at the same time maintaining a high level of diversity within a collection so that the collection can be used to identify developable candidates against any antigen.

Table 12 shows ~60 bold and underlined germline protein pairs which met the thresholds of an embodiment of the disclosure. Of the 95 germline protein pairs selected for further testing, some were chosen because they met the previous criteria, and it was desirable to further test them. Others were chosen, despite not meeting certain thresholds, so that these pairs could be re-evaluated. Again, one of the goals of the present disclosure is to provide a diverse collection that is able to be used to identify antibodies or fragments against any antigen. The 95 germline protein pairs shown in FIGS. 16-24 were synthesized as described in Example 5. After synthesis and expression in Fab and IgG1 formats, the 95 germline protein pairs were further tested in both Fab and IgG1 formats for the following a) purified Fab expression yield in mg/L (expression culture), b) purified Fab monomeric content (% monomer), c) purified Fab thermal stability in ° C., d) purified IgG1 expression yield in mg/L (cell culture), e) purified IgG1 monomeric content (% monomer), f) purified IgG1 thermal stability in ° C., g) IgG1 isoelectric point and h) IgG stress testing with exposure to acid, including differential scanning fluorometry (DSF), absorption, dynamic light scattering and particle staining.

Example 9.1

Purified Fab Testing

Fab fragments representing each of the 95 germline protein pairs selected for further testing were expressed in *E. coli* and purified. Expression of Fab fragments in *E. coli* TG-1 F-cells was carried out in 500 ml cultures of 2xYT medium supplemented with 0.1% glucose and chloramphenicol. Cultures were shaken until the OD600 nm reached 0.5. Fab expression was induced by addition of IPTG (isopropyl-β-D-thiogalactopyranoside) and further over night cultivation. Cells were harvested and disrupted using lysozyme. His6-tagged (SEQ ID NO: 203) Fab fragments were isolated via IMAC (Bio-Rad, Munich, Germany) and eluted using imidazole. Buffer exchange to 1× Dulbecco's PBS (pH 7.2, Invitrogen, Darmstadt, Germany) was performed using PD10 columns (GE Healthcare, Munich, Germany). Samples were sterile filtered (0.2 μm).

Example 9.1.1

Purified Fab Expression Yield Determination

The protein concentrations of purified Fab fragments representing each of the 95 germline protein pairs were determined by UV-spectrophotometry (Nanodrop, peqlab, Erlangen, Germany). The extinction coefficient used was 1.538 mL/mg and measured absorbance at 280 nm. The results are shown in FIGS. 16-18.

Example 9.1.2

Purified Fab Thermal Stability Determination

The thermal stability of purified Fab fragments representing each of the 95 germline protein pairs were determined by differential scanning fluorometry (DSF). Differential scanning fluorometry (DSF) is a fluorescence dye based technique that monitors thermal unfolding (melting point) of a protein of interest. Changes in the fluorescence of a hydrophobic dye interacting with the hydrophobic amino acid side-chains of the unfolding protein are monitored over a temperature ramp.

The following materials were used: Sypro Orange fluorescent dye (Sigma, #S5692); iCycler iQ PCR Plates, 96-well (Biorad, #2239441); Microseal B Adhesive Sealer (Biorad #MSB-1001); 96-well Optical Pad (Biorad, #ADR3296); iCycler iQ5 Thermal cycler (Biorad) and Gibco D-PBS, pH 7.4 (Invitrogen, Paisley, USA).

Diluted Sypro Orange was added to each well of a 96 well iCycler iQ PCR Plate, and the samples were tested at a final concentration of at least 0.1 mg/ml. The iCycler iQ5 Thermal cycler (Biorad) was used for testing. The temperature was scanned from 20° C. to 95° C. at a heating rate of 60° C./h, and the temperature of unfolding was calculated by analysis of the midpoint of the fluorescence transition. The results are shown in FIGS. 16-18 in the Purified Fab Thermafluor column.

Example 9.1.3

Purified Fab Separation by Size Exclusion Chromatography

The monomer contents (% monomer) of purified Fab fragments representing each of the 95 germline protein pairs were determined by size exclusion chromatography (SEC). SEC was performed on an ÄKTA Purifier System (GE Healthcare Europe GmbH, Freiburg, Germany). For separation a Superdex75 HR 10/30 column was used (GE Healthcare Europe GmbH, Freiburg, Germany). For each sample 10 µl of protein was loaded onto the column, separation was performed at a flow rate of 0.05 ml/min and recorded analyzing the UV absorption at 260 and 280 nm. The running buffer was composed of Gibco D-PBS, pH 7.4 (Invitrogen, Paisley, USA). The results are shown in FIGS. 16-18.

Example 9.2

IgG1 Expression and Purification

IgG1s representing each of the 95 germline protein pairs selected for further testing were expressed in HKB11 cells. Eukaryotic HKB11 cells were transfected with a 1:1 ratio of IgG heavy and light chain expression vector DNA. Cell culture supernatant was harvested on day 3 to 4 post transfection and subjected to protein A affinity chromatography (MabSelect SURE, GE Healthcare, Munich, Germany). Buffer exchange was performed with 1× Dulbecco's PBS (pH 7.2, Invitrogen, Darmstadt, Germany) and samples were sterile filtered (0.2 µm pore size).

Example 9.2.1

Purified IgG1 Expression Yield Determination

The protein concentrations of purified IgG1s representing each of the 95 germline protein pairs were determined by UV-spectrophotometry (Nanodrop, peqlab, Erlangen, Germany). The extinction coefficient used was 1.369 mL/mg and measured absorbance at 280 nm. The results are shown in FIGS. 16-18.

Example 9.2.2

Purified IgG1 Thermal Stability Determination

IgG1 thermal stability of purified IgG1s was determined by differential scanning fluorometry (DSF) as described in method 9.1.2. The values shown for each IgG represent the unfolding events that take place within the variable regions of the IgG. The values representing unfolding of the Fc portion are not shown, as they are generally identical for each human IgG1. The results are shown in FIGS. 16-18.

Example 9.2.3

Purified IgG1 Separation by Size Exclusion Chromatography

The monomeric content (% monomer) of purified IgG1 representing each of the 95 germline protein pairs were determined by size exclusion chromatography (SEC). HP-SEC was performed on a Dionex UltiMate 3000 Titanium HPLC system (Dionex Corporation, Germering, Germany) in combination with Wyatt miniDAWN Treos and Wyatt Optilab rEX (Wyatt Technology Europe, Dernbach, Germany). For separation a Tosoh TSK-Gel G3000SWxl column was used (Tosoh Bioscience, Stuttgart, Germany). For each sample 15 µg of protein was loaded onto the column, separation was performed at a flow rate of 0.5 ml/min and recorded analyzing the UV absorption at 280 nm. The running buffer was composed of Gibco D-PBS, pH 7.4 (Invitrogen, Paisley, USA). The results are shown in FIGS. 16-18.

Example 9.2.4

Purified IgG1 Isoelectric Point (pI) Calculation

The Isoelectric point of each germline protein pair in IgG1 format was calculated. Methods of determining the pI of a protein are known to one of skill in the art. For example, the following tools can be used: http://www.expasy.org/tools/pi_tool.html; Vector NTI (Invitrogen, Carlsbad, Calif.). The results are shown in FIGS. 16-18.

Example 9.2.5

Purified IgG1 Stress Testing with Exposure to Acid

As a virus inactivation step is standard during the downstream processing (DSP) of Chemistry, Manufacturing and Control (CMC), the ability of the 95 germline protein pairs to withstand acid was tested by lowering the pH and recording aggregation sensitive data for each of the IgG1s. Each of the germline protein pairs was delivered in a 96-deep-well plate format in a concentration of 2 mg/mL. 150 µL of each was transferred into a 96-well plate. Initial characterization was performed by absorption, dynamic light scattering (DLS), differential scanning fluorometry (DSF) measurements and particle staining. The samples were acidified using 1.8 µL 1M Citrate pH 2.3. Samples were neutralized after 2, 5 hours using 1 M Tris pH9.0.

Example 9.2.5

(a) Purified IgG1 Differential Scanning Fluorometry

In order to evaluate the thermal stability before and after exposure to acid of IgG1s representing each of the 95 germline protein pairs selected for further testing, differential scanning fluorometry (DSF) was performed as described in Example 9.1.2. The values shown for each IgG represent the unfolding events that take place within the variable regions of the IgG. The values representing unfolding of the Fc portion are not shown, as they are generally identical for each IgG. If the Tm (apparent melting point) values before and after exposure to acid are equal then the molecular structure of the antibody was either unaffected by the acid or was able to refold efficiently after exposure. The results are shown in FIGS. 19, 21, and 23.

Example 9.2.5

(b) Purified IgG1 UV/Vis Absorption

In order to identify aggregating samples turbidity was recorded at 320 nm. Turbidity of IgG solutions was assessed before and after acid exposure representing each of the 95 germline protein pairs selected for further testing. The results are shown in FIGS. 19, 21, and 23. Baseline absorption was 0.035 extinction units expected for clear solutions. Increase in absorption is caused by light scattering which results in increasing absorption. Values above 0.039 are likely to contain aggregates. Values above 0.045 indicate clear presence of aggregates. Values above 0.06 represent critical aggregation levels which were found for molecules with strongly unfavourable stability.

Example 9.2.5

(c) Purified IgG1 Dynamic Light Scattering

In addition, Dynamic Light Scattering (DLS) was performed on each IgG1 representing the 95 germline protein pairs selected. Dynamic light scattering (DLS) is a spectroscopic method to assess the hydrodynamic radius of particles in solution. All DLS experiments were performed using a DynaPro Titan cuvette system (Wyatt Technology Europe, Dernbach, Germany).

In case of visible particle contamination after stress testing, the IgGs were centrifuged in order to remove large aggregates. FIGS. 20, 22 and 24 show the apparent particle radius and polydispersity corresponding to the monomeric IgG1 found in the preparations before and after acid treatment. The data was evaluated according to the calculated radius of the cumulant analysis. In addition to the hydrodynamic radius, the % polydispersity of the preparations was assessed. An increase in polydispersity (>15%) indicates potential aggregation of the IgG molecules, leading to heterogeneous particle size distribution. High molecular weight (HMW) particles clearly distinguishable from the IgG (radius >3-fold) are not listed in the table. All DLS results are shown in FIGS. 20, 22 and 24.

Example 9.2.5

(d) Purified IgG1 Particle Staining

In order to evaluate the amount and morphology of visible aggregates, particle staining was performed before and after acid exposure on each IgG1 representing the 95 germline protein pairs selected. The following reagents were used to filter and stain particles in IgG preparations: Ultrafree-CL 0.22 µm sterile filter (Millipore, #UFC40GVOS); Anti-human lambda light chain, AP conjugated (Sigma #A-2904); Developing agent for AP-conjugates, Fast BCIP/NBT, (Sigma #B-5655); Roti®-ImmunoBlock (Roth #T144.1); Alkaline Phosphatase Stop Solution (Sigma #A5852-100ML); TBS: 0.05 M Tris; 0.15 M NaCl; TBS with 0.1% Tween 20; and 5 M NaCl solution.

The protein solution was filtered through a 0.22 µm filter and the remaining antibody aggregates are subsequently stained using the mouse anti human Fab2 alkaline phosphatase conjugated antibody and a western blot developing agent. The assay was performed according to the manufacturer's manual. The samples were subsequently categorized by visual inspection in range from 1-4, with category 1 representing very low particle content and category 4 representing high particle load of the preparation. All particle staining results are shown in FIGS. 20, 22 and 24.

Example 9.2.6

Purified IgG1 Stress Testing with Agitation

The ability of antibodies or antibody fragments to resist sheer forces is a helpful criteria as filtration steps cannot be avoided during processing. Therefore, the 95 germline protein pairs were tested in IgG1 format using a glass pearl that was accelerated in a 96 well plate on an orbital shaker at 550 rpm in a deep well plate. 350 µl of each IgG was subjected to this treatment. 150 µL of each was transferred into a 96-well plate. Initial characterization was performed by absorption, dynamic light scattering (DLS), differential scanning fluorometry (DSF) measurements and particle staining.

Example 9.2.6

(a) Purified IgG1 UV/Vis Absorption

In order to identify aggregating samples turbidity was recorded at 320 nm. Turbidity of IgG solutions representing each of the 95 germline protein pairs selected for further testing was assessed before and after stress exposure. The results are shown in FIGS. 49, 51 and 53. Baseline absorption was 0.035 extinction units expected for clear solutions. Increase in absorption is caused by light scattering which results in increasing absorption. Values above 0.039 are likely to contain aggregates. Values above 0.045 indicate clear presence of aggregates. Values above 0.06 were found for critical aggregation levels which were found for molecules with strongly unfavourable stability.

Example 9.2.6

(b) Purified IgG1 Differential Scanning Fluorometry

In order to evaluate the thermal stability before and after exposure to acid of IgG1s representing each of the 95 germline protein pairs selected for further testing, differential scanning fluorometry (DSF) was performed as described in Example 9.1.2. The values shown for each IgG represent the unfolding events that take place within the variable regions of the IgG. The values representing unfolding of the Fc portion are not shown, as they are generally identical for each human IgG1. The results are shown in FIGS. 50, 52 and 54.

Example 9.2.6

(c) Purified IgG1 Dynamic Light Scattering

In addition, Dynamic Light Scattering (DLS) was performed on each IgG1 representing the 95 germline protein pairs selected. Dynamic light scattering (DLS) is a spectroscopic method to assess the hydrodynamic radius of particles in solution. All DLS experiments were performed using a DynaPro Titan cuvette system (Wyatt Technology Europe, Dernbach, Germany).

In case of visible particle contamination after stress testing, the IgGs were centrifuged in order to remove large aggregates. FIGS. 50, 52 and 54 show the apparent particle radius and polydispersity corresponding to the monomeric IgG1 found in the preparations after stress treatment. The data was evaluated according to the calculated radius of the cumulant analysis. In addition to the hydrodynamic radius, the % polydispersity of the preparations was assessed. An increase in polydispersity (>15%) indicates potential aggregation of the IgG molecules, leading to heterogeneous particle size distribution. High molecular weight (HMW) particles clearly distinguishable from the IgG (radius >3-fold) are not listed in the table. All DLS results are shown in FIGS. 50, 52 and 54.

Example 9.2.6

(d) Purified IgG1 Particle Staining

In order to evaluate the amount and morphology of visible aggregates, particle staining was performed before and after stress exposure on each IgG1 representing the 95 germline protein pairs selected. The following reagents were used to filter and stain particles in IgG preparations: Ultrafree-CL 0.22 µm sterile filter (Millipore, #UFC40GVOS); Anti-human lambda light chain, AP conjugated (Sigma #A-2904); Developing agent for AP-conjugates, Fast BCIP/NBT, (Sigma #B-5655); Roti®-ImmunoBlock (Roth #T144.1); Alkaline Phosphatase Stop Solution (Sigma #A5852-100ML); TBS: 0.05 M Tris; 0.15 M NaCl; TBS with 0.1% Tween 20; and 5 M NaCl solution.

The protein solution was filtered through a 0.22 µm filter and the remaining antibody aggregates are subsequently stained using the mouse anti human Fab2 alkaline phosphatase conjugated antibody and a western blot developing agent. The assay was performed according to the manufacturer's manual. The samples were subsequently categorized by visual inspection in range from 1-4, with category 1 representing very low particle content and category 4 representing high particle load of the preparation. All particle staining results are shown in FIGS. 50, 52 and 54.

Example 9.2.7

IgG Stress Testing Cumulative Score

In order to help evaluate the stress testing results of both exposure to acid and agitation with glass beads, a scoring system was created so that the germline protein pairs could be compared. Each data point taken in Examples 9.2.5(a-d), results shown in FIGS. 19-24 and Examples 9.2.6(a-d), results shown in FIGS. 49-54 was given a score ranging from 0-100 (0, 25, 75 or 100) and the scores were added together to generate a cumulative score. The thermal stability values identified in Examples 9.2.5(a) and 9.2.6 (b) were not given scores.

FIGS. 55 and 56 show the stress testing scores for the germline protein pairs 1-32 from Examples 9.2.5-9.2.6. Each score is a representation of the raw data points shown in FIGS. 19, 20, 49 and 50. FIGS. 19-20 show the response to acid exposure and FIGS. 49-50 show the response to agitation with glass beads. FIG. 56 shows the cumulative score, which is the addition of each of the scores shown in FIGS. 55 and 56.

FIGS. 57 and 58 show the stress testing scores for the germline protein pairs 33-64 from Examples 9.2.5-9.2.6. Each score is a representation of the raw data points shown in FIGS. 21, 22, 51 and 52. FIGS. 21-22 show the response to acid exposure and FIGS. 51-52 show the response to agitation with glass beads. FIG. 58 shows the cumulative score, which is the addition of each of the scores shown in FIGS. 57 and 58.

FIGS. 59 and 60 show the stress testing scores for the germline protein pairs 65-95 from Examples 9.2.5-9.2.6. Each score is a representation of the raw data points shown in FIGS. 23, 24, 53 and 54. FIGS. 23-24 show the response to acid exposure and FIGS. 53-54 show the response to agitation with glass beads. FIG. 60 shows the cumulative score, which is the addition of each of the scores shown in FIGS. 59 and 60.

Example 10

Selection of Collection Composition

In summary, 400 germline protein pairs were selected, as described in Example 4. These 400 are a representation of the diversity of germline protein pairs that exist in the human immune repertoire. The 400 germline protein pairs were tested as described in Examples 6-7. Of the 400, 95 were further tested as described in Example 9.

The 95 germline protein pairs were compared taking the following factors into consideration: a) Fab display rate; b) Fab expression yield, c) Fab thermal stability; d) Fab serum stability; e) Fab SEC monomeric content (% monomer); f) IgG1 expression yield; g) IgG1 thermal stability; h) IgG1 serum stability; i) IgG1 SEC monomeric content (% monomer); and j) IgG1 isoelectric point (pI). The data for each of these factors are shown in FIGS. 16-18. These factors correlate well to the developability of therapeutic antibodies.

Fab display rate is an important factor in the selection of antibodies or fragments against an antigen. Fabs displaying at a high rate have a higher likelihood to be exposed to the antigen upon selection. A high display rate of each of the various Fabs makes sure that the full diversity of the collection is exposed to an antigen upon selection. The Fab display rate was identified in Example 6.2, where the reference was an internal standard (HuCAL GOLD reference phage preparation (VH3 kappa+lambda)). The HuCAL GOLD VH3 prep is a high displaying preparation. Fab display rate is an important factor and was useful in narrowing the 400 pairs down to 95 for further testing, but in some embodiments was not considered a determinative factor in the selection of germline protein pairs for incorporation into collections.

Expression yield of both Fab and IgG1 are important as antibodies or fragments selected against an antigen, first must be tested, often in vitro or in vivo to determine functional activity, then in tox species and finally in humans for clinical trials. It is very important that the antibodies or fragments selected against an antigen can be efficiently expressed in high enough quantity to support all of the various testing required for therapeutic development and for supply of clinical trial and market. The expression yield (mg purified Fab/L of expression culture) of purified Fabs was identified in Example 9.1.1 (results shown in FIGS. 16-18) and, in an embodiment of the disclosure, a threshold of at least 2.5 mg/L was selected. In other embodiments, other thresholds were selected. The expression yield (mg purified IgG1/L of cell culture) of purified IgG1 was identified in Example 9.2.1 (results shown in FIGS. 16-18) and, in an embodiment of the disclosure, a threshold of at least 30.0 mg/L was selected. In other embodiments, other thresholds were selected.

Thermal stability is an important factor as proteins, such as, antibodies, are susceptible to high temperatures, therefore, antibodies capable of withstanding the requirements associated with the storage and transportation required in order to distribute therapeutics worldwide and have a long shelf life are essential. The thermal stability of purified Fab was determined in Example 9.1.2 (results shown in FIGS. 16-18) and, in an embodiment of the disclosure, a threshold of at least 70° C. was selected. In other embodiments, other thresholds were selected. The thermal stability of purified IgG1 was determined in Example 9.2.2 (results shown in FIGS. 16-18), the listed value represents the de-stabilization of the variable domains and, in an embodiment, a threshold of at least 73° C. was selected. In other embodiments, other thresholds were selected.

Serum stability is an important factor for therapeutic antibodies as therapeutic proteins must maintain efficacy and functional conformation despite being exposed to the serum proteases present in human serum. The serum stability of the germline protein pairs were determined by the methods described in Examples 6.5, and 7.2. Serum stability is important, but was not considered a determinative factor in the selection of germline protein pairs as the assay tended to produce false-negative results in few cases.

Monomeric content (% monomer) as determined by size exclusion chromotagraphy (SEC) is an important factor as it correlates well to aggregation propensity. Aggregation is a common problem in therapeutic protein development, which leads to the inactivation, inhomogeneity and production loss of the protein therapeutic. The monomeric content (% monomer) as determined by size exclusion chromatography (SEC) in both purified Fab and purified IgG1 formats was determined by the methods described in Examples 9.1.3 and 9.2.3 (results shown in FIGS. 16-18). The monomeric content (% monomer) of purified Fab was determined in Example 9.1.3 and, in an embodiment, a threshold of at least 98% was selected. In other embodiments, other thresholds were selected. The monomeric content (% monomer) of purified IgG1 was determined in Example 9.2.3 and, in an embodiment, a threshold of at least 99% was selected. In other embodiments, other thresholds were selected.

Isoelectric point (pI) is predictive of solubility at a certain pH. When the pH of the solution is significantly different from the pI of a given protein, the protein is soluble. Isoelectric point is important, but in some embodiments was not considered a determinative factor in the selection of germline protein pairs.

In an embodiment of the present disclosure, the thresholds for each criteria were selected as follows: a) purified Fab expression yield (as described in Example 9.1.1) of at least 2.5 mg/L; b) purified IgG1 expression yield (as described in Example 9.2.1) of at least 30.0 mg/L; c) thermal stability of purified Fab (as described in Example 9.1.2) of at least 70° C.; d) thermal stability of purified IgG1 (as described in Example 9.2.2) of at least 73° C.; e) monomeric content of purified Fab (as described in Example 9.1.3) of at least 98%; and f) monomeric content of purified IgG1 (as described in Example 9.2.3) of at least 99%. The following germline protein pairs (54) were identified as having these superior functional activities related to developability as each of the following pairs had values equal to or better than these thresholds (data shown in FIGS. 16-24): VH1-18 (SEQ ID NO: 204)/VK1-39 (SEQ ID NO: 236); VH1-18 (SEQ ID NO: 204)/VK3-15 (SEQ ID NO: 238); VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-46 (SEQ ID NO: 205)/VL3-21 (SEQ ID NO: 257); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-16 (SEQ ID NO: 234); VH3-07 (SEQ ID NO: 207)/VK1-27 (SEQ ID NO: 235); VH3-07 (SEQ ID NO: 207)/VK1-39 (SEQ ID NO: 236); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VK1-05 (SEQ ID NO: 230); VH3-11 (SEQ ID NO: 208)/VK1-39 (SEQ ID NO: 236); VH3-11 (SEQ ID NO: 208)/VK3-15 (SEQ ID NO: 238); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-16 (SEQ ID NO: 234); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-40 (SEQ ID NO: 250); VH3-15 (SEQ ID NO: 209)/VL1-47 (SEQ ID NO: 251); VH3-15 (SEQ ID NO: 209)/VL1-51 (SEQ ID NO: 252); VH3-15 (SEQ ID NO: 209)/VL2-14 (SEQ ID NO: 254); VH3-21 (SEQ ID NO: 210)/VK1-12 (SEQ ID NO: 233); VH3-21 (SEQ ID NO: 210)/VK1-27 (SEQ ID NO: 235); VH3-21 (SEQ ID NO: 210)/VL2-11 (SEQ ID NO: 253); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-30 (SEQ ID NO: 212)/VK3-20 (SEQ ID NO: 239); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK1-27 (SEQ ID NO: 235); VH3-74 (SEQ ID NO: 214)/VK3-20 (SEQ ID NO: 239); VH3-74 (SEQ ID NO: 214)/VL1-51 (SEQ ID NO: 252); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-15 (SEQ ID NO: 238); VH6-1 (SEQ ID NO: 216)/VK3-20 (SEQ ID NO: 239) and VH6-1 (SEQ ID NO: 216)/VL1-51 (SEQ ID NO: 252). Therefore, collections comprising any number of these germline protein pairs can be used to identify developable antibodies or fragments thereof against any antigen.

Additionally, a subset of germline protein pairs were selected based upon a comparison of the stress testing data identified using the methods described in Examples 9.2.5 (a-d), data shown in FIGS. 19-24, Example 9.2.6 (a-d), data shown in FIGS. 49-54 and Example 9.2.7, scoring shown in FIGS. 55-60. The stress testing methods evaluated the 95 germline protein pairs in IgG1 format in order to determine their ability to withstand exposure to acid and agitation with glass beads. 36 germline protein pairs, of an embodiment, were selected as they have additional superior functional properties relevant to developability as they showed strong resistance to acid and agitation stress. An antibody's ability to withstand exposure to acid is an increasingly important factor, as a virus inactivation step is standard during the downstream processing (DSP) of Chemistry, Manufacturing and Control (CMC). The acid treatment step denatures virus capsid proteins, which a virus would use for infection. However, lowering the pH has a destabilizing effect on every protein. Unstable antibodies denature and loose native structure during this step. In the virus activation step, after a defined time, the acid treatment is relieved by neutralization and while the virus capsid proteins stay in an inactive conformation, the processed antibody ideally retains its native structure. The ability of antibodies or antibody fragments to resist sheer forces is a helpful criteria as filtration steps cannot be avoided during processing. These 36 germline protein pairs selected in an embodiment, fulfilled all of the previous threshold functional activities and in addition scored at or above 1225 in the stress testing cumulative score. In an embodiment, the thresholds for each criteria were selected as follows: a) purified Fab expression yield (as described in Example 9.1.1) of at least 2.5 mg/L; b) purified IgG1 expression yield (as described in Example 9.2.1) of at least 30.0 mg/L; c) thermal stability of purified Fab (as described in Example 9.1.2) of at least 70° C.; d) thermal stability of purified IgG1 (as described in Example 9.2.2) of at least 73° C.; e) monomeric content of purified Fab (as described in Example 9.1.3) of at least 98%; f) monomeric content of purified IgG1 (as described in Example 9.2.3) of at least 99% and g) stress testing cumulative score (as described in Example 9.2.7) of at least 1225. Therefore, embodiments of the present disclosure comprise collections comprising a subset of the fully functional germline protein pairs (36 of the 54) and have additional superior functional properties relevant to developability. In this embodiment, a collection comprises VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

In another embodiment, the thresholds for each criteria were selected as follows: a) purified Fab expression yield (as described in Example 9.1.1) of at least 2.5 mg/L; b) purified IgG1 expression yield (as described in Example 9.2.1) of at least 30.0 mg/L; c) thermal stability of purified Fab (as described in Example 9.1.2) of at least 70° C.; d) thermal stability of purified IgG1 (as described in Example 9.2.2) of at least 73° C.; e) monomeric content of purified Fab (as described in Example 9.1.3) of at least 99%; f) monomeric content of purified IgG1 (as described in Example 9.2.3) of at least 99%; g) isoelectric point of purified IgG1 (as described in Example 9.2.4) of at least 8.3; and h) stress testing cumulative score (as described in Example 9.2.7) of at least 1225. In this embodiment, a collection comprises (33 pairs): VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK3-15 (SEQ ID NO: 238); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252)

In a further embodiment, pairs were added to a collection even though the pairs themselves did not meet all of the thresholds within each criteria, but were added to the collections in order to enhance diversity. In an embodiment, a collection further comprises: VH3-23 (SEQ ID NO: 211)/VK1-39 (SEQ ID NO: 236); VH3-23 (SEQ ID NO: 211)/VL2-23 (SEQ ID NO: 255); and VH3-23 (SEQ ID NO: 211)/VL3-1 (SEQ ID NO: 256). In this embodiment, a collection comprises (36 pairs): VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO:

207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

Example 11

Beta Testing of Collections

In order to confirm the effectiveness of the collection design, sub-collections, each comprising one germline protein pair or pools of sub-collections were generated and selected against antigens. The antibodies selected were then tested in both Fab and IgG1 formats for developability characteristics, such as, thermal stability in Fab format, pI in IgG1 format, expression yields in both Fab and IgG1 formats, thermal stability in IgG1 format, and % monomer in IgG1 format as determined by SEC. In addition, in some cases the affinity for the antigen in Fab format was determined.

Collection Generation

Sub-collections containing germline protein pairs were synthesized as follows: the FR1-CDR1-FR2-CDR2-FR3 regions from the respective germline protein sequences shown in FIGS. 25-33 were synthesized by GeneArt (Regensburg, Germany). The VHs were cloned via NheI and SalI and VLs via NdeI and Acc65I into the pJPd1 display vector. CDR-H3 cassettes including the constant FR4 region were inserted via BssHII and XhoI with theoretical diversities ranging between $5.5 \times 10^5$ and $1.9 \times 10^{19}$. CDR-H3 cassettes with CDR-H3 lengths from 6-17 amino acids were synthesized by Sloning (Martinsried, Germany). CDR-L3 diversity was achieved by introducing either kappy or lambda TRIM cassettes synthesized by ELLA Biotech (Martinsried, Germany) with theoretical diversity ranging between $4.6 \times 10^6$ and $2.5 \times 10^9$.

Typically 0.25 to 2 µg pJPd1 phagemid DNA of the sub-collections were transformed in *E. coli* MC1061 F' electrocompetent cells and transformants were collected in TB medium and shaken for at 37° C. for 1 h. Dilutions of the outgrowth medium were plated on LB/Cam/Gluc. Amplification of the libraries was performed by shaking o/n in appropriate amounts of LB/cam/1% Glu. Library sizes for sub-collections ranged between $4.6 \times 10^8$ and $4.4 \times 10^9$. The total library size of all sub-collections together is about $1.3 \times 10^{11}$ members. To analyze the quality of the engineered sub-collections at least 30 clones for each sub-collection were picked and CDR-L3 and -H3 regions were sequenced to determine correctness and uniqueness of the sequences. The libraries were stored as *E. coli* glycerol cultures.

Phage displaying the sub-collections in Fab format were prepared as follows. For each library phage preparation 80 ml 2xYT/Cam/Glc medium were inoculated with bacteria from the corresponding library glycerol stock resulting in an $OD_{600nm}$ of 0.2-0.3. Cultures were shaken until an $OD_{600nm}$ of 0.45-0.55 was reached. Then helper phage was added at a multiplicity of infection of 10 to the bacterial culture followed by an incubation for 45 min at 37° C. without shaking and then for 45 min at 37° C. shaking at 120 rpm. Bacteria were spun down and helper phage containing supernatant was discarded. Phage-infected bacteria were resuspended in 400 ml 2xYT/CAM/KAN/IPTG medium and incubated overnight at 22° C. with shaking at 120 rpm. The next day bacteria from the overnight culture were pelleted and the supernatant containing the Fab-presenting phage was collected. Phage precipitation was performed by adding PEG/NaCl to the phage-containing supernatant. The sample was incubated for at least 30 min on ice. Precipitated phage were spun down and resuspended in PBS. The sample was rotated slowly to obtain a homogeneous suspension and residual bacterial debris was pelleted and discarded. From the phage-containing supernatant the phage were precipitated again using PEG/NaCl. Finally, the phage pellet was resuspended in PBS, transferred to a sterile tube and shaken slowly to obtain a homogeneous suspension. Phage titers were determined by spot titration, ELISA and UV absorbance (Nanodrop) at OD268 nm.

Phage titers and display levels of Fab fragments expressed by the tricistronic display vector pJPd1 (shown in FIG. 9) and presented on the phage by CysDisplay® (as described in WO01/05950, U.S. Pat. No. 6,753,136, which is incorporated by reference in its entirety) were evaluated for each individual phage preparation by ELISA Two different antibodies are used for capturing:
(1) The anti-M13 antibody (Amersham #27-9420-01) was used, as it captures phage particles via the major coat protein g8p; therefore, phage titer can be determined.
(2) An anti-Fd antibody (The Binding Site #PC075) was used, which binds to the displayed Fab; therefore, only phage displaying Fabs are captured.

For (1) and (2) separate reference curves are used. A monoclonal anti-M13 (directed against major coat protein of M13 phage, g8p) conjugated to HRP is used as a detection antibody.

The respective capture antibodies were immobilized on 96-well Maxisorp™ plates by dispensing antibody solution for the anti-M13 antibody and for the anti-Fd antibody into different wells, sealing the plate with laminated foil and incubating overnight. The next day, the plates were washed with TBST, and each well was blocked with CTBST.

The starting dilutions of phage supernatants and reference samples (CS) were prepared in CTBST in microtiter plates. The starting dilutions of the phage supernatants for the anti-M13 and anti-Fd antibodies were prepared. The starting dilutions of the reference samples, VH3-23 HuCAL Gold® l+k VCSM13 and HuCAL PLATINUM pooled Hyperphages kappa and lambda were prepared. Serial dilutions of the phage supernatants were prepared by pre-filling microtiter plates with CTBST and adding phage and pre-filling a second microtiter plate with CTBST, and adding phage. For the reference sample, the starting dilution described above was plated and serial dilutions with both the anti-M13 and anti-Fd antibodies were plated.

Both the phage supernatants and reference samples were transferred for detection as follows. The blocked ELISA plates were washed with TBST. The phage supernatants were transferred from the dilution plates to the coated ELISA plates, incubated at room temperature, and washed with TBST. Anti-M13 peroxidase conjugate (Amersham) diluted in CTBST was added, and incubated for 1-2 h at room temperature. The Quanta Blu (Pierce) working solution was prepared by mixing 1 part (e.g. 0.5 ml) peroxide solution with 9 parts (e.g. 4.5 ml) substrate solution. The ELISA plates were washed with TBST, the QuantaBlu working solution was added. The fluorescence was measured after an incubation time of ~2 min (excitation: 320 nm, emission: 430 nm) and subsequently at intervals of 5 min. The evaluation of the ELISA data was completed as follows: calibration curves were created and the titers of the phage supernatants and control were calculated. For each sample, the titer on anti-Fd was divided by the titer on anti-M13 (anti-pVIII), the resulting ratio was the relative display rate. The results are shown in Table 13.

(The Binding Site Cat. PC075) coated ELISA plate followed by detection with goat anti-human IgG F(ab')2 fragment specific antibody conjugated with Alkaline Phosphatase (AP) (Jackson Cat. 109-055-097). Antigen specificity was tested by screening Fab containing cell extracts on DKK3 coupled-Carboxylbeads and BSA coupled-Carboxylbeads (DynaI) with a fluorometric microvolume assay technology (FMATe) for bead based assays (Applied Biosystems 8200 Cellular Detection System/PE Biosystems). Primary Hits were defined as Fabs that result in an FMAT mean fluorescence signal of at least 5-fold above the background which was set to a value of 200. Specificity to DKK3 was confirmed in a secondary ELISA with DKK3 as cognate antigen and CD38_Fc as negative control antigen. Heavy and light chain CDR3 region of 63, 43 and 44 clones for the VH3-23/VK1-39, VH3-23/VL3-1 and HuCAL Platinum® VH3-23/kappa sub-libraries were picked for sequencing in order to estimate the sequence diversity of DKK3 binding antibodies. The sequences of the CDR-H3s and CDR-L3s of selected binders are shown in FIG. 86. In total, 31 out of 56 successful sequences (55%), 20 out of 35 sequences (47%) and 17 out of 44 sequences (39%) for the VH3-23/VK1-39, VH3-23/VL3-1 and HuCAL-Pt VH3-23/kappa sublibraries, respectively were different, showing that the constructed libraries contained a diverse repertoire of DKK3 binders. Results are shown in Table 14.

TABLE 13

| Sub-Library | Framework VH | Framework VL | Titer (Spot-Titration) phageprep I | Titer (Spot-Titration) phageprep II | Titer (ELISA) phageprep I | Titer (ELISA) phageprep II | relative display phageprep I | relative display phageprep II |
|---|---|---|---|---|---|---|---|---|
| I8 | VH3-23 | VK1-39 | 5.7E+12 | 2.9E+12 | 2.9E+13 | 8.0E+12 | 6.1 | 9.3 |
| I19 | VH3-23 | VL3-1 | 6.6E+12 | 2.2E+12 | 2.8E+13 | 9.2E+12 | 6.6 | 8.8 |

Phage Display Selection Against Human DKK3, rhErbB4/her4 Fc Fusion, rhFZD-4 Fc Fusion and eGFP Parallel panning strategies with individual sub-collections or pools of sub-collections were performed in order to maximize the chance of identifying diverse binding antibodies with the desired biophysical characteristics. human Dickkopf-3 (DKK3) (Gene ID 27122), Recombinant human (rh)ErbB4/Her4 (Gene ID 2066) Fc fusion protein, rhFZD-4 (Gene ID 8322) Fc fusion and eGFP (enhanced green fluorescent protein; sequence provided above) were chosen as model antigens for collection validation. Collection screening was performed in a M-450 epoxy bead-based solution panning with the respective antigens covalently coupled to magnetic Dynabeads® (DynaI/Invitrogen Prod. no. 140.11), described below.

Bead-Based Solution Panning Against DKK3

DKK3 and control BSA coated carboxyl-beads (DynaI) were blocked with MPBST at room-temperature (RT) before incubation with pre-adsorbed phages. After several washing steps, bound phage were eluted and amplified by infecting TG1F+ cells for the next round of selection. After 3 rounds of selection, pJPd1 (shown in FIG. 9) phagemid DNA was isolated and Fab encoding fragments (modified ompA-VL and modified phoA-Fd) were excised by restriction digestion with XbaI and EcoRI and ligated into the expression vector pJPx1 (shown in FIG. 10) and transformed into E. coli TG1 F−. The infected cultures were then plated on large LB/Cam/Gluc plates and allowed to grow over night. Single clones were isolated and tested for Fab expression yield and antigen binding by ELISA. Fab expression was detected by incubating Fab containing cell extracts on a sheep anti-human Fd

TABLE 14

| | Dkk-3 | | | | |
|---|---|---|---|---|---|
| library | screened | Hits | Hit-rate [%] | picked for Seq. | (unique/ sequences |
| I8 | 732 | 525 | 72 | 63 | 31/56 |
| I19 | 715 | 536 | 75 | 43 | 20/35 |
| HuCAL-Pt VH3-23/k | 736 | 667 | 91 | 44 | 17/44 |

I8 represents VH3-23/VK1-39, and I19 represents VH3-23/VL3-1.

Bead-Based Solution Panning Against rhErbB4/her4 Fc Fusion, rhFZD-4 Fc Fusion and eGFP rhErbB4/Her4_Fc fusion, rhFZD-4 Fc fusion or eGFP and control BSA epoxy M450-beads (DynaI) were blocked with Chemiblocker for 2 h at room-temperature (RT) before incubation with pre-adsorbed phages for 2 h at RT. After several washing steps, bound phage were eluted and amplified by infecting TG1F+ cells for the next round of selection. After 3 rounds of selection, pJPd1 (shown in FIG. 9) phagemid DNA was isolated and Fab encoding fragments (modified ompA-VL and modified phoA-Fd) were amplified by PCR, purified, and digested with XbaI and EcoRI and ligated into the expression vector pJPx1 (shown in FIG. 10) and transformed into E. coli TG1 F−. The infected cultures were then plated on large LB/Cam/Gluc plates and allowed to grow overnight. Single clones were isolated and tested for Fab expression yield and antigen binding by ELISA. Fab expression was detected by incubating Fab containing cell extracts on a sheep anti-human Fd (The Binding Site Cat. PC075) coated ELISA plate followed by detection with goat anti-human IgG F(ab')2 fragment specific antibody conjugated with Alkaline Phosphatase (AP) (Jackson Cat. 109-055-097). Antigen specificity was tested by ELISA screening with Fab containing cell extracts on rhErbB4/Her4_Fc antigen, rhFZD-4_Fc antigen or eGFP directly coated on MaxiSorp plates. Primary Hits were defined as Fabs that result in an ELISA signal of at least 5-fold above the background. The results are shown in FIGS. 61A-D.

Fc-Capture Panning Against ErbB4/her4 Fc

Three rounds of solid phase Fc-capture panning were performed using human ErbB4/Her4 recombinant Fc-tagged protein immobilized by capturing with goat anti human-IgG Fc specific (Jackson; Cat. 109-005-098) or mouse anti human-IgG Fc specific (Jackson; Cat. 209-005-098) on Maxisorp plates (Nunc). Prior to each selection round, phages were blocked with 0.1 mg/ml human, goat and mouse immunoglobulin in MPBST/BSA. After several washing steps, bound phage were eluted and amplified by infecting TG1F+ cells for the next round of selection. After the third selection round, pJPd1 (shown in FIG. 9) phagemid DNA was isolated and Fab encoding fragments (modified ompA-VL and modified phoA-Fd) were exised by restriction digestion with XbaI and EcoRI and ligated into the expression vector pJPx1(shown in FIG. 10) and transformed into TG1F−. The infected cultures were then plated on large LB/Cam/Gluc plates and allowed to grow overnight. Single clones were isolated and tested for Fab expression yield and antigen binding by ELISA. Fab expression was detected by incubating Fab containing cell extracts on a sheep anti-human Fd (The Binding Site Cat. PC075) coated ELISA plate followed by detection with goat anti-human IgG F(ab')2 fragment specific antibody conjugated with Alkaline Phosphatase (AP) (Jackson Cat. 109 055 097). Antigen specificity was tested by ELISA screening with Fab containing cell extracts on ErbB4/Her4_Fc antigen captured via goat anti-human IgG antibody (Jackson; Cat. 109-005-098) coated on MaxiSorp plates. Primary Hits were defined as Fabs that result in an ELISA signal of at least 5-fold above the background. Specificity to ErbB4/Her4_Fc was confirmed in a secondary Fc-capture ELISA with ErbB4/Her4_Fc as cognate antigen and CD38_Fc as negative control antigen.

Heavy and light chain CDR3 regions of 112, 61 and 95 clones for the VH3-23/VK1-39, VH3-23/VL3-1 and HuCAL-Pt VH3-23/kappa sub-libraries, respectively, were sequenced in order to estimate the sequence diversity of ErbB4/Her4_Fc binding antibodies. In total, 31 out of 106 successful sequences (29%), 30 out of 61 sequences (49%) and 14 out of 91 sequences (15%) for the VH3-23/VK1-39, VH3-23/VL3-1 and HuCAL-Pt VH3-23/kappa sub-libraries were different, showing that the constructed libraries contained a diverse repertoire of binders. The sequence diversity is shown in Table 15.

TABLE 15

Her4_Fc

| | | Hits | | | | | picked for CP** | | | | |
|---|---|---|---|---|---|---|---|---|---|---|---|
| library | screened | 10x Bg | 5x Bg | 2x Bg | Hits* | Hit-rate [%] | 10x Bg | 5x Bg | 2x Bg | total | unique*** |
| I8 | 794 | 112 | 150 | 92 | 262 | 33 | 86 | 19 | 7 | 112 | 31/106 |
| I19 | 1145 | 39 | 7 | 15 | 46 | 4 | 39 | 7 | 15 | 61 | 30/61 |
| HuCAL-Pt VH3-23/k | 1364 | 922 | 105 | 118 | 1027 | 75 | 95 | 0 | 0 | 95 | 14/91 |

*Hits are defined as being reactive at least 5x above background (Bg)
**For compression plates (CP) a few clones were picked that were reactive only 2x above background (Bg)
***unique sequences per analyzable sequences
I8 represents VH3-23/VK1-39, and
I19 represents VH3-23/VL3-1.

Biacore $K_D$ (Affinity) Determination Via Antigen Capture Setup in Fab Format

Binding of monomeric Fab fractions (analyzed by analytical SEC; Superdex75, Amersham Pharmacia) to captured antigen was analyzed as follows: On a CM5 chip (Biacore/GE Healthcare) an appropriate anti-antigen tag capture antibody was covalently immobilized using EDC/NHS chemistry. Kinetic measurements were done by capturing the antigen and subsequent injection of six different Fab concentrations (2' serial dilution). After each cycle the sensor chip was regenerated. A blank injection of running buffer was used for double referencing. All sensorgrams were fitted using BIA evaluation software 3.2 (Biacore/GE Healthcare), to determine $k_{on}$ and $k_{off}$ rate constants, which were used to calculate $K_D$.

The Biacore $K_D$ determinations were performed as follows: Running buffer was PBST (phosphate buffered saline pH 7.2 GIBCO+0.05% Tween-20). Approx. 400 RU antigen with Fc fusion tag (lot#FYY0310041) were captured using an anti-human Fc antibody (Biacore/GE Healthcare). Fab concentrations ranging from 15.6 to 500 nM were used with a flow rate of 20 µl/min, an injection time of 30 s and a dissociation time of 100 s. Regeneration of the surface was done with 2 injections a 15 µl 3 M $MgCl_2$ reagent. The results are shown in FIG. 38.

Developability Testing of Antibodies and Antibody Fragments Identified Against DKK3, rhErbB4/Her4 Fc Fusion, rhFZD-4 Fc Fusion and eGFP The antibodies or fragments specific for the antigens were tested in both Fab and IgG1 formats for developability characteristics, such as, thermal stability in Fab format, affinity in Fab format, pI in IgG1 format, expression yield in both Fab and IgG formats, thermal stability in IgG1 format, and % monomer in IgG1 format as determined by SEC. The serum stability in IgG1 format was tested as described in Example 7.2. The thermal stability testing in Fab and IgG1 formats was completed as described in Examples 9.1.2 and 9.2.2. The pI in IgG1 format was completed as described in Example 9.2.4. The expression yield in IgG1 format was completed as described in Example 9.2.1. The % monomer in IgG1 format as determined by SEC was completed as described in Example 9.2.3. The results are shown in FIGS. 37-39, 45-48 and 62.

Again, the inventors believe that there is a high correlation between the input (antibody collection used for selection against an antigen) and output (antibodies identified as specific for the antigen) regarding the tested functional properties. Therefore, the collections of the invention comprise antibodies or fragments that comprise, in part, the same amino acid sequences as the constructs tested, for example, the framework regions and/or complementarity determining regions. The CDR3s are diversified. Since, in an aspect, the collections comprise the amino acid sequences, or the nucleic acids encoding them, of the tested constructs it is believed that the collections comprise antibodies or fragments having the same superior functional properties related to developability as the constructs tested in Example 9. Therefore, it is expected that many of the antibodies or fragments subsequently selected against an antigen will also have the same superior functional properties relevant to developability.

The data shown in FIGS. 37-39, 45-48 and 62A-C support this conclusion. FIG. 39 shows the Fabs selected against DKK3 or ErbB4/Her4_Fc antigen from collections of the invention and how the Fabs have a similar thermal stability as the control, which was the construct originally tested as described in Example 9. In addition, FIGS. 45-48 show the IgGs specific for DKK3 or ErbB4/Her4_Fc antigen that were selected from the collections of the invention and how the IgGs have similar isoelectric points (pI), thermal stability, expression yield and monomeric content as the controls, which were the constructs originally tested as described in Example 9. FIGS. 62A-C shows IgGs selected against rhErbB4/Her4_Fc fusion, rhFZD-4 Fc fusion and eGFP and how the IgGs have similar isoelectric points (pI), expression yield, thermal stability, and monomeric content as the controls, which were the constructs originally tested as described in Example 9.

Overall, this shows that the collections of the invention contain antibodies or fragments having superior properties relevant to developability and supports the inventors' hypothesis that the input, collections using sequences, for example, framework regions and/or complementarity determining regions from the germline protein pairs tested and shown to have superior functional properties, correlates well to the output, antibodies or fragments selected against any antigen having the same superior functional properties related to development.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

We claim:

1. A collection of nucleic acids encoding synthetic antibodies or functional fragments thereof, wherein the antibodies or functional fragments comprise variable heavy chain and variable light chain pairs, wherein the framework regions of the variable heavy chain and variable light chain pairs comprise germline protein sequences selected from twenty or more of the variable heavy chain and variable light chain pairs VH1-18 (SEQ ID NO: 204)/VK1-39 (SEQ ID NO: 236); VH1-18 (SEQ ID NO: 204)/VK3-15 (SEQ ID NO: 238); VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-46 (SEQ ID NO: 205)/VL3-21 (SEQ ID NO: 257); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-16 (SEQ ID NO: 234); VH3-07 (SEQ ID NO: 207)/VK1-27 (SEQ ID NO: 235); VH3-07 (SEQ ID NO: 207)/VK1-39 (SEQ ID NO: 236); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VK1-05 (SEQ ID NO: 230); VH3-11 (SEQ ID NO: 208)/VK1-39 (SEQ ID NO: 236); VH3-11 (SEQ ID NO: 208)/VK3-15 (SEQ ID NO: 238); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-16 (SEQ ID NO: 234); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-40 (SEQ ID NO: 250); VH3-15 (SEQ ID NO: 209)/VL1-47 (SEQ ID NO: 251); VH3-15 (SEQ ID NO: 209)/VL1-51 (SEQ ID NO: 252); VH3-15 (SEQ ID NO: 209)/VL2-14 (SEQ ID NO: 254); VH3-21 (SEQ ID NO: 210)/VK1-12 (SEQ ID NO: 233); VH3-21 (SEQ ID NO: 210)/VK1-27 (SEQ ID NO: 235); VH3-21 (SEQ ID NO: 210)/VL2-11 (SEQ ID NO: 253); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-30 (SEQ ID NO: 212)/VK3-20 (SEQ ID NO: 239); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK1-27 (SEQ ID NO: 235); VH3-74 (SEQ ID NO: 214)/VK3-20 (SEQ ID NO: 239); VH3-74 (SEQ ID NO: 214)/VL1-51 (SEQ ID NO: 252); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-15 (SEQ ID NO: 238); VH6-1 (SEQ ID NO: 216)/VK3-20 (SEQ ID NO: 239) and VH6-1 (SEQ ID NO: 216)/VL1-51 (SEQ ID NO: 252).

2. A collection of nucleic acids according to claim 1, wherein the antibodies or functional fragments comprise variable heavy chain and variable light chain framework regions comprising germline protein sequences of a germline protein pair, wherein said germline protein pair comprises the following properties:
i) an expression yield in Fab format of at least 2.5 mg/L;
ii) thermal stability at 70° C. or above in Fab format;
iii) monomeric content (% monomer) in Fab format of at least 98% as determined by SEC;
iv) an expression yield in IgG1 format of at least 30 mg/L;
v) thermal stability at 73° C. or above in IgG1 format; and
vii) monomeric content (% monomer) in IgG1 format of at least 99% as determined by SEC.

3. A collection of nucleic acids according to claim 1, wherein the framework regions of the variable heavy chain and variable light chain pairs comprise germline protein sequences selected from twenty five or more of the variable heavy chain and variable light chain pairs.

4. A collection of nucleic acids according to claim 3, wherein the framework regions of the variable heavy chain and variable light chain pairs comprise germline protein sequences selected from thirty or more of the variable heavy chain and variable light chain pairs.

5. A collection of nucleic acids according to claim 4, wherein the framework regions of the variable heavy chain and variable light chain pairs comprise germline protein sequences selected from thirty three or more of the variable heavy chain and variable light chain pairs.

6. A collection of nucleic acids according to claim 5, wherein the antibodies or fragments thereof comprise variable heavy chain and variable light chain pairs, wherein the framework regions of the variable heavy chain and variable light chain pairs comprise the germline protein sequences of the variable heavy chain and variable light chain pairs VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK3-15 (SEQ ID NO: 238); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

7. A collection of nucleic acids according to claim 6, wherein the antibodies or fragments comprise variable heavy chain and variable light chain framework regions comprising germline protein sequences of a germline protein pair, wherein said germline protein pair comprises the following properties:
  i) an expression yield in Fab format of at least 2.5 mg/L;
  ii) thermal stability at 70° C. or above in Fab format;
  iii) monomeric content (% monomer) in Fab format of at least 99% as determined by SEC;
  iv) an expression yield in IgG1 format of at least 30 mg/L;
  v) thermal stability at 73° C. or above in IgG1 format;
  vi) monomeric content (% monomer) in IgG1 format of at least 99% as determined by SEC, and
  vii) an isoelectric point in IgG1 format of at least 8.3.

8. A collection of nucleic acids according to claim 6, wherein the framework regions of the variable heavy chain and variable light chain pairs comprise germline protein sequences further selected from the variable heavy chain and variable light chain pairs VH3-23 (SEQ ID NO: 211)/VK1-39 (SEQ ID NO: 236); VH3-23 (SEQ ID NO: 211)/VL2-23 (SEQ ID NO: 255); and VH3-23 (SEQ ID NO: 211)/VL3-1 (SEQ ID NO: 256).

9. A collection of nucleic acids according to claim 5, wherein the framework regions of the variable heavy chain and variable light chain pairs comprise germline protein sequences selected from thirty six or more of the variable heavy chain and variable light chain pairs.

10. A collection of nucleic acids according to claim 9, wherein the antibodies or functional fragments comprise variable heavy chain and variable light chain pairs, wherein the framework regions of the variable heavy chain and variable light chain pairs comprise germline protein sequences of the variable heavy chain and variable light chain pairs VH1-18 (SEQ ID NO: 204)/VK3-20 (SEQ ID NO: 239); VH1-46 (SEQ ID NO: 205)/VK3-15 (SEQ ID NO: 238); VH1-46 (SEQ ID NO: 205)/VL1-51 (SEQ ID NO: 252); VH1-69*01 (SEQ ID NO: 206)/VL1-51 (SEQ ID NO: 252); VH3-07 (SEQ ID NO: 207)/VK1-12 (SEQ ID NO: 233); VH3-07 (SEQ ID NO: 207)/VK1-27 (SEQ ID NO: 235); VH3-07 (SEQ ID NO: 207)/VK3-15 (SEQ ID NO: 238); VH3-07 (SEQ ID NO: 207)/VL1-47 (SEQ ID NO: 251); VH3-07 (SEQ ID NO: 207)/VL1-51 (SEQ ID NO: 252); VH3-11 (SEQ ID NO: 208)/VL1-40 (SEQ ID NO: 250); VH3-11 (SEQ ID NO: 208)/VL1-47 (SEQ ID NO: 251); VH3-11 (SEQ ID NO: 208)/VL1-51 (SEQ ID NO: 252); VH3-11 (SEQ ID NO: 208)/VL2-23 (SEQ ID NO: 255); VH3-15 (SEQ ID NO: 209)/VK1-05 (SEQ ID NO: 230); VH3-15 (SEQ ID NO: 209)/VK1-06 (SEQ ID NO: 231); VH3-15 (SEQ ID NO: 209)/VK1-12 (SEQ ID NO: 233); VH3-15 (SEQ ID NO: 209)/VK1-27 (SEQ ID NO: 235); VH3-15 (SEQ ID NO: 209)/VK3-11 (SEQ ID NO: 237); VH3-15 (SEQ ID NO: 209)/VL1-51 (SEQ ID NO: 252); VH3-21 (SEQ ID NO: 210)/VK1-12 (SEQ ID NO: 233); VH3-23 (SEQ ID NO: 211)/VK1-39 (SEQ ID NO: 236); VH3-23 (SEQ ID NO: 211)/VK3-15 (SEQ ID NO: 238); VH3-23 (SEQ ID NO: 211)/VL2-23 (SEQ ID NO: 255); VH3-23 (SEQ ID NO: 211)/VL3-1 (SEQ ID NO: 256); VH3-53 (SEQ ID NO: 213)/VK3-15 (SEQ ID NO: 238); VH3-53 (SEQ ID NO: 213)/VL2-11 (SEQ ID NO: 253); VH3-74 (SEQ ID NO: 214)/VK1-05 (SEQ ID NO: 230); VH3-74 (SEQ ID NO: 214)/VK1-06 (SEQ ID NO: 231); VH3-74 (SEQ ID NO: 214)/VK1-12 (SEQ ID NO: 233); VH3-74 (SEQ ID NO: 214)/VK3-20 (SEQ ID NO: 239); VH5-51 (SEQ ID NO: 215)/VK1-39 (SEQ ID NO: 236); VH5-51 (SEQ ID NO: 215)/VL1-40 (SEQ ID NO: 250); VH5-51 (SEQ ID NO: 215)/VL1-51 (SEQ ID NO: 252); VH6-1 (SEQ ID NO: 216)/VK1-09 (SEQ ID NO: 232); VH6-1 (SEQ ID NO: 216)/VK3-20 (SEQ ID NO: 239) and VH6-1 (SEQ ID NO: 216)/VL1-51 (SEQ ID NO: 252).

11. A collection of nucleic acids according to claim 10, wherein the antibodies or functional fragments comprise variable heavy chain and variable light chain framework regions comprising germline protein sequences of a germline protein pair, wherein said germline protein pair comprises the following properties:
  i) an expression yield in Fab format of at least 2.5 mg/L;
  ii) thermal stability at 70° C. or above in Fab format;
  iii) monomeric content (% monomer) in Fab format of at least 98% as determined by SEC;
  iv) an expression yield in IgG1 format of at least 30 mg/L;
  v) thermal stability at 73° C. or above in IgG1 format; and
  vii) monomeric content (% monomer) in IgG1 format of at least 99% as determined by SEC.

12. A collection of nucleic acids according to claim 11, wherein
  i) the expression yield in Fab format is determined by UV-spectrophotometry using an extinction coefficient of 1.538 mL/mg and measuring absorbance at 280 nm;
  ii) the thermal stability in Fab format is determined by differential scanning fluorometry using PBS buffer;
  iii) the monomeric content (% monomer) in Fab format is determined by size exclusion chromatography using a Superdex75 HR10/30 column and Gibco D-PBS buffer at pH 7.4;
  iv) the expression yield in IgG1 format is determined by UV-spectrophotometry using an extinction coefficient of 1.369 mL/mg and measuring absorbance at 280 nm;
  v) the thermal stability in IgG1 format is determined by differential scanning fluorometry using PBS buffer; and
  vi) the monomeric content (% monomer) in IgG1 format is determined by size exclusion chromatography using a Tosoh TSK-Gel G3000SWxl column and Gibco D-PBS buffer at pH 7.4.

13. The collection of nucleic acids according to claim 10, wherein said antibodies or functional fragments thereof comprise one or more complementarity determining regions comprising germline protein sequences from the respective variable heavy chain and variable light chain pairs.

14. The collection of nucleic acids according to claim 13, wherein said antibodies or functional fragments thereof comprise CDR1 regions comprising germline protein sequences from the respective variable heavy chain and variable light chain pairs depicted in SEQ ID NOs: 204-216, 230-239 and 250-257.

15. The collection of nucleic acids according to claim 14, wherein said antibodies or fragments thereof comprise HCDR1 regions from the respective HCDR1 regions depicted in SEQ ID NOs: 204-216.

16. The collection of nucleic acids according to claim 14, wherein said antibodies or fragments thereof comprise LCDR1 regions from the respective LCDR1 regions depicted in SEQ ID NOs: 230-239 and 250-257.

17. The collection of nucleic acids according to claim 13, wherein said antibodies or functional fragments thereof comprise CDR2 regions comprising germline protein sequences from the respective variable heavy chain and variable light chain pairs depicted in SEQ ID NOs: 204-216, 230-239 and 250-257.

18. The collection of nucleic acids according to claim 17, wherein said antibodies or fragments thereof comprise HCDR2 regions from the respective HCDR2 regions depicted in SEQ ID NOs: 204-216.

19. The collection of nucleic acids according to claim 17, wherein said antibodies or fragments thereof comprise LCDR2 regions from the respective LCDR2 regions depicted in SEQ ID NOs: 230-239 and 250-257.

20. The collection of nucleic acids according to claim 10, wherein said antibodies or functional fragments thereof comprise one or more complementarity determining regions comprising amino acid modifications that remove potential post translational modification sites.

21. The collection of nucleic acids according to claim 20, wherein said antibodies or functional fragments thereof comprise one or more heavy chain complementarity determining regions comprising the complementarity determining region sequences from the respective variable heavy chains depicted in SEQ ID NOs: 266-278.

22. The collection of nucleic acids according to claim 21, wherein said antibodies or functional fragments thereof comprise HCDR1 regions from the respective HCDR1 region depicted in SEQ ID NOs: 266-278.

23. The collection of nucleic acids according to claim 21, wherein said antibodies or functional fragments thereof comprise HCDR2 regions from the respective HCDR2 region depicted in SEQ ID NOs: 266-278.

24. The collection of nucleic acids according to claim 10, wherein said antibodies or functional fragments thereof comprise a FR4 region selected from the group consisting of JH4 (SEQ ID NO:293), Jκ1 (SEQ ID NO:297), and Jλ2/3 (SEQ ID NO:301).

25. The collection of nucleic acids according to claim 10, wherein said antibodies or functional fragments thereof comprise a diversified HCDR3 region.

26. The collection of nucleic acids according to claim 10, wherein said antibodies or functional fragments thereof comprise a diversified LCDR3 region.

27. The collection of nucleic acids according to claim 10, wherein the collection comprises at least $1 \times 10^4$ antibodies or functional fragments thereof.

28. The collection of nucleic acids according to claim 10, wherein said antibodies are selected from the groups consisting of human IgG1, IgG2, IgG3, IgG4, IgA, IgE, IgM and IgD.

29. The collection of nucleic acids according to claim 10, wherein said functional fragments of said antibodies are selected from the group consisting of Fab, F(ab')2, Fab', Fv, and scFv.

30. A vector comprising the collection of nucleic acids according to claim 10.

31. A recombinant host cell comprising the vector of claim 30.

32. A method of producing a collection of nucleic acids encoding synthetic antibodies or functional fragments thereof, comprising
   a) identifying the variable heavy chain and variable light chain germline gene pairs present in the human immune repertoire;
   b) testing the variable heavy chain and variable light chain germline protein pairs identified in step a) for the following properties:
      i) an expression yield in Fab format of at least 2.5 mg/L;
      ii) thermal stability at 70° C. or above in Fab format;
      iii) monomeric content (% monomer) in Fab format of at least 98% as determined by SEC;
      iv) an expression yield in IgG1 format of at least 30 mg/L;
      v) thermal stability at 73° C. or above in IgG1 format; and
      vii) monomeric content (% monomer) in IgG1 format of at least 99% as determined by SEC; and
   c) generating a collection, wherein the antibodies or functional fragments thereof comprise variable heavy chain and variable light chain pairs, wherein the framework regions of the variable heavy chain and variable light chain pairs comprise germline protein sequences of the germline protein pairs fulfilling the properties of step b), wherein the collection encodes the germline protein sequences according to claim 1.

* * * * *